(12) United States Patent     (10) Patent No.:    US 7,977,071 B2
Nuttal et al.                                                 (45) Date of Patent:     Jul. 12, 2011

(54) BINDING MOIETIES BASED ON SHARK IGNAR DOMAINS

(75) Inventors: Stewart Nuttal, Ivanhoe (AU); Victor Streltsov, Templestowe (AU); Katherine Merne Griffiths, Eltham (AU); Jennifer Ann Carmichael, East Brunswick (AU); Peter Hudson, Blackburn (AU); Robert Alexander Irving, Pakenham (AU); Joseph Noozhumurry Varghese, East Brunswick (AU); Miles Mackay Barraclough, Bondi (AU); David Peter Simmons, North Melbourne (AU); Kylie Anne Henderson, Southport (AU)

(73) Assignee: Adalta Pty Ltd., Bundodra (AU)

( * ) Notice: Subject to any disclaimer, the term of this patent is extended or adjusted under 35 U.S.C. 154(b) by 0 days.

(21) Appl. No.: 11/628,475

(22) PCT Filed: Jun. 2, 2005

(86) PCT No.: PCT/AU2005/000789
§ 371 (c)(1),
(2), (4) Date: Jun. 16, 2008

(87) PCT Pub. No.: WO2005/118629
PCT Pub. Date: Dec. 15, 2005

(65) Prior Publication Data
US 2009/0148438 A1    Jun. 11, 2009

(51) Int. Cl.
*C12P 21/04* (2006.01)
*C12P 21/08* (2006.01)
*A61K 39/00* (2006.01)
(52) U.S. Cl. .................. 435/69.6; 530/387.3; 424/133.1
(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | 435/181 |
| 5,955,363 A | 9/1999 | Lewis et al. | 435/440 |
| 7,166,697 B1 * | 1/2007 | Galanis et al. | 530/350 |

FOREIGN PATENT DOCUMENTS

| | | |
|---|---|---|
| EP | 368684 | 3/1994 |
| EP | 239400 | 8/1994 |
| WO | WO 90/05144 | 5/1990 |
| WO | WO 91/08482 | 6/1991 |
| WO | WO 94/25591 | 11/1994 |
| WO | WO 96/34103 | 10/1996 |
| WO | WO 97/27213 | 7/1997 |
| WO | WO 03/014161 | 2/2003 |
| WO | WO 03/050531 | 6/2003 |

OTHER PUBLICATIONS

Nuttall, Humberstone, Krishnan, Carmichael, Doughty, Hattarki, Coley, Casey, Anders, Foley, Irving and Hudson. Selection and affinity maturation of IgNAR variable domains targeting *Plasmodium falciparum* AMA1. Proteins, 2004. vol. 55, pp. 187-197.*

Nuttall, Krishnan, Doughty, Pearson, Ryan, Hoogenraad, Hattarki, Carmichael, Irving, and Hudson. Isolation and characterization of an IgNAR variable domain specific for the human mitochondrial translocase receptor Tom70. European Journal of Biochemistry, 2003. vol. 270, pp. 3543-3554.*

Agrawal, A. et al. 'Implications of transposition mediated by V(D)J-recombination proteins RAG1 and RAG2 for origins of antigen-specific immunity', *Nature* 394: 744-751 (1998).

Blundell et al., 'Knowledge-based protein modeling and design', *Eur. J. Biochem*, 172: 513-520 (1988).

Bork, P. et al. 'The immunoglobulin fold: structural classification, sequence patterns and common core', *J. Mol. Biol.*, 242: 309-320 (1994).

Brandl, M. et al. 'π-Interactions in Proteins', *J. Mol. Biol.*, 307: 357-377 (2001).

Brünger, A.T. et al., 'Recent developments for the efficient crystallographic refinement of macromolecular structures', *Current Opinions in Structural Biology*, 8(5): 606-611 (1998a).

Bruns, C.M. et al., 'Human Glutathione Transferase A4-4 Crystal Structures and Mutagenesis Reveal the Basis of High Catalytic Efficiency with Toxic Lipid Peroxidation Products', *J. Mol. Biol.* 288(3): 427-439 (1999).

Casasnovas, J.M. et al. 'A Dimeric crystal structure for the N-terminal two domains of intercellular adhesion molecular-1', *Proc. Natl. Acad. Sci. USA*, 95: 4134-4139 (1998).

Casey, J.L. et al., 'Tumour targeting of humanised cross-linked divalent-fab' antibody fragments: a clinical phase I/II study', *Br J Cancer*, 86(9): 1401-10 (2002).

Chothia, C. et al., 'Conformations of immunoglobulin hypervariable regions', *Nature* 342: 877-883 (1989).

Chothia, C. & Jones, E.Y. 'The molecular structure of cell adhesion molecules' *Annu. Rev. Biochem.*, 66: 823-862 (1997).

Chothia, C. et al., 'Structural determinants in the sequences of immunoglobulin variable domain', *J. Mol. Biol.* 278: 457-479 (1998).

Davies, J. & Riechmann, L., 'Camelising human antibody fragments: NMR studies on VH domains', *FEBS Lett.*, 339(3): 285-290 (1994).

Davies, J. & Riechmann, L., 'Single antibody domains as small recognition units: design and in vitro antigen selection of camelized, human VH domains with improved protein stability', *Protein Eng.*, 9(6): 531-537 (1996).

Desmyter, A. et al., 'Crystal structure of a camel single-domain VH antibody fragment in complex with lysozyme', *Nat. Struct. Biol.* 3: 803-811 (1996).

Desmyter, A. et al., 'Three camelid VHH domains in complex with porcine pancreatic alpha-amylase. Inhibition and versatility of binding topology', *J. Biol. Chem.* 277: 23645-23650 (2002).

(Continued)

*Primary Examiner* — Anne M. Gussow
(74) *Attorney, Agent, or Firm* — Medlen & Carroll, LLP

(57) ABSTRACT

The present invention relates to immunoglobulin new antigen receptors (IgNARs) from fish and uses thereof. In particular, the present invention relates to modified IgNAR variable domains and to domains from members of the immunoglobulin superfamily that have been modified to include structural features derived from IgNAR variable domains.

8 Claims, 50 Drawing Sheets

OTHER PUBLICATIONS

Diaz, et al., Somatic hypermutation of the new antigen receptor gene (NAR) in the nurse shark does not generate the repertoire: Possible role in antigen-driven reactions in the absence of germinal centers. Proc. Natl. Acad. Sci. USA 95:14343-14348 (1998).

Diaz, M. et al., 'Mutational paterns of nurse shark antigen receptor gene (NAR) is similar to that of mammalian Ig genes to spontaneous mutations in evolution: the translesion synthesis model of somatic hypermutation', *Int. Immunol.*, 11: 825-833 (1999).

Diaz, M. et al., 'Structural analysis, selection and ontogeny of the shark new antigen receptor (IgNAR): identification of a new locus preferentially expressed in early development', *Immunogenetics*, 54: 501-512 (2002).

Dooley, H. et al., 'Selection and characterization of naturally occurring single-domain (IgNAR) antibody fragments from immunized sharks by phage display', *Mol. Immunol.* 40: 25-33 (2003).

Dunbrak et al., 'Meeting review: the second meeting on the critical assessment of techniques for protein structure prediction (CASP2), Asilomar, California, Dec. 13-16, 1996' *Folding and Design*, 2: 27-42 (1997).

Greenberg, A.S. et al., 'A new antigen receptor gene family that undergoes rearrangement and extensive somatic diversification in sharks', *Nature*, 374: 168-173 (1995).

Greer, 'Model structure for the inflammatory protein C5a', *Science*, 228: 1055 (1985).

Harpaz, Y. & Chothia, C. 'Many of the immunoglobulin superfamily domains in cell adhesion molecules and surface receptors belong to a new structural set which is close to that containing variable domains', *J. Mol. Biol.*, 238: 528-539 (1994).

Hodder, A.N. et al., 'The disulfide bond structure of *Plasmodium* apical membrane antigen-1', *J. Biol. Chem.* 271: 29446-29452 (1996).

Holden, H.M. et al., 'X-ray structure determination of telokin, the C-terminal domain of myosin light chain kinase, at 2.8 angstroms resolution', *J. Mol. Biol.*, 227: 840-851 (1992).

Hong, L. et al., 'Structure of the protease domain of memapsin 2 (β-Secretase) complexed with inhibitor', *Science*, 290: 150-153 (2000).

Jespers, L. et al., 'Crystal structure of HEL$_4$, a soluble, refoldable human VH single domain with a germ-line scaffold', *J. Mol. Biol.*, 337: 893-903 (2004).

Kortt, A.A. et al., 'Solution properties of *E. coli* epressed VH domain of anti-neuraminidase antibody NC$_{41}$', *J. Protein Chem.*, 14: 167-178 (1995).

La Fortelle, E. & Bricogne, G., 'Maximum likelihood heavy-atom parameter refinement program for the Multiple Isomorphous Replacement and Multiwavelength Anomalous Diffraction methods', in Carter, C.W. & Sweet, R.M. eds., *Meth. Enzym.*, 276: 472-494, Academic Press: Orlando, FL (1997).

Lamzin, V.S. & Wilson, K.S. 'Automated refinement for protein crystallography', *Methods Enzymol.*, 277: 269-305 (1997).

Lee, Y.S. & Mrksich, M., 'Protein chips: from concept to practice' *Trends Biotechnol.*, 20(12 Suppl.): S14-8 (2002).

Lo Conte, L. et al., 'The atomatic structure of protein-protein recognition sites', *J. Mol. Biol.*, 285: 2177-2198 (1999).

Low, N.M. et al., 'Mimicking somatic hypermutation: affinity maturation of antibodies displayed on bacteriophage using a bacterial mutator strain' *J Mol Biol*, 26o: 359-368 (1996).

Lu, G., 'TOP: a new method for protein structure comparisons and similarity searches', *J Appl Crystellog*, 33: 176-183 (2000).

McLachan, 'Gene duplications in the structural evolution of chymotrypsin' *J. Mol. Biol.*, 128: 49 (1979).

McRee, D.E. 'Xtal/view/xfit—a versatile program for manipulating atomic coordinates and electron density', *J. Struct. Biol.*, 125: 156-165 (1999).

Minsky, A. et al., 'Secretion of beta-lactamase into the periplasm pf *Escherichia coli*: evidence for distinct release step associated with a conformational change', *Proc. Natl. Acad. Sci. USA*, 83: 4180-4184 (1986).

Muyldermans, S. et al., 'Sequence and structure of VH domain from naturally occurring camel heavy chain immunoglobulins lacking light chains', *Protein Eng.* 7: 1129-1135 (1994).

Nieba, L. et al., 'Disrupting the hydrophobic patches at the antibody variable/constant domain interface: improved in vivo folding and physical characterization of an engineered scFv fragment', *Protein Eng.*, 10(4): 435-444 (1997).

Nguyen, V.K. et al., 'Heavy-chain antibodies in Camelidae: a case of evolutionary innovation', *Immunogenetics*, 54: 38-47 (2002).

Novotny, J. et al., 'A soluble, single-chained T-cell receptor fragment endowed with antigen-combining properties', *PNAS USA*, 88(19): 8646-8650 (1991).

Nuttall, S.D. et al. 'Isolation of the new antigen receptor from Wobbegong Sharks, and use as a scaffold for the display of protein loop libraries', *Mol. Immunol.*, 38: 313-326 (2001).

Nuttall, S.D. et al., 'A naturally occurring NAR variable domain against the Gingipain K protease from *Porphyromonas gingivalis*', *FEBS Lett.*, 516: 8o-86 (2002).

Nuttall, S.D. et al., 'Isolation and characterization of an IgNAR variable domain specific for the human mitochondrial translocase receptor Tom70', *Eur. J. Biochem.*, 270: 3543-3554 (2003).

Nuttall, S.D. et al., 'Selection and affinity maturation of IgNAR variable domains targeting *Plasmodium falciparum* AMA1', *Proteins*, 55: 187-197 (2004).

Otwinowski, Z. & Minor, W., 'Processing of X-ray diffraction data collected in an oscillation mode', *Methods Enzymol.*, 276: 307-326 (1997).

Queen, M. et al., 'A humanized antibody that binds to interleukin-2 receptor', *Proc. Natl. Acad. USA*, 86: 10029-10033 (1989).

Riechmann, L. et al., 'Reshaping human antibodies for therapy', *Nature*, 332: 323-327 (1988).

Riechmann, L. 'Rearrangement of the former VL interface in the solution structure of a camelised, single antibody VH domain', *J. Mol. Biol.*, 259: 957-969 (1996).

Rossman & Argos, 'A comparison of the heme binding pocket in globins and cytochrome b5' *J. Biol. Chem.*, 250: 7525 (1975).

Roux, K.H. et al., 'Structural analysis of a nurse shark (new) antigen receptor (NAR): molecular convergence of Nar and unusual mammalian immunoglobulins', *Proc. Acad. Natl. Sci. USA*, 95: 11804-11809 (1998).

Rumfelf et al., 'The development of primary and secondary lymphoid tissues in the nurse shark *Ginglymostroma cirratum*: B-cell zones precede dendritic cell immigration and T-cell zone formation during ontogeny of the spleen', *Scand. J. Immunol.*, 56: 130-148 (2002).

Saphire, E.O. et al., 'Crystal structure of a neutralizing human IgG against HIV-1: A template for vaccine design', *Science*, 293: 1155-1159 (2001).

Sayle et al., 'RASMOL: biomolecular graphics for all', *TIBS*, 20: 374 (1995).

Skerra, Arne, Engineered protein scaffolds for molecular recognition. Journal of Molecular Recognition, vol. 13:167-187 (2000).

Snow & Amzel, 'Calculating three-dimensional changes in protein structure due to amino acid substitutions: the variable region of immunoglobulins', *Protein: Structure, Function and Genetics*, Alan R. Liss, Inc., 1: 267-279 (1986).

Soroka, V. et al., 'Structure and interactions of NCAM Ig1-2-3 suggest a novel zipper mechanism for homophilic adhesion', *Structure*, 11(10): 1291-1301 (2003).

Spada, S. et al., 'Reproducing the natural evolution of protein structural features with the selectively infective phage (SIP) technology. The kink in the first strand of antibody kappa domains', *J. Mol. Biol.*, 283: 395-407 (1998).

Streltsov, V.A. et al., 'Structural evidence for evolution of shark Ig new antigen receptor variable domain antibodies from a cell-surface receptor' *Proc Natl Acad Sci USA* 101(34): 12444-12449 (2004).

Sutcliffe, M.J. et al., 'Knowledge-based modeling of homologous. proteins, part I: three-dimensional frameworks derived from the simultaneous superposition of multiple structures', *Protein Enqineenng*, 1:377-384 (1987).

Winn, M.D. et al., 'Use of TLS parameters to model anisotrophic displacements in macromolecular refinement', *Acta. Crystallog D.*, 57: 122-133 (2001).

Wolfson, H.J. et al., 'From structure to function: methods and applications', *Curr. Protein Pept. Sci.*, 6(2): 171-183 (2005).

Wu, T.T. et al., 'Length distribution of CDRH$_3$ in antibodies', *Proteins* 16: 1-7 (1993).

Wulfing, C. & Pluckthun, A., 'Correctly folded T-cell receptor fragments in the periplasm of *Escherichia coli*—influence of folding catalysts', *J. Mol. Biol.* 242(5): 655-669 (1994).

Xu, D. et al., 'Computational tools for protein modeling', *Curr. Protein Pept. Sci.*, 1(1): 1-21 (.2000).

Yau, et al., Emerging trends in the synthesis and improvement of hapten-specific recombinant antibodies. Biotechnology Advances, vol. 21(7):599-637 (2003).

Yelamos, J. et al., 'Targeting of non-Ig sequences in place of the V segment by somatic hypermutation', *Nature*, 376: 225-9 (1995).

Zaccolo, M. et al., 'An approach to random mutagenesis of DNA using mixtures of triphosphate derivatives of neucleotide analogues', *J Mol Biol*, 255: 589-603 (1996).

* cited by examiner

Figure 1

| SEQ ID NO: | | 1 | 10 | 20 | 30 | 40 |
|---|---|---|---|---|---|---|
| 1 | 12Y-1 | AWVDQTPRTATKETGESLTINCVLRDASYGLESTGWYRTK | | | | |
| 3 | 12Y-2 | ---------------------------FE-KD------- | | | | |
| 9 | 12A-9 | -R------I----------------TACA-DS-N----- | | | | |
| 5 | 1A-7 | --------SV------------A-KN-ADD--R-D----T | | | | |
| 17 | 7E-22 | VR-----H-E---------------STNCAFS--R----- | | | | |
| 18 | 7E-23 | -LT------V----------------THCA-SD-Y----- | | | | |
| 19 | 7E-51 | ---E-P---------G--------V-N-RCA-LR-D----- | | | | |
| 20 | 7E-54 | -R------------------H-A---SECA-GD-Y----- | | | | |
| 21 | 7E-56 | -R------------------------S--K--------- | | | | |
| 22 | 7E-58 | G------TS---------------ET-CA-SE-Y----- | | | | |
| 23 | 7E-68 | ----------------------------S-R------- | | | | |
| 24 | 7E-77 | -RA-----P----------------T-CSFT--Y----- | | | | |
| 25 | 7E-80 | -R------P----------------T-CAFS-------- | | | | |
| 26 | 7E-87 | ----PK--PV---------------TNCA-GD-D----R | | | | |
| 27 | 7E-91 | QR-----K-----R------Y---K-TPCS-SI-W----- | | | | |
| 28 | 7E-93 | -------KS-----------S--I---T--V--------- | | | | |

Figure 1 cont.

| SEQ ID NO: | | 41      50       60       70       80 |
|---|---|---|
| 1 | 12Y-1 | LGSTNEQTISIGGRYVETVNKGSKSFSLRIRDLRVEDSGT |
| 3 | 12Y-2 | -------S----------------------S--------- |
| 9 | 12A-9 | ----K----------S---DE--N-A--T----------- |
| 5 | 1A-7  | -------K-------------------------------- |
| 17 | 7E-22 | -------KV------L---DR------------------- |
| 18 | 7E-23 | -------F----------------------S--------- |
| 19 | 7E-51 | -D----------------DL----------S--------- |
| 20 | 7E-54 | ------------------D RT------S---------A |
| 21 | 7E-56 | ---------------------------------------- |
| 22 | 7E-58 | -------S----------------------S--------- |
| 23 | 7E-68 | ---------------------------------------- |
| 24 | 7E-77 | -------SM---------------------S--------- |
| 25 | 7E-80 | -------S----------------------S--------- |
| 26 | 7E-87 | ----KL-K---------------------SE-S----S- |
| 27 | 7E-91 | -------KMTL---H---E--E--------S--------- |
| 28 | 7E-93 | -------A-------------------------------- |

Figure 1 cont.

| SEQ ID NO: |  | 81         90 | 104         113 |  |
|---|---|---|---|---|
| 1  | 12Y-1  | YKCGAFRFWLP | YGYGSLPLSEKGAGTVLTVK | [111] |
| 3  | 12Y-2  | ---Q--YSLPLGD | -N-SL-FRG------A---- | [113] |
| 9  | 12A-9  | ---K-YRRCAFNTGVGYKE | --------- | [108] |
| 5  | 1A-7   | -----YFSDAMSNYSYPIPGEK | --------- | [111] |
| 17 | 7E-22  | FQ-Q-YGTL-RQSGLSCYNGDG | LE-GL------ | [113] |
| 18 | 7E-23  | ---H-Y-DTRYDRECYDWRYP | ---V------R | [112] |
| 19 | 7E-51  | ------S-MVYGLSCYG- | VWW--------- | [110] |
| 20 | 7E-54  | -Q-Q-WGEKPR | YGETRYACNGDY--GD-L---- | [113] |
| 21 | 7E-56  | ---S-CDDVAN | -YRRYTY ------I---- | [109] |
| 22 | 7E-58  | ---Q-Y | TVYD-SCYGDYS ----------- | [109] |
| 23 | 7E-68  | ----GLATLTA | PYEQLYS Y---------- | [110] |
| 24 | 7E-77  | ------GAT-TGPLLTLE-Y | ---------- | [111] |
| 25 | 7E-80  | ---Q-YVIATMAP | LC-A-YSWN---------- | [113] |
| 26 | 7E-87  | ---Q-S | RKWGRSCAGDRPYDY---------- | [112] |
| 27 | 7E-91  | ---QVYNPHR | SCPWTYA DP-F--D---T | [108] |
| 28 | 7E-93  | ----NCGYITT | ITFRCDGRD-E--------- | [111] |
|    |        | 81         90 | 104         113 |  |

Figure 13
(a)
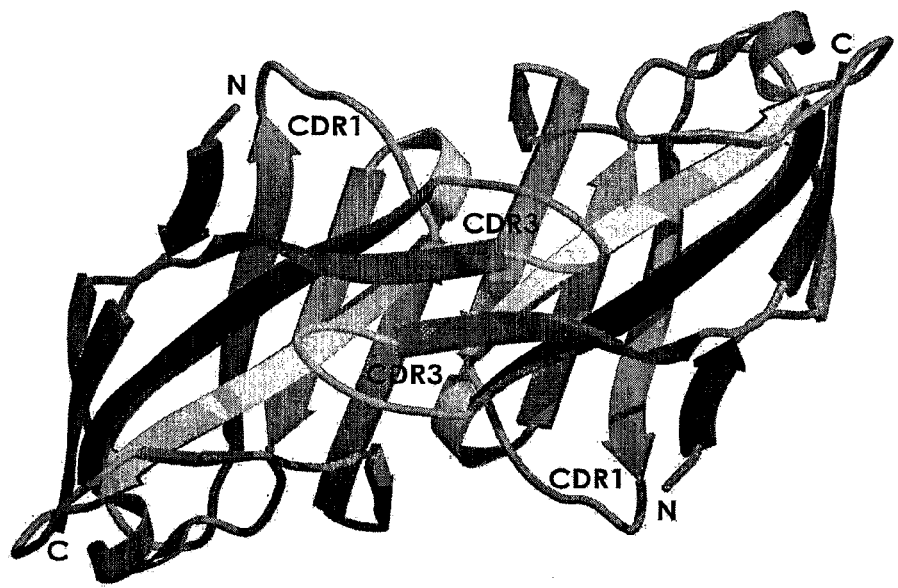
(b)
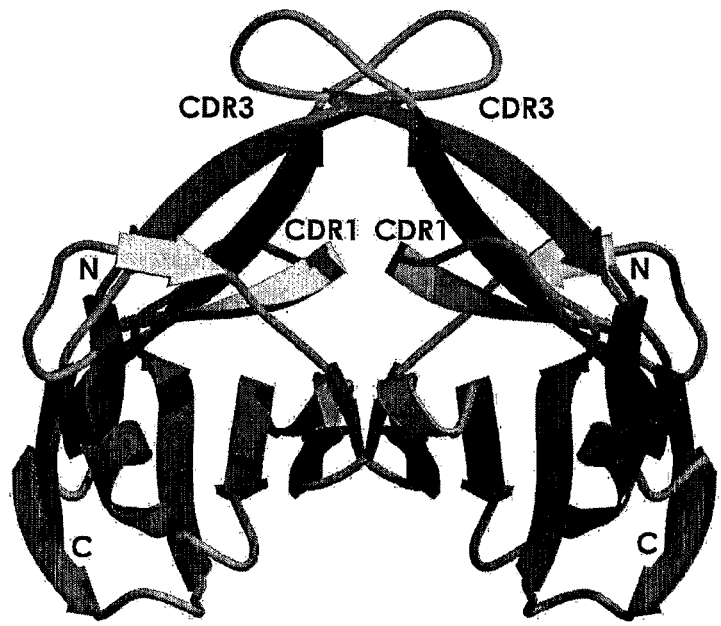

Figure 17

| SEQ ID NO: | | | |
|---|---|---|---|
| 11 | 14M-15 | 1 | AWVDQIPRIATKEIGESLTINCVIRDASFELKDIGWYRTKLGSTNEQSISIGGRYVETVN |
| 15 | 22A-2 | 1 | AWVDQIPRIATKEIGESLTINCVIRDASFELKDIGWYRSKLGSTNEQSISIGGRYVETVN |
| 102 | 24A-82 | 1 | AWVDQIPRIATKEIGESLTINCVIRDSNDALGSTIWYRTKLGSTNEQIISIGGRYVETVN |
| 103 | 24A-72 | 1 | AWVDQIPRSVIKEIGESVTINCVIEDSPCDLANTIWYRTKLGSKYEQIVSIGGRYVETVN |
| 104 | 24A-58 | 1 | AWVDQIPRSVTKEIGESLTINCVIRDTSCAFSSTGWYRTKLGSTNEQSISIGGRYVETVN |
| 105 | 24A-75 | 1 | AWVDQIPRSATKEIGESLTINCVIRDTSCAFSSTGWYRTKLGSTNEQSISIGGRYVETVN |
| 106 | 24A-46 | 1 | AWVDQIQFTATKEIGESLTINCVIRDTSCAFSSTGWYRTKLGSTNEQSISIGGRYVETVN |
| 107 | 24A-24 | 1 | AWVDQIPRTTTKEIGESLTINCVITDTICVFSNTGWYRTKLGSTNEQSISIGGRYVETVN |
| 108 | 24A-28 | 1 | AWVDQIPRIATKEIGESLTINCVIRDTSCAFSSTGWYRTKLGSTNEQRISIGGRYVETVN |
| 109 | 24A-33 | 1 | AWVDQIPRIATKEIGESLTINCVIRYTSCAFDNIGWYRTKLGSRNERSISIGGRYVETVN |
| 110 | 24A-10 | 1 | AWVDQIPRIVIKEIGESLTINCVIRGTEHGLCRADWARTKLGSTNEQKMIIGGRYVETVN |
| 111 | 24A-19 | 1 | AWVDQIPRIATKEIGESLTINCVIREGGCAIGSTYWFRTKLGSTNEQKLSIGGRYVETVN |

| 11 | 14M-15 | 61 | KGSKSFSLRISDLRVEDSGTYKCQAFYSLLLGDYNYSLLFRGEKGAGTALTVF |
| 15 | 22A-2 | 61 | KGSKSFSLRISDLRVEDSGTYKCQAFYSLLLGDYNYSLLFRGEKGAGTALTVF |
| 102 | 24A-82 | 61 | KGSKSFSLRISDLRVEDSGTYKCQAFYSLLLGDYNYSLLFRGEKGAGTALTVF |
| 103 | 24A-72 | 61 | KGSKSFSLRISDLRVEDSGTYKCQAFYSLLLGDYNYSLLFRGEKGAGTALTVF |
| 104 | 24A-58 | 61 | KGSKSFSLRISDLRVEDSGTYKCQAFYSLLLGDYNYSLLFRGEKGAGTALTVF |
| 105 | 24A-75 | 61 | KGSKSFSLRISDLRVEDSGTYKCQAFYSLLLGDYNYSLLFRGEKGAGTALTVF |
| 106 | 24A-46 | 61 | KGSKSFSLRISDLRVEDSGTYKCQAFYSLLLGDYNYSLLFRGEKGAGTALTVF |
| 107 | 24A-24 | 61 | KGSKSFSLRISDLRVEDSGTYKCQAFYSLLLGDYNYSLLFRGEKGAGTALTVF |
| 108 | 24A-28 | 61 | KGSKSFSLRISDLRVEDSGTYKCQAFYSLLLGDYNYSLLFRGEKGAGTALTVF |
| 109 | 24A-33 | 61 | KGSKSFSLRISDLRVEDSGTYKCQAFYSLLLGDYNYSLLFRGEKGAGTALTVF |
| 110 | 24A-10 | 61 | KGSKSFSLRISDLRVEDSGTYKCQAFYSLLLGDYNYSLLFRGEKGAGTALTVF |
| 111 | 24A-19 | 61 | KGSKSFSLRISDLRVEDSGTYKCQAFYSLLLGDYNYSLLFRGEKGAGTALTVF |

| | FR | CDR | FR | | Oligo |
|---|---|---|---|---|---|
| | | | | SEQ ID NO: | |
| | CQA | FYSLFLGDYWYSLLFRGE | KGAGTALTVK | 140 | |
| | CQA | FYSLFXXXYXXBLFRGE | KGAGTALTVK | 141 | KH0001RC |
| | CQA | FYSXXXXXXYXXBLFRGE | KGAGTALTVK | 142 | KH0002RC |
| | CQA | FYSXSXSXXSXZBBFRGE | KGAGTALTVK | 143 | KH0003RC |
| | CQA | FYSYXXSZZZXXBLFRGE | KGAGTALTVK | 144 | KH0004RC |
| | CQA | FYSXXXJXXJXXJXXLFRGE | KGAGTALTVK | 145 | KH0005RC |
| | CQA | FYBJXXJXXJXXJXXLFRGE | KGAGTALTVK | 146 | KH0006RC |

X = any residue
B = hydrophobic bias: Leu, Val, Pro, Ala, His, Gln, Glu, Asp, Gly, Arg
Z = ring bias: Ser, Tyr, His, Pro
J = aromatic bias : Phe, Tyr, Cys, Ile, Met, Asn Lys, Arg, Ser, Trp, Leu

```
SEQ
ID NO:
 4    241 - TATAAGTGTCAAGCATTCTATTCTCTTCCGTTGGGCGATTATAACTATTCTCTGCTGTTT - 300
 3          - Y   K   C   Q   A   F   Y   S   L   P   L   G   D   Y   N   Y   S   L   L   F
                                86 87 88 89 90 91 92 93 94 95 96 97 98 99 100

4    301 - AGGGGTGAGAAAGGAGCTGGCACCGCATTAACCGTGAAAGCGGCCGCAGATTATAAAGAT - 360
 3          - R   G   E   K   G   A   G   T   A   L   T   V   K   A   A   A   D   Y   K   D
              101 102 103
```

| SEQ ID NO: | | |
|---|---|---|
| 4 | 14M-15 | AWVDQTPRTATKETGESLTINCVLRDASFELKDTGWYRTKLGSTNEQSISIGGRYVETVN |
| 3 | 22A-2 | AWVDQTPRTATKETGESLTINCVLRDASFELKDTGWYRSKLGSTNEQSISIGGRYVETVN |
| | | ************************************ * *********************** |
| 4 | 14M-15 | KGSKSFSLRISDLRVEDSGTYKCQAFYSLLLGDYNYSLLFRGEKGAGTALTVK |
| 3 | 22A-2 | KGSKSFSLRISDLRVEDSGTYKCQAFYSLLLGDYNYSLLFRGEKGAGTALTVK |
| | | **************************************************** |

Figure 23(a)

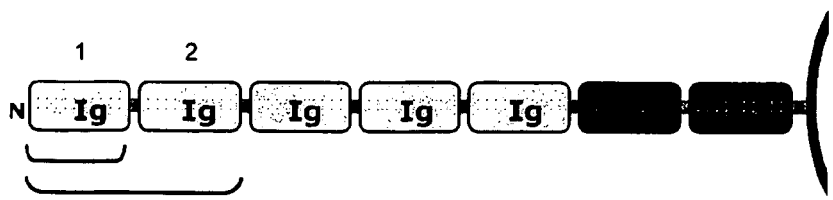

Figure 23(b)

NCAM domain 1: 21H-5 (SEQ ID NO: 36)
LQVDIVPSQGEISVGESKFFLCQVAGDAKDKDISWFSPNGEKLTPNQQR
ISVVWNDDSSSTLTIYNANIDDAGIYKCVVTGEDGSESEATVNVKIFQ

NCAM domain 1+2: 21G-1 (SEQ ID NO: 38)
LQVDIVPSQGEISVGESKFFLCQVAGDAKDKDISWFSPNGEKLTPNQQR
ISVVWNDDSSSTLTIYNANIDDAGIYKCVVTGEDGSESEATVNVKIFQK
LMFKNAPTPQEFREGEDAVIVCDVVSSLPPTIIWKHKGRDVILKKDVRF
IVLSNNYLQIRGIKKTDEGTYRCEGRILARGEINFKDIQVIVN Figure 23(c)
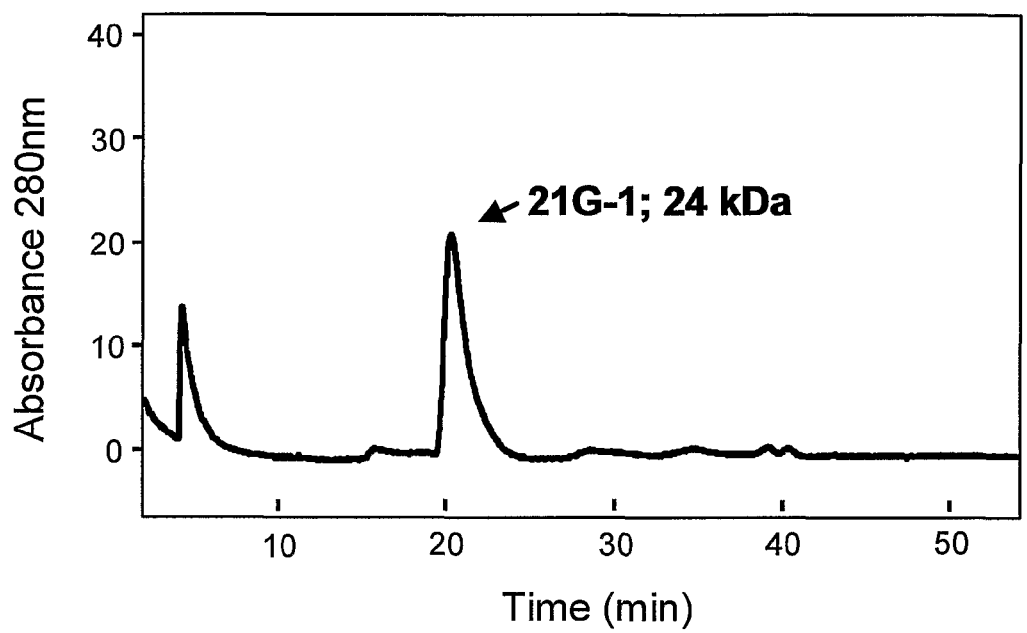
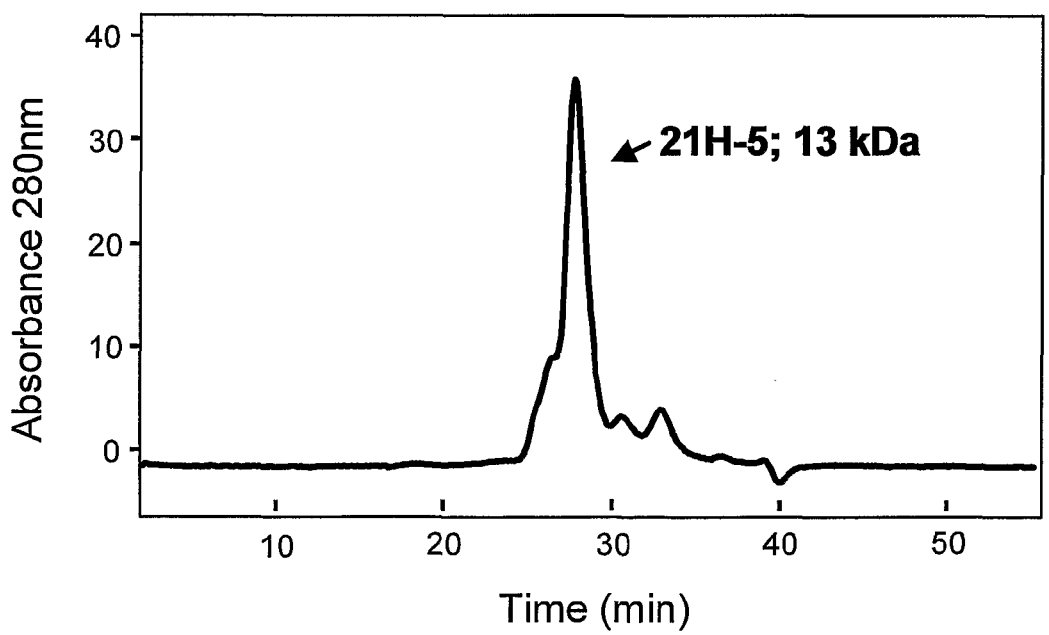

Figure 24(a)
Figure 24(b)
Telokin: 21J-4 (SEQ ID NO: 41)
PYFSKTIRDLEVVEGSAARFDCKIEGYPDPEVVWFKDDQSIRESRHFQIDYDED
GNCSLIISDVCGDDDAKYTCKAVNSLGEATCTAELIVE
Figure 24(c)
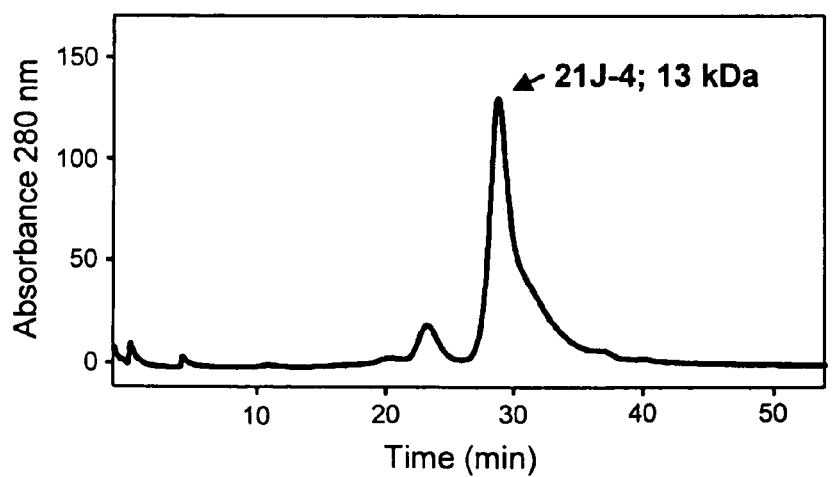

| SEQ ID NO: | | |
|---|---|---|
| 36 | 21H-5 | LQVDIVPSQGEISVGESKFFLCQVAGDAKDKDISWFSPNGEKLTPNQQRISVVWNDDSSS |
| 40 | 23B-2 | LQVDIVPSQGEISVGESKFFLCQVAGDAKDKDISWFSPNGEKLTPNQQRISVVWNDDSSS |
| | | ************************************************************ |

| 36 | 21H-5 | TLTIYNANIDDAGIYKCVVTGEDG--------SESEATVNVKIFQ |
|---|---|---|
| 40 | 23B-2 | TLTIYNANIDDAGIYKCVVTGSDAMSNYSYPISESEATVNVKIFQ |
| | | ******************* *            ************ |

Figure 26(a)

```
SEQ ID
NO:
41  21J-4_w/t    PYFSKTIRDLEVVEGSAARFDCKIEGYPDPEVVWFKDDQSIRESRHFQIDYDEDGNCSLI
45  23C-7_Mdl5   PYFSKTIRDLEVVEGSAARFDCKIEGYPDPEVVWFKDDQSIRESRHFQIDYDEDGNCSLI
43  24F-4_Mdl3   PYFSKTIRDLEVVEGSAARFDCKIEGYPDPEVVWFKDDQSIRESRHFQIDYDEDGNCSLI
                 ************************************************************

41  21J-4_w/t    ISDVCGDDDAKYTCKAVNS---------LGEATCTAELIVE
45  23C-7_Mdl5   ISDVCGDDDAKYTCKAVNSDAMSNYSYPIGEATCTAELIVE
43  24F-4_Mdl3   ISDVCGDDDAKYTCKYFSDAMSN-YSYPIPGATCTAELIVE
                 ***************  ...     : *********
```

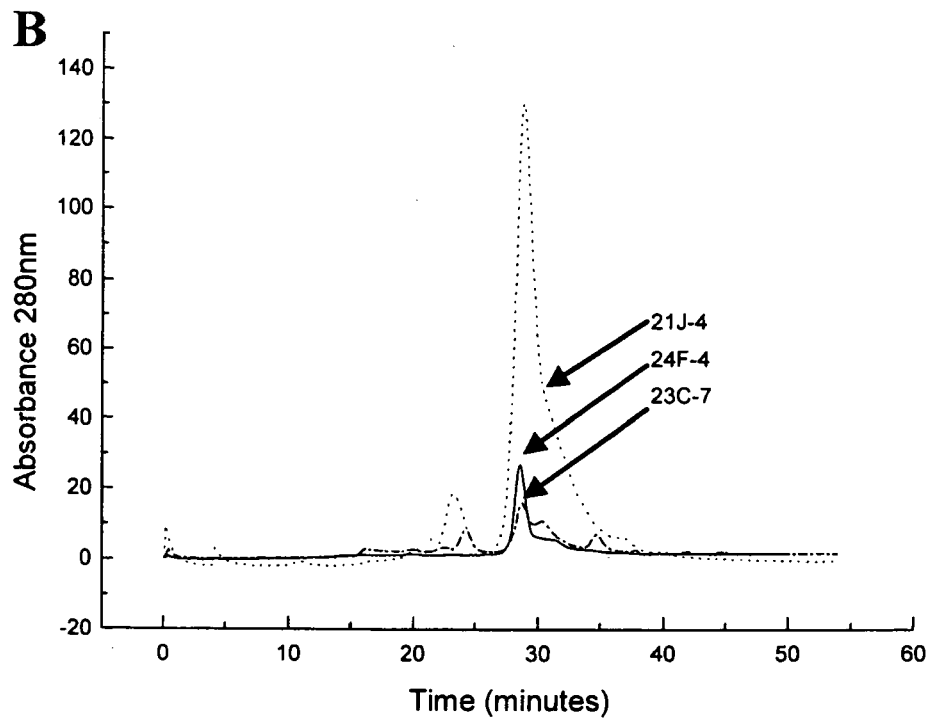

| | | | | SEQ ID NO: | Oligo |
|---|---|---|---|---|---|
| xxxxxx | VAG | DAKDKD | ISWF... | 153 | |
| ~~~~~~ | VAG | XXXXXX | ISWF... | 154 | A0980 |
| xxxxxx | VAG | XXXXXXX | ISWF... | 155 | A0981 |

| | | | | | Oligo |
|---|---|---|---|---|---|
| xxxxxx | CVV | TGEDSSES | EATVNVKIFQ | 156 | |
| ~~~~~~ | CVV | XXXXXXXX | EATVNVKIFQ | 157 | A0982 |
| ~~~~~~ | CVV | XXXXXXXXXXX | EATVNVKIFQ | 158 | A0987 |
| ~~~~~~ | CVV | XXXXXXXXXXXXX | EATVNVKIFQ | 159 | A1018 |
| ~~~~~~ | CVV | TGXXXXXXXSES | EATVNVKIFQ | 160 | A0988 |

Figure 29

| | | | SEQ ID NO: | Oligo |
|---|---|---|---|---|
| CR1 | EGYPDPE | VVWF... | 161 | |
| CR1 | XXXXXX | VVWF... | 162 | A1801 |
| CR1 | XXXXXXXX | VVWF... | 163 | A1802 |

| | | | | Oligo |
|---|---|---|---|---|
| CKA | VNSLGE | ATCTAELVE | 164 | |
| CKA | XXXXXX | ATCTAELVE | 165 | A1800 |
| CKA | XXXXXXXX | ATCTAELVE | 166 | A1803 |
| CKA | XXXXXXXXXX | ATCTAELVE | 167 | A1804 |
| CKA | VNSLXXXXXXXGE | ATCTAELVE | 168 | A1817 |

Figure 33  (SEQ ID NO: 31)

```
   1    A   W   V   D   Q   T   P   R   T   A   T   K   E   T   D   E   S   L   T   I
   1    GCATGGGTAGACCAAACACCAAGAACAGCAACAAAAGAGACGGACGAATCACTGACCATC
   1    N   C   V   L   R   E   S   P   Y   E   L   Y   N   T   G   W   Y   R   T   K
  61    AATTGCGTCCTCAGAGAGAGTCCCTACGAATTGTACAACACGGGCTGGTATCGGACAAAA
  41    L   G   S   T   K   E   Q   R   I   S   I   G   G   R   Y   V   E   T   V   D
 121    TTGGGTTCAACAAAGGAGCAGAGAATATCAATTGGCGGACGATATGTTGAAACAGTCGAC
  61    K   E   S   K   S   F   S   L   R   I   S   D   L   R   I   E   D   S   G   T
 181    AAAGAATCAAAGTCCTTTTCTCTGAGAATTAGTGATCTGAGAATTGAAGACAGTGGCACG
  81    Y   K   C   G   A   C   D   E   P   D   G   G   Y   G   K   Y   S   C   F   T
 241    TATAAGTGTGGAGCATGTGATGAACCTGACGGGGGCTACGGTAAGTATAGCTGTTTCACC
 101    Y   K   K   G   T   G   T   G   L   T   V   K   P   G   V   Q   P   S   P   P
 301    TACAAGAAAGGAACTGGCACCGGACTGACCGTGAAACCTGGAGTACAGCCTTCTCCACCA
 121    V   I   S   L   L   Y   S   A   T   E   E   Q   R   G   N   G   F   V   Q   L
 361    GTCATCAGTCTACTTTACTCTGCAACTGAAGAACAGAGAGGAAACGGGTTTGTGCAGCTG
 141    I   C   L   I   S   G   Y   Y   P   E   N   I   A   V   S   W   Q   K   N   R
 421    ATTTGTCTAATCAGCGGATACTATCCTGAAAACATTGCAGTGAGCTGGCAAAAGAACAGA
 161    N   D   I   S   S   G   F   T   T   S   P   S   M   K   T   S   T   N   D   F
 481    AACGACATAAGTTCTGGCTTTACAACTTCACCCTCAATGAAAACATCGACCAATGACTTT
 181    S   S   T   S   L   L   N   V   P   L   Q   E   W   S   S   G   S   V   Y   S
 541    AGCTCTACAAGTTTACTTAATGTGCCCCTGCAGGAATGGAGCAGCGGTTCTGTGTACAGT
 201    C   R   V   S   H   S   A   T   N   S   N   Q   R   K   E   I   R   S   T   S
 601    TGTCGAGTTTCTCATTCTGCAACCAACAGTAACCAAAGGAAAGAAATTAGATCAACATCA
 221    E   I   A   V   F   L   R   D   P   S   V   E   E   I   W   I   N   K   S   A
 661    GAGATTGCTGTATTCCTAAGAGATCCATCAGTTGAAGAAATCTGGATCAATAAAAGTGCC
 241    T   V   V   C   E   V   L   S   T   V   S   T   G   V   V   I   S   W   M   V
 721    ACTGTGGTTTGCGAAGTTCTTTCTACAGTTTCCACTGGAGTCGTCATCTCTTGGATGGTG
 261    D   G   K   V   R   T   E   G   V   R   I   E   A   A   K   M   D   G   N   Q
 781    GATGGAAAGGTAAGGACCGAAGGCGTTCGAATCGAAGCAGCTAAAATGGATGGAAACCAA
 281    Y   L   T   I   S   R   L   S   S   S   V   E   E   W   Q   S   G   V   E   Y
 841    TATCTGACCATCAGCCGCTTGAGCAGCAGCGTGGAAGAGTGGCAGAGTGGGGTGGAATAC
 301    T   C   S   A   K   Q   D   Q   S   S   T   P   V   S   K   R   T   G   K   T
 901    ACATGCTCCGCAAAACAGGATCAATCATCGACCCCGGTATCAAAACGAACAGGAAAAACA
 321    K   V   E   P   M   K   P   Y   L   R   L   L   P   P   S   P   E   E   I   Q
 961    AAAGTCGAGCCAATGAAGCCATATCTTCGCCTCCTGCCCCCATCACCAGAGGAGATTCAA
 341    N   I   S   S   A   I   L   T   C   L   I   R   G   F   Y   P   D   K   I   R
1021    AACATCAGTTCTGCTATTCTCACATGTTTGATAAGAGGATTCTACCCTGACAAGATACGC
 361    V   S   W   E   K   D   G   A   A   V   S   G   N   I   T   S   F   P   T   A
1081    GTTTCCTGGGAGAAGGACGGAGCTGCTGTGAGTGGGAACATCACCAGTTTCCCGACTGCT
 381    L   E   Q   D   L   T   F   S   T   R   S   L   L   I   L   P   A   V   E   W
1141    CTGGAACAGGACCTGACCTTCAGCACCCGGAGCCTCCTCATTTTGCCTGCAGTGGAATGG
 401    K   S   G   A   K   Y   T   C   I   A   S   H   P   P   S   Q   S   T   V   K
1201    AAGAGCGGAGCAAAATACACCTGTATCGCCTCACATCCACCGTCACAATCCACTGTGAAG
 421    R   V   I   R   S   P   K   G   D   C   G   Q   P   D   I   S   V   N   L   L
1261    AGGGTCATCAGGAGCCCGAAAGGTGATTGCGGTCAGCCAGACATTTCTGTCAATCTACTG
 441    N   P   P   F   E   E   I   W   T   Q   K   T   A   T   I   V   C   E   I   V
1321    AACCCTCCGTTTGAAGAGATTTGGACACAAAAAGACAGCGACCATTGTTTGTGAAATCGTT
 461    Y   S   D   L   E   N   V   N   V   F   W   Q   V   N   G   S   E   R   T   E
1381    TACAGTGACTTAGAAAACGTCAACGTGTTCTGGCAGGTGAATGGGAGTGAGAGAACGGAG
 481    G   V   E   T   Q   N   P   E   W   S   G   S   K   S   T   I   V   S   K   L
1441    GGAGTCGAGACACAAAATCCTGAGTGGAGTGGAAGCAAATCCACCATTGTCAGCAAACTA
 501    K   V   T   S   S   E   W   D   S   G   V   E   Y   V   C   L   V   E   D   S
1501    AAAGTAACGTCTTCGGAGTGGGACAGTGGTGTGGAATATGTCTGCTTGGTAGAAGACAGT
 521    E   L   P   T   P   V   K   S   S   I   R   K   A   K   D   R   E   M   Y   P
1561    GAATTACCAACACCAGTGAAATCGTCCATCAGGAAGGCAAAGGACCGCGAAATGTACCCT
 541    P   K   V   Y   V   L   H   P   S   T   D   E   I   D   T   E   N   S   A   T
1621    CCTAAGGTTTATGTCCTGCATCCATCGACGGACGAGATTGACACTGAGAATTCGGCTACC
 561    L   V   C   L   A   T   G   F   S   P   A   E   I   Y   V   G   W   M   A   N
1681    CTGGTGTGTCTAGCCACCGGCTTTTCCCCAGCTGAGATTTACGTCGGTTGGATGGCCAAT
 581    D   T   L   L   N   S   G   Y   R   S   Q   V   E   N   E   K   G   N   G   S
1741    GACACACTTTTGAATTCCGGGTACCGGAGCCAAGTAGAGAACGAGAAAGGGAATGGTTCC
 601    N   F   I   I   N   R   L   R   L   T   A   A   E   W   D   S   D   T   T   Y
1801    AATTTCATTATCAACAGATTAAGACTCACAGCGGCGGAATGGGACAGTGACACCACTTAC
 621    S   C   L   V   G   H   P   S   L   S   R   D   L   I   R   S   I   N   K   S
1861    TCCTGTTTAGTGGGTCACCCGTCCCTCAGCCGGGATTTAATCAGAAGTATAAATAAATCT
 641    H   G   K   P   T   L   V   N   L   S   V   V   L   S   D   T   V   K   S   C
1921    CACGGTAAACCCGACATTAGTTAATCTTTCAGTTGTACTAAGCGACACTGTTAAATCCGT
 661    T   *
1981    ACATAATTTGCAGTGATTGACTAATTGTTTTCTATAGATAAGTTCATGTTGTTCTGGCAA
2041    TAACGGTTTAAGCAACCGAACCAATGCGTTTTCAATTCAACGCAAGGCACAGTCACATTT
2101    CTGATGAGAGAACACGTTTGTAAAAATAATTAGCTACTATTTGAAATTTTATCTGTCAAT
2161    GAAGGACAATTATGATTAGAATCTGATATGCAAGGATAACCTGATCTTGTCAGTGCAATC
2221    GTTCTGAAGATCCCTTGACGTGTTTCACGCCGTTATTGAAAGAACAGAAAATGATGCTTT
        AGTGTGTATGTGGCGCCGATAGTTGCAATAAACGCAGAATGAAAACTT
```

BINDING MOIETIES BASED ON SHARK IGNAR DOMAINS

FIELD OF THE INVENTION

The present invention relates to immunoglobulin new antigen receptors (IgNARs) from fish and uses thereof. In particular, the present invention relates to modified IgNAR variable domains and to domains from members of the immunoglobulin superfamily that have been modified to include structural features derived from IgNAR variable domains.

BACKGROUND OF THE INVENTION

The immunoglobulin superfamily (IgSF) includes immunoglobulins and numerous other cell surface and soluble molecules that mediate recognition, adhesion or binding functions in the immune system. They share partial amino acid sequence homology and tertiary structural features that were originally identified in immunoglobulin (Ig) heavy and light chains.

Molecules of the IgSF are identified by a characteristic IgSF fold structure, a sandwich structure formed by two β-sheets, packed face-to-face and linked by a disulphide bond between the B and F strands (Bork 1994; Chothia 1998). IgSF frameworks are further classified into 3-4 major categories, the Variable (V)-, Constant (C)-, I- and I2-sets, based on β-strand number, configuration and hydrogen bond patterns (Bork 1994; Cassasnovas 1998).

Conventional immunoglobulins have two heavy polypeptide chains linked by disulphide bonds at a hinge portion, and two light polypeptide chains, each of which is linked to a respective heavy chain by disulphide bonding. Each heavy chain comprises a variable (VH) domain at the N-terminal end and a number of constant (CH) domains. Each light chain has a variable (VL) domain at the N-terminal end and a constant (CL) domain at the C-terminal end, the VL and CL domains aligning with the VH domain and the first CH domain, respectively. Unlike immunoglobulins, T-cell receptors (TCRs) are heterodimers having α and β chains of equal size, each chain consisting of an N-terminal variable domain (Vα or Vβ) and a constant domain.

Typically, the variable domains on different polypeptide chains interact across hydrophobic interfaces to form binding sites designed to receive a particular target molecule. In the case of immunoglobulins, each pair of VH/VL domains form an antigen binding site, the CH and CL domains not being directly involved in binding the antibody to the antigen. Similarly, in the case of TCRs, the Vα and Vβ domains form the binding site for target molecules, namely peptides presented by a histocompatibility antigen.

The amino acid sequences of variable domains vary particularly from one molecule to another. This variation in sequence enables the molecules to recognise an extremely wide variety of target molecules. Variable domains are often viewed as comprising four framework regions, whose sequences are relatively conserved, connected by three hypervariable or complementarity determining loop regions (CDRs) (Kabat 1983 & 1987; Bork 1994). The CDRs are held in close proximity by the framework regions and, with the CDRs from the other variable domain, contribute to the formation of the binding site.

With the development of new molecular biology and recombinant DNA techniques, research interest in the IgSF field has increased. Among the main reasons for this increased interest is the desire to develop novel therapeutics and diagnostics based on immunoglobulins or other IgSF molecules.

Using the hybridoma technique developed by Kohler and Milstein, the production of monoclonal antibodies (MAbs) of almost any specificity is now well known. However, the production of human antibodies remains difficult, with the vast majority of MAbs produced being of rodent, in particular mouse, origin. Such antibodies are often antigenic in humans.

Researchers have therefore investigated producing modified immunoglobulins which are as "human" as possible, but which still retain the appropriate specificity. For example, "chimeric" antibodies have been constructed in which an animal antigen-binding variable domain is coupled to a human constant domain. The isotype of the human constant domain may be selected to tailor the chimeric antibody for participation in antibody-dependent cellular cytotoxicity (ADCC) and complement dependent cytotoxicity. However, chimeric antibodies typically may contain about one third rodent (or other non-human species) sequence and consequently are often still capable of eliciting a significant antigenic response in humans.

In a further effort to resolve the antigen binding functions of antibodies and to minimize the use of heterologous sequences in human antibodies, others have modified the specific domains by, for example, substituting rodent CDRs for CDR sequences from the corresponding segments of a human antibody. In some cases, substituting CDRs from rodent antibodies for the human CDRs in human frameworks is sufficient to transfer high antigen binding affinity as described in EP 239400.

An alternative approach has been to use fragments of immunoglobulins or other molecules of the IgSF. For example, specific binding reagents can be formed by association of only the VH and VL domains into a Fv module. Bacterial expression is then enhanced by joining the variable domains with a linker polypeptide into a single-chain scFv molecule.

Methods to improve the expression and folding characteristics of single-chain Fv molecules have been described by Nieba (1997). The properties of single V-domains, derived from natural mammalian antibodies, have been described in WO 90/05144, EP 368684 and WO 91/08482. Single camelid V-domains have been described by WO/96/34103 and in WO/94/25591. A method for reducing the hydrophobicity of the surface of a human VH domain by replacing human amino acid sequences with camelid amino acid sequences was described by Davies and Riechmann (1994). Methods to exchange other regions of human VH sequences with camel sequences to further enhance protein stability, including the insertion of cysteine residues in CDR loops, were described by Davies and Riechmann (1996).

Several attempts to engineer high-affinity single domain binding reagents using either the VH or VL domains alone have been unsuccessful, due to lack of binding specificity and the inherent insolubility of single domains exposing unpaired hydrophobic VH/VL binding faces (Kortt 1995).

The TCR has two variable domains that combine into a structure similar to the Fv module of an antibody that results from combination of the VH and VL domains. Novotny (1991) described how the Vα and Vβ domains of the TCR can be fused and expressed as a single chain polypeptide and, further, how to alter surface residues to reduce the hydrophobicity directly analogous to an antibody scFv. Other publications describe the expression characteristics of single-chain TCRs comprising two Vα and Vβ domains (Wulfing 1994; Ward 1991).

The three-dimensional crystal structures have been published for intact immunoglobulins, a variety of immunoglobulin fragments, antibody-antigen complexes and for other IgSF molecules such as the TCR. It is known that the function of IgSF molecules is dependent on their three dimensional structure, and that amino acid substitutions can change the three-dimensional structure of, for example, an antibody (Snow and Amzel 1986). Based upon molecular modelling, it has been shown that the antigen binding affinity of a humanized antibody can be increased by mutagenesis (Riechmann 1988; Queen 1989).

The Immunoglobulin New Antigen Receptors (IgNARs) are an unconventional subset of antibodies recently identified in fish. In domain structure, IgNAR proteins are reportedly similar to other immune effector molecules, being disulphide-bonded homodimers of two polypeptide chains having five constant domains ($C_{NAR}$s) and one variable domain ($V_{NAR}$) (Greenberg 1995). However, unlike conventional antibodies, there are no associated light chains and the individual variable domains are independent in solution and do not appear to associate across a hydrophobic interface (as seen for conventional VH/VL type antibodies) (Roux 1998).

IgNARs have been identified in all shark species studied to date. In particular, IgNARs have been identified in the serum of nurse sharks *Ginglymostoma cirratum* (Greenberg 1995) and wobbegong sharks *Orectolobus maculatus* (Nuttall 2001). The cell-surface expression of IgNARs has also been reported (Rumfelt 2002). Research has implicated IgNARs as true molecules of the immune armoury, and as the most probable agents of the shark antigen-driven affinity-maturation antibody response (Diaz 1999; Nuttall 2002; Dooley 2003).

IgNARs identified to date have been placed into three categories based on their time of appearance during the shark development and on their postulated disulphide bonding pattern within the variable domains (Diaz 2002; Nuttall 2003). Type 1 $V_{NAR}$ topology is characterised by an extra framework disulphide linkage and, usually, cysteines in the extended loop region analogous to a conventional CDR3 loop, which it has been suggested may form intra-loop disulphide bonds. Type 2 $V_{NAR}$ topology is characterised by cysteines in the loop regions analogous to conventional CDR1 and CDR3 loops in approximately two thirds of cases, which it has been postulated may form inter-loop disulphide bonds. Type 3 $V_{NAR}$ topology is characterised by a relatively constant sized loop region analogous to a conventional CDR3 loop of limited diversity and a characteristic conserved tryptophan residue within the loop region analogous to a CDR1 loop.

Regardless of type, all IgNARs identified to date are reported as having minimally variable loop regions analogous to conventional CDR1 and CDR2 loops, with diversity being concentrated in an elongated loop region analogous to a conventional CDR3 loop (Greenberg 1995; Nuttall 2001; Diaz 2002). The elongated loop region can reportedly vary in length from 5 to 23 residues in length, though the modal classes are more in the order of 15 to 17 residues (Nuttall 2003). This is significantly larger than for conventional murine and human antibodies, but approximate to the extended CDR3 loops found in camelid single VH antibodies (Wu 1993; Muyldermans 1994).

Large bacteriophage libraries have been generated based upon the Type 2 $V_{NAR}$ repertoire from wobbegong sharks and used to isolate a number of Type 2 $V_{NAR}$s proteins encapsulating significant variability within the framework and the loop region analogous to a conventional CDR1 loop. However, the most significant diversity was within the extended loop region analogous to a conventional CDR3 loop, the extended loop region varying in both length and amino acid composition (Nuttall 2001; Nuttall 2003).

Various computer-modelled structures for Type 2 $V_{NAR}$s have been reported in the literature (Roux 1998; Nuttall 2001; Diaz 2002; Nuttall 2004). Although such computer modelling can offer key insights into structure, the definitive structure remains to be determined from crystallographic analysis. In the case of $V_{NAR}$s, the elucidation of the crystal structure is particularly important.

SUMMARY OF THE INVENTION

In a first aspect, the present invention provides a crystal of a variable domain of a Type 2 IgNAR that effectively diffracts X-rays for the determination of the atomic coordinates of the variable domain of the IgNAR to a resolution of better than 4.0 Å, wherein the variable domain of the Type 2 IgNAR consists of 105 to 125 amino acid residues and comprises an amino acid sequence according to Table 1 and/or FIG. 1.

In another aspect, the present invention provides a crystal of a variable domain of a Type 2 IgNAR comprising a structure defined by all or a portion of the coordinates of Appendix I(a), (b), (c) or (d)±a root mean square deviation from the Cα atoms of less than 0.5 Å.

In another aspect, the present invention provides a method of homology modelling comprising the steps of: (a) aligning a representation of an amino acid sequence of an IgSF domain with the amino acid sequence of 12Y-1, 12Y-2, 12A-9 or 1A-7 as shown in FIG. 1 to match homologous regions of the amino acid sequences; (b) modelling the structure of the matched homologous regions of said IgSF domain on the corresponding regions of the 12Y-1, 12Y-2, 12A-9 or 1A-7 structure as defined by Appendix I(a), (b), (c) or (d); and (c) determining a conformation (e.g. so that favourable interactions are formed within the IgSF domain and/or so that a low energy conformation is formed) for said IgSF domain which substantially preserves the structure of said matched homologous regions.

In another aspect, the present invention provides a method for determining the structure of a protein, which method comprises; providing the co-ordinates of Appendix I(a), (b), (c) or (d), and either (a) positioning the co-ordinates in the crystal unit cell of said protein so as to provide a structure for said protein or (b) assigning NMR spectra Peaks of said protein by manipulating the coordinates of Appendix I(a), (b), (c) or (d).

In another aspect, the present invention provides systems, particularly a computer system, the systems containing at least one of the following: (a) atomic coordinate data according to Appendix I, said data defining the three-dimensional structure of 12Y-1, 12Y-2, 12A-9 or 1A-7 or at least selected coordinates thereof; (b) structure factor data (where a structure factor comprises the amplitude and phase of the diffracted wave) for 12Y-1, 12Y-2, 12A-9 or 1A-7, said structure factor data being derivable from the atomic coordinate data of Appendix I; (c) atomic coordinate data of an IgSF domain generated by homology modelling of the IgSF domain based on the data of Appendix I; (d) atomic coordinate data of the IgSF domain generated by interpreting X-ray crystallographic data or NMR data by reference to the data of Appendix I; and (e) structure factor data derivable from the atomic coordinate data of (c) or (d).

In another aspect, the present invention provides a computer-readable storage medium, comprising a data storage material encoded with computer readable data, wherein the data are defined by all or a portion (e.g. selected coordinates as defined herein) of the structure coordinates of 12Y-1, 12Y-

2, 12A-9 or 1A-7, or a variant of 12Y-1, 12Y-2, 12A-9 or 1A-7, wherein said variant comprises backbone atoms that have a root mean square deviation from the Cα or backbone atoms (nitrogen-carbonα-carbon) of Appendix I of less than 2 Å, such as not more than 1.5 Å, preferably less than 1.5 Å, more preferably less than 1.0 Å, even more preferably less than 0.74 Å, even more preferably less than 0.72 Å and most preferably less than 0.5 Å.

In another aspect, the present invention provides a computer-readable data storage medium comprising a data storage material encoded with a first set of computer-readable data comprising a Fourier transform of at least a portion (e.g. selected coordinates as defined herein) of the structural coordinates for 12Y-1, 12Y-2, 12A-9 or 1A-7 according to Appendix I; which, when combined with a second set of machine readable data comprising an X-ray diffraction pattern of a molecule or molecular complex of unknown structure, using a machine programmed with the instructions for using said first set of data and said second set of data, can determine at least a portion of the structure coordinates corresponding to the second set of machine readable data.

In another aspect, the present invention provides computer readable media with at least one of: (a) atomic coordinate data according to Appendix I recorded thereon, said data defining the three-dimensional structure of 12Y-1, 12Y-2, 12A-9 or 1A-7, or at least selected coordinates thereof; (b) structure factor data for 12Y-1, 12Y-2, 12A-9 or 1A-7 recorded thereon, the structure factor data being derivable from the atomic coordinate data of Appendix I; (c) atomic coordinate data of a target IgSF domain generated by homology modelling of the IgSF domain based on the data of Appendix 1; (d) atomic coordinate data of a modified IgSF domain generated by interpreting X-ray crystallographic data or NMR data by reference to the data of Appendix I; and (e) structure factor data derivable from the atomic coordinate data of (c) or (d).

In another aspect, the present invention provides a method of providing data for generating structures and/or performing rational drug design for IgSF domains, the method comprising: (i) establishing communication with a remote device containing computer-readable data comprising at least one of: (a) atomic coordinate data according to Appendix I, said data defining the three-dimensional structure of 12Y-1, 12Y-2, 12A-9 or 1A-7, at least one sub-domain of the three-dimensional structure of 12Y-1, 12Y-2, 12A-9 or 1A-7, or the coordinates of a plurality of atoms of 12Y-1, 12Y-2, 12A-9 or 1A-7; (b) structure factor data for 12Y-1, 12Y-2, 12A-9 or 1A-7, said structure factor data being derivable from the atomic coordinate data of Appendix I; (c) atomic coordinate data of a modified IgSF domain generated by homology modelling of the domain based on the data of Appendix I; (d) atomic coordinate data of a protein generated by interpreting X-ray crystallographic data or NMR data by reference to the data of Appendix I; and (e) structure factor data derivable from the atomic coordinate data of (c) or (d); and (ii) receiving said computer-readable data from said remote device.

In another aspect, the present invention provides a method of altering a property of an IgNAR variable domain comprising eight β-strand regions, designated A, A', B, C, D, E, F and G according to FIG. 2, and nine loop regions, designated 1 to 9 according to FIG. 2, said method comprising modifying the IgNAR variable domain within at least one of the β-strand regions or loop regions.

In another aspect, the present invention provides a binding moiety comprising a modified IgNAR variable domain produced by a method according to any one of claims 1 to 5.

In another aspect, the present invention provides a binding moiety comprising an IgNAR variable domain comprising eight β-strand regions, designated A, A', B, C, D, E, F and G according to FIG. 2, and nine loop regions, designated 1 to 9 according to FIG. 2, wherein the IgNAR variable domain has been modified within at least one of the β-strand regions or loop regions.

In a further aspect, the present invention provides a method of modifying an I-set domain, said method comprising inserting and/or substituting one or more structural features from an IgNAR variable domain into the I-set domain.

In another aspect, the present invention provides a binding moiety comprising a I-set domain, wherein the I-set domain has been modified by insertion and/or substitution of one or more structural features from an IgNAR variable domain into the I-set domain and/or by introducing a modification into a region equivalent to loop region 4 or loop region 8 of an IgNAR variable domain In a further aspect, the present invention provides a method of modifying a V-set domain, said method comprising inserting and/or substituting one or more structural features from an IgNAR variable domain into the V-set domain.

In another aspect, the present invention provides a binding moiety comprising a V-set domain, wherein the V-set domain has been modified by insertion and/or substitution of one or more structural features from an IgNAR variable domain into the V-set domain and/or by introducing a modification into a region equivalent to loop region 4 or loop region 8 of an IgNAR variable domain.

In another aspect, the present invention provides a binding moiety comprising a multimer comprising:
(i) at least two IgNAR domains, which may be the same or different, and at least one of which is a IgNAR variable domain;
(ii) at least two I-set domains, which may be the same or different, and at least one of which is a I-set domain according to the present invention; or
(iii) at least two V-set domains, which may be the same or different, and at least one of which is a V-set domain according to the present invention.

In another aspect, the present invention provides a binding moiety according to the invention linked to a diagnostic reagent.

In another aspect, the present invention provides a binding moiety according to the invention immobilised on a solid support or coupled to a biosensor surface.

In another aspect, the present invention provides a polynucleotide encoding a binding moiety according to the invention.

In another aspect, the present invention provides a vector comprising a polynucleotide according to the present invention.

In another aspect, the present invention contemplates a host cell comprising a vector according to the invention.

In another aspect, the present invention provides a method of producing a binding moiety according to the invention which comprises culturing a host cell of the present invention under conditions enabling expression of the binding moiety according to the invention and optionally recovering the a binding moiety.

In another aspect, the present invention provides a pharmaceutical composition comprising a binding moiety according to the invention and a pharmaceutically acceptable carrier or diluent.

In another aspect, the present invention provides a method of treating a pathological condition in a subject, which method comprises administering to the subject a binding moiety according to the invention.

In another aspect, the present invention provides a method of selecting a binding moiety according to the invention with an affinity for a target molecule which comprises screening a library of polynucleotides of the present invention for expression of a binding moiety according to the invention with an affinity for the target molecule.

In a further aspect, the present invention provides a polynucleotide library comprising a plurality of polynucleotides encoding binding moieties according to the invention, which polynucleotides comprise one or more modifications in the IgNAR variable domain, I-set domain or V-set domain.

BRIEF DESCRIPTION OF THE FIGURES

FIG. 1. Amino acid sequence alignment of $V_{NAR}$s 12Y-1, 12Y-2, 12A-9 and 1A-7 with 12 naturally occurring Type 2 IgNAR variable domain sequences.

FIG. 13. Structures of the $V_{NAR}$ 12Y-2 2-fold symmetry dimer. (a) View from the top of the CDR3 analogous region (loop region 8) and (b) side view. Each chain is shown in ribbon representation. The N and C termini, and the CDR1 analogous region (loop region 4) and CDR3 analogous region (loop region 8) of each chain are labelled.

FIG. 17. Amino acid sequence alignment of 14M-15 variant IgNAR clones in which the CDR1 analogous region (loop region 4) has been shuffled. Five clones with affinity for the AMA-1 antigen (24A-82, 24A-72, 24A-58, 24A-75, 24A-46) and five with no affinity (24A-24, 24A-28, 24A-33, 24A-10, 24A-19) are shown. Sequence differences map predominantly to the CDR1 analogous region (loop region 4), with some contribution from framework residues.

Figure 19:
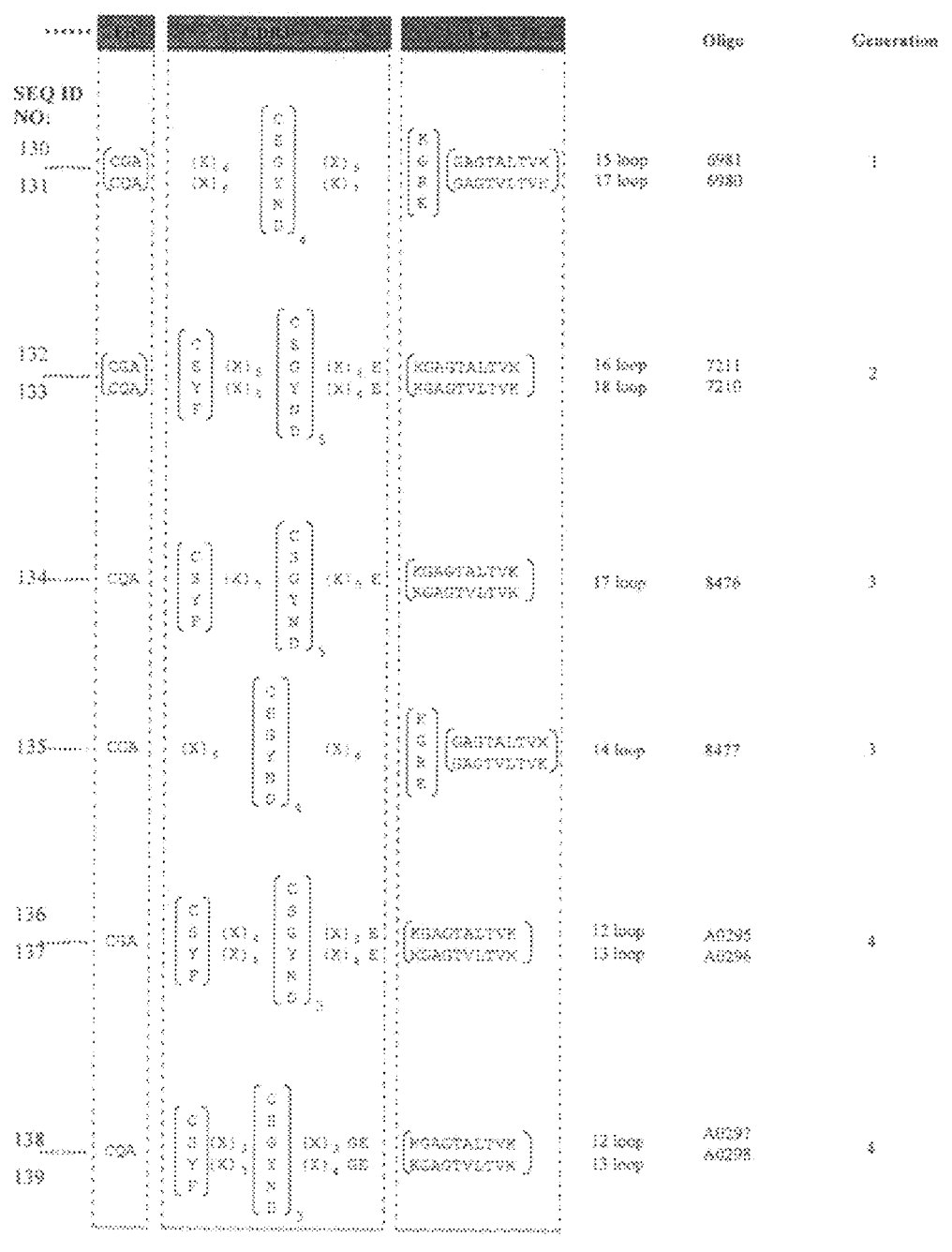

FIG. 19. Schematic diagram of loop region 8 (analogous to CDR3) variability for IgNAR libraries. Loop region 8 varies in length and in coding sequence and randomisation strategy (SEQ ID NOs: 130-139). Generations 1 to 3 are based on the existing shark libraries. Generation 4 libraries were designed with reference to the structures of 12Y-1 and 12Y-2. Oligonucleotides A0298, A0296, A0297, A0295, 8477, 8476, 7210, 7211, 6980 and 6981 correspond to SEQ ID Nos: 61-70, respectively.

FIG. 20. Schematic diagram of loop region 8 (analogous to CDR3) variability for IgNAR libraries based on the 12Y-2 structure. The tip of the 12Y02 loop region 8 is modified by 6 different strategies, varying in amino acid randomisation, loop length and amino acid variation pattern (SEQ ID NOs: 140-146). Oligonucleotides KH0001RC, KH0002RC, KH0003RC, KH0004RC, KH0005RC and KH0006RC correspond to SEQ ID Nos: 71-76, respectively.

FIG. 23: (a) Schematic figure of NCAM (CD56) ectodomain showing Ig superfamily and fibronectin domains. (b) Amino acid sequences of NCAM domain 1 (21H-5) and domain 1+2 (21G-1) recombinant proteins. Dual C-terminal FLAG affinity tags are not shown. (c) FPLC traces of NCAM domain 1 (21H-5) and domain 1+2 (21 G-1) recombinant proteins.

FIG. 24: (a) Schematic figure of Myosin Light Chain Kinase showing Ig, catalytic, and Telokin domains. (b) Protein sequences of human wild type Telokin (21J-4). Dual C-terminal FLAG affinity tags are not shown. (c) FPLC trace of Telokin (21J-4) recombinant protein.

FIG. 28: Schematic diagram of CDR1 and CDR3 variability for NCAM domain 1 libraries. CDR1 and CDR3 both vary in length and in coding sequence and randomisation strategy (SEQ ID NOs: 154-155 and 157-160). The NCAM wild type sequences (SEQ ID NOs: 153 and 156, respectively) are is given for comparison. Framework residues N- and C-terminal to the CDR loop regions are also shown.

FIG. 29: Schematic diagram of CDR1 and CDR3 variability for Telokin libraries. CDR1 and CDR3 both vary in length and in coding sequence and randomisation strategy (SEQ ID NOs: 162-163 and 165-168). The Telokin wild type sequences are given for comparison (SEQ ID NOs: 161 and 164, respectively). Framework residues N- and C-terminal to the CDR loop regions are also shown.

FIG. 33: The full wobbegong shark (*Orectolobus maculatus*) IgNAR coding sequence.

DETAILED DESCRIPTION OF THE INVENTION

Figure 2:
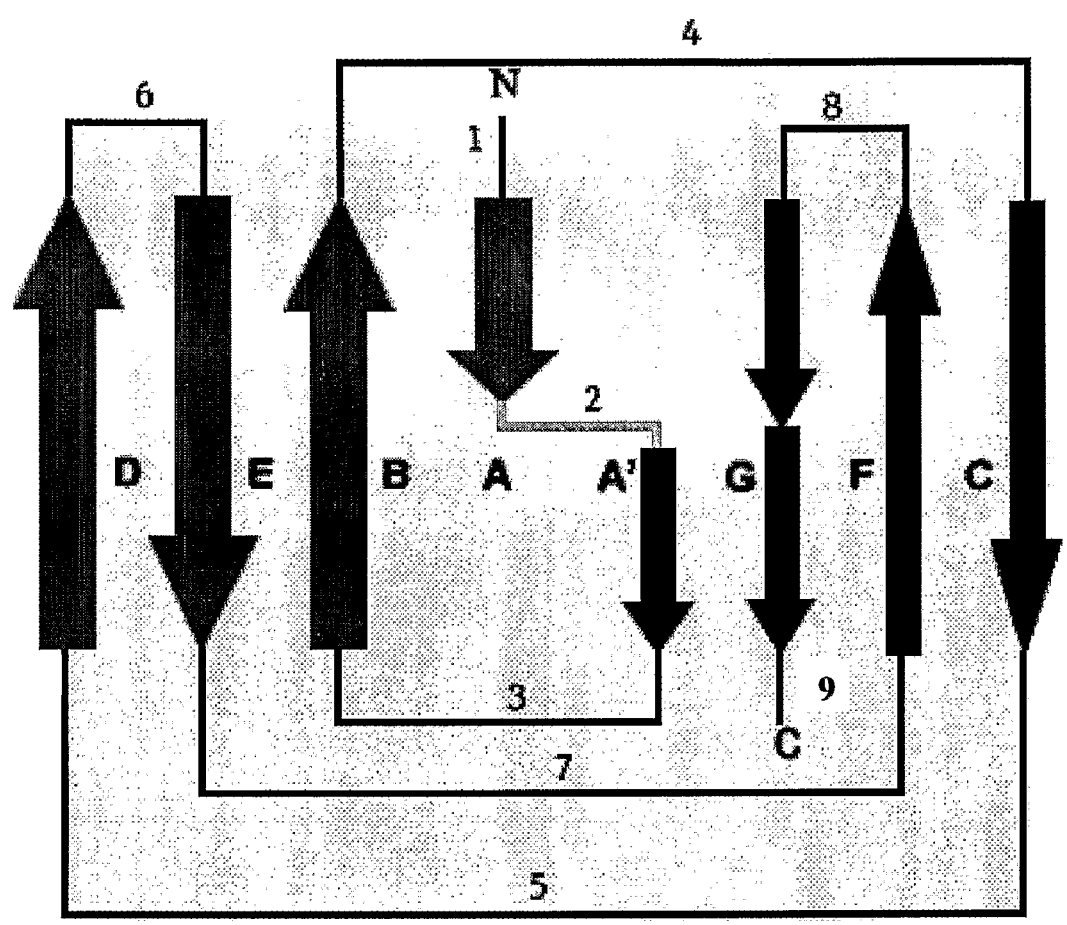
FIG. 2. 2D topology diagram of the 12Y-1, 12Y-2, 12A-9 and 1A-7 folds showing the loop regions and β-strand regions. The labelled 8 strands form a sandwich of 2 sheets: front and back sheets are shown with thick and thin arrows, respectively. The switch of N-terminal strand A to A', adjacent to the bulge in the C-terminal strand G, is shown as a kink between the A and A' strands.

All publications discussed above are incorporated herein in their entirety.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Unless defined otherwise, all technical and scientific terms used herein have the same meaning as commonly understood by one of ordinary skill in the art (e.g., in molecular biology and biochemistry). Standard techniques are used for molecular and biochemical methods (see generally, Sambrook et al., Molecular Cloning: A Laboratory Manual, 3rd ed. (2001) Cold Spring Harbor Laboratory Press, Cold Spring Harbor, N.Y. and Ausubel et al., Short Protocols in Molecular Biology (1999) 4th Ed, John Wiley & Sons, Inc. —and the full version entitled Current Protocols in Molecular Biology, which are incorporated herein by reference) and chemical methods.

Throughout the specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

By "hydrophobic residues" or "nonpolar residues" as used herein is meant valine, leucine, isoleucine, methionine, phenylalanine, tyrosine, and tryptophan.

By "polar residues" herein is meant serine, threonine, histidine, aspartic acid, asparagine, glutamic acid, glutamine, arginine, and lysine.

We have previously identified two closely related IgNAR variable domains ($V_{NAR}$s) targeting the apical membrane antigen-1 (AMA1) of *Plasmodium falciparum* malarial parasites (Nuttall 2004). These proteins, designated 12Y-1 (SEQ ID NOs: 1 & 2) and 12Y-2 (SEQ ID NOs: 3 & 4), were isolated from a library containing a broad mixture of Type 2 $V_{NAR}$ framework scaffolds derived from the native wobbegong shark repertoire, combined with both naturally occurring and synthetic loop regions analogous to CDR3 sequences (Nuttall 2003).

We have now isolated two further IgNAR variable domains designated 12A-9 and 1A-7.

$V_{NAR}$12A-9 (SEQ ID NOs: 9 & 10) was isolated from a library containing a broad mixture of naturally occurring Type 2 $V_{NAR}$ framework scaffolds derived from the wobbegong shark by biopanning against the Gingipain K protease from *Porphyromonas gingivalis* (Nuttall et al. 2002). This IgNAR is completely natural, including the CDR3 analogous loop region (loop region 8). In common with many IgNAR variable domains, a disulphide bridge links and stabilises the CDR1 and CDR3 analogous loop regions, in this case connecting residues Cys29 and Cys89.

$V_{NAR}$ 1A-7 (SEQ ID NOs: 5 & 6) is specific for the anti-AMA-1 mouse IgG 5G8 and was isolated using the same procedure as described for the isolation of 12Y-1 and 12Y-2, i.e. biopanning of the phage displayed IgNAR library. Binding is through an "SYP" motif found in the 1A-7 "synthetic" CDR3 analogous loop region (i.e. loop region 8).

While the 12Y-1, 12Y-2 and 1A-7 loop regions analogous to conventional CDR3 loops fit into the synthetic category, their lengths (16, 18 and 16 residues, respectively) and amino acid composition are typical of naturally occurring IgNAR antibodies. 12A-9 is a naturally occurring shark IgNAR and has a loop region of length 13 residues analogous to a conventional CDR3 loop.

FIG. 1 presents the sequence alignments of 12Y-1, 12Y-2, 12A-9, 1A-7 and twelve naturally occurring Type 2 $V_{NAR}$s: 7E-22 (SEQ ID NO: 17), 7E-23 (SEQ ID NO: 18), 7E-51 (SEQ ID NO: 19), 7E-54 (SEQ ID NO: 20), 7E-56 (SEQ ID NO: 21), 7E-58 (SEQ ID NO: 22), 7E-68 (SEQ ID NO: 23), 7E-77 (SEQ ID NO: 24), 7E-80 (SEQ ID NO: 25), 7E-87 (SEQ ID NO: 26), 7E-91 (SEQ ID NO: 27), 7E-93 (SEQ ID NO: 28). Half cysteine residues occur in ~⅔rds of cases in loop regions 4 and 8 (as defined herein), forming a disulphide bridge between the loops analogous to conventional CDR1 and CDR3 loops. 12A-9 has cysteine residues is both loop region 4 and loop region 8. 12Y-1, 12Y2 and 1A-7 contain no cysteine residues in loop regions 4 and 8.

Table 1 shows the amino acid variation across the sixteen Type 2 $V_{NAR}$s sequences in FIG. 1 and the Type 2 $V_{NAR}$s sequences reported by Nuttall (2002 & 2003). It is evident from FIG. 1 and Table 1 that there is a large degree of conservation of sequence outside of the loop regions analogous to conventional CDR1 and CDR3 loops.

We have now successfully generated crystals of 12Y-1, 12Y-2, 12A-9 and 1A-7 and have determined the structures of these proteins. Furthermore, we have compared these structures with a range of known immune molecules, i.e. members of the immunoglobulin superfamily.

12Y-1 and 12Y-2 $V_{NAR}$s were expressed in *Escherichia coli* and placed into crystallization trials in the presence or absence of AMA1 antigen. No crystal leads were observed in the presence of antigen, possibly due to the intrinsically flexible domain structure of the AMA1 protein (Hodder 1996). In contrast, good quality crystals were obtained for both 12Y-1 (space group $I4_1 22$) and 12Y-2 (space group $I2_1 2_1 2$) in the absence of antigen.

12A-9 and 1A-7 $V_{NAR}$s were expressed in *Escherichia coli* and placed into crystallization trials. Successful conditions were scaled up and diffraction quality crystals obtained for both 12A-9 (space group $P2_1 2_1 2$) and 1A-7 (space group $I2_1 2_1 2_1$).

Data sets generated for 12Y-1 and 12Y-2 crystal forms resisted solution by standard molecular replacement techniques, using a broad range of immunoglobulin superfamily proteins as template. We believed this was indicative of the unique nature of these proteins, thus the 12Y-1 structure was solved ab initio by phasing with two isomorphous heavy atom derivatives (Lutetium (III) Acetate Hydrate: LAH, and Potassium Hexachloro Rhenium: PHR). However, this structure was incomplete, lacking residues Phe88 to Pro98, most likely due to inherent flexibility of the loop region analogous to a conventional CDR3 loop within this crystal form. The complete 12Y-2 structure was then solved by molecular replacement using the 2.8 Å 12Y-1 structure as a model.

Whereas the 12Y-1 asymmetric unit contains one molecule, the 12Y-2 crystal asymmetric units contain two molecules (Chains A; B); the relative disposition of these two 12Y-2 monomers requires rotation by 176.20 and screw translation by −1.1 Å to overlay the Cα atoms. The final 12Y-2 structure was refined to 2.18 Å resolution, with 93.4% of residues in the most favoured regions of the Ramachandran plot with no residues in the generously allowed or disallowed regions. Details of the diffraction data and refinement statistics are presented in Table 2. The coordinates for 12Y-1 and 12Y-2 are attached as Appendix I(a) and (b) respectively.

The structures of 12A-9 and 1A-7 were determined by molecular replacement. The search model for 12A-9 was the 12Y-1 structure (above) without the CDR3 loop. The search model for 1A-7 was the 12Y-1 two-fold dimer structure without the CDR3 loops. In the final 12A-9 structure, 88.4% of the residues are in the most favoured regions of the Ramachandran plot, with one residue in the generously allowed or disallowed regions. In the final 1A-7 structure, 90.9% of the residues are in the most favoured regions of the Ramachandran plot, with two residues for chain C in the generously allowed or disallowed regions. Details of the diffraction data and refinement statistics are presented in Table 2. The coordinates for 12A-9 and 1A-7 are attached as Appendix I(c) and (d), respectively.

Thus, is a first aspect, the present invention provides a crystal of a variable domain of a Type 2 IgNAR that effectively diffracts X-rays for the determination of the atomic coordinates of the variable domain of the IgNAR to a resolution of better than 4.0 Å, wherein the variable domain of the Type 2 IgNAR consists of 105 to 125 amino acid residues and comprises an amino acid sequence according to Table 1 and/or FIG. 1.

It will be understood that reference herein to comprising an amino acid sequence according to Table 1 includes amino acid sequences having a high degree of sequence homology with the consensus sequence given in Table 1. Preferably, amino acid sequences will have at least 80%, more preferably at least 85% and yet more preferably at least 90% sequence identity with the consensus sequence in Table 1. Preferably, amino acid sequences will have at least 90%, more preferably at least 95% sequence identity with those residues in the consensus sequence in Table 1 that are totally conserved.

It will be understood that reference herein to comprising an amino acid sequence according to FIG. 1 includes amino acid sequences having at least at least 80%, more preferably at least 85% and yet more preferably at least 90% sequence identity with a sequence shown in FIG. 1.

For the avoidance of doubt, the sequence identity figures given above in respect of Table 1 and FIG. 1 exclude the variable regions in Table 1 and corresponding variable regions in FIG. 1.

In one embodiment, the crystal has a space group $I4_122$ with unit cell dimensions of a=97.26 Å, b=97.26 Å and c=65.23 Å, and a unit cell variability of 5% in all dimensions.

In another embodiment, the crystal has a space group $I2_12_12_1$ with unit cell dimensions of a=65.28 Å, b=92.05 Å and c=98.22 Å, and a unit cell variability of 5% in all dimensions.

In another embodiment, the crystal has a space group $P2_12_12$ with unit cell dimensions of a=38.27 Å, b=68.32 Å and c=39.51 Å, and a unit cell variability of 5% in all dimensions.

In another embodiment, the crystal has a space group $I2_12_12_1$ with unit cell dimensions of a=80.50 Å, b=88.66 Å and c=101.75 Å, and a unit cell variability of 5% in all dimensions.

Preferably, the crystals effectively diffract X-rays to a resolution of better than 3.0 Å, more preferably better than 2.5 Å.

In a further aspect, the present invention provides a crystal of a variable domain of a Type 2 IgNAR comprising a structure defined by all or a portion of the coordinates of Appendix I(a), (b), (c) or (d)± a root mean square deviation from the Cα atoms of less than 0.5 Å.

The IgNAR domain structures set out in Appendices I(a), (b), (c) and (d) are monomer structures. This is the first time that a monomer has been observed crystallographically for an IgNAR variable domain.

In Appendices I(a), (b), (c) and (d), the third column denotes the atom type, the fourth column the residue type, the fifth column the chain identification, the sixth column the residue number (the atom numbering as described in Hong (2000)), the seventh, eighth and ninth columns the X, Y, Z coordinates, respectively, of the atom in question, the tenth column the occupancy of the atom, the eleventh column the temperature factor of the atom, and the last the atom type.

Each of the Appendices is presented in an internally consistent format. For example, the coordinates of the atoms of each amino acid residue are listed such that the backbone nitrogen atom is first, followed by the C-α backbone carbon atom, designated CA, followed by the carbon and oxygen of the protein backbone and finally side chain residues (designated according to one standard convention). Alternative file formats (e.g. such as a format consistent with that of the EBI Macromolecular Structure Database (Hinxton, UK)) which may include a different ordering of these atoms, or a different designation of the side-chain residues, may be used or preferred by others of skill in the art. However it will be apparent that the use of a different file format to present or manipulate the coordinates of the Appendices is within the scope of the present invention.

As discussed herein, we have identified structural features in 12Y-1, 12Y-2, 12A-9 and 1A-7 IgNAR variable domains that are important for antigen binding or solubility/stability of these domains. These features can be introduced into domains of other members of the IgSF (for example, I-set or V-set domains) in order to alter binding properties or to improve solubility and/or stability. The information presented in Appendix I can be used, for example, to compare structures of IgSF domains that have been modified so as to more closely resemble the structure of IgNAR variable domains.

Protein structure similarity is routinely expressed and measured by the root mean square deviation (r.m.s.d.), which measures the difference in positioning in space between two sets of atoms. By "root mean square deviation" we mean the square root of the arithmetic mean of the squares of the deviations from the mean. The r.m.s.d. measures distance between equivalent atoms after their optimal superposition. The r.m.s.d. can be calculated over all atoms, over residue backbone atoms (i.e. the nitrogen-carbon-carbon backbone atoms of the protein amino acid residues), main chain atoms only (i.e. the nitrogen-carbon-oxygen-carbon backbone atoms of the protein amino acid residues), side chain atoms only or more usually over C-α atoms only. For the purposes of this invention, the r.m.s.d. can be calculated over any of these, using any of the methods outlined below.

Methods of comparing protein structures are discussed in Methods of Enzymology, vol 115, pg 397-420. The necessary least-squares algebra to calculate r.m.s.d. has been given by Rossman (1975) although faster methods have been described by Kabsch (1976 & 1978), Hendrickson (1979) and McLachan (1979). Some algorithms use an iterative procedure in which the one molecule is moved relative to the other, such as that described by Ferro (1977). Other methods e.g. Kabsch's algorithm locate the best fit directly.

It is usual to consider C-α atoms and the r.m.s.d. can then be calculated using programs such as LSQKAB (Collaborative Computational Project 4. (CCP4 1994)), MNYFIT (part of a collection of programs called COMPOSER) (Sutcliffe (1987)), MAPS (Lu 1998), QUANTA (Jones 1991 and commercially available from Accelerys, San Diego, Calif.), Insight (commercially available from Accelerys, San Diego, Calif.), Sybyl® (commercially available from Tripos, Inc., St Louis), O (Jones 1991) and other coordinate fitting programs.

In, for example, the programs LSQKAB and O, the user can define the residues in the two proteins that are to be paired for the purpose of the calculation. Alternatively, the pairing of residues can be determined by generating a sequence alignment of the two proteins. The atomic coordinates can then be superimposed according to this alignment and an r.m.s.d. value calculated. The program *Sequoia* (Bruns 1999) performs the alignment of homologous protein sequences, and the superposition of homologous protein atomic coordinates. Once aligned, the r.m.s.d. can be calculated using programs detailed above. For sequence identical, or highly identical, the structural alignment of proteins can be done manually or automatically as outlined above. Another approach would be to generate a superposition of protein atomic coordinates without considering the sequence.

It is more normal when comparing significantly different sets of coordinates to calculate the r.m.s.d. value over C-α atoms only. It is particularly useful when analysing side chain movement to calculate the r.m.s.d. over all atoms and this can be done using LSQKAB and other programs.

Varying the atomic positions of the atoms of the structure by up to about 0.5 Å in a concerted way, preferably up to about 0.3 Å in any direction will result in a structure which is substantially the same as the structure of Appendix I(a) or (b) in terms of both its structural characteristics and utility e.g. for molecular structure-based analysis.

Those of skill in the art will appreciate that in many applications of the invention, it is not necessary to utilise all the coordinates of Appendix I(a), (b), (c) or (d), but merely a portion of them. The term portion is intended to define a sub-set of the coordinates, which may or may not represent contiguous amino acid residues in the 12Y-1, 12Y-2, 12A-9 or 1A-7 structure.

The invention also provides a means for homology modelling of other IgSF domains. By "homology modelling", it is meant the prediction of related IgSF domain structures based either on X-ray crystallographic data or computer-assisted de novo prediction of structure, based upon manipulation of the coordinate data of Appendix I.

The term "homologous regions" describes amino acid residues in two sequences that are identical or have similar (e.g. aliphatic, aromatic, polar, negatively charged, or positively charged) side-chain chemical groups. Identical and similar residues in homologous regions are sometimes described as being respectively "invariant" and "conserved" by those skilled in the art.

In general, the method involves comparing the amino acid sequences of the IgNAR domain of Appendix I(a), (b), (c) or (d) with a modified IgSF domain by aligning the amino acid sequences (Dunbrack (1997)). Amino acids in the sequences are then compared and groups of amino acids that are homologous (conveniently referred to as "corresponding regions") are grouped together. This method detects conserved regions of the polypeptides and accounts for amino acid insertions or deletions.

Homology between amino acid sequences can be determined using commercially available algorithms. The programs BLAST, gapped BLAST, BLASTN, PSI-BLAST and BLAST 2 sequences (provided by the National Center for Biotechnology Information) are widely used in the art for this purpose, and can align homologous regions of two amino acid sequences. These may be used with default parameters to determine the degree of homology between the amino acid sequence of the 12Y-1, 12Y-2, 12A-9 or 1A-7 protein and other IgSF domains, which are to be modelled.

Homology modelling as such is a technique that is well known to those skilled in the art (see e.g. Greer 1985 and Blundell 1988). The techniques described in these references, as well as other homology modelling techniques, generally available in the art, may be used in performing the present invention Thus the invention provides a method of homology modelling comprising the steps of: (a) aligning a representation of an amino acid sequence of an IgSF domain with the amino acid sequence of 12Y-1, 12Y-2, 12A-9 or 1A-9 as shown in FIG. 1 to match homologous regions of the amino acid sequences; (b) modelling the structure of the matched homologous regions of said IgSF domain on the corresponding regions of the 12Y-1, 12Y-2, 12A-9 or 1A-7 structure as defined by Appendix I(a), (b), (c) or (d); and (c) determining a conformation (e.g. so that favourable interactions are formed within the IgSF domain and/or so that a low energy conformation is formed) for said IgSF domain which substantially preserves the structure of said matched homologous regions.

Preferably one or all of steps (a) to (c) are performed by computer modelling.

The aspects of the invention described herein which utilise the 12Y-1, 12Y-2, 12A-9 or 1A-7 structure in silico may be equally applied to models of modified IgSF domains obtained by methods of the present invention, and this application forms a further aspect of the present invention. Thus having determined the conformation of 12Y-1, 12Y-2, 12A-9 or 1A-7, such conformation may be used in a computer-based method of rational design of modified domains for diagnostic or therapeutic applications as described herein.

The structure of 12Y-1, 12Y-2, 12A-9 or 1A-7 can also be used to solve the crystal structure of other IgNAR domains, where X-ray diffraction data or NMR spectroscopic data of these other domains has been generated and requires interpretation in order to provide a structure.

One method that may be employed for these purposes is molecular replacement. In this method, the unknown IgNAR domain crystal structure, may be determined using the 12Y-1, 12Y-2, 12A-9 or 1A-7 structure coordinates as provided herein. This method will provide an accurate structural form for the unknown crystal more quickly and efficiently than attempting to determine such information ab initio.

Examples of computer programs known in the art for performing molecular replacement are CNX (Brunger 1998a (also commercially available from Accelerys San Diego, Calif.)) or AMORE (Navaza 1994).

Thus, in a further aspect, the invention provides a method for determining the structure of a protein, which method comprises; providing the co-ordinates of Appendix I(a), (b), (c) or (d), and either (a) positioning the co-ordinates in the crystal unit cell of said protein so as to provide a structure for said protein or (b) assigning NMR spectra Peaks of said protein by manipulating the coordinates of Appendix I(a), (b), (c) or (d).

In another aspect, the present invention provides systems, particularly a computer system, the systems containing at least one of the following: (a) atomic coordinate data according to Appendix I, said data defining the three-dimensional structure of 12Y-1, 12Y-2, 12A-9 or 1A-7 or at least selected coordinates thereof; (b) structure factor data (where a structure factor comprises the amplitude and phase of the diffracted wave) for 12Y-1, 12Y-2, 12A-9 or 1A-7, said structure factor data being derivable from the atomic coordinate data of Appendix I; (c) atomic coordinate data of an IgSF domain generated by homology modelling of the IgSF domain based on the data of Appendix I; (d) atomic coordinate data of the IgSF domain generated by interpreting X-ray crystallographic data or NMR data by reference to the data of Appendix I; and (e) structure factor data derivable from the atomic coordinate data of (c) or (d).

For example the computer system may comprise: (i) a computer-readable data storage medium comprising data storage material encoded with the computer-readable data; (ii) a working memory for storing instructions for processing said computer-readable data; and (iii) a central-processing unit coupled to said working memory and to said computer-readable data storage medium for processing said computer-readable data and thereby generating structures and/or performing rational drug design. The computer system may further comprise a display coupled to said central-processing unit for displaying said structures.

The invention also provides such systems containing atomic coordinate data of modified IgSF domains wherein such data has been generated according to the methods of the invention described herein based on the starting data provided by Appendix I.

Such data is useful for a number of purposes, including the generation of structures to analyze the mechanisms of action of IgSF domains and/or to perform rational design of IgSF domains for diagnostic or therapeutic purposes.

In another aspect, the invention provides a computer-readable storage medium, comprising a data storage material encoded with computer readable data, wherein the data are defined by all or a portion (e.g. selected coordinates as defined herein) of the structure coordinates of 12Y-1, 12Y-2, 12A-9 or 1A-7, or a variant of 12Y-1, 12Y-2, 12A-9 or 1A-7, wherein said variant comprises backbone atoms that have a root mean square deviation from the Cα or backbone atoms (nitrogen-carbonα-carbon) of Appendix I of less than 2 Å, such as not more than 1.5 Å, preferably less than 1.5 Å, more preferably less than 1.0 Å, even more preferably less than 0.74 Å, even more preferably less than 0.72 Å and most preferably less than 0.5 Å.

The invention also provides a computer-readable data storage medium comprising a data storage material encoded with a first set of computer-readable data comprising a Fourier transformation of at least a portion (e.g. selected coordinates as defined herein) of the structural coordinates for 12Y-1, 12Y-2, 12A-9 or 1A-7 according to Appendix I; which, when combined with a second set of machine readable data comprising an X-ray diffraction pattern of a molecule or molecular complex of unknown structure, using a machine programmed with the instructions for using said first set of data and said second set of data, can determine at least a portion of the structure coordinates corresponding to the second set of machine readable data.

In a further aspect, the present invention provides computer readable media with at least one of: (a) atomic coordinate data according to Appendix I recorded thereon, said data defining the three-dimensional structure of 12Y-1, 12Y-2, 12A-9 or 1A-7, or at least selected coordinates thereof; (b) structure factor data for 12Y-1, 12Y-2, 12A-9 or 1A-7 recorded thereon, the structure factor data being derivable from the atomic coordinate data of Appendix I; (c) atomic coordinate data of a target IgSF domain generated by homology modelling of the IgSF domain based on the data of Appendix 1; (d) atomic coordinate data of a modified IgSF domain generated by interpreting X-ray crystallographic data or NMR data by reference to the data of Appendix I; and (e) structure factor data derivable from the atomic coordinate data of (c) or (d).

By providing such computer readable media, the atomic coordinate data can be routinely accessed to model IgSF domains or selected coordinates thereof. For example, RASMOL (Sayle 1995) is a publicly available computer software package which allows access and analysis of atomic coordinate data for structure determination and/or rational drug design.

On the other hand, structure factor data, which are derivable from atomic coordinate data (see e.g. Blundell 1976), are particularly useful for calculating e.g. difference Fourier electron density maps.

A further aspect of the invention provides a method of providing data for generating structures and/or performing rational drug design for IgSF domains, the method comprising: (i) establishing communication with a remote device containing computer-readable data comprising at least one of: (a) atomic coordinate data according to Appendix I, said data defining the three-dimensional structure of 12Y-1, 12Y-2, 12A-9 or 1A-7, at least one sub-domain of the three-dimensional structure of 12Y-1, 12Y-2, 12A-9 or 1A-7, or the coordinates of a plurality of atoms of 12Y-1, 12Y-2, 12A-9 or 1A-7; (b) structure factor data for 12Y-1, 12Y-2, 12A-9 or 1A-7, said structure factor data being derivable from the atomic coordinate data of Appendix I; (c) atomic coordinate data of a modified IgSF domain generated by homology modelling of the domain based on the data of Appendix I; (d) atomic coordinate data of a protein generated by interpreting X-ray crystallographic data or NMR data by reference to the data of Appendix I; and (e) structure factor data derivable from the atomic coordinate data of (c) or (d); and (ii) receiving said computer-readable data from said remote device.

A further aspect of the invention provides a method of providing data for generating structures and/or performing rational drug design for IgSF domains, the method comprising: (i) establishing communication with a remote device containing computer-readable data comprising at least one of: (a) atomic coordinate data according to Appendix I, said data defining the three-dimensional structure of 12Y-1, 12Y-2, 12A-9 or 1A-7, at least one sub-domain of the three-dimensional structure of 12Y-1, 12Y-2, 12A-9 or 1A-7, or the coordinates of a plurality of atoms of 12Y-1, 12Y-2, 12A-9 or 1A-7; (b) structure factor data for 12Y-1, 12Y-2, 12A-9 or 1A-7, said structure factor data being derivable from the atomic coordinate data of Appendix I; (c) atomic coordinate data of a modified IgSF domain generated by homology modelling of the domain based on the data of Appendix I; (d) atomic coordinate data of a protein generated by interpreting X-ray crystallographic data or NMR data by reference to the data of Appendix I; and (e) structure factor data derivable from the atomic coordinate data of (c) or (d); and (ii) receiving said computer-readable data from said remote device.

Thus the remote device may comprise, for example, a computer system or computer readable media of one of the previous aspects of the invention. The device may be in a different country or jurisdiction from where the computer-readable data is received. The communication may be via the internet, intranet, email etc. Typically the communication will be electronic in nature, but some or all of the communication pathway may be optical, for example, over optical fibres. Additionally, the communication may be through radio signals or satellite transmissions.

The folding topologies of the 12Y-1, 12Y-2, 12A-9 and 1A-7 structures show the characteristic immunoglobulin superfamily (IgSF) fold, identified by a β-sandwich structure formed by two β-sheets, packed face-to-face and linked by a disulfide bond between strands B and F (Bork 1994, Chothia 1998). The inner-strand features are turns, coils and loops including two loop regions analogous to CDR1 and CDR3 loops.

The structures comprise eight β-strand regions, designated A, A', B, C, D, E, F and G according to FIG. 2, and nine loop regions, designated 1 to 9 according to FIG. 2. As used herein, a "loop region" is a portion of peptide sequence that extends either from or between a β-strand conformation or β-strand conformations. As used herein, a "β-strand region" contains an extended β-strand conformation, i.e. β-strands comprising at least 4, preferably at least 5 amino acids. Loop regions are typically free of extended β-strand conformations but may include shortened β-strand conformations, i.e. β-strands comprising less than 4 amino acids. Apart from N- and C-terminal loop regions, the loop regions connect β-strands running in opposite directions.

Preferably, loop region 5 contains shortened β-strand conformations. We have also found that loop region 8 may contain β-strand conformations, which may be either shortened or extended, and these are discussed in more detail below. Preferably, no other loop regions contain β-strand conformations.

Detailed analysis of the 12Y-1, 12Y-2, 12A-9 and 1A-7 frameworks indicates a novel folding topology which resembles the intermediate (I-set) fold in a number of important characteristics, but also with distinct structural features found in variable (V-set) domains. More particularly, the structures comprise 8 β-strand regions, designated A, A', B, C, D, E, F and G according to FIG. 2, and nine loop regions, designated 1 to 9 according to FIG. 2, in which loop region 5 comprises 2 shortened β-strand regions, designated D' and C', and 3 loop regions, designated 5a, 5b and 5c, according to FIG. 3.

From the data assimilated, Table 3 presents a breakdown of the number of amino acid residues present in the various loop and β-strand regions of Type 2 $V_{NAR}$s. Loop region 4 is analogous to a conventional CDR1 loop. Loop region 8 is analogous to a conventional CDR3 loop. As loop region 8 can contain a variable number of amino acids ranging from about 5 to 30, a default value of 18 is used on which to base the residue numbering for subsequent regions. Consequently, the residue numbering does not necessarily correlate with the total number of amino acid residues present in the sequence. It is based on loop region 8 having a default value of 18 amino acid residues.

Table 3A presents a breakdown of the number of amino acid residues present in the loop region 5 of Type 2 $V_{NAR}$s. Loop region 5 comprises 2 shortened β-strand regions, designated D' and C', and 3 loop regions, designated 5a, 5b and 5c.

Both V-set and I-set proteins have a typical kink in the first strand (A'), which allows the first part of the strand (A) to hydrogen bond to one part of the β-sandwich sheet and the second part (A') to the extended G strand of the other β-sheet. This first-strand kink is found in the $V_{NAR}$ proteins as depicted in FIG. 4. It starts with the highly conserved cis-proline (Pro7), the most typical residue in first-strand kinks of variable domains (Spada 1998). Like V-set proteins, 12Y-1, 12Y-2, 12A-9 and 1A-7 also have bulges in the C terminal G strand (conserved Gly-Ala-Gly motif) and in the C' strand. Most significantly, 12Y-1, 12Y-2, 12A-9 and 1A-7 resemble I-set proteins in having a short C' strand (three H-bonds) and a very short C" strand (labelled as D' in FIG. 3) which atypically switches from one β-sheet to the other, such that a single hydrogen bond links it to the D strand rather than the C' strand as in V-set domains.

Figure 5:
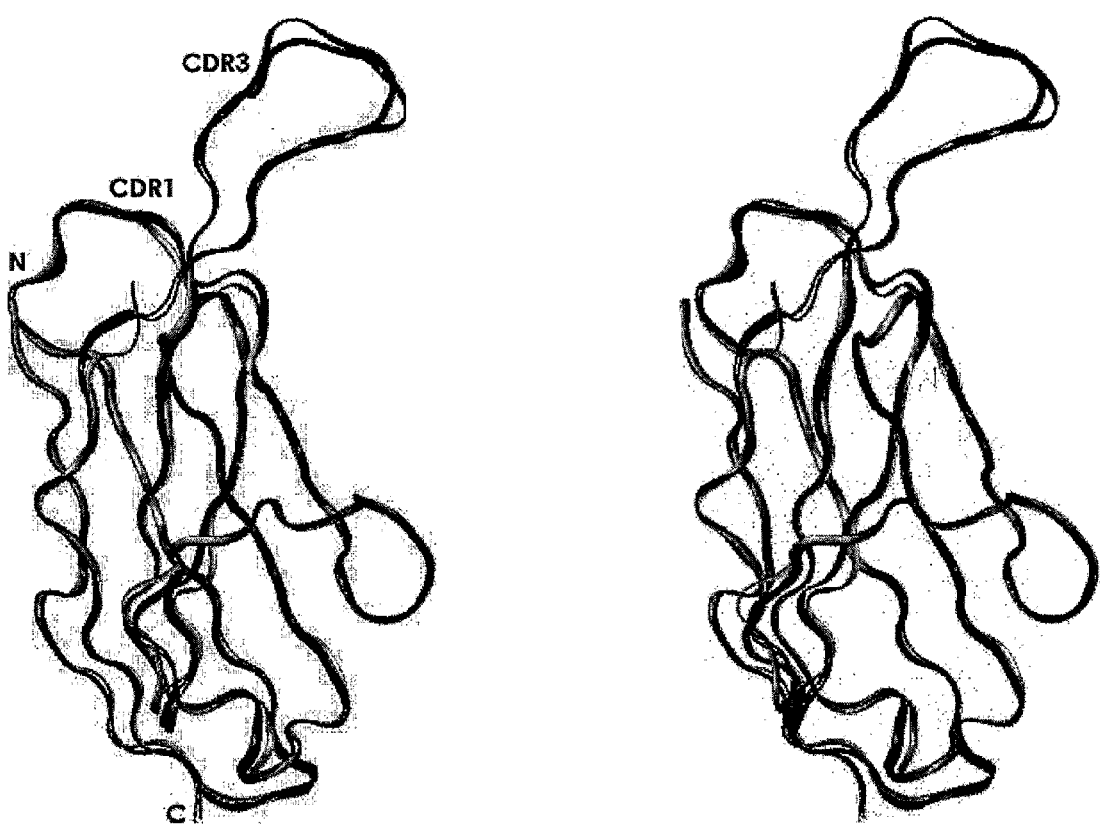
FIG. 5. Stereo images of superimposed IgSF domains in ribbon representation of the 12Y-2 A chain, the 12Y-2 B chain and the 12Y-1 chain. Figures were produced using VMD. The CDR1 analogous region (loop region 4) and CDR3 analogous region (loop region 8) are labelled.
Figure 6:
FIG. 6. Stereo images of superimposed IgSF domains in ribbon representation of the 12Y-2 A chain, Telokin (1FHG) and the NCAM domain 1 (1QZ1). Figures were produced using VMD.
Figure 7:
FIG. 7. Stereo images of superimposed IgSF domains in ribbon representation of the 12Y-2 A chain, human TCR $V_\alpha$ (1A07), human $V_H$ and $V_L$ (1IGM), and camel $V_H$H (1 MEL). Figures were produced using VMD.

The 12Y-2 chain A and B (r.m.s.d. of 0.53 Å for $C_\alpha$ of 113 residues), and the 12Y-1 framework (r.m.s.d. of 0.72 Å for $C_\alpha$ of 100 residues) are closely related (see FIG. 5). Further structural comparison (see FIGS. 6 and 7) of the 12Y-2 chain A to diverse variable and intermediate set proteins for which structural information is available, shows $V_{NAR}$s to be most closely related to I-set molecules such as the Neural Cell Adhesion Molecules (NCAMs) (Harpaz 1994; Chothia 1997; Soroka 2003,) and Telokin (Chothia 1997; Holden 1992). This similarity is heavily biased by the absence of extended C' and C" strands, connected by a CDR2 loop, that in conventional antibodies extends up to the top of the molecule and participates in immune recognition. In contrast, comparison of the 12Y-2 chain A to conventional T cell receptor (TCR) Vα, and $V_H$, $V_L$, and single-domain $V_H$H antibodies, shows little consistent structural identity beyond a core of residues based around the major strands, minus the C', C" and CDR regions. The single $V_H$H domains found in the Camelidae may be expected to be similar to the $V_{NAR}$ structure, however, these single domain antibodies clearly arose from a mammalian IgG-like progenitor, successively acquiring solubilizing, stabilizing, and extensive CDR3 mutations (Nguyen 2002). The low structural homology between $V_H$H and $V_{NAR}$s is consistent with their very low sequence homology, and reflects convergent evolutionary solutions to the problem of achieving solvent solubility and binding affinity.

Figure 8:
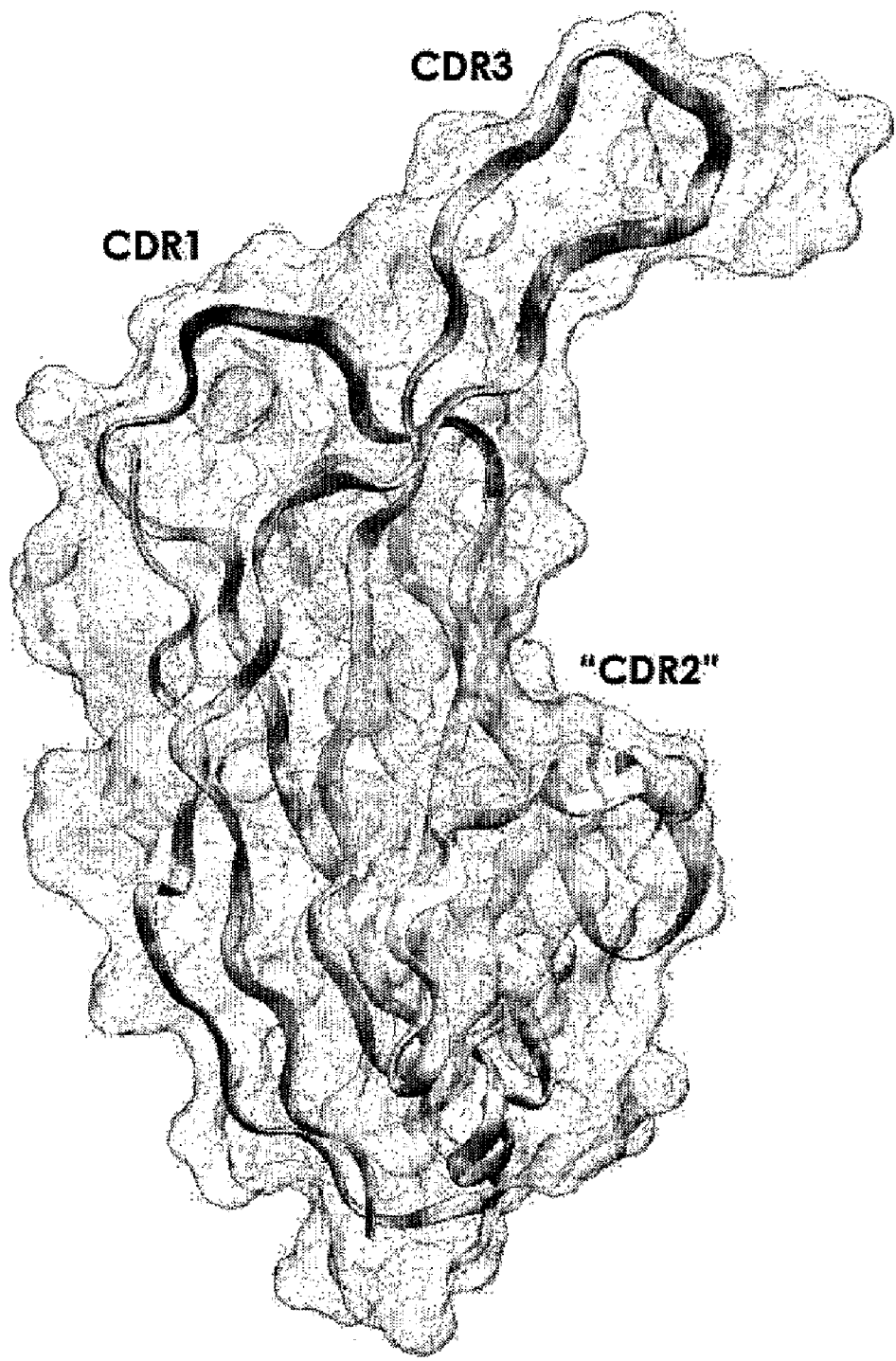
FIG. 8. CDR analogous regions in $V_{NAR}$ 12Y-2. The 12Y-2 chain A structure in ribbon representation is overlayed with transparent molecular surface. The positions of the CDR1, "CDR2" and CDR3 analogous regions are indicated.
Figure 9:
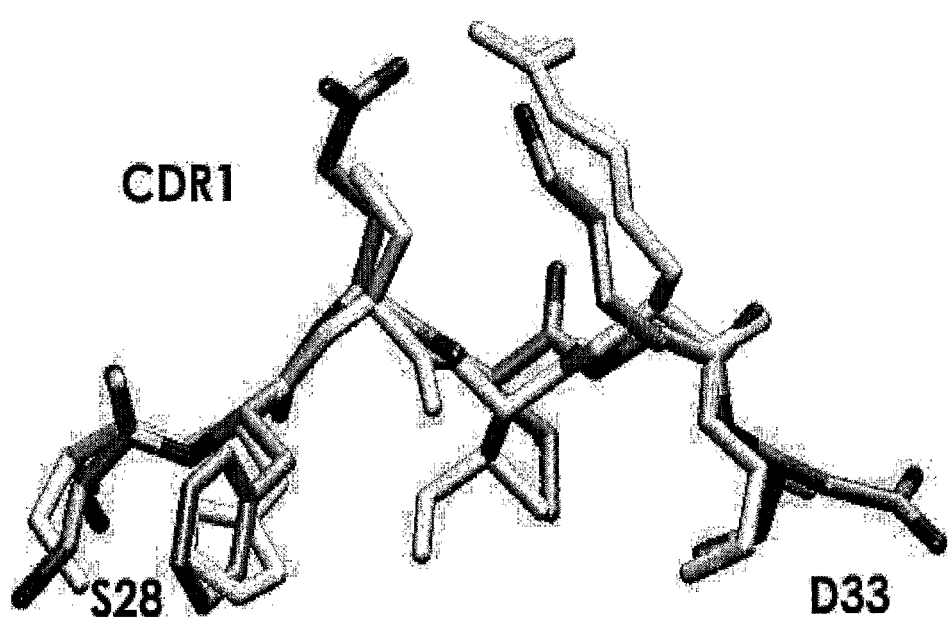
FIG. 9. CDR analogous regions in $V_{NAR}$ 12Y-2. Overlay of the CDR1 analogous region (loop region 4) of the 12Y-2 chain A and the CDR1 of human $V_L$ (1 HZH) (r.m.s.d. 1.22 Å²) in liquorice representation.
Figure 10:
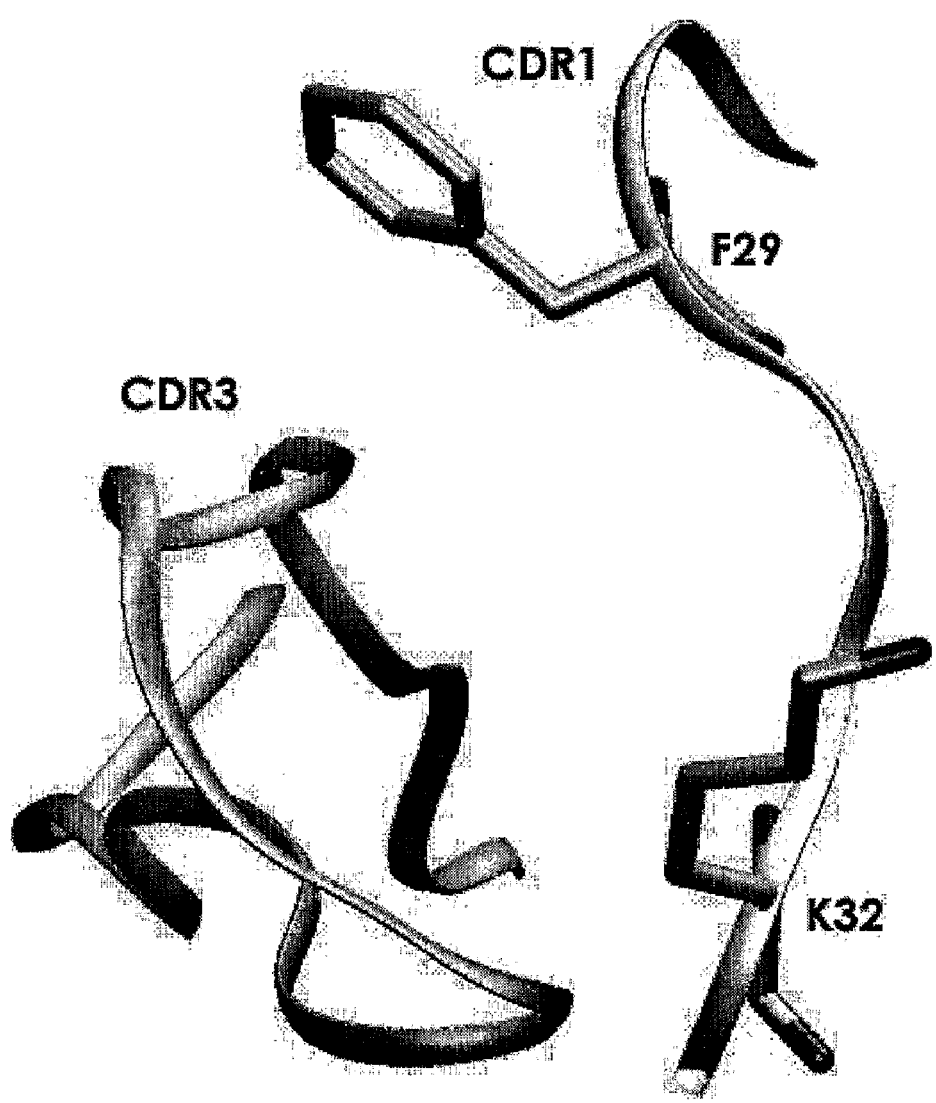
FIG. 10. CDR analogous regions in $V_{NAR}$ 12Y-2. Positioning of the CDR1 analogous region (loop region 4) and the CDR3 analogous region (loop region 8) in the 12Y-2 chain A in ribbon representation. Residues Phe29 and Lys32 (possible half-cystine positions) are oriented toward the CDR3 analogous region (loop region 8), ideally placed to make inter-loop contacts.

In FIG. 8, the relative positions of the three classically defined antibody CDR or hypervariable loop regions are shown. Sequence alignments show IgNAR antibody variability confined to the loop regions 4 and 8 corresponding to conventional CDR1 and CDR-3 regions, and this is confirmed by our structural analysis where a loop region analogous to a typical "CDR2 loop" is missing and its bottom turn appears to be well separated from the antigen-binding face (or paratope). Sequence analysis also suggests that loop region 4 is the minor loop component, invariant in length and limited in diversity. This region is confined to residues 28-33 (12Y-1: $^N$SYGLES$^C$; SEQ ID NO: 112; 12Y-2: $^N$SFELKD$^C$; SEQ ID NO: 113), with a topology close to that of canonical structure 2 observed in antibody light chain variable domains (see FIG. 9; $C_\alpha$ r.m.s.d. of 1.22 Å with 1 hzh$V_L$) (Chothia 1989). Where a half cysteine is present in the $V_{NAR}$ loop region 4, it is exclusively found at positions 29 or 32. The side chains of these two residues extend outward and upward towards the extended loop region 8, and are ideally positioned to make contact with the concomitant half cysteine in this region (see FIG. 10). Given the enormous topological latitude inherent in the highly diverse loop regions 8, a wide variety of conformations can clearly be adopted by loop region 8, despite the restraints of these stabilizing disulphide linkages. Such extreme diversity has also been observed for the CDR3 loop of $V_{HH}$ single domain antibodies, with a single antigen eliciting a highly varied immune response with significantly different loop topologies (Desmyter 2002).

Figure 11:
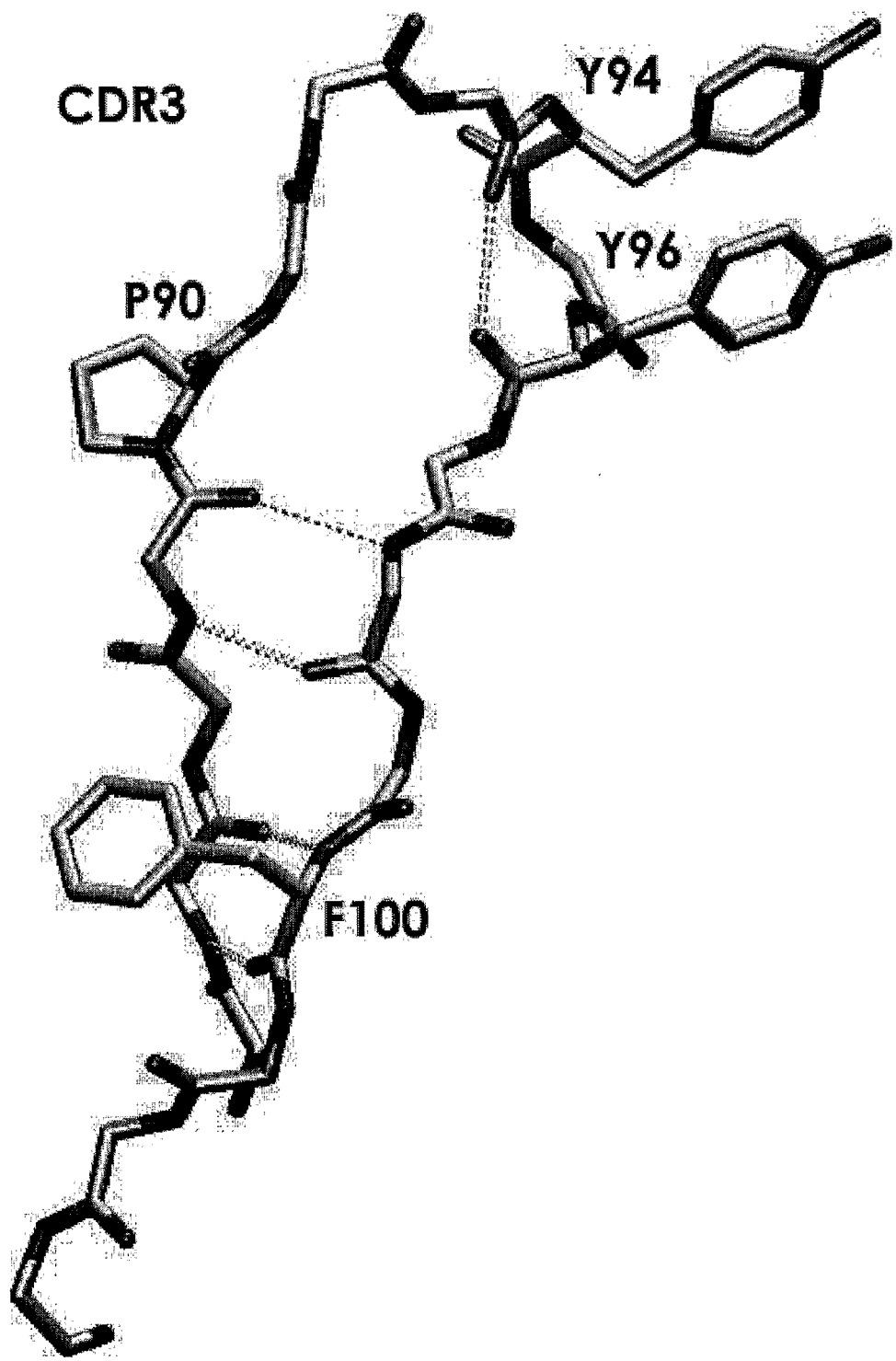
FIG. 11. CDR analogous regions in $V_{NAR}$ 12Y-2. Backbone of CDR3 analogous region (loop region 8) in the 12Y-2 chain A (86-103). β-hairpin main-chain hydrogen bonds are shown by dashed lines. Residues at the mutation positions (Pro90Leu and Phe100Leu) and residues at the tip of the loop (Tyr94 and Tyr96) are shown with side-chains.

The 12Y-2 CDR3 loop is present in two crystal forms, corresponding to chains A and B, and extends from residues Phe86 to Glu103. Unusually, the chain A loop region 8 adopts a clear β-hairpin configuration with β-strands from Phe86-Leu89, and Leu98-Glu103, separated by a flexible loop (Pro90-Ser97). For chain B, the β-hairpin extends even further into loop region 8 with residues Phe86-Asp93 and Tyr96-Glu103 involved in β-strand formation (see FIG. 11). Structurally, the β-hairpins are formed by the main chain hydrogen bonds (<3A): Tyr87 (O)-Phe100(N); Tyr87 (N)-Phe100(O); Leu89 (N)-Leu98 (O); Leu89 (O)-Leu98 (N), and, Asp93(O)-Tyr96(O) (FIG. 11). Additional H-bonds for loop region 8 of chain B are: Asp93 (N)-Tyr96 (O); Asp93 (O)-Tyr96 (N); and, Leu91 (O)-Tyr96 (O). Thus, the 12Y-2 loop region 8 extends outward and upward from the immunoglobulin framework, at the furthest point extending ~20A above the conserved β-sheet framework, and tipped by the bulky side-chains of tyrosine residues at positions 94 and 96 (see FIGS. 8 and 11). Such extended antigen binding paratopes have been observed in but a limited number of antibodies, for example the camel anti-lysozyme $V_H$H cAb-Lys3 (Desmyter 1996), and the H3 loop of human antibody b12, which penetrates deeply into the HIV gp120 binding cleft (Sapphire 2001). A comparison of the extended loop lengths of the 12Y-2 region 8 with these antibodies reveals that the 12Y-2 loop region 8 is of greater length and may bind antigen in a similar manner. Thus, it is apparent that structures based on the 12Y-2 loop region 8 with its extended β-hairpin structure may prove ideal for penetrating buried clefts and cavities in for example enzyme active sites, parasite coat proteins, or viral canyons.

We previously identified two mutations in the 12Y-2 loop region 8 which independently enhanced AMA1 antigen binding affinity 10-fold (Nuttall 2004). Without being limited by theory, it is believed that these mutations (Pro90Leu and Phe100Leu) probably act to increase the flexibility of the β-hairpin around hinge regions relative to the rest of the framework (see FIG. 11). For example, the three aromatic residues: Phe29 of CDR1, and Tyr87 and Phe100 of loop region 8 have side chains involved in stabilizing C—H.π- interactions ($d_{c-x}$<4.8A, where X is the centre-of-mass of the π-system (Brandl 2001)). Additional stability comes from hydrogen bond Tyr87 (OH)-Glu103(Oε). Thus, binding of 12Y-2 to the AMA1 target is probably mediated by the rigid β-hairpin, with increased access to the antigen mediated by flexibility at the bottom of the loop structure. In contrast, the 12Y-1 loop region 8 is unresolved in the crystal structure and is probably highly flexible in solution around similar hinge-like residues. The aromatic loop region 8 residues of 12Y-2 are replaced with Arg87 and Pro98 in 12Y-1, reducing the stability of the loop region, i.e. the Phe29 of loop region 4 is now hydrogen bonded to Glu101 (Glu103 in 12Y-2) (Tyr29 (OH)-Glu101(Oε)) leaving the hinges of the loop region 8 unsupported.

Figure 12:
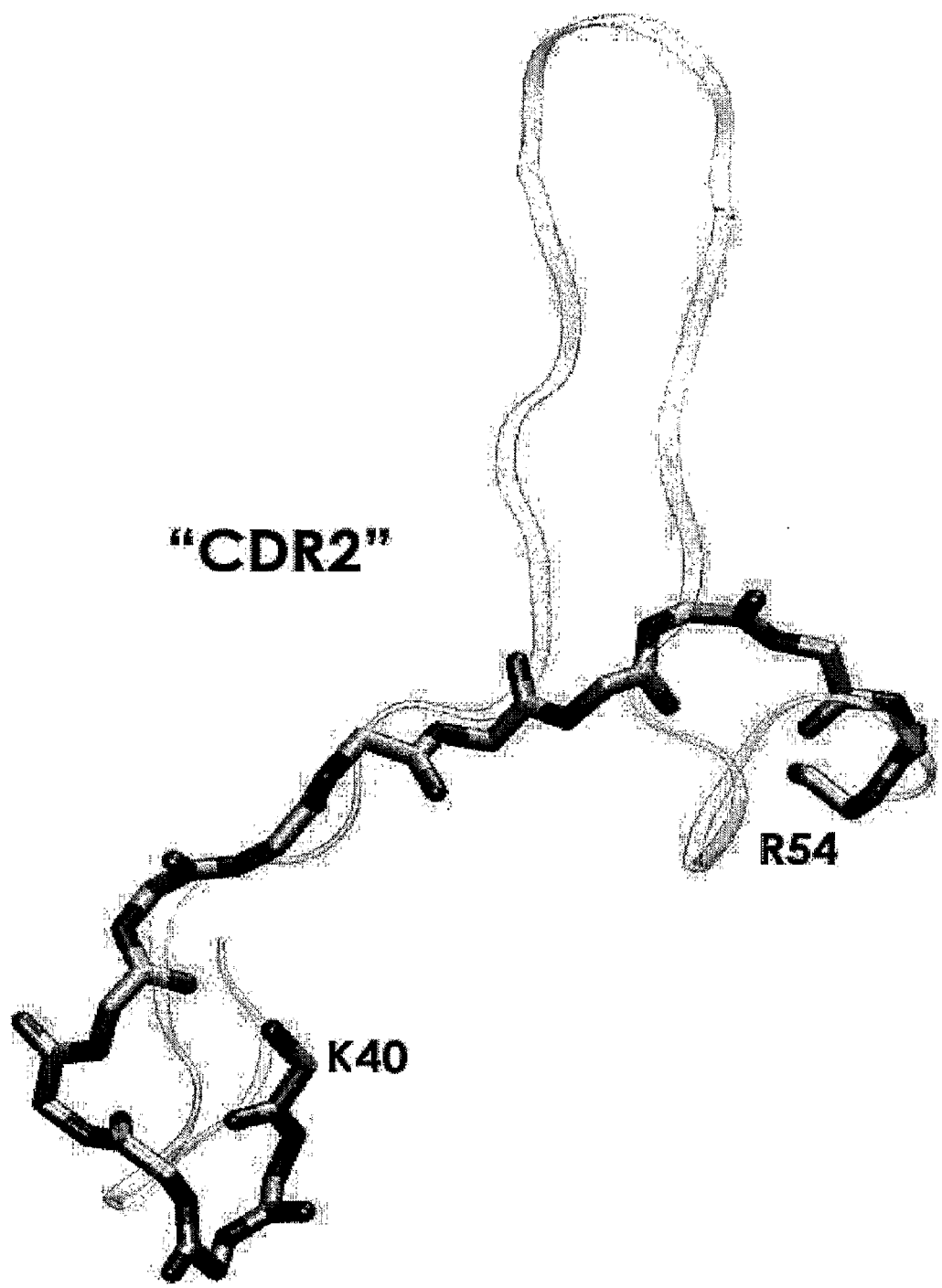
FIG. 12. CDR analogous regions in $V_{NAR}$ 12Y-2. Overlay of the backbone "CDR2" region (loop region 5) of the 12Y-2 chain A in liquorice representation and CDR2 of human $V_H$ (1 hzh) in ribbon semitransparent representation. This figure was produced using VMD.

We turn now to the impact of the unusual $V_{NAR}$ C'C"D strand topology on antigen recognition. The $V_{NAR}$ "CDR2" loop is non-existent, replaced by a short β-turn at the bottom of the molecule. This is graphically illustrated in FIG. 12, where the $V_{NAR}$ "CDR2" is aligned with that of a typical human antibody. The "bottom" position of this loop, combined with the low sequence variability, strongly suggests that this region has little impact on the interaction with antigen. However, the loss of the conventional C" and D strands suggests a possible alternative model for antigen binding, where the extended 12Y-2 loop region 8 combines with the large concave pocket opened in the absence of the conventional CDR2 (FIG. 8). Additional structural variability is also observed in the 12Y-1 and 12Y-2 structures for the C strand loop ranging from residues Lys40 to Glu46, just prior to the "CDR2" (FIG. 12). Comparison of $V_{NAR}$s from different shark species shows significant sequence heterogeneity in this region, which most likely reflects an area under less intensive selection pressure than the rest of the molecule, and susceptible to some degree of structural plasticity.

Lack of an extended CDR2 loop also has a significant impact on the interaction between isolated $V_{NAR}$s. Both 12Y-1 and 12Y-2 form crystallographic 2-fold symmetry dimers, which form a continuous 8-stranded β-sheet underneath the loop regions 4 and 8, which correspond to conventional CDR1 and CDR3 loops respectively (see FIG. 13). Contact areas are highly conserved between the 12Y-1 and 12Y-2 proteins, despite different crystal forms (12Y-1 tetragonal; 12Y-2 orthorhombic). A comparison of the 12Y-2 and 12Y-1 dimeric forms shows that the interaction surface between the 2-fold monomers is not continuous and can be subdivide into three areas: (i) the main-chain β-sheet interactions between D strands; (ii) the interaction between loop regions 4; and (iii) the interactions between loop regions 8 (see FIG. 13 and Table 4). While the contact between loop regions 8 in 12Y-2 is extensive, the dimeric arrangement is preserved in 12Y-1 crystals notwithstanding the more flexible and significantly distorted loop region 8, indicating that the conformation of loop region 8 is not absolutely required. Thus, the most significant dimer contacts are probably mediated by the loop regions 4 and especially by the D strands, where the main-chain interactions are independent of side-chain variation. With a buried surface area of ~1760 Å$^2$, the 12Y-2 dimer appears to be a true protein-protein interaction site, as the statistical probability of finding a non-specific interface of such dimensions in a crystal is <1% (Lo Conte 1999). We suggest that this configuration is a general phenomenon for independent IgNAR variable domains (i.e. not tethered to constant domains), as we have also observed such dimeric species in other recombinant $V_{NAR}$s (Nuttall 2002).

In heterodimeric immune receptors such as $V_H/V_L$ antibodies and Vα/Vβ TCRs, the paired domains interact across a broad hydrophobic interface. This non-solvent exposed region is formed by a conserved patch of residues on the AGFCC' β-strands, with additional CDR3 interactions. In contrast, many IgSF-based cell surface receptors are single domains in solution and this face of the β-sandwich takes on a more charged/polar character. We have compared this region on the 12Y-2 $V_{NAR}$, a camel $V_HH$, a TCR $V_α$, an antibody $V_H$, and NCAM and Telokin domains. The hydrophobic region of inter-domain contact is immediately apparent for the TCR and antibody domains, centred around aromatic residues at the centre of the interface. The surface character is altered for $V_HH$ domains, for example by mutations Leu45Arg and Gly44Glu, to give a more charged character. However, the relatively short evolutionary time since the development of these single domain antibodies in the Camelidae mean that other solutions have also been adopted, for example the illustrated antibody where part of the loop region 8 (analogous to a conventional CDR3 loop) descends to partly cover the former $V_L$ interface, for example residues Asp121 and Tyr120. Although these camelid adaptations can be directly transplanted to murine and human antibody variable domains, the resulting proteins often achieve increased solubility by non-predictable conformational changes (Riechmann 1996). Isolation of soluble human single variable domains can also depend on conformational perturbations, for example the side chain of conserved residue Trp47 flipping into a cavity on the $V_L$ interface (Jespers 2004).

In contrast, for the $V_{NAR}$s this face is dominated by the charged and polar residues Tyr37, Glu46, Lys82, Gln84, Arg101, and Lys104. Residues Glu46, Lys82, and Lys104 especially are well conserved across type 2 $V_{NAR}$s, and in this instance form a charged pocket with a pattern of hydrogen bonds between side-chains (i.e. Glu46Oε1-Lys104 Nζ) and to adjacent water molecules (i.e. Glu46Oε2-H$_2$0-Lys82 Nζ). The central Tyr37 is well-conserved as an aromatic species across the immunoglobulin superfamily, and it and residues Gln84 and Arg101 also participate in forming a framework-CDR3 hydrogen bond network (Arg101(NH2)-Gln84(Nζ2); Tyr87(OH)-Arg101(NH$_2$). The combined effect of these residues is to form a conserved charged pocket, which displays a high degree of solvent solubility such that it is ringed by water molecules in the crystal forms. The conservation of the Glu46, Lys82, and Lys104 trio suggests a stable and well-established face. A similar situation is observed in NCAM, where this face is dominated by the charged residues Lys76 and Glu88, and for Telokin, where a charged and polar interface is maintained by a combination of hydrogen bonds.

Modifications to the IgNAR Variable Domain

Analysis of the crystal structures has revealed the potential of $V_{NAR}$ proteins as, for example, therapeutic, diagnostic and bioarray reagents. For example, $V_{NAR}$ proteins have potential to act as cleft-binding antibodies in which the β-hairpin structures are extended to form paratopes capable of penetrating otherwise cryptic antigenic sites. Furthermore, these proteins have a high degree of stability which offers significant advantages in terms of their manipulation and practical application.

Thus, the present invention provides a method of altering a property of an IgNAR variable domain comprising eight N-strand regions, designated A, A', B, C, D, E, F and G according to FIG. 2, and nine loop regions, designated 1 to 9 according to FIG. 2, said method comprising modifying the IgNAR variable domain within at least one of the β-strand regions or loop regions.

The IgNAR variable domain is modified such that a property of the IgNAR variable domains is altered. A property of an IgNAR variable domain, I-set domain or V-set domain is altered if any characteristic or attribute of the domain differs from the corresponding property of the unmodified domain.

These properties include, but are not limited to, substrate specificity, substrate affinity, binding affinity, binding selectivity, catalytic activity, thermal stability, alkaline stability, pH activity profile, resistance to proteolytic degradation, kinetic association, kinetic dissociation, immunogenicity, ability to be secreted, ability to activate receptors, ability to treat disease, solubility, cytotoxic activity and oxidative stability.

Unless otherwise specified, a property of an IgNAR variable domain, I-set domain or V-set domain is considered to be altered when the property exhibits at least a 5%, preferably at least 10%, more preferably at least a 20%, yet more preferably at least a 50%, and most preferably at least a 2-fold increase or decrease relative to the corresponding property in the unmodified domain.

In a preferred embodiment, the solubility of the modified IgNAR variable domain, and concomitantly the binding moiety, is altered, preferably improved, relative to the corresponding unmodified IgNAR variable domain.

In another preferred embodiment, the stability of the IgNAR variable domain, and concomitantly the binding moiety, is altered, preferably improved, relative to the corresponding unmodified IgNAR variable domain. Examples of altering the stability include changing one of the following properties:—thermal stability, alkaline stability, pH activity profile and resistance to proteolytic degradation.

In a particularly preferred embodiment, the binding characteristics of the IgNAR variable domain are altered relative to the corresponding unmodified IgNAR variable domain. Examples of altering the binding characteristics include changing one of the following properties: substrate specificity, substrate affinity, catalytic activity, kinetic association, kinetic dissociation, binding affinity and binding selectivity.

In another preferred embodiment, the modification increases or decreases the propensity for IgNAR variable domain to form homodimers compared to the unmodified IgNAR variable domains.

The present invention also provides a binding moiety comprising a modified IgNAR variable domain produced by a method according to the invention.

The present invention also provides a binding moiety comprising an IgNAR variable domain comprising eight β-strand regions, designated A, A', B, C, D, E, F and G according to FIG. 2, and nine loop regions, designated 1 to 9 according to FIG. 2, wherein the IgNAR variable domain has been modified within at least one of the β-strand regions or loop regions.

Preferably, the unmodified β-strand regions and loop regions have the amino acid residue numbering according to Table 3.

Figure 3:
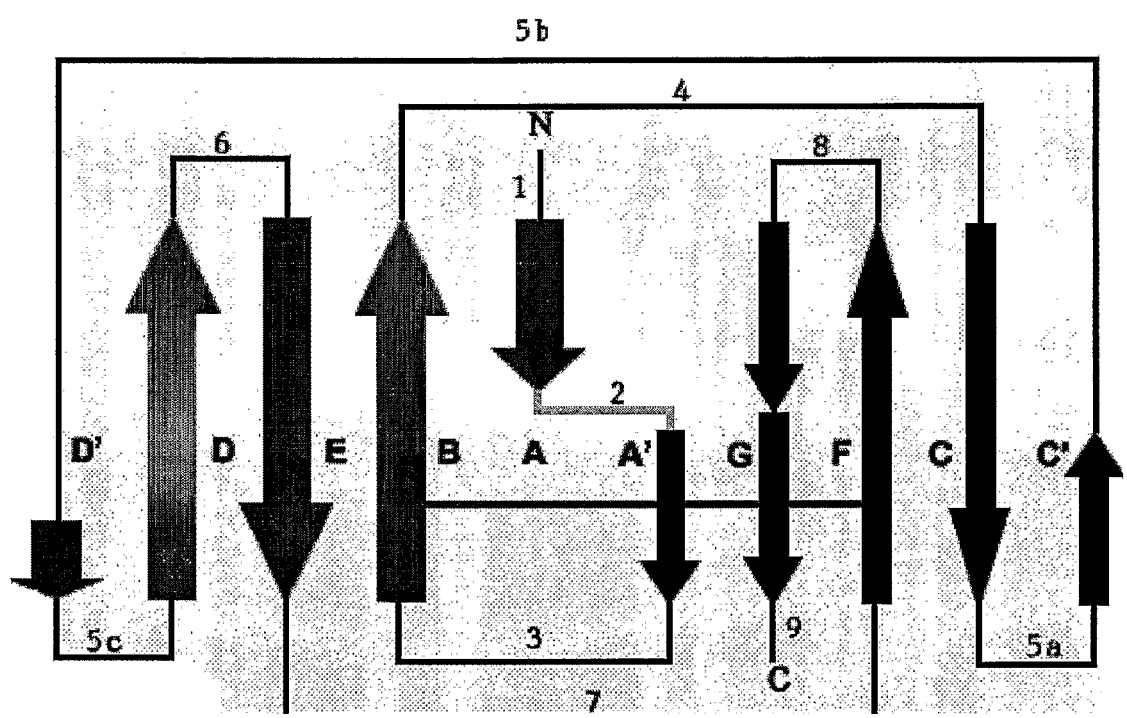
FIG. 3. Detailed 2D topology diagram of the 12Y-1, 12Y-2, 12A-9 and 1A-7 folds showing the loop regions and β-strand regions. The labelled 10 strands form a sandwich of 2 sheets: front and back sheets are shown with thick and thin arrows, respectively. The disulfide bond is indicated as a horizontal line connecting the B and F strands. The switch of N-terminal strand A to A', adjacent to the bulge in the C-terminal strand G, is shown as a kink between the A and A' strands.
Figure 4:
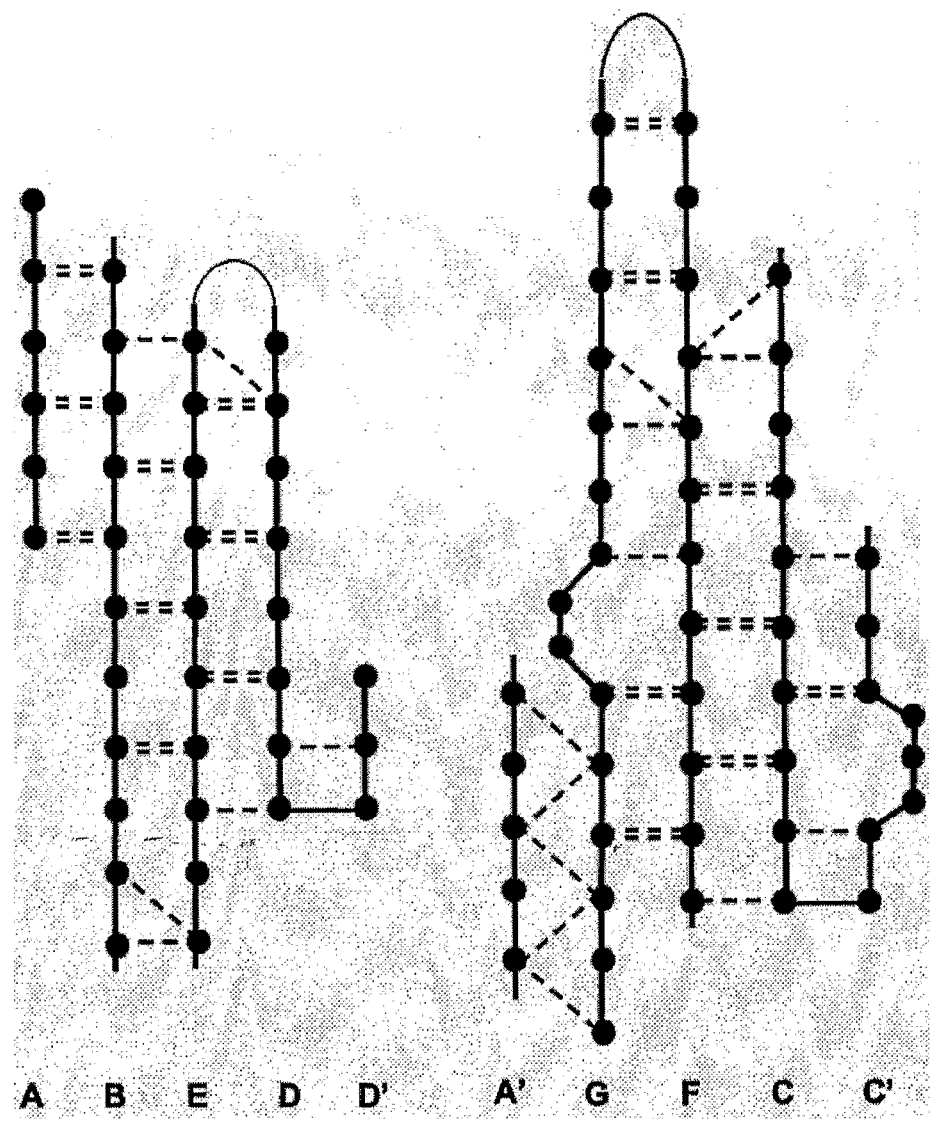
FIG. 4. H-bond pattern of the 12Y-2 β-sheets. β-sheets are presented as filled circles, and broken lines represent H-bonds between main-chain atoms.

Preferably, the unmodified loop region 5 comprises two β-strand regions designated C' and D' and three loop regions designated 5a, 5b and 5c, all according to FIG. 3. Thus, in a preferred embodiment, an IgNAR variable comprises 10 β-strand regions, designated A, A', B, C, C', D', D, E, F and G according to FIG. 3, and eleven loop regions, designated 1, 2, 3, 4, 5a, 5b, 5c, 6, 7, 8 and 9 according to FIG. 3. Preferably, the loop regions 5a, 5b and 5c, and β-strand regions C, C' and D' have the amino acid residue numbering according to Table 3A.

In a preferred embodiment, where an IgNAR variable domain is to be modified, prior to the modification, the $C_\alpha$ trace of loop region 5b extends no more than 5A above the plane formed by the $C_\alpha$ trace of residues 22, 83 and 36 as defined in Table 1.

In a preferred embodiment, the amino acid sequence of the unmodified β-strand regions A, A', B, C, D, E, F and G and loop regions 1, 2, 3, 6, 7 and 9 comprises an amino acid sequence according to FIG. 1 and/or Table 1.

In a preferred embodiment, the IgNAR is a Type 2 or Type 3 IgNAR, preferably Type 2. Preferably, the IgNAR is derived from a shark, preferably a wobbegong shark.

In a further preferred embodiment, the unmodified IgNAR variable domain has a sequence as shown in FIG. 1. More preferably, the unmodified IgNAR is 12Y-1, 12Y-2, 12A-9 or 1A-7.

Suitable modifications include substitutions, insertions and deletions within at least one at least one of the β-strand regions or loop regions. A combination of deletion, insertion and substitution can be made to generate the IgNAR modified variable domain.

Modifications can be prepared by introducing appropriate nucleotide changes into a nucleic acid of the present invention, or by in vitro synthesis of the desired polypeptide. Such mutants include, for example, deletions, insertions or substitutions of residues within the amino acid sequence.

In designing amino acid sequence mutants, the location of the mutation site and the nature of the mutation will depend on characteristic(s) to be modified. The sites for mutation can be modified individually or in series, for example by (1) substituting first with conservative amino acid choices and then with more radical selections depending upon the results achieved, (2) deleting the target residue, or (3) inserting other residues adjacent to the located site.

Encompassed within the scope of the invention are modifications which are tantamount to conservative substitutions but which alter a property of the IgNAR variable domain. Examples of conservative substitutions are given in as follows:

| Original Residue | Exemplary Substitutions |
|---|---|
| Ala (A) | val; leu; ile; gly |
| Arg (R) | lys |
| Asn (N) | gln; his; |
| Asp (D) | glu |
| Cys (C) | ser |
| Gln (Q) | asn; his |
| Glu (E) | asp |
| Gly (G) | pro, ala |
| His (H) | asn; gln |
| Ile (I) | leu; val; ala |
| Leu (L) | ile; val; met; ala; phe |
| Lys (K) | arg |
| Met (M) | leu; phe; |
| Phe (F) | leu; val; ala |
| Pro (P) | gly |
| Ser (S) | thr |
| Thr (T) | ser |
| Trp (W) | tyr |
| Tyr (Y) | trp; phe |
| Val (V) | ile; leu; met; phe, ala |

Furthermore, if desired, unnatural amino acids or chemical amino acid analogues can be introduced as a substitution or addition into the polypeptides of the present invention. Such amino acids include, but are not limited to, the D-isomers of the common amino acids, 2,4-diaminobutyric acid, α-amino isobutyric acid, 4-aminobutyric acid, 2-aminobutyric acid, 6-amino hexanoic acid, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogues in general.

Also included within the scope of the invention are chemically modified derivates of IgNAR variable domains which may provide advantages such as increasing stability and circulating time of the polypeptide, or decreasing immunogenicity (see U.S. Pat. No. 4,179,337). The chemical moieties for derivatization may be selected from water-soluble polymers such as polyethylene glycol, ethylene glycol/propylene glycol copolymers. carboxymethylcellulose, dextran, polyvinyl alcohol and the like.

Also included within the scope of the invention are variable domains of the present invention that are differentially modified during or after synthesis, for example, by biotinylation, benzylation, glycosylation, acetylation, phosphorylation, amidation, derivatization by known protecting/blocking groups, proteolytic cleavage, linkage to an antibody molecule or other cellular ligand, etc. The IgNAR variable domain may be modified at random positions within the molecule or at predetermined positions within the molecule and may include one, two, three or more attached chemical moieties. These modifications may, for example, serve to increase the stability and/or bioactivity of the modified domains of the invention.

The IgNAR variable domains may also be modified by having C- or N-terminal truncations. However, the scope for such modifications is limited and it is preferred that no more than 8, preferably no more than 6 and more preferably no more than 4 residues be removed. Preferably there is no truncation at the N-terminal and more preferably there is no truncation at either the N- or C-terminals.

Modified domains of the present invention can be produced in a variety of ways, including production and recovery of natural proteins, production and recovery of recombinant proteins, and chemical synthesis of the proteins. In one embodiment, an isolated polypeptide of the present invention is produced by culturing a cell capable of expressing the polypeptide under conditions effective to produce the polypeptide, and recovering the polypeptide.

In a preferred embodiment the modification comprises insertion of 1, 2, 3, 4, 5, 6, 7, 8, 9, 10, 11, 12, 13, 14, 15, 16, 17, 18, 19, 20 or more amino acids.

In another preferred embodiment the modification comprises deletion of 1, 2, 3, 4, 5, 6, 7, 8, 9, 10, 11, 12, 13, 14, 15, 16, 17, 18, 19, 20 or more amino acids.

In a further preferred embodiment, the modification involves more than mere substitution of a cysteine residue in one loop region, the cysteine residue being involved in disulphide formation with another cysteine residue in another loop region.

In a further preferred embodiment, the modification is not substitution of residue 43 as shown in Table 1 or involves more than mere substitution of the residue 43.

In another preferred embodiment, the modification is made to one or more amino acid residues within the patch defined by residues 33, 37, 46, 48, 50, 51, 59, 61, 86, 94, 95, 96, 98, 99 and 101 as shown in Table 1.

In a preferred embodiment, when loop region 4 or loop region 8 of the IgNAR is modified, at least one of the β-strand regions or loop regions 1-3, 5-7 or 9 is also modified.

In a further preferred embodiment, at least one of β-strand regions C, D, E or F or loop regions 5, 6 or 7 has been modified. In a further preferred embodiment, at least one of β-strand regions C or D or loop region 5 has been modified. In a further preferred embodiment, loop region 5 has been modified.

In one preferred embodiment, the modification involves point mutations within loop region 8. For example, residues Pro90 and/or Phe100 may be replaced in order to enhance flexibility of loop region 8.

In another embodiment of the invention, the modification involves randomisation of loop region 8.

In yet another embodiment, the modification involves insertion of amino acids into loop region 8.

In yet another embodiment the modification involves grafting a CDR loop or portion thereof from a V-set or an I-set domain onto the IgNAR variable domain. For example, the CDR3 loop of an antibody may be grafted onto the IgNAR variable domain in the vicinity of loop region 8. The grafting may involve, for example, replacing amino acids from loop region 8 (for example amino acids 86 to 103 as defined in Table 1 or a portion thereof) with amino acids that constitute an antibody CDR 3 loop or portion thereof. The modification may further involve replacing amino acids from loop region 4 (for example amino acids 28 to 33 as defined in Table 1 or a portion thereof) with amino acids that constitute an antibody CDR 1 loop or portion thereof.

In a further preferred embodiment, when the amino acid residues at the N-terminal and C-terminal ends of loop region 8 are each capable of adopting a β-strand configuration, loop region 8 is modified by substitution, deletion or addition, preferably by addition, of at least one amino acid within that part of the loop not capable of adopting the β-strand configuration.

In a further preferred embodiment from 2 to 10, preferably from the 3 to 8, amino acid residues at the N-terminal and C-terminal ends of loop region 8 are capable of adopting β-strand configurations.

In a further preferred embodiment, loop region 8 is modified by substitution, deletion or addition, preferably by addition or substitution, of one or more amino acid residues at the C- and/or N-terminal ends of the loop region to facilitate the adoption of β-strand configurations at the C- and/or N-terminal ends.

In a further preferred embodiment, loop region 8 is modified so as to facilitate the adoption of β-strand configurations at the C- and/or N-terminal ends of 2 to 10, preferably from 3 to 8, amino acid residues in length.

It will be appreciated by those skilled in the art that it is possible to predict whether or not any given sequence is capable of forming a β-strand configuration by in silico modelling. Many computer programs are available and are know to the skilled person (see, for example, Wolfson et al. 2005 and Xu et al. 2000). Examples of suitable programs can also be found on the secondary structure prediction server at world wide web.predictprotein.org.

In one embodiment, the modification increases or decreases the binding characteristics, e.g. the affinity, of the modified IgNAR variable domain for a predetermined target molecule compared to the unmodified IgNAR variable domain.

That part of the IgNAR variable domain which normally contacts a ligand (e.g. an antigen) or which appear, from the studies we have undertaken, to be available for interacting with a ligand (e.g. a receptor, enzyme etc.) are typically the solvent exposed regions of the IgNAR variable domain. In particular, they are generally made up of the surface exposed loops, and in particular loop regions 8 and 4 of the IgNAR variable domain.

Preferably, the unmodified IgNAR variable domain has had one or more loop regions modified. In particular, this can be achieved by replacing one or more solvent exposed loops of the IgNAR variable domain with one or more loops from the variable domains of other members of the IgSF. Preferably, loop regions 4 and/or 8, or part thereof, is modified, preferably replaced, by a corresponding loop structure (e.g. a CDR1 or CDR3 loop structure, respectively) from another molecule.

Modifications can also be made to regions of the IgNAR variable domain that are not solvent exposed and/or which do not form part of a binding loop, e.g. the β strand regions.

In another preferred embodiment, the modification increases or decreases the propensity for the IgNAR variable domain to form homodimers compared to the unmodified IgNAR variable domains.

In another preferred embodiment, the modification increases the solubility of the IgNAR variable domain compared to the unmodified IgNAR variable domain.

In a preferred embodiment, one or more solvent exposed loops is/are modified to improve solubility. Solubility may be improved by, for example, either removing disulphide bond-forming cysteines and/or replacing disulphide bond-forming cysteines from within the solvent exposed loops with amino acids such as alanine or serine.

Modifications to improve solubility may be desirable where the IgNAR variable domains are being designed to function in an intracellular context and/or their method of production favours expression in a soluble form. It will also be evident to the skilled person that it may be necessary to modify the solubility characteristics of the IgNAR variable domains at the same time or even prior to making other modifications, such as, changing the binding characteristics.

The physicochemical properties, such as stability and solubility, of the IgNAR variable domains may be qualitatively and/or quantitatively determined using a wide range of methods known in the art. Methods which may find use in the present invention for characterizing the biophysical/physicochemical properties of the binding moieties include gel electrophoresis, chromatography such as size exclusion chromatography, reversed-phase high performance liquid chromatography, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use.

Protein stability (e.g. structural integrity) may, for example, be determined by measuring the thermodynamic equilibrium between folded and unfolded states.

In one embodiment, stability and/or solubility may be measured by determining the amount of soluble protein after some defined period of time. In such an assay, the protein may or may not be exposed to some extreme condition, for example elevated temperature, low pH, or the presence of denaturant. Because unfolded and aggregated protein is not expected to maintain its function, e.g. be capable of binding to a predetermined target molecule, the amount of activity remaining provides a measure of the binding moieties stability and solubility. Thus, one method of assessing solubility and/or stability is to assay a solution comprising a binding moiety for its ability to bind a target molecule, then expose the solution to elevated temperature for one or more defined periods of time, then assay for antigen binding again.

Alternatively, the modified IgNAR binding domains could be expressed in prokaryotic expression systems and the protein isolated from the cell lysate by a series of biochemical purification steps including differential centrifugation, affinity isolation chromatography using attached tags such as poly histidine, ion-exchange chromatography and gel filtration chromatography. A measure of the improvement in the solubility of the modified polypeptide can be obtained by making a comparison of the amount of soluble protein obtained at the end of the purification procedure to that obtained using the unmodified polypeptide, when starting with a similar amount of expressed unfractionated product. Levels of expression of product in culture can be normalized by a comparison of product band densities after polyacrylamide gel electrophoresis of equivalent aliquots of SDS detergent-solubilised cell lysate.

In addition, IgNAR variable domains can be unfolded using chemical denaturant, heat, or pH, and this transition be monitored using methods including, but not limited to, circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques.

The solubility of the IgNAR variable domains of the present invention preferably correlates with the production of correctly folded, monomeric polypeptide. The solubility of the modified IgNAR variable domains may therefore also be assessed by HPLC or FPLC. For example, soluble (non-aggregated) domains will give rise to a single peak on a HPLC or FPLC chromatograph, whereas insoluble (aggregated) domains will give rise to a plurality of peaks. Furthermore, the ability to be able to correctly fold and form ordered crystal leads and structures is also often indicative of good solubility.

As an example of an accelerated stability trial, aliquots of the IgNAR variable domain can be stored at different temperatures, such as −20° C., 4° C., 20° C. and 37° C. and an activity of the IgNAR variable domain assayed at different time intervals. For example, successful maintenance of activity during storage at 37° C. for 12 weeks is roughly equivalent to storage stability for 12 months at 4° C. The trial can also be conducted to compare the effect of different protecting additives in the storage buffer on the stability of the protein. Such additives can include compounds such as glycerol, sorbitol, non-specific protein such as bovine serum albumin, or other protectants that might be used to increase the shelf life of the protein.

Modifications of Members of the IgSF Based on the IgNAR Variable Domain

The results presented herein also identify structural features in IgNAR variable domains that are important for antigen binding or solubility/stability of these domains. These features can be introduced into domains of other members of the IgSF (for example, I-set or V-set domains) in order to alter binding properties or to improve solubility and/or stability.

Accordingly, in a further aspect the present invention provides a method of modifying an I- or V-set domain, said method comprising inserting and/or substituting one or more structural features from an IgNAR variable domain into the I- or V-set domain.

In a further aspect, the present invention provides a binding moiety comprising an I- or V-set domain, wherein the I- or V-set domain has been modified by substitution or insertion of one or more structural features from an IgNAR variable domain into the I- or V-set domain.

By "I-set domain" is meant a domain comprising nine β-strand regions, designated A, A', B, C, C', D, E, F and G, as set out and according to Chothia (1997).

Examples of representative I-set domain molecules include NCAM, VCAM, ICAM, Telokin, MADCAM-1, Twitchin and Titin.

By "V-set domain" is meant a domain comprising ten β-strand regions, designated A, A', B, C, C', C", D, E, F and G, as, as set out and according to Chothia (1997).

Examples of representative V-set domain molecules include antibodies, T cell receptors (TCRs), CTLA-4, CD28, ICOS, CD2, CD4, Cd7, CD22, CD33, CD80, CD86, CD48 and CD58.

Preferably, the I-set or V-set domain is modified such that a property of the domain is altered.

In one embodiment, the structural feature is a loop region from an IgNAR variable domain. For example, loop region 8 and/or loop region 4 from an IgNAR variable domain may be grafted onto the I- or V-set domain. The grafting may involve, for example, replacing suitable (e.g. predetermined) amino acids of the I- or V-set domain with amino acids 86 to 103 as defined in Table 1 or a portion thereof.

In another embodiment, the method comprises removing all or a portion of the CDR2 loop of the I- or V-set domain.

In another embodiment the structural feature is the solvent exposed face of an IgNAR variable domain at the C-terminus of loop region 4 and in the C and D β-strands (for example comprising residues 32, 33, 34, 35, 55, 57 and 58 as defined in Table 1). The method may involve modifying amino acids of the I- or V-set domain equivalent to amino acids 32, 33, 34, 35, 55, 57 and 58 as defined in Table 1 or a portion thereof. The method may involve grafting the solvent exposed face of an IgNAR variable domain (for example comprising residues 32, 33, 34, 35, 55, 57 and 58 as defined in Table 1) or a portion thereof onto the I- or V-set domain. Grafting may involve replacing amino acids of the I- or V-set domain with amino acids derived from the solvent exposed face of an IgNAR variable domain. Grafting of the solvent exposed face onto the I- or V-set domain preferably occurs after removal of all or a portion of the CDR2 loop. Preferably, the modification introduces charged or polar amino acids at these positions. Preferably, this modification improves the solubility of the I- or V-set domain.

In one preferred embodiment, the V-set domain is a TCRVα or Vβ domain and the equivalent amino acids to the solvent exposed surface of am IgNAR variable domain are Gly30, Ser31, Phe32, Phe33, Phe62, Thr63, Ala64 and Gln65. Preferably, the modification involves the introduction of polar or charged amino acids in these positions.

In another embodiment, the method involves modifying one or more residues of a TCR Vα or Vβ domain, wherein the one or more residues is located at the interface between the Vα and Vβ domains. In a preferred embodiment, the one or more amino acid residue is selected from the group consisting of Ser31, Pro43, Leu89 and Phe106 and combinations thereof. Preferably, the modification involves the introduction of one or more charged amino acids in these positions.

In another embodiment, the method involves modifying one or more residues of an antibody $V_H$ or $V_L$ domain, wherein the one or more residues is located at the interface between the $V_H$ and $V_L$ domains. In a preferred embodiment, the one or more amino acid residue is equivalent to an amino acid of the TCR Vα or Vβ domain selected from the group consisting of Ser31, Pro43, Leu89 and Phe106 and combinations thereof. Preferably, the modification involves the introduction of one or more charged amino acids in these positions.

In a preferred embodiment the modification improves the solubility of the I- or V-set domain.

In a further aspect, the present invention provides a method of modifying an I- or V-set domain, said method comprising introducing a modification into a region of the I- or V-set domain equivalent to loop region 4 and/or loop region 8 of an IgNAR variable domain as defined by FIG. 2.

In another aspect, the present invention provides a modified V-set domain produced by a method of the present invention.

Multimers

The present invention also provides a binding moiety comprising a multimer comprising:

(i) at least two IgNAR domains, which may be the same or different, and at least one of which is a IgNAR variable domain;

(ii) at least two I-set domains, which may be the same or different, and at least one of which is a I-set domain according to the present invention; or (iii) at least two V-set domains, which may be the same or different, and at least one of which is a V-set domain according to the present invention.

The two domains may be derived from the same or different sources.

The following description is directed to IgNAR domain multimers. It will, however, be apparent to the skilled person that many of the embodiments described with respect to IgNAR domain multimers can equally be applied to I-set and V-set domain multimers. Furthermore, it will be apparent to the skilled person that the various embodiments of the invention described herein in relation to IgNAR variable domains, I-set domains and V-set domains equally apply to IgNAR variable domains, I-set domains and V-set domains, respectively, present in the multimer embodiments of the invention.

Preferably, the multimer comprises two IgNAR variable domains.

In a preferred embodiment, the one or the at least two of the IgNAR domains is/are variable IgNAR domains(s) comprising eight β-strand regions, designated A, A', B, C, D, E, F and G according to FIG. 2, and nine loop regions, designated 1 to 9 according to FIG. 2.

In a preferred embodiment, at least one IgNAR variable domains is modified by substitution, deletion or addition of at least one amino acid within in at least one of the β-strand or loop regions as described hereinabove.

Where the multimer comprises at least two IgNAR variable domains, the two domains preferably form stable homodimers, preferably at least partially through salt bridges. Thus, a preferred modification is one in which at least one of the IgNAR variable domains has been modified such that the propensity to form a stable homodimer is increased. In a further preferred embodiment, the least one IgNAR variable domain has been modified so as to increase the dissociation constant of the homodimer formed compared to the homodimer formed by the unmodified IgNAR variable domain.

Preferably both IgNAR variable domains have been modified such that the propensity to form a stable homodimer is increased. Preferably, this is achieved by replacing the following residues of one or both of the unmodified monomers (as defined in Table 1) with cysteine residues: residues 57 and/or 61; residues 51 and either 61 or 62; residues 32 and/or 33; residue 99; or residue 59.

We have now cloned the full wobbegong shark (*Orectolobus maculatus*) IgNAR coding sequence (see FIG. 33). The coding sequence encodes a single polypeptide chain encompassing one IgNAR I-set domain and 5 C-domains. In the mature IgNAR antibody, these chains form a dimer mediated by half-cystine residues at positions Cys430 and Cys660. The resulting two disulphide bridges are located (1) C-terminal to constant domain 3 and N-terminal to constant domain 4 and (2) C-terminal to constant domain 5.

Thus in a further embodiment, the multimer comprises at least one IgNAR variable domain and at least one IgNAR constant domain. Preferably the constant domain is the C1 constant domain of an IgNAR, i.e. the constant domain closest to the IgNAR variable domain in nature. We have found that connecting an IgNAR variable domain to an IgNAR constant domain has no effect on the level of binding affinity (see Example 16). This means it is possible to add mass to the binding moieties without facilitating multimerisation or loss of binding affinity. Therefore, such multimer constructs have potential as commercial biosensor reagents.

Multimers are one preferred design for therapeutic reagents since they have the potential to provide increased avidity and slower blood clearance rates which may provide favorable pharmacokinetic and biodistribution properties. The IgNAR domains may be connected either through covalent linkage or non-covalent linkage or a combination of linkages, including the use of chemical or genetically-encoded linkers. Linkers used to link protein domains are well-known and well understood in the art, in particular in relation to proteins in the immunoglobulin superfamilies (e.g. Casey J L et al., 2002 Br J. Cancer., 86(9):1401-10; Plutckthun, A., and Pack, P 1997. Immunotechnology, 3, 83-105). Therefore, the skilled person will appreciate that any suitable hinge or means of connection may be used to connect the two at least IgNAR domains. Examples of suitable chemical linkage include linking the two domains using a suitable cross-linker such as dimaleimide. Alternatively, the two domains may be linked by providing cysteine residues at the respective C- and N-terminals and forming a disulphide bond. In addition, they could be linked using single chain GlySer linkers such as GlyGlyGlyGlySer (SEQ ID NO: 114). The domains may also be linked genetically using techniques well-know in the art.

The resulting multimers from any of these linker strategies described may possess the same, or different target specificities thus providing multivalent or multispecific reagents. In a preferred embodiment, two IgNAR variable domains may be joined to form a heterodimer through either covalent linkage or non-covalent linkage or a combination of linkages thereby providing two target binding affinities. If two or more IgNAR variable domains in the multimer have the same target specificity, the multimer will be multivalent and have increased avidity (functional affinity) for binding to two or more target molecules.

In the case of multimers, it will be appreciated by the skilled person that the IgNAR domains must be suitably orientated with respect to each other. The first IgNAR domain should be suitably hinged or connected to the second IgNAR domain. Where the multimer comprises an IgNAR variable domain and an IgNAR constant domain, the domains are preferably orientated with respect to each other as they would be in the respective native protein(s) from which they are derived.

Binding Moieties

With regards to binding moieties of the present invention comprising IgNAR variable domains, such binding moieties comprise an IgNAR variable domain which has been modified such that at least one property of the IgNAR variable domain is altered. It will be understood that such binding moieties do not encompass and do not relate to the full-length, wild-type proteins from which suitable IgNAR variable domains may be derived. Rather, they encompass and relate to portions of IgNARs comprising the variable domain, which have been removed or isolated from their natural environments.

In a preferred embodiment, the IgNAR variable domain of the binding moiety accounts for at least 25%, preferably at least 40%, more preferably at least 50%, yet more preferably at least 70%, even more preferably at least 80%, yet more preferably at least 90% and most preferably at least 95% by weight of the total molecular weight of and/or number of amino acid residues in the binding moiety. In a particularly preferred embodiment, the binding moiety consists essentially of the CBD.

Preferably, the only binding domains present in the binding moieties of the present invention are the modified IgNAR variable domain, the I-set domain or the V-set domain.

The binding moieties of the invention may be in a substantially isolated form. It will be understood that the protein may be mixed with carriers or diluents which will not interfere with the intended purpose of the protein and still be regarded as substantially isolated. Binding moieties of the invention may also be in a substantially purified form, in which case they will generally comprise the protein in a preparation in which more than 90%, e.g. 95%, 98% or 99% of the protein in the preparation is a binding moiety of the invention.

The binding moieties of the invention may also be linked to other molecules, for example by covalent or non-covalent means. In preferred embodiments, the binding moieties of the invention may be linked (without restriction) to molecules such as enzymes, drugs, lipids, sugars, nucleic acids and viruses.

In one aspect, the present invention provides a binding moiety of the present invention linked to a diagnostic reagent.

In a preferred embodiment of this aspect, the diagnostic reagent is selected from the group consisting of streptavidin, biotin, a radioisotope, dye marker, other imaging reagent and combinations thereof.

In another aspect, the present invention provides a binding moiety of the present invention immobilised on a solid support or coupled to a biosensor surface.

In one embodiment, the binding moiety may contain solvent exposed cysteine residues for the site-specific attachment of other entities.

Binding moieties of the invention can be linked to other molecules, typically by covalent or non-covalent means. For example, binding moieties may be produced as fusion proteins, linked to other polypeptide sequences. Fusion partners can include enzymes, detectable labels and/or affinity tags for numerous diagnostic applications or to aid in purification. Fusion partners, without restriction, may be GFP (green fluorescent protein), GST (glutathione S-transferase), thioredoxin or hexahistidine. Other fusion partners include targeting sequences that direct binding moieties to particular subcellular locations or direct binding moieties to extracellular locations e.g. secretion signals. In a preferred embodiment, binding moieties of the invention do not comprise other regions of the protein from which they are derived i.e. any fusion partners are heterologous to the IgNAR or protein from which I-set or V-set domains are derived. The heterologous sequence may be any sequence which allows the resulting fusion protein to retain the activity of the modified IgNAR variable domain, modified I-set domain or modified V-set domain. The heterologous sequences include for example, immunoglobulin fusions, such as Fc fusions, or fusions to other cellular ligands which may increase stability or aid in purification of the protein.

Diagnostic or therapeutic agents that can be linked to the binding moieties of the invention include pharmacologically active substances such as toxins or prodrugs, immunomodulatory agents, nucleic acids, such as inhibitory nucleic acids or nucleic acids encoding polypeptides, molecules that enhance the in vivo stability or lipophilic behaviour of the binding moieties such as PEG, and detectable labels such as radioactive compounds, dyes, chromophores, fluorophores or other imaging reagents.

Binding moieties may also be immobilised to a solid phase, such as a substantially planar surface (e.g. a chip or a microtitre plate) or beads. Techniques for immobilising polypeptides to a solid phase are known in the art. In addition, where libraries of binding moieties are used (e.g. in screening methods), arrays of binding moieties immobilised to a solid phase can be produced (Lee Y S and Mrksich, M, 2002 Trends Biotechnol. 20(12 Suppl):S14-8. and references contained therein).

In another embodiment of the invention, the binding moieties of the invention function as a protein scaffold with other polypeptide sequences being inserted into solvent-exposed regions of the binding moiety for display on the surface of the scaffold. Such scaffolds may, for example, serve as a convenient means to present peptides in a conformationally constrained manner. The scaffolds may be used to produce IgNAR variable domains, I-set domains or V-set domains with altered binding specificities and also to produce and/or screen for binding moieties having specificity for any target molecule of interest.

Heterologous polypeptide sequences may be inserted into one or more solvent exposed regions such as, for example, one or more loops of the IgNAR variable domains, I-set domains or V-set domains. The IgNAR variable domain, I-set domain or V-set domain of the binding moiety functions as a protein scaffold for the inserted heterologous sequences, displaying the heterologous sequences on the surface of the binding moiety.

The heterologous sequences may replace all or part of the loop of the IgNAR variable domain, I-set domain or V-set domain into which they are inserted, or may simply form additional sequence. Preferably, a plurality of heterologous sequences are inserted into a plurality of loops.

The heterologous sequences may be derived from solvent exposed regions such as, for example, loops of another IgNAR variable domain, I-set domains or V-set domains. They may also be derived from other molecules or be partially of fully randomised.

Polynucleotides Vectors and Hosts

The present invention provides a polynucleotide encoding a IgNAR variable domain or multimeric reagent according to the present invention.

The present invention also provides a vector comprising a polynucleotide of the present invention.

The present invention further provides a host cell comprising the vector of the invention.

The present invention also provides a method of producing a binding moiety according to the present invention which comprises culturing a host cell of the present invention under conditions enabling expression of the binding moiety and optionally recovering the IgNAR variable domain. In a preferred embodiment of this aspect the IgNAR variable domain or multimeric reagent is unglycosylated.

Polynucleotides of the invention may comprise DNA or RNA. They may be single-stranded or double-stranded. They may also be polynucleotides which include within them synthetic or modified nucleotides. A number of different types of modifications to oligonucleotides are known in the art. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or life span of polynucleotides of the invention.

Polynucleotides of the invention can be incorporated into a recombinant replicable vector. The vector may be used to replicate the nucleic acid in a compatible host cell.

Preferably, a polynucleotide of the invention in a vector is operably linked to a control sequence that is capable of providing for the expression of the coding sequence by a host cell or using an in vitro transcription/translation system, i.e. the vector is an expression vector. The term "operably linked" means that the components described are in a relationship permitting them to function in their intended manner. A regulatory sequence "operably linked" to a coding sequence is ligated in such a way that expression of the coding sequence is achieved under condition compatible with the control sequences.

The control sequences may be modified, for example by the addition of further transcriptional regulatory elements to make the level of transcription directed by the control sequences more responsive to transcriptional modulators.

Vectors of the invention may be transformed or transfected into a suitable host cell to provide for expression of a binding moiety according to the invention. This process may comprise culturing a host cell transformed with an expression vector under conditions to provide for expression by the vector of a coding sequence encoding the binding moiety, and optionally recovering the expressed binding moiety.

The vectors may be, for example, plasmid, phagemid or virus vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used, for example, to transfect or transform a host cell.

Control sequences operably linked to sequences encoding the protein of the invention include promoters/enhancers and other expression regulation signals. These control sequences may be selected to be compatible with the host cell for which the expression vector is designed to be used in. The term "promoter" is well-known in the art and encompasses nucleic acid regions ranging in size and complexity from minimal promoters to promoters including upstream elements and enhancers.

The promoter is typically selected from promoters which are functional in prokaryotic or eukaryotic cells. With respect to eukaryotic promoters, they may be promoters that function in a ubiquitous manner or, alternatively, a tissue-specific manner. They may also be promoters that respond to specific stimuli. Viral promoters may also be used, for example the Moloney murine leukaemia virus long terminal repeat (MMLV LTR) promoter, the rous sarcoma virus (RSV) LTR promoter or the human cytomegalovirus (CMV) IE promoter.

It may also be advantageous for the promoters to be inducible so that the levels of expression of the binding moiety can be regulated during the life-time of the cell. Inducible means that the levels of expression obtained using the promoter can be regulated.

In a number of embodiments of the present invention, heterologous sequences are inserted into the various domains (including IgNAR variable domains, I-set domains and V-set domains) of the present invention. Such modifications are generally made by manipulating polynucleotides of the invention encoding the respective domain. This may conveniently be achieved by providing cloning vectors that comprise a sequence encoding a domain which sequence comprises one or more unique insertion sites to allow for easy insertion of nucleotide sequences encoding heterologous sequences into the appropriate region of the domain.

Each "unique" insertion site typically contains a nucleotide sequence that is recognised and cleaved by a type II restriction endonuclease, the nucleotide sequence not being present elsewhere in the cloning vector such that the cloning vector is cleaved by the restriction endonuclease only at the "unique" insertion site. This allows for easy insertion of nucleotide sequences having the appropriate ends by ligation with cut vector using standard techniques well know by persons skilled in the art. Preferably the insertion site is engineered— i.e. where the domain is derived from a naturally occurring sequence, the insertion site does not naturally occur in the natural sequence.

Vectors and polynucleotides of the invention may be introduced into host cells for the purpose of replicating the vectors/polynucleotides and/or expressing the binding moiety according to the invention encoded by the polynucleotides. Any suitable host cell may be used, including prokaryotic host cells (such as *Escherichia coli, Streptomyces* spp. and *Bacillus subtilis*) and eukaryotic host cells. Suitable eukaryotic host cells include insect cells (e.g. using the baculovirus expression system), mammalian cells, fungal (e.g. yeast) cells and plant cells. Preferred mammalian cells are animal cells such as CHO, COS, C 127, 3T3, HeLa, HEK 293, NIH 3T3, BHK and Bowes melanoma (particularly preferred being CHO-K1, COS7, Y1 adrenal and carcinoma cells).

Vectors/polynucleotides of the invention may introduced into suitable host cells using any of a large number of techniques known in the art such as, for example, transfection (for example calcium phosphate transfection or DEAE-Dextran mediated transfection), transformation and electroporation. Where vectors/polynucleotides of the invention are to be administered to animals, several techniques are known in the art, for example infection with recombinant viral vectors such as retroviruses, herpes simplex viruses and adenoviruses, direct injection of nucleic acids and biolistic transformation.

Host cells comprising polynucleotides of the invention may be used to express proteins of the invention. Host cells are cultured under suitable conditions which allow for expression of the binding moieties according to the invention. Expression of the binding moieties may be constitutive such that they are continually produced, or inducible, requiring a stimulus to initiate expression. In the case of inducible expression, protein production can be initiated when required by, for example, addition of an inducer substance to the culture medium, for example dexamethasone or IPTG, or inducible expression may achieved through heat-induction, thereby denaturing the repressor and initiating protein synthesis.

Binding moieties according to the invention can be extracted from host cells by a variety of techniques known in the art, including enzymatic, chemical and/or osmotic lysis and physical disruption.

Cell-free translation systems can also be used to produce the peptides of the invention. Appropriate cloning and expression vectors for use with prokaryotic and eukaryotic hosts are described in Sambrook (1989).

Libraries of Binding Moieties

Binding moieties according to the invention may be provided as libraries comprising a plurality of binding moieties which have different sequences in the IgNAR variable domains, I-set domains or V-set domains. Preferably, the variations reside in one or more loops. These libraries can typically be used in screening methods to identify a binding reagent with an activity of interest, such as affinity for a specific target molecule of interest.

Libraries of binding moieties are conveniently provided as libraries of polynucleotides encoding the binding moieties. The polynucleotides are generally mutagenized or randomised to produce a large number of different sequences which differ at one or more positions within at least one β strand or loop region.

Mutations can be introduced using a variety of techniques known in the art, such as site-directed mutagenesis. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.). Academic Press, New York, 1990). Another technique is to use the commercially available "Altered Sites II in vitro Mutagenesis System" (Promega— U.S. Pat. No. 5,955,363). Techniques for site-directed mutagenesis are described above. Pluralities of randomly mutated sequences can be made by introducing mutations into a nucleotide sequence or pool of nucleotide sequences 'randomly' by a variety of techniques in vivo, including; using 'mutator strains', of bacteria such as *E. coli* mutD5 (Low et al., 1996, J Mol Biol 60: 9-68); and using the antibody hypermutation system of B-lymphocytes (Yelamos et al., 1995, Nature 376: 225-9). Random mutations can also be introduced both in vivo and in vitro by chemical mutagens, and ionising or UV irradiation (Friedberg et al., 1995, DNA repair and mutagenesis. SM Press, Washington D.C.), or incorporation of mutagenic base analogues (Zaccolo et al., 1996 J Mol Biol 255: 589-603). 'Random' mutations can also be introduced into genes in vitro during polymerisation for example by using error-prone polymerases (Leung et al., 1989, Technique 1: 11-15).

It is generally preferred to use mutagenesis techniques that vary the sequences present in the loop regions of the IgNAR variable domains, although framework changes (e.g. changes in the β stands) may also occur which may or may not be desirable. One method for targeting the loop regions is to provide a plurality of relatively short nucleotide sequences that are partially or fully mutagenized/randomised and clone these sequences into specific insertion sites in the IgNAR variable domains.

Another approach is to synthesise a plurality of random synthetic oligonucleotides and then insert the oligonucleotides into a sequence encoding the IgNAR variable domain, I-set domain or V-set domain and/or replace a sequence encoding the IgNAR variable domains, I-set domain or V-set domain with the random synthetic oligonucleotides. A suitable method is described in WO 97/27213 where degenerate oligonucleotides are produced by adding more than one nucleotide precursor to the reaction at each step. The advantage of this method is that there is complete control over the extent to which each nucleotide position is held constant or randomised. Furthermore, if only C, G or T are allowed at the third base of each codon, the likelihood of producing premature stop codons is significantly reduced since two of the three stop codons have an A at this position (TAA and TGA).

Oligonucleotide synthesis is performed using techniques that are well known in the art (see Eckstein, Oligonucleotides and Analogues: A Practical Approach, IRL Press at Oxford University Press 1991). Libraries can also be specified and purchased commercially. The synthetic process can be performed to allow the generation of all or most possible combinations over the length of the nucleic acid, thus generating a library of randomised nucleic acids. These randomised sequences are synthesised such that they allow in frame expression of the randomised peptide with any fusion partner.

In one embodiment, the library is fully randomised, with no sequence preferences or constants at any position. In another embodiment, the library is biased, i.e. partially randomised in which some positions within the sequence are either held constant, or are selected from a limited number of possible variations. Thus some nucleic acid or amino acid positions are kept constant with a view to maintaining certain structural or chemical characteristics.

The randomised oligonucleotides can then be inserted into a suitable site and/or replace a suitable sequence encoding a IgNAR variable domains, I-set domain or V-set domain.

Generally the library of sequences will be large enough such that a structurally diverse population of random sequences is presented. This ensures that a large subset of shapes and structures is represented and maximises the probability of a functional interaction.

It is preferred that the library comprises at least 1000 different nucleotide sequences, more preferably at least $10^4$, $10^5$ or $10^6$ different sequences. Preferably, the library comprises from $10^4$ to $10^{10}$ different sequences. Preferably at least 5, 10, 15 or 20 amino acid residues of the peptides encoded by the nucleotide sequences are randomised.

Typically, the inserted peptides encoded by the randomised nucleotide sequences comprise at least 5, 8, 10 or 20 amino acids. Preferably, they also comprise fewer than 50, 30 or 25 amino acids.

In another aspect, the present invention provides a method of selecting a binding moiety of the present invention with an affinity for a target molecule which comprises screening a library of polynucleotides of the present invention for expression of a binding moiety with an affinity for the target molecule.

The libraries of polynucleotides encoding binding moieties can be screened using any suitable technique to identify a binding moiety having an activity of interest. For example, to identify a binding moiety that binds to a target molecule of interest, the library of polynucleotides is incubated under conditions that allow for expression of the binding moiety polypeptides encoded by the polynucleotides and binding of the polypeptides to the target molecule assessed. Binding is typically assessed in vitro or using whole cell assays.

Suitable techniques for screening the library for binding moieties having an activity of interest include phage display and ribosome display as well as the use of viral vectors, such as retroviral vectors and in vivo compartmentalisation screening by protein bioarray.

In a preferred embodiment this method involves displaying the IgNAR variable domain or multimeric reagent of the present invention as gene III protein fusions on the surface of bacteriophage particles.

In another preferred embodiment the method involves displaying the IgNAR variable domain or multimeric reagent of the present invention in a ribosomal display selection system.

The sequence of binding moieties identified in the screen can conveniently be determined using standard DNA sequencing techniques.

Diagnostic/Therapeutic Uses of Binding Moieties

Binding moieties of the invention, including those identified in the screening methods of the invention, may be used in methods of diagnosis/therapy by virtue of their specific binding to a target molecule of interest. Such uses will be analogous to the plethora of diagnostic/therapeutic applications already known in relation to antibodies and fragments thereof. For example, binding moieties of the invention may be used to detect the presence or absence of molecules of interest in a biological sample.

For diagnostic purposes, it may be convenient to immobilise the binding reagent to a solid phase, such as a dipstick, microtitre plate or chip.

As discussed above, binding moieties of the invention when used diagnostically will typically be linked to a diagnostic reagent such as a detectable label to allow easy detection of binding events in vitro or in vivo. Suitable labels include radioisotopes, dye markers or other imaging reagents for in vivo detection and/or localisation of target molecules.

Binding moieties may also be used therapeutically. For example, binding moieties may be used to target ligands that bind to extracellular receptors.

In addition, binding moieties of the invention may be used, in a similar manner to antibodies, to target pharmacologically active substances to a cell of interest, such as a tumour cell, by virtue of binding to a cell surface molecule present specifically on the tumour cell to which the binding moiety binds specifically.

Administration

In another aspect the present invention provides a pharmaceutical composition comprising an IgNAR variable domain or multimeric reagent according to the present invention and a pharmaceutically acceptable carrier or diluent.

In another aspect the present invention provides a method of treating a pathological condition in a subject, which method comprises administering to the subject a pharmaceutical composition according to the present invention.

Binding moieties of the invention including binding moieties identified by the screening methods of the invention may preferably be combined with various components to produce compositions of the invention. Preferably the compositions are combined with a pharmaceutically acceptable carrier, adjuvant or diluent to produce a pharmaceutical composition (which may be for human or animal use). Suitable carriers and diluents include isotonic saline solutions, for example phosphate-buffered saline. The composition of the invention may be administered by direct injection. The composition may be formulated for parenteral, intramuscular, intravenous, subcutaneous, intraocular, oral or transdermal administration. Typically, each protein may be administered at a dose of from 0.01 to 30 mg/kg body weight, preferably from 0.1 to 10 mg/kg, more preferably from 0.1 to 1 mg/kg body weight.

Polynucleotides/vectors encoding binding moieties may be administered directly as a naked nucleic acid construct. When the polynucleotides/vectors are administered as a naked nucleic acid, the amount of nucleic acid administered may typically be in the range of from 1 µg to 10 mg, preferably from 100 µg to 1 mg.

Uptake of naked nucleic acid constructs by mammalian cells is enhanced by several known transfection techniques for example those including the use of transfection agents. Example of these agents include cationic agents (for example calcium phosphate and DEAE-dextran) and lipofectants (for example Lipofectam™ and Transfectam™). Typically, nucleic acid constructs are mixed with the transfection agent to produce a composition.

Preferably the polynucleotide or vector of the invention is combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, oral, intraocular or transdermal administration.

The routes of administration and dosages described are intended only as a guide since a skilled practitioner will be able to determine readily the optimum route of administration and dosage for any particular patient and condition.

The various features and embodiments of the present invention, referred to in individual sections above apply, as appropriate, to other sections, mutatis mutandis. Consequently features specified in one section may be combined with features specified in other sections, as appropriate.

The present invention will now be further described in the following non-limiting Examples.

EXAMPLES

Example 1

Expression of $V_{NAR}$ 12Y-1 and 12Y-2 Proteins

Recombinant proteins 12Y-1 (SEQ ID NOs: 1 & 2) and 12Y-2 (SEQ ID NOs: 3 & 4) were expressed into the *E. coli* periplasm in frame with 21 residue C-terminal dual octapeptide FLAG epitopes and linker regions ($^N$-AAADYKDDDD-KAADYKDDDDK$^C$; SEQ ID NO: 115) as described (Nuttall 2004). Briefly, *E. coli* TG1 starter cultures were grown overnight in 2YT medium/ampicillin (100 µg/mL)/glucose (2.0% w/v.), diluted 1/100 into fresh 2YT/100 µg/mL ampicillin/glucose (0.1% w/v) and then grown at 37° C./200 rpm until $OD_{550}$ nm=0.2-0.4. Cultures were then induced with IPTG (1 mM final), grown for a further 16 hours at 28° C. and harvested by centrifugation (Beckman JA-14/6K/10 min/4° C.). Periplasmic fractions were isolated by the method of Minsky (Minsky 1994) and recombinant protein purified by affinity chromatography through an anti-FLAG antibody-Sepharose column (10×1 cm). The affinity column was equilibrated in TBS, pH 7.4 and bound protein eluted with ImmunoPure™ gentle elution buffer (Pierce). Eluted proteins were dialysed against two changes of 0.02M Tris pH7.5, concentrated by ultrafiltration over a 3000 Da cutoff membrane (YM3, Diaflo), and analysed for purity and activity by size exclusion chromatography, SDS-polyacrylamide gel electrophoresis, and biosensor.

Example 1a

Expression of $V_{NAR}$ 1A-7 and 12A-9 Proteins

Recombinant proteins 1A-7 (SEQ ID NOs: 5 & 6) and 12A-9 (SEQ ID NOs: 9 & 10) were expressed into the *E. coli* periplasm, purified and analysed exactly as described in Example 1 above.

Example 2

Crystallization of $V_{NAR}$ 12Y-1 and 12Y-2 Proteins

Recombinant protein 12Y-2 (14 mg/ml) was set up in 2 µl hanging drops using the Hampton Research sparse matrix crystallization screening kit. Plates were incubated at 25° C. Final crystallization conditions were 0.1M Sodium citrate pH4.6/20% v/v iso-Propanol/20% PEG4000. Diffraction quality crystals were obtained after 48 h.

Recombinant protein 12Y-1 (6 mg/ml) was set up as 0.2 µl sitting drops using a Cartesian Honey Bee robot. Plates were incubated at 25° C. Successful conditions were scaled up to 2 µl hanging drops, using 12Y-1 protein at 13 mg/ml. Final crystallization conditions were 0.1M bis-tris Propane pH6.5/45% PPG P400. Diffraction quality crystals were obtained after 7 days.

Example 2a

Crystallization of $V_{NAR}$ 12A-9 and 1A-7 Proteins

Recombinant protein 12A-9 (7 mg/ml) was set up as 0.2 µl sitting drops using a Cartesian Honey Bee robot. Plates were incubated at 25° C. Successful conditions were scaled up to 2 µl hanging drops. Final crystallization conditions were 0.1M CHES pH 9.5/50% PEG200. Diffraction quality crystals (space group $P2_12_12_1$) were obtained after 40 days.

Recombinant protein 1A-7 (6 mg/ml) was set up as 0.2 µl sitting drops using a Cartesian Honey Bee robot. Plates were incubated at 25° C. Successful conditions were scaled up to 2 µl hanging drops. Final crystallization conditions were 0.1M acetate pH 4.6/20% PEP (17/8 PO/OH). Diffraction quality crystals (space group $I2_12_12_1$) were obtained after 10 days.

Example 3

Data Collection and Structure Determination for 12Y-1 and 12Y-2

X-ray diffraction data collections from all crystals were conducted in-house using Rigaku RAXIS IV (Rigaku-MSC) and Mar 180 (MarResearch) image plate detectors mounted on a Rigaku HR3 HB X-ray generator equipped with monocapillary focusing optics (AXCO). Data were collected at −160° C.; the crystals required no added cryoprotectant. All data processing was carried out using the DENZO/SCALEPACK suite (Otwinoski 1997). Diffraction data statistics are summarized in Table 2.

Initial heavy atom screening for 12Y-1 protein was performed by native polyacrylamide gel electrophoresis using the Heavy Atom Screen M2 kit (Hampton Research. Band shifts were observed for Lutetium (III) Acetate Hydrate (LAH; $Lu(O_2C_2H_3)_2$) and Potassium Hexachloro Rhenium (PHR; $K_2ReCl_6$). Isomorphous heavy atom derivatives were obtained by soaking 12Y-1 crystals for ~30 min in 0.8 l of 50 mM of LAH or PHR. Heavy atom sites were identified and refined with the statistical phasing program SHARP (La fortell 1997), and solvent-fattening procedures DM and SOLOMON used to resolve the phase ambiguity. The residual and anomalous difference Fourier maps produced by SHARP were examined in order to locate further heavy atom peaks, which were included in subsequent cycles of phase refinement and calculation using SHARP. Several iterations of this cycle located additional positions and improved phases to 2.82 Å. This result was achieved using the phasing power of both Lu and Re.

The model was manually built using XtalView (McRee 1999) into the electron-density map (centroid map) produced by SHARP. The model was then refined against the native 12Y-1 data using CNS (Brunger 1998) and CCP4 (CCP) packages. Difference electron density maps $2m|F_o|-D|F_c|$ and $m|F_o|-|F_c|$ were used to improve the model in the XtalView program. During the model building and refinement, 5% of the data was flagged for cross-validation to monitor the progress of refinement.

The electron density map allowed unambiguous tracing of all residues except the CDR3 analogous loop residues (88-98), which disordered. Water molecules were located automatically with the program ARP (Lamzin 1997) for >2σ peaks in the $m|F_o|-|F_c|$ map and retained if they satisfied H-bond criteria and returned 2 $m|F_o|-D|F_c|$ density after refinement. Following the convergence in standard refinement, a further improvement of more than 2% in R factors was achieved by refining all protein atoms as one anisotropic domain with the TLS procedure in CCP4 REFMAC5 (Wins 2001). The libration tensor showed significant anisotropy. The final R and $R_{free}$ values were 0.166 and 0.254, respectively for a 6-2.82 Å range of refined data. The final 12Y-1 model contains 100 amino acids (residues 1-87 and 99-111) and 97 water molecules. Of the residues in the 12Y-1 model, 84.5% fall in the most favourable regions of a Ramachandran plot generated by CCP4 PROCHECK (Laskowski 1993) with no residues in the generously allowed or disallowed regions. Further details are given in Table 2.

The structure of 12Y-2 was determined by molecular replacement using CCP4 MOLREP. The search model was the 12Y-1 structure (above) without the CDR3 analogous loop. Two 12Y-2 monomers (A and B) were identified in the asymmetric unit of the $I2_12_12_1$, space group. Iterative model building using XtalView and refinement using REFMAC5 allowed a complete trace of A and B monomers including extended CDR3 analogous loops. The electron density was well defined in the CDR3 analogous loop region. Progress of the refinement was monitored using the $R_{free}$ statistic based on a set encompassing 5% of the observed diffraction amplitudes. Water molecules were added automatically with the program ARP as described for 12Y-1. The final refinement included the TLS parameters for each molecule individually as a TLS group in the asymmetric unit and converged to R and $R_{free}$ values of 0.176 and 0.247, respectively, for the 18.12-2.18 Å range of experimental data. As for 12Y-1, only the liberation tensor was significant, though less anisotropic. The final model comprises residues 1 to 113 of the 12Y-2 A and B chains, and 358 water molecules. In total, 93.4% of residues are in the most favoured regions of the Ramachandran plot, with no residues in the generously allowed or disallowed regions. This indicates that the 12Y-2 model is consistent with a highly refined protein structure. Further details are in Table 2.

Example 3a

Data Collection and Structure Determination for 12A-9 and 1A-7

X-ray diffraction data collection for 1A-7 crystal was conducted in-house using Mar 180 (MarResearch) image plate detectors mounted on a Rigaku HR3 HB X-ray generator equipped with monocapillary focusing optics (AXCO). X-ray diffraction data for 12A-9 crystal was collected at the Photon Factory synchrotron BL5 beamline in Japan. Data for both crystals were collected at –160° C.; the crystals required no added cryoprotectant. All data processing was carried out using the DENZO/SCALEPACK suite (Otwinoski 1997). Diffraction data statistics are summarized in Table 2.

Figure 5A:
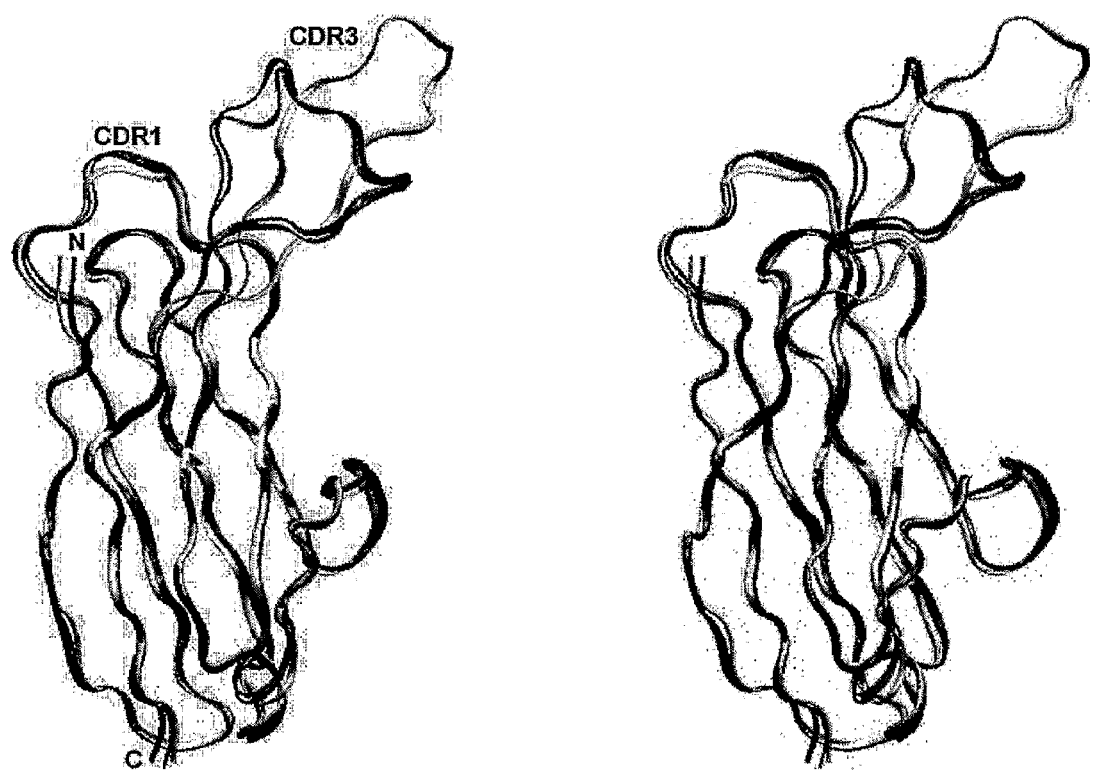
FIG. 5a. Stereo images of superimposed 1A-7 A chain, 1A-7 C chain and 12Y-2 A chain. Figures were produced using VMD. The CDR1 analogous region (loop region 4) and CDR3 analogous region (loop region 8) are labeled.
Figure 15:
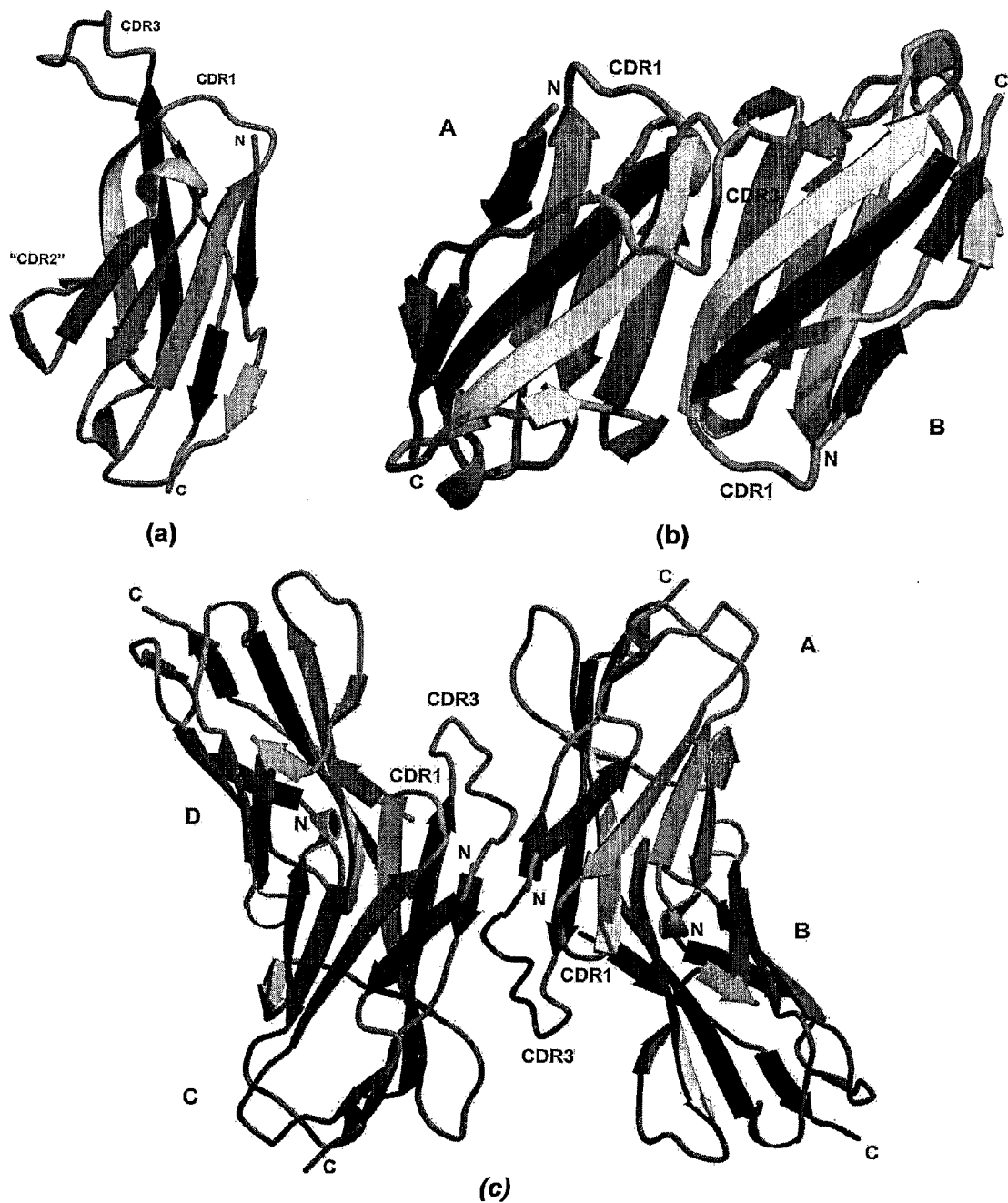
FIG. 15. MOLSCRIPT/RASTERED3D diagrams of (a) 1A-7 chain A, (b) 1A-7 chain A and B dimer, and (c) 1A-7 chains A, B, C and D in the asymmetric unit of crystal structure. Each chain is shown as a ribbon representation. The N- and C-termini and the CDR analogous regions are labeled.

The structures of 1A-7 and 12A-9 were determined by molecular replacement using CCP4 MOLREP. The search model for 1A-7 was the 12Y-1 two-fold dimer without the CDR3 analogous loops. Four 1A-7 monomers (A, B, C and D) were identified in the asymmetric unit of the $I2_12_12_1$ space group. Iterative model building using XtalView and refinement using REFMAC5 allowed a complete trace of A and C monomers including CDR3 analogous loops. The electron density was not well defined in the CDR3 analogous loop region (89-98) for monomers B and D. The A & B and C & D chains form two approximately 2-fold dimers (see FIG. 15) similar to those observed in 12Y-1 and 12Y-2 structures. Water molecules were added and progress of the refinement was monitored as described for 12Y-1 and 12Y-2. The final refinement included the TLS parameters for each molecule individually as a TLS group in the asymmetric unit and converged to R and $R_{free}$ values of 0.176 and 0.265, respectively, for the full 21.6-2.7 Å range of experimental data. The final model comprises residues 1 to 111 of the 1A-7 A and C chains, and residues 1-88 and 99-111 for B and D chains, and 489 water molecules. In total, 90.9% of residues are in the most favoured regions of the Ramachandran plot, with 2 residues for chain C in the generously allowed or disallowed regions. Overlay of 1A-7 full chains A and C, and 12Y-2 chain A is shown in FIG. 5a. Further details are given in Table 2.

Figure 14:
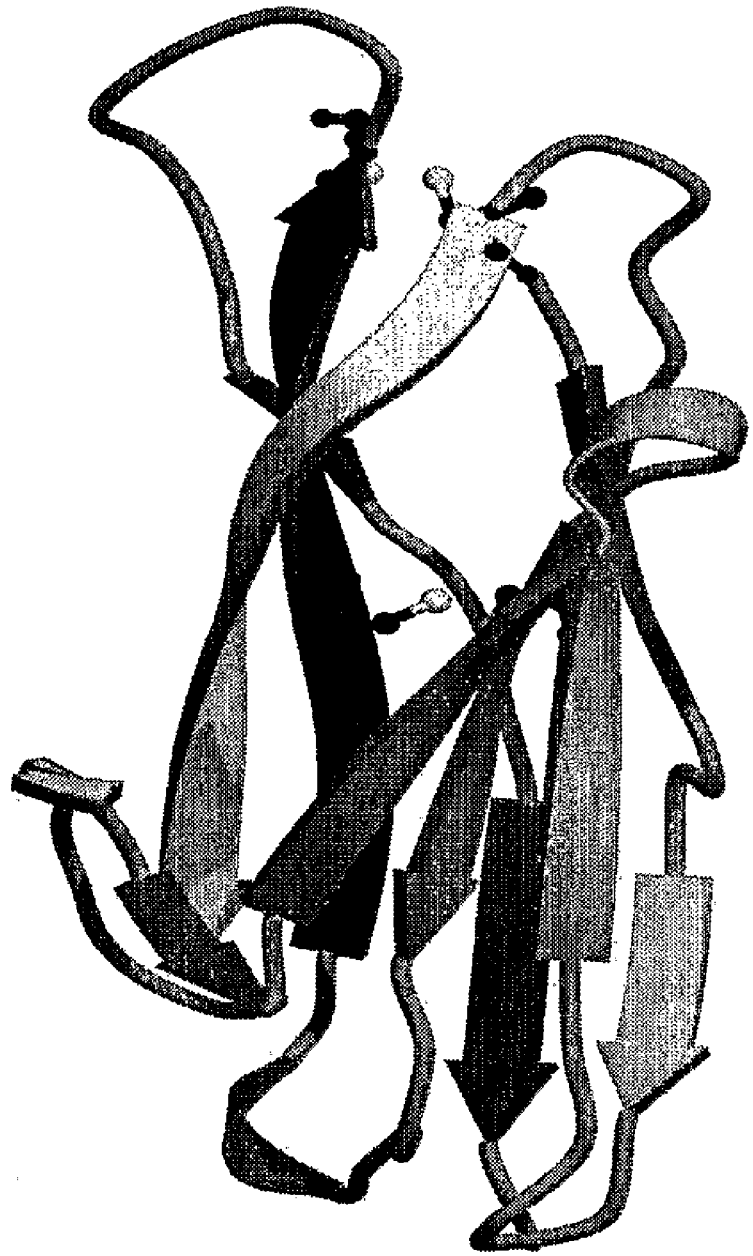
FIG. 14. MOLSCRIPT/RASTERED3D diagram of the 12A-9 chain. The chain is shown in ribbon representation. Cysteine residues are shown as ball-and-sticks.

The search model for 12A-9 was the 12Y-1 structure (above) without the CDR3 analogous loop. One molecule of 12A-9 was identified in the asymmetric unit of the $P2_12_12$ space group. The electron density was traceable in the CDR3 analogous loop, however with somewhat diffuse 92-95 region. The final refinement included the TLS parameters for whole molecule and converged to R and $R_{free}$ values of 0.217 and 0.280, respectively, for the full 39.5-2.1 Å range of experimental data. The final model comprises residues 1 to 108 of the 12A-9 (see FIG. 14) and 140 water molecules. In total, 88.4% of residues are in the most favoured regions of the Ramachandran plot, with 1 residue in the generously allowed regions. Further details are in Table 2.

Example 4

Structure of the Crystallographic Dimer

The inter-dimer relative disposition of monomers can be described as rotation by 6.9° and screw translation by –0.43 Å. This was calculated as follows. The 12Y-1 dimer was overlaid onto that of the 12Y-2 dimer using a least-squares superposition of corresponding Cα atoms selected from a single monomer only, then the magnitude of the rotation (about the centre of mass) and translation then required to superimpose the remaining monomer from the first crystal form onto that from the second crystal form was calculated.

Example 5

Coordinates for 12Y-1 and 12Y-2

The coordinates for 12Y-1 and 12Y-2 are attached as Appendices I(a) and I(b) respectively.

Example 5a

Coordinates for 12A-9 and 1A-7

The coordinates for 12A-9 and 1A-7 are attached as Appendices I(c) and I(d) respectively.

Example 6

Modifications to Loop Regions of 12Y-2

Loop region 8 of 12Y-2 adopts a β-hairpin configuration with β-strands extending for a significant portion of its length, stabilized by main-chain hydrogen bonds. This β-hairpin configuration is conserved by main-chain hydrogen bonds, for example, between: Tyr87 (O)-Phe100(N); Leu89 (N)-Leu98 (O); Leu89 (O)-Leu98 (N). The elongated loop extends outward and upward from the immunoglobulin framework and creates a structure ideal for penetrating buried clefts and cavities in, for example, enzyme active sites, parasite coat proteins, or viral canyons. The following table is a comparison of the length of loop region 8 of 12Y-2 with long CDR3 loops from cleft binding antibodies such as b12 Ig (targeting HIV gp120; Saphire 2001); camelid VHH 1MEL (targeting lysozyme, Desmyter 1994); and T cell receptor 1QRN.

| Domain | Framework | Loop Tip | Distance b/w residues | Comments |
|---|---|---|---|---|
| 12Y-2 $V_{NAR}$ | Phe86 | Gly93 | 20 Å | β-hairpin |
| b12 VH 1HZH | Val99 | Trp104 | 15 Å | anti-HIV gp120 |
| VHH 1MEL | Asp99 | Ala104 | 14 Å | Anti-lysozyme |
| TCR Vα 1QRN | Thr93 | Trp101 | 09 Å | Comparison |

These figures show that the 12Y-2 loop region 8 is relatively long, suggesting that the $V_{NAR}$ scaffold is ideal for displaying such long CDR3-like loops. This analysis indicates that modifications to loop region 8 may lead to the generation of novel diagnostic or therapeutic binding moieties. Additionally, modifications to other regions of the $V_{NAR}$ scaffold, and in particular the 12Y-2 scaffold, may also lead to the generation of novel diagnostic or therapeutic binding moieties. Examples of modifications include:

1. Grafting of Extended CDR3 Loops with Specifically Designed Amino Acid Sequences onto the $V_{NAR}$ Scaffold in the Vicinity of Loop Region 8

For example, the sequence RVGPYSWDDSPQDNYYM (SEQ ID NO: 116) may be grafted onto the 12Y-2 scaffold in the vicinity of loop region 8 to form an extended loop corresponding to the anti-HIV antibody b12 (1 HZH) and thereby provide novel binding moiety with an IgNAR scaffold capable of binding HIV gp120. The grafting may involve, for example, replacement of amino acid residues 86 to 103 of 12Y-2 (or a portion of these residues) with RVGPYSWDDSPQDNYYM (SEQ ID NO: 116).

In another example, the sequence CSKPSDSNC (SEQ ID NO: 117), representing a protruding loop of the major surface antigen (HBsAg) from hepatitis B virus (HBV) may be grafted onto the $V_{NAR}$ scaffold 24G-3 (SEQ ID NO: 101), in place of the CDR3 loop. The resulting IgNAR could then be used to assess the interaction of the HBsAg loop with other HBV proteins.

2. Grafting of CDR1 Loops with Specifically Designed Amino Acid Sequences onto the $V_{NAR}$ Scaffold in the Vicinity of Loop Region 4.

For example, the sequence GYRFSNFVI (SEQ ID NO: 118) of the anti-HIV antibody b12 (1 HZH) may be grafted onto the 12Y-2 scaffold in the vicinity of loop region 4 and, when combined with the CDR3 loop graft of the anti-HIV antibody b12 described in (1) above, will enhance the binding affinity to gp120. The grafting may involve, for example, replacement of amino acid residues 28 to 33 of 12Y-2 (or a portion of these residues) with the sequence GYRFSNFVI (SEQ ID NO: 118).

Figure 16:
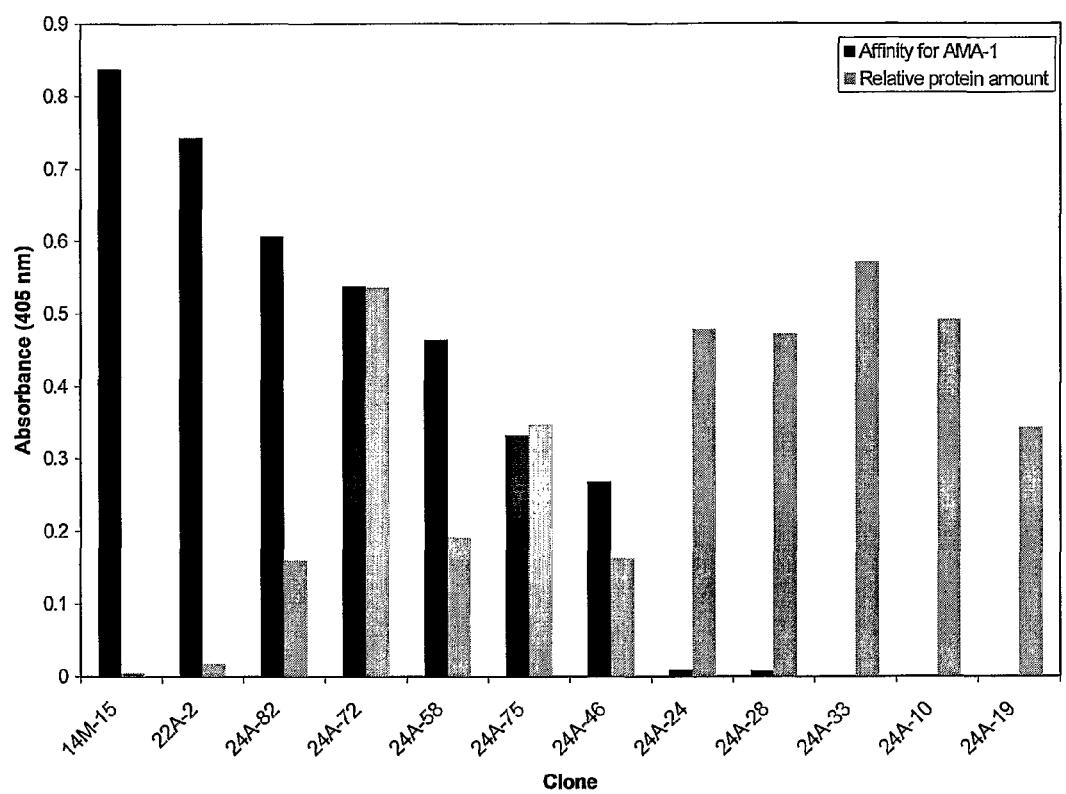
FIG. 16. ELISA analysis of 12 14M-15 variants (12Y-2 with Pro90Leu) for binding to AMA1 and a control negative antigen. Comparative expression levels are also shown. The CDR1 analogous region (loop region 4) has been shuffled in the variants.

To determine if CDR1 loop grafting would change the affinity and expression qualities of the 12Y-2 $V_{NAR}$, the N-terminal half of the 14M-15 clone (SEQ ID NOs: 11 & 12) of 12Y-2 was replaced with a library of sequences. This effectively produced a library of CDR1/N-terminus framework variants combined with a fixed CDR3. 88 CDR1 shuffled $V_{NA}$ clones were analysed by ELISA for binding to AMA1 antigen. Nineteen clones had affinity for AM-1, whilst the remaining 69 showed no binding. No clones had detectable affinity for a negative control antigen (bovine serum albumin). This indicates that the CDR1 sequence and conformation is vital to IgNAR binding. FIG. 16 presents the results of ELISA analysis of five clones with high affinity and 5 clones with no detectable affinity. Comparative expression levels are also given. FIG. 17 presents the amino acid sequence alignment of the clones from FIG. 16 (SEQ ID NOs: 11, 15 and 102-111, respectively).

Of the clones with highest affinity, three had similar CDR1 sequences (24A-58, 24A-75, 24A-46) but the remaining two were significantly different (24A-82 and 24A-72). The similar clones shared the common CDR1 sequence "RDTSCAFSSTG" (SEQ ID NO: 119) and had 1-3 residues differing in the framework region near the N-terminus. The sequences for 5 clones with no detectable antigen affinity also had significant variability. Additionally, the amount of IgNAR protein present varied among the clones (only 4 of 88 produced no detectable protein). This indicates that the CDR1 sequence and conformation are also vital to IgNAR expression levels and protein production. Sequence differences map predominantly to the CDR1 loop region, with some contribution from framework residues, and have a marked affect on both affinity and protein expression levels.

3. Mutation or Insertion of Specific Residues in Loop Region 8.

For example, mutating residues Pro90 and/or Phe100 may enhance the flexibility of loop region 8 thereby resulting in improved antigen binding.

A randomly generated library of 12Y-2 variant containing on average one amino acid change per 100 residues was screened against AMA1 antigen. Two high affinity clones were isolated each separately showing 10-fold enhanced affinity over the wild type 12Y-2. These were designated 14M-15 (Pro90Leu) (SEQ ID NOs: 11 & 12) and 14M-8 (Phe100Leu) (Nuttall et al. 2004).

4. Randomisation of the Entire Loop Region 8, Varying in Length and Amino Acid Composition.

This is in effect the creation of new shark libraries which are described in various Examples below.

5. Randomisation of the Entire Loop Region 8, Varying in Length and Amino Acid Composition Together with Improvement of the Loop Region-Framework Junctions by Incorporation of the Combinations of Paired Junction Residues: Gly84+Glu103, or Gln84+Gly102.

The $V_{NAR}$ library was expanded by designing new degenerate oligonucleotide primers for CDR3 (loop region 8) with loop lengths of either 12 or 13 residues and framework residue combination of either: Gly84+Glu103, or Gln84+Gly102. These and other CDR3 combinations were used to construct a further $V_{NAR}$ library of >2×10$^8$ members.

The following new primer oligonucleotides were used: A0295 (SEQ ID NO: 64), A0296 (SEQ ID NO: 62), A0297 (SEQ ID NO: 63) and A0298 (SEQ ID NO: 61). The IgNAR domain was completed using combinations of the primers disclosed in SEQ ID Nos: 47-60.

6. Randomisation of the Residues at the Tip of Loop Region 8, for Example, from Residues Pro90-Ser97, or Other Such Variations, and Expansion or Contraction of this Loop by Incorporation or Removal of Residues, and Differing Number and Strategy of Randomised Residues.

Modification of loop region 8 residues Leu98, Leu99 may be made in a similar manner. For example:

Set 1 (Short Loop 8 Residues)

Leu89 to Ser97 replaced by 7 randomised residues; Leu98 constrained modification according to the nucleic acid encoding formula: (NNK)7+(SNK)1.

Set 2 (Randomised Loop 10 Residues)

Leu89 to Ser97 replaced by 9 randomised residues; Leu98 constrained modification according to the nucleic acid encoding formula: (NNK)9+(SNK)1.

Set 3 (Long Loop Leu98-99)

Leu89 to Ser97 replaced by 8 randomised residues with a tyrosine/ring amino acid bias and Leu99 constrained modifications according to the nucleic acid encoding formula: $(NNK)1\ (YMC)1\ (NNK)1\ (YMC)1\ (NNK)2\ (YMC)1\ (NNK)1\ (SNK)1\ (SNK)1$.

Set 4 (Long Loop 11 Residues)

Leu89 to Ser97 replaced by 10 randomised residues with a central tyrosine/ring amino acid bias and Leu98 constrained modification according to the nucleic acid encoding formula: $(NNK)3\ (YMC)4\ (NNK)3\ (SNK)1$.

Set 5 (Long Loop 12 Residues)

Leu89 to Ser97 replaced by 12 randomised residues with an aromatic bias and no Leu98 constraints according to the nucleic acid encoding formula: $(NNK)_3\ (WDB)_1\ (NNB)_2\ (WDB)_1\ (NNK)_2\ (WDS)_1\ (NNB)_2$ Set 6 (Long Loop 12 Residues)

Leu89 to Ser97 replaced by 12 randomised residues with an aromatic bias and no Leu98 constraints according to the nucleic acid encoding formula: $(WDB)_1\ (K)_2\ (WDS)_1\ (NNB)_2\ (WDB)_1\ (NNK)_2\ (WDB)_1\ (NNB)_2$ A library based on 12Y-2 of size ~1×10⁸ independent clones was constructed using equal representations of these 6 oligonucleotide primers. The library was screened against different strains of Plasmodium falciparum AMA1, i.e. W2MEF and HB3 (not recognised by the parent 12Y-2), and original antigen AMA-1 3D7 (positive control).

Figure 18:
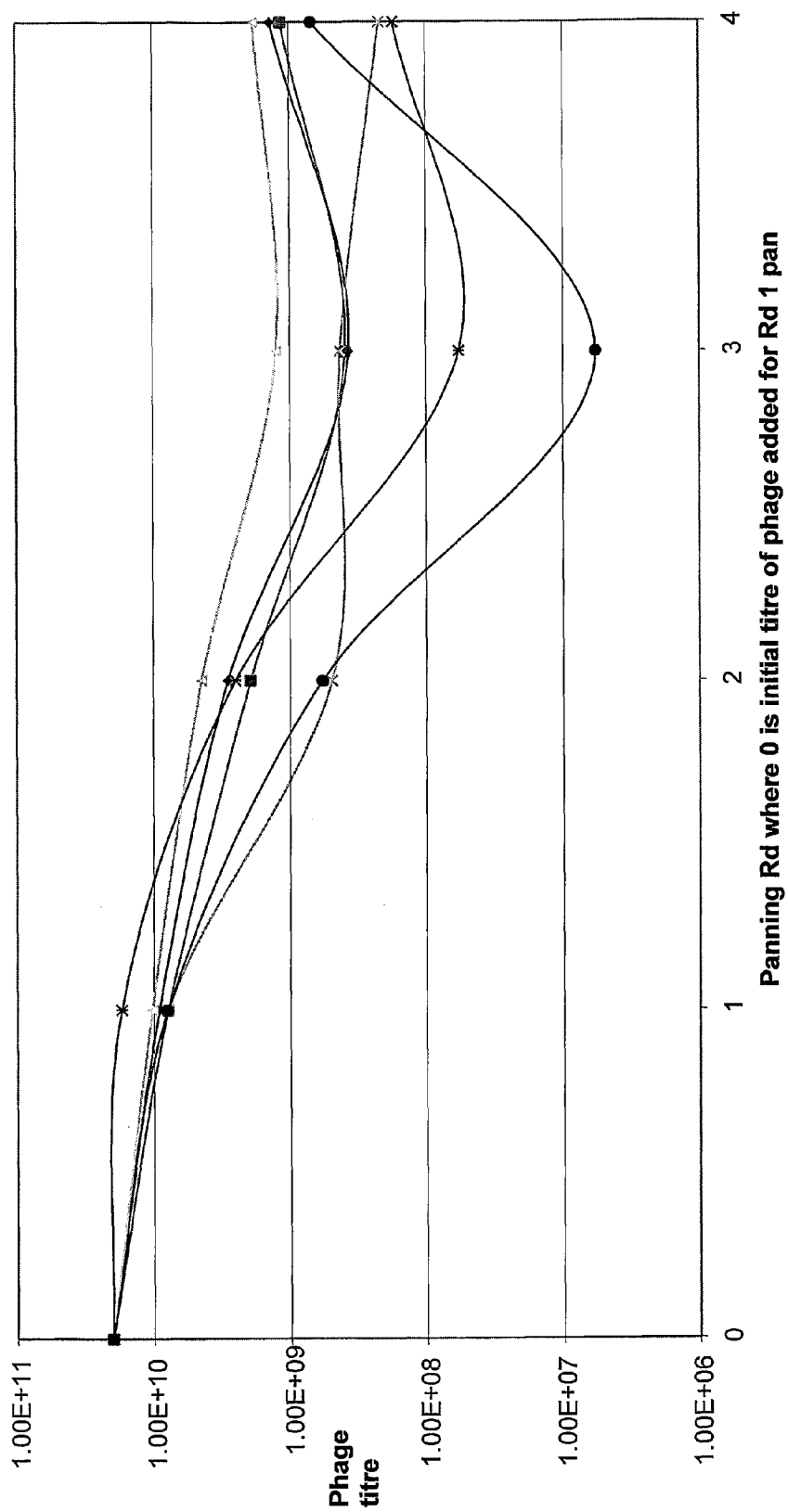
FIG. 18. Titers of total eluted phage from 12Y-2 loop library panned against different malarial strains: W2MEF (-♦-), W2MEF (-■-), W2/HB/W2/3D7 (-▲-), HB3 (-x-), HB3 (-*-), HB/W2/HB/3D7 (-●-). The initial titre of phage added for reading 1 pan is taken as the zero reading.
Figures 21A, 21B:
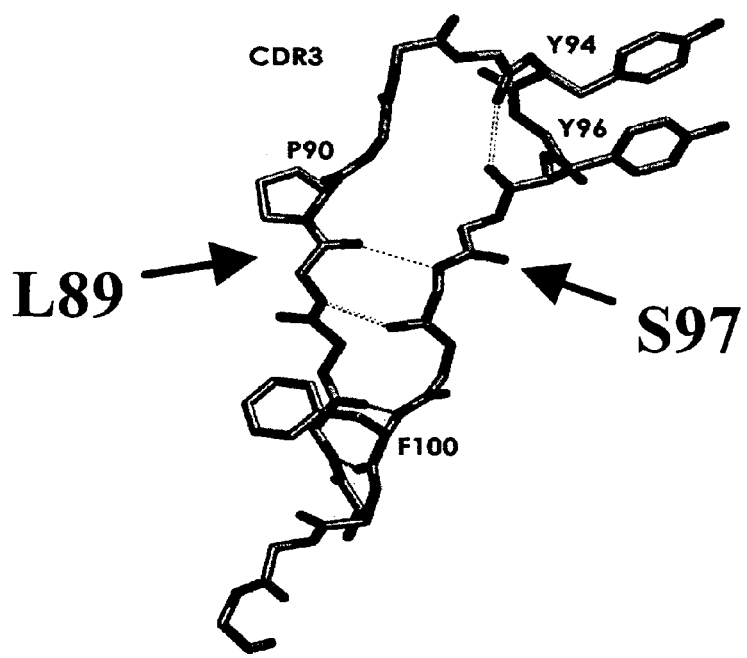
FIG. 21. (a) Modelled liquorice representation of CDR3 analogous loop (loop region 8) of the 12Y-2 structure showing the position of the Leu89 and Ser97 residues. (b) Portion of the 12Y-2 nucleotide/amino acid sequences showing the CDR3 analogous region (light shade). (c) Schematic diagram of loop region 8 (analogous to CDR3) libraries based on the 12Y-2 structure, where the tip of the 12Y-2 loop region 8 has been modified by 6 different strategies, varying in amino acid randomisation, loop length, and amino acid variation pattern (SEQ ID NOs: 147-152).
Figure 21C:
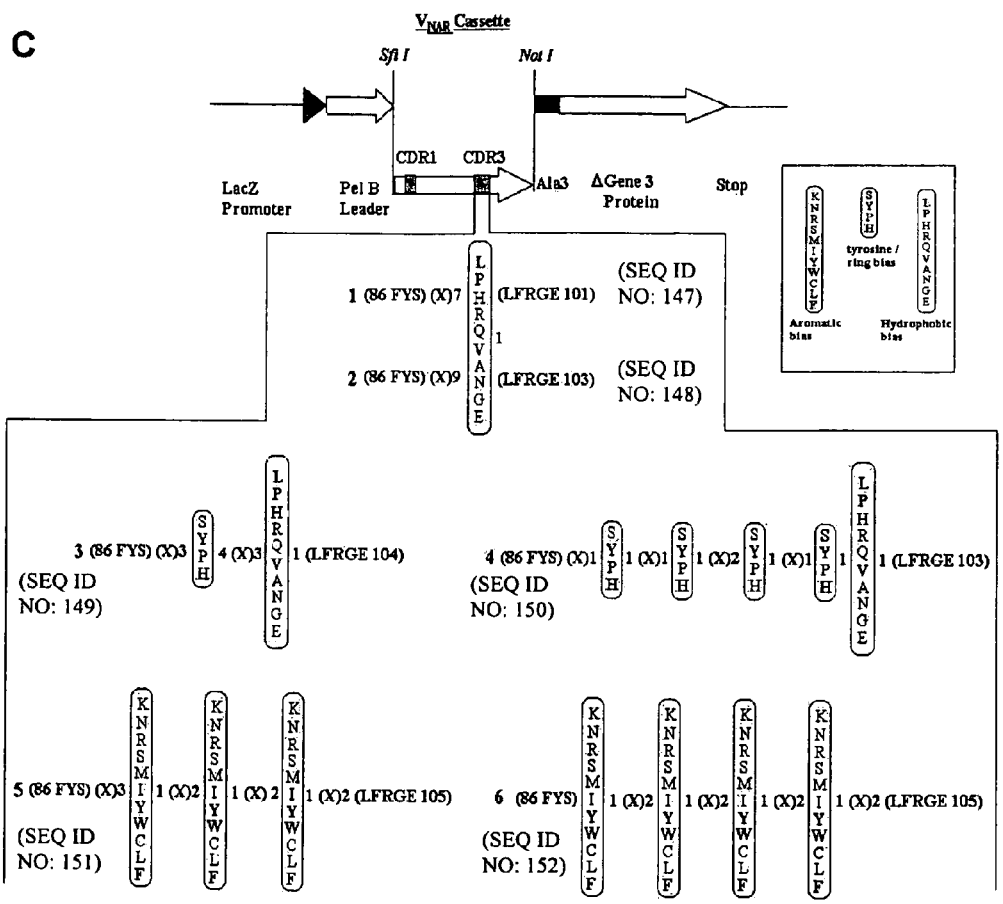

FIG. 18 shows the KH (12Y-2 loop) library panned against different malarial strains.

Example 7

Proposed Modifications to Expand the Binding Face of the $V_{NAR}$

Results presented herein show that the $V_{NAR}$ "CDR2" loop is non-existent, replaced by a short β-turn at the bottom of the molecule. This is graphically illustrated in FIG. 12, where the $V_{NAR}$ "CDR2" is aligned with that of a typical human antibody. The "bottom" position of this loop, combined with the low sequence variability, strongly suggests that this region has little impact on the interaction with antigen. However, the loss of the conventional C" and D strands suggests a possible alternative model for antigen binding, where the extended 12Y-2 loop region 8 combines with the large concave pocket opened in the absence of the conventional CDR2. This concave pocket is a potential antigen binding face. The pocket comprises residues loop region 8, loop region 5 and C & D β-strands. These residues (for 12Y-2) include: Asp33, Tyr37, Glu46, Ser48, Ser50, Ile51, Val59, Lys61, Phe86, Tyr94, Asn95, Tyr96, Leu98, Leu99 & Arg101. This antigen binding surface is unlike any antibody paratope (the antigen-binding surface of an antibody), since the loop regions are distant from each other (are not in contact) and the antigen contact residues may include framework residues between the loop regions.

This analysis suggests that the randomisation of selected residues within the C, C', D strands, and the loop regions 5 and 8, can be used to construct "pincerbody" molecular libraries, which will bind antigen by a combination of loop and framework residues. Suitable target residues (for the 12Y-2 structure) are, singly and in combination:

| Residue 12Y-2 | Residue 12Y-1 | Designation | Position |
|---|---|---|---|
| Tyr37 | Tyr37 | Bottom jaw | C strand |
| Glu46 | Glu46 | Bottom jaw | C' strand |
| Ser48 | Thr48 | Bottom jaw | C' strand (Loop region 5) |
| Ser50 | Ser50 | Bottom jaw | Loop region 5 |
| Ile51 | Ile51 | Bottom jaw | Loop region 5 |
| Asp33 | Ser33 | Top jaw | Loop region 4 |
| Val59 | Val59 | Top jaw | D strand |
| Lys61 | Lys61 | Top jaw | Loop region 6 |
| Phe86 | Phe86 | Top jaw | Loop region 8 |
| Arg101 | N/A | Top jaw | Loop region 8 |
| Tyr94 | N/A | Overbite | Loop region 8 |
| Asn95 | N/A | Overbite | Loop region 8 |
| Tyr96 | N/A | Overbite | Loop region 8 |
| Leu98 | N/A | Overbite | Loop region 8 |
| Leu99 | N/A | Overbite | Loop region 8 |

Figures 22A, 22B:
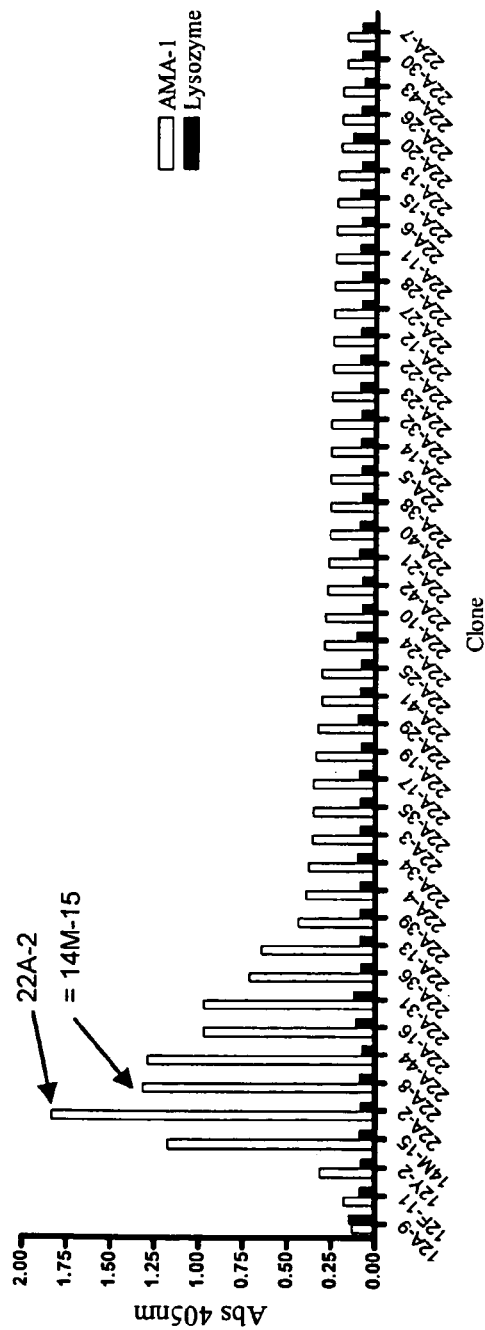
FIG. 22: (a) ELISA analysis of 40 12Y-2 variants binding to AMA-1 and a control negative antigen. (b) Alignment of 12Y-2 variants 22A-2 (Thr39Ser; Pro90Leu) and 14M-15 (Pro90Leu). (c) Three-dimensional structure of 12Y-2 illustrating affinity-enhancing CDR1 and CDR3 mutation and the framework affinity-enhancing mutation Thr39Ser. (d) FPLC traces of 12Y-2 variants 14M-15 and 22A-2. Both show identical expression and folding characteristics. (e) Biosensor traces of purified 12Y-2 variant proteins 14M-15 and 22A-2. 22A-2 shows 2-fold enhanced affinity over 14M-15 (20-fold better affinity than 12Y-2).
Figure 22C:
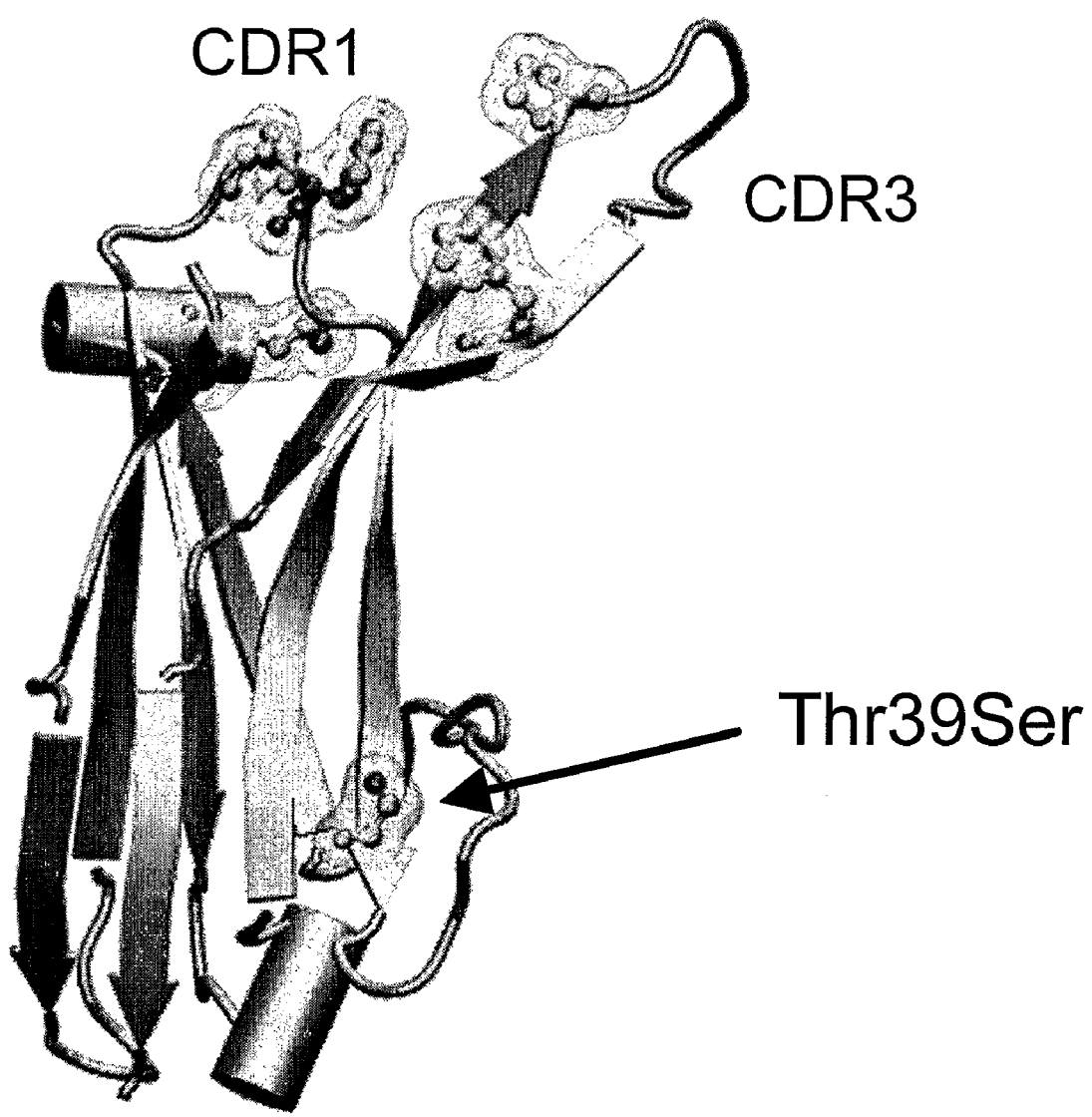
Figure 22D:
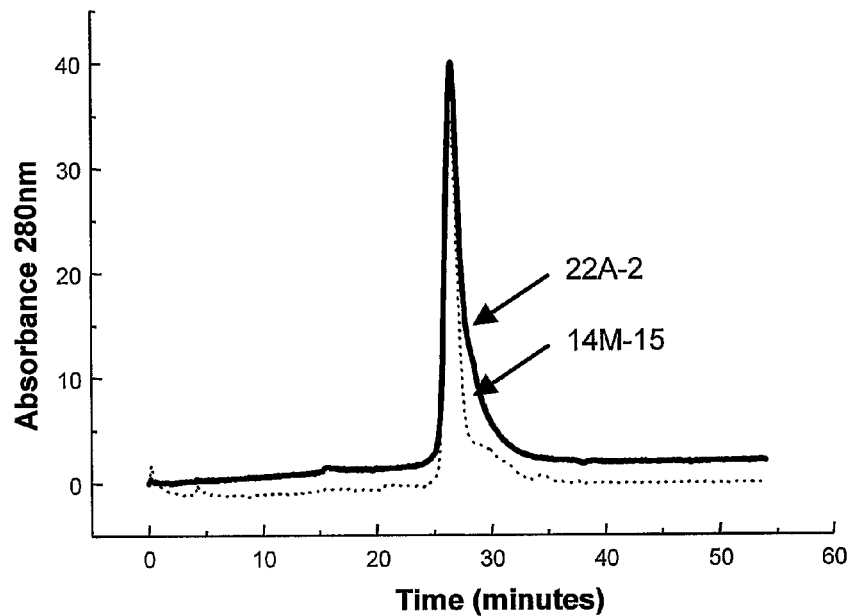
Figure 22E:
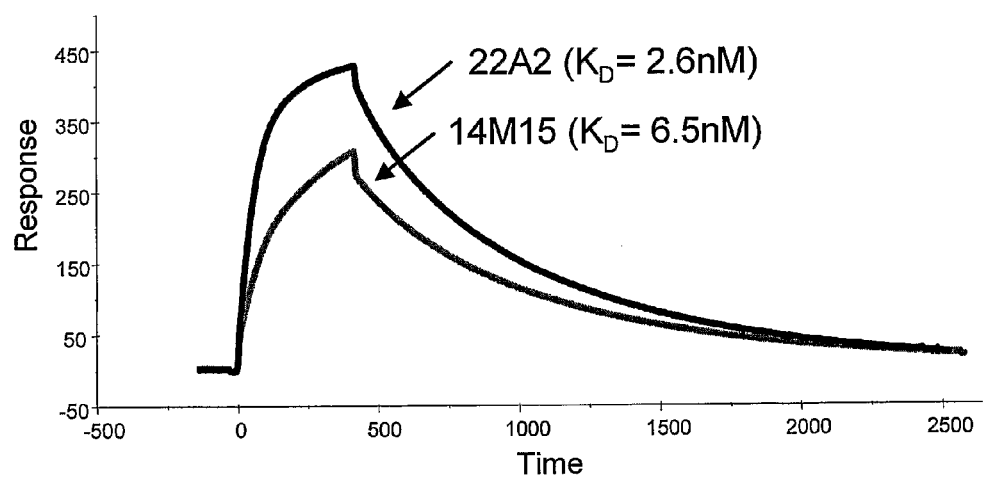

A randomly generated library of 12Y-2 variants containing on average one amino acid change per 100 residues was screened against AMA1 antigen. A high affinity clone was isolated incorporating the mutations Pro90Leu (identical to 14M-15) and the additional mutation Thr39Ser. This protein (22A-2: SEQ ID NO: 15) had two-fold better affinity than 14M-15, by ELISA (see FIG. 22(a)), biosensor (see FIG. 22(e)), and protein bioarray ($K_D$ 2.6 nM vs $K_D$ 6.5 nM). Protein expression characteristics were unchanged (see FIG. 22(d)). This mutation is at position 39 in the framework just N-terminal to β-strand region C (see FIGS. 22(b) and (c)). This indicates that framework region mutations can have a significant effect upon affinity, especially in the vicinity of "CDR2". Without being limited by theory, it is believed that this may affect the torsions of the strands which alter the CDR conformations sufficiently to enhance binding.

Example 8

Generation of Therapeutics or Diagnostics by Loop Grafting from Shark to Human Domains The structures of IgNARs and human Immunoglobulin superfamily I-set domains are homologous enough to allow prediction of framework/loop region junctions, take-off angles of strands, and loop orientations. Binding loops discovered for $V_{NAR}$s can be grafted to human I-set frameworks such as but not limited to NCAM, ICAM, and Telokin. This will form a human binding domain Ig-like reagent with only the variable loop regions derived from non-human sources. These may be particularly useful as cleft-binding "human-Ig-like" reagents, since they possess antigen-binding surfaces different from any known naturally occurring antibody.

The following modifications may, for example, be made to I-set framework molecules such as NCAM, ICAM or Telokin:

1. Grafting of anti-AMA1 loop region 8 from 12Y-2 onto I-set framework.
2. Grafting of anti-AMA1 loop region 4 and 8 from 12Y-2 onto I-set framework.
3. Grafting of anti-AMA1 loop region 8 from 12Y-1 onto I-set framework.
4. Grafting of anti-AMA1 loop region 4 and 8 from 12Y-1 onto I-set framework.
5. Grafting other $V_{NAR}$ loop region 8 onto I-set framework.
6. Grafting other $V_{NAR}$ loop region 4 onto I-set framework.
7. Grafting of loop regions 4 and 8 from $V_{NAR}$s onto I-set framework, where these loops are linked by a disulphide bridge.

8. Incorporation of loop region 4-8 disulphide bridges into loops grafted onto I-set framework.
9. Generation of a library of I-set frameworks by randomising equivalent loops the loop regions 4 and 8.
10. Generation of a library of I-set frameworks by randomising equivalent loops to loop regions 4 and 8, and use as a set of variable "virus traps" for identifying viruses targeting the cell adhesion molecules.

Cloning of NCAM and Telokin.

The Neural Cell Adhesion Molecule 1 (NCAM; CD56) is a mammalian cell-surface glycoprotein which mediates neuronal cell adhesion. The extracellular domain consists of 51 g superfamily domains followed by 2 fibronectin Type 3 domains (see FIG. 23(a)). Domain 1 of NCAM is classified within the I-set of the Ig superfamily and is unmodified by glycosylation or other post-translational modification.

Coding sequences for the wild-type human NCAM domain 1 (SEQ ID NO: 37) and wild-type human NCAM domains 1+2 (SEQ ID NO: 39) were amplified from a human cDNA library and cloned in-frame into the *E. coli* cloning/expression vector pGC. A0657 (SEQ ID No: 77) was used as the forward 5' primer for domain 1. A0658 (SEQ ID No: 78) was used as the reverse 3' primer for domain 1. A0659 (SEQ ID NO: 79) was used as the reverse primer for domain 2. A0979 (SEQ ID NO: 80) was used as the NCAM secondary extension primer.

Clones were verified by DNA sequencing. Both the wild-type domain 1 (clone 21H-5: SEQ ID NO: 36) and wild-type domains 1+2 (clone 21G-1: SEQ ID NO: 38) were successfully expressed as soluble protein into the *E. coli* periplasmic space as measured by Fast Protein Liquid Chromatography (FPLC) (see FIG. 23(c)) and SDS-PAGE. Crystal leads were obtained for providing evidence for folding into an ordered conformation.

Myosin Light Chain Kinase (MLCK) consists of 3 N-terminal Ig-like domains, a calmodulin-binding catalytic domain, and one C-terminal Ig-like domain (see FIG. 24(a)). Activation of MLCK following binding by calcium-calmodulin results in phosphorylation of a specific serine in the N-terminus of a myosin light chain, leading to the formation of calmodulin/MLCK signal transduction complexes which allow selective transduction of calcium signals, ultimately causing muscle contraction. The Ig-like domains flanking the catalytic domain enable binding of MLCK to myosin. Independent transcription of the C-terminal Ig-like domain of MLCK from an internal promoter gives rise to the production of the mature protein, Telokin. Telokin is an I-set Ig domain and has phosphorylation sites at Ser-12 and Ser-18. It appears to modulate MLCK activity by binding to unphosphorylated myosin thus preventing phosphorylation by MLCK.

The coding sequence for the human Telokin domain 1 was amplified from a human cDNA library and cloned in-frame into the *E. coli* cloning/expression vector pGC. A0678 (SEQ ID No: 88) was used as the forward 5' primer. A0677 (SEQ ID NO: 89) was used as the reverse 3' primer. A0999 (SEQ ID NO: 96) was used as the Telokin N-terminus secondary extension primer. Clone 21J-4 was correct as verified by DNA sequencing (SEQ ID NO: 42). Telokin domain was successfully expressed as soluble protein (SEQ ID NO: 41) into the *E. coli* periplasmic space as measured by FPLC (see FIG. 24(c)) and SDS-PAGE.

Modeling and Loop Grafts

In order to produce human binding domain Ig-like reagent with only the variable loop regions derived from non-human sources, i.e. shark IgNAR antibodies, the CDR3 loop from $V_{NAR}$ 1A-7 was modeled for loop-grafting to NCAM domain 1 and Telokin I-set domains. Shark $V_{NAR}$s, NCAM domain 1 and Telokin were least squares aligned to determine where framework structural homology was greatest to assess grafting points for variable "$V_{NAR}$ CDR3" loops. These loops varied in both length and sequence and were modelled as chimeras onto NCAM domain 1 and Telokin frameworks to produce human binding domain Ig-like reagents.

A variety of chimeras were then designed and constructed using Modeller6v2 with variation of the $V_{NAR}$ CDR3 (i.e. loop region 8) length and sequence according to Table 5 (SEQ ID NOs: 120-129). Each model was then assessed for deviation from the human framework and $V_{NAR}$ CDR3 structures by visual inspection and for potential stability (energy) according to the modeler objective scores.

The best scoring models were for NCAM model 5 (SEQ ID NO: 124), and for Telokin model 3 and model 5 (SEQ ID NOs: 127 and 129, respectively).

NCAM—1A-7 Loop Grafts:

The best NCAM/shark 1A-7 CDR3 loop graft (model 5) (SEQ ID NO: 124) was constructed by overlap PCR using oligonucleotide primer A0989 (SEQ ID NO: 81). The resulting clone designated 23B-2 was verified by DNA sequencing (SEQ ID NO: 40).

Figures 25A, 25B:
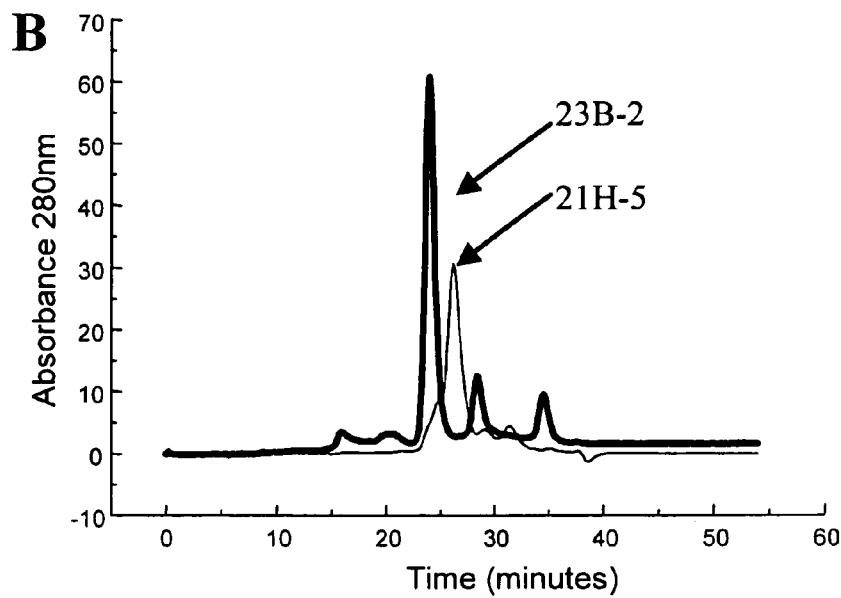
FIG. 25: (a) Alignment of NCAM domain 1 (21H-5) and loop-graft variant 23B-2. Dual C-terminal FLAG affinity tags are not shown. (b) FPLC traces of NCAM domain 1 (21H-5) and loop-graft variant 23B-2 recombinant proteins. Protein 23B-2 shows a "cleaner" profile. (c) SDS-PAGE profiles of NCAM domain 1 (21H-5) and domain 1 loop-graft variant 23B-2. NCAM domain 1+2 (21G-1) is shown for comparison. (d) ELISA analysis showing binding of NCAM domain 1 loop-graft variant 23B-2 to the target antigen (monoclonal antibody 5G-8) but not to negative control antigens. The parental anti-5G-8 IgNAR (1A-7) similarly binds, but not the wild type NCAM domain 1 or domain 1+2. (e) Biosensor traces of NCAM domain 1 (21H-5) and loop-graft variant 23B-2 recombinant proteins. The loop graft protein binds. The wild type does not.
Figure 25C:
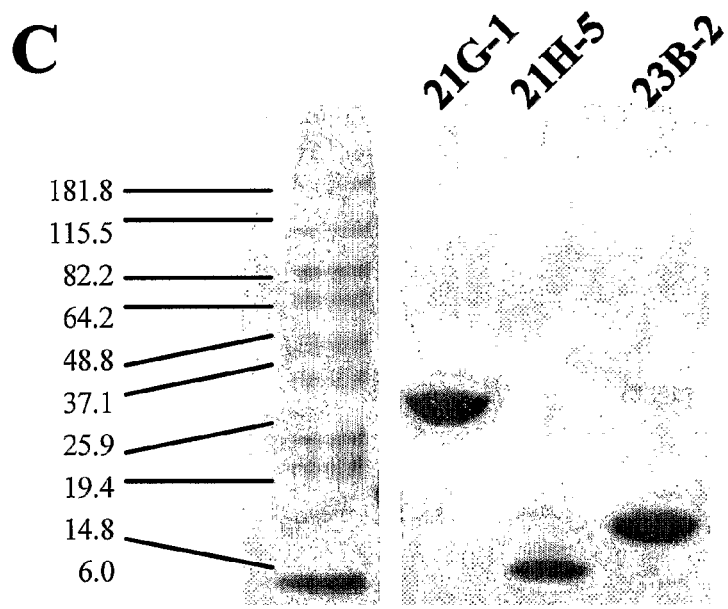
Figure 25D:
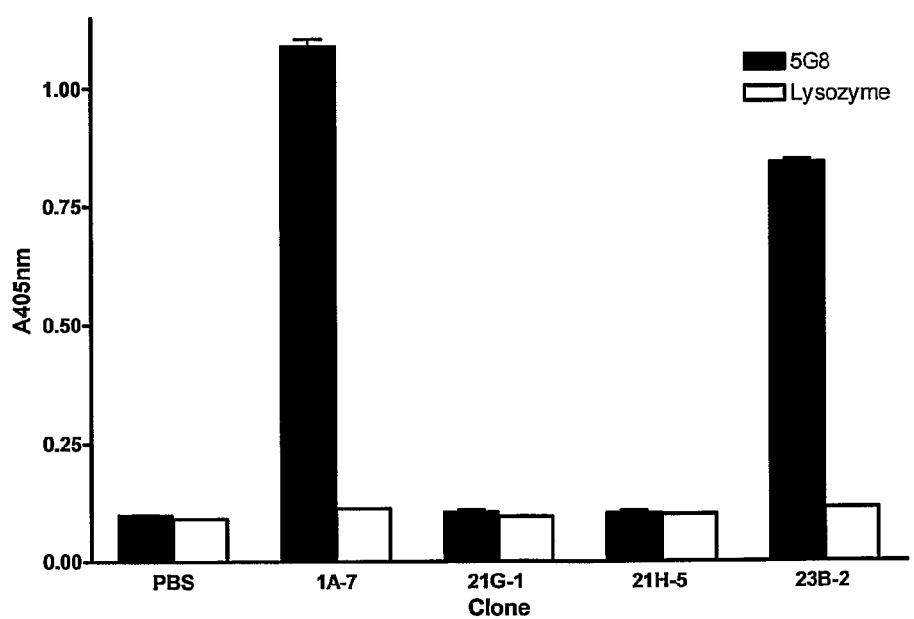
Figure 25E:
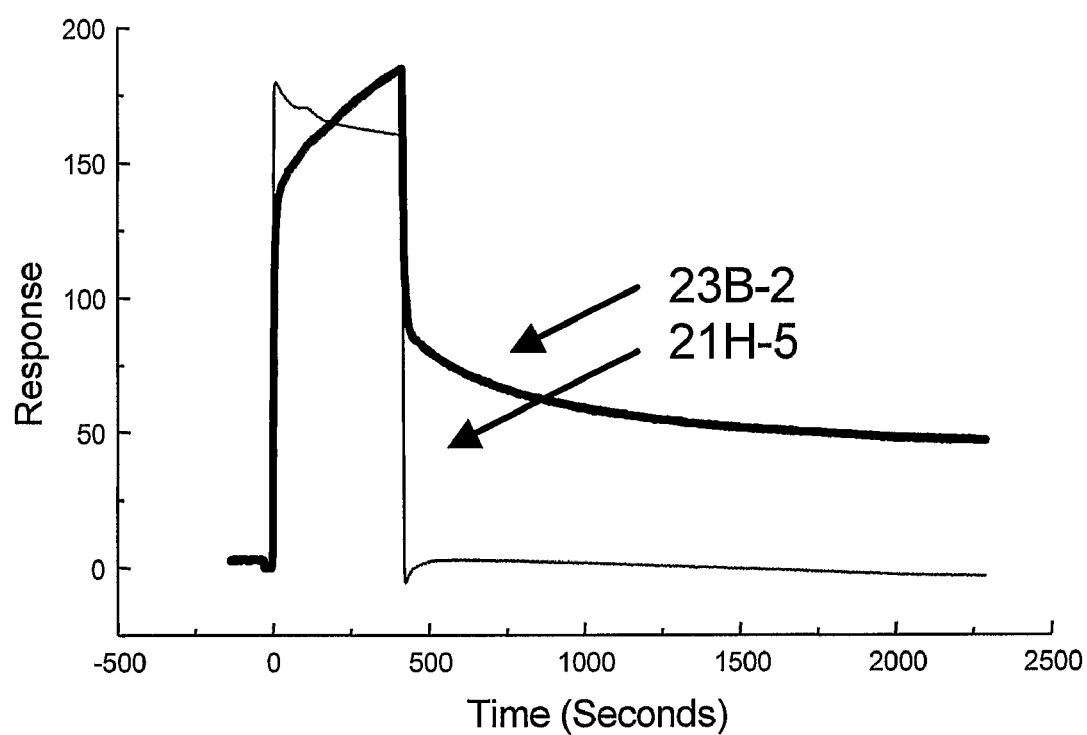

Protein expression and purification showed that the resulting recombinant protein appeared more stable than the wild type, for example there appeared little degradation by SDS-PAGE (see FIG. 25(c)), and a single peak by FPLC (see FIG. 25(b)). This protein when placed in crystallisation trials gave several strong crystal leads, indicating that it was folded into a stable and ordered structure. Recombinant protein 23B-2 specifically interacted with the target antigen (monoclonal antibody 5G-8) but not to a negative control antigen (lysozyme) in an ELISA (see FIG. 25(d)). Specific binding of the 23B-2 but not wild type NCAM domain 1 was confirmed by Biosensor (see FIG. 25(e)).

Telokin 1A-7 Loop Grafts

The best Telokin/shark 1A-7 CDR3 loop grafts (models 3 & 5) were constructed by overlap PCR using oligonucleotide primers A1022 (primary extension primer) (SEQ ID NO: 90) and A1023 (secondary extension primer) (SEQ ID NO: 91) (Model 3) (SEQ ID NO: 127), and primers A1024 (primary extension primer) (SEQ ID NO: 92) and A1025 (secondary extension primer) (SEQ ID NO: 93) (Model 5) (SEQ ID NO: 129). The resulting clones were designated 24F-4 (SEQ ID NOs: 43 & 44) (model 3) and 23C-7 (SEQ ID NOs: 45 & 46) (model 5), and were verified by DNA sequencing.

Figure 26C:
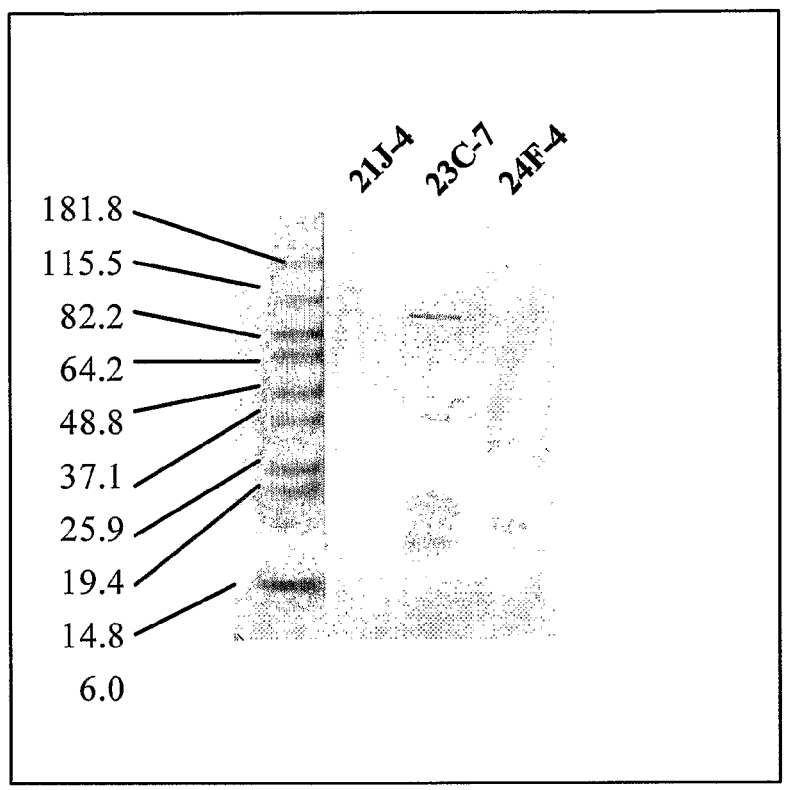
FIG. 26: (a) Alignment of Telokin (21J-4) and loop-graft variants 23C-7 and 23F-4. Dual C-terminal FLAG affinity tags are not shown. (b) FPLC traces of recombinant proteins 21J-4, 23C-7, and 23F-4. (c) SDS-PAGE profiles of recombinant proteins 21J-4, 23C-7, and 23F-4. (d) ELISA analysis showing binding of Telokin loop-graft variants 23C-7 and 23F-4 to the target antigen (monoclonal antibody 5G-8) but not to negative control antigens. The parental anti-5G-8 IgNAR (1A-7) similarly binds, but not the wild type Telokin (21J-4). (e) Biosensor traces of Telokin (21J-4) and loop-graft variant 23F-4 recombinant proteins. The loop graft protein binds. The wild type does not.
Figure 26D:
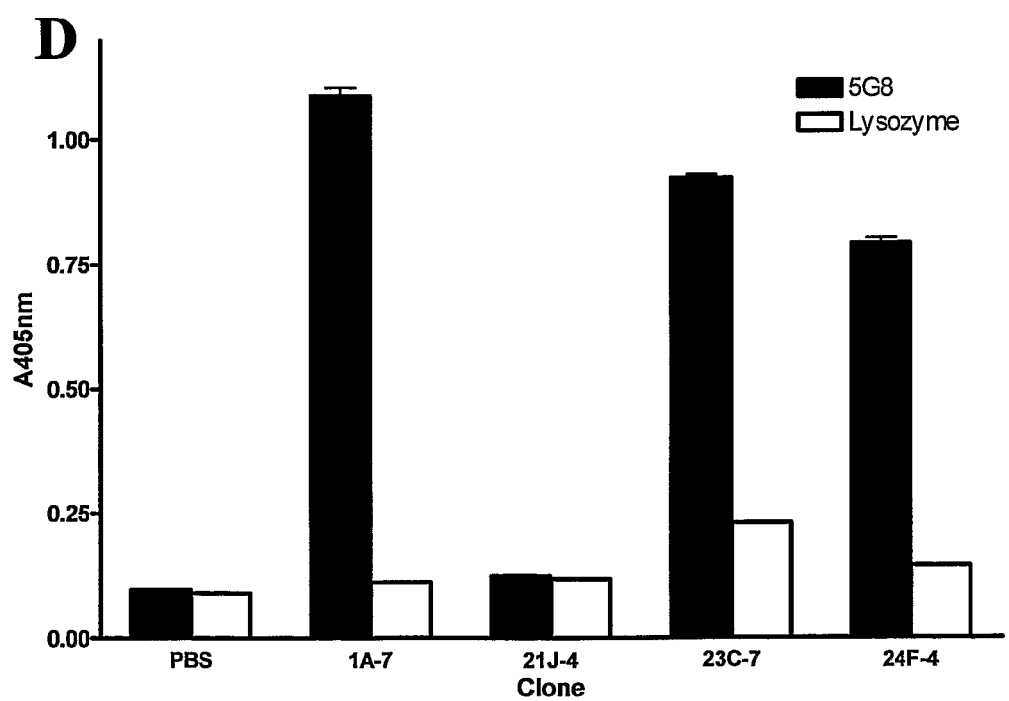
Figure 26E:
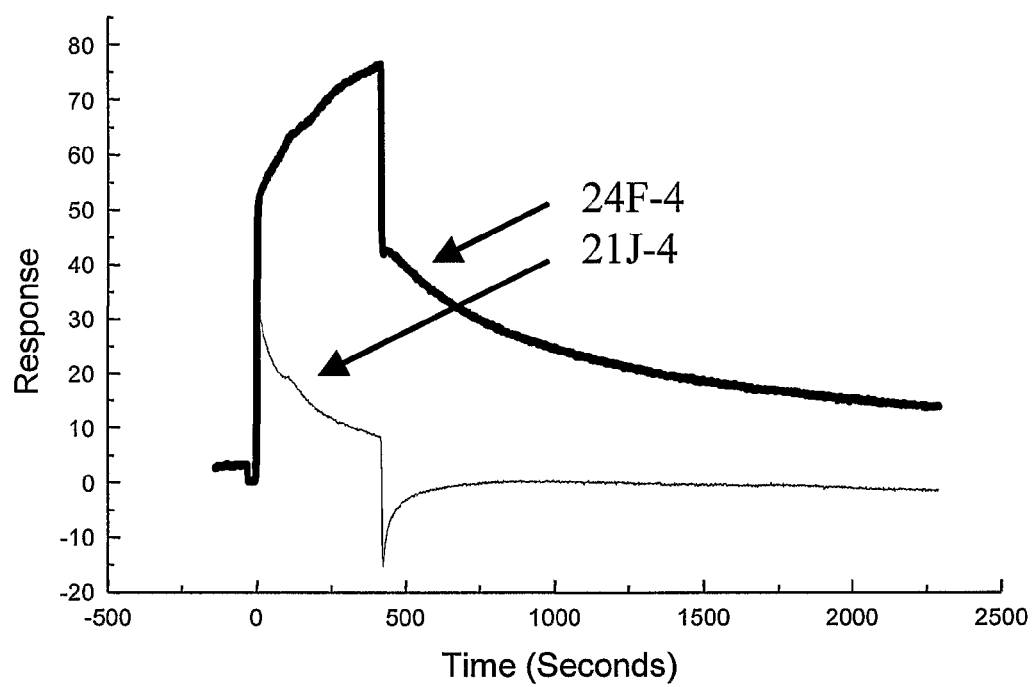

Protein expression and purification showed that the resulting recombinant proteins were expressed into the *E. coli* periplasmic space. FPLC traces and SDS-PAGE profiles of the recombinant proteins are shown in FIG. 26(b) & (c). Both loop graft model recombinant protein (23C-7, 24F-4) specifically interacted with the target antigen (monoclonal antibody 5G-8) but not a negative control antigen (lysozyme) (see FIG. 26(d)). Specific binding of the 24F-4, but not wild type Telokin, was confirmed by Biosensor (see FIG. 26(e)).

Example 9

Generation of Therapeutics or Diagnostics by Loop Grafting from Human Domains to Shark $V_{NAR}$s The structures of IgNARs human Immunoglobulin superfamily I-set domains are homologous enough to allow prediction of framework/loop region junctions, take-off angles of strands, and loop orientations. I-set domains such as ICAM-1 have been implicated as receptors for viruses such a rhinovirus. Binding loops on ICAM-1 specific for rhinovirus binding can be grafted to $V_{NAR}$ frameworks, giving rise to novel binding moieties. This can be further expanded to other viral diagnostics based on I-set domains.

For example, the following modifications may be made to shark NARs:
1. Grafting of rhinovirus-binding ICAM-1 VLR loops onto the 12Y-2 framework.
2. Grafting of rhinovirus-binding ICAM-1 VLR loops onto the 12Y-1 framework.
3. Grafting of rhinovirus-binding ICAM-1 VLR loops onto a $V_{NAR}$ framework.
4. Grafting of rhinovirus-binding ICAM-1 VLR loops onto a dimeric or multimeric $V_{NAR}$ framework.
5. Grafting of rabies virus-binding NCAM VLR loops onto the 12Y-2 framework.
6. Grafting of rabies virus-binding NCAM VLR loops onto the 12Y-1 framework.
7. Grafting of rabies virus-binding NCAM VLR loops onto a $V_{NAR}$ framework.
8. Grafting of rabies virus-binding NCAM VLR loops onto a dimeric or multimeric $V_{NAR}$ framework.
9. Grafting of virus-binding I-set VLR loops onto a $V_{NAR}$ framework.
10. Grafting of virus-binding I-set VLR loops onto a dimeric or multimeric $V_{NAR}$ framework.

VLRs are the variable loop regions of V-set and I-set domains, these being the loop regions which typically extend between β-strand conformations and which demonstrate natural amino acid variation without compromising the framework structure of the domain. VLRs include those regions typically referred to as CDRs.

Example 10

Generation of Soluble Human Variable Domains by "Sharkisation": CDR2 Region

CDR2 loops generated by the C' and C" strands of the V-set immunoglobulin superfamily proteins are important in antigen binding and maintenance of the solvent solubility of the immunoglobulin. With the shark domain CDR2 loop equivalent in "bottom" position, there is now a solvent-exposed patch of residues at the C-terminus of loop region 4 and in the C and D β-strands, which in other immunoglobulin domains is shielded by the CDR2 loop. This solvent-exposed face consists mainly of the 12Y-2 residues Lys32, Asp33, Thr34, Gly35, Tyr55, Glu57, Thr58. The charged and polar patch formed by residues Asp33-Thr34-Glu57 appears to be particularly significant.

In one example, these residues may be "transferred" to I-set variable domains, for example neural cell adhesion molecules (NCAMs), to render these proteins more soluble when expressed in a single domain format.

In another example, these residues may be "transferred" to V-set domains such as TCRs and antibodies, where the CDR2 loop has been removed to avoid superantigen stimulation. See, for example, the following table:

| Residue 12Y-2 | Residue 12Y-1 | Conservation | TCR α§ | TCR α conservation |
|---|---|---|---|---|
| Lys32 | Glu32 | minimal | Gly30 | minimal |
| Asp33 | Ser33 | Charged/polar | Ser31 | S, F, P, T |
| Thr34 | Thr34 | 100%* | Phe32 | F, L, I |
| Gly35 | Gly35 | G, Y, D, S¶ | Phe33 | F, L, H, Q |
| Tyr55 | Tyr55 | 100%* | Phe62 | F, M, L |
| Glu57 | Glu57 | 100%* | Thr63/Ala64 | varies |
| Thr58 | Thr58 | 100%* | Gln65 | Q, F, E, L |

§For TCR α of 1ao7.
¶In Nurse shark Type1, this position occupied by half-cysteine.
*Across Wobbegong, Nurse, and Bamboo sharks, Types 1, 2, & 3 IgNARs.

Example 11

Generation of Soluble Human TCRs by "Sharkisation": VH/VL Interface

Attempts in the past to produce single human TCR domains have been problematic at best, due to low solubility and difficulty in expression. Comparison of the 12Y-1 and 12Y-2 $V_{NAR}$s to the TCR α (and β) domains show a number of aspects where the human TCR could be modified by reference to the shark structure. "Sharkisation" gives us the opportunity to separately produce the TCR Vα or Vβ domain and enhance its solubility by directed mutation.

Table 6 presents a comparison of TCR interfaces with the 12Y-2 and camelid variable domains. This analysis suggests that the following modifications may be made to enhance solubility of TCR domains:
1. Residue Ser31 in the TCR interface is almost always a serine or tyrosine: thus a polar residue. In $V_{NAR}$s it can be a charged (Asp) residue, or a serine in ~50% of cases. Mutation of residue 31 of a TCR domain to Asp may therefore enhance solubility.
2. Significant residues in the TCR domain interface are Pro43/Leu89/Phe106 (and equivalents). This is an extensive hydrophobic patch in TCR Vα and Vβ domains. Mutation of these residues to form a charged pocket, similar to that formed by residues Glu46, Lys82, Lys104 of 12Y-2 may therefore enhance solubility.

Example 12

Generation of Soluble Antibody Variable Domains by "Sharkisation": VH/VL Interface Attempts in the past to produce single antibody variable domains have encountered solubility and expression problems. Comparison of the 12Y-1 and 12Y-2 $V_{NAR}$s to antibody VH and VL domains shows a number of aspects where these individual domains could be modified by reference to the shark structure, to improve solubility and expression levels. For example:
1. Modification of the VH or VL interface to enhance solubility of the isolated single domain, using residues described in Example 11 above. Mutation of these residues to form a charged pocket, similar to that formed by residues Glu46, Lys82, Lys104 of 12 Y-2 may therefore enhance solubility.

Example 13

Modification of $V_{NAR}$ Dimers

The 12Y-1 & 12Y-2 dimer forms are a continuous 8-stranded β-sheet underneath the loop regions (buried surface area at interface ~1760 Å$^2$). The interactions between the 2-fold monomers involve main-chain β sheet interactions between D strands and between loop region 8 as well as side-chain interactions and water mediated contacts. This suggests a significant propensity for dimer interactions with non-standard involvement of loop regions in complex formation.

The dimer form may act as a single binding entity with the loop region 8 residues and framework residues of the dimer available for mutation and library selection. This suggests that the following modifications may be made to generate binding moieties with potential diagnostic or therapeutic applications:
1. Stabilisation of a recombinant dimer by introduction of cysteine residues at positions Lys61 and Glu57 in the D strand of a $V_{NAR}$. Alternatively, stabilisation may be achieved by the introduction of cysteine residues at positions Ile51 and either Lys61 or Gly62 in the D strand.
2. Stabilisation of the recombinant dimer by introduction of cysteine residues at positions Lys32 and Asp33 in loop region 4 of the $V_{NAR}$.
3. Stabilisation of the recombinant dimer by introduction of cysteine residues at position Val 59.
4. Stabilisation of a recombinant dimer by introduction of cysteine residues at positions Leu98 and/or Leu99 in loop region 8 of the $V_{NAR}$ region.
5. Randomisation of loop region 8 of 12Y-2 and β sheet residues to form a binding surface. For eg 12Y-2 residues Asp26-Glu30 inclusive (27 should be hydrophobic); Tyr87-Glu103, though buried residues should be hydrophobic. In this case residues Asp93-Tyr96 are from the symmetry related molecules.
6. Randomisation of the loop regions 4 and 8 of the $V_{NAR}$ and β sheet residues to form a binding surface. It will be appreciated that the loop region sequences will be different for each example.
7. Multimerisation by using the dimer to present two copies of the same binding specificity.
8. Multimerisation by using the dimer to present two different binding specificities.

Modification of the $V_{NAR}$ Dimer

If the crystallographic dimer is a natural form, and the continuous 8-stranded β-sheet is formed under physiological conditions, then various residues are paired across the dimer interface. Thus, in the crystallographic structure the side chains of Leu99 residue are adjacent, in the correct orientation, and of appropriate distance (~3A) to from a disulphide bridge.

To test this hypothesis, the double 12Y-2 mutant Pro90Leu and Leu99Cys was created. These mutations enhance the natural affinity for the target antigen (Pro90Leu), making binding easier to detect, and are in the correct position to moderate dimerisation (Leu99Cys).

Overlap PCR using oligonucleotide primers was used to construct DNA clone 21B-5 (SEQ ID NO: 13 & 14). This was confirmed as correct by DNA sequencing.

Figures 27A, 27B:
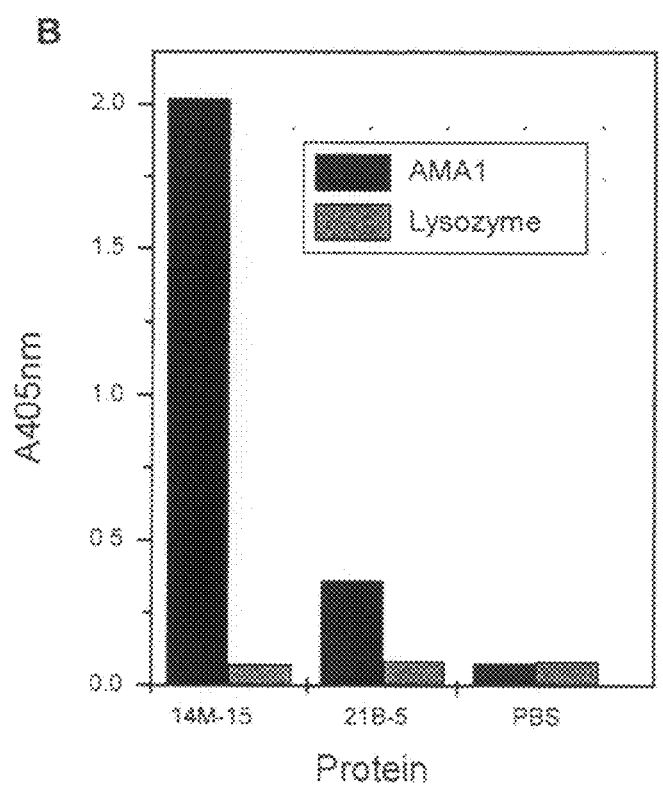
FIG. 27: (a) Alignment of 12Y-2 variants 14M-15 and 21B-5. (b) Affinity purified proteins 21B-5 and 14M-15 binding to the target antigen AMA1 and a negative control antigen. (c) FPLC traces of 12Y-2 variants 14M-15 and 21B-5, the disulphide-bonded dimer runs as a dimer. (d) Biosensor traces of purified 21B-5 monomeric and dimeric forms. The disulphide-bonded dimer does not bind the target antigen, demonstrating both the importance of the CDR3 and that the novel dimer form presents a different interface to antigen than the monomeric protein. (e) SDS-PAGE and western blot analysis 12Y-2 variants 14M-15 and 21B-5. The disulphide-bonded dimer runs as a dimeric form in the absence of reducing agent (β-mercaptoethanol). Incorporation of Leu99Cys drives the dominant protein form to dimer.
Figure 27C:
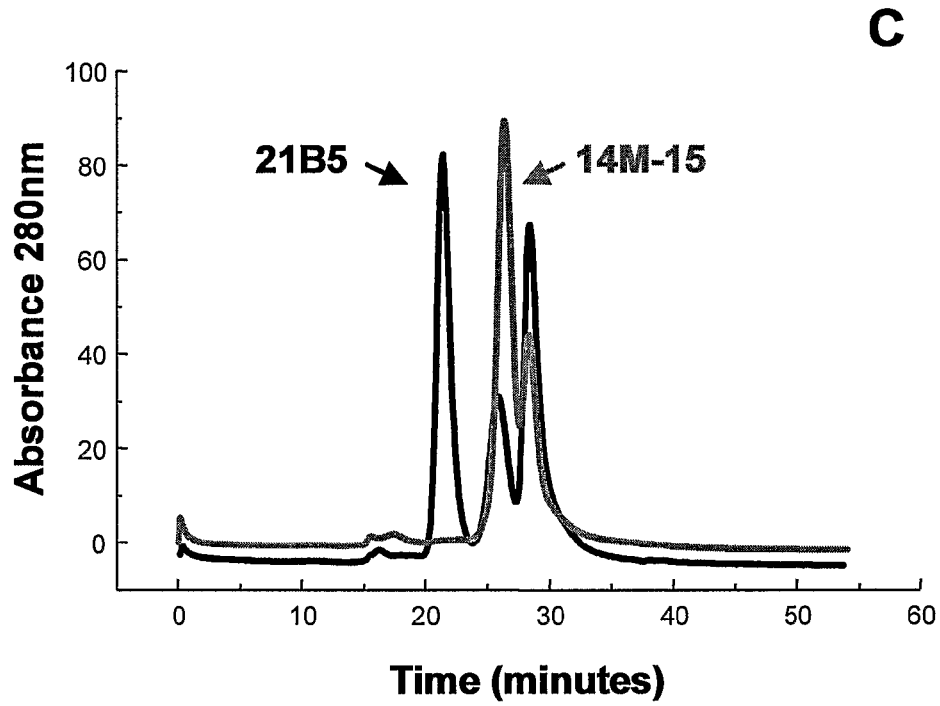
Figure 27D:
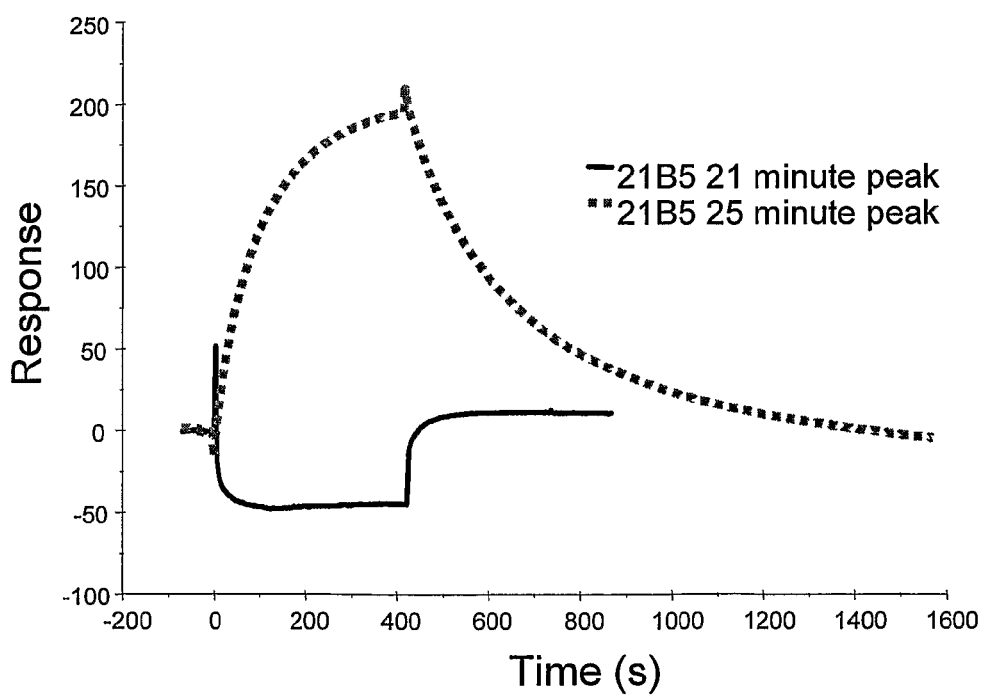
Figure 27E:
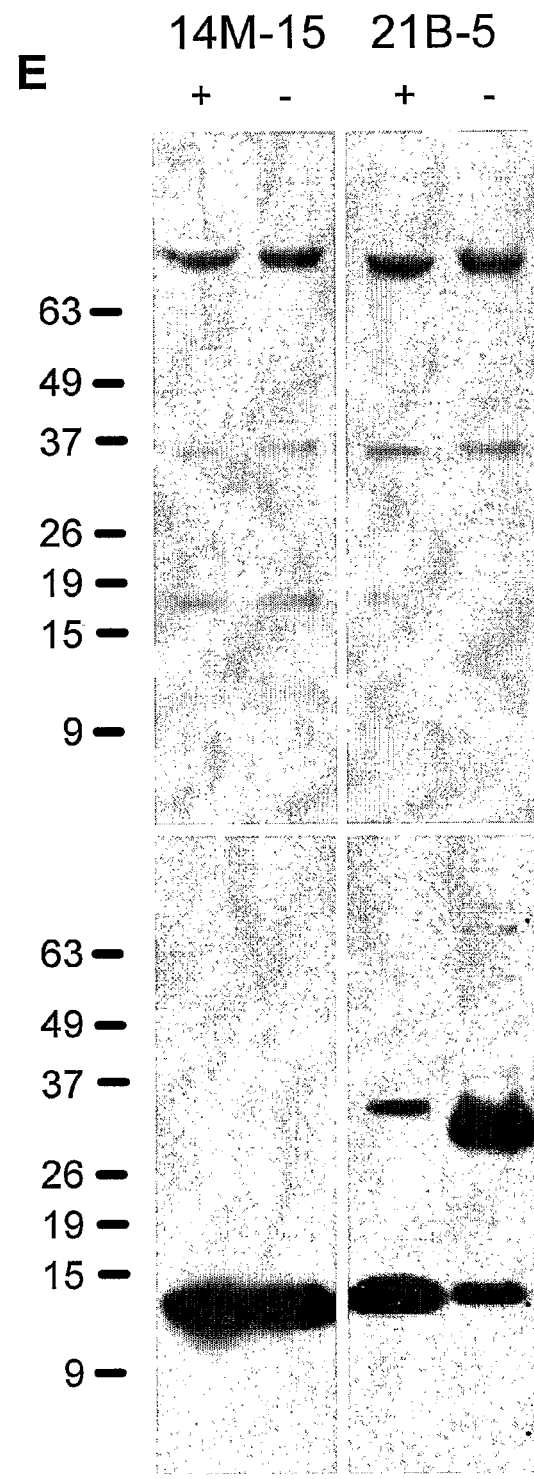

The resultant clone 21B-5 was clearly visible as a dimer form by FPLC and by SDS-PAGE in the absence of reducing agent (see FIG. 27(c) & (e)), compared to the wild type (14M-15, Pro90Leu only). Purified monomer bound immobilised AMA1 by ELISA and by biosensor (See FIG. 27(b) & (d)). The purified disulphide-linked dimer did not bind the target antigen, demonstrating both the importance of the CDR3 and that the novel dimer form appears to present a different interface to antigen than the monomeric protein. The dimer species could be crystallised, is stable, and may form the basis of a binding interface different from that of monomeric IgNAR forms.

Example 14

Design, Construction, and Screening of Human I-Set Domains Based on Shark IgNAR Principles Shark IgNAR antibodies are structurally close to I-set domain immunoglobulins such as Telokin and domain 1 of NCAM. Specifically, what would otherwise be a CDR2 loop is at the "bottom" of the molecule. The foregoing structural, protein engineering, and library selection experiments suggest that the principles learnt from shark IgNAR antibody structures can be successfully applied to the generation of binding repertoires of human I-set immunoglobulins. Such libraries are anticipated to primarily contain variability in the CDR1 and CDR3 analogous regions. The foregoing experiments also indicated that downstream affinity maturation strategies targeting framework regions (as well as the loop regions) of the NCAM and Telokin domains may result in altered and enhanced binding affinities and specificities.

Shark IgNAR antibodies and NCAM domain 1 and Telokin were modelled to determine the best CDR-framework junction residues for mutation and incorporation of library randomisation. This allowed incorporation of randomised "CDR" loops which varied in both length and sequence. Additionally, in at least one variant for each of NCAM and Telokin, the human CDR3 framework was extended by analogy with the successful human/shark model 5 loop grafts, to provide a CDR3 loop extending several residues above the NCAM or Telokin scaffold (NCAM/A0988 library; Telokin/ A1017 library).

Following identification of framework junctions, oligonucleotide primers were designed to build human-scaffold-based libraries, based on both NCAM domain 1 and Telokin domain.

NCAM library oligonucleotide primers: A0980 NCAM CDR1 randomisation 6-loop (SEQ ID NO: 82); A0981 NCAM CDR1 randomisation 7-loop (SEQ ID NO: 83); A0982 NCAM CDR3 randomisation: rev compl; 8 loop (SEQ ID NO: 84); A0987 NCAM CDR3 randomisation: rev compl; 11 loop (SEQ ID NO: 85); A1018 NCAM CDR3 randomisation: rev compl; 14 loop (SEQ ID NO: 86); A0988 NCAM CDR3 randomisation: rev compl; 8 loop based on Model 5 (SEQ ID NO: 87).

Telokin library oligonucleotide primers: A1001 Telokin CDR1 randomisation; 7 loop (SEQ ID NO: 94); A1002 Telokin CDR1 randomisation; 9 loop (SEQ ID NO: 95); A1000 Telokin CDR3 randomisation: rev compl; 6 loop (SEQ ID NO: 97); A1003 Telokin CDR3 randomisation: rev compl; 9 loop (SEQ ID NO: 98); A1004 Telokin CDR3 randomisation: rev compl; 12 loop (SEQ ID NO: 99); A1017 Telokin CDR3 randomisation: rev compl; 9 loop based on Model 5 (SEQ ID NO: 100).

Three molecular libraries were constructed as follows:

| No | Library | CDR coverage | Final Size |
|----|---------|--------------|------------|
| 1 | NCAM 1 + 3 | CDR1, CDR3 | $6 \times 10^7$ |
| 2 | NCAM 3 | CDR3 | $7 \times 10^4$ |
| 3 | Telokin 1 | CDR1 | $5. \times 10^6$ |

Figure 30:
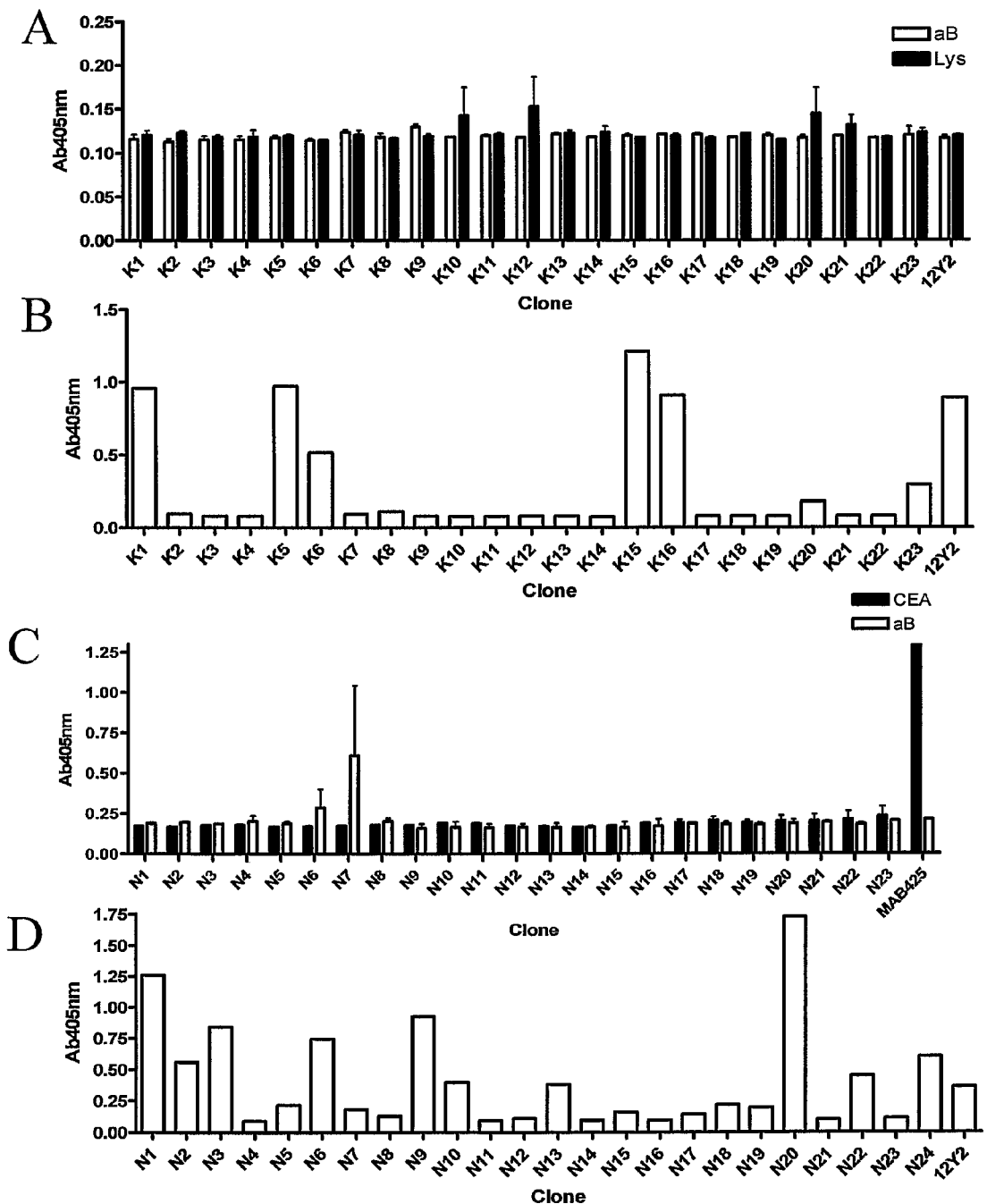
FIG. 30. Immunopanning of NCAM domain 1 library by bacteriophage display against amyloid aβ (1-42) peptide (panels A & B) and the Carcino Embryonic Antigen (CEA) (panels C & D). Binding to antigens (panels A & C) and comparative expression levels of individual clones (panels B & D) are shown.
Figure 31:
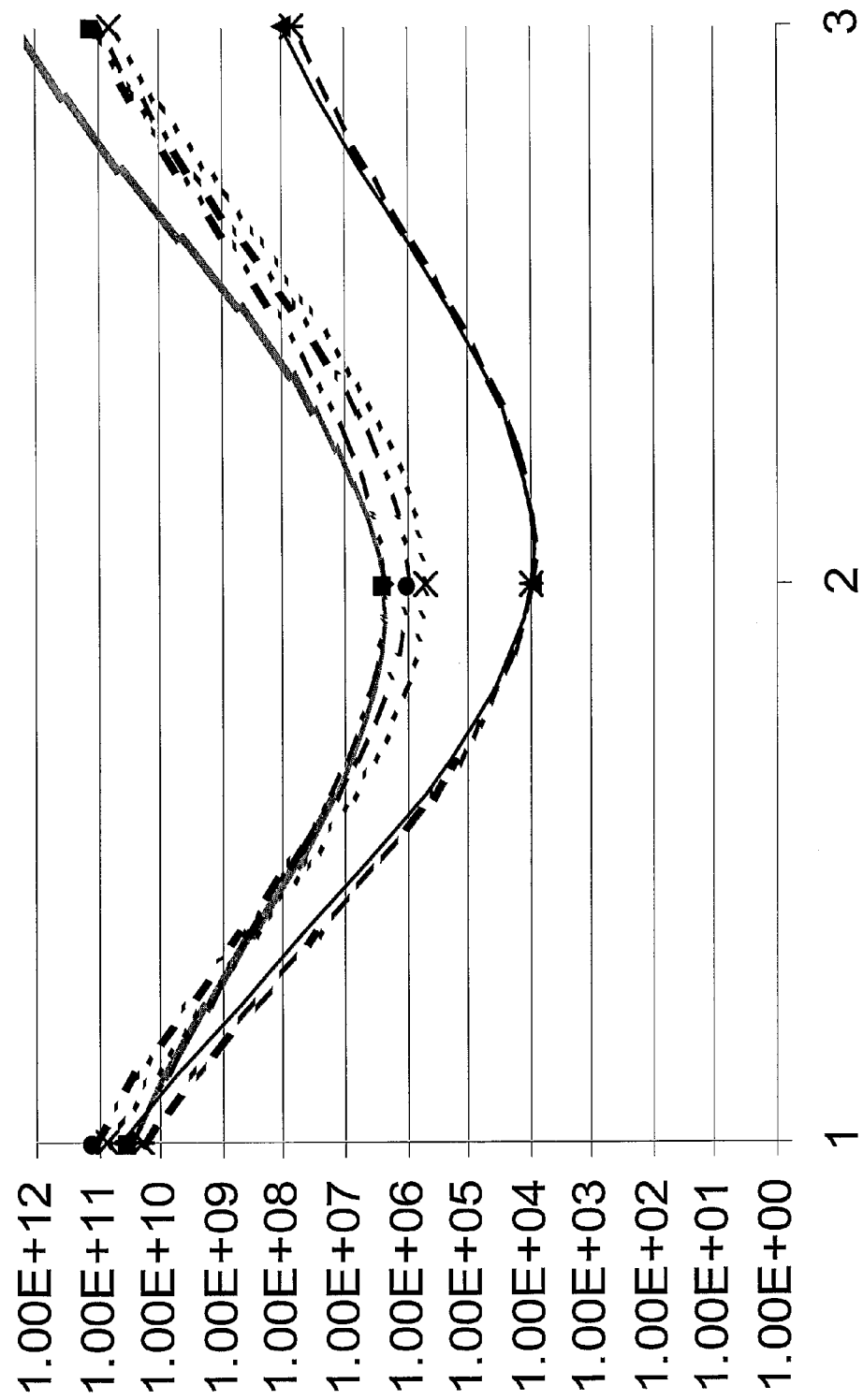
FIG. 31. Titers of eluted phage/ml from NCAM library panned against monoclonal antibody 5G8 (♦), AMA1 (■), Hepatitis B virus E antigen (▲-), ab 1-42 peptide (-x-), Carcino Embryonic Antigen (*); and, the Telokin library panned against monoclonal antibody 5G8 (●).

Library numbers 1 and 2 from the above table were pooled and immunopanned by bacteriophage display against amyloid aβ (1-42) peptide and the Carcino Embryonic Antigen (CEA). FIG. 30 shows the results of the panning against amyloid aβ (1-42) peptide (panels and A and B) and CEA (panels and C and D). In particular, binding to antigens (panels A & C) and comparative expression levels of individual clones (panels B & D) are shown. FIG. 31 shows the titers of eluted phage from the NCAM library panned against monoclonal antibody 5G8 (-♦-), AMA1 (-■-), Hepatitis B virus E antigen (-▲-), ab 1-42 peptide (-x-), Carcino Embryonic Antigen (*); and, the Telokin library panned against monoclonal antibody 5G8 (●).

Example 15

12Y-2 IgNAR Protein Stability

Figure 32:
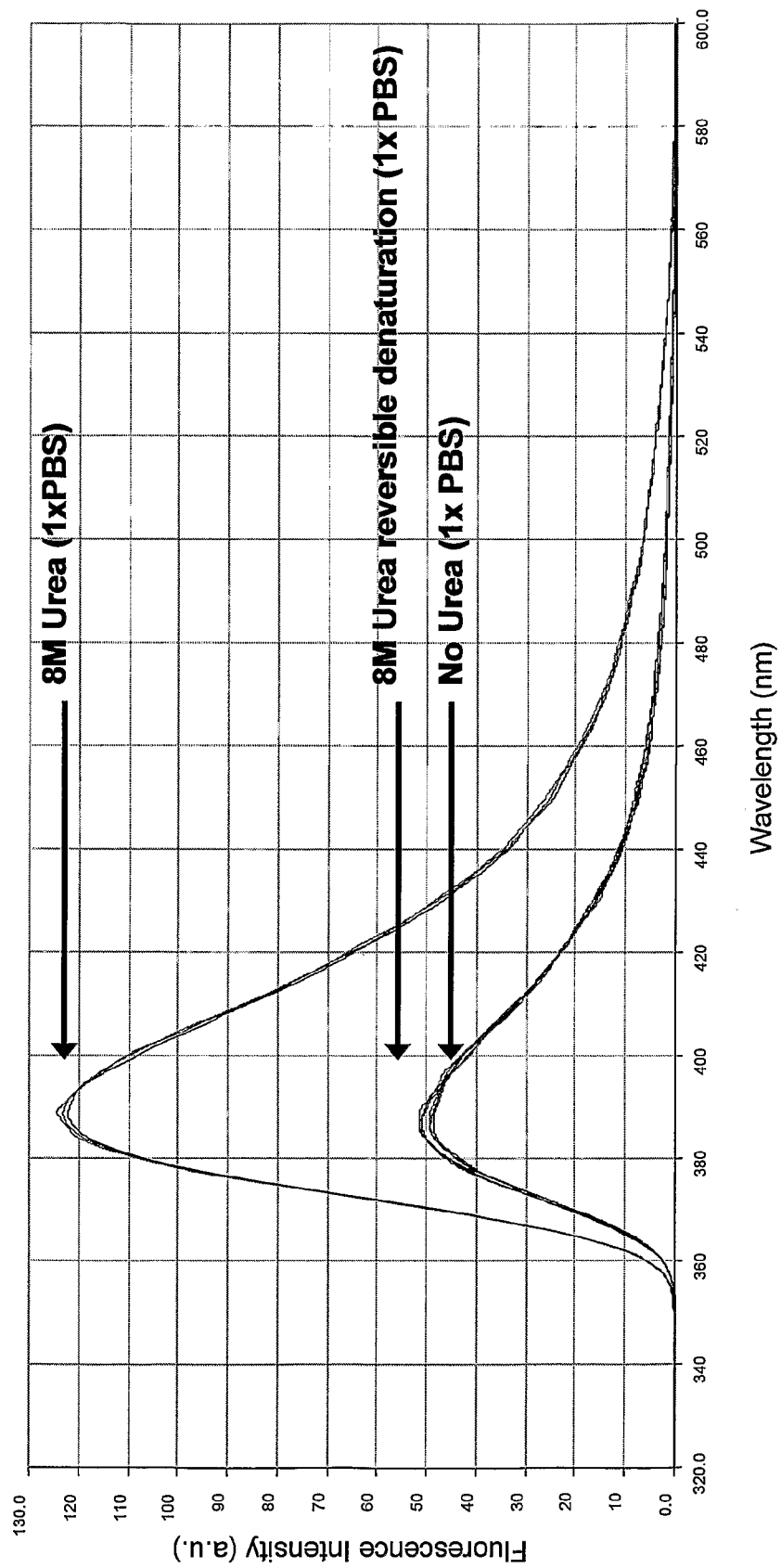
FIG. 32: Fluorescent intensity graph following regeneration of $V_{NAR}$ 14M-15 (12Y-2 Pro90Leu variant) after denaturation in 8M urea.
Figure 34A:
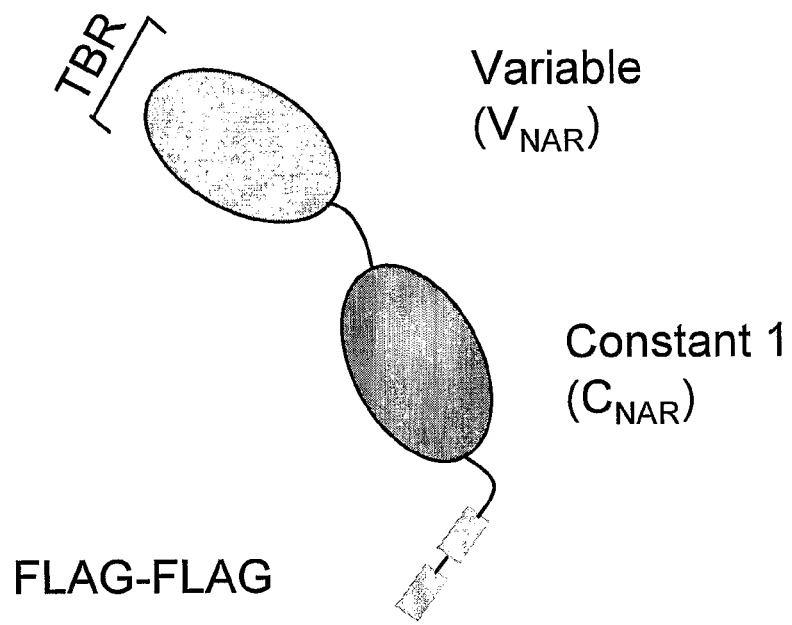
FIG. 34: (a) Cartoon of 17T-6 protein, with 12Y-2 variable and constant domain. 1. (b) Comparative FPLC traces of IgNARs 12Y-2 and 17T-6. (c) SDS PAGE of IgNARs 12Y-2 and 17T-6. (d) Biosensor traces of equal masses of IgNARs 12Y-2 and 17T-6 binding to immobilized AMA1.
Figure 34B:
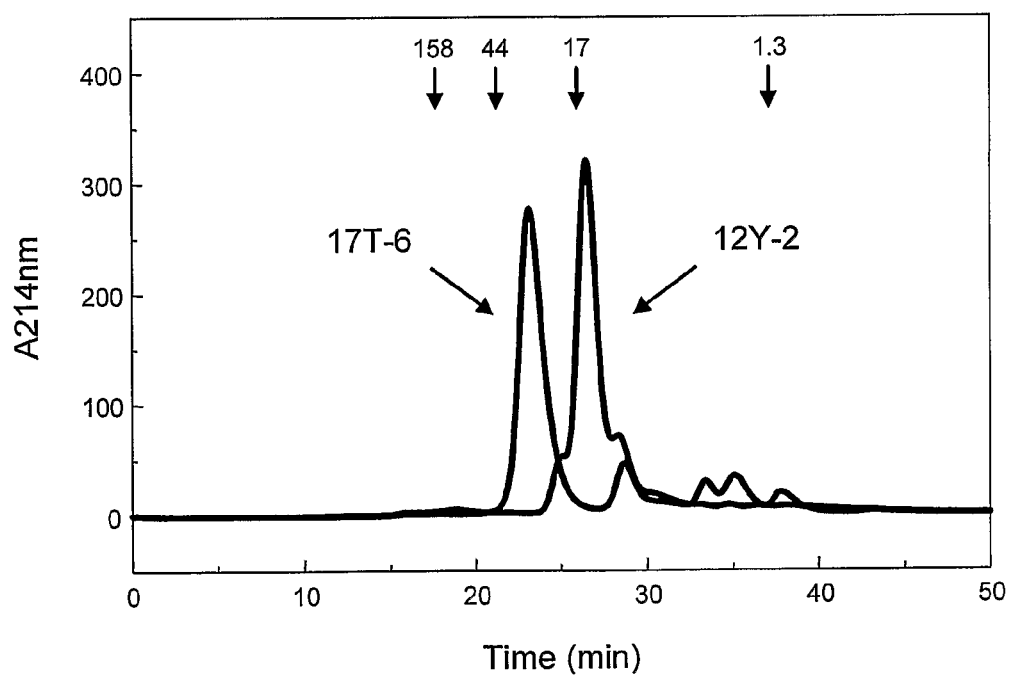
Figure 34C:
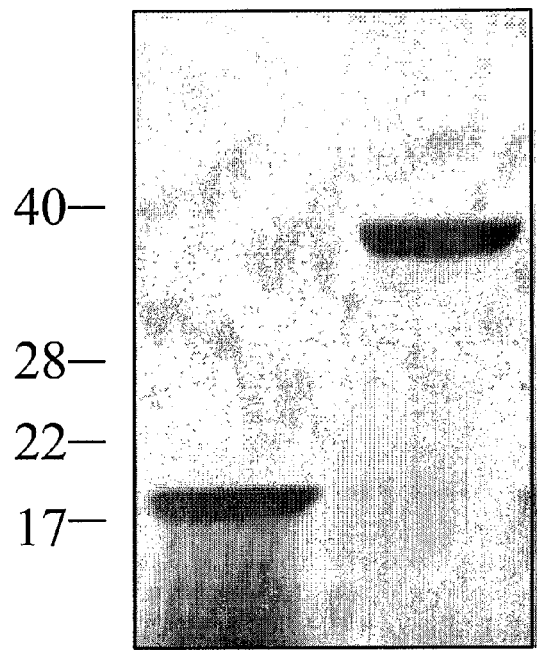
Figure 34D:
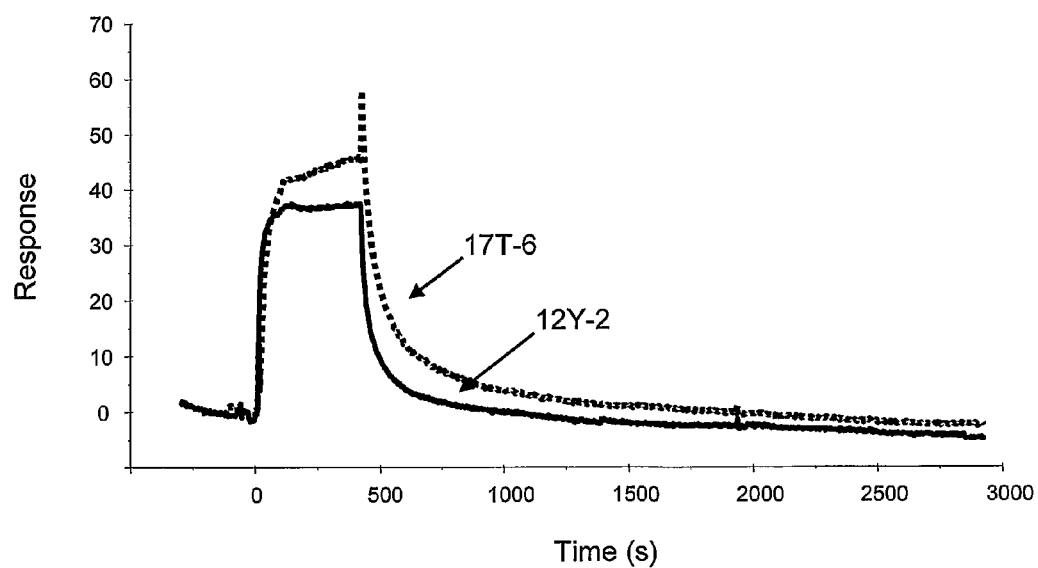

Shark blood is rich in urea. Thus IgNAR domains may be hypothesised to have evolved to be unusually resistant to treatment with such harsh chemical agents. Recombinant IgNAR 14M-15 (12Y-2 Pro90Leu variant) (SEQ ID NO: 11) was tested for its ability to refold after denaturation in 8M urea. Regeneration was measured by intrinsic fluorescent intensity (see FIG. 32). The IgNAR domain re-folded to its native conformation following removal of the urea.

Example 16

Full IgNAR Coding Sequence and the Production of Variable and Constant Domain Reagents for Biosensor Analysis The full wobbegong shark (*Orectolobus maculatus*) IgNAR coding sequence was cloned from shark cDNA (clone designated 18H-2 (SEQ ID NOs: 31 & 32)). The full DNA and amino acid sequences are given in FIG. 33. The DNA sequence encodes a single polypeptide chain encompassing one IgNAR I-set domain and 5 C-domains (see FIG. 34(*a*)). In the mature IgNAR antibody, these chains form a dimer mediated by half-cystine residues at positions Cys430 and Cys660. The resulting two disulphide bridges are located (1) C-terminal to constant domain 3 and N-terminal to constant domain 4 and (2) C-terminal to constant domain 5. The numbering adopted is for protein 18H-2; residues numbers will be different in each IgNAR due to the size differences in the variable domains.

Each constant domain is ~12 kDa in molecular weight. Sequential addition of constant domains 1, 2, and 3 to an IgNAR variable domain produce a set of single chain monovalent proteins with identical affinity for antigen, but varying in their molecular weight (see table below). For example, addition of the 12Y-2 variable domain to varying numbers of constant domains produces a set of molecules with identical affinities for the target antigen AMA1, but with varying molecular weights. Of the variety of biosensors available, many rely on mass differences. These reagents provide an ideal test system of measuring the effect of mass differences for a single affinity.

| Clone Designation | SEQ ID NOs | Format | Product MW | No. of Residues |
|---|---|---|---|---|
| 12Y-2 | 3 & 4 | V | 12,469 | 113 |
| 17T-6 | 33 | V + C1 | 24,260 | 219 |
| 18C-4 | 34 | V + C1 + C2 | 35,092 | 319 |
| 18J-1 | 35 | V + C1 + C2 + C3 | 46,821 | 425 |

12Y-2 and 17T-6 proteins were compared by protein chemistry and biosensor (see FIG. 34(*b*)-(*d*)). Results indicate that 17T-6 (i.e. 12Y-2+constant domain 1) is produced as a soluble monomeric protein of the correct molecular weight. It has identical binding affinity for the target AMA1 as does the parent 12Y-2, when adjusted for mass.

Example 17

Modelling of Type 3 IgNAR

One of the Type 2 IgNAR variable domains solved structures is 12A-9. This structure has a disulphide linkage between loops regions 4 and 8 (i.e. between the CDR1-CDR3 analogous regions). This particular IgNAR is similar in CDR3 length and disulphide-bond position to Type 3 IgNARs, which are found in embryonic sharks. See Genbank AAM77190 (SEQ ID NO: 29) and AAM77191 (SEQ ID NO: 30) (Nurse shark Type 3 IgNARs).

As a class, the Type 3 IgNAR variable domains are characterized by constant length loop regions analogous to CDR3s, disulphide bonds connecting the CDR1 and CDR3 analogous loops (which happens to be in the same position as in 12A-9), and a conserved tryptophan residue at position 31. Alignment of 12A-9 with Two Type 3 IgNARs
CLUSTAL W (1.74) Multiple Sequence Alignment

```
12A9      ARVDQTPRIATKETGESLTTNCVLRDTACALDSTNWYRTKLGSTKEQTISIGGRYSETVD
AAM77190  ARVDQTPKTITKETGESLTTNCVLSDTSCAWDSTYWYRKKLDSTNEESTSKGGRYVETVN
AAM77191  ARVDQTPKTITKETGESLTTNCVLSDTSCAWDSTYWYRKKLDSTNEESTSKGGRYVETVN
          *******:**************.**:** *** ***.**.**:*:: * **** ***:

12A-9     EGSNSASLTIRDLRVEDSGTYKCKAYRRCAFNTGVGYKEGAGTVLTVK
AAM77190  SESTSFSLRTNDLTVEDSGTYRCRAYLYCGSQLDSFDEYGGGTIVTVS
AAM77191  SESTSFSLRINDLTVEDSGTYRCRAYLYCGAELDSFDEYGGGTIVTVN
          . *.* ** *.** *******.*:**  *.  :      : *.**:.**.

12A-9     ARVDQTPRIATKETGESLTINCVLRDTACALDSTNWYRTKLGSTKEQTISIGGRYSETVD
AAM77191  ARVDQTPKTITKETGESLTINCVLSDTSCAWDSTYWYRKKLDSTNEESTSKGGRYVETVN
          *******:**************.**:** *** ***.**.**:*:: * **** ***:

12A-9     EGSNSASLTIRDLRVEDSGTYKCKAYRRCAFNTGVGYKEGAGTVLTVK
AAM77191  SESTSFSLRINDLTVEDSGTYRCRAYLYCGAELDSFDEYGGGTIVTVN
          . *.* ** *.** *******.*:**  *.  :      : *.**:**:
```

Figure 35:
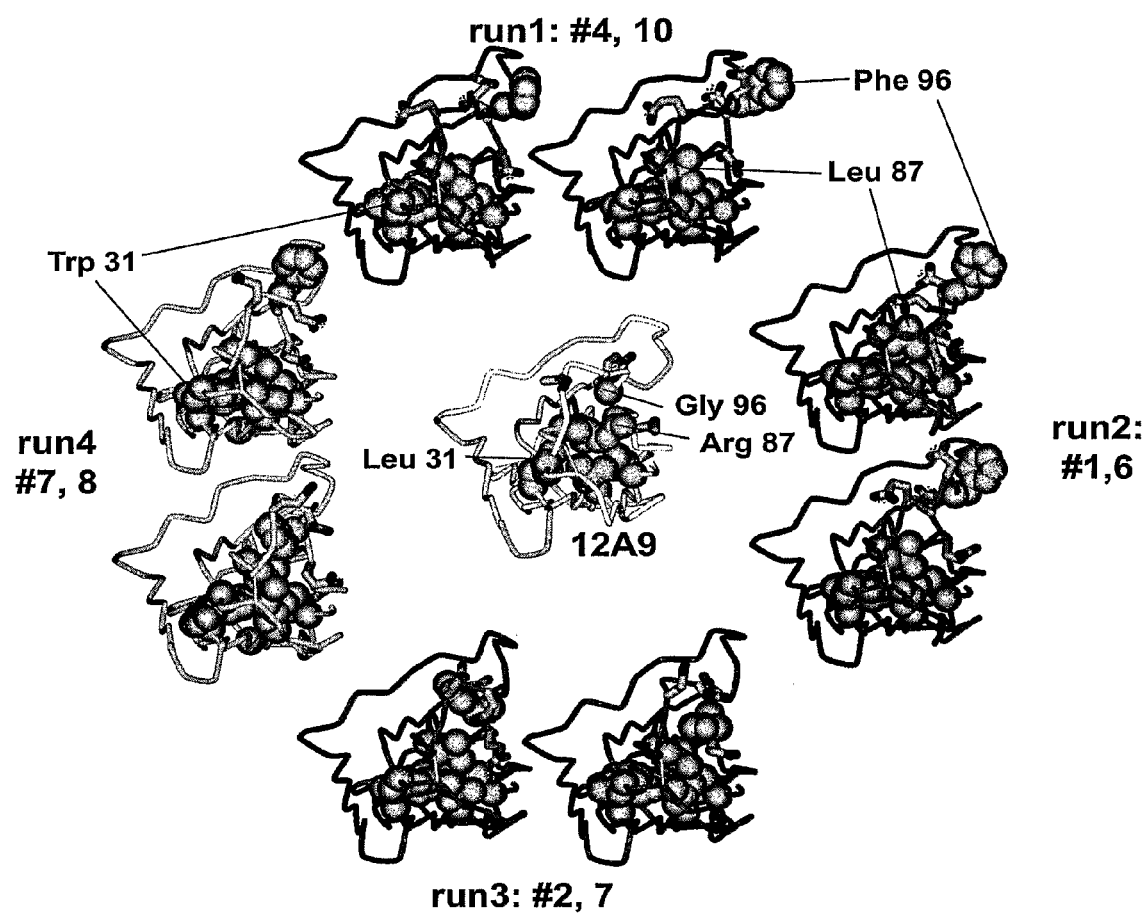
FIG. 35. Modelling of Type 3 IgNAR AAM77191 based on the 12A-9 crystal structure. The results of four modelling runs are shown compared with the template 12A-9. Run 1=Loopref; run 2=Loopref cis; run 3=Nolloopref; run 4=Noloopref_cis. Two solutions were selected from the top ten of each with buried Trp 31 residues and illustrating the variability of the Phe 96 in the modelling solutions.

FIG. 35 shows the modeling of Type 3 $V_{NAR}$ AAM77191 based on the 12A-9 crystal structure. The results of four modelling runs are shown compared with the template 12A-9.

Figure 36:
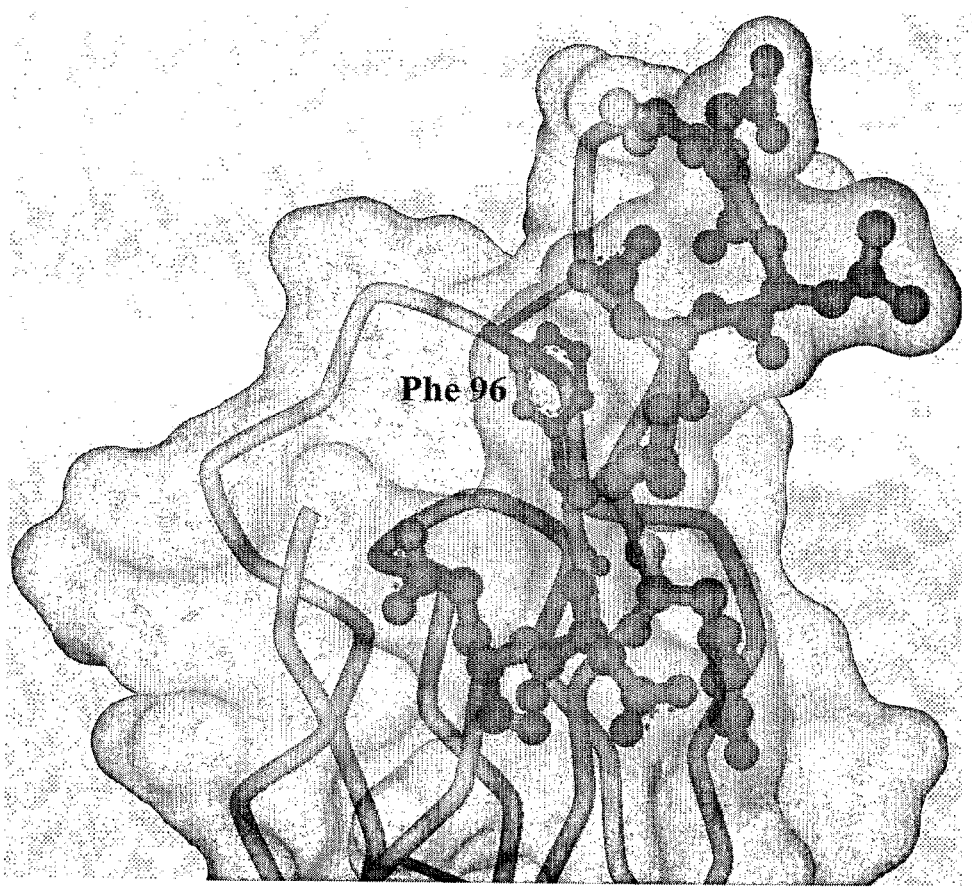
FIG. 36. Model of IgNAR Type 3 CDR1 and CDR3 analogous regions (and some framework residues) based on the 12A-9 structure. This isotype has limited diversity. Hypervariable residues (by sequence alignment) are shown in dark grey.

FIG. 36 shows a model of a $V_{NAR}$ Type 3 CDR1 and CDR3 analogous regions based on the 12A-9 structure. The isotype has limited diversity with the hypervariable residues (by sequence alignment) depicted in dark grey. The modeling suggests that the conserved Phe96 can adopt a number of structural conformations, dramatically enhancing the antigen-binding range of this antibody, despite the low sequence variability It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

Agrawal, A., Eastman, Q. M. & Schatz, D. G. Transposition mediated by RAG1 and RAG2 and its implications for the evolution of the immune system. *Nature* 394, 744-751 (1998).

Blundell et al., in Protein Crystallography, Academic Press, New York, London and San Francisco, (1976).

Blundell et al., *Eur. J. Biochem,* 172, 513 (1988).

Bork, P., Holm, L. & Sander, C. The immunoglobulin fold: structural classification, sequence patterns and common core. *J. Mol. Biol.* 242, 309-320 (1994).

Brandl, M., Weiss, M. S., Jabs A., Sühnel, J. & Hilgenfeld, R. C—H. P-I-Interactions in Proteins. *J. Mol. Biol.* 307, 357-377 (2001).

Brunger, A. T. et al. Crystallography & NMR system: a new software suite for macromolecular structure determination. *Acta Crystallog.* 54, 905-921 (1998).

Brunger A. T., Adams P. D. & Rice L. M., *Current Opinion in Structural Biology,* 8(5), 606-611 (1998a).

Bruns, C. M., Hubatsch, I., Ridderstrom, M., Mannervik, B. & Tainer, J. A. Human Glutathione Transferase A4-4 Crystal Structures and Mutagenesis Reveal the Basis of High Catalytic Efficiency with Toxic Lipid Peroxidation Products, *J. Mol. Biol.,* 288(3): 427-439 (1999).

Casasnovas, J. M., Stehle, T., Liu, J-H., Wang, J-H. & Springer, T. A. A dimeric crystal structure for the N-terminal two domains of ICAM-1. *Proc. Natl. Acad. Sci. USA;* 95, 4134-4139 (1998).

Chothia, C., et al. Conformations of immunoglobulin hypervariable regions. *Nature,* 342, 877-883 (1989).

Chothia, C. & Jones, E. Y. The molecular Structure of Cell Adhesion Molecules. *Annu. Rev. Biochem.* 66, 823-862 (1997).

Chothia, C., Gelfand, I. & Kister, A. Structural Determinants in the Sequences of Immunoglobulin Variable Domain. *J. Mol. Biol.* 278, 457-479 (1998).

Collaborative Computational Project Number 4. The CCP.4 suite: programs for protein crystallography. *Acta Crystallogr.* D50, 760-763 (1994).

Davies, J. & Riechmann, L. Camelising human antibody fragments: NMR studies on $V_H$ domains. *FEBS Lett.* 339 (3):285-90 (1994).

Davies, J. & Riechmann, L. Single antibody domains as small recognition units: design and in vitro antigen selection of camelized, human $V_H$ domains with improved protein stability. *Protein Eng* 9(6):531-7 (1996).

Desmyter, A., Transue, T. R., Ghahroudi, M. A., Dao Thi, M.-H., Poortnans, F., Hamers, R., Muyldermans, S. & Wyns, L. Crystal structure of a camel single-domain VH antibody fragment in complex with lysozyme. *Nat. Struct. Biol.* 3, 803-811 (1996).

Desmyter A., Crystal structure of a camel single-domain VH antibody fragment in complex with lysozyme. *Nat. Struct. Biol.* 3, 803-811 (1996).

Desmyter, A. et al. Three camelid VHH domains in complex with porcine pancreatic alpha-amylase. Inhibition and versatility of binding topology. *J. Biol. Chem.* 277, 23645-23650 (2002).

Diaz, M., Velez, J., Singh, M., Cemy, J. & Flajnik, M. F. Mutational pattern of the nurse shark antigen receptor gene (NAR) is similar to that of mammalian Ig genes and to spontaneous mutations in evolution: the translesion synthesis model of somatic hypermutation. *Int. Immunol.* 11, 825-833 (1999).

Diaz, M., Stanfield, R. L., Greenberg, A. S. & Flajnik, M. F. Structural analysis, selection, and ontogeny of the shark new antigen receptor (IgNAR): identification of a new locus preferentially expressed in early development. *Immunogenetics* 54, 501-512 (2002).

Dooley, H., Flajnik, M. F. & Porter, A. J. Selection and characterization of naturally occurring single-domain (IgNAR) antibody fragments from immunized sharks by phage display. *Mol. Immunol.* 40, 25-33 (2003).

Dunbrack et al., Folding and Design, 2, 27-42 (1997).

Ferro & Hermans. *Acta Cryst., A*33, 345-347 (1977).

Greenberg, A. S. et al. A new antigen receptor gene family that undergoes rearrangement and extensive somatic diversification in sharks. *Nature* 374, 168-173 (1995).

Greer. *Science,* 228, 1055 (1985),

Harpaz, Y. & Chothia, C. Many of the immunoglobulin superfamily domains in cell adhesion molecules and surface receptors belong to a new structural set which is close to that containing variable domains. *J. Mol. Biol.* 238, 528-539 (1994).

Hendrickson. *Acta Cryst., Section A, A*35, 158 (1979)

Hodder, A. N. et al. The disulfide bond structure of *Plasmodium* apical membrane antigen-1. *J. Biol. Chem.* 271, 29446-29452 (1996).

Holden, H. M., Ito, M., Hartshorne, D. J. & Rayment, I. X-Ray Structure Determination of Telokin, the C-Terminal Domain of Myosin Light Chain Kinase, at 2.8 Angstroms Resolution. *J. Mol. Biol.* 227, 840-851 (1992).

Hong, L., Koelsch, G., Lin, X., Wu, S., Terzyan, S., Ghosh, A. K., Zhang, X. C. and Tang, J. *Science,* 290, 150-153.

Jespers, L., Schon, O., James, L. C., Veprintsev, D. & Winter, G. Crystal Structure of HEL4, a Soluble, Refoldable Human VH Single Domain with a Germ-line Scaffold. *J. Mol. Biol.,* 337, 893-903 (2004).

Jones et al., *Acta Cryst., A*47, 110-119 (1991)

Kabat, E. A., Wu, T. T., Bilofsky, H., Reid-Miller, M. & Perry, H., in "Sequences of Proteins of Immunological Interest", U.S. Dept. Health and Human Services, 1983 and 1987.

Kabsch. *Acta Cryst., Section A*, A92, 922 (1976).

Kabsch. *Acta Cryst., A*34, 827-828 (1978).

Kortt, A. A., Guthrie, R. E., Hinds, M. G., Power, B. E., Ivancic, C., Caldwell, J. B., Gruen, L. C., Norton, R. S, and Hudson, P. J. Solution properties of *E. coli* expressed VH domain of anti-neuraminidase antibody NC41. *J. Protein Chem.* 14, 167-178 (1995).

La Fortelle, E. de, & Bricogne, G. "SHARP: A Maximum-Likelihood Heavy-Atom Parameter Refinement Program for the MIR and MAD Methods". In Carter, C. W., and Sweet, R. M., eds, *Meth. Enzym.* 276, 472-494. Academic Press, Orlando, Fla., 1997.

Lamzin, V. S. & Wilson, K. S. Automated refinement for protein crystallography. *Methods Enzymol.* 277, 269-305 (1997).

Laskowski, R. A., MacArthur, M. W., Moss, D. S. & Thornton, J. M. PROCHECK: a program to check the stereochemical quality of protein structures. *J. Appl. Crystallog.* 26, 283-291 (1993).

Lo Conte, L., Chothia, C. & Janin, J. The atomic structure of protein-protein recognition sites. *J. Mol. Biol.* 285, 2177-2198 (1999).

Lu, G. An Approach for Multiple Alignment of Protein Structures, in manuscript (1998).

McLachan. *J. Mol. Biol.*, 128, 49 (1979).

McRee, D. E. XtalView/Xfit—a versatile program for manipulating atomic coordinates and electron density. *J. Struct. Biol.* 125, 156-165 (1999).

Minsky, A., Summers, R. G. & Knowles, J. R. Secretion of beta-lactamase into the periplasm of *Escherichia coli*: evidence for a distinct release step associated with a conformational change. *Proc. Natl. Acad. Sci. USA.* 83, 4180-4184 (1986).

Muyldermans, S., Atarhouch, T., Saldanha, J., Barbosa, J. A. & Hamers, R. Sequence and structure of VH domain from naturally occurring camel heavy chain immunoglobulins lacking light chains. *Protein Eng.* 7, 1129-1135 (1994).

Navaza, J. AMoRe: an automated package for molecular replacement. *Acta Cryst.*, A50, 157-163 (1994).

Nieba, L., Honegger, A., Krebber, C. & Pluckthun, A. Disrupting the hydrophobic patches at the antibody variable/constant domain interface: improved in vivo folding and physical characterization of an engineered scFv fragment. *Protein Eng.* 4, 435-444 (1997).

Nguyen V. K., Su, C., Muyldermans, S. & van der Loo, W. Heavy-chain antibodies in Camelidae; a case of evolutionary innovation. *Immunogenetics* 54, 39-47 (2002).

Novotny, J., Ganju, R. K., Smiley, S. T., Hussey, R. E., Luther, M. A., Recny, M. A., Siliciano, R. F., Reinherz, E. L. A soluble, single-chain T-cell receptor fragment endowed with antigen-combining properties. *PNAS USA.* 88(19), 8646-8650 (1991).

Nuttall, S. D. et al. Isolation of the New Antigen Receptor from Wobbegong Sharks, and Use as a Scaffold for the Display of Protein Loop Libraries. *Mol. Immunol.* 38, 313-326 (2001).

Nuttall, S. D. et al. A naturally occurring NAR variable domain against the Gingipain K protease from *Porphyromonas gingivalis*. *FEBS Lett.* 516, 80-86 (2002).

Nuttall, S. D. et al. Isolation and characterisation of an IgNAR variable domain specific for the human mitochondrial translocase receptor Tom70. *Eur. J. Biochem.* 270, 3543-3554 (2003).

Nuttall, S. D., et al. S election and affinity maturation of IgNAR variable domains targeting *Plasmodium falciparum* AMA1. *Proteins* 55, 187-197 (2004).

Otwinowski, Z. & Minor, W. Processing of X-ray diffraction data collected in oscillation mode. *Methods Enzymol.* 276, 307-326 (1997).

Queen, M. et al. A humanized antibody that binds to the interleukin 2 receptor. *Proc. Natl. Acad. Sci. USA* 86:10029-10033 (1989).

Riechmann, L. et al. Reshaping human antibodies for therapy. *Nature* 332:323-327 (1988).

Riechmann, L. Rearrangement of the former VL interface in the solution structure of a camelised, single antibody VH domain. *J. Mol. Biol.* 259, 957-69 (1996).

Rossman & Argos. *J. Biol. Chem.*, 250, 7525 (1975).

Roux, K. H. et al. Structural analysis of the nurse shark (new) antigen receptor (NAR): molecular convergence of NAR and unusual mammalian immunoglobulins. *Proc. Natl. Acad. Sci. USA* 95, 11804-11809 (1998).

Rumfelt et al. The development of primary and secondary lymphoid tissues in the nurse shark *Ginglymostoma cirratum*: B-cell zones precede dendritic cell immigration and T-cell zone formation during ontogeny of the spleen *Scand. J. Immunol.* 56:130-148 (2002).

Saphire, E. O. et al. Structure of an intact human IgG with potent and broad activity against primary HIV-1 isolates: A template for HIV vaccine design. *Science* 293, 1155-1159 (2001).

Sambrook et al. Molecular Cloning: A Laboratory Manual, Second Edition, Cold Spring Harbor, N.Y., (1989).

Sayle et al. *TIBS*, 20, 374 (1995).

Snow & Amzel. Calculating three-dimensional changes in protein structure due to amino acid substitutions: the variable region of immunoglobulins" *Protein: Structure, Function and Genetics*, Alan R. Liss, Inc 1:267-279 (1986).

Soroka V. et al. Structure and Interactions of NCAM Ig1-2-3 Suggest a Novel Zipper Mechanism for Homophilic Adhesion. *Structure* 10, 1291-301 (2003).

Spada, S., Honegger, A. & Plückthun, A. Reproducing the natural evolution of protein structural features with the selectively infective phage (SIP) technology. The kink in the first strand of antibody kappa domains. *J. Mol. Biol.* 283, 395-407 (1998).

Sutcliffe, M. J., Haneef, I., Carney, D. & Blundell, T. L. *Protein Engineering*, 1, 377-384 (1987).

Ward, E. S. Expression and secretion of T-cell receptor V alpha and V beta domains using *Escherichia coli* as a host. *Scand. J. Immunol.* 34(2), 215-220 (1991).

Winn, M. D., Isupov, M. N. & Murshudov, G. N. Use of TLS parameters to model anisotropic displacements in macromolecular refinement. *Acta. Crystallog.* 57, 122-133 (2001).

Wolfson, H. J., Shatsky, M., Schneidman-Duhovny, D., Dror, O., Shulman-Peleg, A., Ma, B. & Nussinov, R. From structure to function: methods and applications. *Curr. Protein Pept. Sci.*, 6(2):171-83 (2005).

Wu, T. T., Johnson, G. & Kabat, E. A. Length distribution of CDRH3 in antibodies. *Proteins* 16, 1-7 (1993).

Wulfing, C. & Pluckthun, A. Correctly folded T-cell receptor fragments in the periplasm of *Escherichia coli*—Influence of folding catalysts. *J. Mol. Biol.* 245(5), 655-669 (1994).

The CCP4 Suite: Programs for Protein Crystallography, *Acta Cryst.*, D50, 760-763 (1994).

Xu, D., Xu, Y. & Uberbacher, E. C. Computational tools for protein modeling, Curr. Protein Pept. Sci., 1(1), 1-21 (2000).

TABLE 1

Amino acid variation across the 14 Type 2 $V_{NAR}$s sequences in FIG. 1

| No | 12Y-1<br>12Y-2<br>12A-9<br>1A-7 | Var | Con |
|---|---|---|---|
| 1 | A | VQGT | AVQGT |
| 2 | WR | L | WRL |
| 3 | V | AT | VAT |
| 4 | D | E | DE |
| 5 | Q | P | QP |
| 6 | T | KP | TKP |
| 7 | P | — | P |
| 8 | R | KTH | RKTH |
| 9 | TIS | P | TISP |
| 10 | AV | E | AVE |
| 11 | T | — | T |
| 12 | K | — | K |
| 13 | E | — | E |
| 14 | T | R | TR |
| 15 | G | — | G |
| 16 | E | G | EG |
| 17 | S | — | S |
| 18 | L | — | L |

TABLE 1-continued

Amino acid variation across the 14 Type 2 $V_{NAR}s$ sequences in FIG. 1

| No | 12Y-1 12Y-2 12A-9 1A-7 | Var | Con |
|---|---|---|---|
| 19 | T | — | T |
| 20 | I | — | I |
| 21 | N | SYH | NSYH |
| 22 | C | — | C |
| 23 | VA | — | VA |
| 24 | L | VI | LVI |
| 25 | RK | — | RK |
| 26 | DN | ES | DNES |
| 27 | AT | S | ATS |
| | Variable region | | |
| 34 | T | — | T |
| 35 | GND | RYW | GNDRYW |
| 36 | W | — | W |
| 37 | Y | — | Y |
| 38 | R | — | R |
| 39 | T | absent | T or absent |
| 40 | KT | R | KTR |
| 41 | L | F | LF |
| 42 | G | DS | GDS |
| 43 | S | — | S |
| 44 | T | — | T |
| 45 | NK | — | NK |
| 46 | E | L | EL |
| 47 | Q | — | Q |
| 48 | TSK | FAH | TSKFAH |
| 49 | I | M | IM |
| 50 | S | TP | STP |
| 51 | I | L | IL |
| 52 | G | — | G |
| 53 | G | — | G |
| 54 | R | — | R |
| 55 | Y | H | YH |
| 56 | VS | L | VSL |
| 57 | E | — | E |
| 58 | T | — | T |
| 59 | V | E | VE |
| 60 | ND | S | NDS |
| 61 | KE | RL | KERL |
| 62 | G | TER | GTER |
| 63 | S | — | S |
| 64 | KN | E | KNE |
| 65 | S | — | S |
| 66 | FA | — | FA |
| 67 | S | — | S |
| 68 | L | — | L |
| 69 | RT | S | RTS |
| 70 | I | — | I |
| 71 | RS | — | RS |
| 72 | D | E | DE |
| 73 | L | — | L |
| 74 | R | S | RS |
| 75 | V | — | V |
| 76 | E | — | E |
| 77 | D | — | D |
| 78 | S | — | S |
| 79 | G | SA | GSA |
| 80 | T | — | T |
| 81 | Y | F | YF |
| 82 | K | QR | KQR |
| 83 | C | — | C |
| 84 | GQK | SH | GQKSH |
| 85 | A | GNV | AGNV |
| | Variable region | | |
| 104 | KE | PW | KEPW |
| 105 | G | — | G |
| 106 | A | GFV | AGFV |
| 107 | G | DL | GDL |
| 108 | T | — | T |
| 109 | VA | DLI | VADLI |
| 110 | L | — | L |
| 111 | T | — | T |
| 112 | V | — | V |
| 113 | K | RT | KRT |

Var: Variant amino acids: These columns show the variation in amino acid residues found in the corresponding positions in the twelve other Type 2 $V_{NAR}s$ sequences in FIG. 1 and in other Type 2 $V_{NAR}s$ reported in Nuttall 2002 and 2003.
Con: Consensus sequence

TABLE 2

Diffraction data and refinement statistics

| | | Native 12Y-1 | LAH 12Y-1 | PHR 12Y-1 | Native 12Y-2 | Native 12A-9 | Native 1A-7 |
|---|---|---|---|---|---|---|---|
| Diffraction data | | | | | | | |
| Space Group | | I4₁22 | I4₁22 | I4₁22 | I2₁2₁2₁ | P2₁2₁2 | I2₁2₁2₁ |
| Unit cell (Å) | (a) | 97.26 | 97.97 | 97.60 | 65.28 | 38.27 | 80.50 |
| | (b) | 97.26 | 97.97 | 97.60 | 92.05 | 68.32 | 88.66 |
| | (c) | 65.23 | 65.61 | 65.27 | 98.22 | 39.51 | 101.75 |
| Resolution (Å) | | 69-2.8 | 20-3.0 | 20-2.5 | 67.4-2.18 | 39.5-2.1 | 21.6-2.7 |
| - (outer shell) | | (2.9-2.8) | (3.11-3.0) | (2.6-2.5) | (2.24-2.18) | (2.15-2.1) | (2.78-2.7) |
| Measured reflections | | 60022 | 42615 | 48364 | 99606 | 43653 | 52866 |
| Unique reflections | | 3975 | 3304 | 5472 | 15764 | 6048 | 18372 |
| Multiplicity | | 15.1 (4.3) | 12.9 (8.3) | 8.8 (5.0) | 6.6 (6.3) | 7.2 (6.3) | 2.9 (2.2) |
| Completeness (%) (outer shell) | | 99 (94.3) | 97.2 (82.5) | 96 (77) | 100 (99.4) | 98.6 (100) | 95.1 (87.9) |
| I/σ(I) (outer shell) | | 18.1 (1.8) | 18.4 (1.8) | 8.6 (1.5) | 32.5 (4.0) | 15.2 (2.0) | 7.6 (1.2) |
| $\chi^2$ (outer shell) | | 1.21 (1.10) | 1.74 (1.60) | 1.09 (1.40) | 1.19 (0.95) | 1.03 (0.97) | 1.27 (1.03) |
| $R_{merge}$ (%) | | 4.5 | 10.2 | 10.0 | 5.4 | 12.6 | 14.8 |
| Refinement | | | | | | | |
| Resolution range (Å) | | 6.0-2.82 | | | 18.12-2.18 | 34.2-2.10 | 21.6-2.7 |
| R % (outer shell) | | 16.6 (33.9) | | | 17.6 (22.5) | 21.7 (29.5) | 17.6 (32.7) |
| $R_{free}$ % (outer shell) | | 25.4 (54.3) | | | 24.7 (31.1) | 28.0 (39.9) | 26.5 (32.8) |

TABLE 2-continued

Diffraction data and refinement statistics

| | Native 12Y-1 | LAH 12Y-1 | PHR 12Y-1 | Native 12Y-2 | Native 12A-9 | Native 1A-7 |
|---|---|---|---|---|---|---|
| RMS deviations: | | | | | | |
| Bond length (Å) | 0.0012 | | | 0.012 | 0.012 | 0.012 |
| Bond angles (deg.) | 1.552 | | | 1.484 | 1.494 | 1.453 |
| Average B values (Å$^2$) | 40.2 | | | 21.3 | 49.9 | 43.3 |

TABLE 3

Number and numbering of amino acid residues in each region

| Region | Number of residues | Residue Numbering |
|---|---|---|
| Loop region 1 | 1-2 | 1 to 2 |
| β-strand region A | 5-6 | 2 to 6-7 |
| Loop region 2 | 2-3 | 6-7 to 8-9 |
| β-strand region A | 5-6 | 8-9 to 13-14 |
| Loop region 3 | 4-5 | 13-14 to 17-18 |
| β-strand region B | 8-10 | 17-18 to 26-28 |
| Loop region 4 | 5-9 | 26-28 to 32-34 |
| β-strand region C | 7-9 | 32-34 to 40-41 |
| Loop region 5 | 14-17 | 40-41 to 54-55 |
| β-strand region D | 6-7 | 54-55 to 60-61 |
| Loop region 6 | 4-5 | 60-61 to 64-65 |
| β-strand region E | 6-7 | 64-65 to 70-71 |
| Loop region 7 | 8-9 | 70-71 to 78-79 |
| β-strand region F | 6-8 | 78-79 to 85-86 |
| Loop region 8 | 5-25 | 85-86 to # |
| β-strand region G | 10-12 | 97-98 to 105-120* |

TABLE 3A

Number and numbering of amino acid residues in loop region 5

| Region | Number of residues | Residue Numbering |
|---|---|---|
| Loop region 5 | 14-17 | 40-41 to 54-55 |
| β-strand region C | ... 1 | ... 40 |
| Loop region 5a | 6 | 41-46 |
| β-strand region C' | 2 | 47, 48 |
| Loop region 5b | 3 | 49-51 |
| β-strand region D' | 1 | 52 |
| Loop region 5c | 2 | 53, 54 |

TABLE 4

Dimer interactions

| | | | Hydrogen bond distance (Å) < 4 Å | | |
|---|---|---|---|---|---|
| Interface* | Hydrogen bonds | | 12Y-2 A | 12Y-2 B | 12Y-1 |
| D-D$_s$ | Main-chain H-bonds: | | | | |
| strands | Val59(N)-Val59(O)$_s$ | | 2.88 | 2.93 | 3.15 |
| | Val59(O)-Val59(N)$_s$ | | 2.88 | 2.93 | 3.15 |
| | Side-chain H-bonds: | | | | |
| | Lys61(NZ)-Glu57(OE1)$_s$ | | 2.65 | | 3.16 |
| | Water mediated H-bonds: | | | | |
| | W(20)/W(37)-Lys61(N) | | 3.37 | 3.12 | |
| | W(20)/W(37)-Gly62(N) | | 3.09 | 2.64 | |
| | W(20)/W(37)-Glu57(O)$_s$ | | 2.73 | 2.88 | |
| | W(20)/W(37)-Glu57(N)$_s$ | | 2.75 | 2.92 | |
| | W(1)/W(11)-Glu57(OE1)$_s$ | | 2.96 | 2.66 | |
| | W(1)/W(11)-Lys61(N) | | 2.81 | 3.00 | |
| | W(1)/W(11)-Val59(O) | | 2.81 | 3.13 | |
| | W(81)-Thr58(OG1) | | | | 3.01 |
| | W(81)-Asn60(OD1))$_s$ | | | | 3.13 |
| CDR3-CDR3$_s$ | Main-chain H-bonds: | | | | |
| | Asn95(N)-Arg101(O)$_s$ | | 3.25 | 3.05 | |
| | Arg101(N)-Asn95(O)$_s$ | | 3.25 | 3.05 | |
| | Ser97(N)-Leu99(O)$_s$ | | 2.9 | 3.11 | |
| | Ser97(O)-Leu99(N)$_s$ | | 3.09 | 2.74 | |
| | Side-chain H-bonds: | | | | |
| | Asn95(OD1)-Arg101(NE)$_s$ | | 2.72 | | |
| | Tyr94(O)-Arg101(NE)$_s$ | | | 2.69 | |
| | Tyr94(OH)-Arg101(NH1)$_s$ | | | 3.36 | |
| CDR1-CDR1$_s$ | Side-chain H-bonds: | | | | |
| | Lys 32(O)-Asp33(OD1)$_s$ | | 2.42 | 3.25 | |
| | Lys 32(O)-Lys61(NZ)$_s$ | | | 2.84 | |

*Subscript "s" is for a symmetry (2-fold) related molecule.

TABLE 5

Amino acid sequences of NCAM/IgNAR and Telokin/IgNAR chimeras

| | SEQ ID NO: | |
|---|---|---|
| NCAM | 36 | LQVDIVPSQGEISVGESKFFLCQVAGDAKDKDISWFSPNGEKLTPNQQRISVVWNDDSSS |
| | | TLTIYNANIDDAGIYKCVVTGED--------------------GSESEA-TVNVKIFQ |
| N1A7_1 | 120 | |
| N1A7_2 | 121 | TLTIYNANIDDAGIYKC------GAYFSDAMSNYSYPIPGEK-------A-TVNVKIFQ |
| N1A7_3 | 122 | TLTIYNANTDDAGIYKCV------AYFSDAMSNYSYPIPGE-------SA-TVNVKIFQ |
| N1A7_4 | 123 | TLTIYNANIDDAGIYKCVV------YFSDAMSNYSYPIPG-------SEA-TVNVKIFQ |
| N1A7_5 | 124 | TLTIYNANIDDAGIYKCVVT------FSDAMSNYSYPIP-------ESEA-TVNVKIFQ |
| | | TLTIYNANIDDAGIYKCVVTG------SDAMSNYSYPI-------SESEA-TVNVKIFQ |
| TELOKIN | 41 | ---PYFSKTIRDLEVVEGSAARFDCKTEGYPDPEVVWFKDDQSIRESRHFQIDYDEDGN |
| | | CSLTISEVCGDDDAKYTCKAVNS--------------------LGEATC-TAELIVE |
| T1A7_1 | 125 | CSLIISDVCGDDDAKYTC-----GAYFSDAMSNYSYPIPGEK-------C-TAELIVE- |
| T1A7_2 | 126 | CSLIISDVCGDDDAKYTCK-----AYFSDAMSNYSYPIPGE-------TC-TAELIVE- |

TABLE 5-continued

Amino acid sequences of NCAM/IgNAR and Telokin/IgNAR chimeras

| | SEQ ID NO: | |
|---|---|---|
| T1A7_3 | 127 | CSLIISDVCGDDDAKYTCKA-----YFSDAMSNYSYPIPG-------ATC-TAELIVE- |
| T1A7_4 | 128 | CSLIISDVCGDDDAKYTCKAV-----FSDAMSNYSYPIP-------EATC-TAELIVE- |
| T1A7_5 | 129 | CSLIISDVCGDDDAKYTCKAVN-----SDAMSNYSYPI-------GEATC-TAELIVE- |

TABLE 6

Comparison of TCR interfaces:

| TCR Vα 1AO7 | TCR Vα 1J8H | TCR Vα 1KGC | TCR Vα 1KB5 | 12Y-2 | Camelid | Comments |
|---|---|---|---|---|---|---|
| Ser31 | Tyr31 | Tyr31 | Tyr31 | Asp33 | | |
| Phe33 | Phe33 | His33 | Pro33 | Gly35 | | |
| Tyr35 | Tyr35 | Tyr35 | Tyr35 | Tyr37 | V37F£ | |
| Gln37 | Gln37 | Gln37 | Gln37 | Thr39 | | |
| Ser42 | Gly42 | Gly42 | Gly42 | Asn45 | G44E£ | Deviation¥ |
| Pro43 | Pro43 | Pro43 | Pro43 | Glu46 | L45R£ | |
| Leu45 | Leu45 | Tyr45 | Leu45 | Ser48 | W47G/S£ | |
| Ser48 | Lys48 | His48 | Ser48 | —* | | CDR2 |
| Tyr50 | Thr50 | Leu50 | Arg50 | —* | | CDR2 |
| Ser51 | Ser51 | Thr51 | Ser51 | —* | | CDR2 |
| Asn52 | Ala52 | Ser52 | Val52 | —* | | CDR2 |
| Leu89 | Phe89 | Tyr89 | Phe89 | Lys82 | | |
| Thr93 | Ser93 | Pro93 | Arg93 | Phe86 | | Deviation¥ |
| Leu104 | Leu104 | Leu104 | Leu104 | Gly102 | | Deviation¥ |
| Phe106 | Phe106 | Phe106 | Phe106 | Lys104 | | |

*Residues is TCR CDR2 loop, no equivalent position in IgNAR variable domains.
¥Deviation between Cα traces of shark and TCR structures.
£Camelisation of human domains, difficult to correlate.
NB: This does not include interface residues incorporated within the highly variable VLR3 loop regions. For example 12Y-2 residue Arg101 would also contribute to covering the hydrophobic interface if modelled onto the TCR domain.

APPENDIX I(a)

```
HEADER      IMMUNE SYSTEM                        05-APR-04   1VER
TITLE       STRUCTURE OF NEW ANTIGEN RECEPTOR VARIABLE DOMAIN FROM SHARKS
COMPND      MOL_ID: 1;
COMPND    2   MOLECULE: NEW ANTIGEN RECEPTOR;
COMPND    3   CHAIN: A;
COMPND    4   FRAGMENT: VARIABLE DOMAIN;
COMPND    5   SYNONYM: VNAR;
COMPND    6   ENGINEERED: YES
SOURCE      MOL_ID: 1;
SOURCE    2   ORGANISM_SCIENTIFIC: ORECTOLOBUS MACULATUS;
SOURCE    3   ORGANISM_COMMON: SPOTTED WOBBEGONG;
SOURCE    4   EXPRESSION_SYSTEM: ESCHERICHIA COLI;
SOURCE    5   EXPRESSION_SYSTEM_COMMON: BACTERIA
KEYWDS      IG VNAR, NATIVE, 12Y-1
EXPDTA      X-RAY DIFFRACTION
AUTHOR      V. A. STRELTSOV
JRNL        AUTH     V. A. STRELTSOV, J. N. VARGHESE, P. J. HUDSON, R. A. IRVING,
JRNL        AUTH 2   J. A. CARMICHAEL, S. D. NUTTALL
JRNL        TITL     CRYSTAL STRUCTURE OF A SHARK NEW ANTIGEN RECEPTOR
JRNL        TITL 2   (IGNAR) VARIABLE DOMAIN
JRNL        REF      TO BE PUBLISHED
JRNL        REFN
REMARK   1
REMARK   2
REMARK   2   RESOLUTION. 2.82 ANGSTROMS.
REMARK   3
REMARK   3   REFINEMENT.
REMARK   3     PROGRAM     : REFMAC 5.1.24
REMARK   3     AUTHORS     : MURSHUDOV, VAGIN, DODSON
REMARK   3
REMARK   3     REFINEMENT TARGET: MAXIMUM LIKELIHOOD
REMARK   3
REMARK   3   DATA USED IN REFINEMENT.
REMARK   3     RESOLUTION RANGE HIGH       (ANGSTROMS) : 2.82
REMARK   3     RESOLUTION RANGE LOW        (ANGSTROMS) : 6.00
REMARK   3     DATA CUTOFF                  (SIGMA(F)) : NULL
REMARK   3     COMPLETENESS FOR RANGE             (%) : 99.3
REMARK   3     NUMBER OF REFLECTIONS                  : 3353
REMARK   3
REMARK   3   FIT TO DATA USED IN REFINEMENT.
REMARK   3     CROSS-VALIDATION METHOD          : THROUGHOUT
REMARK   3     FREE R VALUE TEST SET SELECTION  : RANDOM
REMARK   3     R VALUE     (WORKING + TEST SET) : 0.170
REMARK   3     R VALUE            (WORKING SET) : 0.166
```

APPENDIX I(a)-continued

```
REMARK   3      FREE R VALUE                                  : 0.254
REMARK   3      FREE R VALUE TEST SET SIZE          (%)  : 4.400
REMARK   3      FREE R VALUE TEST SET COUNT           : 153
REMARK   3
REMARK   3      FIT IN THE HIGHEST RESOLUTION BIN.
REMARK   3         TOTAL NUMBER OF BINS USED                 : 20
REMARK   3         BIN RESOLUTION RANGE HIGH                 : 2.82
REMARK   3         BIN RESOLUTION RANGE LOW                  : 2.88
REMARK   3         REFLECTION IN BIN           (WORKING SET) : 195
REMARK   3         BIN COMPLETENESS      (WORKING + TEST) (%) : NULL
REMARK   3         BIN R VALUE                 (WORKING SET) : 0.3390
REMARK   3         BIN FREE R VALUE SET COUNT                : 11
REMARK   3         BIN FREE R VALUE                          : 0.5430
REMARK   3
REMARK   3      NUMBER OF NON-HYDROGEN ATOMS USED IN REFINEMENT.
REMARK   3         ALL ATOMS                  : 867
REMARK   3
REMARK   3      B VALUES.
REMARK   3         FROM WILSON PLOT              (A**2)  : NULL
REMARK   3         MEAN B VALUE           (OVERALL, A**2) : 40.21
REMARK   3      OVERALL ANISOTROPIC B VALUE.
REMARK   3         B11 (A**2): 3.53000
REMARK   3         B22 (A**2): 3.53000
REMARK   3         B33 (A**2): −7.06000
REMARK   3         B12 (A**2): 0.00000
REMARK   3         B13 (A**2): 0.00000
REMARK   3         B23 (A**2): 0.00000
REMARK   3
REMARK   3      ESTIMATED OVERALL COORDINATE ERROR.
REMARK   3         ESU BASED ON R VALUE                         (A): NULL
REMARK   3         ESU BASED ON FREE R VALUE                    (A): 0.370
REMARK   3         ESU BASED ON MAXIMUM LIKELIHOOD              (A): 0.288
REMARK   3         ESU FOR B VALUES BASED ON MAXIMUM LIKELIHOOD (A**2): 16.179
REMARK   3
REMARK   3      CORRELATION COEFFICIENTS.
REMARK   3         CORRELATION COEFFICIENT FO-FC       : 0.965
REMARK   3         CORRELATION COEFFICIENT FO-FC FREE  : 0.911
REMARK   3
REMARK   3      RMS DEVIATIONS FROM IDEAL VALUES            COUNT    RMS    WEIGHT
REMARK   3         BOND LENGTHS REFINED ATOMS        (A):    780 ;  0.012 ;  0.021
REMARK   3         BOND LENGTHS OTHERS               (A):    710 ;  0.002 ;  0.020
REMARK   3         BOND ANGLES REFINED ATOMS   (DEGREES):   1050 ;  1.552 ;  1.955
REMARK   3         BOND ANGLES OTHERS          (DEGREES):   1648 ;  0.838 ;  3.000
REMARK   3         TORSION ANGLES, PERIOD 1    (DEGREES):     98 ;  8.873 ;  5.000
REMARK   3         TORSION ANGLES, PERIOD 2    (DEGREES):   NULL ;  NULL ;   NULL
REMARK   3         TORSION ANGLES, PERIOD 3    (DEGREES):   NULL ;  NULL ;   NULL
REMARK   3         TORSION ANGLES, PERIOD 4    (DEGREES):   NULL ;  NULL ;   NULL
REMARK   3         CHIRAL-CENTER RESTRAINTS       (A**3):    121 ;  0.085 ;  0.200
REMARK   3         GENERAL PLANES REFINED ATOMS      (A):    857 ;  0.005 ;  0.020
REMARK   3         GENERAL PLANES OTHERS             (A):    165 ;  0.001 ;  0.020
REMARK   3         NON-BONDED CONTACTS REFINED ATOMS (A):    147 ;  0.220 ;  0.200
REMARK   3         NON-BONDED CONTACTS OTHERS        (A):    841 ;  0.224 ;  0.200
REMARK   3         NON-BONDED TORSION REFINED ATOMS  (A):   NULL ;  NULL ;   NULL
REMARK   3         NON-BONDED TORSION OTHERS         (A):    558 ;  0.089 ;  0.200
REMARK   3         H-BOND (X...Y) REFINED ATOMS      (A):     32 ;  0.220 ;  0.200
REMARK   3         H-BOND (X...Y) OTHERS             (A):   NULL ;  NULL ;   NULL
REMARK   3         POTENTIAL METAL-ION REFINED ATOMS (A):   NULL ;  NULL ;   NULL
REMARK   3         POTENTIAL METAL-ION OTHERS        (A):   NULL ;  NULL ;   NULL
REMARK   3         SYMMETRY VDW REFINED ATOMS        (A):     11 ;  0.370 ;  0.200
REMARK   3         SYMMETRY VDW OTHERS               (A):     26 ;  0.364 ;  0.200
REMARK   3         SYMMETRY H-BOND REFINED ATOMS     (A):     11 ;  0.160 ;  0.200
REMARK   3         SYMMETRY H-BOND OTHERS            (A):   NULL ;  NULL ;   NULL
REMARK   3
REMARK   3      ISOTROPIC THERMAL FACTOR RESTRAINTS.         COUNT    RMS    WEIGHT
REMARK   3         MAIN-CHAIN BOND REFINED ATOMS   (A**2):    488 ;  0.363 ;  1.500
REMARK   3         MAIN-CHAIN BOND OTHER ATOMS     (A**2):   NULL ;  NULL ;   NULL
REMARK   3         MAIN-CHAIN ANGLE REFINED ATOMS  (A**2):    783 ;  0.690 ;  2.000
REMARK   3         SIDE-CHAIN BOND REFINED ATOMS   (A**2):    292 ;  1.038 ;  3.000
REMARK   3         SIDE-CHAIN ANGLE REFINED ATOMS  (A**2):    267 ;  1.864 ;  4.500
REMARK   3
REMARK   3      ANISOTROPIC THERMAL FACTOR RESTRAINTS.       COUNT    RMS    WEIGHT
REMARK   3         RIGID-BOND RESTRAINTS           (A**2):   NULL ;  NULL ;   NULL
REMARK   3         SPHERICITY; FREE ATOMS          (A**2):   NULL ;  NULL ;   NULL
REMARK   3         SPHERICITY; BONDED ATOMS        (A**2):   NULL ;  NULL ;   NULL
REMARK   3
REMARK   3      NCS RESTRAINTS STATISTICS
REMARK   3        NUMBER OF DIFFERENT NCS GROUPS: 0
REMARK   3
REMARK   3      TLS DETAILS
REMARK   3        NUMBER OF TLS GROUPS  : 1
```

APPENDIX I(a)-continued

```
REMARK    3
REMARK    3     TLS GROUP : 1
REMARK    3      NUMBER OF COMPONENTS GROUP : 1
REMARK    3      COMPONENTS       C    SSSEQI  TO  C    SSSEQI
REMARK    3      RESIDUE RANGE:   A      1       A      111
REMARK    3      ORIGIN FOR THE GROUP (A):  45.6110   36.4110   14.2350
REMARK    3      T TENSOR
REMARK    3        T11:    0.0948 T22:     0.2124
REMARK    3        T33:    0.2758 T12:    -0.1415
REMARK    3        T13:   -0.1115 T23:     0.1801
REMARK    3      L TENSOR
REMARK    3        L11:    3.5582 L22:     7.2854
REMARK    3        L33:   17.6513 L12:     0.4045
REMARK    3        L13:   -0.8273 L23:    -0.9129
REMARK    3      S TENSOR
REMARK    3        S11:    0.1545 S12:    -0.6840 S13:   -0.0196
REMARK    3        S21:    0.7097 S22:    -0.6861 S23:   -0.3902
REMARK    3        S31:   -0.4080 S32:     0.6079 S33:    0.5316
REMARK    3
REMARK    3  BULK SOLVENT MODELLING.
REMARK    3     METHOD USED : BABINET MODEL WITH MASK
REMARK    3     PARAMETERS FOR MASK CALCULATION
REMARK    3     VDW PROBE RADIUS    : 1.40
REMARK    3     ION PROBE RADIUS    : 0.80
REMARK    3     SHRINKAGE RADIUS    : 0.80
REMARK    3
REMARK    3  OTHER REFINEMENT REMARKS: NULL
REMARK    4
REMARK    4 1VER COMPLIES WITH FORMAT V. 2.3, 09-JULY-1998
REMARK  100
REMARK  100 THIS ENTRY HAS BEEN PROCESSED BY PDBJ ON 07-APR-2004.
REMARK  100 THE RCSB ID CODE IS RCSB006537.
REMARK  200
REMARK  200 EXPERIMENTAL DETAILS
REMARK  200   EXPERIMENT TYPE                : X-RAY DIFFRACTION
REMARK  200   DATE OF DATA COLLECTION        : OCT-03
REMARK  200   TEMPERATURE           (KELVIN) : 113.0
REMARK  200   PH                             : 6.50
REMARK  200   NUMBER OF CRYSTALS USED        : 1
REMARK  200
REMARK  200   SYNCHROTRON              (Y/N) : N
REMARK  200   RADIATION SOURCE               : ROTATING ANODE
REMARK  200   BEAMLINE                       : NULL
REMARK  200   X-RAY GENERATOR MODEL          : RIGAKU HR3 HB
REMARK  200   MONOCHROMATIC OR LAUE    (M/L) : M
REMARK  200   WAVELENGTH OR RANGE        (A) : 1.5418
REMARK  200   MONOCHROMATOR                  : NI FILTER
REMARK  200   OPTICS                         : AXCO MICROCAPILLARY FOCUSING
REMARK  200                                    OPTICS
REMARK  200
REMARK  200   DETECTOR TYPE                  : IMAGE PLATE
REMARK  200   DETECTOR MANUFACTURER          : MAR 180
REMARK  200   INTENSITY-INTEGRATION SOFTWARE : DENZO
REMARK  200   DATA SCALING SOFTWARE          : SCALEPACK
REMARK  200
REMARK  200   NUMBER OF UNIQUE REFLECTIONS   : 3975
REMARK  200   RESOLUTION RANGE HIGH      (A) : 2.820
REMARK  200   RESOLUTION RANGE LOW       (A) : 69.010
REMARK  200   REJECTION CRITERIA  (SIGMA(I)) : 0.000
REMARK  200
REMARK  200 OVERALL.
REMARK  200   COMPLETENESS FOR RANGE     (%) : 99.0
REMARK  200   DATA REDUNDANCY                : 15.100
REMARK  200   R MERGE                    (I) : 0.04500
REMARK  200   R SYM                      (I) : 0.04500
REMARK  200   <I/SIGMA(I)> FOR THE DATA SET  : 18.1000
REMARK  200
REMARK  200 IN THE HIGHEST RESOLUTION SHELL.
REMARK  200   HIGHEST RESOLUTION SHELL, RANGE HIGH (A) : 2.82
REMARK  200   HIGHEST RESOLUTION SHELL, RANGE LOW  (A) : 2.90
REMARK  200   COMPLETENESS FOR SHELL     (%) : 94.3
REMARK  200   DATA REDUNDANCY IN SHELL       : 4.30
REMARK  200   R MERGE FOR SHELL          (I) : NULL
REMARK  200   R SYM FOR SHELL            (I) : NULL
REMARK  200   <I/SIGMA(I)> FOR SHELL         : 1.800
REMARK  200
REMARK  200 DIFFRACTION PROTOCOL: SINGLE WAVELENGTH
REMARK  200 METHOD USED TO DETERMINE THE STRUCTURE: MIR
REMARK  200 SOFTWARE USED: SHARP
REMARK  200 STARTING MODEL: NULL
```

APPENDIX I(a)-continued

```
REMARK   200
REMARK   200  REMARK: NULL
REMARK   280
REMARK   280  CRYSTAL
REMARK   280  SOLVENT CONTENT, VS      (%): NULL
REMARK   280  MATTHEWS COEFFICIENT, VM (ANGSTROMS**3/DA): NULL
REMARK   280
REMARK   280  CRYSTALLIZATION CONDITIONS: 0.1M BIS-TRIS PROPANE, 45% PPG
REMARK   280   P400, PH 6.50, VAPOR DIFFUSION, HANGING DROP, TEMPERATURE 298K
REMARK   290
REMARK   290  CRYSTALLOGRAPHIC SYMMETRY
REMARK   290  SYMMETRY OPERATORS FOR SPACE GROUP: I 41 2 2
REMARK   290
REMARK   290        SYMOP   SYMMETRY
REMARK   290        NNNMMM  OPERATOR
REMARK   290          1555  X, Y, Z
REMARK   290          2555  ½ − X, ½ − Y, ½ + Z
REMARK   290          3555  −Y, ½ + X, ¼ + Z
REMARK   290          4555  ½ + Y, −X, ¾ + Z
REMARK   290          5555  ½ − X, Y, ¾ − Z
REMARK   290          6555  X, ½ − Y, ¼ − Z
REMARK   290          7555  ½ + Y, ½ + X, ½ − Z
REMARK   290          8555  −Y, −X, −Z
REMARK   290          9555  ½ + X, ½ + Y, ½ + Z
REMARK   290         10555  1/1 − X, 1/1 − Y, 1/1 + Z
REMARK   290         11555  ½ − Y, 1/1 + X, ¾ + Z
REMARK   290         12555  1/1 + Y, ½ − X, ⁵/4 + Z
REMARK   290         13555  1/1 − X, ½ + Y, ⁵/4 − Z
REMARK   290         14555  ½ + X, 1/1 − Y, ¾ − Z
REMARK   290         15555  1/1 + Y, 1/1 + X, 1/1 − Z
REMARK   290         16555  ½ − Y, ½ − X, ½ − Z
REMARK   290
REMARK   290     WHERE NNN -> OPERATOR NUMBER
REMARK   290           MMM -> TRANSLATION VECTOR
REMARK   290
REMARK   290  CRYSTALLOGRAPHIC SYMMETRY TRANSFORMATIONS
REMARK   290  THE FOLLOWING TRANSFORMATIONS OPERATE ON THE ATOM/HETATM
REMARK   290  RECORDS IN THIS ENTRY TO PRODUCE CRYSTALLOGRAPHICALLY
REMARK   290  RELATED MOLECULES.
REMARK   290      SMTRY1    1    1.000000    0.000000    0.000000     0.00000
REMARK   290      SMTRY2    1    0.000000    1.000000    0.000000     0.00000
REMARK   290      SMTRY3    1    0.000000    0.000000    1.000000     0.00000
REMARK   290      SMTRY1    2   −1.000000    0.000000    0.000000    48.62950
REMARK   290      SMTRY2    2    0.000000   −1.000000    0.000000    48.62950
REMARK   290      SMTRY3    2    0.000000    0.000000    1.000000    32.61400
REMARK   290      SMTRY1    3    0.000000   −1.000000    0.000000     0.00000
REMARK   290      SMTRY2    3    1.000000    0.000000    0.000000    48.62950
REMARK   290      SMTRY3    3    0.000000    0.000000    1.000000    16.30700
REMARK   290      SMTRY1    4    0.000000    1.000000    0.000000    48.62950
REMARK   290      SMTRY2    4   −1.000000    0.000000    0.000000     0.00000
REMARK   290      SMTRY3    4    0.000000    0.000000    1.000000    48.92100
REMARK   290      SMTRY1    5   −1.000000    0.000000    0.000000    48.62950
REMARK   290      SMTRY2    5    0.000000    1.000000    0.000000     0.00000
REMARK   290      SMTRY3    5    0.000000    0.000000   −1.000000    48.92100
REMARK   290      SMTRY1    6    1.000000    0.000000    0.000000     0.00000
REMARK   290      SMTRY2    6    0.000000   −1.000000    0.000000    48.62950
REMARK   290      SMTRY3    6    0.000000    0.000000   −1.000000    16.30700
REMARK   290      SMTRY1    7    0.000000    1.000000    0.000000    48.62950
REMARK   290      SMTRY2    7    1.000000    0.000000    0.000000    48.62950
REMARK   290      SMTRY3    7    0.000000    0.000000   −1.000000    32.61400
REMARK   290      SMTRY1    8    0.000000   −1.000000    0.000000     0.00000
REMARK   290      SMTRY2    8   −1.000000    0.000000    0.000000     0.00000
REMARK   290      SMTRY3    8    0.000000    0.000000   −1.000000     0.00000
REMARK   290      SMTRY1    9    1.000000    0.000000    0.000000    48.62950
REMARK   290      SMTRY2    9    0.000000    1.000000    0.000000    48.62950
REMARK   290      SMTRY3    9    0.000000    0.000000    1.000000    32.61400
REMARK   290      SMTRY1   10   −1.000000    0.000000    0.000000    97.25900
REMARK   290      SMTRY2   10    0.000000   −1.000000    0.000000    97.25900
REMARK   290      SMTRY3   10    0.000000    0.000000    1.000000    65.22800
REMARK   290      SMTRY1   11    0.000000   −1.000000    0.000000    48.62950
REMARK   290      SMTRY2   11    1.000000    0.000000    0.000000    97.25900
REMARK   290      SMTRY3   11    0.000000    0.000000    1.000000    48.92100
REMARK   290      SMTRY1   12    0.000000    1.000000    0.000000    97.25900
REMARK   290      SMTRY2   12   −1.000000    0.000000    0.000000    48.62950
REMARK   290      SMTRY3   12    0.000000    0.000000    1.000000    81.53500
REMARK   290      SMTRY1   13   −1.000000    0.000000    0.000000    97.25900
REMARK   290      SMTRY2   13    0.000000    1.000000    0.000000    48.62950
REMARK   290      SMTRY3   13    0.000000    0.000000   −1.000000    81.53500
REMARK   290      SMTRY1   14    1.000000    0.000000    0.000000    48.62950
REMARK   290      SMTRY2   14    0.000000   −1.000000    0.000000    97.25900
```

APPENDIX I(a)-continued

```
REMARK   290    SMTRY3   14    0.000000    0.000000   -1.000000   48.92100
REMARK   290    SMTRY1   15    0.000000    1.000000    0.000000   97.25900
REMARK   290    SMTRY2   15    1.000000    0.000000    0.000000   97.25900
REMARK   290    SMTRY3   15    0.000000    0.000000   -1.000000   65.22800
REMARK   290    SMTRY1   16    0.000000   -1.000000    0.000000   48.62950
REMARK   290    SMTRY2   16   -1.000000    0.000000    0.000000   48.62950
REMARK   290    SMTRY3   16    0.000000    0.000000   -1.000000   32.61400
REMARK   290
REMARK   290   REMARK: NULL
REMARK   300
REMARK   300   BIOMOLECULE: 1
REMARK   300   THIS ENTRY CONTAINS THE CRYSTALLOGRAPHIC ASYMMETRIC UNIT
REMARK   300   WHICH CONSISTS OF 1 CHAIN(S). SEE REMARK 350 FOR
REMARK   300   INFORMATION ON GENERATING THE BIOLOGICAL MOLECULE(S).
REMARK   350
REMARK   350   GENERATING THE BIOMOLECULE
REMARK   350   COORDINATES FOR A COMPLETE MULTIMER REPRESENTING THE KNOWN
REMARK   350   BIOLOGICALLY SIGNIFICANT OLIGOMERIZATION STATE OF THE
REMARK   350   MOLECULE CAN BE GENERATED BY APPLYING BIOMT TRANSFORMATIONS
REMARK   350   GIVEN BELOW. BOTH NON-CRYSTALLOGRAPHIC AND
REMARK   350   CRYSTALLOGRAPHIC OPERATIONS ARE GIVEN.
REMARK   350
REMARK   350   BIOMOLECULE: 1
REMARK   350   APPLY THE FOLLOWING TO CHAINS: A
REMARK   350     BIOMT1   1    1.000000    0.000000    0.000000    0.00000
REMARK   350     BIOMT2   1    0.000000    1.000000    0.000000    0.00000
REMARK   350     BIOMT3   1    0.000000    0.000000    1.000000    0.00000
REMARK   465
REMARK   465   MISSING RESIDUES
REMARK   465   THE FOLLOWING RESIDUES WERE NOT LOCATED IN THE
REMARK   465   EXPERIMENT. (M = MODEL NUMBER; RES = RESIDUE NAME; C = CHAIN
REMARK   465   IDENTIFIER; SSSEQ = SEQUENCE NUMBER; I = INSERTION CODE.)
REMARK   465
REMARK   465     M   RES  C   SSSEQI
REMARK   465         PHE  A     88
REMARK   465         TRP  A     89
REMARK   465         LEU  A     90
REMARK   465         PRO  A     91
REMARK   465         TYR  A     92
REMARK   465         GLY  A     93
REMARK   465         TYR  A     94
REMARK   465         GLY  A     95
REMARK   465         SER  A     96
REMARK   465         LEU  A     97
REMARK   465         PRO  A     98
REMARK   500
REMARK   500   GEOMETRY AND STEREOCHEMISTRY
REMARK   500   SUBTOPIC: CLOSE CONTACTS IN SAME ASYMMETRIC UNIT
REMARK   500
REMARK   500   THE FOLLOWING ATOMS ARE IN CLOSE CONTACT.
REMARK   500
REMARK   500    ATM1 RES  C   SSEQI    ATM2 RES  C   SSEQI
REMARK   500     N   ALA  A    1        O   HOH        54       1.94
REMARK   500
REMARK   500   GEOMETRY AND STEREOCHEMISTRY
REMARK   500   SUBTOPIC: CLOSE CONTACTS
REMARK   500
REMARK   500   THE FOLLOWING ATOMS THAT ARE RELATED BY CRYSTALLOGRAPHIC
REMARK   500   SYMMETRY ARE IN CLOSE CONTACT. AN ATOM LOCATED WITHIN 0.15
REMARK   500   ANGSTROMS OF A SYMMETRY RELATED ATOM IS ASSUMED TO BE ON A
REMARK   500   SPECIAL POSITION AND IS, THEREFORE, LISTED IN REMARK 375
REMARK   500   INSTEAD OF REMARK 500. ATOMS WITH NON-BLANK ALTERNATE
REMARK   500   LOCATION INDICATORS ARE NOT INCLUDED IN THE CALCULATIONS.
REMARK   500
REMARK   500   DISTANCE CUTOFF:
REMARK   500   2.2 ANGSTROMS FOR CONTACTS NOT INVOLVING HYDROGEN ATOMS
REMARK   500   1.6 ANGSTROMS FOR CONTACTS INVOLVING HYDROGEN ATOMS
REMARK   500
REMARK   500    ATM1 RES  C   SSEQI    ATM2 RES  C   SSEQI    SSYMOP  DISTANCE
REMARK   500     O   ALA  A    1        O   ALA  A    1         8665    2.07
REMARK   500
REMARK   500   GEOMETRY AND STEREOCHEMISTRY
REMARK   500   SUBTOPIC: NON-CIS, NON-TRANS
REMARK   500
REMARK   500   THE FOLLOWING PEPTIDE BONDS DEVIATE SIGNIFICANTLY FROM BOTH
REMARK   500   CIS AND TRANS CONFORMATION. CIS BONDS, IF ANY, ARE LISTED
REMARK   500   ON CISPEP RECORDS. TRANS IS DEFINED AS 180 +/- 30 AND
REMARK   500   CIS IS DEFINED AS 0 +/- 30 DEGREES.
REMARK   500                                               MODEL    OMEGA
REMARK   500   SER   A    100   GLU  A   101                        144.45
```

APPENDIX I(a)-continued

```
REMARK   525
REMARK   525  SOLVENT
REMARK   525  THE FOLLOWING SOLVENT MOLECULES LIE FARTHER THAN EXPECTED
REMARK   525  FROM THE PROTEIN OR NUCLEIC ACID MOLECULE AND MAY BE
REMARK   525  ASSOCIATED WITH A SYMMETRY RELATED MOLECULE (M = MODEL
REMARK   525  NUMBER; RES = RESIDUE NAME; C = CHAIN IDENTIFIER; SSEQ = SEQUENCE
REMARK   525  NUMBER; I = INSERTION CODE):
REMARK   525
REMARK   525   M RES     CSSEQI
REMARK   525     HOH      28    DISTANCE =    5.01 ANGSTROMS
REMARK   525     HOH      60    DISTANCE =    9.08 ANGSTROMS
REMARK   525     HOH      75    DISTANCE =    5.80 ANGSTROMS
REMARK   525     HOH      86    DISTANCE =    9.33 ANGSTROMS
REMARK   525     HOH      90    DISTANCE =    5.58 ANGSTROMS
REMARK   525     HOH      92    DISTANCE =    7.18 ANGSTROMS
REMARK   525     HOH      94    DISTANCE =   11.83 ANGSTROMS
REMARK   900
REMARK   900  RELATED ENTRIES
REMARK   900  RELATED ID: 1VES    RELATED DB: PDB
REMARK   900  THE SAME PROTEIN (12Y-2)
REMARK   999
REMARK   999  SEQUENCE
REMARK   999  A SEQUENCE DATABASE REFERENCE FOR THIS PROTEIN DOES
REMARK   999    NOT CURRENTLY EXIST.
SEQRES    1 A  111  ALA TRP VAL ASP GLN THR PRO ARG THR ALA THR LYS GLU
SEQRES    2 A  111  THR GLY GLU SER LEU THR ILE ASN CYS VAL LEU ARG ASP
SEQRES    3 A  111  ALA SER TYR GLY LEU GLU SER THR GLY TRP TYR ARG THR
SEQRES    4 A  111  LYS LEU GLY SER THR ASN GLU GLN THR ILE SER ILE GLY
SEQRES    5 A  111  GLY ARG TYR VAL GLU THR VAL ASN LYS GLY SER LYS SER
SEQRES    6 A  111  PHE SER LEU ARG ILE ARG ASP LEU ARG VAL GLU ASP SER
SEQRES    7 A  111  GLY THR TYR LYS CYS GLY ALA PHE ARG PHE TRP LEU PRO
SEQRES    8 A  111  TYR GLY TYR GLY SER LEU PRO LEU SER GLU LYS GLY ALA
SEQRES    9 A  111  GLY THR VAL LEU THR VAL LYS
FORMUL    2  HOH     *97(H2 O1)
HELIX     1   1 ARG A    74  SER A   78 5                                     5
SHEET     1   A 4 TRP A    2  THR A    6  0
SHEET     2   A 4 LEU A   18  ARG A   25 -1 O  ARG A   25  N  TRP A    2
SHEET     3   A 4 SER A   65  ILE A   70 -1 O  ILE A   70  N  LEU A   18
SHEET     4   A 4 TYR A   55  ASN A   60 -1 N  ASN A   60  O  SER A   65
SHEET     1   B 5 THR A    9  ALA A   10  0
SHEET     2   B 5 THR A  106  LEU A  108  1 O  VAL A  107  N  ALA A   10
SHEET     3   B 5 GLY A   79  ALA A   85 -1 N  GLY A   79  O  LEU A  108
SHEET     4   B 5 THR A   34  ARG A   38 -1 N  TYR A   37  O  LYS A   82
SHEET     5   B 5 GLN A   47  THR A   48 -1 O  GLN A   47  N  ARG A   38
SHEET     1   C 4 THR A    9  ALA A   10  0
SHEET     2   C 4 THR A  106  LEU A  108  1 O  VAL A  107  N  ALA A   10
SHEET     3   C 4 GLY A   79  ALA A   85 -1 N  GLY A   79  O  LEU A  108
SEEET     4   C 4 GLU A  101  LYS A  102 -1 O  GLU A  101  N  ALA A   85
SSBOND    1 CYS A   22  CYS A   83
CISPEP    1 THR A    6  PRO A    7           0        -3.12
CRYST1   97.259    97.259    65.228  90.00  90.00  90.00  I 41 2 2     16
ORIGX1      1.000000   0.000000   0.000000      0.00000
ORIGX2      0.000000   1.000000   0.000000      0.00000
ORIGX3      0.000000   0.000000   1.000000      0.00000
SCALE1      0.010282   0.000000   0.000000      0.00000
SCALE2      0.000000   0.010282   0.000000      0.00000
SCALE3      0.000000   0.000000   0.015331      0.00000
ATOM      1  N    ALA  A   1      55.513  40.915  -1.352  1.00  39.81   N
ATOM      2  CA   ALA  A   1      54.244  40.231  -0.986  1.00  39.92   C
ATOM      3  C    ALA  A   1      53.526  40.997   0.141  1.00  40.10   C
ATOM      4  O    ALA  A   1      53.961  42.071   0.568  1.00  39.99   O
ATOM      5  CB   ALA  A   1      54.548  38.792  -0.565  1.00  39.81   C
ATOM      6  N    TRP  A   2      52.424  40.457   0.635  1.00  40.03   N
ATOM      7  CA   TRP  A   2      51.839  41.010   1.842  1.00  40.13   C
ATOM      8  C    TRP  A   2      50.807  40.092   2.398  1.00  40.02   C
ATOM      9  O    TRP  A   2      50.312  39.214   1.691  1.00  39.96   O
ATOM     10  CB   TRP  A   2      51.215  42.378   1.578  1.00  40.30   C
ATOM     11  CG   TRP  A   2      50.173  42.417   0.480  1.00  41.25   C
ATOM     12  CD1  TRP  A   2      50.368  42.203  -0.853  1.00  41.78   C
ATOM     13  CD2  TRP  A   2      48.787  42.751   0.629  1.00  41.72   C
ATOM     14  NE1  TRP  A   2      49.188  42.376  -1.533  1.00  41.43   N
ATOM     15  CE2  TRP  A   2      48.206  42.712  -0.641  1.00  41.13   C
ATOM     16  CE3  TRP  A   2      47.977  43.089   1.723  1.00  43.91   C
ATOM     17  CZ2  TRP  A   2      46.867  42.980  -0.851  1.00  42.60   C
ATOM     18  CZ3  TRP  A   2      46.637  43.363   1.506  1.00  43.85   C
ATOM     19  CH2  TRP  A   2      46.100  43.300   0.233  1.00  43.32   C
ATOM     20  N    VAL  A   3      50.489  40.299   3.675  1.00  39.97   N
ATOM     21  CA   VAL  A   3      49.447  39.528   4.356  1.00  39.89   C
ATOM     22  C    VAL  A   3      48.257  40.456   4.600  1.00  40.16   C
ATOM     23  O    VAL  A   3      48.404  41.631   4.929  1.00  40.00   O
```

APPENDIX I(a)-continued

| ATOM | 24 | CB | VAL | A | 3 | 49.958 | 38.817 | 5.658 | 1.00 | 39.49 | C |
|---|---|---|---|---|---|---|---|---|---|---|---|
| ATOM | 25 | CG1 | VAL | A | 3 | 48.829 | 38.221 | 6.441 | 1.00 | 39.82 | C |
| ATOM | 26 | CG2 | VAL | A | 3 | 50.923 | 37.704 | 5.310 | 1.00 | 38.65 | C |
| ATOM | 27 | N | ASP | A | 4 | 47.075 | 39.886 | 4.397 | 1.00 | 40.79 | N |
| ATOM | 28 | CA | ASP | A | 4 | 45.818 | 40.616 | 4.341 | 1.00 | 40.59 | C |
| ATOM | 29 | C | ASP | A | 4 | 45.024 | 40.126 | 5.538 | 1.00 | 40.13 | C |
| ATOM | 30 | O | ASP | A | 4 | 44.435 | 39.061 | 5.532 | 1.00 | 38.36 | O |
| ATOM | 31 | CB | ASP | A | 4 | 45.110 | 40.349 | 2.990 | 1.00 | 40.76 | C |
| ATOM | 32 | CG | ASP | A | 4 | 44.054 | 41.400 | 2.640 | 1.00 | 40.56 | C |
| ATOM | 33 | OD1 | ASP | A | 4 | 43.544 | 41.358 | 1.487 | 1.00 | 37.98 | O |
| ATOM | 34 | OD2 | ASP | A | 4 | 43.664 | 42.283 | 3.449 | 1.00 | 39.55 | O |
| ATOM | 35 | N | GLN | A | 5 | 45.083 | 40.921 | 6.591 | 1.00 | 40.81 | N |
| ATOM | 36 | CA | GLN | A | 5 | 44.451 | 40.587 | 7.845 | 1.00 | 41.30 | C |
| ATOM | 37 | C | GLN | A | 5 | 43.186 | 41.395 | 8.027 | 1.00 | 41.46 | C |
| ATOM | 38 | O | GLN | A | 5 | 43.123 | 42.577 | 7.702 | 1.00 | 41.23 | O |
| ATOM | 39 | CB | GLN | A | 5 | 45.400 | 40.847 | 9.003 | 1.00 | 41.37 | C |
| ATOM | 40 | CG | GLN | A | 5 | 44.887 | 40.277 | 10.299 | 1.00 | 42.10 | C |
| ATOM | 41 | CD | GLN | A | 5 | 45.861 | 40.424 | 11.402 | 1.00 | 42.51 | C |
| ATOM | 42 | OE1 | GLN | A | 5 | 47.069 | 40.451 | 11.166 | 1.00 | 44.78 | O |
| ATOM | 43 | NE2 | GLN | A | 5 | 45.352 | 40.534 | 12.624 | 1.00 | 41.68 | N |
| ATOM | 44 | N | THR | A | 6 | 42.214 | 40.738 | 8.641 | 1.00 | 42.08 | N |
| ATOM | 45 | CA | THR | A | 6 | 40.819 | 41.137 | 8.591 | 1.00 | 42.22 | C |
| ATOM | 46 | C | THR | A | 6 | 40.083 | 40.525 | 9.824 | 1.00 | 42.57 | C |
| ATOM | 47 | O | THR | A | 6 | 40.242 | 39.345 | 10.099 | 1.00 | 43.00 | O |
| ATOM | 48 | CB | THR | A | 6 | 40.290 | 40.612 | 7.239 | 1.00 | 41.88 | C |
| ATOM | 49 | OG1 | THR | A | 6 | 39.946 | 41.711 | 6.391 | 1.00 | 41.95 | O |
| ATOM | 50 | CG2 | THR | A | 6 | 39.025 | 39.834 | 7.380 | 1.00 | 42.09 | C |
| ATOM | 51 | N | PRO | A | 7 | 39.344 | 41.292 | 10.619 | 1.00 | 42.73 | N |
| ATOM | 52 | CA | PRO | A | 7 | 39.187 | 42.740 | 10.490 | 1.00 | 42.90 | C |
| ATOM | 53 | C | PRO | A | 7 | 40.330 | 43.531 | 11.124 | 1.00 | 42.96 | C |
| ATOM | 54 | O | PRO | A | 7 | 41.152 | 42.995 | 11.849 | 1.00 | 42.51 | O |
| ATOM | 55 | CB | PRO | A | 7 | 37.880 | 43.001 | 11.256 | 1.00 | 42.96 | C |
| ATOM | 56 | CG | PRO | A | 7 | 37.869 | 41.963 | 12.343 | 1.00 | 42.75 | C |
| ATOM | 57 | CD | PRO | A | 7 | 38.595 | 40.759 | 11.773 | 1.00 | 42.62 | C |
| ATOM | 58 | N | ARG | A | 8 | 40.342 | 44.827 | 10.863 | 1.00 | 43.73 | N |
| ATOM | 59 | CA | ARG | A | 8 | 41.356 | 45.709 | 11.405 | 1.00 | 44.66 | C |
| ATOM | 60 | C | ARG | A | 8 | 40.985 | 46.138 | 12.829 | 1.00 | 44.54 | C |
| ATOM | 61 | O | ARG | A | 8 | 41.804 | 46.687 | 13.565 | 1.00 | 44.09 | O |
| ATOM | 62 | CB | ARG | A | 8 | 41.542 | 46.920 | 10.471 | 1.00 | 45.24 | C |
| ATOM | 63 | CG | ARG | A | 8 | 42.962 | 47.049 | 9.838 | 1.00 | 47.41 | C |
| ATOM | 64 | CD | ARG | A | 8 | 43.159 | 46.295 | 8.519 | 1.00 | 49.70 | C |
| ATOM | 65 | NE | ARG | A | 8 | 43.473 | 47.198 | 7.407 | 1.00 | 52.43 | N |
| ATOM | 66 | CZ | ARG | A | 8 | 43.429 | 46.856 | 6.105 | 1.00 | 54.91 | C |
| ATOM | 67 | NH1 | ARG | A | 8 | 43.082 | 45.621 | 5.715 | 1.00 | 54.18 | N |
| ATOM | 68 | NH2 | ARG | A | 8 | 43.739 | 47.765 | 5.175 | 1.00 | 55.49 | N |
| ATOM | 69 | N | THR | A | 9 | 39.736 | 45.876 | 13.195 | 1.00 | 45.02 | N |
| ATOM | 70 | CA | THR | A | 9 | 39.191 | 46.199 | 14.512 | 1.00 | 45.42 | C |
| ATOM | 71 | C | THR | A | 9 | 38.029 | 45.259 | 14.826 | 1.00 | 45.80 | C |
| ATOM | 72 | O | THR | A | 9 | 37.109 | 45.112 | 14.013 | 1.00 | 46.14 | O |
| ATOM | 73 | CB | THR | A | 9 | 38.648 | 47.646 | 14.554 | 1.00 | 45.22 | C |
| ATOM | 74 | OG1 | THR | A | 9 | 38.000 | 47.954 | 13.311 | 1.00 | 45.04 | O |
| ATOM | 75 | CG2 | THR | A | 9 | 39.777 | 48.670 | 14.677 | 1.00 | 45.18 | C |
| ATOM | 76 | N | ALA | A | 10 | 38.057 | 44.646 | 16.007 | 1.00 | 45.93 | N |
| ATOM | 77 | CA | ALA | A | 10 | 36.911 | 43.887 | 16.487 | 1.00 | 45.99 | C |
| ATOM | 78 | C | ALA | A | 10 | 36.711 | 44.153 | 17.968 | 1.00 | 46.02 | C |
| ATOM | 79 | O | ALA | A | 10 | 37.496 | 43.675 | 18.785 | 1.00 | 46.26 | O |
| ATOM | 80 | CB | ALA | A | 10 | 37.100 | 42.385 | 16.221 | 1.00 | 45.95 | C |
| ATOM | 81 | N | THR | A | 11 | 35.679 | 44.937 | 18.302 | 1.00 | 45.89 | N |
| ATOM | 82 | CA | THR | A | 11 | 35.211 | 45.069 | 19.687 | 1.00 | 45.55 | C |
| ATOM | 83 | C | THR | A | 11 | 34.095 | 44.051 | 19.970 | 1.00 | 45.47 | C |
| ATOM | 84 | O | THR | A | 11 | 32.901 | 44.352 | 19.936 | 1.00 | 45.09 | O |
| ATOM | 85 | CB | THR | A | 11 | 34.806 | 46.535 | 20.052 | 1.00 | 45.51 | C |
| ATOM | 86 | OG1 | THR | A | 11 | 34.375 | 46.597 | 21.420 | 1.00 | 44.83 | O |
| ATOM | 87 | CG2 | THR | A | 11 | 33.601 | 47.035 | 19.257 | 1.00 | 45.59 | C |
| ATOM | 88 | N | LYS | A | 12 | 34.536 | 42.821 | 20.219 | 1.00 | 45.62 | N |
| ATOM | 89 | CA | LYS | A | 12 | 33.681 | 41.730 | 20.660 | 1.00 | 45.76 | C |
| ATOM | 90 | C | LYS | A | 12 | 33.400 | 41.907 | 22.149 | 1.00 | 45.70 | C |
| ATOM | 91 | O | LYS | A | 12 | 33.885 | 42.864 | 22.765 | 1.00 | 45.63 | O |
| ATOM | 92 | CB | LYS | A | 12 | 34.386 | 40.390 | 20.416 | 1.00 | 45.92 | C |
| ATOM | 93 | CG | LYS | A | 12 | 34.484 | 39.985 | 18.949 | 1.00 | 46.82 | C |
| ATOM | 94 | CD | LYS | A | 12 | 33.149 | 39.399 | 18.453 | 1.00 | 47.89 | C |
| ATOM | 95 | CE | LYS | A | 12 | 33.151 | 39.145 | 16.934 | 1.00 | 48.84 | C |
| ATOM | 96 | NZ | LYS | A | 12 | 31.796 | 39.348 | 16.320 | 1.00 | 48.93 | N |
| ATOM | 97 | N | GLU | A | 13 | 32.612 | 41.002 | 22.731 | 1.00 | 45.55 | N |
| ATOM | 98 | CA | GLU | A | 13 | 32.409 | 41.008 | 24.181 | 1.00 | 45.41 | C |
| ATOM | 99 | C | GLU | A | 13 | 32.642 | 39.635 | 24.805 | 1.00 | 45.16 | C |
| ATOM | 100 | O | GLU | A | 13 | 32.848 | 38.657 | 24.088 | 1.00 | 45.05 | O |
| ATOM | 101 | CB | GLU | A | 13 | 31.046 | 41.606 | 24.567 | 1.00 | 45.43 | C |
| ATOM | 102 | CG | GLU | A | 13 | 29.861 | 41.148 | 23.742 | 1.00 | 45.72 | C |
| ATOM | 103 | CD | GLU | A | 13 | 28.564 | 41.822 | 24.170 | 1.00 | 46.47 | C |

APPENDIX I(a)-continued

| ATOM | 104 | OE1 | GLU | A | 13 | 28.600 | 42.702 | 25.066 | 1.00 | 46.24 | O |
|---|---|---|---|---|---|---|---|---|---|---|---|
| ATOM | 105 | OE2 | GLU | A | 13 | 27.500 | 41.468 | 23.610 | 1.00 | 46.90 | O |
| ATOM | 106 | N | THR | A | 14 | 32.644 | 39.593 | 26.140 | 1.00 | 44.90 | N |
| ATOM | 107 | CA | THR | A | 14 | 33.083 | 38.428 | 26.911 | 1.00 | 44.71 | C |
| ATOM | 108 | C | THR | A | 14 | 32.125 | 37.269 | 26.709 | 1.00 | 44.50 | C |
| ATOM | 109 | O | THR | A | 14 | 30.911 | 37.449 | 26.735 | 1.00 | 44.21 | O |
| ATOM | 110 | CB | THR | A | 14 | 33.238 | 38.792 | 28.435 | 1.00 | 44.82 | C |
| ATOM | 111 | OG1 | THR | A | 14 | 34.553 | 39.314 | 28.685 | 1.00 | 44.93 | O |
| ATOM | 112 | CG2 | THR | A | 14 | 33.164 | 37.561 | 29.361 | 1.00 | 44.75 | C |
| ATOM | 113 | N | GLY | A | 15 | 32.694 | 36.085 | 26.496 | 1.00 | 44.50 | N |
| ATOM | 114 | CA | GLY | A | 15 | 31.931 | 34.889 | 26.197 | 1.00 | 44.65 | C |
| ATOM | 115 | C | GLY | A | 15 | 31.896 | 34.603 | 24.710 | 1.00 | 44.80 | C |
| ATOM | 116 | O | GLY | A | 15 | 31.830 | 33.436 | 24.318 | 1.00 | 44.91 | O |
| ATOM | 117 | N | GLU | A | 16 | 31.938 | 35.667 | 23.896 | 1.00 | 44.95 | N |
| ATOM | 118 | CA | GLU | A | 16 | 31.877 | 35.577 | 22.428 | 1.00 | 44.98 | C |
| ATOM | 119 | C | GLU | A | 16 | 33.187 | 35.043 | 21.885 | 1.00 | 44.72 | C |
| ATOM | 120 | O | GLU | A | 16 | 34.108 | 34.803 | 22.648 | 1.00 | 44.90 | O |
| ATOM | 121 | CB | GLU | A | 16 | 31.594 | 36.948 | 21.789 | 1.00 | 45.01 | C |
| ATOM | 122 | CG | GLU | A | 16 | 30.329 | 37.640 | 22.280 | 1.00 | 45.66 | C |
| ATOM | 123 | CD | GLU | A | 16 | 29.871 | 38.772 | 21.368 | 1.00 | 46.88 | C |
| ATOM | 124 | OE1 | GLU | A | 16 | 28.712 | 39.223 | 21.498 | 1.00 | 47.16 | O |
| ATOM | 125 | OE2 | GLU | A | 16 | 30.668 | 39.221 | 20.518 | 1.00 | 48.78 | O |
| ATOM | 126 | N | SER | A | 17 | 33.267 | 34.847 | 20.572 | 1.00 | 44.36 | N |
| ATOM | 127 | CA | SER | A | 17 | 34.525 | 34.452 | 19.945 | 1.00 | 44.22 | C |
| ATOM | 128 | C | SER | A | 17 | 34.950 | 35.435 | 18.848 | 1.00 | 43.95 | C |
| ATOM | 129 | O | SER | A | 17 | 34.197 | 36.323 | 18.477 | 1.00 | 43.90 | O |
| ATOM | 130 | CB | SER | A | 17 | 34.430 | 33.018 | 19.417 | 1.00 | 44.27 | C |
| ATOM | 131 | OG | SER | A | 17 | 33.581 | 32.935 | 18.296 | 1.00 | 44.57 | O |
| ATOM | 132 | N | LEU | A | 18 | 36.173 | 35.281 | 18.361 | 1.00 | 43.92 | N |
| ATOM | 133 | CA | LEU | A | 18 | 36.724 | 36.130 | 17.302 | 1.00 | 44.02 | C |
| ATOM | 134 | C | LEU | A | 18 | 37.370 | 35.255 | 16.226 | 1.00 | 43.55 | C |
| ATOM | 135 | O | LEU | A | 18 | 38.128 | 34.358 | 16.549 | 1.00 | 43.25 | O |
| ATOM | 136 | CB | LEU | A | 18 | 37.782 | 37.064 | 17.905 | 1.00 | 44.33 | C |
| ATOM | 137 | CG | LEU | A | 18 | 38.245 | 38.374 | 17.238 | 1.00 | 45.16 | C |
| ATOM | 138 | CD1 | LEU | A | 18 | 39.734 | 38.631 | 17.509 | 1.00 | 45.46 | C |
| ATOM | 139 | CD2 | LEU | A | 18 | 37.995 | 38.410 | 15.752 | 1.00 | 46.71 | C |
| ATOM | 140 | N | THR | A | 19 | 37.068 | 35.503 | 14.961 | 1.00 | 43.45 | N |
| ATOM | 141 | CA | THR | A | 19 | 37.811 | 34.883 | 13.873 | 1.00 | 43.78 | C |
| ATOM | 142 | C | THR | A | 19 | 38.532 | 35.969 | 13.100 | 1.00 | 44.14 | C |
| ATOM | 143 | O | THR | A | 19 | 37.898 | 36.792 | 12.447 | 1.00 | 43.91 | O |
| ATOM | 144 | CB | THR | A | 19 | 36.883 | 34.098 | 12.919 | 1.00 | 44.21 | C |
| ATOM | 145 | OG1 | THR | A | 19 | 36.260 | 32.974 | 13.596 | 1.00 | 43.80 | O |
| ATOM | 146 | CG2 | THR | A | 19 | 37.701 | 33.482 | 11.751 | 1.00 | 43.99 | C |
| ATOM | 147 | N | ILE | A | 20 | 39.855 | 35.995 | 13.228 | 1.00 | 44.85 | N |
| ATOM | 148 | CA | ILE | A | 20 | 40.724 | 36.824 | 12.400 | 1.00 | 45.39 | C |
| ATOM | 149 | C | ILE | A | 20 | 41.108 | 36.004 | 11.155 | 1.00 | 45.61 | C |
| ATOM | 150 | O | ILE | A | 20 | 41.388 | 34.805 | 11.253 | 1.00 | 45.68 | O |
| ATOM | 151 | CB | ILE | A | 20 | 42.012 | 37.231 | 13.181 | 1.00 | 45.75 | C |
| ATOM | 152 | CG1 | ILE | A | 20 | 41.681 | 37.954 | 14.485 | 1.00 | 45.74 | C |
| ATOM | 153 | CG2 | ILE | A | 20 | 42.932 | 38.125 | 12.340 | 1.00 | 46.03 | C |
| ATOM | 154 | CD1 | ILE | A | 20 | 42.736 | 37.725 | 15.527 | 1.00 | 45.77 | C |
| ATOM | 155 | N | ASN | A | 21 | 41.139 | 36.664 | 9.997 | 1.00 | 45.69 | N |
| ATOM | 156 | CA | ASN | A | 21 | 41.425 | 36.011 | 8.731 | 1.00 | 45.87 | C |
| ATOM | 157 | C | ASN | A | 21 | 42.566 | 36.673 | 8.007 | 1.00 | 45.77 | C |
| ATOM | 158 | O | ASN | A | 21 | 42.517 | 37.865 | 7.702 | 1.00 | 45.99 | O |
| ATOM | 159 | CB | ASN | A | 21 | 40.197 | 36.006 | 7.832 | 1.00 | 45.95 | C |
| ATOM | 160 | CG | ASN | A | 21 | 39.197 | 34.957 | 8.240 | 1.00 | 46.88 | C |
| ATOM | 161 | OD1 | ASN | A | 21 | 38.008 | 35.241 | 8.394 | 1.00 | 45.42 | O |
| ATOM | 162 | ND2 | ASN | A | 21 | 39.678 | 33.729 | 8.444 | 1.00 | 49.22 | N |
| ATOM | 163 | N | CYS | A | 22 | 43.589 | 35.867 | 7.733 | 1.00 | 45.61 | N |
| ATOM | 164 | CA | CYS | A | 22 | 44.744 | 36.274 | 6.942 | 1.00 | 45.36 | C |
| ATOM | 165 | C | CYS | A | 22 | 44.808 | 35.587 | 5.576 | 1.00 | 44.39 | C |
| ATOM | 166 | O | CYS | A | 22 | 44.397 | 34.437 | 5.442 | 1.00 | 44.02 | O |
| ATOM | 167 | CB | CYS | A | 22 | 46.018 | 36.007 | 7.733 | 1.00 | 45.38 | C |
| ATOM | 168 | SG | CYS | A | 22 | 46.155 | 37.120 | 9.136 | 1.00 | 47.07 | S |
| ATOM | 169 | N | VAL | A | 23 | 45.299 | 36.314 | 4.564 | 1.00 | 43.69 | N |
| ATOM | 170 | CA | VAL | A | 23 | 45.610 | 35.707 | 3.272 | 1.00 | 42.87 | C |
| ATOM | 171 | C | VAL | A | 23 | 46.930 | 36.260 | 2.699 | 1.00 | 42.09 | C |
| ATOM | 172 | O | VAL | A | 23 | 47.175 | 37.458 | 2.743 | 1.00 | 41.16 | O |
| ATOM | 173 | CB | VAL | A | 23 | 44.411 | 35.789 | 2.289 | 1.00 | 42.69 | C |
| ATOM | 174 | CG1 | VAL | A | 23 | 44.004 | 37.187 | 2.072 | 1.00 | 42.87 | C |
| ATOM | 175 | CG2 | VAL | A | 23 | 44.734 | 35.101 | 0.943 | 1.00 | 43.10 | C |
| ATOM | 176 | N | LEU | A | 24 | 47.789 | 35.346 | 2.229 | 1.00 | 41.64 | N |
| ATOM | 177 | CA | LEU | A | 24 | 49.057 | 35.682 | 1.605 | 1.00 | 41.41 | C |
| ATOM | 178 | C | LEU | A | 24 | 48.809 | 36.129 | 0.181 | 1.00 | 41.77 | C |
| ATOM | 179 | O | LEU | A | 24 | 48.420 | 35.330 | −0.689 | 1.00 | 41.43 | O |
| ATOM | 180 | CB | LEU | A | 24 | 50.032 | 34.502 | 1.614 | 1.00 | 41.29 | C |
| ATOM | 181 | CG | LEU | A | 24 | 51.469 | 34.832 | 1.175 | 1.00 | 41.13 | C |
| ATOM | 182 | CD1 | LEU | A | 24 | 52.229 | 35.654 | 2.232 | 1.00 | 41.67 | C |
| ATOM | 183 | CD2 | LEU | A | 24 | 52.248 | 33.586 | 0.829 | 1.00 | 40.60 | C |

APPENDIX I(a)-continued

| ATOM | 184 | N   | ARG | A | 25 | 49.090 | 37.411 | -0.055 | 1.00 | 41.98 | N |
|------|-----|-----|-----|---|----|--------|--------|--------|------|-------|---|
| ATOM | 185 | CA  | ARG | A | 25 | 48.726 | 38.075 | -1.287 | 1.00 | 42.00 | C |
| ATOM | 186 | C   | ARG | A | 25 | 49.889 | 38.325 | -2.241 | 1.00 | 42.03 | C |
| ATOM | 187 | O   | ARG | A | 25 | 51.012 | 38.537 | -1.824 | 1.00 | 41.90 | O |
| ATOM | 188 | CB  | ARG | A | 25 | 48.032 | 39.373 | -0.938 | 1.00 | 42.03 | C |
| ATOM | 189 | CG  | ARG | A | 25 | 46.623 | 39.140 | -0.474 | 1.00 | 42.99 | C |
| ATOM | 190 | CD  | ARG | A | 25 | 45.621 | 39.047 | -1.599 | 1.00 | 44.97 | C |
| ATOM | 191 | NE  | ARG | A | 25 | 44.560 | 40.014 | -1.353 | 1.00 | 47.71 | N |
| ATOM | 192 | CZ  | ARG | A | 25 | 44.099 | 40.915 | -2.219 | 1.00 | 47.44 | C |
| ATOM | 193 | NH1 | ARG | A | 25 | 43.147 | 41.739 | -1.836 | 1.00 | 46.78 | N |
| ATOM | 194 | NH2 | ARG | A | 25 | 44.563 | 41.001 | -3.456 | 1.00 | 48.53 | N |
| ATOM | 195 | N   | ASP | A | 26 | 49.588 | 38.295 | -3.536 | 1.00 | 42.42 | N |
| ATOM | 196 | CA  | ASP | A | 26 | 50.527 | 38.682 | -4.575 | 1.00 | 42.66 | C |
| ATOM | 197 | C   | ASP | A | 26 | 51.931 | 38.119 | -4.330 | 1.00 | 43.02 | C |
| ATOM | 198 | O   | ASP | A | 26 | 52.910 | 38.831 | -4.519 | 1.00 | 43.38 | O |
| ATOM | 199 | CB  | ASP | A | 26 | 50.554 | 40.217 | -4.690 | 1.00 | 42.63 | C |
| ATOM | 200 | CG  | ASP | A | 26 | 49.267 | 40.784 | -5.308 | 1.00 | 42.95 | C |
| ATOM | 201 | OD1 | ASP | A | 26 | 48.444 | 41.361 | -4.570 | 1.00 | 41.75 | O |
| ATOM | 202 | OD2 | ASP | A | 26 | 48.985 | 40.699 | -6.526 | 1.00 | 43.93 | O |
| ATOM | 203 | N   | ALA | A | 27 | 52.019 | 36.849 | -3.918 | 1.00 | 43.15 | N |
| ATOM | 204 | CA  | ALA | A | 27 | 53.298 | 36.200 | -3.589 | 1.00 | 43.42 | C |
| ATOM | 205 | C   | ALA | A | 27 | 53.539 | 34.998 | -4.486 | 1.00 | 43.84 | C |
| ATOM | 206 | O   | ALA | A | 27 | 52.683 | 34.130 | -4.576 | 1.00 | 44.30 | O |
| ATOM | 207 | CB  | ALA | A | 27 | 53.320 | 35.760 | -2.119 | 1.00 | 43.12 | C |
| ATOM | 208 | N   | SER | A | 28 | 54.707 | 34.934 | -5.118 | 1.00 | 44.23 | N |
| ATOM | 209 | CA  | SER | A | 28 | 55.060 | 33.830 | -6.031 | 1.00 | 45.06 | C |
| ATOM | 210 | C   | SER | A | 28 | 55.236 | 32.425 | -5.371 | 1.00 | 45.41 | C |
| ATOM | 211 | O   | SER | A | 28 | 55.084 | 31.382 | -6.024 | 1.00 | 45.34 | O |
| ATOM | 212 | CB  | SER | A | 28 | 56.347 | 34.192 | -6.792 | 1.00 | 45.26 | C |
| ATOM | 213 | OG  | SER | A | 28 | 57.380 | 34.588 | -5.892 | 1.00 | 45.67 | O |
| ATOM | 214 | N   | TYR | A | 29 | 55.569 | 32.417 | -4.087 | 1.00 | 45.63 | N |
| ATOM | 215 | CA  | TYR | A | 29 | 55.743 | 31.191 | -3.322 | 1.00 | 46.00 | C |
| ATOM | 216 | C   | TYR | A | 29 | 54.418 | 30.837 | -2.637 | 1.00 | 46.01 | C |
| ATOM | 217 | O   | TYR | A | 29 | 53.559 | 31.681 | -2.501 | 1.00 | 45.94 | O |
| ATOM | 218 | CB  | TYR | A | 29 | 56.864 | 31.377 | -2.283 | 1.00 | 46.23 | C |
| ATOM | 219 | CG  | TYR | A | 29 | 56.797 | 32.700 | -1.550 | 1.00 | 46.49 | C |
| ATOM | 220 | CD1 | TYR | A | 29 | 57.416 | 33.832 | -2.066 | 1.00 | 46.98 | C |
| ATOM | 221 | CD2 | TYR | A | 29 | 56.085 | 32.824 | -0.361 | 1.00 | 48.01 | C |
| ATOM | 222 | CE1 | TYR | A | 29 | 57.343 | 35.050 | -1.415 | 1.00 | 47.91 | C |
| ATOM | 223 | CE2 | TYR | A | 29 | 55.998 | 34.044 | 0.307  | 1.00 | 49.09 | C |
| ATOM | 224 | CZ  | TYR | A | 29 | 56.635 | 35.156 | -0.229 | 1.00 | 49.16 | C |
| ATOM | 225 | OH  | TYR | A | 29 | 56.559 | 36.376 | 0.412  | 1.00 | 49.69 | O |
| ATOM | 226 | N   | GLY | A | 30 | 54.259 | 29.594 | -2.202 | 1.00 | 46.34 | N |
| ATOM | 227 | CA  | GLY | A | 30 | 53.046 | 29.169 | -1.518 | 1.00 | 46.80 | C |
| ATOM | 228 | C   | GLY | A | 30 | 53.063 | 29.488 | -0.029 | 1.00 | 47.05 | C |
| ATOM | 229 | O   | GLY | A | 30 | 53.892 | 30.277 | 0.419  | 1.00 | 47.34 | O |
| ATOM | 230 | N   | LEU | A | 31 | 52.168 | 28.870 | 0.741  | 1.00 | 47.02 | N |
| ATOM | 231 | CA  | LEU | A | 31 | 52.073 | 29.121 | 2.180  | 1.00 | 47.04 | C |
| ATOM | 232 | C   | LEU | A | 31 | 52.846 | 28.046 | 2.918  | 1.00 | 47.34 | C |
| ATOM | 233 | O   | LEU | A | 31 | 52.657 | 26.854 | 2.672  | 1.00 | 47.29 | O |
| ATOM | 234 | CB  | LEU | A | 31 | 50.620 | 29.072 | 2.653  | 1.00 | 46.88 | C |
| ATOM | 235 | CG  | LEU | A | 31 | 50.129 | 30.133 | 3.642  | 1.00 | 46.91 | C |
| ATOM | 236 | CD1 | LEU | A | 31 | 48.959 | 29.592 | 4.454  | 1.00 | 47.38 | C |
| ATOM | 237 | CD2 | LEU | A | 31 | 51.222 | 30.614 | 4.558  | 1.00 | 47.01 | C |
| ATOM | 238 | N   | GLU | A | 32 | 53.712 | 28.452 | 3.832  | 1.00 | 47.44 | N |
| ATOM | 239 | CA  | GLU | A | 32 | 54.431 | 27.474 | 4.604  | 1.00 | 47.70 | C |
| ATOM | 240 | C   | GLU | A | 32 | 54.182 | 27.729 | 6.092  | 1.00 | 47.35 | C |
| ATOM | 241 | O   | GLU | A | 32 | 53.023 | 27.704 | 6.485  | 1.00 | 47.96 | O |
| ATOM | 242 | CB  | GLU | A | 32 | 55.882 | 27.401 | 4.135  | 1.00 | 48.20 | C |
| ATOM | 243 | CG  | GLU | A | 32 | 56.334 | 25.976 | 3.750  | 1.00 | 50.58 | C |
| ATOM | 244 | CD  | GLU | A | 32 | 55.433 | 25.258 | 2.727  | 1.00 | 52.14 | C |
| ATOM | 245 | OE1 | GLU | A | 32 | 54.939 | 25.923 | 1.779  | 1.00 | 52.31 | O |
| ATOM | 246 | OE2 | GLU | A | 32 | 55.240 | 24.015 | 2.871  | 1.00 | 52.34 | O |
| ATOM | 247 | N   | SER | A | 33 | 55.178 | 27.958 | 6.940  | 1.00 | 46.79 | N |
| ATOM | 248 | CA  | SER | A | 33 | 54.873 | 28.132 | 8.367  | 1.00 | 46.45 | C |
| ATOM | 249 | C   | SER | A | 33 | 53.863 | 29.273 | 8.593  | 1.00 | 46.08 | C |
| ATOM | 250 | O   | SER | A | 33 | 53.672 | 30.135 | 7.739  | 1.00 | 46.14 | O |
| ATOM | 251 | CB  | SER | A | 33 | 56.152 | 28.351 | 9.188  | 1.00 | 46.57 | C |
| ATOM | 252 | OG  | SER | A | 33 | 55.888 | 28.890 | 10.475 | 1.00 | 46.71 | O |
| ATOM | 253 | N   | THR | A | 34 | 53.188 | 29.239 | 9.730  | 1.00 | 45.62 | N |
| ATOM | 254 | CA  | THR | A | 34 | 52.243 | 30.289 | 10.107 | 1.00 | 45.56 | C |
| ATOM | 255 | C   | THR | A | 34 | 52.425 | 30.607 | 11.569 | 1.00 | 44.81 | C |
| ATOM | 256 | O   | THR | A | 34 | 52.995 | 29.815 | 12.293 | 1.00 | 45.14 | O |
| ATOM | 257 | CB  | THR | A | 34 | 50.802 | 29.825 | 9.885  | 1.00 | 45.92 | C |
| ATOM | 258 | OG1 | THR | A | 34 | 50.659 | 28.479 | 10.376 | 1.00 | 47.83 | O |
| ATOM | 259 | CG2 | THR | A | 34 | 50.459 | 29.745 | 8.384  | 1.00 | 45.65 | C |
| ATOM | 260 | N   | GLY | A | 35 | 51.910 | 31.742 | 12.016 | 1.00 | 44.17 | N |
| ATOM | 261 | CA  | GLY | A | 35 | 52.193 | 32.203 | 13.362 | 1.00 | 43.84 | C |
| ATOM | 262 | C   | GLY | A | 35 | 51.335 | 33.355 | 13.829 | 1.00 | 43.55 | C |
| ATOM | 263 | O   | GLY | A | 35 | 51.044 | 34.257 | 13.065 | 1.00 | 43.37 | O |

APPENDIX I(a)-continued

| ATOM | 264 | N | TRP | A | 36 | 50.951 | 33.333 | 15.098 | 1.00 | 43.43 | N |
|---|---|---|---|---|---|---|---|---|---|---|---|
| ATOM | 265 | CA | TRP | A | 36 | 50.125 | 34.387 | 15.662 | 1.00 | 43.65 | C |
| ATOM | 266 | C | TRP | A | 36 | 50.808 | 35.017 | 16.862 | 1.00 | 43.76 | C |
| ATOM | 267 | O | TRP | A | 36 | 51.562 | 34.348 | 17.536 | 1.00 | 44.10 | O |
| ATOM | 268 | CB | TRP | A | 36 | 48.736 | 33.832 | 16.015 | 1.00 | 43.66 | C |
| ATOM | 269 | CG | TRP | A | 36 | 48.035 | 33.281 | 14.791 | 1.00 | 43.52 | C |
| ATOM | 270 | CD1 | TRP | A | 36 | 48.228 | 32.056 | 14.203 | 1.00 | 43.11 | C |
| ATOM | 271 | CD2 | TRP | A | 36 | 47.066 | 33.955 | 13.989 | 1.00 | 43.23 | C |
| ATOM | 272 | NE1 | TRP | A | 36 | 47.429 | 31.932 | 13.091 | 1.00 | 42.76 | N |
| ATOM | 273 | CE2 | TRP | A | 36 | 46.708 | 33.079 | 12.933 | 1.00 | 42.13 | C |
| ATOM | 274 | CE3 | TRP | A | 36 | 46.465 | 35.212 | 14.052 | 1.00 | 42.31 | C |
| ATOM | 275 | CZ2 | TRP | A | 36 | 45.786 | 33.412 | 11.970 | 1.00 | 42.17 | C |
| ATOM | 276 | CZ3 | TRP | A | 36 | 45.545 | 35.541 | 13.101 | 1.00 | 42.77 | C |
| ATOM | 277 | CH2 | TRP | A | 36 | 45.213 | 34.645 | 12.060 | 1.00 | 43.22 | C |
| ATOM | 278 | N | TYR | A | 37 | 50.547 | 36.306 | 17.100 | 1.00 | 44.26 | N |
| ATOM | 279 | CA | TYR | A | 37 | 51.155 | 37.090 | 18.178 | 1.00 | 44.69 | C |
| ATOM | 280 | C | TYR | A | 37 | 50.145 | 38.050 | 18.793 | 1.00 | 45.68 | C |
| ATOM | 281 | O | TYR | A | 37 | 49.574 | 38.884 | 18.132 | 1.00 | 45.58 | O |
| ATOM | 282 | CB | TYR | A | 37 | 52.357 | 37.862 | 17.660 | 1.00 | 44.51 | C |
| ATOM | 283 | CG | TYR | A | 37 | 53.257 | 36.964 | 16.865 | 1.00 | 44.82 | C |
| ATOM | 284 | CD1 | TYR | A | 37 | 54.326 | 36.311 | 17.461 | 1.00 | 45.09 | C |
| ATOM | 285 | CD2 | TYR | A | 37 | 52.993 | 36.705 | 15.529 | 1.00 | 45.84 | C |
| ATOM | 286 | CE1 | TYR | A | 37 | 55.114 | 35.452 | 16.740 | 1.00 | 45.33 | C |
| ATOM | 287 | CE2 | TYR | A | 37 | 53.776 | 35.854 | 14.802 | 1.00 | 45.95 | C |
| ATOM | 288 | CZ | TYR | A | 37 | 54.826 | 35.232 | 15.411 | 1.00 | 45.91 | C |
| ATOM | 289 | OH | TYR | A | 37 | 55.589 | 34.380 | 14.672 | 1.00 | 49.07 | O |
| ATOM | 290 | N | ARG | A | 38 | 49.900 | 37.872 | 20.079 | 1.00 | 47.31 | N |
| ATOM | 291 | CA | ARG | A | 38 | 49.134 | 38.801 | 20.909 | 1.00 | 48.10 | C |
| ATOM | 292 | C | ARG | A | 38 | 50.091 | 39.931 | 21.209 | 1.00 | 47.87 | C |
| ATOM | 293 | O | ARG | A | 38 | 51.303 | 39.726 | 21.173 | 1.00 | 47.88 | O |
| ATOM | 294 | CB | ARG | A | 38 | 48.759 | 38.111 | 22.249 | 1.00 | 48.62 | C |
| ATOM | 295 | CG | ARG | A | 38 | 47.377 | 38.432 | 22.831 | 1.00 | 50.71 | C |
| ATOM | 296 | CD | ARG | A | 38 | 46.603 | 37.207 | 23.407 | 1.00 | 53.44 | C |
| ATOM | 297 | NE | ARG | A | 38 | 46.786 | 37.089 | 24.850 | 1.00 | 55.90 | N |
| ATOM | 298 | CZ | ARG | A | 38 | 47.813 | 36.479 | 25.449 | 1.00 | 58.69 | C |
| ATOM | 299 | NH1 | ARG | A | 38 | 47.882 | 36.457 | 26.782 | 1.00 | 59.57 | N |
| ATOM | 300 | NH2 | ARG | A | 38 | 48.779 | 35.889 | 24.738 | 1.00 | 59.59 | N |
| ATOM | 301 | N | THR | A | 39 | 49.567 | 41.114 | 21.489 | 1.00 | 47.47 | N |
| ATOM | 302 | CA | THR | A | 39 | 50.306 | 42.060 | 22.309 | 1.00 | 47.36 | C |
| ATOM | 303 | C | THR | A | 39 | 49.306 | 42.440 | 23.385 | 1.00 | 47.23 | C |
| ATOM | 304 | O | THR | A | 39 | 48.311 | 43.116 | 23.131 | 1.00 | 47.09 | O |
| ATOM | 305 | CB | THR | A | 39 | 50.927 | 43.249 | 21.480 | 1.00 | 47.47 | C |
| ATOM | 306 | OG1 | THR | A | 39 | 52.344 | 43.323 | 21.720 | 1.00 | 47.03 | O |
| ATOM | 307 | CG2 | THR | A | 39 | 50.436 | 44.627 | 21.920 | 1.00 | 47.35 | C |
| ATOM | 308 | N | LYS | A | 40 | 49.535 | 41.920 | 24.582 | 1.00 | 47.19 | N |
| ATOM | 309 | CA | LYS | A | 40 | 48.558 | 42.086 | 25.633 | 1.00 | 47.13 | C |
| ATOM | 310 | C | LYS | A | 40 | 48.444 | 43.571 | 25.866 | 1.00 | 47.19 | C |
| ATOM | 311 | O | LYS | A | 40 | 49.445 | 44.248 | 26.082 | 1.00 | 47.17 | O |
| ATOM | 312 | CB | LYS | A | 40 | 48.928 | 41.324 | 26.921 | 1.00 | 47.02 | C |
| ATOM | 313 | CG | LYS | A | 40 | 47.688 | 40.729 | 27.623 | 1.00 | 46.82 | C |
| ATOM | 314 | CD | LYS | A | 40 | 48.015 | 39.740 | 28.748 | 1.00 | 46.47 | C |
| ATOM | 315 | CE | LYS | A | 40 | 47.890 | 40.377 | 30.145 | 1.00 | 46.50 | C |
| ATOM | 316 | NZ | LYS | A | 40 | 46.755 | 41.347 | 30.294 | 1.00 | 45.86 | N |
| ATOM | 317 | N | LEU | A | 41 | 47.225 | 44.076 | 25.723 | 1.00 | 47.30 | N |
| ATOM | 318 | CA | LEU | A | 41 | 46.871 | 45.412 | 26.180 | 1.00 | 47.33 | C |
| ATOM | 319 | C | LEU | A | 41 | 47.530 | 45.674 | 27.555 | 1.00 | 47.66 | C |
| ATOM | 320 | O | LEU | A | 41 | 47.133 | 45.093 | 28.587 | 1.00 | 47.69 | O |
| ATOM | 321 | CB | LEU | A | 41 | 45.346 | 45.509 | 26.247 | 1.00 | 47.14 | C |
| ATOM | 322 | CG | LEU | A | 41 | 44.683 | 46.802 | 26.698 | 1.00 | 46.34 | C |
| ATOM | 323 | CD1 | LEU | A | 41 | 43.722 | 47.282 | 25.653 | 1.00 | 45.95 | C |
| ATOM | 324 | CD2 | LEU | A | 41 | 43.951 | 46.576 | 28.014 | 1.00 | 46.62 | C |
| ATOM | 325 | N | GLY | A | 42 | 48.559 | 46.526 | 27.547 | 1.00 | 47.83 | N |
| ATOM | 326 | CA | GLY | A | 42 | 49.360 | 46.802 | 28.732 | 1.00 | 47.73 | C |
| ATOM | 327 | C | GLY | A | 42 | 50.836 | 46.954 | 28.413 | 1.00 | 47.74 | C |
| ATOM | 328 | O | GLY | A | 42 | 51.489 | 47.872 | 28.901 | 1.00 | 47.48 | O |
| ATOM | 329 | N | SER | A | 43 | 51.351 | 46.050 | 27.583 | 1.00 | 48.04 | N |
| ATOM | 330 | CA | SER | A | 43 | 52.779 | 45.973 | 27.275 | 1.00 | 48.28 | C |
| ATOM | 331 | C | SER | A | 43 | 53.132 | 46.240 | 25.793 | 1.00 | 48.76 | C |
| ATOM | 332 | O | SER | A | 43 | 52.263 | 46.291 | 24.909 | 1.00 | 48.44 | O |
| ATOM | 333 | CB | SER | A | 43 | 53.307 | 44.595 | 27.691 | 1.00 | 48.30 | C |
| ATOM | 334 | OG | SER | A | 43 | 52.660 | 43.559 | 26.975 | 1.00 | 47.00 | O |
| ATOM | 335 | N | THR | A | 44 | 54.429 | 46.431 | 25.548 | 1.00 | 49.30 | N |
| ATOM | 336 | CA | THR | A | 44 | 54.965 | 46.557 | 24.185 | 1.00 | 49.61 | C |
| ATOM | 337 | C | THR | A | 44 | 55.542 | 45.219 | 23.671 | 1.00 | 49.81 | C |
| ATOM | 338 | O | THR | A | 44 | 55.581 | 44.967 | 22.450 | 1.00 | 49.86 | O |
| ATOM | 339 | CB | THR | A | 44 | 56.019 | 47.712 | 24.113 | 1.00 | 49.63 | C |
| ATOM | 340 | OG1 | THR | A | 44 | 56.404 | 47.937 | 22.748 | 1.00 | 49.78 | O |
| ATOM | 341 | CG2 | THR | A | 44 | 57.330 | 47.364 | 24.847 | 1.00 | 49.19 | C |
| ATOM | 342 | N | ASN | A | 45 | 55.995 | 44.395 | 24.627 | 1.00 | 49.77 | N |
| ATOM | 343 | CA | ASN | A | 45 | 56.406 | 43.001 | 24.416 | 1.00 | 49.48 | C |

APPENDIX I(a)-continued

| ATOM | 344 | C | ASN | A | 45 | 55.386 | 42.201 | 23.612 | 1.00 | 49.23 | C |
|---|---|---|---|---|---|---|---|---|---|---|---|
| ATOM | 345 | O | ASN | A | 45 | 54.319 | 41.857 | 24.120 | 1.00 | 49.15 | O |
| ATOM | 346 | CB | ASN | A | 45 | 56.617 | 42.324 | 25.786 | 1.00 | 49.49 | C |
| ATOM | 347 | CG | ASN | A | 45 | 57.451 | 41.059 | 25.705 | 1.00 | 49.18 | C |
| ATOM | 348 | OD1 | ASN | A | 45 | 56.931 | 39.971 | 25.446 | 1.00 | 47.89 | O |
| ATOM | 349 | ND2 | ASN | A | 45 | 58.755 | 41.195 | 25.957 | 1.00 | 48.90 | N |
| ATOM | 350 | N | GLU | A | 46 | 55.703 | 41.923 | 22.352 | 1.00 | 49.07 | N |
| ATOM | 351 | CA | GLU | A | 46 | 54.849 | 41.064 | 21.544 | 1.00 | 49.04 | C |
| ATOM | 352 | C | GLU | A | 46 | 55.201 | 39.618 | 21.828 | 1.00 | 48.82 | C |
| ATOM | 353 | O | GLU | A | 46 | 56.369 | 39.233 | 21.815 | 1.00 | 48.78 | O |
| ATOM | 354 | CB | GLU | A | 46 | 54.967 | 41.353 | 20.047 | 1.00 | 49.09 | C |
| ATOM | 355 | CG | GLU | A | 46 | 53.704 | 40.968 | 19.284 | 1.00 | 49.83 | C |
| ATOM | 356 | CD | GLU | A | 46 | 53.952 | 40.570 | 17.838 | 1.00 | 51.36 | C |
| ATOM | 357 | OE1 | GLU | A | 46 | 53.070 | 40.860 | 16.976 | 1.00 | 51.15 | O |
| ATOM | 358 | OE2 | GLU | A | 46 | 55.014 | 39.951 | 17.570 | 1.00 | 51.52 | O |
| ATOM | 359 | N | GLN | A | 47 | 54.166 | 38.828 | 22.082 | 1.00 | 48.68 | N |
| ATOM | 360 | CA | GLN | A | 47 | 54.310 | 37.447 | 22.519 | 1.00 | 48.37 | C |
| ATOM | 361 | C | GLN | A | 47 | 53.572 | 36.493 | 21.577 | 1.00 | 47.51 | C |
| ATOM | 362 | O | GLN | A | 47 | 52.394 | 36.706 | 21.249 | 1.00 | 47.38 | O |
| ATOM | 363 | CB | GLN | A | 47 | 53.787 | 37.293 | 23.954 | 1.00 | 48.68 | C |
| ATOM | 364 | CG | GLN | A | 47 | 52.342 | 37.807 | 24.195 | 1.00 | 49.39 | C |
| ATOM | 365 | CD | GLN | A | 47 | 51.875 | 37.558 | 25.625 | 1.00 | 50.87 | C |
| ATOM | 366 | OE1 | GLN | A | 47 | 50.669 | 37.523 | 25.893 | 1.00 | 51.36 | O |
| ATOM | 367 | NE2 | GLN | A | 47 | 52.832 | 37.379 | 26.546 | 1.00 | 50.64 | N |
| ATOM | 368 | N | THR | A | 48 | 54.288 | 35.448 | 21.159 | 1.00 | 46.35 | N |
| ATOM | 369 | CA | THR | A | 48 | 53.721 | 34.349 | 20.381 | 1.00 | 45.37 | C |
| ATOM | 370 | C | THR | A | 48 | 52.475 | 33.751 | 21.058 | 1.00 | 44.66 | C |
| ATOM | 371 | O | THR | A | 48 | 52.422 | 33.619 | 22.271 | 1.00 | 44.42 | O |
| ATOM | 372 | CB | THR | A | 48 | 54.795 | 33.240 | 20.174 | 1.00 | 45.26 | C |
| ATOM | 373 | OG1 | THR | A | 48 | 56.010 | 33.809 | 19.668 | 1.00 | 43.92 | O |
| ATOM | 374 | CG2 | THR | A | 48 | 54.372 | 32.261 | 19.087 | 1.00 | 45.53 | C |
| ATOM | 375 | N | ILE | A | 49 | 51.470 | 33.420 | 20.262 | 1.00 | 43.99 | N |
| ATOM | 376 | CA | ILE | A | 49 | 50.325 | 32.645 | 20.724 | 1.00 | 43.43 | C |
| ATOM | 377 | C | ILE | A | 49 | 50.598 | 31.154 | 20.458 | 1.00 | 43.66 | C |
| ATOM | 378 | O | ILE | A | 49 | 51.019 | 30.794 | 19.352 | 1.00 | 44.12 | O |
| ATOM | 379 | CB | ILE | A | 49 | 49.060 | 33.106 | 19.994 | 1.00 | 42.82 | C |
| ATOM | 380 | CG1 | ILE | A | 49 | 48.633 | 34.473 | 20.529 | 1.00 | 41.60 | C |
| ATOM | 381 | CG2 | ILE | A | 49 | 47.949 | 32.065 | 20.138 | 1.00 | 42.75 | C |
| ATOM | 382 | CD1 | ILE | A | 49 | 47.627 | 35.211 | 19.649 | 1.00 | 40.71 | C |
| ATOM | 383 | N | SER | A | 50 | 50.357 | 30.302 | 21.457 | 1.00 | 43.62 | N |
| ATOM | 384 | CA | SER | A | 50 | 50.546 | 28.846 | 21.321 | 1.00 | 43.72 | C |
| ATOM | 385 | C | SER | A | 50 | 49.252 | 28.069 | 21.024 | 1.00 | 43.40 | C |
| ATOM | 386 | O | SER | A | 50 | 48.505 | 27.736 | 21.944 | 1.00 | 43.31 | O |
| ATOM | 387 | CB | SER | A | 50 | 51.169 | 28.288 | 22.586 | 1.00 | 43.69 | C |
| ATOM | 388 | OG | SER | A | 50 | 52.525 | 28.670 | 22.645 | 1.00 | 45.22 | O |
| ATOM | 389 | N | ILE | A | 51 | 49.051 | 27.741 | 19.744 | 1.00 | 43.11 | N |
| ATOM | 390 | CA | ILE | A | 51 | 47.804 | 27.170 | 19.211 | 1.00 | 42.81 | C |
| ATOM | 391 | C | ILE | A | 51 | 47.340 | 25.902 | 19.933 | 1.00 | 42.89 | C |
| ATOM | 392 | O | ILE | A | 51 | 48.044 | 24.893 | 19.973 | 1.00 | 43.22 | O |
| ATOM | 393 | CB | ILE | A | 51 | 47.928 | 26.862 | 17.691 | 1.00 | 42.60 | C |
| ATOM | 394 | CG1 | ILE | A | 51 | 48.287 | 28.126 | 16.869 | 1.00 | 42.42 | C |
| ATOM | 395 | CG2 | ILE | A | 51 | 46.646 | 26.231 | 17.177 | 1.00 | 42.42 | C |
| ATOM | 396 | CD1 | ILE | A | 51 | 47.368 | 29.346 | 17.030 | 1.00 | 41.97 | C |
| ATOM | 397 | N | GLY | A | 52 | 46.125 | 25.975 | 20.464 | 1.00 | 42.68 | N |
| ATOM | 398 | CA | GLY | A | 52 | 45.517 | 24.912 | 21.226 | 1.00 | 42.57 | C |
| ATOM | 399 | C | GLY | A | 52 | 44.403 | 25.490 | 22.076 | 1.00 | 42.68 | C |
| ATOM | 400 | O | GLY | A | 52 | 44.396 | 26.683 | 22.359 | 1.00 | 42.51 | O |
| ATOM | 401 | N | GLY | A | 53 | 43.467 | 24.636 | 22.488 | 1.00 | 42.80 | N |
| ATOM | 402 | CA | GLY | A | 53 | 42.378 | 25.025 | 23.372 | 1.00 | 42.58 | C |
| ATOM | 403 | C | GLY | A | 53 | 41.385 | 26.025 | 22.801 | 1.00 | 42.38 | C |
| ATOM | 404 | O | GLY | A | 53 | 40.644 | 25.714 | 21.855 | 1.00 | 42.63 | O |
| ATOM | 405 | N | ARG | A | 54 | 41.353 | 27.211 | 23.410 | 1.00 | 41.93 | N |
| ATOM | 406 | CA | ARG | A | 54 | 40.476 | 28.301 | 22.981 | 1.00 | 41.82 | C |
| ATOM | 407 | C | ARG | A | 54 | 40.875 | 28.889 | 21.641 | 1.00 | 41.60 | C |
| ATOM | 408 | O | ARG | A | 54 | 40.031 | 29.296 | 20.881 | 1.00 | 41.77 | O |
| ATOM | 409 | CB | ARG | A | 54 | 40.516 | 29.441 | 23.985 | 1.00 | 41.91 | C |
| ATOM | 410 | CG | ARG | A | 54 | 39.826 | 29.154 | 25.263 | 1.00 | 42.28 | C |
| ATOM | 411 | CD | ARG | A | 54 | 40.540 | 29.674 | 26.510 | 1.00 | 43.07 | C |
| ATOM | 412 | NE | ARG | A | 54 | 41.425 | 30.833 | 26.339 | 1.00 | 42.41 | N |
| ATOM | 413 | CZ | ARG | A | 54 | 41.047 | 32.056 | 25.963 | 1.00 | 42.94 | C |
| ATOM | 414 | NH1 | ARG | A | 54 | 39.789 | 32.339 | 25.636 | 1.00 | 42.52 | N |
| ATOM | 415 | NH2 | ARG | A | 54 | 41.957 | 33.008 | 25.885 | 1.00 | 43.60 | N |
| ATOM | 416 | N | TYR | A | 55 | 42.166 | 28.988 | 21.378 | 1.00 | 41.61 | N |
| ATOM | 417 | CA | TYR | A | 55 | 42.650 | 29.497 | 20.103 | 1.00 | 41.70 | C |
| ATOM | 418 | C | TYR | A | 55 | 42.726 | 28.309 | 19.151 | 1.00 | 41.39 | C |
| ATOM | 419 | O | TYR | A | 55 | 43.364 | 27.317 | 19.490 | 1.00 | 41.66 | O |
| ATOM | 420 | CB | TYR | A | 55 | 44.045 | 30.071 | 20.256 | 1.00 | 41.78 | C |
| ATOM | 421 | CG | TYR | A | 55 | 44.264 | 31.058 | 21.374 | 1.00 | 43.01 | C |
| ATOM | 422 | CD1 | TYR | A | 55 | 44.114 | 32.412 | 21.151 | 1.00 | 45.49 | C |
| ATOM | 423 | CD2 | TYR | A | 55 | 44.698 | 30.648 | 22.625 | 1.00 | 44.41 | C |

APPENDIX I(a)-continued

| ATOM | 424 | CE1 | TYR | A | 55 | 44.364 | 33.356 | 22.149 | 1.00 | 46.84 | C |
|---|---|---|---|---|---|---|---|---|---|---|---|
| ATOM | 425 | CE2 | TYR | A | 55 | 44.951 | 31.580 | 23.642 | 1.00 | 46.64 | C |
| ATOM | 426 | CZ | TYR | A | 55 | 44.783 | 32.942 | 23.394 | 1.00 | 47.72 | C |
| ATOM | 427 | OH | TYR | A | 55 | 45.036 | 33.905 | 24.366 | 1.00 | 49.23 | O |
| ATOM | 428 | N | VAL | A | 56 | 42.074 | 28.395 | 18.004 | 1.00 | 41.05 | N |
| ATOM | 429 | CA | VAL | A | 56 | 42.029 | 27.272 | 17.070 | 1.00 | 41.07 | C |
| ATOM | 430 | C | VAL | A | 56 | 42.311 | 27.777 | 15.674 | 1.00 | 41.10 | C |
| ATOM | 431 | O | VAL | A | 56 | 41.569 | 28.596 | 15.132 | 1.00 | 41.64 | O |
| ATOM | 432 | CB | VAL | A | 56 | 40.694 | 26.430 | 17.153 | 1.00 | 41.25 | C |
| ATOM | 433 | CG1 | VAL | A | 56 | 39.609 | 27.137 | 17.971 | 1.00 | 41.73 | C |
| ATOM | 434 | CG2 | VAL | A | 56 | 40.172 | 26.028 | 15.763 | 1.00 | 40.97 | C |
| ATOM | 435 | N | GLU | A | 57 | 43.409 | 27.292 | 15.105 | 1.00 | 40.96 | N |
| ATOM | 436 | CA | GLU | A | 57 | 43.907 | 27.802 | 13.840 | 1.00 | 40.50 | C |
| ATOM | 437 | C | GLU | A | 57 | 43.551 | 26.841 | 12.720 | 1.00 | 40.33 | C |
| ATOM | 438 | O | GLU | A | 57 | 43.610 | 25.629 | 12.889 | 1.00 | 39.83 | O |
| ATOM | 439 | CB | GLU | A | 57 | 45.415 | 27.998 | 13.907 | 1.00 | 40.54 | C |
| ATOM | 440 | CG | GLU | A | 57 | 46.000 | 28.762 | 12.727 | 1.00 | 39.88 | C |
| ATOM | 441 | CD | GLU | A | 57 | 47.473 | 28.469 | 12.482 | 1.00 | 38.40 | C |
| ATOM | 442 | OE1 | GLU | A | 57 | 48.114 | 29.301 | 11.801 | 1.00 | 38.52 | O |
| ATOM | 443 | OE2 | GLU | A | 57 | 47.983 | 27.414 | 12.932 | 1.00 | 36.20 | O |
| ATOM | 444 | N | THR | A | 58 | 43.186 | 27.423 | 11.578 | 1.00 | 40.58 | N |
| ATOM | 445 | CA | THR | A | 58 | 42.790 | 26.704 | 10.378 | 1.00 | 40.61 | C |
| ATOM | 446 | C | THR | A | 58 | 43.598 | 27.214 | 9.204 | 1.00 | 40.52 | C |
| ATOM | 447 | O | THR | A | 58 | 43.541 | 28.376 | 8.894 | 1.00 | 40.83 | O |
| ATOM | 448 | CB | THR | A | 58 | 41.319 | 26.947 | 10.131 | 1.00 | 40.51 | C |
| ATOM | 449 | OG1 | THR | A | 58 | 40.594 | 26.653 | 11.332 | 1.00 | 40.91 | O |
| ATOM | 450 | CG2 | THR | A | 58 | 40.770 | 25.955 | 9.126 | 1.00 | 40.94 | C |
| ATOM | 451 | N | VAL | A | 59 | 44.354 | 26.342 | 8.559 | 1.00 | 40.88 | N |
| ATOM | 452 | CA | VAL | A | 59 | 45.209 | 26.761 | 7.469 | 1.00 | 41.62 | C |
| ATOM | 453 | C | VAL | A | 59 | 44.781 | 26.118 | 6.177 | 1.00 | 41.67 | C |
| ATOM | 454 | O | VAL | A | 59 | 44.760 | 24.902 | 6.034 | 1.00 | 40.44 | O |
| ATOM | 455 | CB | VAL | A | 59 | 46.709 | 26.454 | 7.729 | 1.00 | 42.11 | C |
| ATOM | 456 | CG1 | VAL | A | 59 | 47.562 | 26.709 | 6.467 | 1.00 | 42.52 | C |
| ATOM | 457 | CG2 | VAL | A | 59 | 47.238 | 27.304 | 8.895 | 1.00 | 42.97 | C |
| ATOM | 458 | N | ASN | A | 60 | 44.438 | 26.981 | 5.234 | 1.00 | 42.73 | N |
| ATOM | 459 | CA | ASN | A | 60 | 44.254 | 26.580 | 3.848 | 1.00 | 43.69 | C |
| ATOM | 460 | C | ASN | A | 60 | 45.350 | 27.108 | 2.904 | 1.00 | 44.08 | C |
| ATOM | 461 | O | ASN | A | 60 | 45.186 | 28.134 | 2.225 | 1.00 | 44.00 | O |
| ATOM | 462 | CB | ASN | A | 60 | 42.850 | 26.963 | 3.411 | 1.00 | 43.92 | C |
| ATOM | 463 | CG | ASN | A | 60 | 41.801 | 26.329 | 4.299 | 1.00 | 44.18 | C |
| ATOM | 464 | OD1 | ASN | A | 60 | 41.512 | 25.128 | 4.195 | 1.00 | 43.39 | O |
| ATOM | 465 | ND2 | ASN | A | 60 | 41.270 | 27.117 | 5.219 | 1.00 | 44.84 | N |
| ATOM | 466 | N | LYS | A | 61 | 46.487 | 26.399 | 2.909 | 1.00 | 44.37 | N |
| ATOM | 467 | CA | LYS | A | 61 | 47.524 | 26.609 | 1.918 | 1.00 | 44.47 | C |
| ATOM | 468 | C | LYS | A | 61 | 46.898 | 26.038 | 0.671 | 1.00 | 44.64 | C |
| ATOM | 469 | O | LYS | A | 61 | 46.173 | 25.035 | 0.742 | 1.00 | 44.99 | O |
| ATOM | 470 | CB | LYS | A | 61 | 48.856 | 25.930 | 2.313 | 1.00 | 44.51 | C |
| ATOM | 471 | CG | LYS | A | 61 | 48.903 | 24.387 | 2.322 | 1.00 | 44.75 | C |
| ATOM | 472 | CD | LYS | A | 61 | 50.173 | 23.793 | 1.630 | 1.00 | 45.19 | C |
| ATOM | 473 | CE | LYS | A | 61 | 51.015 | 22.846 | 2.575 | 1.00 | 46.53 | C |
| ATOM | 474 | NZ | LYS | A | 61 | 50.959 | 21.330 | 2.328 | 1.00 | 45.04 | N |
| ATOM | 475 | N | GLY | A | 62 | 47.119 | 26.692 | −0.457 | 1.00 | 44.60 | N |
| ATOM | 476 | CA | GLY | A | 62 | 46.387 | 26.359 | −1.667 | 1.00 | 44.89 | C |
| ATOM | 477 | C | GLY | A | 62 | 45.563 | 27.560 | −2.050 | 1.00 | 45.08 | C |
| ATOM | 478 | O | GLY | A | 62 | 45.623 | 28.028 | −3.199 | 1.00 | 45.76 | O |
| ATOM | 479 | N | SER | A | 63 | 44.806 | 28.073 | −1.079 | 1.00 | 44.83 | N |
| ATOM | 480 | CA | SER | A | 63 | 44.249 | 29.417 | −1.186 | 1.00 | 44.31 | C |
| ATOM | 481 | C | SER | A | 63 | 45.076 | 30.389 | −0.342 | 1.00 | 44.40 | C |
| ATOM | 482 | O | SER | A | 63 | 44.659 | 31.524 | −0.106 | 1.00 | 45.19 | O |
| ATOM | 483 | CB | SER | A | 63 | 42.765 | 29.447 | −0.796 | 1.00 | 43.91 | C |
| ATOM | 484 | OG | SER | A | 63 | 42.566 | 29.106 | 0.552 | 1.00 | 42.61 | O |
| ATOM | 485 | N | LYS | A | 64 | 46.252 | 29.969 | 0.114 | 1.00 | 44.25 | N |
| ATOM | 486 | CA | LYS | A | 64 | 47.113 | 30.860 | 0.890 | 1.00 | 44.38 | C |
| ATOM | 487 | C | LYS | A | 64 | 46.362 | 31.577 | 2.063 | 1.00 | 44.90 | C |
| ATOM | 488 | O | LYS | A | 64 | 46.748 | 32.662 | 2.520 | 1.00 | 44.39 | O |
| ATOM | 489 | CB | LYS | A | 64 | 47.771 | 31.866 | −0.063 | 1.00 | 43.88 | C |
| ATOM | 490 | CG | LYS | A | 64 | 49.066 | 31.391 | −0.649 | 1.00 | 43.04 | C |
| ATOM | 491 | CD | LYS | A | 64 | 49.237 | 31.859 | −2.077 | 1.00 | 43.15 | C |
| ATOM | 492 | CE | LYS | A | 64 | 50.702 | 31.983 | −2.440 | 1.00 | 43.42 | C |
| ATOM | 493 | NZ | LYS | A | 64 | 51.009 | 31.656 | −3.874 | 1.00 | 43.88 | N |
| ATOM | 494 | N | SER | A | 65 | 45.296 | 30.938 | 2.545 | 1.00 | 45.34 | N |
| ATOM | 495 | CA | SER | A | 65 | 44.506 | 31.436 | 3.657 | 1.00 | 45.55 | C |
| ATOM | 496 | C | SER | A | 65 | 44.859 | 30.722 | 4.949 | 1.00 | 45.70 | C |
| ATOM | 497 | O | SER | A | 65 | 45.151 | 29.524 | 4.968 | 1.00 | 45.65 | O |
| ATOM | 498 | CB | SER | A | 65 | 43.043 | 31.218 | 3.368 | 1.00 | 45.66 | C |
| ATOM | 499 | OG | SER | A | 65 | 42.746 | 31.666 | 2.060 | 1.00 | 47.51 | O |
| ATOM | 500 | N | PHE | A | 66 | 44.879 | 31.496 | 6.022 | 1.00 | 46.04 | N |
| ATOM | 501 | CA | PHE | A | 66 | 44.975 | 30.970 | 7.373 | 1.00 | 46.46 | C |
| ATOM | 502 | C | PHE | A | 66 | 44.180 | 31.868 | 8.289 | 1.00 | 46.96 | C |
| ATOM | 503 | O | PHE | A | 66 | 43.821 | 32.983 | 7.917 | 1.00 | 47.34 | O |

APPENDIX I(a)-continued

| ATOM | 504 | CB | PHE | A | 66 | 46.418 | 30.795 | 7.864 | 1.00 | 46.58 | C |
|---|---|---|---|---|---|---|---|---|---|---|---|
| ATOM | 505 | CG | PHE | A | 66 | 47.295 | 32.024 | 7.739 | 1.00 | 46.03 | C |
| ATOM | 506 | CD1 | PHE | A | 66 | 47.894 | 32.562 | 8.850 | 1.00 | 45.98 | C |
| ATOM | 507 | CD2 | PHE | A | 66 | 47.593 | 32.571 | 6.502 | 1.00 | 45.65 | C |
| ATOM | 508 | CE1 | PHE | A | 66 | 48.736 | 33.644 | 8.736 | 1.00 | 46.45 | C |
| ATOM | 509 | CE2 | PHE | A | 66 | 48.420 | 33.648 | 6.387 | 1.00 | 46.28 | C |
| ATOM | 510 | CZ | PHE | A | 66 | 48.998 | 34.190 | 7.507 | 1.00 | 46.93 | C |
| ATOM | 511 | N | SER | A | 67 | 43.887 | 31.362 | 9.483 | 1.00 | 47.40 | N |
| ATOM | 512 | CA | SER | A | 67 | 42.797 | 31.900 | 10.301 | 1.00 | 47.25 | C |
| ATOM | 513 | C | SER | A | 67 | 42.861 | 31.390 | 11.738 | 1.00 | 47.20 | C |
| ATOM | 514 | O | SER | A | 67 | 43.245 | 30.241 | 12.007 | 1.00 | 46.85 | O |
| ATOM | 515 | CB | SER | A | 67 | 41.445 | 31.534 | 9.663 | 1.00 | 47.08 | C |
| ATOM | 516 | OG | SER | A | 67 | 40.452 | 31.232 | 10.624 | 1.00 | 46.69 | O |
| ATOM | 517 | N | LEU | A | 68 | 42.476 | 32.272 | 12.649 | 1.00 | 47.00 | N |
| ATOM | 518 | CA | LEU | A | 68 | 42.493 | 31.990 | 14.065 | 1.00 | 47.00 | C |
| ATOM | 519 | C | LEU | A | 68 | 41.130 | 32.354 | 14.616 | 1.00 | 47.52 | C |
| ATOM | 520 | O | LEU | A | 68 | 40.742 | 33.530 | 14.551 | 1.00 | 47.90 | O |
| ATOM | 521 | CB | LEU | A | 68 | 43.587 | 32.842 | 14.724 | 1.00 | 46.58 | C |
| ATOM | 522 | CG | LEU | A | 68 | 43.663 | 32.936 | 16.246 | 1.00 | 45.67 | C |
| ATOM | 523 | CD1 | LEU | A | 68 | 44.187 | 31.659 | 16.863 | 1.00 | 44.93 | C |
| ATOM | 524 | CD2 | LEU | A | 68 | 44.549 | 34.085 | 16.631 | 1.00 | 46.07 | C |
| ATOM | 525 | N | ARG | A | 69 | 40.394 | 31.355 | 15.124 | 1.00 | 47.58 | N |
| ATOM | 526 | CA | ARG | A | 69 | 39.227 | 31.612 | 15.975 | 1.00 | 47.49 | C |
| ATOM | 527 | C | ARG | A | 69 | 39.629 | 31.518 | 17.432 | 1.00 | 47.38 | C |
| ATOM | 528 | O | ARG | A | 69 | 40.130 | 30.483 | 17.850 | 1.00 | 46.69 | O |
| ATOM | 529 | CB | ARG | A | 69 | 38.084 | 30.631 | 15.698 | 1.00 | 47.74 | C |
| ATOM | 530 | CG | ARG | A | 69 | 36.735 | 31.107 | 16.207 | 1.00 | 48.05 | C |
| ATOM | 531 | CD | ARG | A | 69 | 35.559 | 30.284 | 15.720 | 1.00 | 50.06 | C |
| ATOM | 532 | NE | ARG | A | 69 | 34.814 | 29.685 | 16.848 | 1.00 | 52.61 | N |
| ATOM | 533 | CZ | ARG | A | 69 | 33.507 | 29.870 | 17.130 | 1.00 | 52.39 | C |
| ATOM | 534 | NH1 | ARG | A | 69 | 32.724 | 30.653 | 16.378 | 1.00 | 52.14 | N |
| ATOM | 535 | NH2 | ARG | A | 69 | 32.982 | 29.261 | 18.189 | 1.00 | 51.54 | N |
| ATOM | 536 | N | ILE | A | 70 | 39.427 | 32.603 | 18.187 | 1.00 | 47.73 | N |
| ATOM | 537 | CA | ILE | A | 70 | 39.636 | 32.606 | 19.643 | 1.00 | 48.12 | C |
| ATOM | 538 | C | ILE | A | 70 | 38.291 | 32.469 | 20.350 | 1.00 | 48.27 | C |
| ATOM | 539 | O | ILE | A | 70 | 37.476 | 33.380 | 20.289 | 1.00 | 48.45 | O |
| ATOM | 540 | CB | ILE | A | 70 | 40.311 | 33.899 | 20.149 | 1.00 | 48.01 | C |
| ATOM | 541 | CG1 | ILE | A | 70 | 41.379 | 34.400 | 19.189 | 1.00 | 48.22 | C |
| ATOM | 542 | CG2 | ILE | A | 70 | 40.912 | 33.652 | 21.524 | 1.00 | 47.97 | C |
| ATOM | 543 | CD1 | ILE | A | 70 | 41.707 | 35.866 | 19.402 | 1.00 | 49.26 | C |
| ATOM | 544 | N | ARG | A | 71 | 38.091 | 31.353 | 21.048 | 1.00 | 48.47 | N |
| ATOM | 545 | CA | ARG | A | 71 | 36.793 | 30.972 | 21.600 | 1.00 | 48.71 | C |
| ATOM | 546 | C | ARG | A | 71 | 36.670 | 31.511 | 22.987 | 1.00 | 48.26 | C |
| ATOM | 547 | O | ARG | A | 71 | 37.671 | 31.684 | 23.675 | 1.00 | 48.07 | O |
| ATOM | 548 | CB | ARG | A | 71 | 36.661 | 29.448 | 21.702 | 1.00 | 49.15 | C |
| ATOM | 549 | CG | ARG | A | 71 | 36.940 | 28.673 | 20.415 | 1.00 | 51.24 | C |
| ATOM | 550 | CD | ARG | A | 71 | 37.414 | 27.240 | 20.664 | 1.00 | 53.73 | C |
| ATOM | 551 | NE | ARG | A | 71 | 36.868 | 26.293 | 19.682 | 1.00 | 56.03 | N |
| ATOM | 552 | CZ | ARG | A | 71 | 36.941 | 24.966 | 19.790 | 1.00 | 56.30 | C |
| ATOM | 553 | NH1 | ARG | A | 71 | 36.417 | 24.190 | 18.841 | 1.00 | 56.29 | N |
| ATOM | 554 | NH2 | ARG | A | 71 | 37.542 | 24.412 | 20.838 | 1.00 | 56.89 | N |
| ATOM | 555 | N | ASP | A | 72 | 35.435 | 31.734 | 23.416 | 1.00 | 48.12 | N |
| ATOM | 556 | CA | ASP | A | 72 | 35.173 | 32.117 | 24.795 | 1.00 | 48.04 | C |
| ATOM | 557 | C | ASP | A | 72 | 36.106 | 33.276 | 25.179 | 1.00 | 47.53 | C |
| ATOM | 558 | O | ASP | A | 72 | 37.067 | 33.104 | 25.928 | 1.00 | 47.76 | O |
| ATOM | 559 | CB | ASP | A | 72 | 35.350 | 30.890 | 25.705 | 1.00 | 48.14 | C |
| ATOM | 560 | CG | ASP | A | 72 | 35.188 | 31.210 | 27.176 | 1.00 | 49.09 | C |
| ATOM | 561 | OD1 | ASP | A | 72 | 34.318 | 32.035 | 27.531 | 1.00 | 51.07 | O |
| ATOM | 562 | OD2 | ASP | A | 72 | 35.891 | 30.667 | 28.051 | 1.00 | 49.87 | O |
| ATOM | 563 | N | LEU | A | 73 | 35.810 | 34.456 | 24.646 | 1.00 | 46.77 | N |
| ATOM | 564 | CA | LEU | A | 73 | 36.660 | 35.618 | 24.835 | 1.00 | 46.24 | C |
| ATOM | 565 | C | LEU | A | 73 | 36.615 | 36.074 | 26.282 | 1.00 | 45.94 | C |
| ATOM | 566 | O | LEU | A | 73 | 35.542 | 36.191 | 26.874 | 1.00 | 45.87 | O |
| ATOM | 567 | CB | LEU | A | 73 | 36.222 | 36.772 | 23.939 | 1.00 | 46.11 | C |
| ATOM | 568 | CG | LEU | A | 73 | 36.560 | 36.698 | 22.459 | 1.00 | 45.54 | C |
| ATOM | 569 | CD1 | LEU | A | 73 | 35.845 | 37.825 | 21.761 | 1.00 | 45.64 | C |
| ATOM | 570 | CD2 | LEU | A | 73 | 38.049 | 36.783 | 22.216 | 1.00 | 45.68 | C |
| ATOM | 571 | N | ARG | A | 74 | 37.794 | 36.314 | 26.843 | 1.00 | 45.60 | N |
| ATOM | 572 | CA | ARG | A | 74 | 37.927 | 36.893 | 28.175 | 1.00 | 45.37 | C |
| ATOM | 573 | C | ARG | A | 74 | 38.273 | 38.376 | 28.000 | 1.00 | 45.01 | C |
| ATOM | 574 | O | ARG | A | 74 | 38.583 | 38.817 | 26.891 | 1.00 | 44.82 | O |
| ATOM | 575 | CB | ARG | A | 74 | 39.010 | 36.146 | 28.980 | 1.00 | 45.33 | C |
| ATOM | 576 | CG | ARG | A | 74 | 38.584 | 34.734 | 29.475 | 1.00 | 45.30 | C |
| ATOM | 577 | CD | ARG | A | 74 | 39.360 | 33.541 | 28.851 | 1.00 | 44.76 | C |
| ATOM | 578 | NE | ARG | A | 74 | 38.631 | 32.259 | 28.955 | 1.00 | 43.64 | N |
| ATOM | 579 | CZ | ARG | A | 74 | 39.075 | 31.144 | 29.556 | 1.00 | 42.68 | C |
| ATOM | 580 | NH1 | ARG | A | 74 | 38.322 | 30.052 | 29.576 | 1.00 | 42.05 | N |
| ATOM | 581 | NH2 | ARG | A | 74 | 40.266 | 31.094 | 30.134 | 1.00 | 42.74 | N |
| ATOM | 582 | N | VAL | A | 75 | 38.209 | 39.146 | 29.079 | 1.00 | 44.67 | N |
| ATOM | 583 | CA | VAL | A | 75 | 38.682 | 40.533 | 29.036 | 1.00 | 44.47 | C |

APPENDIX I(a)-continued

| ATOM | 584 | C   | VAL | A | 75 | 40.205 | 40.543 | 28.869 | 1.00 | 44.30 | C |
| ---- | --- | --- | --- | - | -- | ------ | ------ | ------ | ---- | ----- | - |
| ATOM | 585 | O   | VAL | A | 75 | 40.744 | 41.405 | 28.175 | 1.00 | 44.10 | O |
| ATOM | 586 | CB  | VAL | A | 75 | 38.319 | 41.335 | 30.307 | 1.00 | 44.42 | C |
| ATOM | 587 | CG1 | VAL | A | 75 | 38.693 | 42.808 | 30.125 | 1.00 | 44.06 | C |
| ATOM | 588 | CG2 | VAL | A | 75 | 36.833 | 41.170 | 30.660 | 1.00 | 44.41 | C |
| ATOM | 589 | N   | GLU | A | 76 | 40.873 | 39.573 | 29.514 | 1.00 | 44.03 | N |
| ATOM | 590 | CA  | GLU | A | 76 | 42.327 | 39.344 | 29.397 | 1.00 | 43.64 | C |
| ATOM | 591 | C   | GLU | A | 76 | 42.840 | 39.312 | 27.962 | 1.00 | 43.24 | C |
| ATOM | 592 | O   | GLU | A | 76 | 44.036 | 39.503 | 27.733 | 1.00 | 42.95 | O |
| ATOM | 593 | CB  | GLU | A | 76 | 42.726 | 38.014 | 30.062 | 1.00 | 43.51 | C |
| ATOM | 594 | CG  | GLU | A | 76 | 43.101 | 38.123 | 31.531 | 1.00 | 43.72 | C |
| ATOM | 595 | CD  | GLU | A | 76 | 44.528 | 38.599 | 31.769 | 1.00 | 43.87 | C |
| ATOM | 596 | OE1 | GLU | A | 76 | 45.099 | 38.292 | 32.839 | 1.00 | 43.97 | O |
| ATOM | 597 | OE2 | GLU | A | 76 | 45.085 | 39.296 | 30.904 | 1.00 | 44.56 | O |
| ATOM | 598 | N   | ASP | A | 77 | 41.934 | 39.055 | 27.018 | 1.00 | 42.97 | N |
| ATOM | 599 | CA  | ASP | A | 77 | 42.277 | 38.875 | 25.609 | 1.00 | 42.98 | C |
| ATOM | 600 | C   | ASP | A | 77 | 42.373 | 40.157 | 24.790 | 1.00 | 42.77 | C |
| ATOM | 601 | O   | ASP | A | 77 | 42.913 | 40.136 | 23.703 | 1.00 | 42.39 | O |
| ATOM | 602 | CB  | ASP | A | 77 | 41.279 | 37.912 | 24.954 | 1.00 | 43.02 | C |
| ATOM | 603 | CG  | ASP | A | 77 | 41.334 | 36.537 | 25.560 | 1.00 | 43.11 | C |
| ATOM | 604 | OD1 | ASP | A | 77 | 42.385 | 36.208 | 26.154 | 1.00 | 43.48 | O |
| ATOM | 605 | OD2 | ASP | A | 77 | 40.386 | 35.725 | 25.510 | 1.00 | 43.48 | O |
| ATOM | 606 | N   | SER | A | 78 | 41.859 | 41.263 | 25.304 | 1.00 | 43.07 | N |
| ATOM | 607 | CA  | SER | A | 78 | 41.994 | 42.532 | 24.613 | 1.00 | 43.54 | C |
| ATOM | 608 | C   | SER | A | 78 | 43.462 | 42.791 | 24.304 | 1.00 | 44.00 | C |
| ATOM | 609 | O   | SER | A | 78 | 44.327 | 42.631 | 25.167 | 1.00 | 43.80 | O |
| ATOM | 610 | CB  | SER | A | 78 | 41.445 | 43.691 | 25.441 | 1.00 | 43.62 | C |
| ATOM | 611 | OG  | SER | A | 78 | 40.216 | 43.356 | 26.048 | 1.00 | 44.60 | O |
| ATOM | 612 | N   | GLY | A | 79 | 43.715 | 43.187 | 23.058 | 1.00 | 44.73 | N |
| ATOM | 613 | CA  | GLY | A | 79 | 45.050 | 43.480 | 22.558 | 1.00 | 45.12 | C |
| ATOM | 614 | C   | GLY | A | 79 | 45.102 | 43.517 | 21.037 | 1.00 | 45.35 | C |
| ATOM | 615 | O   | GLY | A | 79 | 44.062 | 43.549 | 20.369 | 1.00 | 45.53 | O |
| ATOM | 616 | N   | THR | A | 80 | 46.317 | 43.496 | 20.492 | 1.00 | 45.41 | N |
| ATOM | 617 | CA  | THR | A | 80 | 46.524 | 43.585 | 19.054 | 1.00 | 45.52 | C |
| ATOM | 618 | C   | THR | A | 80 | 47.169 | 42.327 | 18.490 | 1.00 | 45.73 | C |
| ATOM | 619 | O   | THR | A | 80 | 48.314 | 42.017 | 18.796 | 1.00 | 45.71 | O |
| ATOM | 620 | CB  | THR | A | 80 | 47.366 | 44.798 | 18.741 | 1.00 | 45.47 | C |
| ATOM | 621 | OG1 | THR | A | 80 | 46.544 | 45.965 | 18.844 | 1.00 | 45.71 | O |
| ATOM | 622 | CG2 | THR | A | 80 | 47.818 | 44.794 | 17.300 | 1.00 | 45.82 | C |
| ATOM | 623 | N   | TYR | A | 81 | 46.416 | 41.641 | 17.632 | 1.00 | 46.25 | N |
| ATOM | 624 | CA  | TYR | A | 81 | 46.764 | 40.329 | 17.103 | 1.00 | 46.37 | C |
| ATOM | 625 | C   | TYR | A | 81 | 47.323 | 40.466 | 15.717 | 1.00 | 46.94 | C |
| ATOM | 626 | O   | TYR | A | 81 | 46.771 | 41.180 | 14.900 | 1.00 | 46.88 | O |
| ATOM | 627 | CB  | TYR | A | 81 | 45.528 | 39.444 | 17.046 | 1.00 | 46.07 | C |
| ATOM | 628 | CG  | TYR | A | 81 | 44.964 | 39.157 | 18.407 | 1.00 | 45.69 | C |
| ATOM | 629 | CD1 | TYR | A | 81 | 45.211 | 37.938 | 19.033 | 1.00 | 45.97 | C |
| ATOM | 630 | CD2 | TYR | A | 81 | 44.203 | 40.109 | 19.089 | 1.00 | 45.33 | C |
| ATOM | 631 | CE1 | TYR | A | 81 | 44.705 | 37.660 | 20.297 | 1.00 | 45.78 | C |
| ATOM | 632 | CE2 | TYR | A | 81 | 43.700 | 39.843 | 20.354 | 1.00 | 45.41 | C |
| ATOM | 633 | CZ  | TYR | A | 81 | 43.955 | 38.618 | 20.947 | 1.00 | 45.24 | C |
| ATOM | 634 | OH  | TYR | A | 81 | 43.477 | 38.341 | 22.195 | 1.00 | 45.03 | O |
| ATOM | 635 | N   | LYS | A | 82 | 48.429 | 39.779 | 15.464 | 1.00 | 47.75 | N |
| ATOM | 636 | CA  | LYS | A | 82 | 49.024 | 39.725 | 14.140 | 1.00 | 48.32 | C |
| ATOM | 637 | C   | LYS | A | 82 | 49.286 | 38.281 | 13.752 | 1.00 | 48.72 | C |
| ATOM | 638 | O   | LYS | A | 82 | 49.633 | 37.451 | 14.579 | 1.00 | 48.30 | O |
| ATOM | 639 | CB  | LYS | A | 82 | 50.311 | 40.541 | 14.073 | 1.00 | 48.32 | C |
| ATOM | 640 | CG  | LYS | A | 82 | 50.043 | 42.030 | 13.997 | 1.00 | 48.91 | C |
| ATOM | 641 | CD  | LYS | A | 82 | 51.254 | 42.821 | 14.378 | 1.00 | 50.39 | C |
| ATOM | 642 | CE  | LYS | A | 82 | 50.900 | 44.278 | 14.589 | 1.00 | 52.20 | C |
| ATOM | 643 | NZ  | LYS | A | 82 | 51.775 | 44.922 | 15.629 | 1.00 | 53.56 | N |
| ATOM | 644 | N   | CYS | A | 83 | 49.074 | 37.995 | 12.475 | 1.00 | 49.15 | N |
| ATOM | 645 | CA  | CYS | A | 83 | 49.442 | 36.717 | 11.920 | 1.00 | 49.17 | C |
| ATOM | 646 | C   | CYS | A | 83 | 50.727 | 36.864 | 11.140 | 1.00 | 49.28 | C |
| ATOM | 647 | O   | CYS | A | 83 | 51.136 | 37.983 | 10.811 | 1.00 | 49.33 | O |
| ATOM | 648 | CB  | CYS | A | 83 | 48.351 | 36.228 | 11.017 | 1.00 | 49.00 | C |
| ATOM | 649 | SG  | CYS | A | 83 | 48.139 | 37.232 | 9.569  | 1.00 | 49.18 | S |
| ATOM | 650 | N   | GLY | A | 84 | 51.341 | 35.724 | 10.836 | 1.00 | 49.33 | N |
| ATOM | 651 | CA  | GLY | A | 84 | 52.629 | 35.673 | 10.166 | 1.00 | 49.19 | C |
| ATOM | 652 | C   | GLY | A | 84 | 52.664 | 34.559 | 9.141  | 1.00 | 49.12 | C |
| ATOM | 653 | O   | GLY | A | 84 | 52.266 | 33.442 | 9.430  | 1.00 | 49.28 | O |
| ATOM | 654 | N   | ALA | A | 85 | 53.114 | 34.862 | 7.935  | 1.00 | 49.01 | N |
| ATOM | 655 | CA  | ALA | A | 85 | 53.339 | 33.844 | 6.937  | 1.00 | 49.26 | C |
| ATOM | 656 | C   | ALA | A | 85 | 54.841 | 33.726 | 6.775  | 1.00 | 49.76 | C |
| ATOM | 657 | O   | ALA | A | 85 | 55.508 | 34.740 | 6.569  | 1.00 | 49.89 | O |
| ATOM | 658 | CB  | ALA | A | 85 | 52.687 | 34.240 | 5.632  | 1.00 | 49.16 | C |
| ATOM | 659 | N   | PHE | A | 86 | 55.369 | 32.504 | 6.901  | 1.00 | 50.29 | N |
| ATOM | 660 | CA  | PHE | A | 86 | 56.787 | 32.209 | 6.632  | 1.00 | 50.83 | C |
| ATOM | 661 | C   | PHE | A | 86 | 56.962 | 31.172 | 5.505  | 1.00 | 51.30 | C |
| ATOM | 662 | O   | PHE | A | 86 | 56.044 | 30.388 | 5.203  | 1.00 | 51.47 | O |
| ATOM | 663 | CB  | PHE | A | 86 | 57.500 | 31.686 | 7.874  | 1.00 | 50.78 | C |

APPENDIX I(a)-continued

| ATOM | 664 | CG  | PHE | A | 86  | 57.296 | 32.520 | 9.099  | 1.00 | 51.53 | C |
|------|-----|-----|-----|---|-----|--------|--------|--------|------|-------|---|
| ATOM | 665 | CD1 | PHE | A | 86  | 58.337 | 33.299 | 9.603  | 1.00 | 52.02 | C |
| ATOM | 666 | CD2 | PHE | A | 86  | 56.073 | 32.502 | 9.777  | 1.00 | 52.06 | C |
| ATOM | 667 | CE1 | PHE | A | 86  | 58.158 | 34.064 | 10.757 | 1.00 | 52.26 | C |
| ATOM | 668 | CE2 | PHE | A | 86  | 55.876 | 33.270 | 10.928 | 1.00 | 52.10 | C |
| ATOM | 669 | CZ  | PHE | A | 86  | 56.920 | 34.056 | 11.417 | 1.00 | 52.60 | C |
| ATOM | 670 | N   | ARG | A | 87  | 58.163 | 31.168 | 4.915  | 1.00 | 51.82 | N |
| ATOM | 671 | CA  | ARG | A | 87  | 58.515 | 30.298 | 3.781  | 1.00 | 51.91 | C |
| ATOM | 672 | C   | ARG | A | 87  | 59.001 | 28.925 | 4.242  | 1.00 | 51.90 | C |
| ATOM | 673 | O   | ARG | A | 87  | 58.918 | 27.952 | 3.493  | 1.00 | 51.72 | O |
| ATOM | 674 | CB  | ARG | A | 87  | 59.609 | 30.946 | 2.925  | 1.00 | 51.90 | C |
| ATOM | 675 | CG  | ARG | A | 87  | 59.285 | 31.033 | 1.440  | 1.00 | 52.27 | C |
| ATOM | 676 | CD  | ARG | A | 87  | 59.985 | 32.196 | 0.751  | 1.00 | 52.53 | C |
| ATOM | 677 | NE  | ARG | A | 87  | 59.902 | 32.136 | -0.707 | 1.00 | 53.38 | N |
| ATOM | 678 | CZ  | ARG | A | 87  | 60.590 | 31.293 | -1.486 | 1.00 | 54.43 | C |
| ATOM | 679 | NH1 | ARG | A | 87  | 60.423 | 31.344 | -2.809 | 1.00 | 54.34 | N |
| ATOM | 680 | NH2 | ARG | A | 87  | 61.453 | 30.411 | -0.969 | 1.00 | 54.98 | N |
| ATOM | 681 | N   | LEU | A | 99  | 62.366 | 34.803 | 7.148  | 1.00 | 48.13 | N |
| ATOM | 682 | CA  | LEU | A | 99  | 61.580 | 35.970 | 6.729  | 1.00 | 48.11 | C |
| ATOM | 683 | C   | LEU | A | 99  | 60.051 | 35.873 | 6.978  | 1.00 | 47.80 | C |
| ATOM | 684 | O   | LEU | A | 99  | 59.295 | 35.253 | 6.215  | 1.00 | 47.42 | O |
| ATOM | 685 | CB  | LEU | A | 99  | 61.848 | 36.317 | 5.256  | 1.00 | 48.34 | C |
| ATOM | 686 | CG  | LEU | A | 99  | 61.841 | 35.196 | 4.211  | 1.00 | 48.54 | C |
| ATOM | 687 | CD1 | LEU | A | 99  | 60.746 | 35.451 | 3.132  | 1.00 | 48.20 | C |
| ATOM | 688 | CD2 | LEU | A | 99  | 63.255 | 35.054 | 3.600  | 1.00 | 47.97 | C |
| ATOM | 689 | N   | SER | A | 100 | 59.641 | 36.505 | 8.076  | 1.00 | 47.37 | N |
| ATOM | 690 | CA  | SER | A | 100 | 58.263 | 36.875 | 8.346  | 1.00 | 47.04 | C |
| ATOM | 691 | C   | SER | A | 100 | 57.684 | 37.768 | 7.233  | 1.00 | 46.75 | C |
| ATOM | 692 | O   | SER | A | 100 | 58.413 | 38.487 | 6.570  | 1.00 | 46.99 | O |
| ATOM | 693 | CB  | SER | A | 100 | 58.229 | 37.667 | 9.673  | 1.00 | 46.92 | C |
| ATOM | 694 | OG  | SER | A | 100 | 57.110 | 37.317 | 10.475 | 1.00 | 47.46 | O |
| ATOM | 695 | N   | GLU | A | 101 | 56.376 | 37.721 | 7.023  | 1.00 | 46.31 | N |
| ATOM | 696 | CA  | GLU | A | 101 | 55.660 | 38.937 | 6.639  | 1.00 | 46.11 | C |
| ATOM | 697 | C   | GLU | A | 101 | 54.328 | 38.924 | 7.349  | 1.00 | 44.85 | C |
| ATOM | 698 | O   | GLU | A | 101 | 53.675 | 37.918 | 7.372  | 1.00 | 44.33 | O |
| ATOM | 699 | CB  | GLU | A | 101 | 55.524 | 39.113 | 5.132  | 1.00 | 46.54 | C |
| ATOM | 700 | CG  | GLU | A | 101 | 54.675 | 38.081 | 4.410  | 1.00 | 49.34 | C |
| ATOM | 701 | CD  | GLU | A | 101 | 55.438 | 37.372 | 3.300  | 1.00 | 52.97 | C |
| ATOM | 702 | OE1 | GLU | A | 101 | 55.890 | 38.064 | 2.356  | 1.00 | 55.23 | O |
| ATOM | 703 | OE2 | GLU | A | 101 | 55.598 | 36.123 | 3.376  | 1.00 | 55.84 | O |
| ATOM | 704 | N   | LYS | A | 102 | 53.950 | 40.050 | 7.939  | 1.00 | 44.25 | N |
| ATOM | 705 | CA  | LYS | A | 102 | 52.908 | 40.088 | 8.953  | 1.00 | 43.97 | C |
| ATOM | 706 | C   | LYS | A | 102 | 51.747 | 41.024 | 8.619  | 1.00 | 43.73 | C |
| ATOM | 707 | O   | LYS | A | 102 | 51.950 | 42.118 | 8.109  | 1.00 | 43.86 | O |
| ATOM | 708 | CB  | LYS | A | 102 | 53.548 | 40.502 | 10.279 | 1.00 | 44.02 | C |
| ATOM | 709 | CG  | LYS | A | 102 | 54.611 | 39.507 | 10.770 | 1.00 | 44.31 | C |
| ATOM | 710 | CD  | LYS | A | 102 | 54.571 | 39.285 | 12.286 | 1.00 | 44.93 | C |
| ATOM | 711 | CE  | LYS | A | 102 | 54.919 | 40.565 | 13.066 | 1.00 | 45.78 | C |
| ATOM | 712 | NZ  | LYS | A | 102 | 55.844 | 40.345 | 14.224 | 1.00 | 45.77 | N |
| ATOM | 713 | N   | GLY | A | 103 | 50.523 | 40.600 | 8.923  | 1.00 | 43.50 | N |
| ATOM | 714 | CA  | GLY | A | 103 | 49.358 | 41.453 | 8.754  | 1.00 | 43.47 | C |
| ATOM | 715 | C   | GLY | A | 103 | 49.452 | 42.664 | 9.652  | 1.00 | 43.24 | C |
| ATOM | 716 | O   | GLY | A | 103 | 50.251 | 42.663 | 10.554 | 1.00 | 44.06 | O |
| ATOM | 717 | N   | ALA | A | 104 | 48.665 | 43.705 | 9.422  | 1.00 | 43.06 | N |
| ATOM | 718 | CA  | ALA | A | 104 | 48.750 | 44.902 | 10.262 | 1.00 | 42.99 | C |
| ATOM | 719 | C   | ALA | A | 104 | 47.958 | 44.776 | 11.576 | 1.00 | 42.96 | C |
| ATOM | 720 | O   | ALA | A | 104 | 47.924 | 45.701 | 12.406 | 1.00 | 42.63 | O |
| ATOM | 721 | CB  | ALA | A | 104 | 48.295 | 46.085 | 9.505  | 1.00 | 43.28 | C |
| ATOM | 722 | N   | GLY | A | 105 | 47.306 | 43.637 | 11.767 | 1.00 | 42.51 | N |
| ATOM | 723 | CA  | GLY | A | 105 | 46.757 | 43.346 | 13.067 | 1.00 | 42.31 | C |
| ATOM | 724 | C   | GLY | A | 105 | 45.302 | 43.726 | 13.257 | 1.00 | 41.97 | C |
| ATOM | 725 | O   | GLY | A | 105 | 44.699 | 44.464 | 12.477 | 1.00 | 41.85 | O |
| ATOM | 726 | N   | THR | A | 106 | 44.753 | 43.187 | 14.334 | 1.00 | 41.36 | N |
| ATOM | 727 | CA  | THR | A | 106 | 43.365 | 43.308 | 14.680 | 1.00 | 40.73 | C |
| ATOM | 728 | C   | THR | A | 106 | 43.414 | 43.897 | 16.077 | 1.00 | 40.07 | C |
| ATOM | 729 | O   | THR | A | 106 | 43.987 | 43.294 | 16.972 | 1.00 | 40.05 | O |
| ATOM | 730 | CB  | THR | A | 106 | 42.723 | 41.874 | 14.678 | 1.00 | 41.01 | C |
| ATOM | 731 | OG1 | THR | A | 106 | 42.896 | 41.244 | 13.393 | 1.00 | 41.37 | O |
| ATOM | 732 | CG2 | THR | A | 106 | 41.192 | 41.909 | 14.880 | 1.00 | 40.73 | C |
| ATOM | 733 | N   | VAL | A | 107 | 42.850 | 45.078 | 16.280 | 1.00 | 39.30 | N |
| ATOM | 734 | CA  | VAL | A | 107 | 42.791 | 45.629 | 17.628 | 1.00 | 38.84 | C |
| ATOM | 735 | C   | VAL | A | 107 | 41.513 | 45.153 | 18.341 | 1.00 | 38.25 | C |
| ATOM | 736 | O   | VAL | A | 107 | 40.449 | 45.765 | 18.230 | 1.00 | 37.76 | O |
| ATOM | 737 | CB  | VAL | A | 107 | 42.903 | 47.153 | 17.609 | 1.00 | 38.89 | C |
| ATOM | 738 | CG1 | VAL | A | 107 | 42.771 | 47.696 | 19.003 | 1.00 | 39.50 | C |
| ATOM | 739 | CG2 | VAL | A | 107 | 44.250 | 47.583 | 17.018 | 1.00 | 38.81 | C |
| ATOM | 740 | N   | LEU | A | 108 | 41.628 | 44.033 | 19.047 | 1.00 | 37.85 | N |
| ATOM | 741 | CA  | LEU | A | 108 | 40.480 | 43.435 | 19.720 | 1.00 | 37.95 | C |
| ATOM | 742 | C   | LEU | A | 108 | 40.263 | 44.075 | 21.076 | 1.00 | 37.90 | C |
| ATOM | 743 | O   | LEU | A | 108 | 41.218 | 44.325 | 21.827 | 1.00 | 37.90 | O |

APPENDIX I(a)-continued

| | | | | | | | | | | | |
|---|---|---|---|---|---|---|---|---|---|---|---|
| ATOM | 744 | CB | LEU | A | 108 | 40.641 | 41.921 | 19.875 | 1.00 | 38.13 | C |
| ATOM | 745 | CG | LEU | A | 108 | 39.674 | 41.188 | 20.817 | 1.00 | 38.58 | C |
| ATOM | 746 | CD1 | LEU | A | 108 | 38.324 | 40.947 | 20.132 | 1.00 | 39.30 | C |
| ATOM | 747 | CD2 | LEU | A | 108 | 40.275 | 39.883 | 21.355 | 1.00 | 37.97 | C |
| ATOM | 748 | N | THR | A | 109 | 38.988 | 44.328 | 21.376 | 1.00 | 37.62 | N |
| ATOM | 749 | CA | THR | A | 109 | 38.567 | 45.006 | 22.592 | 1.00 | 37.27 | C |
| ATOM | 750 | C | THR | A | 109 | 37.389 | 44.227 | 23.139 | 1.00 | 36.65 | C |
| ATOM | 751 | O | THR | A | 109 | 36.394 | 44.059 | 22.454 | 1.00 | 36.27 | O |
| ATOM | 752 | CB | THR | A | 109 | 38.171 | 46.458 | 22.265 | 1.00 | 37.47 | C |
| ATOM | 753 | OG1 | THR | A | 109 | 39.347 | 47.266 | 22.112 | 1.00 | 37.69 | O |
| ATOM | 754 | CG2 | THR | A | 109 | 37.446 | 47.111 | 23.426 | 1.00 | 38.07 | C |
| ATOM | 755 | N | VAL | A | 110 | 37.510 | 43.763 | 24.378 | 1.00 | 36.34 | N |
| ATOM | 756 | CA | VAL | A | 110 | 36.562 | 42.815 | 24.957 | 1.00 | 36.14 | C |
| ATOM | 757 | C | VAL | A | 110 | 35.880 | 43.403 | 26.157 | 1.00 | 35.82 | C |
| ATOM | 758 | O | VAL | A | 110 | 36.546 | 43.920 | 27.035 | 1.00 | 35.99 | O |
| ATOM | 759 | CB | VAL | A | 110 | 37.267 | 41.549 | 25.429 | 1.00 | 36.16 | C |
| ATOM | 760 | CG1 | VAL | A | 110 | 36.267 | 40.606 | 26.101 | 1.00 | 36.38 | C |
| ATOM | 761 | CG2 | VAL | A | 110 | 37.976 | 40.871 | 24.252 | 1.00 | 36.41 | C |
| ATOM | 762 | N | LYS | A | 111 | 34.556 | 43.280 | 26.196 | 1.00 | 35.74 | N |
| ATOM | 763 | CA | LYS | A | 111 | 33.712 | 43.808 | 27.277 | 1.00 | 35.65 | C |
| ATOM | 764 | C | LYS | A | 111 | 33.882 | 45.319 | 27.426 | 1.00 | 35.69 | C |
| ATOM | 765 | O | LYS | A | 111 | 33.593 | 46.069 | 26.493 | 1.00 | 35.75 | O |
| ATOM | 766 | CB | LYS | A | 111 | 33.971 | 43.086 | 28.607 | 1.00 | 35.42 | C |
| ATOM | 767 | CG | LYS | A | 111 | 33.345 | 43.774 | 29.823 | 1.00 | 35.29 | C |
| ATOM | 768 | CD | LYS | A | 111 | 33.221 | 42.838 | 31.025 | 1.00 | 34.49 | C |
| ATOM | 769 | CE | LYS | A | 111 | 31.800 | 42.353 | 31.211 | 1.00 | 33.74 | C |
| ATOM | 770 | NZ | LYS | A | 111 | 31.760 | 41.205 | 32.135 | 1.00 | 33.10 | N |
| TER | 771 | | LYS | A | 111 | | | | | | |
| HETATM | 772 | O | HOH | | 1 | 49.245 | 46.328 | 5.022 | 1.00 | 62.33 | O |
| HETATM | 773 | O | HOH | | 2 | 51.667 | 42.393 | 5.253 | 1.00 | 64.26 | O |
| HETATM | 774 | O | HOH | | 3 | 45.146 | 47.489 | 13.258 | 1.00 | 72.01 | O |
| HETATM | 775 | O | HOH | | 4 | 34.352 | 33.440 | 15.578 | 1.00 | 45.87 | O |
| HETATM | 776 | O | HOH | | 5 | 45.505 | 44.955 | 4.778 | 1.00 | 64.32 | O |
| HETATM | 777 | O | HOH | | 6 | 52.352 | 45.006 | 8.090 | 1.00 | 59.13 | O |
| HETATM | 778 | O | HOH | | 7 | 47.204 | 46.514 | 3.486 | 1.00 | 68.76 | O |
| HETATM | 779 | O | HOH | | 8 | 52.395 | 44.051 | 10.998 | 1.00 | 71.90 | O |
| HETATM | 780 | O | HOH | | 9 | 52.999 | 37.102 | −8.462 | 1.00 | 86.85 | O |
| HETATM | 781 | O | HOH | | 10 | 41.419 | 38.464 | 5.175 | 1.00 | 59.45 | O |
| HETATM | 782 | O | HOH | | 11 | 49.959 | 34.680 | −3.470 | 1.00 | 67.87 | O |
| HETATM | 783 | O | HOH | | 12 | 53.994 | 41.486 | −5.678 | 1.00 | 65.92 | O |
| HETATM | 784 | O | HOH | | 13 | 51.536 | 27.053 | 17.915 | 1.00 | 74.52 | O |
| HETATM | 785 | O | HOH | | 14 | 47.163 | 43.295 | 6.450 | 0.50 | 37.28 | O |
| HETATM | 786 | O | HOH | | 15 | 40.047 | 28.796 | 12.708 | 1.00 | 49.93 | O |
| HETATM | 787 | O | HOH | | 16 | 40.421 | 33.389 | 3.038 | 1.00 | 72.11 | O |
| HETATM | 788 | O | HOH | | 17 | 55.257 | 43.445 | 8.358 | 1.00 | 69.83 | O |
| HETATM | 789 | O | HOH | | 18 | 46.613 | 34.179 | −2.484 | 1.00 | 75.26 | O |
| HETATM | 790 | O | HOH | | 19 | 41.926 | 30.672 | −4.416 | 1.00 | 69.47 | O |
| HETATM | 791 | O | HOH | | 20 | 38.111 | 45.323 | 8.830 | 1.00 | 71.05 | O |
| HETATM | 792 | O | HOH | | 21 | 33.282 | 42.452 | 35.017 | 1.00 | 56.31 | O |
| HETATM | 793 | O | HOH | | 22 | 38.097 | 28.022 | 27.567 | 1.00 | 82.82 | O |
| HETATM | 794 | O | HOH | | 23 | 36.861 | 38.358 | 7.741 | 1.00 | 59.93 | O |
| HETATM | 795 | O | HOH | | 24 | 35.632 | 41.106 | 33.951 | 1.00 | 64.85 | O |
| HETATM | 796 | O | HOH | | 25 | 39.694 | 51.545 | 17.552 | 1.00 | 88.01 | O |
| HETATM | 797 | O | HOH | | 26 | 38.301 | 46.295 | 27.232 | 1.00 | 79.40 | O |
| HETATM | 798 | O | HOH | | 27 | 46.017 | 40.012 | −5.952 | 1.00 | 71.49 | O |
| HETATM | 799 | O | HOH | | 28 | 33.459 | 47.017 | 11.159 | 1.00 | 91.29 | O |
| HETATM | 800 | O | HOH | | 29 | 54.056 | 48.074 | 21.658 | 1.00 | 87.62 | O |
| HETATM | 801 | O | HOH | | 30 | 42.698 | 30.957 | −9.926 | 1.00 | 85.37 | O |
| HETATM | 802 | O | HOH | | 31 | 49.053 | 46.541 | 23.570 | 0.50 | 40.58 | O |
| HETATM | 803 | O | HOH | | 32 | 36.644 | 26.866 | 16.515 | 1.00 | 63.49 | O |
| HETATM | 804 | O | HOH | | 33 | 35.842 | 41.211 | 8.228 | 1.00 | 61.91 | O |
| HETATM | 805 | O | HOH | | 34 | 45.847 | 31.003 | −4.217 | 1.00 | 60.17 | O |
| HETATM | 806 | O | HOH | | 35 | 36.559 | 42.530 | 6.037 | 1.00 | 80.60 | O |
| HETATM | 807 | O | HOH | | 36 | 41.738 | 38.583 | −0.756 | 1.00 | 78.58 | O |
| HETATM | 808 | O | HOH | | 37 | 41.721 | 37.198 | −2.911 | 1.00 | 70.53 | O |
| HETATM | 809 | O | HOH | | 38 | 55.564 | 31.245 | 15.877 | 1.00 | 66.47 | O |
| HETATM | 810 | O | HOH | | 39 | 48.594 | 26.834 | −5.493 | 1.00 | 71.61 | O |
| HETATM | 811 | O | HOH | | 40 | 57.648 | 37.697 | 17.683 | 1.00 | 76.43 | O |
| HETATM | 812 | O | HOH | | 41 | 54.466 | 30.209 | 22.435 | 1.00 | 82.25 | O |
| HETATM | 813 | O | HOH | | 42 | 46.207 | 40.360 | 32.941 | 1.00 | 74.06 | O |
| HETATM | 814 | O | HOH | | 43 | 29.341 | 42.492 | 20.689 | 1.00 | 80.60 | O |
| HETATM | 815 | O | HOH | | 44 | 50.735 | 47.197 | 19.342 | 1.00 | 88.78 | O |
| HETATM | 816 | O | HOH | | 45 | 39.469 | 48.751 | 19.274 | 1.00 | 64.53 | O |
| HETATM | 817 | O | HOH | | 46 | 54.578 | 43.702 | 3.150 | 1.00 | 53.90 | O |
| HETATM | 818 | O | HOH | | 47 | 51.878 | 45.740 | 1.436 | 0.50 | 43.20 | O |
| HETATM | 819 | O | HOH | | 48 | 26.610 | 38.072 | 22.759 | 1.00 | 73.32 | O |
| HETATM | 820 | O | HOH | | 49 | 33.027 | 41.919 | 15.357 | 1.00 | 89.15 | O |
| HETATM | 821 | O | HOH | | 50 | 49.309 | 31.953 | 24.818 | 1.00 | 75.95 | O |
| HETATM | 822 | O | HOH | | 51 | 44.607 | 44.158 | 29.925 | 0.50 | 38.52 | O |
| HETATM | 823 | O | HOH | | 52 | 42.536 | 26.524 | 0.006 | 1.00 | 74.15 | O |

APPENDIX I(a)-continued

| | | | | | | | | | | |
|---|---|---|---|---|---|---|---|---|---|---|
| HETATM | 824 | O | HOH | 53 | 51.130 | 19.337 | 0.472 | 1.00 | 89.67 | O |
| HETATM | 825 | O | HOH | 54 | 56.592 | 41.377 | −2.899 | 1.00 | 52.63 | O |
| HETATM | 826 | O | HOH | 55 | 30.159 | 45.430 | 25.057 | 1.00 | 75.58 | O |
| HETATM | 827 | O | HOH | 56 | 59.017 | 28.005 | 8.578 | 1.00 | 83.63 | O |
| HETATM | 828 | O | HOH | 57 | 50.030 | 33.674 | −8.476 | 1.00 | 76.97 | O |
| HETATM | 829 | O | HOH | 58 | 41.264 | 29.369 | 5.970 | 1.00 | 70.36 | O |
| HETATM | 830 | O | HOH | 59 | 35.397 | 35.904 | 9.882 | 1.00 | 66.45 | O |
| HETATM | 831 | O | HOH | 60 | 29.699 | 24.263 | 29.792 | 1.00 | 77.96 | O |
| HETATM | 832 | O | HOH | 61 | 41.632 | 39.734 | 2.099 | 1.00 | 49.35 | O |
| HETATM | 833 | O | HOH | 62 | 26.312 | 40.818 | 31.981 | 1.00 | 87.48 | O |
| HETATM | 834 | O | HOH | 63 | 43.409 | 32.875 | −2.653 | 1.00 | 97.68 | O |
| HETATM | 835 | O | HOH | 64 | 39.233 | 30.631 | 0.994 | 1.00 | 60.94 | O |
| HETATM | 836 | O | HOH | 65 | 50.583 | 48.025 | 0.811 | 0.50 | 55.46 | O |
| HETATM | 837 | O | HOH | 66 | 59.008 | 24.532 | 6.787 | 0.50 | 41.79 | O |
| HETATM | 838 | O | HOH | 67 | 57.610 | 30.961 | 12.027 | 1.00 | 68.40 | O |
| HETATM | 839 | O | HOH | 68 | 54.850 | 26.829 | −1.181 | 1.00 | 81.14 | O |
| HETATM | 840 | O | HOH | 69 | 34.060 | 39.827 | 6.446 | 1.00 | 72.84 | O |
| HETATM | 841 | O | HOH | 70 | 27.701 | 35.938 | 20.953 | 1.00 | 71.47 | O |
| HETATM | 842 | O | HOH | 71 | 47.661 | 26.712 | 24.623 | 1.00 | 78.24 | O |
| HETATM | 843 | O | HOH | 72 | 43.403 | 49.234 | 14.571 | 1.00 | 81.06 | O |
| HETATM | 844 | O | HOH | 73 | 40.989 | 30.459 | −7.252 | 1.00 | 75.18 | O |
| HETATM | 845 | O | HOH | 74 | 50.187 | 28.078 | −0.705 | 1.00 | 88.41 | O |
| HETATM | 846 | O | HOH | 75 | 52.501 | 22.888 | 23.124 | 1.00 | 72.12 | O |
| HETATM | 847 | O | HOH | 76 | 51.937 | 26.536 | 26.291 | 1.00 | 76.44 | O |
| HETATM | 848 | O | HOH | 77 | 57.772 | 29.623 | −5.664 | 1.00 | 67.63 | O |
| HETATM | 849 | O | HOH | 78 | 50.926 | 25.600 | 5.056 | 1.00 | 80.32 | O |
| HETATM | 850 | O | HOH | 79 | 61.922 | 29.045 | 9.305 | 1.00 | 77.07 | O |
| HETATM | 851 | O | HOH | 80 | 54.189 | 23.727 | 5.680 | 1.00 | 76.46 | O |
| HETATM | 852 | O | HOH | 81 | 38.768 | 24.307 | 10.848 | 1.00 | 69.70 | O |
| HETATM | 853 | O | HOH | 82 | 36.445 | 22.153 | 24.035 | 1.00 | 78.79 | O |
| HETATM | 854 | O | HOH | 83 | 47.196 | 46.033 | 21.492 | 1.00 | 74.35 | O |
| HETATM | 855 | O | HOH | 84 | 35.057 | 43.461 | 13.870 | 1.00 | 69.66 | O |
| HETATM | 856 | O | HOH | 85 | 51.118 | 42.221 | 17.798 | 1.00 | 84.91 | O |
| HETATM | 857 | O | HOH | 86 | 50.992 | 23.568 | 30.307 | 1.00 | 85.90 | O |
| HETATM | 858 | O | HOH | 87 | 24.118 | 39.727 | 34.347 | 1.00 | 68.74 | O |
| HETATM | 859 | O | HOH | 88 | 38.823 | 28.953 | 8.669 | 1.00 | 85.42 | O |
| HETATM | 860 | O | HOH | 89 | 49.288 | 26.659 | 27.113 | 1.00 | 85.90 | O |
| HETATM | 861 | O | HOH | 90 | 37.335 | 18.846 | 21.135 | 1.00 | 92.05 | O |
| HETATM | 862 | O | HOH | 91 | 57.599 | 27.914 | 1.058 | 1.00 | 76.63 | O |
| HETATM | 863 | O | HOH | 92 | 60.682 | 24.384 | −4.788 | 1.00 | 91.50 | O |
| HETATM | 864 | O | HOH | 93 | 34.218 | 35.108 | 7.727 | 1.00 | 61.57 | O |
| HETATM | 865 | O | HOH | 94 | 62.389 | 21.875 | −9.626 | 1.00 | 83.23 | O |
| HETATM | 866 | O | HOH | 95 | 44.801 | 42.200 | 27.630 | 1.00 | 93.68 | O |
| HETATM | 867 | O | HOH | 96 | 56.200 | 28.893 | 20.739 | 1.00 | 76.88 | O |
| HETATM | 868 | O | HOH | 97 | 57.817 | 39.521 | 1.149 | 0.50 | 33.39 | O |
| CONECT | 168 | 649 | | | | | | | | |
| CONECT | 649 | 168 | | | | | | | | |
| MASTER | | 365 | 0 | 0 | 1 | 13 | 0 | 0 | 6 | 867 | 1 | 2 | 9 |
| END | | | | | | | | | | | |

APPENDIX I(b)

| | | |
|---|---|---|
| HEADER | | IMMUNE SYSTEM                   05-APR-04   1VES |
| TITLE | | STRUCTURE OF NEW ANTIGEN RECEPTOR VARIABLE DOMAIN FROM |
| TITLE | 2 | SHARKS |
| COMPND | | MOL_ID: 1; |
| COMPND | 2 | MOLECULE: NEW ANTIGEN RECEPTOR; |
| COMPND | 3 | CHAIN: A, B; |
| COMPND | 4 | FRAGMENT: VARIABLE DOMAIN; |
| COMPND | 5 | SYNONYM: VNAR; |
| COMPND | 6 | ENGINEERED: YES |
| SOURCE | | MOL_ID: 1; |
| SOURCE | 2 | ORGANISM_SCIENTIFIC: ORECTOLOBUS MACULATUS; |
| SOURCE | 3 | ORGANISM_COMMON: SPOTTED WOBBEGONG; |
| SOURCE | 4 | EXPRESSION_SYSTEM: ESCHERICHIA COLI; |
| SOURCE | 5 | EXPRESSION_SYSTEM_COMMON: BACTERIA |
| KEYWDS | | IG VNAR, 12Y-2 |
| EXPDTA | | X-RAY DIFFRACTION |
| AUTHOR | | V. A. STRELTSOV |
| JRNL | | AUTH     V. A. STRELTSOV, J. N. VARGHESE, P. J. HUDSON, R. A. IRVING, |
| JRNL | | AUTH 2   J. A. CARMICHAEL, S. D. NUTTALL |
| JRNL | | TITL     CRYSTAL STRUCTURE OF A SHARK NEW ANTIGEN RECEPTOR |
| JRNL | | TITL 2   (IGNAR) VARIABLE DOMAIN |
| JRNL | | REF      TO BE PUBLISHED |
| JRNL | | REFN |
| REMARK | 1 | |
| REMARK | 2 | |

APPENDIX I(b)-continued

```
REMARK  2   RESOLUTION. 2.18 ANGSTROMS.
REMARK  3
REMARK  3   REFINEMENT.
REMARK  3     PROGRAM     : REFMAC 5.1.24
REMARK  3     AUTHORS     : MURSHUDOV, VAGIN, DODSON
REMARK  3
REMARK  3     REFINEMENT TARGET : MAXIMUM LIKELIHOOD
REMARK  3
REMARK  3   DATA USED IN REFINEMENT.
REMARK  3     RESOLUTION RANGE HIGH     (ANGSTROMS) : 2.18
REMARK  3     RESOLUTION RANGE LOW      (ANGSTROMS) : 18.12
REMARK  3     DATA CUTOFF               (SIGMA(F))  : NULL
REMARK  3     COMPLETENESS FOR RANGE        (%)     : 99.9
REMARK  3     NUMBER OF REFLECTIONS                 : 14981
REMARK  3
REMARK  3   FIT TO DATA USED IN REFINEMENT.
REMARK  3     CROSS-VALIDATION METHOD         : THROUGHOUT
REMARK  3     FREE R VALUE TEST SET SELECTION : RANDOM
REMARK  3     R VALUE      (WORKING + TEST SET) : 0.179
REMARK  3     R VALUE              (WORKING SET) : 0.176
REMARK  3     FREE R VALUE                       : 0.247
REMARK  3     FREE R VALUE TEST SET SIZE    (%)  : 5.000
REMARK  3     FREE R VALUE TEST SET COUNT        : 783
REMARK  3
REMARK  3   FIT IN THE HIGHEST RESOLUTION BIN.
REMARK  3     TOTAL NUMBER OF BINS USED            : 20
REMARK  3     BIN RESOLUTION RANGE HIGH            : 2.18
REMARK  3     BIN RESOLUTION RANGE LOW             : 2.23
REMARK  3     REFLECTION IN BIN     (WORKING SET)  : 1057
REMARK  3     BIN COMPLETENESS    (WORKING + TEST) (%) : NULL
REMARK  3     BIN R VALUE           (WORKING SET)  : 0.2250
REMARK  3     BIN FREE R VALUE SET COUNT           : 46
REMARK  3     BIN FREE R VALUE                     : 0.3110
REMARK  3
REMARK  3   NUMBER OF NON-HYDROGEN ATOMS USED IN REFINEMENT.
REMARK  3     ALL ATOMS            : 2120
REMARK  3
REMARK  3   B VALUES.
REMARK  3     FROM WILSON PLOT          (A**2) : NULL
REMARK  3     MEAN B VALUE      (OVERALL, A**2) : 21.29
REMARK  3     OVERALL ANISOTROPIC B VALUE.
REMARK  3      B11 (A**2) : -1.07000
REMARK  3      B22 (A**2) : 0.07000
REMARK  3      B33 (A**2) : 1.00000
REMARK  3      B12 (A**2) : 0.00000
REMARK  3      B13 (A**2) : 0.00000
REMARK  3      B23 (A**2) : 0.00000
REMARK  3
REMARK  3   ESTIMATED OVERALL COORDINATE ERROR.
REMARK  3     ESU BASED ON R VALUE                         (A): 0.223
REMARK  3     ESU BASED ON FREE R VALUE                    (A): 0.206
REMARK  3     ESU BASED ON MAXIMUM LIKELIHOOD              (A): 0.140
REMARK  3     ESU FOR B VALUES BASED ON MAXIMUM LIKELIHOOD (A**2): 5.392
REMARK  3
REMARK  3   CORRELATION COEFFICIENTS.
REMARK  3     CORRELATION COEFFICIENT FO-FC       : 0.961
REMARK  3     CORRELATION COEFFICIENT FO-FC FREE  : 0.922
REMARK  3
REMARK  3   RMS DEVIATIONS FROM IDEAL VALUES           COUNT    RMS    WEIGHT
REMARK  3     BOND LENGTHS REFINED ATOMS        (A):   1794;   0.012;   0.021
REMARK  3     BOND LENGTHS OTHERS               (A):   1596;   0.002;   0.020
REMARK  3     BOND ANGLES REFINED ATOMS   (DEGREES):   2422;   1.484;   1.958
REMARK  3     BOND ANGLES OTHERS          (DEGREES):   3716;   0.868;   3.000
REMARK  3     TORSION ANGLES, PERIOD 1    (DEGREES):    224;   6.648;   5.000
REMARK  3     TORSION ANGLES, PERIOD 2    (DEGREES):   NULL;   NULL;    NULL
REMARK  3     TORSION ANGLES, PERIOD 3    (DEGREES):   NULL;   NULL;    NULL
REMARK  3     TORSION ANGLES, PERIOD 4    (DEGREES):   NULL;   NULL;    NULL
REMARK  3     CHIRAL-CENTER RESTRAINTS      (A**3):    270;   0.101;   0.200
REMARK  3     GENERAL PLANES REFINED ATOMS      (A):   1994;   0.005;   0.020
REMARK  3     GENERAL PLANES OTHERS             (A):    384;   0.002;   0.020
REMARK  3     NON-BONDED CONTACTS REFINED ATOMS (A):    303;   0.193;   0.200
REMARK  3     NON-BONDED CONTACTS OTHERS        (A):   1944;   0.251;   0.200
REMARK  3     NON-BONDED TORSION REFINED ATOMS  (A):   NULL;   NULL;    NULL
REMARK  3     NON-BONDED TORSION OTHERS         (A):   1227;   0.086;   0.200
REMARK  3     H-BOND (X . . . Y) REFINED ATOMS  (A):    216;   0.188;   0.200
REMARK  3     H-BOND (X . . . Y) OTHERS         (A):   NULL;   NULL;    NULL
REMARK  3     POTENTIAL METAL-ION REFINED ATOMS (A):   NULL;   NULL;    NULL
REMARK  3     POTENTIAL METAL-ION OTHERS        (A):   NULL;   NULL;    NULL
REMARK  3     SYMMETRY VDW REFINED ATOMS        (A):     29;   0.208;   0.200
REMARK  3     SYMMETRY VDW OTHERS               (A):    115;   0.251;   0.200
```

APPENDIX I(b)-continued

| | | | | | | | |
|---|---|---|---|---|---|---|---|
| REMARK | 3 | SYMMETRY H-BOND REFINED ATOMS | (A): | 43; | 0.199; | 0.200 | |
| REMARK | 3 | SYMMETRY H-BOND OTHERS | (A): | NULL; | NULL; | NULL | |
| REMARK | 3 | | | | | | |
| REMARK | 3 | ISOTROPIC THERMAL FACTOR RESTRAINTS. | | COUNT | RMS | WEIGHT | |
| REMARK | 3 | MAIN-CHAIN BOND REFINED ATOMS | (A**2): | 1110; | 0.591; | 1.500 | |
| REMARK | 3 | MAIN-CHAIN BOND OTHER ATOMS | (A**2): | NULL; | NULL; | NULL | |
| REMARK | 3 | MAIN-CHAIN ANGLE REFINED ATOMS | (A**2): | 1780; | 1.140; | 2.000 | |
| REMARK | 3 | SIDE-CHAIN BOND REFINED ATOMS | (A**2): | 684; | 1.826; | 3.000 | |
| REMARK | 3 | SIDE-CHAIN ANGLE REFINED ATOMS | (A**2): | 642; | 3.050; | 4.500 | |
| REMARK | 3 | | | | | | |
| REMARK | 3 | ANISOTROPIC THERMAL FACTOR RESTRAINTS. | | COUNT | RMS | WEIGHT | |
| REMARK | 3 | RIGID-BOND RESTRAINTS | (A**2): | NULL; | NULL; | NULL | |
| REMARK | 3 | SPHERICITY; FREE ATOMS | (A**2): | NULL; | NULL; | NULL | |
| REMARK | 3 | SPHERICITY; BONDED ATOMS | (A**2): | NULL; | NULL; | NULL | |
| REMARK | 3 | | | | | | |
| REMARK | 3 | NCS RESTRAINTS STATISTICS | | | | | |
| REMARK | 3 | NUMBER OF DIFFERENT NCS GROUPS : 0 | | | | | |
| REMARK | 3 | | | | | | |
| REMARK | 3 | TLS DETAILS | | | | | |
| REMARK | 3 | NUMBER OF TLS GROUPS : 2 | | | | | |
| REMARK | 3 | | | | | | |
| REMARK | 3 | TLS GROUP : 1 | | | | | |
| REMARK | 3 | NUMBER OF COMPONENTS GROUP : 1 | | | | | |
| REMARK | 3 | COMPONENTS C SSSEQI TO C SSSEQI | | | | | |
| REMARK | 3 | RESIDUE RANGE : A 1 A 113 | | | | | |
| REMARK | 3 | ORIGIN FOR THE GROUP (A): 5.3834 33.1578 25.0745 | | | | | |
| REMARK | 3 | T TENSOR | | | | | |
| REMARK | 3 | T11: 0.1096 T22: 0.0299 | | | | | |
| REMARK | 3 | T33: 0.1185 T12: 0.0303 | | | | | |
| REMARK | 3 | T13: −0.0055 T23: −0.0341 | | | | | |
| REMARK | 3 | L TENSOR | | | | | |
| REMARK | 3 | L11: 3.3390 L22: 4.7309 | | | | | |
| REMARK | 3 | L33: 3.2713 L12: −0.1654 | | | | | |
| REMARK | 3 | L13: 0.6888 L23: −0.6154 | | | | | |
| REMARK | 3 | S TENSOR | | | | | |
| REMARK | 3 | S11: 0.1195 S12: 0.0442 S13: −0.2338 | | | | | |
| REMARK | 3 | S21: −0.2682 S22: 0.0273 S23: −0.3948 | | | | | |
| REMARK | 3 | S31: 0.1461 S32: 0.1933 S33: −0.1468 | | | | | |
| REMARK | 3 | | | | | | |
| REMARK | 3 | TLS GROUP : 2 | | | | | |
| REMARK | 3 | NUMBER OF COMPONENTS GROUP : 1 | | | | | |
| REMARK | 3 | COMPONENTS C SSSEQI TO C SSSEQI | | | | | |
| REMARK | 3 | RESIDUE RANGE : B 1 B 113 | | | | | |
| REMARK | 3 | ORIGIN FOR THE GROUP (A): −20.7040 46.2053 38.5402 | | | | | |
| REMARK | 3 | T TENSOR | | | | | |
| REMARK | 3 | T11: 0.1451 T22: 0.2403 | | | | | |
| REMARK | 3 | T33: 0.1040 T12: −0.0402 | | | | | |
| REMARK | 3 | T13: 0.0700 T23: −0.0394 | | | | | |
| REMARK | 3 | L TENSOR | | | | | |
| REMARK | 3 | L11: 3.2727 L22: 4.0810 | | | | | |
| REMARK | 3 | L33: 5.0389 L12: 0.5719 | | | | | |
| REMARK | 3 | L13: 0.1006 L23: 0.6479 | | | | | |
| REMARK | 3 | S TENSOR | | | | | |
| REMARK | 3 | S11: 0.1393 S12: −0.0589 S13: −0.0029 | | | | | |
| REMARK | 3 | S21: 0.1389 S22: −0.3008 S23: 0.2593 | | | | | |
| REMARK | 3 | S31: −0.0779 S32: −0.5470 S33: 0.1615 | | | | | |
| REMARK | 3 | | | | | | |
| REMARK | 3 | BULK SOLVENT MODELLING. | | | | | |
| REMARK | 3 | METHOD USED : BABINET MODEL WITH MASK | | | | | |
| REMARK | 3 | PARAMETERS FOR MASK CALCULATION | | | | | |
| REMARK | 3 | VDW PROBE RADIUS : 1.40 | | | | | |
| REMARK | 3 | ION PROBE RADIUS : 0.80 | | | | | |
| REMARK | 3 | SHRINKAGE RADIUS : 0.80 | | | | | |
| REMARK | 3 | | | | | | |
| REMARK | 3 | OTHER REFINEMENT REMARKS: HYDROGENS HAVE BEEN ADDED IN THE | | | | | |
| REMARK | 3 | RIDING POSITIONS | | | | | |
| REMARK | 4 | | | | | | |
| REMARK | 4 | 1VES COMPLIES WITH FORMAT V. 2.3, 09-JULY-1998 | | | | | |
| REMARK | 100 | | | | | | |
| REMARK | 100 | THIS ENTRY HAS BEEN PROCESSED BY PDBJ ON 07-APR-2004. | | | | | |
| REMARK | 100 | THE RCSB ID CODE IS RCSB006538. | | | | | |
| REMARK | 200 | | | | | | |
| REMARK | 200 | EXPERIMENTAL DETAILS | | | | | |
| REMARK | 200 | EXPERIMENT TYPE : X-RAY DIFFRACTION | | | | | |
| REMARK | 200 | DATE OF DATA COLLECTION : NULL | | | | | |
| REMARK | 200 | TEMPERATURE (KELVIN) : 113.0 | | | | | |
| REMARK | 200 | PH : 4.60 | | | | | |
| REMARK | 200 | NUMBER OF CRYSTALS USED : 1 | | | | | |
| REMARK | 200 | | | | | | |
| REMARK | 200 | SYNCHROTRON (Y/N) : N | | | | | |

APPENDIX I(b)-continued

```
REMARK   200   RADIATION SOURCE                        : ROTATING ANODE
REMARK   200   BEAMLINE                                : NULL
REMARK   200   X-RAY GENERATOR MODEL                   : RIGAKU HR3 HB
REMARK   200   MONOCHROMATIC OR LAUE         (M/L) : M
REMARK   200   WAVELENGTH OR RANGE             (A) : 1.5418
REMARK   200   MONOCHROMATOR                           : NI FILTER
REMARK   200   OPTICS                                  : AXCO MICROCAPILLARY FOCUSING
REMARK   200                                             OPTICS
REMARK   200
REMARK   200   DETECTOR TYPE                           : IMAGE PLATE
REMARK   200   DETECTOR MANUFACTURER                   : MAR 180
REMARK   200   INTENSITY-INTEGRATION SOFTWARE          : DENZO
REMARK   200   DATA SCALING SOFTWARE                   : SCALEPACK
REMARK   200
REMARK   200   NUMBER OF UNIQUE REFLECTIONS         : 14981
REMARK   200   RESOLUTION RANGE HIGH            (A) : 2.180
REMARK   200   RESOLUTION RANGE LOW             (A) : 18.120
REMARK   200   REJECTION CRITERIA          (SIGMA(I)) : 0.000
REMARK   200
REMARK   200   OVERALL.
REMARK   200    COMPLETENESS FOR RANGE         (%) : 100.0
REMARK   200    DATA REDUNDANCY                    : 6.600
REMARK   200    R MERGE                        (I) : 0.05400
REMARK   200    R SYM                          (I) : 0.05400
REMARK   200    <I/SIGMA(I)> FOR THE DATA SET      : 32.5000
REMARK   200
REMARK   200   IN THE HIGHEST RESOLUTION SHELL.
REMARK   200    HIGHEST RESOLUTION SHELL, RANGE HIGH  (A) : 2.18
REMARK   200    HIGHEST RESOLUTION SHELL, RANGE LOW   (A) : 2.24
REMARK   200    COMPLETENESS FOR SHELL         (%) : 99.4
REMARK   200    DATA REDUNDANCY IN SHELL           : 6.30
REMARK   200    R MERGE FOR SHELL              (I) : NULL
REMARK   200    R SYM FOR SHELL                (I) : NULL
REMARK   200    <I/SIGMA(I)> FOR SHELL             : 4.000
REMARK   200
REMARK   200   DIFFRACTION PROTOCOL: SINGLE WAVELENGTH
REMARK   200   METHOD USED TO DETERMINE THE STRUCTURE: MOLECULAR REPLACEMENT
REMARK   200   SOFTWARE USED: MOLREP
REMARK   200   STARTING MODEL: 12Y-1 VNAR PDB ENTRY 1VER
REMARK   200
REMARK   200   REMARK: NULL
REMARK   280
REMARK   280   CRYSTAL
REMARK   280   SOLVENT CONTENT, VS    (%): NULL
REMARK   280   MATTHEWS COEFFICIENT, VM (ANGSTROMS**3/DA): NULL
REMARK   280
REMARK   280   CRYSTALLIZATION CONDITIONS: 0.1M SODIUM CITRATE, 20% V/V ISO-
REMARK   280    PROPANOL, 20% PEG4000, PH 4.6, VAPOR DIFFUSION, HANGING DROP,
REMARK   280    TEMPERATURE 298 K
REMARK   290
REMARK   290   CRYSTALLOGRAPHIC SYMMETRY
REMARK   290   SYMMETRY OPERATORS FOR SPACE GROUP: I 21 21 21
REMARK   290
REMARK   290         SYMOP   SYMMETRY
REMARK   290        NNNMMM   OPERATOR
REMARK   290          1555   X, Y, Z
REMARK   290          2555   ½ – X, –Y, ½ + Z
REMARK   290          3555   –X, ½ + Y, ½ – Z
REMARK   290          4555   ½ + X, ½ – Y, –Z
REMARK   290          5555   ½ + X, ½ + Y, ½ + Z
REMARK   290          6555   –X, ½ – Y, Z
REMARK   290          7555   ½ – X, Y, –Z
REMARK   290          8555   X, –Y, ½ – Z
REMARK   290
REMARK   290     WHERE NNN -> OPERATOR NUMBER
REMARK   290            MMM -> TRANSLATION VECTOR
REMARK   290
REMARK   290   CRYSTALLOGRAPHIC SYMMETRY TRANSFORMATIONS
REMARK   290   THE FOLLOWING TRANSFORMATIONS OPERATE ON THE ATOM/HETATM
REMARK   290   RECORDS IN THIS ENTRY TO PRODUCE CRYSTALLOGRAPHICALLY
REMARK   290   RELATED MOLECULES.
REMARK   290    SMTRY1   1     1.000000    0.000000    0.000000      0.00000
REMARK   290    SMTRY2   1     0.000000    1.000000    0.000000      0.00000
REMARK   290    SMTRY3   1     0.000000    0.000000    1.000000      0.00000
REMARK   290    SMTRY1   2    –1.000000    0.000000    0.000000     32.64150
REMARK   290    SMTRY2   2     0.000000   –1.000000    0.000000      0.00000
REMARK   290    SMTRY3   2     0.000000    0.000000    1.000000     49.11200
REMARK   290    SMTRY1   3    –1.000000    0.000000    0.000000      0.00000
REMARK   290    SMTRY2   3     0.000000    1.000000    0.000000     46.02300
REMARK   290    SMTRY3   3     0.000000    0.000000   –1.000000     49.11200
```

APPENDIX I(b)-continued

```
REMARK   290  SMTRY1 4    1.000000   0.000000   0.000000   32.64150
REMARK   290  SMTRY2 4    0.000000  -1.000000   0.000000   46.02300
REMARK   290  SMTRY3 4    0.000000   0.000000  -1.000000    0.00000
REMARK   290  SMTRY1 5    1.000000   0.000000   0.000000   32.64150
REMARK   290  SMTRY2 5    0.000000   1.000000   0.000000   46.02300
REMARK   290  SMTRY3 5    0.000000   0.000000   1.000000   49.11200
REMARK   290  SMTRY1 6   -1.000000   0.000000   0.000000    0.00000
REMARK   290  SMTRY2 6    0.000000  -1.000000   0.000000   46.02300
REMARK   290  SMTRY3 6    0.000000   0.000000   1.000000    0.00000
REMARK   290  SMTRY1 7   -1.000000   0.000000   0.000000   32.64150
REMARK   290  SMTRY2 7    0.000000   1.000000   0.000000    0.00000
REMARK   290  SMTRY3 7    0.000000   0.000000  -1.000000    0.00000
REMARK   290  SMTRY1 8    1.000000   0.000000   0.000000    0.00000
REMARK   290  SMTRY2 8    0.000000  -1.000000   0.000000    0.00000
REMARK   290  SMTRY3 8    0.000000   0.000000  -1.000000   49.11200
REMARK   290
REMARK   290  REMARK: NULL
REMARK   300
REMARK   300  BIOMOLECULE: 1, 2
REMARK   300  THIS ENTRY CONTAINS THE CRYSTALLOGRAPHIC ASYMMETRIC UNIT
REMARK   300  WHICH CONSISTS OF 2 CHAIN(S). SEE REMARK 350 FOR
REMARK   300  INFORMATION ON GENERATING THE BIOLOGICAL MOLECULE(S).
REMARK   350
REMARK   350  GENERATING THE BIOMOLECULE
REMARK   350  COORDINATES FOR A COMPLETE MULTIMER REPRESENTING THE KNOWN
REMARK   350  BIOLOGICALLY SIGNIFICANT OLIGOMERIZATION STATE OF THE
REMARK   350  MOLECULE CAN BE GENERATED BY APPLYING BIOMT TRANSFORMATIONS
REMARK   350  GIVEN BELOW. BOTH NON-CRYSTALLOGRAPHIC AND
REMARK   350  CRYSTALLOGRAPHIC OPERATIONS ARE GIVEN.
REMARK   350
REMARK   350  BIOMOLECULE: 1
REMARK   350  APPLY THE FOLLOWING TO CHAINS: A
REMARK   350    BIOMT1   1   1.000000   0.000000   0.000000    0.00000
REMARK   350    BIOMT2   1   0.000000   1.000000   0.000000    0.00000
REMARK   350    BIOMT3   1   0.000000   0.000000   1.000000    0.00000
REMARK   350  BIOMOLECULE: 2
REMARK   350  APPLY THE FOLLOWING TO CHAINS: B
REMARK   350    BIOMT1   2   1.000000   0.000000   0.000000    0.00000
REMARK   350    BIOMT2   2   0.000000   1.000000   0.000000    0.00000
REMARK   350    BIOMT3   2   0.000000   0.000000   1.000000    0.00000
REMARK   375
REMARK   375  SPECIAL POSITION
REMARK   375  THE FOLLOWING ATOMS ARE FOUND TO BE WITHIN 0.15 ANGSTROMS
REMARK   375  OF A SYMMETRY RELATED ATOM AND ARE ASSUMED TO BE ON SPECIAL
REMARK   375  POSITIONS.
REMARK   375
REMARK   375  ATOM    RES CSSEQI
REMARK   375        HOH 60        LIES ON A SPECIAL POSITION.
REMARK   375        HOH 67        LIES ON A SPECIAL POSITION.
REMARK   500
REMARK   500  GEOMETRY AND STEREOCHEMISTRY
REMARK   500  SUBTOPIC: CLOSE CONTACTS IN SAME ASYMMETRIC UNIT
REMARK   500
REMARK   500  THE FOLLOWING ATOMS ARE IN CLOSE CONTACT.
REMARK   500
REMARK   500  ATM1  RES C  SSEQI  ATM2  RES C  SSEQI
REMARK   500   O    HOH      132   O    HOH      324             2.11
REMARK   500   OE1  GLU A     76   O    HOH      319             2.14
REMARK   500   O    HOH       55   O    HOH      162             2.14
REMARK   500   O    HOH      262   O    HOH      326             2.14
REMARK   500   O    HOH       47   O    HOH      268             2.15
REMARK   500
REMARK   500  GEOMETRY AND STEREOCHEMISTRY
REMARK   500  SUBTOPIC: COVALENT BOND LENGTHS
REMARK   500
REMARK   500  THE STEREOCHEMICAL PARAMETERS OF THE FOLLOWING RESIDUES
REMARK   500  HAVE VALUES WHICH DEVIATE FROM EXPECTED VALUES BY MORE
REMARK   500  THAN 6*RMSD (M = MODEL NUMBER; RES = RESIDUE NAME; C = CHAIN
REMARK   500  IDENTIFIER; SSEQ = SEQUENCE NUMBER; I = INSERTION CODE).
REMARK   500
REMARK   500  STANDARD TABLE:
REMARK   500  FORMAT: (10X, I3, 1X, 2(A3, 1X, A1, I4, A1, 1X, A4, 3X), F6.3)
REMARK   500
REMARK   500  EXPECTED VALUES: ENGH AND HUBER, 1991
REMARK   500
REMARK   500  M RES  CSSEQI     ATM1 RES   CSSEQI     ATM2 DEVIATION
REMARK   500    LYS  A  61       CG  LYS   A  61       CD    0.080
REMARK   500    ARG  B  25       CG  ARG   B  25       CD   -0.072
REMARK   500
REMARK   500  GEOMETRY AND STEREOCHEMISTRY
```

APPENDIX I(b)-continued

```
REMARK  500  SUBTOPIC: COVALENT BOND ANGLES
REMARK  500
REMARK  500  THE STEREOCHEMICAL PARAMETERS OF THE FOLLOWING RESIDUES
REMARK  500  HAVE VALUES WHICH DEVIATE FROM EXPECTED VALUES BY MORE
REMARK  500  THAN 6*RMSD (M = MODEL NUMBER; RES = RESIDUE NAME; C = CHAIN
REMARK  500  IDENTIFIER; SSEQ = SEQUENCE NUMBER; I = INSERTION CODE).
REMARK  500
REMARK  500  STANDARD TABLE:
REMARK  500  FORMAT: (10X, I3, 1X, A3, 1X, A1, I4, A1, 3(1X, A4, 2X), 12X, F5.1)
REMARK  500
REMARK  500  EXPECTED VALUES: ENGH AND HUBER, 1991
REMARK  500
REMARK  500    M  RES  CSSEQI    ATM1       ATM2       ATM3
REMARK  500       TYR  A  94     CA    -  C      -  N       ANGL. DEV. = 10.7 DEGREES
REMARK  500       ASN  A  95     C     -  N      -  CA      ANGL. DEV. = 10.8 DEGREES
REMARK  500
REMARK  500  GEOMETRY AND STEREOCHEMISTRY
REMARK  500  SUBTOPIC: NON-CIS, NON-TRANS
REMARK  500
REMARK  500  THE FOLLOWING PEPTIDE BONDS DEVIATE SIGNIFICANTLY FROM BOTH
REMARK  500  CIS AND TRANS CONFORMATION. CIS BONDS, IF ANY, ARE LISTED
REMARK  500  ON CISPEP RECORDS. TRANS IS DEFINED AS 180 +/- 30 AND
REMARK  500  CIS IS DEFINED AS 0 +/- 30 DEGREES.
REMARK  500                                    MODEL    OMEGA
REMARK  500  VAL A  112    LYS A  113                   149.69
REMARK  525
REMARK  525  SOLVENT
REMARK  525  THE FOLLOWING SOLVENT MOLECULES LIE FARTHER THAN EXPECTED
REMARK  525  FROM THE PROTEIN OR NUCLEIC ACID MOLECULE AND MAY BE
REMARK  525  ASSOCIATED WITH A SYMMETRY RELATED MOLECULE (M = MODEL
REMARK  525  NUMBER; RES = RESIDUE NAME; C = CHAIN IDENTIFIER; SSEQ = SEQUENCE
REMARK  525  NUMBER; I = INSERTION CODE):
REMARK  525
REMARK  525    M  RES CSSEQI
REMARK  525       HOH     298      DISTANCE =  8.93 ANGSTROMS
REMARK  525       HOH     311      DISTANCE =  5.86 ANGSTROMS
REMARK  525       HOH     312      DISTANCE =  7.03 ANGSTROMS
REMARK  525       HOH     313      DISTANCE =  7.02 ANGSTROMS
REMARK  525       HOH     341      DISTANCE =  5.38 ANGSTROMS
REMARK  525       HOH     342      DISTANCE =  5.10 ANGSTROMS
REMARK  525       HOH     350      DISTANCE =  8.50 ANGSTROMS
REMARK  525       HOH     351      DISTANCE =  8.05 ANGSTROMS
REMARK  525       HOH     353      DISTANCE =  6.37 ANGSTROMS
REMARK  525       HOH     354      DISTANCE =  6.80 ANGSTROMS
REMARK  525       HOH     355      DISTANCE = 12.75 ANGSTROMS
REMARK  525       HOH     356      DISTANCE =  6.59 ANGSTROMS
REMARK  525       HOH     357      DISTANCE =  5.98 ANGSTROMS
REMARK  525       HOH     358      DISTANCE = 13.58 ANGSTROMS
REMARK  900
REMARK  900  RELATED ENTRIES
REMARK  900  RELATED ID: 1VER    RELATED DB: PDB
REMARK  900  THE SAME PROTEIN (12Y-1)
REMARK  999
REMARK  999  SEQUENCE
REMARK  999  A SEQUENCE DATABASE REFERENCE FOR THIS PROTEIN DOES
REMARK  999    NOT CURRENTLY EXIST.
SEQRES    1 A  113  ALA  TRP  VAL  ASP  GLN  THR  PRO  ARG  THR  ALA  THR  LYS  GLU
SEQRES    2 A  113  THR  GLY  GLU  SER  LEU  THR  ILE  ASN  CYS  VAL  LEU  ARG  ASP
SEQRES    3 A  113  ALA  SER  PHE  GLU  LEU  LYS  ASP  THR  GLY  TRP  TYR  ARG  THR
SEQRES    4 A  113  LYS  LEU  GLY  SER  THR  ASN  GLU  GLN  SER  ILE  SER  ILE  GLY
SEQRES    5 A  113  GLY  ARG  TYR  VAL  GLU  THR  VAL  ASN  LYS  GLY  SER  LYS  SER
SEQRES    6 A  113  PHE  SER  LEU  ARG  ILE  SER  ASP  LEU  ARG  VAL  GLU  ASP  SER
SEQRES    7 A  113  GLY  THR  TYR  LYS  CYS  GLN  ALA  PHE  TYR  SER  LEU  PRO  LEU
SEQRES    8 A  113  GLY  ASP  TYR  ASN  TYR  SER  LEU  LEU  PHE  ARG  GLY  GLU  LYS
SEQRES    9 A  113  GLY  ALA  GLY  THR  ALA  LEU  THR  VAL  LYS
SEQRES    1 B  113  ALA  TRP  VAL  ASP  GLN  THR  PRO  ARG  THR  ALA  THR  LYS  GLU
SEQRES    2 B  113  THR  GLY  GLU  SER  LEU  THR  ILE  ASN  CYS  VAL  LEU  ARG  ASP
SEQRES    3 B  113  ALA  SER  PHE  GLU  LEU  LYS  ASP  THR  GLY  TRP  TYR  ARG  THR
SEQRES    4 B  113  LYS  LEU  GLY  SER  THR  ASN  GLU  GLN  SER  ILE  SER  ILE  GLY
SEQRES    5 B  113  GLY  ARG  TYR  VAL  GLU  THR  VAL  ASN  LYS  GLY  SER  LYS  SER
SEQRES    6 B  113  PHE  SER  LEU  ARG  ILE  SER  ASP  LEU  ARG  VAL  GLU  ASP  SER
SEQRES    7 B  113  GLY  THR  TYR  LYS  CYS  GLN  ALA  PHE  TYR  SER  LEU  PRO  LEU
SEQRES    8 B  113  GLY  ASP  TYR  ASN  TYR  SER  LEU  LEU  PHE  ARG  GLY  GLU  LYS
SEQRES    9 B  113  GLY  ALA  GLY  THR  ALA  LEU  THR  VAL  LYS
FORMUL    3   HOH   *358(H2 O1)
HELIX     1 1  ARG A      74  ASP  A     77  5                                      4
HELIX     2 2  ARG B      74  ASP  B     77  5                                      4
SHEET     1 A 4  TRP  A    2  THR  A    6  0
SHEET     2 A 4  LEU  A   18  ARG  A   25 -1 O  ARG  A   25  N  TRP  A     2
SHEET     3 A 4  SER  A   65  ILE  A   70 -1 O  LEU  A   68  N  ILE  A    20
```

APPENDIX I(b)-continued

| | | | | | | | | | | | | | | | |
|---|---|---|---|---|---|---|---|---|---|---|---|---|---|---|---|
| SHEET | 4 | A | 4 | TYR | A | 55 | ASN | A | 60 | −1 N | ASN | A | 60 O | SER | A | 65 |
| SHEET | 1 | B | 5 | THR | A | 9 | GLU | A | 13 | 0 | | | | | | |
| SHEET | 2 | B | 5 | THR | A | 108 | LYS | A | 113 | 1 O | THR | A | 111 N | LYS | A | 12 |
| SHEET | 3 | B | 5 | GLY | A | 79 | LEU | A | 89 | −1 N | GLY | A | 79 O | LEU | A | 110 |
| SHEET | 4 | B | 5 | ASP | A | 33 | LYS | A | 40 | −1 N | TYR | A | 37 Q | LYS | A | 82 |
| SHEET | 5 | B | 5 | GLN | A | 47 | SER | A | 48 | −1 O | GLN | A | 47 N | ARG | A | 38 |
| SHEET | 1 | C | 4 | THR | A | 9 | GLU | A | 13 | 0 | | | | | | |
| SHEET | 2 | C | 4 | THR | A | 108 | LYS | A | 113 | 1 O | THR | A | 111 N | LYS | A | 12 |
| SHEET | 3 | C | 4 | GLY | A | 79 | LEU | A | 89 | −1 N | GLY | A | 79 O | LEU | A | 110 |
| SHEET | 4 | C | 4 | LEU | A | 98 | LYS | A | 104 | −1 O | PHE | A | 100 N | TYR | A | 87 |
| SHEET | 1 | D | 4 | TRP | B | 2 | THR | B | 6 | 0 | | | | | | |
| SHEET | 2 | D | 4 | LEU | B | 18 | ARG | B | 25 | −1 O | ARG | B | 25 N | TRP | B | 2 |
| SHEET | 3 | D | 4 | SER | B | 65 | ILE | B | 70 | −1 O | ILE | B | 70 N | LEU | B | 18 |
| SHEET | 4 | D | 4 | TYR | B | 55 | ASN | B | 60 | −1 N | ASN | B | 60 O | SER | B | 65 |
| SHEET | 1 | E | 5 | THR | B | 9 | GLU | B | 13 | 0 | | | | | | |
| SHEET | 2 | E | 5 | THR | B | 108 | LYS | B | 113 | 1 O | THR | B | 111 N | LYS | B | 12 |
| SHEET | 3 | E | 5 | GLY | B | 79 | LEU | B | 89 | −1 N | GLY | B | 79 O | LEU | B | 110 |
| SHEET | 4 | E | 5 | ASP | B | 33 | LYS | B | 40 | −1 N | TYR | B | 37 O | LYS | B | 82 |
| SHEET | 5 | E | 5 | GLN | B | 47 | SER | B | 48 | −1 O | GLN | B | 47 N | ARG | B | 38 |
| SHEET | 1 | F | 4 | THR | B | 9 | GLU | B | 13 | 0 | | | | | | |
| SHEET | 2 | F | 4 | THR | B | 108 | LYS | B | 113 | 1 O | THR | B | 111 N | LYS | B | 12 |
| SHEET | 3 | F | 4 | GLY | B | 79 | LEU | B | 89 | −1 N | GLY | B | 79 O | LEU | B | 110 |
| SHEET | 4 | F | 4 | LEU | B | 98 | LYS | B | 104 | −1 O | PHE | B | 100 N | TYR | B | 87 |
| SSBOND | 1 | CYS | A | 22 | CYS | A | 83 | | | | | | | | | |
| SSBOND | 2 | CYS | B | 22 | CYS | B | 83 | | | | | | | | | |
| CISPEP | 1 | THR | A | 6 | PRO | A | 7 | 0 | −8.21 | | | | | | | |
| CISPEP | 2 | TYR | A | 94 | ASN | A | 95 | 0 | −6.39 | | | | | | | |
| CISPEP | 3 | THR | B | 6 | PRO | B | 7 | 0 | −3.51 | | | | | | | |
| CISPEP | 4 | PRO | B | 90 | LEU | B | 91 | 0 | 3.64 | | | | | | | |
| CRYST1 | 65.283 | 92.046 | 98.224 | 90.00 | 90.00 | 90.00 I 21 21 21 | 16 | | | | | | | | | |
| ORIGX1 | | 1.000000 | 0.000000 | 0.000000 | 0.00000 | | | | | | | | | | | |
| ORIGX2 | | 0.000000 | 1.000000 | 0.000000 | 0.00000 | | | | | | | | | | | |
| ORIGX3 | | 0.000000 | 0.000000 | 1.000000 | 0.00000 | | | | | | | | | | | |
| SCALE1 | | 0.015318 | 0.000000 | 0.000000 | 0.00000 | | | | | | | | | | | |
| SCALE2 | | 0.000000 | 0.010864 | 0.000000 | 0.00000 | | | | | | | | | | | |
| SCALE3 | | 0.000000 | 0.000000 | 0.010181 | 0.00000 | | | | | | | | | | | |
| ATOM | 1 | N | ALA | A | 1 | −9.545 | 39.140 | 18.378 | 1.00 | 15.32 | N | | | | | |
| ATOM | 2 | CA | ALA | A | 1 | −8.794 | 38.432 | 19.437 | 1.00 | 16.13 | C | | | | | |
| ATOM | 3 | C | ALA | A | 1 | −7.548 | 39.217 | 19.826 | 1.00 | 16.68 | C | | | | | |
| ATOM | 4 | O | ALA | A | 1 | −7.010 | 39.977 | 19.012 | 1.00 | 16.60 | O | | | | | |
| ATOM | 5 | CB | ALA | A | 1 | −8.408 | 37.046 | 18.960 | 1.00 | 16.79 | C | | | | | |
| ATOM | 6 | N | TRP | A | 2 | −7.111 | 39.048 | 21.078 | 1.00 | 16.98 | N | | | | | |
| ATOM | 7 | CA | TRP | A | 2 | −5.862 | 39.620 | 21.552 | 1.00 | 17.64 | C | | | | | |
| ATOM | 8 | C | TRP | A | 2 | −5.260 | 38.787 | 22.680 | 1.00 | 18.87 | C | | | | | |
| ATOM | 9 | O | TRP | A | 2 | −5.963 | 38.059 | 23.370 | 1.00 | 19.72 | O | | | | | |
| ATOM | 10 | CB | TRP | A | 2 | −6.069 | 41.092 | 21.974 | 1.00 | 18.44 | C | | | | | |
| ATOM | 11 | CG | TRP | A | 2 | −6.976 | 41.289 | 23.105 | 1.00 | 18.44 | C | | | | | |
| ATOM | 12 | CD1 | TRP | A | 2 | −8.346 | 41.195 | 23.092 | 1.00 | 21.94 | C | | | | | |
| ATOM | 13 | CD2 | TRP | A | 2 | −6.613 | 41.616 | 24.447 | 1.00 | 19.52 | C | | | | | |
| ATOM | 14 | NE1 | TRP | A | 2 | −8.849 | 41.469 | 24.338 | 1.00 | 22.38 | N | | | | | |
| ATOM | 15 | CE2 | TRP | A | 2 | −7.811 | 41.725 | 25.193 | 1.00 | 20.62 | C | | | | | |
| ATOM | 16 | CE3 | TRP | A | 2 | −5.399 | 41.870 | 25.095 | 1.00 | 18.50 | C | | | | | |
| ATOM | 17 | CZ2 | TRP | A | 2 | −7.825 | 42.048 | 26.558 | 1.00 | 19.76 | C | | | | | |
| ATOM | 18 | CZ3 | TRP | A | 2 | −5.422 | 42.212 | 26.453 | 1.00 | 20.59 | C | | | | | |
| ATOM | 19 | CH2 | TRP | A | 2 | −6.625 | 42.294 | 27.161 | 1.00 | 18.64 | C | | | | | |
| ATOM | 20 | N | VAL | A | 3 | −3.943 | 38.845 | 22.809 | 1.00 | 19.14 | N | | | | | |
| ATOM | 21 | CA | VAL | A | 3 | −3.232 | 38.167 | 23.869 | 1.00 | 19.37 | C | | | | | |
| ATOM | 22 | C | VAL | A | 3 | −2.927 | 39.147 | 24.993 | 1.00 | 18.82 | C | | | | | |
| ATOM | 23 | O | VAL | A | 3 | −2.330 | 40.236 | 24.792 | 1.00 | 17.99 | O | | | | | |
| ATOM | 24 | CB | VAL | A | 3 | −1.929 | 37.489 | 23.381 | 1.00 | 19.52 | C | | | | | |
| ATOM | 25 | CG1 | VAL | A | 3 | −1.186 | 36.857 | 24.535 | 1.00 | 20.40 | C | | | | | |
| ATOM | 26 | CG2 | VAL | A | 3 | −2.251 | 36.437 | 22.333 | 1.00 | 18.97 | C | | | | | |
| ATOM | 27 | N | ASP | A | 4 | −3.365 | 38.725 | 26.175 | 1.00 | 17.88 | N | | | | | |
| ATOM | 28 | CA | ASP | A | 4 | −3.223 | 39.473 | 27.406 | 1.00 | 18.63 | C | | | | | |
| ATOM | 29 | C | ASP | A | 4 | −1.983 | 38.946 | 28.134 | 1.00 | 18.37 | C | | | | | |
| ATOM | 30 | O | ASP | A | 4 | −2.035 | 37.909 | 28.778 | 1.00 | 18.22 | O | | | | | |
| ATOM | 31 | CB | ASP | A | 4 | −4.489 | 39.238 | 28.221 | 1.00 | 19.11 | C | | | | | |
| ATOM | 32 | CG | ASP | A | 4 | −4.542 | 40.031 | 29.474 | 1.00 | 19.12 | C | | | | | |
| ATOM | 33 | OD1 | ASP | A | 4 | −3.571 | 40.746 | 29.799 | 1.00 | 18.98 | O | | | | | |
| ATOM | 34 | OD2 | ASP | A | 4 | −5.553 | 40.002 | 30.189 | 1.00 | 19.61 | O | | | | | |
| ATOM | 35 | N | GLN | A | 5 | −0.872 | 39.673 | 28.022 | 1.00 | 18.58 | N | | | | | |
| ATOM | 36 | CA | GLN | A | 5 | 0.425 | 39.258 | 28.554 | 1.00 | 19.07 | C | | | | | |
| ATOM | 37 | C | GLN | A | 5 | 0.820 | 40.096 | 29.787 | 1.00 | 19.50 | C | | | | | |
| ATOM | 38 | O | GLN | A | 5 | 0.930 | 41.331 | 29.694 | 1.00 | 19.48 | O | | | | | |
| ATOM | 39 | CB | GLN | A | 5 | 1.522 | 39.386 | 27.498 | 1.00 | 19.16 | C | | | | | |
| ATOM | 40 | CG | GLN | A | 5 | 2.892 | 38.959 | 28.076 | 1.00 | 18.91 | C | | | | | |
| ATOM | 41 | CD | GLN | A | 5 | 4.025 | 38.930 | 27.080 | 1.00 | 20.12 | C | | | | | |
| ATOM | 42 | OE1 | GLN | A | 5 | 3.808 | 38.996 | 25.860 | 1.00 | 19.01 | O | | | | | |
| ATOM | 43 | NE2 | GLN | A | 5 | 5.257 | 38.774 | 27.601 | 1.00 | 21.06 | N | | | | | |
| ATOM | 44 | N | THR | A | 6 | 1.012 | 39.408 | 30.922 | 1.00 | 19.09 | N | | | | | |

APPENDIX I(b)-continued

| ATOM | 45 | CA | THR | A | 6 | 1.455 | 39.999 | 32.185 | 1.00 | 19.10 | C |
|---|---|---|---|---|---|---|---|---|---|---|---|
| ATOM | 46 | C | THR | A | 6 | 2.649 | 39.241 | 32.756 | 1.00 | 18.83 | C |
| ATOM | 47 | O | THR | A | 6 | 2.811 | 38.051 | 32.503 | 1.00 | 18.32 | O |
| ATOM | 48 | CB | THR | A | 6 | 0.336 | 39.996 | 33.272 | 1.00 | 19.25 | C |
| ATOM | 49 | OG1 | THR | A | 6 | −0.242 | 38.695 | 33.415 | 1.00 | 20.21 | O |
| ATOM | 50 | CG2 | THR | A | 6 | −0.839 | 40.879 | 32.862 | 1.00 | 20.66 | C |
| ATOM | 51 | N | PRO | A | 7 | 3.490 | 39.909 | 33.536 | 1.00 | 18.47 | N |
| ATOM | 52 | CA | PRO | A | 7 | 3.446 | 41.358 | 33.746 | 1.00 | 18.39 | C |
| ATOM | 53 | C | PRO | A | 7 | 4.101 | 42.136 | 32.581 | 1.00 | 18.90 | C |
| ATOM | 54 | O | PRO | A | 7 | 4.863 | 41.586 | 31.800 | 1.00 | 19.06 | O |
| ATOM | 55 | CB | PRO | A | 7 | 4.249 | 41.535 | 35.035 | 1.00 | 18.51 | C |
| ATOM | 56 | CG | PRO | A | 7 | 5.270 | 40.458 | 34.979 | 1.00 | 18.08 | C |
| ATOM | 57 | CD | PRO | A | 7 | 4.567 | 39.269 | 34.305 | 1.00 | 18.29 | C |
| ATOM | 58 | N | ARG | A | 8 | 3.824 | 43.428 | 32.481 | 1.00 | 19.39 | N |
| ATOM | 59 | CA | ARG | A | 8 | 4.423 | 44.236 | 31.427 | 1.00 | 20.40 | C |
| ATOM | 60 | C | ARG | A | 8 | 5.901 | 44.520 | 31.671 | 1.00 | 20.17 | C |
| ATOM | 61 | O | ARG | A | 8 | 6.677 | 44.614 | 30.731 | 1.00 | 20.60 | O |
| ATOM | 62 | CB | ARG | A | 8 | 3.729 | 45.562 | 31.330 | 1.00 | 21.36 | C |
| ATOM | 63 | CG | ARG | A | 8 | 2.267 | 45.512 | 31.058 | 1.00 | 26.32 | C |
| ATOM | 64 | CD | ARG | A | 8 | 1.723 | 46.911 | 30.612 | 1.00 | 32.78 | C |
| ATOM | 65 | NE | ARG | A | 8 | 0.712 | 46.823 | 29.555 | 1.00 | 39.53 | N |
| ATOM | 66 | CZ | ARG | A | 8 | 0.909 | 46.247 | 28.363 | 1.00 | 41.67 | C |
| ATOM | 67 | NH1 | ARG | A | 8 | 2.081 | 45.690 | 28.054 | 1.00 | 41.52 | N |
| ATOM | 68 | NH2 | ARG | A | 8 | −0.081 | 46.223 | 27.483 | 1.00 | 44.76 | N |
| ATOM | 69 | N | THR | A | 9 | 6.257 | 44.755 | 32.922 | 1.00 | 19.16 | N |
| ATOM | 70 | CA | THR | A | 9 | 7.650 | 44.901 | 33.306 | 1.00 | 19.79 | C |
| ATOM | 71 | C | THR | A | 9 | 7.915 | 44.061 | 34.546 | 1.00 | 19.40 | C |
| ATOM | 72 | O | THR | A | 9 | 7.002 | 43.753 | 35.316 | 1.00 | 19.52 | O |
| ATOM | 73 | CB | THR | A | 9 | 8.035 | 46.376 | 33.619 | 1.00 | 19.33 | C |
| ATOM | 74 | OG1 | THR | A | 9 | 7.222 | 46.871 | 34.684 | 1.00 | 20.29 | O |
| ATOM | 75 | CG2 | THR | A | 9 | 7.730 | 47.333 | 32.449 | 1.00 | 20.56 | C |
| ATOM | 76 | N | ALA | A | 10 | 9.181 | 43.716 | 34.731 | 1.00 | 19.17 | N |
| ATOM | 77 | CA | ALA | A | 10 | 9.621 | 43.034 | 35.927 | 1.00 | 18.67 | C |
| ATOM | 78 | C | ALA | A | 10 | 11.091 | 43.315 | 36.193 | 1.00 | 18.87 | C |
| ATOM | 79 | O | ALA | A | 10 | 11.874 | 43.475 | 35.265 | 1.00 | 18.47 | O |
| ATOM | 80 | CB | ALA | A | 10 | 9.388 | 41.559 | 35.780 | 1.00 | 18.21 | C |
| ATOM | 81 | N | THR | A | 11 | 11.434 | 43.391 | 37.479 | 1.00 | 19.55 | N |
| ATOM | 82 | CA | THR | A | 11 | 12.804 | 43.457 | 37.960 | 1.00 | 20.22 | C |
| ATOM | 83 | C | THR | A | 11 | 13.033 | 42.289 | 38.912 | 1.00 | 20.63 | C |
| ATOM | 84 | O | THR | A | 11 | 12.264 | 42.070 | 39.845 | 1.00 | 20.97 | O |
| ATOM | 85 | CB | THR | A | 11 | 13.033 | 44.787 | 38.690 | 1.00 | 20.37 | C |
| ATOM | 86 | OG1 | THR | A | 11 | 12.846 | 45.867 | 37.770 | 1.00 | 20.04 | O |
| ATOM | 87 | CG2 | THR | A | 11 | 14.489 | 44.931 | 39.151 | 1.00 | 20.37 | C |
| ATOM | 88 | N | LYS | A | 12 | 14.082 | 41.530 | 38.655 | 1.00 | 21.26 | N |
| ATOM | 89 | CA | LYS | A | 12 | 14.424 | 40.372 | 39.459 | 1.00 | 21.82 | C |
| ATOM | 90 | C | LYS | A | 12 | 15.893 | 40.438 | 39.791 | 1.00 | 22.04 | C |
| ATOM | 91 | O | LYS | A | 12 | 16.651 | 41.144 | 39.126 | 1.00 | 22.38 | O |
| ATOM | 92 | CB | LYS | A | 12 | 14.105 | 39.091 | 38.683 | 1.00 | 21.97 | C |
| ATOM | 93 | CG | LYS | A | 12 | 12.634 | 38.936 | 38.327 | 1.00 | 22.31 | C |
| ATOM | 94 | CD | LYS | A | 12 | 11.764 | 38.741 | 39.565 | 1.00 | 24.83 | C |
| ATOM | 95 | CE | LYS | A | 12 | 10.287 | 38.577 | 39.202 | 1.00 | 26.64 | C |
| ATOM | 96 | NZ | LYS | A | 12 | 9.480 | 37.955 | 40.305 | 1.00 | 29.33 | N |
| ATOM | 97 | N | GLU | A | 13 | 16.284 | 39.750 | 40.857 | 1.00 | 22.55 | N |
| ATOM | 98 | CA | GLU | A | 13 | 17.689 | 39.566 | 41.190 | 1.00 | 22.57 | C |
| ATOM | 99 | C | GLU | A | 13 | 18.116 | 38.280 | 40.506 | 1.00 | 22.01 | C |
| ATOM | 100 | O | GLU | A | 13 | 17.271 | 37.462 | 40.150 | 1.00 | 21.38 | O |
| ATOM | 101 | CB | GLU | A | 13 | 17.881 | 39.456 | 42.710 | 1.00 | 23.24 | C |
| ATOM | 102 | CG | GLU | A | 13 | 17.221 | 40.587 | 43.496 | 1.00 | 25.57 | C |
| ATOM | 103 | CD | GLU | A | 13 | 17.761 | 40.775 | 44.916 | 1.00 | 29.95 | C |
| ATOM | 104 | OE1 | GLU | A | 13 | 18.899 | 40.333 | 45.239 | 1.00 | 31.64 | O |
| ATOM | 105 | OE2 | GLU | A | 13 | 17.032 | 41.393 | 45.733 | 1.00 | 33.30 | O |
| ATOM | 106 | N | THR | A | 14 | 19.419 | 38.098 | 40.314 | 1.00 | 21.84 | N |
| ATOM | 107 | CA | THR | A | 14 | 19.942 | 36.855 | 39.760 | 1.00 | 21.60 | C |
| ATOM | 108 | C | THR | A | 14 | 19.574 | 35.713 | 40.711 | 1.00 | 21.52 | C |
| ATOM | 109 | O | THR | A | 14 | 19.536 | 35.898 | 41.932 | 1.00 | 20.88 | O |
| ATOM | 110 | CB | THR | A | 14 | 21.494 | 36.916 | 39.555 | 1.00 | 21.62 | C |
| ATOM | 111 | OG1 | THR | A | 14 | 22.147 | 37.283 | 40.775 | 1.00 | 21.67 | O |
| ATOM | 112 | CG2 | THR | A | 14 | 21.894 | 38.012 | 38.574 | 1.00 | 21.13 | C |
| ATOM | 113 | N | GLY | A | 15 | 19.249 | 34.549 | 40.150 | 1.00 | 21.90 | N |
| ATOM | 114 | CA | GLY | A | 15 | 18.859 | 33.401 | 40.955 | 1.00 | 22.03 | C |
| ATOM | 115 | C | GLY | A | 15 | 17.361 | 33.283 | 41.186 | 1.00 | 22.17 | C |
| ATOM | 116 | O | GLY | A | 15 | 16.888 | 32.210 | 41.554 | 1.00 | 21.94 | O |
| ATOM | 117 | N | GLU | A | 16 | 16.610 | 34.369 | 40.982 | 1.00 | 22.35 | N |
| ATOM | 118 | CA | GLU | A | 16 | 15.150 | 34.339 | 41.162 | 1.00 | 22.54 | C |
| ATOM | 119 | C | GLU | A | 16 | 14.486 | 33.740 | 39.927 | 1.00 | 22.68 | C |
| ATOM | 120 | O | GLU | A | 16 | 15.175 | 33.386 | 38.962 | 1.00 | 22.39 | O |
| ATOM | 121 | CB | GLU | A | 16 | 14.602 | 35.749 | 41.433 | 1.00 | 22.57 | C |
| ATOM | 122 | CG | GLU | A | 16 | 15.079 | 36.337 | 42.746 | 1.00 | 23.97 | C |
| ATOM | 123 | CD | GLU | A | 16 | 14.377 | 37.629 | 43.137 | 1.00 | 24.41 | C |
| ATOM | 124 | OE1 | GLU | A | 16 | 14.028 | 38.434 | 42.262 | 1.00 | 22.72 | O |

APPENDIX I(b)-continued

| ATOM | 125 | OE2 | GLU | A | 16 | 14.205 | 37.853 | 44.354 | 1.00 | 28.36 | O |
|---|---|---|---|---|---|---|---|---|---|---|---|
| ATOM | 126 | N | SER | A | 17 | 13.152 | 33.630 | 39.971 | 1.00 | 22.69 | N |
| ATOM | 127 | CA | SER | A | 17 | 12.336 | 33.179 | 38.838 | 1.00 | 22.73 | C |
| ATOM | 128 | C | SER | A | 17 | 11.374 | 34.262 | 38.378 | 1.00 | 21.71 | C |
| ATOM | 129 | O | SER | A | 17 | 10.951 | 35.079 | 39.167 | 1.00 | 21.49 | O |
| ATOM | 130 | CB | SER | A | 17 | 11.486 | 31.970 | 39.228 | 1.00 | 22.48 | C |
| ATOM | 131 | OG | SER | A | 17 | 12.316 | 30.895 | 39.591 | 1.00 | 26.64 | O |
| ATOM | 132 | N | LEU | A | 18 | 11.030 | 34.234 | 37.092 | 1.00 | 21.08 | N |
| ATOM | 133 | CA | LEU | A | 18 | 9.965 | 35.047 | 36.536 | 1.00 | 20.89 | C |
| ATOM | 134 | C | LEU | A | 18 | 8.886 | 34.144 | 35.952 | 1.00 | 20.71 | C |
| ATOM | 135 | O | LEU | A | 18 | 9.189 | 33.225 | 35.204 | 1.00 | 21.21 | O |
| ATOM | 136 | CB | LEU | A | 18 | 10.519 | 35.882 | 35.402 | 1.00 | 21.29 | C |
| ATOM | 137 | CG | LEU | A | 18 | 9.809 | 37.138 | 34.870 | 1.00 | 21.60 | C |
| ATOM | 138 | CD1 | LEU | A | 18 | 9.814 | 37.122 | 33.381 | 1.00 | 21.64 | C |
| ATOM | 139 | CD2 | LEU | A | 18 | 8.433 | 37.400 | 35.427 | 1.00 | 23.34 | C |
| ATOM | 140 | N | THR | A | 19 | 7.630 | 34.423 | 36.251 | 1.00 | 20.13 | N |
| ATOM | 141 | CA | THR | A | 19 | 6.526 | 33.784 | 35.550 | 1.00 | 19.98 | C |
| ATOM | 142 | C | THR | A | 19 | 5.861 | 34.824 | 34.686 | 1.00 | 19.47 | C |
| ATOM | 143 | O | THR | A | 19 | 5.528 | 35.897 | 35.160 | 1.00 | 20.11 | O |
| ATOM | 144 | CB | THR | A | 19 | 5.553 | 33.199 | 36.573 | 1.00 | 20.46 | C |
| ATOM | 145 | OG1 | THR | A | 19 | 6.197 | 32.115 | 37.255 | 1.00 | 17.99 | O |
| ATOM | 146 | CG2 | THR | A | 19 | 4.325 | 32.538 | 35.876 | 1.00 | 19.65 | C |
| ATOM | 147 | N | ILE | A | 20 | 5.710 | 34.538 | 33.403 | 1.00 | 19.31 | N |
| ATOM | 148 | CA | ILE | A | 20 | 4.965 | 35.398 | 32.489 | 1.00 | 18.89 | C |
| ATOM | 149 | C | ILE | A | 20 | 3.702 | 34.640 | 32.137 | 1.00 | 18.68 | C |
| ATOM | 150 | O | ILE | A | 20 | 3.780 | 33.481 | 31.737 | 1.00 | 18.03 | O |
| ATOM | 151 | CB | ILE | A | 20 | 5.765 | 35.676 | 31.218 | 1.00 | 18.83 | C |
| ATOM | 152 | CG1 | ILE | A | 20 | 7.142 | 36.265 | 31.574 | 1.00 | 21.66 | C |
| ATOM | 153 | CG2 | ILE | A | 20 | 4.935 | 36.550 | 30.252 | 1.00 | 19.66 | C |
| ATOM | 154 | CD1 | ILE | A | 20 | 8.099 | 36.433 | 30.374 | 1.00 | 23.01 | C |
| ATOM | 155 | N | ASN | A | 21 | 2.549 | 35.293 | 32.277 | 1.00 | 18.35 | N |
| ATOM | 156 | CA | ASN | A | 21 | 1.260 | 34.685 | 31.989 | 1.00 | 19.67 | C |
| ATOM | 157 | C | ASN | A | 21 | 0.644 | 35.318 | 30.746 | 1.00 | 20.00 | C |
| ATOM | 158 | O | ASN | A | 21 | 0.570 | 36.546 | 30.640 | 1.00 | 20.11 | O |
| ATOM | 159 | CB | ASN | A | 21 | 0.310 | 34.883 | 33.179 | 1.00 | 20.34 | C |
| ATOM | 160 | CG | ASN | A | 21 | 0.743 | 34.107 | 34.414 | 1.00 | 23.88 | C |
| ATOM | 161 | OD1 | ASN | A | 21 | 0.884 | 32.884 | 34.364 | 1.00 | 27.13 | O |
| ATOM | 162 | ND2 | ASN | A | 21 | 0.943 | 34.807 | 35.531 | 1.00 | 22.89 | N |
| ATOM | 163 | N | CYS | A | 22 | 0.155 | 34.472 | 29.841 | 1.00 | 19.78 | N |
| ATOM | 164 | CA | CYS | A | 22 | −0.550 | 34.913 | 28.653 | 1.00 | 18.87 | C |
| ATOM | 165 | C | CYS | A | 22 | −1.932 | 34.294 | 28.600 | 1.00 | 18.28 | C |
| ATOM | 166 | O | CYS | A | 22 | −2.099 | 33.099 | 28.874 | 1.00 | 18.57 | O |
| ATOM | 167 | CB | CYS | A | 22 | 0.251 | 34.591 | 27.375 | 1.00 | 18.23 | C |
| ATOM | 168 | SG | CYS | A | 22 | 1.687 | 35.685 | 27.122 | 1.00 | 22.18 | S |
| ATOM | 169 | N | VAL | A | 23 | −2.930 | 35.099 | 28.241 | 1.00 | 17.04 | N |
| ATOM | 170 | CA | VAL | A | 23 | −4.289 | 34.573 | 28.085 | 1.00 | 17.69 | C |
| ATOM | 171 | C | VAL | A | 23 | −4.780 | 35.074 | 26.736 | 1.00 | 17.84 | C |
| ATOM | 172 | O | VAL | A | 23 | −4.752 | 36.272 | 26.452 | 1.00 | 17.82 | O |
| ATOM | 173 | CB | VAL | A | 23 | −5.257 | 35.034 | 29.209 | 1.00 | 16.92 | C |
| ATOM | 174 | CG1 | VAL | A | 23 | −6.628 | 34.402 | 29.040 | 1.00 | 16.56 | C |
| ATOM | 175 | CG2 | VAL | A | 23 | −4.682 | 34.676 | 30.574 | 1.00 | 18.84 | C |
| ATOM | 176 | N | LEU | A | 24 | −5.205 | 34.150 | 25.896 | 1.00 | 18.50 | N |
| ATOM | 177 | CA | LEU | A | 24 | −5.848 | 34.505 | 24.625 | 1.00 | 18.68 | C |
| ATOM | 178 | C | LEU | A | 24 | −7.287 | 34.970 | 24.888 | 1.00 | 18.14 | C |
| ATOM | 179 | O | LEU | A | 24 | −8.116 | 34.183 | 25.284 | 1.00 | 18.93 | O |
| ATOM | 180 | CB | LEU | A | 24 | −5.870 | 33.273 | 23.754 | 1.00 | 19.49 | C |
| ATOM | 181 | CG | LEU | A | 24 | −5.907 | 33.369 | 22.218 | 1.00 | 21.72 | C |
| ATOM | 182 | CD1 | LEU | A | 24 | −6.724 | 32.226 | 21.629 | 1.00 | 21.29 | C |
| ATOM | 183 | CD2 | LEU | A | 24 | −6.311 | 34.697 | 21.692 | 1.00 | 20.69 | C |
| ATOM | 184 | N | ARG | A | 25 | −7.569 | 36.242 | 24.642 | 1.00 | 17.64 | N |
| ATOM | 185 | CA | ARG | A | 25 | −8.868 | 36.862 | 24.894 | 1.00 | 17.04 | C |
| ATOM | 186 | C | ARG | A | 25 | −9.727 | 37.050 | 23.621 | 1.00 | 17.73 | C |
| ATOM | 187 | O | ARG | A | 25 | −9.215 | 37.396 | 22.549 | 1.00 | 16.17 | O |
| ATOM | 188 | CB | ARG | A | 25 | −8.647 | 38.248 | 25.479 | 1.00 | 17.56 | C |
| ATOM | 189 | CG | ARG | A | 25 | −7.649 | 38.332 | 26.652 | 1.00 | 17.53 | C |
| ATOM | 190 | CD | ARG | A | 25 | −8.169 | 37.706 | 27.893 | 1.00 | 15.71 | C |
| ATOM | 191 | NE | ARG | A | 25 | −9.439 | 38.300 | 28.305 | 1.00 | 15.64 | N |
| ATOM | 192 | CZ | ARG | A | 25 | −9.622 | 39.154 | 29.313 | 1.00 | 14.07 | C |
| ATOM | 193 | NH1 | ARG | A | 25 | −8.604 | 39.617 | 30.029 | 1.00 | 15.08 | N |
| ATOM | 194 | NH2 | ARG | A | 25 | −10.841 | 39.592 | 29.562 | 1.00 | 13.06 | N |
| ATOM | 195 | N | ASP | A | 26 | −11.036 | 36.867 | 23.764 | 1.00 | 18.00 | N |
| ATOM | 196 | CA | ASP | A | 26 | −11.988 | 37.148 | 22.696 | 1.00 | 19.25 | C |
| ATOM | 197 | C | ASP | A | 26 | −11.575 | 36.398 | 21.429 | 1.00 | 19.75 | C |
| ATOM | 198 | O | ASP | A | 26 | −11.446 | 36.979 | 20.340 | 1.00 | 20.42 | O |
| ATOM | 199 | CB | ASP | A | 26 | −12.075 | 38.658 | 22.424 | 1.00 | 19.21 | C |
| ATOM | 200 | CG | ASP | A | 26 | −13.200 | 39.012 | 21.457 | 1.00 | 21.12 | C |
| ATOM | 201 | OD1 | ASP | A | 26 | −13.038 | 39.948 | 20.634 | 1.00 | 23.28 | O |
| ATOM | 202 | OD2 | ASP | A | 26 | −14.288 | 38.390 | 21.446 | 1.00 | 22.43 | O |
| ATOM | 203 | N | ALA | A | 27 | −11.367 | 35.101 | 21.596 | 1.00 | 19.84 | N |
| ATOM | 204 | CA | ALA | A | 27 | −10.842 | 34.247 | 20.552 | 1.00 | 20.65 | C |

APPENDIX I(b)-continued

| ATOM | 205 | C | ALA | A | 27 | −11.891 | 33.953 | 19.486 | 1.00 | 21.01 | C |
|---|---|---|---|---|---|---|---|---|---|---|---|
| ATOM | 206 | O | ALA | A | 27 | −13.064 | 33.807 | 19.789 | 1.00 | 21.53 | O |
| ATOM | 207 | CB | ALA | A | 27 | −10.311 | 32.928 | 21.173 | 1.00 | 20.13 | C |
| ATOM | 208 | N | SER | A | 28 | −11.453 | 33.887 | 18.233 | 1.00 | 21.92 | N |
| ATOM | 209 | CA | SER | A | 28 | −12.274 | 33.408 | 17.128 | 1.00 | 22.37 | C |
| ATOM | 210 | C | SER | A | 28 | −11.935 | 31.949 | 16.842 | 1.00 | 22.77 | C |
| ATOM | 211 | O | SER | A | 28 | −12.830 | 31.137 | 16.616 | 1.00 | 23.65 | O |
| ATOM | 212 | CB | SER | A | 28 | −12.036 | 34.237 | 15.853 | 1.00 | 22.37 | C |
| ATOM | 213 | OG | SER | A | 28 | −12.317 | 35.605 | 16.069 | 1.00 | 22.84 | O |
| ATOM | 214 | N | PHE | A | 29 | −10.641 | 31.638 | 16.835 | 1.00 | 22.53 | N |
| ATOM | 215 | CA | PHE | A | 29 | −10.137 | 30.321 | 16.469 | 1.00 | 22.25 | C |
| ATOM | 216 | C | PHE | A | 29 | −9.596 | 29.606 | 17.697 | 1.00 | 22.55 | C |
| ATOM | 217 | O | PHE | A | 29 | −9.297 | 30.236 | 18.716 | 1.00 | 21.65 | O |
| ATOM | 218 | CB | PHE | A | 29 | −9.050 | 30.465 | 15.410 | 1.00 | 21.99 | C |
| ATOM | 219 | CG | PHE | A | 29 | −9.491 | 31.247 | 14.202 | 1.00 | 22.87 | C |
| ATOM | 220 | CD1 | PHE | A | 29 | −10.415 | 30.715 | 13.324 | 1.00 | 22.45 | C |
| ATOM | 221 | CD2 | PHE | A | 29 | −8.999 | 32.528 | 13.959 | 1.00 | 22.23 | C |
| ATOM | 222 | CE1 | PHE | A | 29 | −10.841 | 31.441 | 12.224 | 1.00 | 23.02 | C |
| ATOM | 223 | CE2 | PHE | A | 29 | −9.409 | 33.249 | 12.861 | 1.00 | 22.01 | C |
| ATOM | 224 | CZ | PHE | A | 29 | −10.333 | 32.715 | 11.992 | 1.00 | 23.18 | C |
| ATOM | 225 | N | GLU | A | 30 | −9.487 | 28.285 | 17.594 | 1.00 | 23.28 | N |
| ATOM | 226 | CA | GLU | A | 30 | −9.087 | 27.435 | 18.716 | 1.00 | 24.16 | C |
| ATOM | 227 | C | GLU | A | 30 | −7.578 | 27.456 | 18.866 | 1.00 | 23.70 | C |
| ATOM | 228 | O | GLU | A | 30 | −6.846 | 27.260 | 17.901 | 1.00 | 22.38 | O |
| ATOM | 229 | CB | GLU | A | 30 | −9.509 | 25.975 | 18.500 | 1.00 | 24.28 | C |
| ATOM | 230 | CG | GLU | A | 30 | −10.965 | 25.743 | 18.147 | 1.00 | 27.72 | C |
| ATOM | 231 | CD | GLU | A | 30 | −11.183 | 24.367 | 17.543 | 1.00 | 30.78 | C |
| ATOM | 232 | OE1 | GLU | A | 30 | −11.872 | 24.247 | 16.501 | 1.00 | 33.08 | O |
| ATOM | 233 | OE2 | GLU | A | 30 | −10.648 | 23.395 | 18.122 | 1.00 | 34.13 | O |
| ATOM | 234 | N | LEU | A | 31 | −7.110 | 27.670 | 20.083 | 1.00 | 25.10 | N |
| ATOM | 235 | CA | LEU | A | 31 | −5.674 | 27.654 | 20.347 | 1.00 | 25.75 | C |
| ATOM | 236 | C | LEU | A | 31 | −5.098 | 26.262 | 20.072 | 1.00 | 26.30 | C |
| ATOM | 237 | O | LEU | A | 31 | −5.584 | 25.272 | 20.610 | 1.00 | 27.18 | O |
| ATOM | 238 | CB | LEU | A | 31 | −5.412 | 28.059 | 21.791 | 1.00 | 26.27 | C |
| ATOM | 239 | CG | LEU | A | 31 | −3.944 | 28.189 | 22.199 | 1.00 | 26.18 | C |
| ATOM | 240 | CD1 | LEU | A | 31 | −3.256 | 29.266 | 21.376 | 1.00 | 27.21 | C |
| ATOM | 241 | CD2 | LEU | A | 31 | −3.871 | 28.497 | 23.665 | 1.00 | 24.85 | C |
| ATOM | 242 | N | LYS | A | 32 | −4.093 | 26.191 | 19.204 | 1.00 | 26.63 | N |
| ATOM | 243 | CA | LYS | A | 32 | −3.472 | 24.920 | 18.830 | 1.00 | 27.19 | C |
| ATOM | 244 | C | LYS | A | 32 | −2.050 | 24.735 | 19.399 | 1.00 | 27.32 | C |
| ATOM | 245 | O | LYS | A | 32 | −1.738 | 23.676 | 19.959 | 1.00 | 29.44 | O |
| ATOM | 246 | CB | LYS | A | 32 | −3.465 | 24.784 | 17.311 | 1.00 | 27.22 | C |
| ATOM | 247 | CG | LYS | A | 32 | −4.868 | 24.598 | 16.683 | 1.00 | 28.87 | C |
| ATOM | 248 | CD | LYS | A | 32 | −5.729 | 23.562 | 17.425 | 1.00 | 30.06 | C |
| ATOM | 249 | CE | LYS | A | 32 | −7.067 | 23.300 | 16.738 | 1.00 | 31.53 | C |
| ATOM | 250 | NZ | LYS | A | 32 | −8.044 | 22.702 | 17.719 | 1.00 | 32.23 | N |
| ATOM | 251 | N | ASP | A | 33 | −1.205 | 25.745 | 19.235 | 1.00 | 25.91 | N |
| ATOM | 252 | CA | ASP | A | 33 | 0.173 | 25.738 | 19.692 | 1.00 | 25.17 | C |
| ATOM | 253 | C | ASP | A | 33 | 0.501 | 27.137 | 20.232 | 1.00 | 24.01 | C |
| ATOM | 254 | O | ASP | A | 33 | −0.299 | 28.066 | 20.103 | 1.00 | 22.47 | O |
| ATOM | 255 | CB | ASP | A | 33 | 1.128 | 25.388 | 18.555 | 1.00 | 25.62 | C |
| ATOM | 256 | CG | ASP | A | 33 | 2.537 | 24.989 | 19.043 | 1.00 | 28.98 | C |
| ATOM | 257 | OD1 | ASP | A | 33 | 2.698 | 24.558 | 20.216 | 1.00 | 32.36 | O |
| ATOM | 258 | OD2 | ASP | A | 33 | 3.560 | 25.093 | 18.322 | 1.00 | 32.29 | O |
| ATOM | 259 | N | THR | A | 34 | 1.662 | 27.243 | 20.872 | 1.00 | 22.48 | N |
| ATOM | 260 | CA | THR | A | 34 | 2.151 | 28.470 | 21.460 | 1.00 | 22.17 | C |
| ATOM | 261 | C | THR | A | 34 | 3.646 | 28.602 | 21.244 | 1.00 | 21.74 | C |
| ATOM | 262 | O | THR | A | 34 | 4.358 | 27.618 | 21.122 | 1.00 | 21.43 | O |
| ATOM | 263 | CB | THR | A | 34 | 1.888 | 28.485 | 22.961 | 1.00 | 21.97 | C |
| ATOM | 264 | OG1 | THR | A | 34 | 2.412 | 27.294 | 23.557 | 1.00 | 23.15 | O |
| ATOM | 265 | CG2 | THR | A | 34 | 0.409 | 28.455 | 23.278 | 1.00 | 22.95 | C |
| ATOM | 266 | N | GLY | A | 35 | 4.121 | 29.838 | 21.250 | 1.00 | 21.66 | N |
| ATOM | 267 | CA | GLY | A | 35 | 5.534 | 30.118 | 21.096 | 1.00 | 21.46 | C |
| ATOM | 268 | C | GLY | A | 35 | 5.966 | 31.234 | 22.008 | 1.00 | 20.74 | C |
| ATOM | 269 | O | GLY | A | 35 | 5.136 | 32.033 | 22.416 | 1.00 | 21.18 | O |
| ATOM | 270 | N | TRP | A | 36 | 7.261 | 31.259 | 22.322 | 1.00 | 20.14 | N |
| ATOM | 271 | CA | TRP | A | 36 | 7.865 | 32.251 | 23.196 | 1.00 | 19.89 | C |
| ATOM | 272 | C | TRP | A | 36 | 9.108 | 32.819 | 22.516 | 1.00 | 20.02 | C |
| ATOM | 273 | O | TRP | A | 36 | 9.907 | 32.078 | 21.925 | 1.00 | 19.67 | O |
| ATOM | 274 | CB | TRP | A | 36 | 8.209 | 31.632 | 24.541 | 1.00 | 19.58 | C |
| ATOM | 275 | CG | TRP | A | 36 | 6.975 | 31.292 | 25.283 | 1.00 | 20.08 | C |
| ATOM | 276 | CD1 | TRP | A | 36 | 6.239 | 30.125 | 25.181 | 1.00 | 17.81 | C |
| ATOM | 277 | CD2 | TRP | A | 36 | 6.255 | 32.141 | 26.182 | 1.00 | 19.53 | C |
| ATOM | 278 | NE1 | TRP | A | 36 | 5.123 | 30.216 | 25.975 | 1.00 | 17.93 | N |
| ATOM | 279 | CE2 | TRP | A | 36 | 5.116 | 31.426 | 26.619 | 1.00 | 20.01 | C |
| ATOM | 280 | CE3 | TRP | A | 36 | 6.462 | 33.427 | 26.678 | 1.00 | 20.31 | C |
| ATOM | 281 | CZ2 | TRP | A | 36 | 4.208 | 31.954 | 27.537 | 1.00 | 17.18 | C |
| ATOM | 282 | CZ3 | TRP | A | 36 | 5.576 | 33.940 | 27.584 | 1.00 | 18.90 | C |
| ATOM | 283 | CH2 | TRP | A | 36 | 4.447 | 33.216 | 27.997 | 1.00 | 20.01 | C |
| ATOM | 284 | N | TYR | A | 37 | 9.237 | 34.132 | 22.568 | 1.00 | 19.65 | N |

APPENDIX I(b)-continued

| ATOM | 285 | CA | TYR | A | 37 | 10.324 | 34.829 | 21.888 | 1.00 | 20.62 | C |
|---|---|---|---|---|---|---|---|---|---|---|---|
| ATOM | 286 | C | TYR | A | 37 | 10.939 | 35.874 | 22.815 | 1.00 | 20.41 | C |
| ATOM | 287 | O | TYR | A | 37 | 10.273 | 36.379 | 23.721 | 1.00 | 20.08 | O |
| ATOM | 288 | CB | TYR | A | 37 | 9.811 | 35.508 | 20.613 | 1.00 | 20.67 | C |
| ATOM | 289 | CG | TYR | A | 37 | 9.135 | 34.556 | 19.685 | 1.00 | 22.11 | C |
| ATOM | 290 | CD1 | TYR | A | 37 | 9.860 | 33.886 | 18.710 | 1.00 | 21.85 | C |
| ATOM | 291 | CD2 | TYR | A | 37 | 7.775 | 34.281 | 19.815 | 1.00 | 22.28 | C |
| ATOM | 292 | CE1 | TYR | A | 37 | 9.244 | 33.001 | 17.853 | 1.00 | 23.13 | C |
| ATOM | 293 | CE2 | TYR | A | 37 | 7.146 | 33.390 | 18.974 | 1.00 | 24.22 | C |
| ATOM | 294 | CZ | TYR | A | 37 | 7.887 | 32.746 | 17.999 | 1.00 | 25.26 | C |
| ATOM | 295 | OH | TYR | A | 37 | 7.279 | 31.839 | 17.172 | 1.00 | 28.45 | O |
| ATOM | 296 | N | ARG | A | 38 | 12.213 | 36.178 | 22.589 | 1.00 | 20.59 | N |
| ATOM | 297 | CA | ARG | A | 38 | 12.916 | 37.187 | 23.372 | 1.00 | 21.53 | C |
| ATOM | 298 | C | ARG | A | 38 | 13.924 | 37.949 | 22.522 | 1.00 | 20.82 | C |
| ATOM | 299 | O | ARG | A | 38 | 14.625 | 37.360 | 21.684 | 1.00 | 20.22 | O |
| ATOM | 300 | CB | ARG | A | 38 | 13.675 | 36.540 | 24.541 | 1.00 | 22.61 | C |
| ATOM | 301 | CG | ARG | A | 38 | 14.457 | 35.317 | 24.149 | 1.00 | 25.21 | C |
| ATOM | 302 | CD | ARG | A | 38 | 15.896 | 35.288 | 24.635 | 1.00 | 30.36 | C |
| ATOM | 303 | NE | ARG | A | 38 | 15.951 | 35.051 | 26.073 | 1.00 | 32.29 | N |
| ATOM | 304 | CZ | ARG | A | 38 | 16.900 | 34.374 | 26.707 | 1.00 | 33.39 | C |
| ATOM | 305 | NH1 | ARG | A | 38 | 17.920 | 33.843 | 26.048 | 1.00 | 35.30 | N |
| ATOM | 306 | NH2 | ARG | A | 38 | 16.828 | 34.232 | 28.028 | 1.00 | 33.42 | N |
| ATOM | 307 | N | THR | A | 39 | 13.986 | 39.259 | 22.742 | 1.00 | 20.17 | N |
| ATOM | 308 | CA | THR | A | 39 | 15.114 | 40.050 | 22.319 | 1.00 | 19.76 | C |
| ATOM | 309 | C | THR | A | 39 | 15.921 | 40.363 | 23.569 | 1.00 | 19.85 | C |
| ATOM | 310 | O | THR | A | 39 | 15.501 | 41.152 | 24.420 | 1.00 | 19.60 | O |
| ATOM | 311 | CB | THR | A | 39 | 14.645 | 41.323 | 21.624 | 1.00 | 19.79 | C |
| ATOM | 312 | OG1 | THR | A | 39 | 13.894 | 40.983 | 20.455 | 1.00 | 19.66 | O |
| ATOM | 313 | CG2 | THR | A | 39 | 15.814 | 42.101 | 21.084 | 1.00 | 18.73 | C |
| ATOM | 314 | N | LYS | A | 40 | 17.092 | 39.752 | 23.676 | 1.00 | 19.48 | N |
| ATOM | 315 | CA | LYS | A | 40 | 17.911 | 39.924 | 24.867 | 1.00 | 19.94 | C |
| ATOM | 316 | C | LYS | A | 40 | 18.632 | 41.250 | 24.878 | 1.00 | 18.92 | C |
| ATOM | 317 | O | LYS | A | 40 | 18.852 | 41.865 | 23.831 | 1.00 | 18.69 | O |
| ATOM | 318 | CB | LYS | A | 40 | 18.892 | 38.759 | 25.026 | 1.00 | 20.70 | C |
| ATOM | 319 | CG | LYS | A | 40 | 19.989 | 38.670 | 24.006 | 1.00 | 23.62 | C |
| ATOM | 320 | CD | LYS | A | 40 | 20.384 | 37.199 | 23.759 | 1.00 | 29.14 | C |
| ATOM | 321 | CE | LYS | A | 40 | 20.713 | 36.432 | 25.055 | 1.00 | 31.07 | C |
| ATOM | 322 | NZ | LYS | A | 40 | 19.484 | 35.955 | 25.759 | 1.00 | 31.81 | N |
| ATOM | 323 | N | LEU | A | 41 | 18.963 | 41.696 | 26.084 | 1.00 | 18.33 | N |
| ATOM | 324 | CA | LEU | A | 41 | 19.757 | 42.899 | 26.296 | 1.00 | 18.50 | C |
| ATOM | 325 | C | LEU | A | 41 | 20.999 | 42.826 | 25.425 | 1.00 | 18.22 | C |
| ATOM | 326 | O | LEU | A | 41 | 21.609 | 41.761 | 25.309 | 1.00 | 17.78 | O |
| ATOM | 327 | CB | LEU | A | 41 | 20.141 | 42.998 | 27.781 | 1.00 | 18.70 | C |
| ATOM | 328 | CG | LEU | A | 41 | 21.006 | 44.117 | 28.359 | 1.00 | 18.56 | C |
| ATOM | 329 | CD1 | LEU | A | 41 | 22.449 | 43.720 | 28.319 | 1.00 | 20.25 | C |
| ATOM | 330 | CD2 | LEU | A | 41 | 20.799 | 45.471 | 27.673 | 1.00 | 18.34 | C |
| ATOM | 331 | N | GLY | A | 42 | 21.348 | 43.954 | 24.804 | 1.00 | 18.35 | N |
| ATOM | 332 | CA | GLY | A | 42 | 22.512 | 44.066 | 23.938 | 1.00 | 18.25 | C |
| ATOM | 333 | C | GLY | A | 42 | 22.285 | 43.684 | 22.478 | 1.00 | 18.60 | C |
| ATOM | 334 | O | GLY | A | 42 | 23.143 | 43.927 | 21.632 | 1.00 | 18.22 | O |
| ATOM | 335 | N | SER | A | 43 | 21.130 | 43.103 | 22.176 | 1.00 | 19.23 | N |
| ATOM | 336 | CA | SER | A | 43 | 20.856 | 42.563 | 20.852 | 1.00 | 19.97 | C |
| ATOM | 337 | C | SER | A | 43 | 19.564 | 43.140 | 20.264 | 1.00 | 20.80 | C |
| ATOM | 338 | O | SER | A | 43 | 18.597 | 43.416 | 20.987 | 1.00 | 19.75 | O |
| ATOM | 339 | CB | SER | A | 43 | 20.752 | 41.031 | 20.944 | 1.00 | 20.21 | C |
| ATOM | 340 | OG | SER | A | 43 | 19.979 | 40.482 | 19.895 | 1.00 | 20.83 | O |
| ATOM | 341 | N | THR | A | 44 | 19.564 | 43.282 | 18.941 | 1.00 | 21.88 | N |
| ATOM | 342 | CA | THR | A | 44 | 18.399 | 43.715 | 18.172 | 1.00 | 23.21 | C |
| ATOM | 343 | C | THR | A | 44 | 17.589 | 42.547 | 17.573 | 1.00 | 24.06 | C |
| ATOM | 344 | O | THR | A | 44 | 16.511 | 42.760 | 17.035 | 1.00 | 24.67 | O |
| ATOM | 345 | CB | THR | A | 44 | 18.869 | 44.658 | 17.033 | 1.00 | 23.62 | C |
| ATOM | 346 | OG1 | THR | A | 44 | 19.802 | 45.624 | 17.536 | 1.00 | 23.82 | O |
| ATOM | 347 | CG2 | THR | A | 44 | 17.752 | 45.508 | 16.559 | 1.00 | 24.67 | C |
| ATOM | 348 | N | ASN | A | 45 | 18.097 | 41.320 | 17.681 | 1.00 | 24.92 | N |
| ATOM | 349 | CA | ASN | A | 45 | 17.466 | 40.137 | 17.080 | 1.00 | 25.63 | C |
| ATOM | 350 | C | ASN | A | 45 | 16.523 | 39.406 | 18.032 | 1.00 | 25.35 | C |
| ATOM | 351 | O | ASN | A | 45 | 16.956 | 38.938 | 19.087 | 1.00 | 25.12 | O |
| ATOM | 352 | CB | ASN | A | 45 | 18.566 | 39.159 | 16.607 | 1.00 | 26.48 | C |
| ATOM | 353 | CG | ASN | A | 45 | 18.127 | 38.290 | 15.422 | 1.00 | 28.96 | C |
| ATOM | 354 | OD1 | ASN | A | 45 | 17.167 | 37.517 | 15.520 | 1.00 | 34.50 | O |
| ATOM | 355 | ND2 | ASN | A | 45 | 18.834 | 38.420 | 14.295 | 1.00 | 33.05 | N |
| ATOM | 356 | N | GLU | A | 46 | 15.243 | 39.310 | 17.656 | 1.00 | 25.20 | N |
| ATOM | 357 | CA | GLU | A | 46 | 14.277 | 38.489 | 18.385 | 1.00 | 25.43 | C |
| ATOM | 358 | C | GLU | A | 46 | 14.524 | 37.037 | 18.050 | 1.00 | 25.11 | C |
| ATOM | 359 | O | GLU | A | 46 | 14.639 | 36.680 | 16.882 | 1.00 | 25.36 | O |
| ATOM | 360 | CB | GLU | A | 46 | 12.818 | 38.836 | 18.045 | 1.00 | 25.34 | C |
| ATOM | 361 | CG | GLU | A | 46 | 11.826 | 38.236 | 19.042 | 1.00 | 27.16 | C |
| ATOM | 362 | CD | GLU | A | 46 | 10.364 | 38.576 | 18.756 | 1.00 | 29.67 | C |
| ATOM | 363 | OE1 | GLU | A | 46 | 9.873 | 38.238 | 17.667 | 1.00 | 32.34 | O |
| ATOM | 364 | OE2 | GLU | A | 46 | 9.686 | 39.166 | 19.619 | 1.00 | 30.61 | O |

APPENDIX I(b)-continued

| ATOM | 365 | N | GLN | A | 47 | 14.614 | 36.202 | 19.070 | 1.00 | 24.89 | N |
|---|---|---|---|---|---|---|---|---|---|---|---|
| ATOM | 366 | CA | GLN | A | 47 | 14.818 | 34.783 | 18.845 | 1.00 | 25.04 | C |
| ATOM | 367 | C | GLN | A | 47 | 13.840 | 33.922 | 19.634 | 1.00 | 24.11 | C |
| ATOM | 368 | O | GLN | A | 47 | 13.292 | 34.332 | 20.649 | 1.00 | 23.89 | O |
| ATOM | 369 | CB | GLN | A | 47 | 16.266 | 34.404 | 19.128 | 1.00 | 25.75 | C |
| ATOM | 370 | CG | GLN | A | 47 | 16.667 | 34.505 | 20.582 | 1.00 | 28.80 | C |
| ATOM | 371 | CD | GLN | A | 47 | 18.162 | 34.706 | 20.766 | 1.00 | 31.99 | C |
| ATOM | 372 | OE1 | GLN | A | 47 | 18.579 | 35.306 | 21.755 | 1.00 | 35.39 | O |
| ATOM | 373 | NE2 | GLN | A | 47 | 18.968 | 34.198 | 19.830 | 1.00 | 33.93 | N |
| ATOM | 374 | N | SER | A | 48 | 13.580 | 32.743 | 19.098 | 1.00 | 23.33 | N |
| ATOM | 375 | CA | SER | A | 48 | 12.753 | 31.745 | 19.742 | 1.00 | 23.09 | C |
| ATOM | 376 | C | SER | A | 48 | 13.408 | 31.195 | 21.015 | 1.00 | 22.17 | C |
| ATOM | 377 | O | SER | A | 48 | 14.630 | 31.025 | 21.088 | 1.00 | 22.12 | O |
| ATOM | 378 | CB | SER | A | 48 | 12.523 | 30.588 | 18.758 | 1.00 | 23.69 | C |
| ATOM | 379 | OG | SER | A | 48 | 11.687 | 29.601 | 19.332 | 1.00 | 25.84 | O |
| ATOM | 380 | N | ILE | A | 49 | 12.577 | 30.889 | 21.998 | 1.00 | 21.60 | N |
| ATOM | 381 | CA | ILE | A | 49 | 13.000 | 30.234 | 23.233 | 1.00 | 21.35 | C |
| ATOM | 382 | C | ILE | A | 49 | 12.617 | 28.772 | 23.125 | 1.00 | 21.11 | C |
| ATOM | 383 | O | ILE | A | 49 | 11.453 | 28.458 | 22.908 | 1.00 | 20.72 | O |
| ATOM | 384 | CB | ILE | A | 49 | 12.262 | 30.865 | 24.434 | 1.00 | 21.53 | C |
| ATOM | 385 | CG1 | ILE | A | 49 | 12.625 | 32.331 | 24.552 | 1.00 | 22.11 | C |
| ATOM | 386 | CG2 | ILE | A | 49 | 12.620 | 30.170 | 25.733 | 1.00 | 21.54 | C |
| ATOM | 387 | CD1 | ILE | A | 49 | 11.854 | 33.061 | 25.590 | 1.00 | 22.85 | C |
| ATOM | 388 | N | SER | A | 50 | 13.582 | 27.875 | 23.268 | 1.00 | 21.72 | N |
| ATOM | 389 | CA | SER | A | 50 | 13.290 | 26.445 | 23.322 | 1.00 | 22.28 | C |
| ATOM | 390 | C | SER | A | 50 | 12.803 | 26.065 | 24.704 | 1.00 | 22.38 | C |
| ATOM | 391 | O | SER | A | 50 | 13.495 | 26.313 | 25.680 | 1.00 | 22.36 | O |
| ATOM | 392 | CB | SER | A | 50 | 14.540 | 25.641 | 23.014 | 1.00 | 22.55 | C |
| ATOM | 393 | OG | SER | A | 50 | 15.092 | 26.052 | 21.776 | 1.00 | 25.68 | O |
| ATOM | 394 | N | ILE | A | 51 | 11.609 | 25.477 | 24.791 | 1.00 | 22.85 | N |
| ATOM | 395 | CA | ILE | A | 51 | 11.048 | 25.047 | 26.074 | 1.00 | 22.89 | C |
| ATOM | 396 | C | ILE | A | 51 | 11.789 | 23.819 | 26.591 | 1.00 | 22.70 | C |
| ATOM | 397 | O | ILE | A | 51 | 11.923 | 22.838 | 25.879 | 1.00 | 22.61 | O |
| ATOM | 398 | CB | ILE | A | 51 | 9.531 | 24.744 | 25.960 | 1.00 | 22.93 | C |
| ATOM | 399 | CG1 | ILE | A | 51 | 8.776 | 25.963 | 25.434 | 1.00 | 22.33 | C |
| ATOM | 400 | CG2 | ILE | A | 51 | 8.960 | 24.349 | 27.321 | 1.00 | 22.98 | C |
| ATOM | 401 | CD1 | ILE | A | 51 | 9.133 | 27.260 | 26.103 | 1.00 | 22.64 | C |
| ATOM | 402 | N | GLY | A | 52 | 12.264 | 23.912 | 27.838 | 1.00 | 22.98 | N |
| ATOM | 403 | CA | GLY | A | 52 | 13.061 | 22.887 | 28.488 | 1.00 | 22.87 | C |
| ATOM | 404 | C | GLY | A | 52 | 14.047 | 23.530 | 29.461 | 1.00 | 23.19 | C |
| ATOM | 405 | O | GLY | A | 52 | 14.408 | 24.718 | 29.301 | 1.00 | 22.95 | O |
| ATOM | 406 | N | GLY | A | 53 | 14.453 | 22.760 | 30.477 | 1.00 | 22.92 | N |
| ATOM | 407 | CA | GLY | A | 53 | 15.429 | 23.194 | 31.470 | 1.00 | 23.02 | C |
| ATOM | 408 | C | GLY | A | 53 | 14.970 | 24.311 | 32.405 | 1.00 | 23.04 | C |
| ATOM | 409 | O | GLY | A | 53 | 14.065 | 24.133 | 33.226 | 1.00 | 22.84 | O |
| ATOM | 410 | N | ARG | A | 54 | 15.626 | 25.463 | 32.294 | 1.00 | 23.35 | N |
| ATOM | 411 | CA | ARG | A | 54 | 15.251 | 26.664 | 33.053 | 1.00 | 23.76 | C |
| ATOM | 412 | C | ARG | A | 54 | 13.909 | 27.234 | 32.576 | 1.00 | 23.14 | C |
| ATOM | 413 | O | ARG | A | 54 | 13.253 | 27.954 | 33.310 | 1.00 | 23.45 | O |
| ATOM | 414 | CB | ARG | A | 54 | 16.336 | 27.749 | 32.923 | 1.00 | 23.80 | C |
| ATOM | 415 | CG | ARG | A | 54 | 17.649 | 27.414 | 33.591 | 1.00 | 25.73 | C |
| ATOM | 416 | CD | ARG | A | 54 | 18.552 | 28.632 | 33.876 | 1.00 | 27.25 | C |
| ATOM | 417 | NE | ARG | A | 54 | 18.898 | 29.355 | 32.648 | 1.00 | 28.42 | N |
| ATOM | 418 | CZ | ARG | A | 54 | 18.492 | 30.588 | 32.323 | 1.00 | 29.63 | C |
| ATOM | 419 | NH1 | ARG | A | 54 | 17.700 | 31.296 | 33.130 | 1.00 | 30.29 | N |
| ATOM | 420 | NH2 | ARG | A | 54 | 18.888 | 31.118 | 31.169 | 1.00 | 29.15 | N |
| ATOM | 421 | N | TYR | A | 55 | 13.524 | 26.908 | 31.341 | 1.00 | 22.88 | N |
| ATOM | 422 | CA | TYR | A | 55 | 12.314 | 27.425 | 30.687 | 1.00 | 22.07 | C |
| ATOM | 423 | C | TYR | A | 55 | 11.188 | 26.385 | 30.719 | 1.00 | 21.17 | C |
| ATOM | 424 | O | TYR | A | 55 | 11.243 | 25.395 | 30.009 | 1.00 | 22.31 | O |
| ATOM | 425 | CB | TYR | A | 55 | 12.623 | 27.784 | 29.234 | 1.00 | 21.88 | C |
| ATOM | 426 | CG | TYR | A | 55 | 13.801 | 28.715 | 29.070 | 1.00 | 23.92 | C |
| ATOM | 427 | CD1 | TYR | A | 55 | 15.055 | 28.228 | 28.712 | 1.00 | 26.80 | C |
| ATOM | 428 | CD2 | TYR | A | 55 | 13.667 | 30.090 | 29.282 | 1.00 | 26.62 | C |
| ATOM | 429 | CE1 | TYR | A | 55 | 16.154 | 29.090 | 28.557 | 1.00 | 28.70 | C |
| ATOM | 430 | CE2 | TYR | A | 55 | 14.745 | 30.954 | 29.134 | 1.00 | 28.10 | C |
| ATOM | 431 | CZ | TYR | A | 55 | 15.989 | 30.448 | 28.769 | 1.00 | 29.67 | C |
| ATOM | 432 | OH | TYR | A | 55 | 17.071 | 31.294 | 28.629 | 1.00 | 33.06 | O |
| ATOM | 433 | N | VAL | A | 56 | 10.185 | 26.610 | 31.559 | 1.00 | 20.05 | N |
| ATOM | 434 | CA | VAL | A | 56 | 9.087 | 25.671 | 31.779 | 1.00 | 19.16 | C |
| ATOM | 435 | C | VAL | A | 56 | 7.774 | 26.317 | 31.360 | 1.00 | 18.52 | C |
| ATOM | 436 | O | VAL | A | 56 | 7.357 | 27.357 | 31.901 | 1.00 | 18.12 | O |
| ATOM | 437 | CB | VAL | A | 56 | 9.010 | 25.219 | 33.252 | 1.00 | 19.07 | C |
| ATOM | 438 | CG1 | VAL | A | 56 | 7.790 | 24.279 | 33.487 | 1.00 | 19.53 | C |
| ATOM | 439 | CG2 | VAL | A | 56 | 10.320 | 24.501 | 33.664 | 1.00 | 19.48 | C |
| ATOM | 440 | N | GLU | A | 57 | 7.147 | 25.747 | 30.344 | 1.00 | 18.03 | N |
| ATOM | 441 | CA | GLU | A | 57 | 5.850 | 26.236 | 29.904 | 1.00 | 17.33 | C |
| ATOM | 442 | C | GLU | A | 57 | 4.703 | 25.360 | 30.398 | 1.00 | 17.50 | C |
| ATOM | 443 | O | GLU | A | 57 | 4.778 | 24.125 | 30.351 | 1.00 | 18.48 | O |
| ATOM | 444 | CB | GLU | A | 57 | 5.820 | 26.327 | 28.381 | 1.00 | 17.47 | C |

APPENDIX I(b)-continued

| ATOM | 445 | CG | GLU | A | 57 | 4.663 | 27.191 | 27.861 | 1.00 | 15.92 | C |
|---|---|---|---|---|---|---|---|---|---|---|---|
| ATOM | 446 | CD | GLU | A | 57 | 4.299 | 26.942 | 26.395 | 1.00 | 16.52 | C |
| ATOM | 447 | OE1 | GLU | A | 57 | 4.605 | 25.850 | 25.893 | 1.00 | 14.24 | O |
| ATOM | 448 | OE2 | GLU | A | 57 | 3.678 | 27.830 | 25.749 | 1.00 | 14.65 | O |
| ATOM | 449 | N | THR | A | 58 | 3.633 | 26.008 | 30.835 | 1.00 | 17.44 | N |
| ATOM | 450 | CA | THR | A | 58 | 2.374 | 25.364 | 31.168 | 1.00 | 17.09 | C |
| ATOM | 451 | C | THR | A | 58 | 1.245 | 25.931 | 30.325 | 1.00 | 17.31 | C |
| ATOM | 452 | O | THR | A | 58 | 1.010 | 27.153 | 30.328 | 1.00 | 17.84 | O |
| ATOM | 453 | CB | THR | A | 58 | 2.063 | 25.622 | 32.638 | 1.00 | 17.50 | C |
| ATOM | 454 | OG1 | THR | A | 58 | 3.208 | 25.265 | 33.412 | 1.00 | 17.51 | O |
| ATOM | 455 | CG2 | THR | A | 58 | 0.965 | 24.689 | 33.140 | 1.00 | 18.00 | C |
| ATOM | 456 | N | VAL | A | 59 | 0.545 | 25.045 | 29.625 | 1.00 | 16.46 | N |
| ATOM | 457 | CA | VAL | A | 59 | -0.542 | 25.426 | 28.736 | 1.00 | 16.43 | C |
| ATOM | 458 | C | VAL | A | 59 | -1.832 | 24.740 | 29.183 | 1.00 | 15.86 | C |
| ATOM | 459 | O | VAL | A | 59 | -1.883 | 23.513 | 29.342 | 1.00 | 14.34 | O |
| ATOM | 460 | CB | VAL | A | 59 | -0.251 | 25.040 | 27.252 | 1.00 | 16.37 | C |
| ATOM | 461 | CG1 | VAL | A | 59 | -1.433 | 25.440 | 26.343 | 1.00 | 16.25 | C |
| ATOM | 462 | CG2 | VAL | A | 59 | 1.054 | 25.676 | 26.743 | 1.00 | 16.91 | C |
| ATOM | 463 | N | ASN | A | 60 | -2.863 | 25.554 | 29.391 | 1.00 | 16.01 | N |
| ATOM | 464 | CA | ASN | A | 60 | -4.224 | 25.100 | 29.657 | 1.00 | 16.49 | C |
| ATOM | 465 | C | ASN | A | 60 | -5.142 | 25.565 | 28.542 | 1.00 | 16.38 | C |
| ATOM | 466 | O | ASN | A | 60 | -5.575 | 26.728 | 28.538 | 1.00 | 15.18 | O |
| ATOM | 467 | CB | ASN | A | 60 | -4.673 | 25.660 | 30.994 | 1.00 | 17.22 | C |
| ATOM | 468 | CG | ASN | A | 60 | -3.700 | 25.309 | 32.116 | 1.00 | 21.86 | C |
| ATOM | 469 | OD1 | ASN | A | 60 | -2.920 | 26.170 | 32.564 | 1.00 | 31.74 | O |
| ATOM | 470 | ND2 | ASN | A | 60 | -3.708 | 24.035 | 32.552 | 1.00 | 22.53 | N |
| ATOM | 471 | N | LYS | A | 61 | -5.435 | 24.678 | 27.592 | 1.00 | 16.48 | N |
| ATOM | 472 | CA | LYS | A | 61 | -6.109 | 25.081 | 26.351 | 1.00 | 18.49 | C |
| ATOM | 473 | C | LYS | A | 61 | -7.533 | 25.551 | 26.650 | 1.00 | 19.11 | C |
| ATOM | 474 | O | LYS | A | 61 | -8.031 | 26.453 | 26.006 | 1.00 | 19.85 | O |
| ATOM | 475 | CB | LYS | A | 61 | -6.143 | 23.937 | 25.319 | 1.00 | 19.58 | C |
| ATOM | 476 | CG | LYS | A | 61 | -5.129 | 24.036 | 24.136 | 1.00 | 21.70 | C |
| ATOM | 477 | CD | LYS | A | 61 | -5.345 | 22.853 | 23.081 | 1.00 | 23.52 | C |
| ATOM | 478 | CE | LYS | A | 61 | -4.572 | 21.530 | 23.383 | 1.00 | 23.96 | C |
| ATOM | 479 | NZ | LYS | A | 61 | -5.373 | 20.217 | 23.361 | 1.00 | 22.11 | N |
| ATOM | 480 | N | GLY | A | 62 | -8.165 | 24.952 | 27.657 | 1.00 | 19.79 | N |
| ATOM | 481 | CA | GLY | A | 62 | -9.545 | 25.256 | 28.002 | 1.00 | 20.12 | C |
| ATOM | 482 | C | GLY | A | 62 | -9.743 | 26.668 | 28.515 | 1.00 | 20.10 | C |
| ATOM | 483 | O | GLY | A | 62 | -10.726 | 27.305 | 28.206 | 1.00 | 20.62 | O |
| ATOM | 484 | N | SER | A | 63 | -8.790 | 27.159 | 29.286 | 1.00 | 20.78 | N |
| ATOM | 485 | CA | SER | A | 63 | -8.812 | 28.532 | 29.772 | 1.00 | 21.23 | C |
| ATOM | 486 | C | SER | A | 63 | -8.030 | 29.506 | 28.874 | 1.00 | 21.06 | C |
| ATOM | 487 | O | SER | A | 63 | -7.870 | 30.670 | 29.206 | 1.00 | 21.02 | O |
| ATOM | 488 | CB | SER | A | 63 | -8.252 | 28.543 | 31.171 | 1.00 | 21.10 | C |
| ATOM | 489 | OG | SER | A | 63 | -6.856 | 28.412 | 31.117 | 1.00 | 23.25 | O |
| ATOM | 490 | N | LYS | A | 64 | -7.545 | 29.008 | 27.742 | 1.00 | 21.07 | N |
| ATOM | 491 | CA | LYS | A | 64 | -6.786 | 29.774 | 26.765 | 1.00 | 21.34 | C |
| ATOM | 492 | C | LYS | A | 64 | -5.552 | 30.450 | 27.383 | 1.00 | 20.91 | C |
| ATOM | 493 | O | LYS | A | 64 | -5.128 | 31.527 | 26.953 | 1.00 | 19.71 | O |
| ATOM | 494 | CB | LYS | A | 64 | -7.716 | 30.743 | 26.029 | 1.00 | 22.29 | C |
| ATOM | 495 | CG | LYS | A | 64 | -8.976 | 30.047 | 25.476 | 1.00 | 25.28 | C |
| ATOM | 496 | CD | LYS | A | 64 | -10.033 | 31.046 | 25.074 | 1.00 | 30.88 | C |
| ATOM | 497 | CE | LYS | A | 64 | -11.210 | 30.411 | 24.334 | 1.00 | 32.43 | C |
| ATOM | 498 | NZ | LYS | A | 64 | -11.472 | 28.992 | 24.760 | 1.00 | 35.69 | N |
| ATOM | 499 | N | SER | A | 65 | -4.962 | 29.765 | 28.363 | 1.00 | 19.94 | N |
| ATOM | 500 | CA | SER | A | 65 | -3.825 | 30.267 | 29.102 | 1.00 | 20.67 | C |
| ATOM | 501 | C | SER | A | 65 | -2.559 | 29.472 | 28.830 | 1.00 | 19.83 | C |
| ATOM | 502 | O | SER | A | 65 | -2.584 | 28.250 | 28.720 | 1.00 | 18.60 | O |
| ATOM | 503 | CB | SER | A | 65 | -4.121 | 30.218 | 30.600 | 1.00 | 20.77 | C |
| ATOM | 504 | OG | SER | A | 65 | -5.350 | 30.878 | 30.850 | 1.00 | 25.20 | O |
| ATOM | 505 | N | PHE | A | 66 | -1.460 | 30.205 | 28.769 | 1.00 | 19.55 | N |
| ATOM | 506 | CA | PHE | A | 66 | -0.136 | 29.672 | 28.581 | 1.00 | 19.48 | C |
| ATOM | 507 | C | PHE | A | 66 | 0.856 | 30.619 | 29.278 | 1.00 | 20.09 | C |
| ATOM | 508 | O | PHE | A | 66 | 0.790 | 31.851 | 29.113 | 1.00 | 20.75 | O |
| ATOM | 509 | CB | PHE | A | 66 | 0.208 | 29.430 | 27.091 | 1.00 | 18.76 | C |
| ATOM | 510 | CG | PHE | A | 66 | -0.156 | 30.556 | 26.151 | 1.00 | 20.98 | C |
| ATOM | 511 | CD1 | PHE | A | 66 | -1.490 | 30.838 | 25.849 | 1.00 | 21.10 | C |
| ATOM | 512 | CD2 | PHE | A | 66 | 0.838 | 31.279 | 25.494 | 1.00 | 22.63 | C |
| ATOM | 513 | CE1 | PHE | A | 66 | -1.827 | 31.847 | 24.961 | 1.00 | 21.88 | C |
| ATOM | 514 | CE2 | PHE | A | 66 | 0.506 | 32.282 | 24.577 | 1.00 | 22.52 | C |
| ATOM | 515 | CZ | PHE | A | 66 | -0.837 | 32.573 | 24.329 | 1.00 | 23.43 | C |
| ATOM | 516 | N | SER | A | 67 | 1.743 | 30.001 | 30.062 | 1.00 | 20.70 | N |
| ATOM | 517 | CA | SER | A | 67 | 2.698 | 30.632 | 30.961 | 1.00 | 21.27 | C |
| ATOM | 518 | C | SER | A | 67 | 4.087 | 30.068 | 30.777 | 1.00 | 20.65 | C |
| ATOM | 519 | O | SER | A | 67 | 4.261 | 28.874 | 30.548 | 1.00 | 21.14 | O |
| ATOM | 520 | CB | SER | A | 67 | 2.356 | 30.312 | 32.415 | 1.00 | 21.31 | C |
| ATOM | 521 | OG | SER | A | 67 | 1.311 | 31.136 | 32.822 | 1.00 | 27.23 | O |
| ATOM | 522 | N | LEU | A | 68 | 5.074 | 30.929 | 30.947 | 1.00 | 20.50 | N |
| ATOM | 523 | CA | LEU | A | 68 | 6.469 | 30.538 | 30.937 | 1.00 | 20.82 | C |
| ATOM | 524 | C | LEU | A | 68 | 7.013 | 30.914 | 32.298 | 1.00 | 20.84 | C |

APPENDIX I(b)-continued

| ATOM | 525 | O | LEU | A | 68 | 6.866 | 32.052 | 32.706 | 1.00 | 19.92 | O |
|---|---|---|---|---|---|---|---|---|---|---|---|
| ATOM | 526 | CB | LEU | A | 68 | 7.181 | 31.344 | 29.878 | 1.00 | 20.70 | C |
| ATOM | 527 | CG | LEU | A | 68 | 8.317 | 30.832 | 29.005 | 1.00 | 23.40 | C |
| ATOM | 528 | CD1 | LEU | A | 68 | 9.303 | 31.968 | 28.773 | 1.00 | 22.63 | C |
| ATOM | 529 | CD2 | LEU | A | 68 | 8.988 | 29.587 | 29.503 | 1.00 | 23.71 | C |
| ATOM | 530 | N | ARG | A | 69 | 7.647 | 29.974 | 32.980 | 1.00 | 20.92 | N |
| ATOM | 531 | CA | ARG | A | 69 | 8.411 | 30.263 | 34.187 | 1.00 | 21.67 | C |
| ATOM | 532 | C | ARG | A | 69 | 9.892 | 30.041 | 33.895 | 1.00 | 21.75 | C |
| ATOM | 533 | O | ARG | A | 69 | 10.296 | 28.963 | 33.478 | 1.00 | 21.02 | O |
| ATOM | 534 | CB | ARG | A | 69 | 7.980 | 29.371 | 35.335 | 1.00 | 21.50 | C |
| ATOM | 535 | CG | ARG | A | 69 | 8.705 | 29.694 | 36.648 | 1.00 | 23.03 | C |
| ATOM | 536 | CD | ARG | A | 69 | 8.145 | 28.935 | 37.842 | 1.00 | 23.71 | C |
| ATOM | 537 | NE | ARG | A | 69 | 8.827 | 29.247 | 39.101 | 1.00 | 26.51 | N |
| ATOM | 538 | CZ | ARG | A | 69 | 9.899 | 28.610 | 39.592 | 1.00 | 29.47 | C |
| ATOM | 539 | NH1 | ARG | A | 69 | 10.481 | 27.609 | 38.932 | 1.00 | 31.37 | N |
| ATOM | 540 | NH2 | ARG | A | 69 | 10.411 | 28.986 | 40.762 | 1.00 | 30.68 | N |
| ATOM | 541 | N | ILE | A | 70 | 10.680 | 31.082 | 34.107 | 1.00 | 22.33 | N |
| ATOM | 542 | CA | ILE | A | 70 | 12.120 | 31.054 | 33.892 | 1.00 | 22.69 | C |
| ATOM | 543 | C | ILE | A | 70 | 12.770 | 31.073 | 35.263 | 1.00 | 22.58 | C |
| ATOM | 544 | O | ILE | A | 70 | 12.595 | 32.017 | 36.011 | 1.00 | 22.40 | O |
| ATOM | 545 | CB | ILE | A | 70 | 12.552 | 32.275 | 33.064 | 1.00 | 22.65 | C |
| ATOM | 546 | CG1 | ILE | A | 70 | 11.665 | 32.389 | 31.835 | 1.00 | 23.48 | C |
| ATOM | 547 | CG2 | ILE | A | 70 | 14.039 | 32.178 | 32.641 | 1.00 | 22.68 | C |
| ATOM | 548 | CD1 | ILE | A | 70 | 11.910 | 33.600 | 31.053 | 1.00 | 26.54 | C |
| ATOM | 549 | N | SER | A | 71 | 13.495 | 30.006 | 35.585 | 1.00 | 23.04 | N |
| ATOM | 550 | CA | SER | A | 71 | 14.143 | 29.844 | 36.878 | 1.00 | 23.02 | C |
| ATOM | 551 | C | SER | A | 71 | 15.597 | 30.286 | 36.806 | 1.00 | 22.90 | C |
| ATOM | 552 | O | SER | A | 71 | 16.154 | 30.394 | 35.719 | 1.00 | 22.88 | O |
| ATOM | 553 | CB | SER | A | 71 | 14.080 | 28.367 | 37.301 | 1.00 | 23.74 | C |
| ATOM | 554 | OG | SER | A | 71 | 14.571 | 27.509 | 36.275 | 1.00 | 23.76 | O |
| ATOM | 555 | N | ASP | A | 72 | 16.199 | 30.550 | 37.968 | 1.00 | 22.96 | N |
| ATOM | 556 | CA | ASP | A | 72 | 17.634 | 30.801 | 38.076 | 1.00 | 23.04 | C |
| ATOM | 557 | C | ASP | A | 72 | 18.076 | 31.853 | 37.083 | 1.00 | 22.39 | C |
| ATOM | 558 | O | ASP | A | 72 | 18.929 | 31.604 | 36.236 | 1.00 | 22.72 | O |
| ATOM | 559 | CB | ASP | A | 72 | 18.431 | 29.498 | 37.862 | 1.00 | 23.38 | C |
| ATOM | 560 | CG | ASP | A | 72 | 19.932 | 29.668 | 38.126 | 1.00 | 24.56 | C |
| ATOM | 561 | OD1 | ASP | A | 72 | 20.305 | 30.618 | 38.854 | 1.00 | 24.85 | O |
| ATOM | 562 | OD2 | ASP | A | 72 | 20.800 | 28.892 | 37.649 | 1.00 | 25.90 | O |
| ATOM | 563 | N | LEU | A | 73 | 17.494 | 33.038 | 37.200 | 1.00 | 22.00 | N |
| ATOM | 564 | CA | LEU | A | 73 | 17.729 | 34.078 | 36.216 | 1.00 | 21.94 | C |
| ATOM | 565 | C | LEU | A | 73 | 19.143 | 34.619 | 36.349 | 1.00 | 21.62 | C |
| ATOM | 566 | O | LEU | A | 73 | 19.704 | 34.654 | 37.434 | 1.00 | 20.95 | O |
| ATOM | 567 | CB | LEU | A | 73 | 16.724 | 35.217 | 36.361 | 1.00 | 21.83 | C |
| ATOM | 568 | CG | LEU | A | 73 | 15.270 | 34.871 | 36.009 | 1.00 | 21.51 | C |
| ATOM | 569 | CD1 | LEU | A | 73 | 14.329 | 35.768 | 36.771 | 1.00 | 20.80 | C |
| ATOM | 570 | CD2 | LEU | A | 73 | 14.991 | 34.947 | 34.493 | 1.00 | 22.55 | C |
| ATOM | 571 | N | ARG | A | 74 | 19.709 | 35.011 | 35.217 | 1.00 | 21.85 | N |
| ATOM | 572 | CA | ARG | A | 74 | 20.977 | 35.727 | 35.179 | 1.00 | 22.48 | C |
| ATOM | 573 | C | ARG | A | 74 | 20.777 | 37.032 | 34.419 | 1.00 | 21.94 | C |
| ATOM | 574 | O | ARG | A | 74 | 19.741 | 37.232 | 33.786 | 1.00 | 21.58 | O |
| ATOM | 575 | CB | ARG | A | 74 | 22.103 | 34.885 | 34.564 | 1.00 | 23.01 | C |
| ATOM | 576 | CG | ARG | A | 74 | 21.719 | 33.699 | 33.687 | 1.00 | 25.24 | C |
| ATOM | 577 | CD | ARG | A | 74 | 21.299 | 32.418 | 34.444 | 1.00 | 28.74 | C |
| ATOM | 578 | NE | ARG | A | 74 | 21.739 | 31.104 | 33.907 | 1.00 | 31.12 | N |
| ATOM | 579 | CZ | ARG | A | 74 | 21.911 | 30.754 | 32.613 | 1.00 | 33.00 | C |
| ATOM | 580 | NH1 | ARG | A | 74 | 21.730 | 31.606 | 31.607 | 1.00 | 35.30 | N |
| ATOM | 581 | NH2 | ARG | A | 74 | 22.299 | 29.513 | 32.319 | 1.00 | 33.69 | N |
| ATOM | 582 | N | VAL | A | 75 | 21.752 | 37.932 | 34.489 | 1.00 | 21.59 | N |
| ATOM | 583 | CA | VAL | A | 75 | 21.531 | 39.275 | 33.970 | 1.00 | 21.69 | C |
| ATOM | 584 | C | VAL | A | 75 | 21.395 | 39.261 | 32.443 | 1.00 | 21.72 | C |
| ATOM | 585 | O | VAL | A | 75 | 20.763 | 40.147 | 31.881 | 1.00 | 21.66 | O |
| ATOM | 586 | CB | VAL | A | 75 | 22.578 | 40.354 | 34.481 | 1.00 | 21.62 | C |
| ATOM | 587 | CG1 | VAL | A | 75 | 23.363 | 39.870 | 35.698 | 1.00 | 20.91 | C |
| ATOM | 588 | CG2 | VAL | A | 75 | 23.488 | 40.839 | 33.373 | 1.00 | 21.89 | C |
| ATOM | 589 | N | GLU | A | 76 | 21.975 | 38.263 | 31.778 | 1.00 | 21.76 | N |
| ATOM | 590 | CA | GLU | A | 76 | 21.853 | 38.163 | 30.319 | 1.00 | 21.87 | C |
| ATOM | 591 | C | GLU | A | 76 | 20.441 | 37.747 | 29.866 | 1.00 | 21.85 | C |
| ATOM | 592 | O | GLU | A | 76 | 20.088 | 37.963 | 28.709 | 1.00 | 22.39 | O |
| ATOM | 593 | CB | GLU | A | 76 | 22.916 | 37.233 | 29.714 | 1.00 | 21.99 | C |
| ATOM | 594 | CG | GLU | A | 76 | 22.876 | 35.791 | 30.199 | 1.00 | 22.56 | C |
| ATOM | 595 | CD | GLU | A | 76 | 24.002 | 35.449 | 31.160 | 1.00 | 24.12 | C |
| ATOM | 596 | OE1 | GLU | A | 76 | 24.518 | 36.377 | 31.853 | 1.00 | 22.56 | O |
| ATOM | 597 | OE2 | GLU | A | 76 | 24.360 | 34.245 | 31.225 | 1.00 | 24.41 | O |
| ATOM | 598 | N | ASP | A | 77 | 19.654 | 37.159 | 30.773 | 1.00 | 21.45 | N |
| ATOM | 599 | CA | ASP | A | 77 | 18.227 | 36.896 | 30.540 | 1.00 | 21.34 | C |
| ATOM | 600 | C | ASP | A | 77 | 17.391 | 38.163 | 30.461 | 1.00 | 21.15 | C |
| ATOM | 601 | O | ASP | A | 77 | 16.243 | 38.119 | 30.018 | 1.00 | 21.28 | O |
| ATOM | 602 | CB | ASP | A | 77 | 17.626 | 36.043 | 31.662 | 1.00 | 21.32 | C |
| ATOM | 603 | CG | ASP | A | 77 | 18.151 | 34.641 | 31.670 | 1.00 | 21.44 | C |
| ATOM | 604 | OD1 | ASP | A | 77 | 18.584 | 34.160 | 30.603 | 1.00 | 22.02 | O |

APPENDIX I(b)-continued

| ATOM | 605 | OD2 | ASP | A | 77 | 18.164 | 33.948 | 32.698 | 1.00 | 21.47 | O |
|---|---|---|---|---|---|---|---|---|---|---|---|
| ATOM | 606 | N | SER | A | 78 | 17.929 | 39.278 | 30.934 | 1.00 | 20.42 | N |
| ATOM | 607 | CA | SER | A | 78 | 17.203 | 40.533 | 30.829 | 1.00 | 20.88 | C |
| ATOM | 608 | C | SER | A | 78 | 16.915 | 40.804 | 29.334 | 1.00 | 20.27 | C |
| ATOM | 609 | O | SER | A | 78 | 17.656 | 40.373 | 28.469 | 1.00 | 20.38 | O |
| ATOM | 610 | CB | SER | A | 78 | 17.976 | 41.658 | 31.542 | 1.00 | 21.09 | C |
| ATOM | 611 | OG | SER | A | 78 | 18.806 | 42.351 | 30.650 | 1.00 | 23.22 | O |
| ATOM | 612 | N | GLY | A | 79 | 15.793 | 41.444 | 29.039 | 1.00 | 20.44 | N |
| ATOM | 613 | CA | GLY | A | 79 | 15.346 | 41.653 | 27.669 | 1.00 | 20.21 | C |
| ATOM | 614 | C | GLY | A | 79 | 13.831 | 41.698 | 27.595 | 1.00 | 20.09 | C |
| ATOM | 615 | O | GLY | A | 79 | 13.160 | 41.737 | 28.627 | 1.00 | 20.37 | O |
| ATOM | 616 | N | THR | A | 80 | 13.287 | 41.710 | 26.381 | 1.00 | 19.79 | N |
| ATOM | 617 | CA | THR | A | 80 | 11.837 | 41.728 | 26.191 | 1.00 | 20.31 | C |
| ATOM | 618 | C | THR | A | 80 | 11.367 | 40.356 | 25.727 | 1.00 | 19.48 | C |
| ATOM | 619 | O | THR | A | 80 | 11.904 | 39.818 | 24.781 | 1.00 | 20.27 | O |
| ATOM | 620 | CB | THR | A | 80 | 11.436 | 42.804 | 25.173 | 1.00 | 20.39 | C |
| ATOM | 621 | OG1 | THR | A | 80 | 11.688 | 44.111 | 25.721 | 1.00 | 23.13 | O |
| ATOM | 622 | CG2 | THR | A | 80 | 9.906 | 42.787 | 24.943 | 1.00 | 22.27 | C |
| ATOM | 623 | N | TYR | A | 81 | 10.379 | 39.809 | 26.415 | 1.00 | 19.45 | N |
| ATOM | 624 | CA | TYR | A | 81 | 9.814 | 38.487 | 26.146 | 1.00 | 18.67 | C |
| ATOM | 625 | C | TYR | A | 81 | 8.393 | 38.662 | 25.599 | 1.00 | 19.26 | C |
| ATOM | 626 | O | TYR | A | 81 | 7.633 | 39.512 | 26.075 | 1.00 | 18.23 | O |
| ATOM | 627 | CB | TYR | A | 81 | 9.761 | 37.660 | 27.429 | 1.00 | 18.65 | C |
| ATOM | 628 | CG | TYR | A | 81 | 11.112 | 37.287 | 27.977 | 1.00 | 15.74 | C |
| ATOM | 629 | CD1 | TYR | A | 81 | 11.549 | 35.980 | 27.944 | 1.00 | 18.49 | C |
| ATOM | 630 | CD2 | TYR | A | 81 | 11.952 | 38.238 | 28.529 | 1.00 | 17.22 | C |
| ATOM | 631 | CE1 | TYR | A | 81 | 12.817 | 35.616 | 28.425 | 1.00 | 18.28 | C |
| ATOM | 632 | CE2 | TYR | A | 81 | 13.225 | 37.889 | 29.020 | 1.00 | 16.72 | C |
| ATOM | 633 | CZ | TYR | A | 81 | 13.644 | 36.577 | 28.963 | 1.00 | 17.27 | C |
| ATOM | 634 | OH | TYR | A | 81 | 14.878 | 36.206 | 29.433 | 1.00 | 15.49 | O |
| ATOM | 635 | N | LYS | A | 82 | 8.051 | 37.877 | 24.586 | 1.00 | 19.68 | N |
| ATOM | 636 | CA | LYS | A | 82 | 6.726 | 37.899 | 23.982 | 1.00 | 19.85 | C |
| ATOM | 637 | C | LYS | A | 82 | 6.238 | 36.470 | 23.773 | 1.00 | 19.88 | C |
| ATOM | 638 | O | LYS | A | 82 | 7.005 | 35.613 | 23.348 | 1.00 | 20.39 | O |
| ATOM | 639 | CB | LYS | A | 82 | 6.802 | 38.639 | 22.652 | 1.00 | 20.14 | C |
| ATOM | 640 | CG | LYS | A | 82 | 6.918 | 40.185 | 22.820 | 1.00 | 21.90 | C |
| ATOM | 641 | CD | LYS | A | 82 | 6.840 | 40.903 | 21.446 | 1.00 | 23.26 | C |
| ATOM | 642 | CE | LYS | A | 82 | 6.806 | 42.409 | 21.625 | 1.00 | 24.18 | C |
| ATOM | 643 | NZ | LYS | A | 82 | 6.979 | 43.197 | 20.363 | 1.00 | 24.03 | N |
| ATOM | 644 | N | CYS | A | 83 | 4.966 | 36.214 | 24.064 | 1.00 | 19.38 | N |
| ATOM | 645 | CA | CYS | A | 83 | 4.326 | 34.925 | 23.758 | 1.00 | 19.54 | C |
| ATOM | 646 | C | CYS | A | 83 | 3.495 | 35.063 | 22.498 | 1.00 | 19.13 | C |
| ATOM | 647 | O | CYS | A | 83 | 3.115 | 36.166 | 22.140 | 1.00 | 20.12 | O |
| ATOM | 648 | CB | CYS | A | 83 | 3.383 | 34.516 | 24.881 | 1.00 | 18.81 | C |
| ATOM | 649 | SG | CYS | A | 83 | 2.064 | 35.745 | 25.124 | 1.00 | 19.61 | S |
| ATOM | 650 | N | GLN | A | 84 | 3.155 | 33.940 | 21.873 | 1.00 | 19.01 | N |
| ATOM | 651 | CA | GLN | A | 84 | 2.386 | 33.949 | 20.620 | 1.00 | 18.39 | C |
| ATOM | 652 | C | GLN | A | 84 | 1.471 | 32.748 | 20.533 | 1.00 | 17.66 | C |
| ATOM | 653 | O | GLN | A | 84 | 1.878 | 31.646 | 20.855 | 1.00 | 17.08 | O |
| ATOM | 654 | CB | GLN | A | 84 | 3.302 | 33.945 | 19.400 | 1.00 | 18.68 | C |
| ATOM | 655 | CG | GLN | A | 84 | 2.520 | 34.082 | 18.069 | 1.00 | 20.36 | C |
| ATOM | 656 | CD | GLN | A | 84 | 3.286 | 34.805 | 16.985 | 1.00 | 22.07 | C |
| ATOM | 657 | OE1 | GLN | A | 84 | 2.702 | 35.549 | 16.177 | 1.00 | 25.82 | O |
| ATOM | 658 | NE2 | GLN | A | 84 | 4.580 | 34.620 | 16.970 | 1.00 | 22.45 | N |
| ATOM | 659 | N | ALA | A | 85 | 0.227 | 32.986 | 20.120 | 1.00 | 17.06 | N |
| ATOM | 660 | CA | ALA | A | 85 | −0.752 | 31.946 | 19.883 | 1.00 | 17.04 | C |
| ATOM | 661 | C | ALA | A | 85 | −0.578 | 31.510 | 18.439 | 1.00 | 17.40 | C |
| ATOM | 662 | O | ALA | A | 85 | −0.174 | 32.300 | 17.593 | 1.00 | 17.89 | O |
| ATOM | 663 | CB | ALA | A | 85 | −2.189 | 32.477 | 20.111 | 1.00 | 16.15 | C |
| ATOM | 664 | N | PHE | A | 86 | −0.882 | 30.249 | 18.186 | 1.00 | 17.84 | N |
| ATOM | 665 | CA | PHE | A | 86 | −0.926 | 29.674 | 16.839 | 1.00 | 18.83 | C |
| ATOM | 666 | C | PHE | A | 86 | −2.239 | 28.934 | 16.677 | 1.00 | 18.76 | C |
| ATOM | 667 | O | PHE | A | 86 | −2.756 | 28.351 | 17.623 | 1.00 | 19.07 | O |
| ATOM | 668 | CB | PHE | A | 86 | 0.206 | 28.670 | 16.608 | 1.00 | 19.07 | C |
| ATOM | 669 | CG | PHE | A | 86 | 1.557 | 29.293 | 16.556 | 1.00 | 20.07 | C |
| ATOM | 670 | CD1 | PHE | A | 86 | 2.196 | 29.652 | 17.710 | 1.00 | 21.17 | C |
| ATOM | 671 | CD2 | PHE | A | 86 | 2.192 | 29.507 | 15.341 | 1.00 | 22.69 | C |
| ATOM | 672 | CE1 | PHE | A | 86 | 3.454 | 30.230 | 17.671 | 1.00 | 24.31 | C |
| ATOM | 673 | CE2 | PHE | A | 86 | 3.446 | 30.106 | 15.289 | 1.00 | 24.05 | C |
| ATOM | 674 | CZ | PHE | A | 86 | 4.086 | 30.451 | 16.456 | 1.00 | 23.58 | C |
| ATOM | 675 | N | TYR | A | 87 | −2.747 | 28.949 | 15.455 | 1.00 | 19.72 | N |
| ATOM | 676 | CA | TYR | A | 87 | −4.017 | 28.334 | 15.122 | 1.00 | 19.98 | C |
| ATOM | 677 | C | TYR | A | 87 | −3.833 | 27.437 | 13.920 | 1.00 | 20.47 | C |
| ATOM | 678 | O | TYR | A | 87 | −2.759 | 27.389 | 13.340 | 1.00 | 20.29 | O |
| ATOM | 679 | CB | TYR | A | 87 | −5.023 | 29.428 | 14.726 | 1.00 | 19.55 | C |
| ATOM | 680 | CG | TYR | A | 87 | −5.267 | 30.538 | 15.730 | 1.00 | 18.80 | C |
| ATOM | 681 | CD1 | TYR | A | 87 | −5.009 | 31.865 | 15.394 | 1.00 | 17.12 | C |
| ATOM | 682 | CD2 | TYR | A | 87 | −5.834 | 30.275 | 16.967 | 1.00 | 19.29 | C |
| ATOM | 683 | CE1 | TYR | A | 87 | −5.264 | 32.881 | 16.260 | 1.00 | 18.87 | C |
| ATOM | 684 | CE2 | TYR | A | 87 | −6.096 | 31.298 | 17.859 | 1.00 | 19.95 | C |

APPENDIX I(b)-continued

| ATOM | 685 | CZ | TYR | A | 87 | −5.817 | 32.608 | 17.489 | 1.00 | 19.14 | C |
|---|---|---|---|---|---|---|---|---|---|---|---|
| ATOM | 686 | OH | TYR | A | 87 | −6.068 | 33.645 | 18.340 | 1.00 | 20.15 | O |
| ATOM | 687 | N | SER | A | 88 | −4.898 | 26.764 | 13.512 | 1.00 | 21.28 | N |
| ATOM | 688 | CA | SER | A | 88 | −4.836 | 25.962 | 12.295 | 1.00 | 23.13 | C |
| ATOM | 689 | C | SER | A | 88 | −6.079 | 26.121 | 11.419 | 1.00 | 23.96 | C |
| ATOM | 690 | O | SER | A | 88 | −7.179 | 26.346 | 11.918 | 1.00 | 23.81 | O |
| ATOM | 691 | CB | SER | A | 88 | −4.625 | 24.475 | 12.629 | 1.00 | 22.85 | C |
| ATOM | 692 | OG | SER | A | 88 | −5.821 | 23.903 | 13.115 | 1.00 | 22.43 | O |
| ATOM | 693 | N | LEU | A | 89 | −5.880 | 26.008 | 10.110 | 1.00 | 25.98 | N |
| ATOM | 694 | CA | LEU | A | 89 | −6.990 | 25.886 | 9.165 | 1.00 | 27.25 | C |
| ATOM | 695 | C | LEU | A | 89 | −7.002 | 24.483 | 8.576 | 1.00 | 28.06 | C |
| ATOM | 696 | O | LEU | A | 89 | −5.951 | 23.950 | 8.222 | 1.00 | 27.98 | O |
| ATOM | 697 | CB | LEU | A | 89 | −6.866 | 26.932 | 8.058 | 1.00 | 27.52 | C |
| ATOM | 698 | CG | LEU | A | 89 | −7.803 | 28.155 | 8.114 | 1.00 | 29.73 | C |
| ATOM | 699 | CD1 | LEU | A | 89 | −8.235 | 28.564 | 9.533 | 1.00 | 30.33 | C |
| ATOM | 700 | CD2 | LEU | A | 89 | −7.145 | 29.358 | 7.411 | 1.00 | 31.16 | C |
| ATOM | 701 | N | PRO | A | 90 | −8.187 | 23.883 | 8.443 | 1.00 | 29.63 | N |
| ATOM | 702 | CA | PRO | A | 90 | −8.283 | 22.530 | 7.881 | 1.00 | 30.44 | C |
| ATOM | 703 | C | PRO | A | 90 | −7.902 | 22.525 | 6.417 | 1.00 | 31.06 | C |
| ATOM | 704 | O | PRO | A | 90 | −7.949 | 23.559 | 5.752 | 1.00 | 31.55 | O |
| ATOM | 705 | CB | PRO | A | 90 | −9.768 | 22.177 | 8.033 | 1.00 | 30.50 | C |
| ATOM | 706 | CG | PRO | A | 90 | −10.464 | 23.490 | 8.063 | 1.00 | 30.55 | C |
| ATOM | 707 | CD | PRO | A | 90 | −9.519 | 24.431 | 8.766 | 1.00 | 29.62 | C |
| ATOM | 708 | N | LEU | A | 91 | −7.497 | 21.360 | 5.944 | 1.00 | 31.85 | N |
| ATOM | 709 | CA | LEU | A | 91 | −7.196 | 21.143 | 4.538 | 1.00 | 32.49 | C |
| ATOM | 710 | C | LEU | A | 91 | −7.932 | 19.896 | 4.069 | 1.00 | 32.76 | C |
| ATOM | 711 | O | LEU | A | 91 | −8.475 | 19.142 | 4.882 | 1.00 | 32.71 | O |
| ATOM | 712 | CB | LEU | A | 91 | −5.689 | 20.983 | 4.341 | 1.00 | 32.58 | C |
| ATOM | 713 | CG | LEU | A | 91 | −4.854 | 22.143 | 4.890 | 1.00 | 32.68 | C |
| ATOM | 714 | CD1 | LEU | A | 91 | −3.396 | 21.736 | 5.042 | 1.00 | 32.35 | C |
| ATOM | 715 | CD2 | LEU | A | 91 | −5.001 | 23.362 | 3.984 | 1.00 | 33.25 | C |
| ATOM | 716 | N | GLY | A | 92 | −7.967 | 19.694 | 2.756 | 1.00 | 33.35 | N |
| ATOM | 717 | CA | GLY | A | 92 | −8.603 | 18.519 | 2.186 | 1.00 | 33.87 | C |
| ATOM | 718 | C | GLY | A | 92 | −7.625 | 17.370 | 2.018 | 1.00 | 34.24 | C |
| ATOM | 719 | O | GLY | A | 92 | −7.469 | 16.853 | 0.909 | 1.00 | 34.70 | O |
| ATOM | 720 | N | ASP | A | 93 | −6.982 | 16.962 | 3.114 | 1.00 | 34.68 | N |
| ATOM | 721 | CA | ASP | A | 93 | −5.910 | 15.961 | 3.084 | 1.00 | 34.86 | C |
| ATOM | 722 | C | ASP | A | 93 | −5.524 | 15.542 | 4.505 | 1.00 | 34.75 | C |
| ATOM | 723 | O | ASP | A | 93 | −5.313 | 16.404 | 5.367 | 1.00 | 34.57 | O |
| ATOM | 724 | CB | ASP | A | 93 | −4.674 | 16.526 | 2.365 | 1.00 | 35.11 | C |
| ATOM | 725 | CG | ASP | A | 93 | −3.673 | 15.447 | 1.968 | 1.00 | 35.84 | C |
| ATOM | 726 | OD1 | ASP | A | 93 | −2.481 | 15.594 | 2.311 | 1.00 | 37.57 | O |
| ATOM | 727 | OD2 | ASP | A | 93 | −3.972 | 14.429 | 1.305 | 1.00 | 36.48 | O |
| ATOM | 728 | N | TYR | A | 94 | −5.444 | 14.227 | 4.736 | 1.00 | 34.54 | N |
| ATOM | 729 | CA | TYR | A | 94 | −4.999 | 13.649 | 6.018 | 1.00 | 34.59 | C |
| ATOM | 730 | C | TYR | A | 94 | −5.877 | 14.239 | 7.177 | 1.00 | 34.53 | C |
| ATOM | 731 | O | TYR | A | 94 | −7.063 | 14.418 | 6.898 | 1.00 | 34.76 | O |
| ATOM | 732 | CB | TYR | A | 94 | −3.469 | 13.756 | 6.099 | 1.00 | 34.48 | C |
| ATOM | 733 | CG | TYR | A | 94 | −2.755 | 12.615 | 5.379 | 1.00 | 35.44 | C |
| ATOM | 734 | CD1 | TYR | A | 94 | −2.816 | 12.498 | 3.990 | 1.00 | 35.43 | C |
| ATOM | 735 | CD2 | TYR | A | 94 | −2.027 | 11.650 | 6.084 | 1.00 | 35.46 | C |
| ATOM | 736 | CE1 | TYR | A | 94 | −2.168 | 11.471 | 3.326 | 1.00 | 35.92 | C |
| ATOM | 737 | CE2 | TYR | A | 94 | −1.372 | 10.614 | 5.424 | 1.00 | 35.24 | C |
| ATOM | 738 | CZ | TYR | A | 94 | −1.447 | 10.526 | 4.044 | 1.00 | 36.16 | C |
| ATOM | 739 | OH | TYR | A | 94 | −0.812 | 9.494 | 3.371 | 1.00 | 35.86 | O |
| ATOM | 740 | N | ASN | A | 95 | −5.475 | 14.527 | 8.433 | 1.00 | 34.45 | N |
| ATOM | 741 | CA | ASN | A | 95 | −4.201 | 14.291 | 9.157 | 1.00 | 34.25 | C |
| ATOM | 742 | C | ASN | A | 95 | −3.022 | 15.236 | 8.862 | 1.00 | 33.88 | C |
| ATOM | 743 | O | ASN | A | 95 | −2.011 | 15.209 | 9.573 | 1.00 | 33.88 | O |
| ATOM | 744 | CB | ASN | A | 95 | −3.787 | 12.810 | 9.182 | 1.00 | 34.55 | C |
| ATOM | 745 | CG | ASN | A | 95 | −4.911 | 11.887 | 9.652 | 1.00 | 35.37 | C |
| ATOM | 746 | OD1 | ASN | A | 95 | −5.961 | 12.340 | 10.123 | 1.00 | 36.86 | O |
| ATOM | 747 | ND2 | ASN | A | 95 | −4.684 | 10.586 | 9.535 | 1.00 | 34.95 | N |
| ATOM | 748 | N | TYR | A | 96 | −3.181 | 16.096 | 7.854 | 1.00 | 33.16 | N |
| ATOM | 749 | CA | TYR | A | 96 | −2.272 | 17.219 | 7.616 | 1.00 | 32.52 | C |
| ATOM | 750 | C | TYR | A | 96 | −3.106 | 18.492 | 7.595 | 1.00 | 31.59 | C |
| ATOM | 751 | O | TYR | A | 96 | −3.950 | 18.681 | 6.719 | 1.00 | 31.58 | O |
| ATOM | 752 | CB | TYR | A | 96 | −1.505 | 17.067 | 6.293 | 1.00 | 32.50 | C |
| ATOM | 753 | CG | TYR | A | 96 | −0.684 | 15.793 | 6.168 | 1.00 | 32.98 | C |
| ATOM | 754 | CD1 | TYR | A | 96 | −0.589 | 15.124 | 4.953 | 1.00 | 32.82 | C |
| ATOM | 755 | CD2 | TYR | A | 96 | 0.004 | 15.261 | 7.257 | 1.00 | 33.53 | C |
| ATOM | 756 | CE1 | TYR | A | 96 | 0.163 | 13.958 | 4.829 | 1.00 | 33.77 | C |
| ATOM | 757 | CE2 | TYR | A | 96 | 0.754 | 14.078 | 7.145 | 1.00 | 33.88 | C |
| ATOM | 758 | CZ | TYR | A | 96 | 0.833 | 13.438 | 5.928 | 1.00 | 34.01 | C |
| ATOM | 759 | OH | TYR | A | 96 | 1.573 | 12.273 | 5.796 | 1.00 | 36.25 | O |
| ATOM | 760 | N | SER | A | 97 | −2.880 | 19.346 | 8.581 | 1.00 | 30.72 | N |
| ATOM | 761 | CA | SER | A | 97 | −3.553 | 20.627 | 8.672 | 1.00 | 30.02 | C |
| ATOM | 762 | C | SER | A | 97 | −2.541 | 21.733 | 8.385 | 1.00 | 29.28 | C |
| ATOM | 763 | O | SER | A | 97 | −1.330 | 21.466 | 8.090 | 1.00 | 29.12 | O |
| ATOM | 764 | CB | SER | A | 97 | −4.171 | 20.793 | 10.073 | 1.00 | 30.20 | C |

APPENDIX I(b)-continued

| ATOM | 765 | OG | SER | A | 97 | −5.560 | 21.058 | 9.980 | 1.00 | 30.59 | O |
|---|---|---|---|---|---|---|---|---|---|---|---|
| ATOM | 766 | N | LEU | A | 98 | −3.053 | 22.970 | 8.500 | 1.00 | 28.61 | N |
| ATOM | 767 | CA | LEU | A | 98 | −2.294 | 24.187 | 8.237 | 1.00 | 28.32 | C |
| ATOM | 768 | C | LEU | A | 98 | −2.146 | 25.042 | 9.499 | 1.00 | 27.54 | C |
| ATOM | 769 | O | LEU | A | 98 | −3.081 | 25.719 | 9.893 | 1.00 | 27.36 | O |
| ATOM | 770 | CB | LEU | A | 98 | −3.022 | 24.990 | 7.154 | 1.00 | 28.70 | C |
| ATOM | 771 | CG | LEU | A | 98 | −2.230 | 26.112 | 6.484 | 1.00 | 29.45 | C |
| ATOM | 772 | CD1 | LEU | A | 98 | −2.319 | 25.982 | 4.986 | 1.00 | 30.13 | C |
| ATOM | 773 | CD2 | LEU | A | 98 | −2.737 | 27.483 | 6.936 | 1.00 | 30.42 | C |
| ATOM | 774 | N | LEU | A | 99 | −0.966 | 24.999 | 10.113 | 1.00 | 27.09 | N |
| ATOM | 775 | CA | LEU | A | 99 | −0.634 | 25.803 | 11.291 | 1.00 | 26.86 | C |
| ATOM | 776 | C | LEU | A | 99 | −0.334 | 27.232 | 10.848 | 1.00 | 26.50 | C |
| ATOM | 777 | O | LEU | A | 99 | 0.386 | 27.430 | 9.882 | 1.00 | 26.79 | O |
| ATOM | 778 | CB | LEU | A | 99 | 0.620 | 25.241 | 11.987 | 1.00 | 27.12 | C |
| ATOM | 779 | CG | LEU | A | 99 | 0.716 | 24.913 | 13.491 | 1.00 | 27.84 | C |
| ATOM | 780 | CD1 | LEU | A | 99 | 2.068 | 25.380 | 14.026 | 1.00 | 28.72 | C |
| ATOM | 781 | CD2 | LEU | A | 99 | −0.407 | 25.463 | 14.359 | 1.00 | 27.90 | C |
| ATOM | 782 | N | PHE | A | 100 | −0.873 | 28.225 | 11.539 | 1.00 | 25.62 | N |
| ATOM | 783 | CA | PHE | A | 100 | −0.539 | 29.617 | 11.225 | 1.00 | 25.27 | C |
| ATOM | 784 | C | PHE | A | 100 | −0.417 | 30.504 | 12.463 | 1.00 | 24.37 | C |
| ATOM | 785 | O | PHE | A | 100 | −1.028 | 30.246 | 13.492 | 1.00 | 23.75 | O |
| ATOM | 786 | CB | PHE | A | 100 | −1.508 | 30.206 | 10.188 | 1.00 | 25.37 | C |
| ATOM | 787 | CG | PHE | A | 100 | −2.881 | 30.528 | 10.719 | 1.00 | 25.83 | C |
| ATOM | 788 | CD1 | PHE | A | 100 | −3.156 | 31.790 | 11.251 | 1.00 | 25.42 | C |
| ATOM | 789 | CD2 | PHE | A | 100 | −3.911 | 29.597 | 10.632 | 1.00 | 25.10 | C |
| ATOM | 790 | CE1 | PHE | A | 100 | −4.427 | 32.096 | 11.733 | 1.00 | 25.81 | C |
| ATOM | 791 | CE2 | PHE | A | 100 | −5.193 | 29.899 | 11.100 | 1.00 | 25.01 | C |
| ATOM | 792 | CZ | PHE | A | 100 | −5.458 | 31.150 | 11.643 | 1.00 | 25.23 | C |
| ATOM | 793 | N | ARG | A | 101 | 0.432 | 31.518 | 12.337 | 1.00 | 24.07 | N |
| ATOM | 794 | CA | ARG | A | 101 | 0.744 | 32.458 | 13.403 | 1.00 | 24.11 | C |
| ATOM | 795 | C | ARG | A | 101 | −0.453 | 33.293 | 13.822 | 1.00 | 22.64 | C |
| ATOM | 796 | O | ARG | A | 101 | −1.103 | 33.900 | 12.999 | 1.00 | 21.90 | O |
| ATOM | 797 | CB | ARG | A | 101 | 1.836 | 33.417 | 12.943 | 1.00 | 25.10 | C |
| ATOM | 798 | CG | ARG | A | 101 | 3.199 | 33.076 | 13.483 | 1.00 | 28.74 | C |
| ATOM | 799 | CD | ARG | A | 101 | 4.328 | 33.811 | 12.806 | 1.00 | 31.82 | C |
| ATOM | 800 | NE | ARG | A | 101 | 5.487 | 32.933 | 12.696 | 1.00 | 36.92 | N |
| ATOM | 801 | CZ | ARG | A | 101 | 6.334 | 32.670 | 13.693 | 1.00 | 40.20 | C |
| ATOM | 802 | NH1 | ARG | A | 101 | 7.359 | 31.849 | 13.489 | 1.00 | 42.57 | N |
| ATOM | 803 | NH2 | ARG | A | 101 | 6.172 | 33.215 | 14.891 | 1.00 | 40.80 | N |
| ATOM | 804 | N | GLY | A | 102 | −0.713 | 33.331 | 15.121 | 1.00 | 21.51 | N |
| ATOM | 805 | CA | GLY | A | 102 | −1.791 | 34.111 | 15.670 | 1.00 | 20.54 | C |
| ATOM | 806 | C | GLY | A | 102 | −1.254 | 35.330 | 16.398 | 1.00 | 20.64 | C |
| ATOM | 807 | O | GLY | A | 102 | −0.148 | 35.845 | 16.108 | 1.00 | 20.15 | O |
| ATOM | 808 | N | GLU | A | 103 | −2.040 | 35.777 | 17.366 | 1.00 | 20.11 | N |
| ATOM | 809 | CA | GLU | A | 103 | −1.764 | 37.023 | 18.082 | 1.00 | 20.21 | C |
| ATOM | 810 | C | GLU | A | 103 | −0.595 | 36.863 | 19.039 | 1.00 | 19.74 | C |
| ATOM | 811 | O | GLU | A | 103 | −0.319 | 35.778 | 19.539 | 1.00 | 19.27 | O |
| ATOM | 812 | CB | GLU | A | 103 | −3.005 | 37.520 | 18.834 | 1.00 | 20.37 | C |
| ATOM | 813 | CG | GLU | A | 103 | −4.122 | 38.017 | 17.910 | 1.00 | 19.56 | C |
| ATOM | 814 | CD | GLU | A | 103 | −4.997 | 36.877 | 17.407 | 1.00 | 20.62 | C |
| ATOM | 815 | OE1 | GLU | A | 103 | −5.788 | 37.120 | 16.497 | 1.00 | 18.31 | O |
| ATOM | 816 | OE2 | GLU | A | 103 | −4.887 | 35.735 | 17.938 | 1.00 | 19.67 | O |
| ATOM | 817 | N | LYS | A | 104 | 0.105 | 37.962 | 19.236 | 1.00 | 19.97 | N |
| ATOM | 818 | CA | LYS | A | 104 | 1.308 | 38.022 | 20.041 | 1.00 | 21.39 | C |
| ATOM | 819 | C | LYS | A | 104 | 1.005 | 38.882 | 21.252 | 1.00 | 21.45 | C |
| ATOM | 820 | O | LYS | A | 104 | 0.296 | 39.882 | 21.145 | 1.00 | 21.44 | O |
| ATOM | 821 | CB | LYS | A | 104 | 2.446 | 38.656 | 19.216 | 1.00 | 22.22 | C |
| ATOM | 822 | CG | LYS | A | 104 | 3.791 | 37.935 | 19.294 | 1.00 | 23.77 | C |
| ATOM | 823 | CD | LYS | A | 104 | 4.795 | 38.501 | 18.284 | 1.00 | 25.29 | C |
| ATOM | 824 | CE | LYS | A | 104 | 6.247 | 38.271 | 18.753 | 1.00 | 25.29 | C |
| ATOM | 825 | NZ | LYS | A | 104 | 7.244 | 38.247 | 17.638 | 1.00 | 24.86 | N |
| ATOM | 826 | N | GLY | A | 105 | 1.549 | 38.506 | 22.406 | 1.00 | 21.96 | N |
| ATOM | 827 | CA | GLY | A | 105 | 1.483 | 39.357 | 23.578 | 1.00 | 21.61 | C |
| ATOM | 828 | C | GLY | A | 105 | 2.263 | 40.654 | 23.371 | 1.00 | 21.52 | C |
| ATOM | 829 | O | GLY | A | 105 | 3.169 | 40.740 | 22.540 | 1.00 | 20.89 | O |
| ATOM | 830 | N | ALA | A | 106 | 1.939 | 41.650 | 24.176 | 1.00 | 21.15 | N |
| ATOM | 831 | CA | ALA | A | 106 | 2.552 | 42.977 | 24.030 | 1.00 | 21.77 | C |
| ATOM | 832 | C | ALA | A | 106 | 3.948 | 43.018 | 24.648 | 1.00 | 21.64 | C |
| ATOM | 833 | O | ALA | A | 106 | 4.659 | 43.974 | 24.461 | 1.00 | 22.09 | O |
| ATOM | 834 | CB | ALA | A | 106 | 1.664 | 44.046 | 24.659 | 1.00 | 21.61 | C |
| ATOM | 835 | N | GLY | A | 107 | 4.325 | 41.984 | 25.395 | 1.00 | 21.27 | N |
| ATOM | 836 | CA | GLY | A | 107 | 5.678 | 41.876 | 25.896 | 1.00 | 20.82 | C |
| ATOM | 837 | C | GLY | A | 107 | 5.816 | 42.112 | 27.392 | 1.00 | 20.64 | C |
| ATOM | 838 | O | GLY | A | 107 | 4.971 | 42.748 | 28.029 | 1.00 | 20.50 | O |
| ATOM | 839 | N | THR | A | 108 | 6.896 | 41.549 | 27.927 | 1.00 | 19.91 | N |
| ATOM | 840 | CA | THR | A | 108 | 7.362 | 41.715 | 29.291 | 1.00 | 19.05 | C |
| ATOM | 841 | C | THR | A | 108 | 8.815 | 42.207 | 29.235 | 1.00 | 18.80 | C |
| ATOM | 842 | O | THR | A | 108 | 9.673 | 41.495 | 28.703 | 1.00 | 18.74 | O |
| ATOM | 843 | CB | THR | A | 108 | 7.367 | 40.355 | 30.019 | 1.00 | 18.67 | C |
| ATOM | 844 | OG1 | THR | A | 108 | 6.026 | 39.840 | 30.183 | 1.00 | 19.42 | O |

APPENDIX I(b)-continued

| | | | | | | | | | | | |
|---|---|---|---|---|---|---|---|---|---|---|---|
| ATOM | 845 | CG2 | THR | A | 108 | 7.954 | 40.510 | 31.435 | 1.00 | 18.69 | C |
| ATOM | 846 | N | ALA | A | 109 | 9.096 | 43.390 | 29.783 | 1.00 | 18.07 | N |
| ATOM | 847 | CA | ALA | A | 109 | 10.460 | 43.927 | 29.825 | 1.00 | 17.50 | C |
| ATOM | 848 | C | ALA | A | 109 | 11.078 | 43.528 | 31.144 | 1.00 | 17.58 | C |
| ATOM | 849 | O | ALA | A | 109 | 10.755 | 44.091 | 32.198 | 1.00 | 17.14 | O |
| ATOM | 850 | CB | ALA | A | 109 | 10.461 | 45.464 | 29.673 | 1.00 | 17.07 | C |
| ATOM | 851 | N | LEU | A | 110 | 11.951 | 42.536 | 31.080 | 1.00 | 17.82 | N |
| ATOM | 852 | CA | LEU | A | 110 | 12.601 | 42.003 | 32.265 | 1.00 | 17.96 | C |
| ATOM | 853 | C | LEU | A | 110 | 13.973 | 42.624 | 32.467 | 1.00 | 18.14 | C |
| ATOM | 854 | O | LEU | A | 110 | 14.762 | 42.710 | 31.550 | 1.00 | 17.77 | O |
| ATOM | 855 | CB | LEU | A | 110 | 12.714 | 40.481 | 32.146 | 1.00 | 17.52 | C |
| ATOM | 856 | CG | LEU | A | 110 | 13.640 | 39.772 | 33.158 | 1.00 | 17.20 | C |
| ATOM | 857 | CD1 | LEU | A | 110 | 13.102 | 39.836 | 34.603 | 1.00 | 16.63 | C |
| ATOM | 858 | CD2 | LEU | A | 110 | 13.878 | 38.331 | 32.704 | 1.00 | 16.47 | C |
| ATOM | 859 | N | THR | A | 111 | 14.245 | 43.003 | 33.709 | 1.00 | 18.82 | N |
| ATOM | 860 | CA | THR | A | 111 | 15.523 | 43.520 | 34.138 | 1.00 | 19.38 | C |
| ATOM | 861 | C | THR | A | 111 | 16.042 | 42.609 | 35.241 | 1.00 | 19.63 | C |
| ATOM | 862 | O | THR | A | 111 | 15.412 | 42.494 | 36.289 | 1.00 | 19.13 | O |
| ATOM | 863 | CB | THR | A | 111 | 15.319 | 44.941 | 34.690 | 1.00 | 19.40 | C |
| ATOM | 864 | OG1 | THR | A | 111 | 15.061 | 45.835 | 33.604 | 1.00 | 19.72 | O |
| ATOM | 865 | CG2 | THR | A | 111 | 16.575 | 45.478 | 35.381 | 1.00 | 19.59 | C |
| ATOM | 866 | N | VAL | A | 112 | 17.194 | 41.977 | 35.006 | 1.00 | 20.01 | N |
| ATOM | 867 | CA | VAL | A | 112 | 17.834 | 41.153 | 36.012 | 1.00 | 20.08 | C |
| ATOM | 868 | C | VAL | A | 112 | 19.158 | 41.763 | 36.479 | 1.00 | 21.01 | C |
| ATOM | 869 | O | VAL | A | 112 | 20.018 | 42.101 | 35.663 | 1.00 | 20.26 | O |
| ATOM | 870 | CB | VAL | A | 112 | 18.107 | 39.732 | 35.497 | 1.00 | 20.00 | C |
| ATOM | 871 | CG1 | VAL | A | 112 | 18.756 | 38.892 | 36.586 | 1.00 | 19.88 | C |
| ATOM | 872 | CG2 | VAL | A | 112 | 16.812 | 39.060 | 34.991 | 1.00 | 20.28 | C |
| ATOM | 873 | N | LYS | A | 113 | 19.268 | 41.953 | 37.792 | 1.00 | 21.94 | N |
| ATOM | 874 | CA | LYS | A | 113 | 20.551 | 41.895 | 38.508 | 1.00 | 23.25 | C |
| ATOM | 875 | C | LYS | A | 113 | 20.351 | 41.882 | 40.024 | 1.00 | 23.33 | C |
| ATOM | 876 | O | LYS | A | 113 | 20.719 | 40.909 | 40.703 | 1.00 | 23.34 | O |
| ATOM | 877 | CB | LYS | A | 113 | 21.503 | 43.027 | 38.130 | 1.00 | 23.42 | C |
| ATOM | 878 | CG | LYS | A | 113 | 22.819 | 43.037 | 38.937 | 1.00 | 25.55 | C |
| ATOM | 879 | CD | LYS | A | 113 | 23.597 | 41.700 | 38.876 | 1.00 | 27.66 | C |
| ATOM | 880 | CE | LYS | A | 113 | 24.257 | 41.325 | 40.233 | 1.00 | 27.87 | C |
| ATOM | 881 | NZ | LYS | A | 113 | 23.252 | 40.985 | 41.318 | 1.00 | 27.98 | N |
| TER | 882 | | LYS | A | 113 | | | | | | |
| ATOM | 883 | N | ALA | B | 1 | −5.294 | 52.838 | 33.861 | 1.00 | 15.59 | N |
| ATOM | 884 | CA | ALA | B | 1 | −6.196 | 51.900 | 34.558 | 1.00 | 14.51 | C |
| ATOM | 885 | C | ALA | B | 1 | −7.435 | 51.573 | 33.721 | 1.00 | 14.54 | C |
| ATOM | 886 | O | ALA | B | 1 | −8.023 | 52.453 | 33.056 | 1.00 | 13.96 | O |
| ATOM | 887 | CB | ALA | B | 1 | −6.596 | 52.455 | 35.882 | 1.00 | 15.29 | C |
| ATOM | 888 | N | TRP | B | 2 | −7.792 | 50.292 | 33.747 | 1.00 | 13.89 | N |
| ATOM | 889 | CA | TRP | B | 2 | −8.997 | 49.798 | 33.142 | 1.00 | 14.26 | C |
| ATOM | 890 | C | TRP | B | 2 | −9.652 | 48.680 | 33.968 | 1.00 | 15.11 | C |
| ATOM | 891 | O | TRP | B | 2 | −9.016 | 48.015 | 34.809 | 1.00 | 16.01 | O |
| ATOM | 892 | CB | TRP | B | 2 | −8.729 | 49.330 | 31.723 | 1.00 | 14.66 | C |
| ATOM | 893 | CG | TRP | B | 2 | −7.843 | 48.087 | 31.565 | 1.00 | 14.26 | C |
| ATOM | 894 | CD1 | TRP | B | 2 | −6.506 | 47.993 | 31.797 | 1.00 | 14.52 | C |
| ATOM | 895 | CD2 | TRP | B | 2 | −8.254 | 46.803 | 31.086 | 1.00 | 13.13 | C |
| ATOM | 896 | NE1 | TRP | B | 2 | −6.056 | 46.727 | 31.499 | 1.00 | 15.51 | N |
| ATOM | 897 | CE2 | TRP | B | 2 | −7.106 | 45.978 | 31.045 | 1.00 | 13.67 | C |
| ATOM | 898 | CE3 | TRP | B | 2 | −9.473 | 46.271 | 30.660 | 1.00 | 12.74 | C |
| ATOM | 899 | CZ2 | TRP | B | 2 | −7.144 | 44.653 | 30.609 | 1.00 | 14.07 | C |
| ATOM | 900 | CZ3 | TRP | B | 2 | −9.515 | 44.948 | 30.232 | 1.00 | 14.11 | C |
| ATOM | 901 | CH2 | TRP | B | 2 | −8.361 | 44.152 | 30.218 | 1.00 | 14.28 | C |
| ATOM | 902 | N | VAL | B | 3 | −10.946 | 48.523 | 33.743 | 1.00 | 14.74 | N |
| ATOM | 903 | CA | VAL | B | 3 | −11.725 | 47.514 | 34.399 | 1.00 | 14.76 | C |
| ATOM | 904 | C | VAL | B | 3 | −11.983 | 46.417 | 33.410 | 1.00 | 14.88 | C |
| ATOM | 905 | O | VAL | B | 3 | −12.581 | 46.644 | 32.364 | 1.00 | 14.62 | O |
| ATOM | 906 | CB | VAL | B | 3 | −13.048 | 48.039 | 34.946 | 1.00 | 14.64 | C |
| ATOM | 907 | CG1 | VAL | B | 3 | −13.891 | 46.849 | 35.486 | 1.00 | 15.90 | C |
| ATOM | 908 | CG2 | VAL | B | 3 | −12.788 | 49.051 | 36.036 | 1.00 | 12.79 | C |
| ATOM | 909 | N | ASP | B | 4 | −11.493 | 45.224 | 33.765 | 1.00 | 14.91 | N |
| ATOM | 910 | CA | ASP | B | 4 | −11.605 | 44.027 | 32.955 | 1.00 | 15.16 | C |
| ATOM | 911 | C | ASP | B | 4 | −12.829 | 43.217 | 33.403 | 1.00 | 15.05 | C |
| ATOM | 912 | O | ASP | B | 4 | −12.789 | 42.529 | 34.422 | 1.00 | 15.65 | O |
| ATOM | 913 | CB | ASP | B | 4 | −10.314 | 43.231 | 33.119 | 1.00 | 14.69 | C |
| ATOM | 914 | CG | ASP | B | 4 | −10.240 | 42.019 | 32.220 | 1.00 | 15.63 | C |
| ATOM | 915 | OD1 | ASP | B | 4 | −11.195 | 41.730 | 31.457 | 1.00 | 13.74 | O |
| ATOM | 916 | OD2 | ASP | B | 4 | −9.226 | 41.299 | 32.226 | 1.00 | 14.48 | O |
| ATOM | 917 | N | GLN | B | 5 | −13.917 | 43.340 | 32.650 | 1.00 | 15.33 | N |
| ATOM | 918 | CA | GLN | B | 5 | −15.213 | 42.752 | 33.000 | 1.00 | 15.77 | C |
| ATOM | 919 | C | GLN | B | 5 | −15.519 | 41.512 | 32.150 | 1.00 | 15.63 | C |
| ATOM | 920 | O | GLN | B | 5 | −15.503 | 41.581 | 30.946 | 1.00 | 15.80 | O |
| ATOM | 921 | CB | GLN | B | 5 | −16.339 | 43.795 | 32.845 | 1.00 | 15.67 | C |
| ATOM | 922 | CG | GLN | B | 5 | −17.760 | 43.235 | 33.121 | 1.00 | 16.80 | C |
| ATOM | 923 | CD | GLN | B | 5 | −18.885 | 44.261 | 32.983 | 1.00 | 17.15 | C |
| ATOM | 924 | OE1 | GLN | B | 5 | −18.630 | 45.443 | 32.871 | 1.00 | 18.07 | O |

APPENDIX I(b)-continued

| ATOM | 925 | NE2 | GLN | B | 5 | −20.132 | 43.794 | 33.006 | 1.00 | 16.71 | N |
|---|---|---|---|---|---|---|---|---|---|---|---|
| ATOM | 926 | N | THR | B | 6 | −15.813 | 40.391 | 32.802 | 1.00 | 15.97 | N |
| ATOM | 927 | CA | THR | B | 6 | −16.163 | 39.147 | 32.127 | 1.00 | 15.83 | C |
| ATOM | 928 | C | THR | B | 6 | −17.374 | 38.489 | 32.805 | 1.00 | 16.25 | C |
| ATOM | 929 | O | THR | B | 6 | −17.561 | 38.649 | 34.004 | 1.00 | 15.50 | O |
| ATOM | 930 | CB | THR | B | 6 | −14.995 | 38.146 | 32.194 | 1.00 | 16.30 | C |
| ATOM | 931 | OG1 | THR | B | 6 | −14.547 | 38.023 | 33.550 | 1.00 | 15.78 | O |
| ATOM | 932 | CG2 | THR | B | 6 | −13.767 | 38.649 | 31.413 | 1.00 | 16.41 | C |
| ATOM | 933 | N | PRO | B | 7 | −18.176 | 37.721 | 32.068 | 1.00 | 16.95 | N |
| ATOM | 934 | CA | PRO | B | 7 | −18.021 | 37.519 | 30.628 | 1.00 | 17.42 | C |
| ATOM | 935 | C | PRO | B | 7 | −18.597 | 38.687 | 29.856 | 1.00 | 17.85 | C |
| ATOM | 936 | O | PRO | B | 7 | −19.411 | 39.454 | 30.375 | 1.00 | 17.30 | O |
| ATOM | 937 | CB | PRO | B | 7 | −18.861 | 36.265 | 30.365 | 1.00 | 17.52 | C |
| ATOM | 938 | CG | PRO | B | 7 | −19.937 | 36.316 | 31.380 | 1.00 | 17.28 | C |
| ATOM | 939 | CD | PRO | B | 7 | −19.324 | 36.967 | 32.593 | 1.00 | 17.21 | C |
| ATOM | 940 | N | ARG | B | 8 | −18.184 | 38.802 | 28.605 | 1.00 | 19.10 | N |
| ATOM | 941 | CA | ARG | B | 8 | −18.717 | 39.826 | 27.719 | 1.00 | 20.43 | C |
| ATOM | 942 | C | ARG | B | 8 | −20.149 | 39.521 | 27.296 | 1.00 | 19.68 | C |
| ATOM | 943 | O | ARG | B | 8 | −20.933 | 40.434 | 27.059 | 1.00 | 19.82 | O |
| ATOM | 944 | CB | ARG | B | 8 | −17.823 | 39.985 | 26.483 | 1.00 | 21.79 | C |
| ATOM | 945 | CG | ARG | B | 8 | −16.418 | 40.439 | 26.812 | 1.00 | 25.91 | C |
| ATOM | 946 | CD | ARG | B | 8 | −16.335 | 41.781 | 27.546 | 1.00 | 31.75 | C |
| ATOM | 947 | NE | ARG | B | 8 | −15.643 | 42.783 | 26.732 | 1.00 | 37.11 | N |
| ATOM | 948 | CZ | ARG | B | 8 | −16.233 | 43.675 | 25.925 | 1.00 | 40.95 | C |
| ATOM | 949 | NH1 | ARG | B | 8 | −17.563 | 43.759 | 25.817 | 1.00 | 42.20 | N |
| ATOM | 950 | NH2 | ARG | B | 8 | −15.475 | 44.500 | 25.209 | 1.00 | 42.21 | N |
| ATOM | 951 | N | THR | B | 9 | −20.468 | 38.243 | 27.163 | 1.00 | 19.30 | N |
| ATOM | 952 | CA | THR | B | 9 | −21.836 | 37.810 | 26.904 | 1.00 | 19.45 | C |
| ATOM | 953 | C | THR | B | 9 | −22.125 | 36.529 | 27.644 | 1.00 | 18.89 | C |
| ATOM | 954 | O | THR | B | 9 | −21.230 | 35.774 | 28.021 | 1.00 | 18.82 | O |
| ATOM | 955 | CB | THR | B | 9 | −22.125 | 37.537 | 25.389 | 1.00 | 19.83 | C |
| ATOM | 956 | OG1 | THR | B | 9 | −21.516 | 36.311 | 25.004 | 1.00 | 21.08 | O |
| ATOM | 957 | CG2 | THR | B | 9 | −21.487 | 38.550 | 24.454 | 1.00 | 20.14 | C |
| ATOM | 958 | N | ALA | B | 10 | −23.410 | 36.271 | 27.810 | 1.00 | 18.26 | N |
| ATOM | 959 | CA | ALA | B | 10 | −23.861 | 35.097 | 28.512 | 1.00 | 17.32 | C |
| ATOM | 960 | C | ALA | B | 10 | −25.289 | 34.832 | 28.117 | 1.00 | 17.20 | C |
| ATOM | 961 | O | ALA | B | 10 | −26.077 | 35.749 | 27.930 | 1.00 | 15.99 | O |
| ATOM | 962 | CB | ALA | B | 10 | −23.759 | 35.304 | 30.010 | 1.00 | 17.04 | C |
| ATOM | 963 | N | THR | B | 11 | −25.595 | 33.555 | 27.968 | 1.00 | 17.78 | N |
| ATOM | 964 | CA | THR | B | 11 | −26.949 | 33.102 | 27.803 | 1.00 | 18.49 | C |
| ATOM | 965 | C | THR | B | 11 | −27.249 | 32.171 | 28.946 | 1.00 | 19.15 | C |
| ATOM | 966 | O | THR | B | 11 | −26.481 | 31.250 | 29.230 | 1.00 | 19.45 | O |
| ATOM | 967 | CB | THR | B | 11 | −27.096 | 32.385 | 26.474 | 1.00 | 18.37 | C |
| ATOM | 968 | OG1 | THR | B | 11 | −27.013 | 33.355 | 25.429 | 1.00 | 19.62 | O |
| ATOM | 969 | CG2 | THR | B | 11 | −28.487 | 31.786 | 26.316 | 1.00 | 18.50 | C |
| ATOM | 970 | N | LYS | B | 12 | −28.381 | 32.425 | 29.587 | 1.00 | 19.79 | N |
| ATOM | 971 | CA | LYS | B | 12 | −28.833 | 31.655 | 30.718 | 1.00 | 20.44 | C |
| ATOM | 972 | C | LYS | B | 12 | −30.323 | 31.299 | 30.553 | 1.00 | 20.18 | C |
| ATOM | 973 | O | LYS | B | 12 | −31.035 | 31.916 | 29.776 | 1.00 | 19.79 | O |
| ATOM | 974 | CB | LYS | B | 12 | −28.588 | 32.465 | 31.998 | 1.00 | 20.72 | C |
| ATOM | 975 | CG | LYS | B | 12 | −27.432 | 31.942 | 32.858 | 1.00 | 22.57 | C |
| ATOM | 976 | CD | LYS | B | 12 | −26.102 | 32.568 | 32.529 | 1.00 | 24.40 | C |
| ATOM | 977 | CE | LYS | B | 12 | −24.953 | 31.573 | 32.674 | 1.00 | 25.84 | C |
| ATOM | 978 | NZ | LYS | B | 12 | −24.586 | 31.287 | 34.076 | 1.00 | 26.38 | N |
| ATOM | 979 | N | GLU | B | 13 | −30.763 | 30.282 | 31.275 | 1.00 | 20.44 | N |
| ATOM | 980 | CA | GLU | B | 13 | −32.173 | 29.910 | 31.332 | 1.00 | 20.98 | C |
| ATOM | 981 | C | GLU | B | 13 | −32.757 | 30.643 | 32.525 | 1.00 | 20.99 | C |
| ATOM | 982 | O | GLU | B | 13 | −32.003 | 31.058 | 33.409 | 1.00 | 20.59 | O |
| ATOM | 983 | CB | GLU | B | 13 | −32.321 | 28.404 | 31.536 | 1.00 | 21.11 | C |
| ATOM | 984 | CG | GLU | B | 13 | −31.536 | 27.530 | 30.561 | 1.00 | 22.38 | C |
| ATOM | 985 | CD | GLU | B | 13 | −32.114 | 27.528 | 29.159 | 1.00 | 22.84 | C |
| ATOM | 986 | OE1 | GLU | B | 13 | −33.252 | 27.051 | 28.965 | 1.00 | 22.94 | O |
| ATOM | 987 | OE2 | GLU | B | 13 | −31.422 | 28.010 | 28.244 | 1.00 | 25.76 | O |
| ATOM | 988 | N | THR | B | 14 | −34.078 | 30.811 | 32.582 | 1.00 | 21.09 | N |
| ATOM | 989 | CA | THR | B | 14 | −34.654 | 31.436 | 33.772 | 1.00 | 21.59 | C |
| ATOM | 990 | C | THR | B | 14 | −34.457 | 30.448 | 34.910 | 1.00 | 22.01 | C |
| ATOM | 991 | O | THR | B | 14 | −34.570 | 29.236 | 34.713 | 1.00 | 21.49 | O |
| ATOM | 992 | CB | THR | B | 14 | −36.161 | 31.873 | 33.652 | 1.00 | 21.37 | C |
| ATOM | 993 | OG1 | THR | B | 14 | −37.020 | 30.818 | 34.079 | 1.00 | 21.82 | O |
| ATOM | 994 | CG2 | THR | B | 14 | −36.592 | 32.178 | 32.225 | 1.00 | 21.18 | C |
| ATOM | 995 | N | GLY | B | 15 | −34.098 | 30.970 | 36.082 | 1.00 | 22.66 | N |
| ATOM | 996 | CA | GLY | B | 15 | −33.883 | 30.142 | 37.256 | 1.00 | 23.26 | C |
| ATOM | 997 | C | GLY | B | 15 | −32.410 | 29.995 | 37.566 | 1.00 | 23.45 | C |
| ATOM | 998 | O | GLY | B | 15 | −32.033 | 29.909 | 38.729 | 1.00 | 23.59 | O |
| ATOM | 999 | N | GLU | B | 16 | −31.582 | 29.967 | 36.524 | 1.00 | 24.06 | N |
| ATOM | 1000 | CA | GLU | B | 16 | −30.133 | 29.924 | 36.681 | 1.00 | 24.32 | C |
| ATOM | 1001 | C | GLU | B | 16 | −29.621 | 31.250 | 37.214 | 1.00 | 24.70 | C |
| ATOM | 1002 | O | GLU | B | 16 | −30.382 | 32.215 | 37.327 | 1.00 | 25.07 | O |
| ATOM | 1003 | CB | GLU | B | 16 | −29.458 | 29.604 | 35.348 | 1.00 | 24.49 | C |
| ATOM | 1004 | CG | GLU | B | 16 | −29.883 | 28.252 | 34.783 | 1.00 | 24.62 | C |

APPENDIX I(b)-continued

| ATOM | 1005 | CD | GLU | B | 16 | −28.994 | 27.748 | 33.659 | 1.00 | 25.18 | C |
|---|---|---|---|---|---|---|---|---|---|---|---|
| ATOM | 1006 | OE1 | GLU | B | 16 | −28.404 | 28.574 | 32.920 | 1.00 | 23.51 | O |
| ATOM | 1007 | OE2 | GLU | B | 16 | −28.906 | 26.505 | 33.503 | 1.00 | 27.51 | O |
| ATOM | 1008 | N | SER | B | 17 | −28.330 | 31.286 | 37.538 | 1.00 | 24.45 | N |
| ATOM | 1009 | CA | SER | B | 17 | −27.680 | 32.487 | 38.013 | 1.00 | 24.38 | C |
| ATOM | 1010 | C | SER | B | 17 | −26.524 | 32.917 | 37.097 | 1.00 | 23.43 | C |
| ATOM | 1011 | O | SER | B | 17 | −26.074 | 32.161 | 36.229 | 1.00 | 23.02 | O |
| ATOM | 1012 | CB | SER | B | 17 | −27.181 | 32.267 | 39.441 | 1.00 | 24.82 | C |
| ATOM | 1013 | OG | SER | B | 17 | −26.182 | 31.263 | 39.474 | 1.00 | 27.20 | O |
| ATOM | 1014 | N | LEU | B | 18 | −26.079 | 34.153 | 37.296 | 1.00 | 22.87 | N |
| ATOM | 1015 | CA | LEU | B | 18 | −24.952 | 34.742 | 36.565 | 1.00 | 22.89 | C |
| ATOM | 1016 | C | LEU | B | 18 | −23.964 | 35.355 | 37.532 | 1.00 | 22.41 | C |
| ATOM | 1017 | O | LEU | B | 18 | −24.365 | 36.105 | 38.414 | 1.00 | 22.16 | O |
| ATOM | 1018 | CB | LEU | B | 18 | −25.455 | 35.873 | 35.654 | 1.00 | 22.72 | C |
| ATOM | 1019 | CG | LEU | B | 18 | −24.729 | 36.314 | 34.379 | 1.00 | 23.50 | C |
| ATOM | 1020 | CD1 | LEU | B | 18 | −24.683 | 37.821 | 34.299 | 1.00 | 22.99 | C |
| ATOM | 1021 | CD2 | LEU | B | 18 | −23.348 | 35.686 | 34.150 | 1.00 | 24.23 | C |
| ATOM | 1022 | N | THR | B | 19 | −22.678 | 35.065 | 37.339 | 1.00 | 21.68 | N |
| ATOM | 1023 | CA | THR | B | 19 | −21.605 | 35.809 | 37.980 | 1.00 | 21.02 | C |
| ATOM | 1024 | C | THR | B | 19 | −20.890 | 36.641 | 36.923 | 1.00 | 19.99 | C |
| ATOM | 1025 | O | THR | B | 19 | −20.510 | 36.120 | 35.877 | 1.00 | 20.15 | O |
| ATOM | 1026 | CB | THR | B | 19 | −20.597 | 34.864 | 38.665 | 1.00 | 21.31 | C |
| ATOM | 1027 | OG1 | THR | B | 19 | −21.255 | 34.102 | 39.683 | 1.00 | 20.95 | O |
| ATOM | 1028 | CG2 | THR | B | 19 | −19.544 | 35.654 | 39.448 | 1.00 | 20.49 | C |
| ATOM | 1029 | N | ILE | B | 20 | −20.777 | 37.941 | 37.188 | 1.00 | 18.82 | N |
| ATOM | 1030 | CA | ILE | B | 20 | −19.940 | 38.853 | 36.425 | 1.00 | 18.18 | C |
| ATOM | 1031 | C | ILE | B | 20 | −18.750 | 39.217 | 37.289 | 1.00 | 17.93 | C |
| ATOM | 1032 | O | ILE | B | 20 | −18.909 | 39.593 | 38.456 | 1.00 | 16.31 | O |
| ATOM | 1033 | CB | ILE | B | 20 | −20.697 | 40.134 | 36.059 | 1.00 | 18.01 | C |
| ATOM | 1034 | CG1 | ILE | B | 20 | −22.010 | 39.806 | 35.333 | 1.00 | 19.21 | C |
| ATOM | 1035 | CG2 | ILE | B | 20 | −19.791 | 41.077 | 35.275 | 1.00 | 17.59 | C |
| ATOM | 1036 | CD1 | ILE | B | 20 | −22.927 | 41.015 | 35.129 | 1.00 | 18.61 | C |
| ATOM | 1037 | N | ASN | B | 21 | −17.555 | 39.079 | 36.717 | 1.00 | 18.25 | N |
| ATOM | 1038 | CA | ASN | B | 21 | −16.320 | 39.372 | 37.423 | 1.00 | 18.53 | C |
| ATOM | 1039 | C | ASN | B | 21 | −15.681 | 40.625 | 36.827 | 1.00 | 17.94 | C |
| ATOM | 1040 | O | ASN | B | 21 | −15.519 | 40.729 | 35.600 | 1.00 | 17.76 | O |
| ATOM | 1041 | CB | ASN | B | 21 | −15.371 | 38.171 | 37.294 | 1.00 | 19.21 | C |
| ATOM | 1042 | CG | ASN | B | 21 | −15.909 | 36.916 | 37.998 | 1.00 | 20.45 | C |
| ATOM | 1043 | OD1 | ASN | B | 21 | −16.162 | 36.930 | 39.210 | 1.00 | 22.21 | O |
| ATOM | 1044 | ND2 | ASN | B | 21 | −16.098 | 35.841 | 37.241 | 1.00 | 20.12 | N |
| ATOM | 1045 | N | CYS | B | 22 | −15.288 | 41.537 | 37.707 | 1.00 | 17.20 | N |
| ATOM | 1046 | CA | CYS | B | 22 | −14.600 | 42.758 | 37.346 | 1.00 | 17.12 | C |
| ATOM | 1047 | C | CYS | B | 22 | −13.282 | 42.865 | 38.076 | 1.00 | 16.44 | C |
| ATOM | 1048 | O | CYS | B | 22 | −13.205 | 42.692 | 39.299 | 1.00 | 16.37 | O |
| ATOM | 1049 | CB | CYS | B | 22 | −15.478 | 43.958 | 37.653 | 1.00 | 17.80 | C |
| ATOM | 1050 | SG | CYS | B | 22 | −16.804 | 44.155 | 36.434 | 1.00 | 20.00 | S |
| ATOM | 1051 | N | VAL | B | 23 | −12.226 | 43.149 | 37.330 | 1.00 | 15.88 | N |
| ATOM | 1052 | CA | VAL | B | 23 | −10.920 | 43.356 | 37.919 | 1.00 | 15.42 | C |
| ATOM | 1053 | C | VAL | B | 23 | −10.391 | 44.710 | 37.454 | 1.00 | 15.65 | C |
| ATOM | 1054 | O | VAL | B | 23 | −10.316 | 44.989 | 36.242 | 1.00 | 14.61 | O |
| ATOM | 1055 | CB | VAL | B | 23 | −9.939 | 42.248 | 37.497 | 1.00 | 15.66 | C |
| ATOM | 1056 | CG1 | VAL | B | 23 | −8.606 | 42.369 | 38.272 | 1.00 | 16.38 | C |
| ATOM | 1057 | CG2 | VAL | B | 23 | −10.572 | 40.871 | 37.674 | 1.00 | 17.32 | C |
| ATOM | 1058 | N | LEU | B | 24 | −9.981 | 45.525 | 38.413 | 1.00 | 15.75 | N |
| ATOM | 1059 | CA | LEU | B | 24 | −9.359 | 46.813 | 38.126 | 1.00 | 17.10 | C |
| ATOM | 1060 | C | LEU | B | 24 | −7.861 | 46.601 | 37.940 | 1.00 | 16.81 | C |
| ATOM | 1061 | O | LEU | B | 24 | −7.173 | 46.203 | 38.879 | 1.00 | 16.22 | O |
| ATOM | 1062 | CB | LEU | B | 24 | −9.632 | 47.769 | 39.287 | 1.00 | 17.80 | C |
| ATOM | 1063 | CG | LEU | B | 24 | −9.501 | 49.301 | 39.180 | 1.00 | 21.15 | C |
| ATOM | 1064 | CD1 | LEU | B | 24 | −8.606 | 49.843 | 40.273 | 1.00 | 22.01 | C |
| ATOM | 1065 | CD2 | LEU | B | 24 | −9.090 | 49.806 | 37.868 | 1.00 | 20.50 | C |
| ATOM | 1066 | N | ARG | B | 25 | −7.380 | 46.916 | 36.739 | 1.00 | 16.84 | N |
| ATOM | 1067 | CA | ARG | B | 25 | −6.028 | 46.650 | 36.300 | 1.00 | 17.59 | C |
| ATOM | 1068 | C | ARG | B | 25 | −5.231 | 47.898 | 35.946 | 1.00 | 18.31 | C |
| ATOM | 1069 | O | ARG | B | 25 | −5.787 | 48.885 | 35.476 | 1.00 | 17.08 | O |
| ATOM | 1070 | CB | ARG | B | 25 | −6.094 | 45.782 | 35.057 | 1.00 | 17.34 | C |
| ATOM | 1071 | CG | ARG | B | 25 | −6.879 | 44.498 | 35.348 | 1.00 | 17.33 | C |
| ATOM | 1072 | CD | ARG | B | 25 | −6.852 | 43.502 | 34.297 | 1.00 | 13.60 | C |
| ATOM | 1073 | NE | ARG | B | 25 | −5.497 | 43.263 | 33.810 | 1.00 | 13.84 | N |
| ATOM | 1074 | CZ | ARG | B | 25 | −5.222 | 42.392 | 32.860 | 1.00 | 11.47 | C |
| ATOM | 1075 | NH1 | ARG | B | 25 | −6.199 | 41.653 | 32.333 | 1.00 | 10.08 | N |
| ATOM | 1076 | NH2 | ARG | B | 25 | −3.982 | 42.241 | 32.449 | 1.00 | 9.16 | N |
| ATOM | 1077 | N | ASP | B | 26 | −3.915 | 47.804 | 36.136 | 1.00 | 19.61 | N |
| ATOM | 1078 | CA | ASP | B | 26 | −2.985 | 48.906 | 35.901 | 1.00 | 21.22 | C |
| ATOM | 1079 | C | ASP | B | 26 | −3.494 | 50.171 | 36.568 | 1.00 | 21.82 | C |
| ATOM | 1080 | O | ASP | B | 26 | −3.598 | 51.200 | 35.928 | 1.00 | 21.62 | O |
| ATOM | 1081 | CB | ASP | B | 26 | −2.809 | 49.154 | 34.403 | 1.00 | 21.90 | C |
| ATOM | 1082 | CG | ASP | B | 26 | −2.338 | 47.932 | 33.658 | 1.00 | 24.84 | C |
| ATOM | 1083 | OD1 | ASP | B | 26 | −1.885 | 46.971 | 34.333 | 1.00 | 28.20 | O |
| ATOM | 1084 | OD2 | ASP | B | 26 | −2.362 | 47.846 | 32.398 | 1.00 | 27.28 | O |

APPENDIX I(b)-continued

| | | | | | | | | | | | |
|---|---|---|---|---|---|---|---|---|---|---|---|
| ATOM | 1085 | N | ALA | B | 27 | −3.843 | 50.068 | 37.847 | 1.00 | 22.97 | N |
| ATOM | 1086 | CA | ALA | B | 27 | −4.447 | 51.166 | 38.590 | 1.00 | 23.99 | C |
| ATOM | 1087 | C | ALA | B | 27 | −3.441 | 51.917 | 39.438 | 1.00 | 24.59 | C |
| ATOM | 1088 | O | ALA | B | 27 | −2.510 | 51.332 | 39.989 | 1.00 | 25.39 | O |
| ATOM | 1089 | CB | ALA | B | 27 | −5.545 | 50.662 | 39.473 | 1.00 | 24.37 | C |
| ATOM | 1090 | N | SER | B | 28 | −3.656 | 53.223 | 39.532 | 1.00 | 24.85 | N |
| ATOM | 1091 | CA | SER | B | 28 | −2.864 | 54.109 | 40.385 | 1.00 | 25.14 | C |
| ATOM | 1092 | C | SER | B | 28 | −3.564 | 54.234 | 41.736 | 1.00 | 25.22 | C |
| ATOM | 1093 | O | SER | B | 28 | −2.930 | 54.167 | 42.789 | 1.00 | 25.75 | O |
| ATOM | 1094 | CB | SER | B | 28 | −2.719 | 55.492 | 39.742 | 1.00 | 24.69 | C |
| ATOM | 1095 | OG | SER | B | 28 | −3.158 | 55.481 | 38.395 | 1.00 | 23.71 | O |
| ATOM | 1096 | N | PHE | B | 29 | −4.881 | 54.398 | 41.687 | 1.00 | 25.03 | N |
| ATOM | 1097 | CA | PHE | B | 29 | −5.667 | 54.683 | 42.872 | 1.00 | 24.87 | C |
| ATOM | 1098 | C | PHE | B | 29 | −6.194 | 53.393 | 43.483 | 1.00 | 25.13 | C |
| ATOM | 1099 | O | PHE | B | 29 | −6.483 | 52.430 | 42.776 | 1.00 | 25.12 | O |
| ATOM | 1100 | CB | PHE | B | 29 | −6.813 | 55.629 | 42.510 | 1.00 | 24.68 | C |
| ATOM | 1101 | CG | PHE | B | 29 | −6.347 | 56.966 | 41.964 | 1.00 | 24.08 | C |
| ATOM | 1102 | CD1 | PHE | B | 29 | −5.477 | 57.755 | 42.688 | 1.00 | 23.02 | C |
| ATOM | 1103 | CD2 | PHE | B | 29 | −6.780 | 57.423 | 40.732 | 1.00 | 22.29 | C |
| ATOM | 1104 | CE1 | PHE | B | 29 | −5.045 | 58.957 | 42.188 | 1.00 | 22.75 | C |
| ATOM | 1105 | CE2 | PHE | B | 29 | −6.349 | 58.641 | 40.235 | 1.00 | 21.38 | C |
| ATOM | 1106 | CZ | PHE | B | 29 | −5.492 | 59.402 | 40.960 | 1.00 | 21.68 | C |
| ATOM | 1107 | N | GLU | B | 30 | −6.303 | 53.397 | 44.806 | 1.00 | 25.15 | N |
| ATOM | 1108 | CA | GLU | B | 30 | −6.873 | 52.294 | 45.554 | 1.00 | 25.25 | C |
| ATOM | 1109 | C | GLU | B | 30 | −8.365 | 52.275 | 45.326 | 1.00 | 24.28 | C |
| ATOM | 1110 | O | GLU | B | 30 | −9.011 | 53.315 | 45.373 | 1.00 | 23.91 | O |
| ATOM | 1111 | CB | GLU | B | 30 | −6.626 | 52.465 | 47.062 | 1.00 | 25.56 | C |
| ATOM | 1112 | CG | GLU | B | 30 | −5.300 | 51.916 | 47.562 | 1.00 | 28.36 | C |
| ATOM | 1113 | CD | GLU | B | 30 | −5.210 | 51.924 | 49.090 | 1.00 | 31.12 | C |
| ATOM | 1114 | OE1 | GLU | B | 30 | −4.192 | 52.404 | 49.626 | 1.00 | 33.68 | O |
| ATOM | 1115 | OE2 | GLU | B | 30 | −6.167 | 51.464 | 49.765 | 1.00 | 33.34 | O |
| ATOM | 1116 | N | LEU | B | 31 | −8.902 | 51.083 | 45.105 | 1.00 | 23.64 | N |
| ATOM | 1117 | CA | LEU | B | 31 | −10.335 | 50.901 | 44.925 | 1.00 | 23.41 | C |
| ATOM | 1118 | C | LEU | B | 31 | −11.025 | 51.255 | 46.232 | 1.00 | 23.46 | C |
| ATOM | 1119 | O | LEU | B | 31 | −10.698 | 50.690 | 47.260 | 1.00 | 22.93 | O |
| ATOM | 1120 | CB | LEU | B | 31 | −10.628 | 49.446 | 44.530 | 1.00 | 23.08 | C |
| ATOM | 1121 | CG | LEU | B | 31 | −12.086 | 49.084 | 44.216 | 1.00 | 22.85 | C |
| ATOM | 1122 | CD1 | LEU | B | 31 | −12.580 | 49.784 | 42.952 | 1.00 | 22.62 | C |
| ATOM | 1123 | CD2 | LEU | B | 31 | −12.209 | 47.591 | 44.057 | 1.00 | 21.60 | C |
| ATOM | 1124 | N | LYS | B | 32 | −11.931 | 52.229 | 46.195 | 1.00 | 23.73 | N |
| ATOM | 1125 | CA | LYS | B | 32 | −12.700 | 52.604 | 47.367 | 1.00 | 23.85 | C |
| ATOM | 1126 | C | LYS | B | 32 | −14.096 | 51.978 | 47.350 | 1.00 | 24.25 | C |
| ATOM | 1127 | O | LYS | B | 32 | −14.432 | 51.229 | 48.255 | 1.00 | 26.21 | O |
| ATOM | 1128 | CB | LYS | B | 32 | −12.803 | 54.124 | 47.507 | 1.00 | 24.04 | C |
| ATOM | 1129 | CG | LYS | B | 32 | −11.473 | 54.841 | 47.853 | 1.00 | 24.78 | C |
| ATOM | 1130 | CD | LYS | B | 32 | −10.603 | 54.086 | 48.865 | 1.00 | 25.77 | C |
| ATOM | 1131 | CE | LYS | B | 32 | −9.387 | 54.910 | 49.284 | 1.00 | 27.06 | C |
| ATOM | 1132 | NZ | LYS | B | 32 | −9.419 | 55.331 | 50.735 | 1.00 | 29.57 | N |
| ATOM | 1133 | N | ASP | B | 33 | −14.904 | 52.294 | 46.345 | 1.00 | 23.49 | N |
| ATOM | 1134 | CA | ASP | B | 33 | −16.296 | 51.860 | 46.288 | 1.00 | 22.67 | C |
| ATOM | 1135 | C | ASP | B | 33 | −16.550 | 51.276 | 44.893 | 1.00 | 21.88 | C |
| ATOM | 1136 | O | ASP | B | 33 | −15.689 | 51.354 | 44.023 | 1.00 | 21.30 | O |
| ATOM | 1137 | CB | ASP | B | 33 | −17.205 | 53.064 | 46.591 | 1.00 | 22.52 | C |
| ATOM | 1138 | CG | ASP | B | 33 | −18.693 | 52.694 | 46.790 | 1.00 | 23.90 | C |
| ATOM | 1139 | OD1 | ASP | B | 33 | −19.082 | 51.493 | 46.850 | 1.00 | 20.86 | O |
| ATOM | 1140 | OD2 | ASP | B | 33 | −19.560 | 53.589 | 46.897 | 1.00 | 26.09 | O |
| ATOM | 1141 | N | THR | B | 34 | −17.693 | 50.631 | 44.712 | 1.00 | 20.74 | N |
| ATOM | 1142 | CA | THR | B | 34 | −18.077 | 50.071 | 43.436 | 1.00 | 20.55 | C |
| ATOM | 1143 | C | THR | B | 34 | −19.533 | 50.336 | 43.181 | 1.00 | 20.18 | C |
| ATOM | 1144 | O | THR | B | 34 | −20.303 | 50.579 | 44.099 | 1.00 | 19.74 | O |
| ATOM | 1145 | CB | THR | B | 34 | −17.904 | 48.557 | 43.451 | 1.00 | 20.76 | C |
| ATOM | 1146 | OG1 | THR | B | 34 | −18.595 | 48.017 | 44.592 | 1.00 | 19.54 | O |
| ATOM | 1147 | CG2 | THR | B | 34 | −16.445 | 48.157 | 43.635 | 1.00 | 20.79 | C |
| ATOM | 1148 | N | GLY | B | 35 | −19.911 | 50.250 | 41.914 | 1.00 | 19.65 | N |
| ATOM | 1149 | CA | GLY | B | 35 | −21.296 | 50.368 | 41.521 | 1.00 | 19.23 | C |
| ATOM | 1150 | C | GLY | B | 35 | −21.562 | 49.486 | 40.318 | 1.00 | 18.79 | C |
| ATOM | 1151 | O | GLY | B | 35 | −20.674 | 49.157 | 39.555 | 1.00 | 18.14 | O |
| ATOM | 1152 | N | TRP | B | 36 | −22.815 | 49.103 | 40.182 | 1.00 | 18.24 | N |
| ATOM | 1153 | CA | TRP | B | 36 | −23.269 | 48.213 | 39.155 | 1.00 | 18.12 | C |
| ATOM | 1154 | C | TRP | B | 36 | −24.497 | 48.867 | 38.514 | 1.00 | 18.61 | C |
| ATOM | 1155 | O | TRP | B | 36 | −25.295 | 49.496 | 39.202 | 1.00 | 17.92 | O |
| ATOM | 1156 | CB | TRP | B | 36 | −23.589 | 46.867 | 39.787 | 1.00 | 17.76 | C |
| ATOM | 1157 | CG | TRP | B | 36 | −22.365 | 46.120 | 40.219 | 1.00 | 16.23 | C |
| ATOM | 1158 | CD1 | TRP | B | 36 | −21.729 | 46.213 | 41.421 | 1.00 | 15.56 | C |
| ATOM | 1159 | CD2 | TRP | B | 36 | −21.621 | 45.167 | 39.445 | 1.00 | 16.02 | C |
| ATOM | 1160 | NE1 | TRP | B | 36 | −20.642 | 45.372 | 41.451 | 1.00 | 15.36 | N |
| ATOM | 1161 | CE2 | TRP | B | 36 | −20.540 | 44.728 | 40.247 | 1.00 | 16.32 | C |
| ATOM | 1162 | CE3 | TRP | B | 36 | −21.749 | 44.644 | 38.148 | 1.00 | 15.74 | C |
| ATOM | 1163 | CZ2 | TRP | B | 36 | −19.612 | 43.786 | 39.808 | 1.00 | 14.00 | C |
| ATOM | 1164 | CZ3 | TRP | B | 36 | −20.836 | 43.705 | 37.711 | 1.00 | 15.81 | C |

APPENDIX I(b)-continued

| ATOM | 1165 | CH2 | TRP | B | 36 | −19.770 | 43.290 | 38.537 | 1.00 | 15.63 | C |
|------|------|-----|-----|---|----|---------|--------|--------|------|-------|---|
| ATOM | 1166 | N | TYR | B | 37 | −24.595 | 48.738 | 37.190 | 1.00 | 19.18 | N |
| ATOM | 1167 | CA | TYR | B | 37 | −25.576 | 49.446 | 36.347 | 1.00 | 19.61 | C |
| ATOM | 1168 | C | TYR | B | 37 | −26.075 | 48.525 | 35.243 | 1.00 | 19.35 | C |
| ATOM | 1169 | O | TYR | B | 37 | −25.336 | 47.676 | 34.777 | 1.00 | 18.84 | O |
| ATOM | 1170 | CB | TYR | B | 37 | −24.921 | 50.647 | 35.653 | 1.00 | 19.72 | C |
| ATOM | 1171 | CG | TYR | B | 37 | −24.347 | 51.638 | 36.617 | 1.00 | 21.51 | C |
| ATOM | 1172 | CD1 | TYR | B | 37 | −25.145 | 52.640 | 37.160 | 1.00 | 24.75 | C |
| ATOM | 1173 | CD2 | TYR | B | 37 | −23.021 | 51.554 | 37.023 | 1.00 | 22.63 | C |
| ATOM | 1174 | CE1 | TYR | B | 37 | −24.633 | 53.547 | 38.079 | 1.00 | 25.58 | C |
| ATOM | 1175 | CE2 | TYR | B | 37 | −22.503 | 52.444 | 37.945 | 1.00 | 24.41 | C |
| ATOM | 1176 | CZ | TYR | B | 37 | −23.312 | 53.443 | 38.460 | 1.00 | 26.84 | C |
| ATOM | 1177 | OH | TYR | B | 37 | −22.810 | 54.333 | 39.372 | 1.00 | 30.18 | O |
| ATOM | 1178 | N | ARG | B | 38 | −27.312 | 48.713 | 34.802 | 1.00 | 19.09 | N |
| ATOM | 1179 | CA | ARG | B | 38 | −27.809 | 47.989 | 33.639 | 1.00 | 19.55 | C |
| ATOM | 1180 | C | ARG | B | 38 | −28.798 | 48.765 | 32.791 | 1.00 | 18.49 | C |
| ATOM | 1181 | O | ARG | B | 38 | −29.565 | 49.591 | 33.287 | 1.00 | 18.38 | O |
| ATOM | 1182 | CB | ARG | B | 38 | −28.469 | 46.674 | 34.044 | 1.00 | 19.81 | C |
| ATOM | 1183 | CG | ARG | B | 38 | −29.525 | 46.843 | 35.070 | 1.00 | 22.46 | C |
| ATOM | 1184 | CD | ARG | B | 38 | −30.798 | 46.162 | 34.774 | 1.00 | 25.60 | C |
| ATOM | 1185 | NE | ARG | B | 38 | −30.898 | 44.895 | 35.479 | 1.00 | 27.28 | N |
| ATOM | 1186 | CZ | ARG | B | 38 | −32.035 | 44.353 | 35.887 | 1.00 | 27.55 | C |
| ATOM | 1187 | NH1 | ARG | B | 38 | −33.193 | 44.976 | 35.690 | 1.00 | 29.81 | N |
| ATOM | 1188 | NH2 | ARG | B | 38 | −32.016 | 43.184 | 36.506 | 1.00 | 26.89 | N |
| ATOM | 1189 | N | THR | B | 39 | −28.749 | 48.467 | 31.501 | 1.00 | 17.65 | N |
| ATOM | 1190 | CA | THR | B | 39 | −29.814 | 48.769 | 30.572 | 1.00 | 17.38 | C |
| ATOM | 1191 | C | THR | B | 39 | −30.609 | 47.483 | 30.339 | 1.00 | 16.90 | C |
| ATOM | 1192 | O | THR | B | 39 | −30.148 | 46.579 | 29.661 | 1.00 | 16.35 | O |
| ATOM | 1193 | CB | THR | B | 39 | −29.211 | 49.268 | 29.255 | 1.00 | 17.27 | C |
| ATOM | 1194 | OG1 | THR | B | 39 | −28.274 | 50.310 | 29.534 | 1.00 | 17.58 | O |
| ATOM | 1195 | CG2 | THR | B | 39 | −30.287 | 49.925 | 28.355 | 1.00 | 17.17 | C |
| ATOM | 1196 | N | LYS | B | 40 | −31.803 | 47.394 | 30.906 | 1.00 | 16.71 | N |
| ATOM | 1197 | CA | LYS | B | 40 | −32.592 | 46.182 | 30.757 | 1.00 | 16.42 | C |
| ATOM | 1198 | C | LYS | B | 40 | −33.348 | 46.177 | 29.428 | 1.00 | 16.17 | C |
| ATOM | 1199 | O | LYS | B | 40 | −33.530 | 47.215 | 28.787 | 1.00 | 15.22 | O |
| ATOM | 1200 | CB | LYS | B | 40 | −33.525 | 45.964 | 31.949 | 1.00 | 16.51 | C |
| ATOM | 1201 | CG | LYS | B | 40 | −34.574 | 47.016 | 32.136 | 1.00 | 18.21 | C |
| ATOM | 1202 | CD | LYS | B | 40 | −35.245 | 46.898 | 33.506 | 1.00 | 19.27 | C |
| ATOM | 1203 | CE | LYS | B | 40 | −36.626 | 47.526 | 33.477 | 1.00 | 20.69 | C |
| ATOM | 1204 | NZ | LYS | B | 40 | −37.393 | 47.282 | 34.746 | 1.00 | 22.98 | N |
| ATOM | 1205 | N | LEU | B | 41 | −33.754 | 44.978 | 29.023 | 1.00 | 16.05 | N |
| ATOM | 1206 | CA | LEU | B | 41 | −34.419 | 44.741 | 27.754 | 1.00 | 16.04 | C |
| ATOM | 1207 | C | LEU | B | 41 | −35.694 | 45.576 | 27.639 | 1.00 | 16.59 | C |
| ATOM | 1208 | O | LEU | B | 41 | −36.414 | 45.783 | 28.619 | 1.00 | 16.92 | O |
| ATOM | 1209 | CB | LEU | B | 41 | −34.746 | 43.248 | 27.628 | 1.00 | 15.95 | C |
| ATOM | 1210 | CG | LEU | B | 41 | −35.555 | 42.752 | 26.427 | 1.00 | 16.05 | C |
| ATOM | 1211 | CD1 | LEU | B | 41 | −34.641 | 42.434 | 25.239 | 1.00 | 15.75 | C |
| ATOM | 1212 | CD2 | LEU | B | 41 | −36.408 | 41.535 | 26.800 | 1.00 | 15.80 | C |
| ATOM | 1213 | N | GLY | B | 42 | −35.967 | 46.055 | 26.430 | 1.00 | 16.75 | N |
| ATOM | 1214 | CA | GLY | B | 42 | −37.081 | 46.951 | 26.185 | 1.00 | 16.88 | C |
| ATOM | 1215 | C | GLY | B | 42 | −36.866 | 48.376 | 26.664 | 1.00 | 17.13 | C |
| ATOM | 1216 | O | GLY | B | 42 | −37.767 | 49.201 | 26.530 | 1.00 | 17.20 | O |
| ATOM | 1217 | N | SER | B | 43 | −35.685 | 48.681 | 27.192 | 1.00 | 17.18 | N |
| ATOM | 1218 | CA | SER | B | 43 | −35.417 | 50.000 | 27.745 | 1.00 | 17.77 | C |
| ATOM | 1219 | C | SER | B | 43 | −34.087 | 50.586 | 27.256 | 1.00 | 18.27 | C |
| ATOM | 1220 | O | SER | B | 43 | −33.140 | 49.870 | 26.945 | 1.00 | 17.60 | O |
| ATOM | 1221 | CB | SER | B | 43 | −35.466 | 49.951 | 29.284 | 1.00 | 17.81 | C |
| ATOM | 1222 | OG | SER | B | 43 | −34.746 | 51.026 | 29.864 | 1.00 | 18.04 | O |
| ATOM | 1223 | N | THR | B | 44 | −34.042 | 51.910 | 27.217 | 1.00 | 19.66 | N |
| ATOM | 1224 | CA | THR | B | 44 | −32.907 | 52.670 | 26.711 | 1.00 | 21.11 | C |
| ATOM | 1225 | C | THR | B | 44 | −32.100 | 53.352 | 27.846 | 1.00 | 21.91 | C |
| ATOM | 1226 | O | THR | B | 44 | −31.000 | 53.871 | 27.624 | 1.00 | 22.34 | O |
| ATOM | 1227 | CB | THR | B | 44 | −33.454 | 53.681 | 25.660 | 1.00 | 21.50 | C |
| ATOM | 1228 | OG1 | THR | B | 44 | −32.669 | 53.614 | 24.459 | 1.00 | 23.73 | O |
| ATOM | 1229 | CG2 | THR | B | 44 | −33.377 | 55.141 | 26.129 | 1.00 | 21.82 | C |
| ATOM | 1230 | N | ASN | B | 45 | −32.628 | 53.319 | 29.066 | 1.00 | 22.83 | N |
| ATOM | 1231 | CA | ASN | B | 45 | −32.014 | 54.024 | 30.205 | 1.00 | 23.46 | C |
| ATOM | 1232 | C | ASN | B | 45 | −31.136 | 53.131 | 31.066 | 1.00 | 23.26 | C |
| ATOM | 1233 | O | ASN | B | 45 | −31.591 | 52.099 | 31.558 | 1.00 | 23.12 | O |
| ATOM | 1234 | CB | ASN | B | 45 | −33.106 | 54.667 | 31.077 | 1.00 | 23.67 | C |
| ATOM | 1235 | CG | ASN | B | 45 | −33.466 | 56.067 | 30.609 | 1.00 | 25.41 | C |
| ATOM | 1236 | OD1 | ASN | B | 45 | −34.592 | 56.322 | 30.178 | 1.00 | 26.74 | O |
| ATOM | 1237 | ND2 | ASN | B | 45 | −32.498 | 56.987 | 30.688 | 1.00 | 27.93 | N |
| ATOM | 1238 | N | GLU | B | 46 | −29.881 | 53.532 | 31.252 | 1.00 | 23.42 | N |
| ATOM | 1239 | CA | GLU | B | 46 | −28.997 | 52.825 | 32.171 | 1.00 | 23.74 | C |
| ATOM | 1240 | C | GLU | B | 46 | −29.372 | 53.162 | 33.610 | 1.00 | 23.50 | C |
| ATOM | 1241 | O | GLU | B | 46 | −29.600 | 54.324 | 33.967 | 1.00 | 23.84 | O |
| ATOM | 1242 | CB | GLU | B | 46 | −27.509 | 53.116 | 31.908 | 1.00 | 24.34 | C |
| ATOM | 1243 | CG | GLU | B | 46 | −26.610 | 52.000 | 32.432 | 1.00 | 25.93 | C |
| ATOM | 1244 | CD | GLU | B | 46 | −25.140 | 52.365 | 32.520 | 1.00 | 28.62 | C |

APPENDIX I(b)-continued

| ATOM | 1245 | OE1 | GLU | B | 46 | −24.813 | 53.403 | 33.137 | 1.00 | 32.72 | O |
|---|---|---|---|---|---|---|---|---|---|---|---|
| ATOM | 1246 | OE2 | GLU | B | 46 | −24.306 | 51.589 | 32.008 | 1.00 | 28.07 | O |
| ATOM | 1247 | N | GLN | B | 47 | −29.421 | 52.125 | 34.431 | 1.00 | 23.10 | N |
| ATOM | 1248 | CA | GLN | B | 47 | −30.050 | 52.178 | 35.744 | 1.00 | 22.80 | C |
| ATOM | 1249 | C | GLN | B | 47 | −29.087 | 51.583 | 36.767 | 1.00 | 22.28 | C |
| ATOM | 1250 | O | GLN | B | 47 | −28.519 | 50.516 | 36.546 | 1.00 | 21.53 | O |
| ATOM | 1251 | CB | GLN | B | 47 | −31.325 | 51.328 | 35.716 | 1.00 | 23.05 | C |
| ATOM | 1252 | CG | GLN | B | 47 | −32.607 | 52.035 | 36.047 | 1.00 | 25.12 | C |
| ATOM | 1253 | CD | GLN | B | 47 | −33.784 | 51.074 | 36.091 | 1.00 | 27.20 | C |
| ATOM | 1254 | OE1 | GLN | B | 47 | −33.945 | 50.234 | 35.192 | 1.00 | 28.88 | O |
| ATOM | 1255 | NE2 | GLN | B | 47 | −34.602 | 51.184 | 37.135 | 1.00 | 27.84 | N |
| ATOM | 1256 | N | SER | B | 48 | −28.922 | 52.265 | 37.890 | 1.00 | 21.60 | N |
| ATOM | 1257 | CA | SER | B | 48 | −28.186 | 51.721 | 39.010 | 1.00 | 21.63 | C |
| ATOM | 1258 | C | SER | B | 48 | −28.843 | 50.437 | 39.546 | 1.00 | 21.29 | C |
| ATOM | 1259 | O | SER | B | 48 | −30.048 | 50.361 | 39.660 | 1.00 | 20.52 | O |
| ATOM | 1260 | CB | SER | B | 48 | −28.131 | 52.766 | 40.124 | 1.00 | 22.04 | C |
| ATOM | 1261 | OG | SER | B | 48 | −27.498 | 52.228 | 41.261 | 1.00 | 23.32 | O |
| ATOM | 1262 | N | ILE | B | 49 | −28.031 | 49.440 | 39.875 | 1.00 | 21.21 | N |
| ATOM | 1263 | CA | ILE | B | 49 | −28.505 | 48.225 | 40.529 | 1.00 | 21.20 | C |
| ATOM | 1264 | C | ILE | B | 49 | −28.340 | 48.370 | 42.049 | 1.00 | 21.46 | C |
| ATOM | 1265 | O | ILE | B | 49 | −27.271 | 48.725 | 42.553 | 1.00 | 21.11 | O |
| ATOM | 1266 | CB | ILE | B | 49 | −27.713 | 46.980 | 40.005 | 1.00 | 21.53 | C |
| ATOM | 1267 | CG1 | ILE | B | 49 | −27.996 | 46.756 | 38.511 | 1.00 | 20.53 | C |
| ATOM | 1268 | CG2 | ILE | B | 49 | −28.080 | 45.740 | 40.843 | 1.00 | 21.49 | C |
| ATOM | 1269 | CD1 | ILE | B | 49 | −27.027 | 45.830 | 37.797 | 1.00 | 22.53 | C |
| ATOM | 1270 | N | SER | B | 50 | −29.409 | 48.078 | 42.774 | 1.00 | 22.04 | N |
| ATOM | 1271 | CA | SER | B | 50 | −29.406 | 48.084 | 44.233 | 1.00 | 22.35 | C |
| ATOM | 1272 | C | SER | B | 50 | −28.888 | 46.745 | 44.755 | 1.00 | 22.25 | C |
| ATOM | 1273 | O | SER | B | 50 | −29.509 | 45.708 | 44.539 | 1.00 | 22.62 | O |
| ATOM | 1274 | CB | SER | B | 50 | −30.823 | 48.335 | 44.765 | 1.00 | 22.21 | C |
| ATOM | 1275 | OG | SER | B | 50 | −30.800 | 49.354 | 45.746 | 1.00 | 23.43 | O |
| ATOM | 1276 | N | ILE | B | 51 | −27.744 | 46.771 | 45.428 | 1.00 | 22.47 | N |
| ATOM | 1277 | CA | ILE | B | 51 | −27.136 | 45.539 | 45.918 | 1.00 | 22.78 | C |
| ATOM | 1278 | C | ILE | B | 51 | −27.933 | 45.009 | 47.098 | 1.00 | 22.80 | C |
| ATOM | 1279 | O | ILE | B | 51 | −28.062 | 45.677 | 48.127 | 1.00 | 22.88 | O |
| ATOM | 1280 | CB | ILE | B | 51 | −25.635 | 45.742 | 46.289 | 1.00 | 22.82 | C |
| ATOM | 1281 | CG1 | ILE | B | 51 | −24.833 | 46.198 | 45.059 | 1.00 | 22.79 | C |
| ATOM | 1282 | CG2 | ILE | B | 51 | −25.041 | 44.451 | 46.872 | 1.00 | 22.51 | C |
| ATOM | 1283 | CD1 | ILE | B | 51 | −25.034 | 45.335 | 43.799 | 1.00 | 23.44 | C |
| ATOM | 1284 | N | GLY | B | 52 | −28.470 | 43.808 | 46.922 | 1.00 | 23.07 | N |
| ATOM | 1285 | CA | GLY | B | 52 | −29.354 | 43.185 | 47.899 | 1.00 | 23.46 | C |
| ATOM | 1286 | C | GLY | B | 52 | −30.214 | 42.108 | 47.244 | 1.00 | 23.47 | C |
| ATOM | 1287 | O | GLY | B | 52 | −30.438 | 42.136 | 46.027 | 1.00 | 23.12 | O |
| ATOM | 1288 | N | GLY | B | 53 | −30.673 | 41.149 | 48.043 | 1.00 | 23.65 | N |
| ATOM | 1289 | CA | GLY | B | 53 | −31.579 | 40.111 | 47.571 | 1.00 | 24.06 | C |
| ATOM | 1290 | C | GLY | B | 53 | −30.945 | 39.186 | 46.542 | 1.00 | 24.34 | C |
| ATOM | 1291 | O | GLY | B | 53 | −29.968 | 38.492 | 46.838 | 1.00 | 24.13 | O |
| ATOM | 1292 | N | ARG | B | 54 | −31.513 | 39.178 | 45.334 | 1.00 | 24.75 | N |
| ATOM | 1293 | CA | ARG | B | 54 | −31.014 | 38.374 | 44.210 | 1.00 | 24.67 | C |
| ATOM | 1294 | C | ARG | B | 54 | −29.618 | 38.827 | 43.735 | 1.00 | 23.81 | C |
| ATOM | 1295 | O | ARG | B | 54 | −28.868 | 38.043 | 43.158 | 1.00 | 23.10 | O |
| ATOM | 1296 | CB | ARG | B | 54 | −32.004 | 38.433 | 43.027 | 1.00 | 24.89 | C |
| ATOM | 1297 | CG | ARG | B | 54 | −33.349 | 37.771 | 43.297 | 1.00 | 27.65 | C |
| ATOM | 1298 | CD | ARG | B | 54 | −34.212 | 37.530 | 42.032 | 1.00 | 30.21 | C |
| ATOM | 1299 | NE | ARG | B | 54 | −34.407 | 38.753 | 41.234 | 1.00 | 31.75 | N |
| ATOM | 1300 | CZ | ARG | B | 54 | −33.979 | 38.962 | 39.977 | 1.00 | 32.55 | C |
| ATOM | 1301 | NH1 | ARG | B | 54 | −33.278 | 38.042 | 39.305 | 1.00 | 33.03 | N |
| ATOM | 1302 | NH2 | ARG | B | 54 | −34.248 | 40.126 | 39.390 | 1.00 | 31.95 | N |
| ATOM | 1303 | N | TYR | B | 55 | −29.293 | 40.089 | 43.991 | 1.00 | 23.32 | N |
| ATOM | 1304 | CA | TYR | B | 55 | −28.022 | 40.699 | 43.607 | 1.00 | 23.27 | C |
| ATOM | 1305 | C | TYR | B | 55 | −26.985 | 40.714 | 44.741 | 1.00 | 22.65 | C |
| ATOM | 1306 | O | TYR | B | 55 | −27.022 | 41.627 | 45.569 | 1.00 | 23.40 | O |
| ATOM | 1307 | CB | TYR | B | 55 | −28.280 | 42.156 | 43.200 | 1.00 | 23.51 | C |
| ATOM | 1308 | CG | TYR | B | 55 | −29.332 | 42.366 | 42.128 | 1.00 | 25.16 | C |
| ATOM | 1309 | CD1 | TYR | B | 55 | −30.554 | 42.974 | 42.433 | 1.00 | 27.40 | C |
| ATOM | 1310 | CD2 | TYR | B | 55 | −29.098 | 41.990 | 40.809 | 1.00 | 25.31 | C |
| ATOM | 1311 | CE1 | TYR | B | 55 | −31.526 | 43.176 | 41.448 | 1.00 | 28.63 | C |
| ATOM | 1312 | CE2 | TYR | B | 55 | −30.052 | 42.193 | 39.814 | 1.00 | 27.21 | C |
| ATOM | 1313 | CZ | TYR | B | 55 | −31.262 | 42.784 | 40.136 | 1.00 | 29.16 | C |
| ATOM | 1314 | OH | TYR | B | 55 | −32.216 | 42.985 | 39.165 | 1.00 | 30.31 | O |
| ATOM | 1315 | N | VAL | B | 56 | −26.068 | 39.741 | 44.814 | 1.00 | 21.32 | N |
| ATOM | 1316 | CA | VAL | B | 56 | −25.013 | 39.817 | 45.831 | 1.00 | 20.28 | C |
| ATOM | 1317 | C | VAL | B | 56 | −23.637 | 40.141 | 45.224 | 1.00 | 19.36 | C |
| ATOM | 1318 | O | VAL | B | 56 | −23.141 | 39.458 | 44.307 | 1.00 | 18.27 | O |
| ATOM | 1319 | CB | VAL | B | 56 | −24.976 | 38.592 | 46.817 | 1.00 | 20.58 | C |
| ATOM | 1320 | CG1 | VAL | B | 56 | −26.399 | 38.065 | 47.118 | 1.00 | 20.96 | C |
| ATOM | 1321 | CG2 | VAL | B | 56 | −24.080 | 37.497 | 46.328 | 1.00 | 21.01 | C |
| ATOM | 1322 | N | GLU | B | 57 | −23.075 | 41.249 | 45.707 | 1.00 | 18.11 | N |
| ATOM | 1323 | CA | GLU | B | 57 | −21.745 | 41.689 | 45.348 | 1.00 | 17.19 | C |
| ATOM | 1324 | C | GLU | B | 57 | −20.708 | 41.168 | 46.343 | 1.00 | 16.51 | C |

APPENDIX I(b)-continued

| ATOM | 1325 | O | GLU | B | 57 | −20.935 | 41.148 | 47.548 | 1.00 | 17.87 | O |
|---|---|---|---|---|---|---|---|---|---|---|---|
| ATOM | 1326 | CB | GLU | B | 57 | −21.689 | 43.211 | 45.299 | 1.00 | 17.51 | C |
| ATOM | 1327 | CG | GLU | B | 57 | −20.379 | 43.725 | 44.737 | 1.00 | 16.73 | C |
| ATOM | 1328 | CD | GLU | B | 57 | −20.183 | 45.223 | 44.875 | 1.00 | 17.23 | C |
| ATOM | 1329 | OE1 | GLU | B | 57 | −20.587 | 45.808 | 45.907 | 1.00 | 18.09 | O |
| ATOM | 1330 | OE2 | GLU | B | 57 | −19.597 | 45.818 | 43.938 | 1.00 | 13.96 | O |
| ATOM | 1331 | N | THR | B | 58 | −19.571 | 40.742 | 45.826 | 1.00 | 15.66 | N |
| ATOM | 1332 | CA | THR | B | 58 | −18.425 | 40.374 | 46.630 | 1.00 | 15.37 | C |
| ATOM | 1333 | C | THR | B | 58 | −17.281 | 41.269 | 46.156 | 1.00 | 15.05 | C |
| ATOM | 1334 | O | THR | B | 58 | −16.978 | 41.276 | 44.986 | 1.00 | 14.93 | O |
| ATOM | 1335 | CB | THR | B | 58 | −18.058 | 38.900 | 46.381 | 1.00 | 15.38 | C |
| ATOM | 1336 | OG1 | THR | B | 58 | −19.184 | 38.058 | 46.659 | 1.00 | 14.54 | O |
| ATOM | 1337 | CG2 | THR | B | 58 | −16.981 | 38.447 | 47.346 | 1.00 | 16.33 | C |
| ATOM | 1338 | N | VAL | B | 59 | −16.665 | 42.012 | 47.064 | 1.00 | 14.77 | N |
| ATOM | 1339 | CA | VAL | B | 59 | −15.529 | 42.862 | 46.748 | 1.00 | 15.29 | C |
| ATOM | 1340 | C | VAL | B | 59 | −14.298 | 42.387 | 47.510 | 1.00 | 15.36 | C |
| ATOM | 1341 | O | VAL | B | 59 | −14.342 | 42.194 | 48.728 | 1.00 | 14.34 | O |
| ATOM | 1342 | CB | VAL | B | 59 | −15.814 | 44.337 | 47.101 | 1.00 | 14.87 | C |
| ATOM | 1343 | CG1 | VAL | B | 59 | −14.650 | 45.211 | 46.733 | 1.00 | 15.38 | C |
| ATOM | 1344 | CG2 | VAL | B | 59 | −17.081 | 44.826 | 46.388 | 1.00 | 16.71 | C |
| ATOM | 1345 | N | ASN | B | 60 | −13.209 | 42.205 | 46.767 | 1.00 | 16.17 | N |
| ATOM | 1346 | CA | ASN | B | 60 | −11.895 | 41.886 | 47.303 | 1.00 | 17.20 | C |
| ATOM | 1347 | C | ASN | B | 60 | −10.940 | 43.002 | 46.931 | 1.00 | 17.56 | C |
| ATOM | 1348 | O | ASN | B | 60 | −10.420 | 43.048 | 45.813 | 1.00 | 16.19 | O |
| ATOM | 1349 | CB | ASN | B | 60 | −11.397 | 40.536 | 46.770 | 1.00 | 17.33 | C |
| ATOM | 1350 | CG | ASN | B | 60 | −12.368 | 39.418 | 47.033 | 1.00 | 20.49 | C |
| ATOM | 1351 | OD1 | ASN | B | 60 | −12.978 | 38.869 | 46.103 | 1.00 | 27.00 | O |
| ATOM | 1352 | ND2 | ASN | B | 60 | −12.538 | 39.068 | 48.309 | 1.00 | 24.14 | N |
| ATOM | 1353 | N | LYS | B | 61 | −10.725 | 43.930 | 47.860 | 1.00 | 18.73 | N |
| ATOM | 1354 | CA | LYS | B | 61 | −9.984 | 45.152 | 47.523 | 1.00 | 20.20 | C |
| ATOM | 1355 | C | LYS | B | 61 | −8.524 | 44.868 | 47.247 | 1.00 | 20.68 | C |
| ATOM | 1356 | O | LYS | B | 61 | −7.929 | 45.496 | 46.389 | 1.00 | 20.73 | O |
| ATOM | 1357 | CB | LYS | B | 61 | −10.056 | 46.190 | 48.628 | 1.00 | 20.55 | C |
| ATOM | 1358 | CG | LYS | B | 61 | −11.155 | 47.169 | 48.436 | 1.00 | 22.89 | C |
| ATOM | 1359 | CD | LYS | B | 61 | −11.078 | 48.286 | 49.467 | 1.00 | 26.16 | C |
| ATOM | 1360 | CE | LYS | B | 61 | −12.306 | 49.166 | 49.399 | 1.00 | 27.62 | C |
| ATOM | 1361 | NZ | LYS | B | 61 | −13.300 | 48.623 | 48.388 | 1.00 | 29.13 | N |
| ATOM | 1362 | N | GLY | B | 62 | −7.961 | 43.930 | 47.994 | 1.00 | 21.46 | N |
| ATOM | 1363 | CA | GLY | B | 62 | −6.559 | 43.575 | 47.852 | 1.00 | 22.44 | C |
| ATOM | 1364 | C | GLY | B | 62 | −6.243 | 43.175 | 46.423 | 1.00 | 22.90 | C |
| ATOM | 1365 | O | GLY | B | 62 | −5.297 | 43.708 | 45.842 | 1.00 | 24.02 | O |
| ATOM | 1366 | N | SER | B | 63 | −7.067 | 42.279 | 45.874 | 1.00 | 22.81 | N |
| ATOM | 1367 | CA | SER | B | 63 | −6.944 | 41.770 | 44.511 | 1.00 | 23.15 | C |
| ATOM | 1368 | C | SER | B | 63 | −7.628 | 42.667 | 43.487 | 1.00 | 23.09 | C |
| ATOM | 1369 | O | SER | B | 63 | −7.706 | 42.330 | 42.312 | 1.00 | 23.32 | O |
| ATOM | 1370 | CB | SER | B | 63 | −7.550 | 40.373 | 44.429 | 1.00 | 23.09 | C |
| ATOM | 1371 | OG | SER | B | 63 | −8.972 | 40.441 | 44.436 | 1.00 | 23.15 | O |
| ATOM | 1372 | N | LYS | B | 64 | −8.154 | 43.793 | 43.960 | 1.00 | 22.85 | N |
| ATOM | 1373 | CA | LYS | B | 64 | −8.785 | 44.801 | 43.138 | 1.00 | 22.19 | C |
| ATOM | 1374 | C | LYS | B | 64 | −9.942 | 44.238 | 42.309 | 1.00 | 21.21 | C |
| ATOM | 1375 | O | LYS | B | 64 | −10.214 | 44.712 | 41.204 | 1.00 | 19.51 | O |
| ATOM | 1376 | CB | LYS | B | 64 | −7.737 | 45.482 | 42.255 | 1.00 | 23.45 | C |
| ATOM | 1377 | CG | LYS | B | 64 | −6.574 | 46.121 | 43.043 | 1.00 | 25.37 | C |
| ATOM | 1378 | CD | LYS | B | 64 | −6.368 | 47.592 | 42.640 | 1.00 | 28.91 | C |
| ATOM | 1379 | CE | LYS | B | 64 | −4.962 | 48.125 | 42.973 | 1.00 | 30.56 | C |
| ATOM | 1380 | NZ | LYS | B | 64 | −4.919 | 49.645 | 42.954 | 1.00 | 31.78 | N |
| ATOM | 1381 | N | SER | B | 65 | −10.630 | 43.234 | 42.850 | 1.00 | 19.74 | N |
| ATOM | 1382 | CA | SER | B | 65 | −11.720 | 42.615 | 42.118 | 1.00 | 19.85 | C |
| ATOM | 1383 | C | SER | B | 65 | −13.073 | 42.732 | 42.831 | 1.00 | 18.80 | C |
| ATOM | 1384 | O | SER | B | 65 | −13.165 | 42.809 | 44.057 | 1.00 | 17.00 | O |
| ATOM | 1385 | CB | SER | B | 65 | −11.398 | 41.177 | 41.757 | 1.00 | 20.53 | C |
| ATOM | 1386 | OG | SER | B | 65 | −10.882 | 40.462 | 42.843 | 1.00 | 23.59 | O |
| ATOM | 1387 | N | PHE | B | 66 | −14.104 | 42.817 | 42.010 | 1.00 | 18.42 | N |
| ATOM | 1388 | CA | PHE | B | 66 | −15.463 | 42.953 | 42.454 | 1.00 | 19.37 | C |
| ATOM | 1389 | C | PHE | B | 66 | −16.404 | 42.203 | 41.511 | 1.00 | 19.75 | C |
| ATOM | 1390 | O | PHE | B | 66 | −16.303 | 42.317 | 40.285 | 1.00 | 20.89 | O |
| ATOM | 1391 | CB | PHE | B | 66 | −15.867 | 44.435 | 42.664 | 1.00 | 19.52 | C |
| ATOM | 1392 | CG | PHE | B | 66 | −15.477 | 45.392 | 41.550 | 1.00 | 19.35 | C |
| ATOM | 1393 | CD1 | PHE | B | 66 | −14.162 | 45.594 | 41.201 | 1.00 | 19.89 | C |
| ATOM | 1394 | CD2 | PHE | B | 66 | −16.447 | 46.173 | 40.942 | 1.00 | 22.22 | C |
| ATOM | 1395 | CE1 | PHE | B | 66 | −13.817 | 46.489 | 40.211 | 1.00 | 23.28 | C |
| ATOM | 1396 | CE2 | PHE | B | 66 | −16.121 | 47.079 | 39.942 | 1.00 | 22.06 | C |
| ATOM | 1397 | CZ | PHE | B | 66 | −14.804 | 47.239 | 39.577 | 1.00 | 24.56 | C |
| ATOM | 1398 | N | SER | B | 67 | −17.301 | 41.407 | 42.089 | 1.00 | 19.90 | N |
| ATOM | 1399 | CA | SER | B | 67 | −18.226 | 40.596 | 41.307 | 1.00 | 20.00 | C |
| ATOM | 1400 | C | SER | B | 67 | −19.671 | 40.698 | 41.776 | 1.00 | 19.50 | C |
| ATOM | 1401 | O | SER | B | 67 | −19.951 | 41.023 | 42.915 | 1.00 | 19.54 | O |
| ATOM | 1402 | CB | SER | B | 67 | −17.786 | 39.139 | 41.278 | 1.00 | 19.89 | C |
| ATOM | 1403 | OG | SER | B | 67 | −17.691 | 38.597 | 42.569 | 1.00 | 23.57 | O |
| ATOM | 1404 | N | LEU | B | 68 | −20.580 | 40.428 | 40.848 | 1.00 | 18.79 | N |

APPENDIX I(b)-continued

| | | | | | | | | | | |
|---|---|---|---|---|---|---|---|---|---|---|
| ATOM | 1405 | CA | LEU | B | 68 | −21.998 | 40.461 | 41.082 | 1.00 | 18.33 | C |
| ATOM | 1406 | C | LEU | B | 68 | −22.553 | 39.108 | 40.665 | 1.00 | 18.42 | C |
| ATOM | 1407 | O | LEU | B | 68 | −22.380 | 38.712 | 39.524 | 1.00 | 18.10 | O |
| ATOM | 1408 | CB | LEU | B | 68 | −22.615 | 41.528 | 40.194 | 1.00 | 18.09 | C |
| ATOM | 1409 | CG | LEU | B | 68 | −23.841 | 42.366 | 40.571 | 1.00 | 18.46 | C |
| ATOM | 1410 | CD1 | LEU | B | 68 | −24.726 | 42.505 | 39.396 | 1.00 | 18.36 | C |
| ATOM | 1411 | CD2 | LEU | B | 68 | −24.609 | 41.922 | 41.814 | 1.00 | 17.75 | C |
| ATOM | 1412 | N | ARG | B | 69 | −23.194 | 38.406 | 41.587 | 1.00 | 18.74 | N |
| ATOM | 1413 | CA | ARG | B | 69 | −23.923 | 37.179 | 41.278 | 1.00 | 19.25 | C |
| ATOM | 1414 | C | ARG | B | 69 | −25.429 | 37.453 | 41.352 | 1.00 | 19.35 | C |
| ATOM | 1415 | O | ARG | B | 69 | −25.948 | 37.865 | 42.402 | 1.00 | 18.55 | O |
| ATOM | 1416 | CB | ARG | B | 69 | −23.547 | 36.057 | 42.238 | 1.00 | 19.56 | C |
| ATOM | 1417 | CG | ARG | B | 69 | −24.193 | 34.712 | 41.888 | 1.00 | 21.15 | C |
| ATOM | 1418 | CD | ARG | B | 69 | −23.508 | 33.525 | 42.544 | 1.00 | 23.00 | C |
| ATOM | 1419 | NE | ARG | B | 69 | −23.997 | 32.225 | 42.077 | 1.00 | 23.21 | N |
| ATOM | 1420 | CZ | ARG | B | 69 | −24.973 | 31.514 | 42.651 | 1.00 | 26.91 | C |
| ATOM | 1421 | NH1 | ARG | B | 69 | −25.607 | 31.945 | 43.746 | 1.00 | 27.11 | N |
| ATOM | 1422 | NH2 | ARG | B | 69 | −25.322 | 30.340 | 42.124 | 1.00 | 27.81 | N |
| ATOM | 1423 | N | ILE | B | 70 | −26.108 | 37.270 | 40.222 | 1.00 | 19.75 | N |
| ATOM | 1424 | CA | ILE | B | 70 | −27.553 | 37.452 | 40.117 | 1.00 | 20.46 | C |
| ATOM | 1425 | C | ILE | B | 70 | −28.187 | 36.081 | 40.074 | 1.00 | 20.76 | C |
| ATOM | 1426 | O | ILE | B | 70 | −27.852 | 35.304 | 39.201 | 1.00 | 19.79 | O |
| ATOM | 1427 | CB | ILE | B | 70 | −27.914 | 38.220 | 38.829 | 1.00 | 20.68 | C |
| ATOM | 1428 | CG1 | ILE | B | 70 | −27.058 | 39.472 | 38.680 | 1.00 | 21.64 | C |
| ATOM | 1429 | CG2 | ILE | B | 70 | −29.385 | 38.622 | 38.815 | 1.00 | 20.79 | C |
| ATOM | 1430 | CD1 | ILE | B | 70 | −27.131 | 40.061 | 37.288 | 1.00 | 23.84 | C |
| ATOM | 1431 | N | SER | B | 71 | −29.106 | 35.794 | 41.013 | 1.00 | 21.41 | N |
| ATOM | 1432 | CA | SER | B | 71 | −29.778 | 34.489 | 41.114 | 1.00 | 22.13 | C |
| ATOM | 1433 | C | SER | B | 71 | −31.295 | 34.535 | 40.702 | 1.00 | 22.62 | C |
| ATOM | 1434 | O | SER | B | 71 | −31.913 | 35.609 | 40.661 | 1.00 | 22.56 | O |
| ATOM | 1435 | CB | SER | B | 71 | −29.633 | 33.953 | 42.548 | 1.00 | 22.67 | C |
| ATOM | 1436 | OG | SER | B | 71 | −30.156 | 34.874 | 43.500 | 1.00 | 22.85 | O |
| ATOM | 1437 | N | ASP | B | 72 | −31.867 | 33.370 | 40.373 | 1.00 | 23.13 | N |
| ATOM | 1438 | CA | ASP | B | 72 | −33.302 | 33.248 | 39.942 | 1.00 | 23.77 | C |
| ATOM | 1439 | C | ASP | B | 72 | −33.660 | 34.144 | 38.730 | 1.00 | 23.69 | C |
| ATOM | 1440 | O | ASP | B | 72 | −34.691 | 34.924 | 38.744 | 1.00 | 24.26 | O |
| ATOM | 1441 | CB | ASP | B | 72 | −34.234 | 33.567 | 41.120 | 1.00 | 23.85 | C |
| ATOM | 1442 | CG | ASP | B | 72 | −35.733 | 33.299 | 40.809 | 1.00 | 26.52 | C |
| ATOM | 1443 | OD1 | ASP | B | 72 | −36.086 | 32.403 | 39.975 | 1.00 | 28.52 | O |
| ATOM | 1444 | OD2 | ASP | B | 72 | −36.650 | 33.939 | 41.381 | 1.00 | 27.73 | O |
| ATOM | 1445 | N | LEU | B | 73 | −32.763 | 34.051 | 37.704 | 1.00 | 23.03 | N |
| ATOM | 1446 | CA | LEU | B | 73 | −32.827 | 34.936 | 36.552 | 1.00 | 22.50 | C |
| ATOM | 1447 | C | LEU | B | 73 | −34.185 | 34.813 | 35.870 | 1.00 | 22.48 | C |
| ATOM | 1448 | O | LEU | B | 73 | −34.819 | 33.754 | 35.886 | 1.00 | 22.20 | O |
| ATOM | 1449 | CB | LEU | B | 73 | −31.678 | 34.664 | 35.562 | 1.00 | 22.31 | C |
| ATOM | 1450 | CG | LEU | B | 73 | −30.259 | 35.096 | 35.998 | 1.00 | 20.96 | C |
| ATOM | 1451 | CD1 | LEU | B | 73 | −29.192 | 34.406 | 35.158 | 1.00 | 21.05 | C |
| ATOM | 1452 | CD2 | LEU | B | 73 | −30.062 | 36.598 | 35.937 | 1.00 | 20.29 | C |
| ATOM | 1453 | N | ARG | B | 74 | −34.630 | 35.917 | 35.285 | 1.00 | 22.48 | N |
| ATOM | 1454 | CA | ARG | B | 74 | −35.889 | 35.960 | 34.554 | 1.00 | 22.53 | C |
| ATOM | 1455 | C | ARG | B | 74 | −35.647 | 36.673 | 33.230 | 1.00 | 21.88 | C |
| ATOM | 1456 | O | ARG | B | 74 | −34.612 | 37.320 | 33.046 | 1.00 | 20.92 | O |
| ATOM | 1457 | CB | ARG | B | 74 | −36.939 | 36.677 | 35.391 | 1.00 | 23.31 | C |
| ATOM | 1458 | CG | ARG | B | 74 | −36.941 | 36.233 | 36.866 | 1.00 | 26.36 | C |
| ATOM | 1459 | CD | ARG | B | 74 | −38.018 | 36.857 | 37.719 | 1.00 | 30.47 | C |
| ATOM | 1460 | NE | ARG | B | 74 | −37.625 | 38.189 | 38.197 | 1.00 | 33.76 | N |
| ATOM | 1461 | CZ | ARG | B | 74 | −38.058 | 39.348 | 37.687 | 1.00 | 35.80 | C |
| ATOM | 1462 | NH1 | ARG | B | 74 | −37.633 | 40.495 | 38.218 | 1.00 | 36.67 | N |
| ATOM | 1463 | NH2 | ARG | B | 74 | −38.905 | 39.378 | 36.654 | 1.00 | 35.80 | N |
| ATOM | 1464 | N | VAL | B | 75 | −36.584 | 36.542 | 32.298 | 1.00 | 21.12 | N |
| ATOM | 1465 | CA | VAL | B | 75 | −36.404 | 37.117 | 30.966 | 1.00 | 20.73 | C |
| ATOM | 1466 | C | VAL | B | 75 | −36.158 | 38.627 | 31.034 | 1.00 | 20.51 | C |
| ATOM | 1467 | O | VAL | B | 75 | −35.397 | 39.177 | 30.221 | 1.00 | 19.93 | O |
| ATOM | 1468 | CB | VAL | B | 75 | −37.606 | 36.808 | 30.050 | 1.00 | 20.73 | C |
| ATOM | 1469 | CG1 | VAL | B | 75 | −37.525 | 37.604 | 28.740 | 1.00 | 20.89 | C |
| ATOM | 1470 | CG2 | VAL | B | 75 | −37.661 | 35.314 | 29.753 | 1.00 | 20.79 | C |
| ATOM | 1471 | N | GLU | B | 76 | −36.781 | 39.270 | 32.024 | 1.00 | 20.02 | N |
| ATOM | 1472 | CA | GLU | B | 76 | −36.723 | 40.717 | 32.209 | 1.00 | 20.19 | C |
| ATOM | 1473 | C | GLU | B | 76 | −35.321 | 41.208 | 32.623 | 1.00 | 19.74 | C |
| ATOM | 1474 | O | GLU | B | 76 | −35.004 | 42.382 | 32.440 | 1.00 | 20.00 | O |
| ATOM | 1475 | CB | GLU | B | 76 | −37.790 | 41.154 | 33.244 | 1.00 | 20.38 | C |
| ATOM | 1476 | CG | GLU | B | 76 | −37.555 | 42.511 | 33.904 | 1.00 | 22.07 | C |
| ATOM | 1477 | CD | GLU | B | 76 | −38.751 | 43.040 | 34.673 | 1.00 | 24.50 | C |
| ATOM | 1478 | OE1 | GLU | B | 76 | −38.901 | 42.686 | 35.863 | 1.00 | 26.47 | O |
| ATOM | 1479 | OE2 | GLU | B | 76 | −39.544 | 43.817 | 34.087 | 1.00 | 26.87 | O |
| ATOM | 1480 | N | ASP | B | 77 | −34.504 | 40.314 | 33.185 | 1.00 | 19.27 | N |
| ATOM | 1481 | CA | ASP | B | 77 | −33.105 | 40.609 | 33.542 | 1.00 | 18.84 | C |
| ATOM | 1482 | C | ASP | B | 77 | −32.144 | 40.679 | 32.358 | 1.00 | 18.39 | C |
| ATOM | 1483 | O | ASP | B | 77 | −30.973 | 41.095 | 32.520 | 1.00 | 18.03 | O |
| ATOM | 1484 | CB | ASP | B | 77 | −32.572 | 39.564 | 34.531 | 1.00 | 19.00 | C |

APPENDIX I(b)-continued

| ATOM | 1485 | CG  | ASP | B | 77 | −33.338 | 39.553 | 35.836 | 1.00 | 19.95 | C |
|------|------|-----|-----|---|----|---------|--------|--------|------|-------|---|
| ATOM | 1486 | OD1 | ASP | B | 77 | −33.747 | 40.645 | 36.287 | 1.00 | 20.99 | O |
| ATOM | 1487 | OD2 | ASP | B | 77 | −33.586 | 38.504 | 36.470 | 1.00 | 20.23 | O |
| ATOM | 1488 | N   | SER | B | 78 | −32.603 | 40.255 | 31.183 | 1.00 | 17.22 | N |
| ATOM | 1489 | CA  | SER | B | 78 | −31.825 | 40.445 | 29.973 | 1.00 | 17.27 | C |
| ATOM | 1490 | C   | SER | B | 78 | −31.410 | 41.909 | 29.880 | 1.00 | 16.95 | C |
| ATOM | 1491 | O   | SER | B | 78 | −32.182 | 42.808 | 30.218 | 1.00 | 17.21 | O |
| ATOM | 1492 | CB  | SER | B | 78 | −32.623 | 40.060 | 28.714 | 1.00 | 17.26 | C |
| ATOM | 1493 | OG  | SER | B | 78 | −33.040 | 38.701 | 28.749 | 1.00 | 17.63 | O |
| ATOM | 1494 | N   | GLY | B | 79 | −30.195 | 42.147 | 29.405 | 1.00 | 16.58 | N |
| ATOM | 1495 | CA  | GLY | B | 79 | −29.696 | 43.501 | 29.261 | 1.00 | 16.32 | C |
| ATOM | 1496 | C   | GLY | B | 79 | −28.197 | 43.570 | 29.333 | 1.00 | 15.94 | C |
| ATOM | 1497 | O   | GLY | B | 79 | −27.520 | 42.550 | 29.407 | 1.00 | 15.54 | O |
| ATOM | 1498 | N   | THR | B | 80 | −27.679 | 44.788 | 29.314 | 1.00 | 15.66 | N |
| ATOM | 1499 | CA  | THR | B | 80 | −26.253 | 45.004 | 29.385 | 1.00 | 15.73 | C |
| ATOM | 1500 | C   | THR | B | 80 | −25.903 | 45.522 | 30.770 | 1.00 | 15.82 | C |
| ATOM | 1501 | O   | THR | B | 80 | −26.410 | 46.558 | 31.193 | 1.00 | 16.07 | O |
| ATOM | 1502 | CB  | THR | B | 80 | −25.830 | 45.984 | 28.287 | 1.00 | 15.80 | C |
| ATOM | 1503 | OG1 | THR | B | 80 | −26.002 | 45.369 | 27.000 | 1.00 | 15.74 | O |
| ATOM | 1504 | CG2 | THR | B | 80 | −24.334 | 46.296 | 28.374 | 1.00 | 15.85 | C |
| ATOM | 1505 | N   | TYR | B | 81 | −25.045 | 44.774 | 31.461 | 1.00 | 15.97 | N |
| ATOM | 1506 | CA  | TYR | B | 81 | −24.585 | 45.082 | 32.807 | 1.00 | 16.35 | C |
| ATOM | 1507 | C   | TYR | B | 81 | −23.181 | 45.663 | 32.775 | 1.00 | 16.12 | C |
| ATOM | 1508 | O   | TYR | B | 81 | −22.326 | 45.216 | 31.999 | 1.00 | 16.10 | O |
| ATOM | 1509 | CB  | TYR | B | 81 | −24.590 | 43.808 | 33.669 | 1.00 | 16.87 | C |
| ATOM | 1510 | CG  | TYR | B | 81 | −25.986 | 43.276 | 33.931 | 1.00 | 17.11 | C |
| ATOM | 1511 | CD1 | TYR | B | 81 | −26.565 | 43.384 | 35.186 | 1.00 | 16.85 | C |
| ATOM | 1512 | CD2 | TYR | B | 81 | −26.739 | 42.686 | 32.916 | 1.00 | 16.44 | C |
| ATOM | 1513 | CE1 | TYR | B | 81 | −27.856 | 42.911 | 35.443 | 1.00 | 15.57 | C |
| ATOM | 1514 | CE2 | TYR | B | 81 | −28.051 | 42.219 | 33.163 | 1.00 | 15.21 | C |
| ATOM | 1515 | CZ  | TYR | B | 81 | −28.596 | 42.326 | 34.431 | 1.00 | 14.59 | C |
| ATOM | 1516 | OH  | TYR | B | 81 | −29.886 | 41.875 | 34.722 | 1.00 | 12.32 | O |
| ATOM | 1517 | N   | LYS | B | 82 | −22.943 | 46.662 | 33.611 | 1.00 | 16.11 | N |
| ATOM | 1518 | CA  | LYS | B | 82 | −21.618 | 47.268 | 33.736 | 1.00 | 16.55 | C |
| ATOM | 1519 | C   | LYS | B | 82 | −21.290 | 47.528 | 35.202 | 1.00 | 16.62 | C |
| ATOM | 1520 | O   | LYS | B | 82 | −22.154 | 47.904 | 35.987 | 1.00 | 17.10 | O |
| ATOM | 1521 | CB  | LYS | B | 82 | −21.543 | 48.567 | 32.938 | 1.00 | 16.71 | C |
| ATOM | 1522 | CG  | LYS | B | 82 | −21.334 | 48.337 | 31.463 | 1.00 | 17.46 | C |
| ATOM | 1523 | CD  | LYS | B | 82 | −21.201 | 49.623 | 30.709 | 1.00 | 18.30 | C |
| ATOM | 1524 | CE  | LYS | B | 82 | −21.401 | 49.380 | 29.236 | 1.00 | 19.09 | C |
| ATOM | 1525 | NZ  | LYS | B | 82 | −21.113 | 50.617 | 28.492 | 1.00 | 21.44 | N |
| ATOM | 1526 | N   | CYS | B | 83 | −20.036 | 47.301 | 35.550 | 1.00 | 16.49 | N |
| ATOM | 1527 | CA  | CYS | B | 83 | −19.504 | 47.644 | 36.852 | 1.00 | 17.38 | C |
| ATOM | 1528 | C   | CYS | B | 83 | −18.682 | 48.929 | 36.761 | 1.00 | 17.36 | C |
| ATOM | 1529 | O   | CYS | B | 83 | −18.203 | 49.275 | 35.699 | 1.00 | 18.22 | O |
| ATOM | 1530 | CB  | CYS | B | 83 | −18.606 | 46.514 | 37.328 | 1.00 | 18.04 | C |
| ATOM | 1531 | SG  | CYS | B | 83 | −17.223 | 46.143 | 36.230 | 1.00 | 19.55 | S |
| ATOM | 1532 | N   | GLN | B | 84 | −18.522 | 49.647 | 37.862 | 1.00 | 17.20 | N |
| ATOM | 1533 | CA  | GLN | B | 84 | −17.693 | 50.849 | 37.870 | 1.00 | 17.02 | C |
| ATOM | 1534 | C   | GLN | B | 84 | −16.913 | 50.936 | 39.156 | 1.00 | 16.97 | C |
| ATOM | 1535 | O   | GLN | B | 84 | −17.444 | 50.623 | 40.223 | 1.00 | 16.56 | O |
| ATOM | 1536 | CB  | GLN | B | 84 | −18.525 | 52.109 | 37.748 | 1.00 | 17.35 | C |
| ATOM | 1537 | CG  | GLN | B | 84 | −17.666 | 53.383 | 37.630 | 1.00 | 18.26 | C |
| ATOM | 1538 | CD  | GLN | B | 84 | −18.275 | 54.425 | 36.724 | 1.00 | 20.08 | C |
| ATOM | 1539 | OE1 | GLN | B | 84 | −17.572 | 55.069 | 35.941 | 1.00 | 23.24 | O |
| ATOM | 1540 | NE2 | GLN | B | 84 | −19.570 | 54.603 | 36.828 | 1.00 | 18.52 | N |
| ATOM | 1541 | N   | ALA | B | 85 | −15.653 | 51.358 | 39.031 | 1.00 | 16.63 | N |
| ATOM | 1542 | CA  | ALA | B | 85 | −14.775 | 51.612 | 40.166 | 1.00 | 16.67 | C |
| ATOM | 1543 | C   | ALA | B | 85 | −14.937 | 53.058 | 40.599 | 1.00 | 16.25 | C |
| ATOM | 1544 | O   | ALA | B | 85 | −15.165 | 53.933 | 39.767 | 1.00 | 16.09 | O |
| ATOM | 1545 | CB  | ALA | B | 85 | −13.288 | 51.341 | 39.783 | 1.00 | 16.01 | C |
| ATOM | 1546 | N   | PHE | B | 86 | −14.767 | 53.283 | 41.897 | 1.00 | 16.14 | N |
| ATOM | 1547 | CA  | PHE | B | 86 | −14.710 | 54.606 | 42.488 | 1.00 | 16.71 | C |
| ATOM | 1548 | C   | PHE | B | 86 | −13.449 | 54.774 | 43.339 | 1.00 | 16.53 | C |
| ATOM | 1549 | O   | PHE | B | 86 | −12.977 | 53.828 | 43.967 | 1.00 | 15.05 | O |
| ATOM | 1550 | CB  | PHE | B | 86 | −15.910 | 54.831 | 43.403 | 1.00 | 17.17 | C |
| ATOM | 1551 | CG  | PHE | B | 86 | −17.195 | 54.931 | 42.676 | 1.00 | 18.63 | C |
| ATOM | 1552 | CD1 | PHE | B | 86 | −17.871 | 53.797 | 42.296 | 1.00 | 18.73 | C |
| ATOM | 1553 | CD2 | PHE | B | 86 | −17.730 | 56.170 | 42.371 | 1.00 | 21.86 | C |
| ATOM | 1554 | CE1 | PHE | B | 86 | −19.047 | 53.881 | 41.600 | 1.00 | 20.98 | C |
| ATOM | 1555 | CE2 | PHE | B | 86 | −18.916 | 56.265 | 41.679 | 1.00 | 23.65 | C |
| ATOM | 1556 | CZ  | PHE | B | 86 | −19.578 | 55.103 | 41.290 | 1.00 | 22.79 | C |
| ATOM | 1557 | N   | TYR | B | 87 | −12.961 | 56.014 | 43.379 | 1.00 | 17.00 | N |
| ATOM | 1558 | CA  | TYR | B | 87 | −11.781 | 56.396 | 44.122 | 1.00 | 17.28 | C |
| ATOM | 1559 | C   | TYR | B | 87 | −12.120 | 57.517 | 45.070 | 1.00 | 18.27 | C |
| ATOM | 1560 | O   | TYR | B | 87 | −13.229 | 58.030 | 45.038 | 1.00 | 17.26 | O |
| ATOM | 1561 | CB  | TYR | B | 87 | −10.746 | 56.915 | 43.139 | 1.00 | 17.73 | C |
| ATOM | 1562 | CG  | TYR | B | 87 | −10.346 | 55.916 | 42.097 | 1.00 | 16.88 | C |
| ATOM | 1563 | CD1 | TYR | B | 87 | −10.367 | 56.245 | 40.752 | 1.00 | 17.20 | C |
| ATOM | 1564 | CD2 | TYR | B | 87 | −9.946  | 54.629 | 42.459 | 1.00 | 17.73 | C |

APPENDIX I(b)-continued

| | | | | | | | | | | |
|---|---|---|---|---|---|---|---|---|---|---|
| ATOM | 1565 | CE1 | TYR | B | 87 | −9.982 | 55.327 | 39.782 | 1.00 | 17.23 | C |
| ATOM | 1566 | CE2 | TYR | B | 87 | −9.553 | 53.697 | 41.496 | 1.00 | 18.63 | C |
| ATOM | 1567 | CZ | TYR | B | 87 | −9.577 | 54.054 | 40.154 | 1.00 | 18.65 | C |
| ATOM | 1568 | OH | TYR | B | 87 | −9.190 | 53.137 | 39.183 | 1.00 | 19.23 | O |
| ATOM | 1569 | N | SER | B | 88 | −11.152 | 57.919 | 45.891 | 1.00 | 19.12 | N |
| ATOM | 1570 | CA | SER | B | 88 | −11.294 | 59.134 | 46.674 | 1.00 | 20.75 | C |
| ATOM | 1571 | C | SER | B | 88 | −9.993 | 59.942 | 46.761 | 1.00 | 22.29 | C |
| ATOM | 1572 | O | SER | B | 88 | −8.890 | 59.421 | 46.612 | 1.00 | 22.12 | O |
| ATOM | 1573 | CB | SER | B | 88 | −11.789 | 58.819 | 48.096 | 1.00 | 20.72 | C |
| ATOM | 1574 | OG | SER | B | 88 | −10.788 | 58.145 | 48.827 | 1.00 | 20.04 | O |
| ATOM | 1575 | N | LEU | B | 89 | −10.139 | 61.227 | 47.018 | 1.00 | 24.28 | N |
| ATOM | 1576 | CA | LEU | B | 89 | −8.987 | 62.040 | 47.362 | 1.00 | 26.19 | C |
| ATOM | 1577 | C | LEU | B | 89 | −9.266 | 62.856 | 48.625 | 1.00 | 27.08 | C |
| ATOM | 1578 | O | LEU | B | 89 | −10.419 | 63.118 | 48.968 | 1.00 | 26.58 | O |
| ATOM | 1579 | CB | LEU | B | 89 | −8.557 | 62.907 | 46.171 | 1.00 | 26.68 | C |
| ATOM | 1580 | CG | LEU | B | 89 | −9.445 | 64.001 | 45.544 | 1.00 | 28.47 | C |
| ATOM | 1581 | CD1 | LEU | B | 89 | −9.280 | 63.988 | 44.028 | 1.00 | 28.80 | C |
| ATOM | 1582 | CD2 | LEU | B | 89 | −10.922 | 63.909 | 45.883 | 1.00 | 29.53 | C |
| ATOM | 1583 | N | PRO | B | 90 | −8.223 | 63.187 | 49.372 | 1.00 | 28.97 | N |
| ATOM | 1584 | CA | PRO | B | 90 | −8.336 | 64.275 | 50.351 | 1.00 | 29.81 | C |
| ATOM | 1585 | C | PRO | B | 90 | −8.264 | 65.614 | 49.611 | 1.00 | 30.96 | C |
| ATOM | 1586 | O | PRO | B | 90 | −7.366 | 65.718 | 48.772 | 1.00 | 31.41 | O |
| ATOM | 1587 | CB | PRO | B | 90 | −7.118 | 64.072 | 51.260 | 1.00 | 29.62 | C |
| ATOM | 1588 | CG | PRO | B | 90 | −6.516 | 62.752 | 50.856 | 1.00 | 29.50 | C |
| ATOM | 1589 | CD | PRO | B | 90 | −6.899 | 62.539 | 49.417 | 1.00 | 29.26 | C |
| ATOM | 1590 | N | LEU | B | 91 | −9.127 | 66.610 | 49.864 | 1.00 | 32.14 | N |
| ATOM | 1591 | CA | LEU | B | 91 | −10.181 | 66.619 | 50.890 | 1.00 | 32.64 | C |
| ATOM | 1592 | C | LEU | B | 91 | −9.654 | 66.206 | 52.261 | 1.00 | 32.94 | C |
| ATOM | 1593 | O | LEU | B | 91 | −9.912 | 65.096 | 52.744 | 1.00 | 33.37 | O |
| ATOM | 1594 | CB | LEU | B | 91 | −11.402 | 65.789 | 50.453 | 1.00 | 33.03 | C |
| ATOM | 1595 | CG | LEU | B | 91 | −12.780 | 66.333 | 50.876 | 1.00 | 33.50 | C |
| ATOM | 1596 | CD1 | LEU | B | 91 | −12.873 | 66.545 | 52.382 | 1.00 | 33.54 | C |
| ATOM | 1597 | CD2 | LEU | B | 91 | −13.093 | 67.641 | 50.143 | 1.00 | 33.79 | C |
| ATOM | 1598 | N | GLY | B | 92 | −8.924 | 67.132 | 52.874 | 1.00 | 32.78 | N |
| ATOM | 1599 | CA | GLY | B | 92 | −8.174 | 66.865 | 54.078 | 1.00 | 32.66 | C |
| ATOM | 1600 | C | GLY | B | 92 | −8.970 | 67.126 | 55.336 | 1.00 | 32.67 | C |
| ATOM | 1601 | O | GLY | B | 92 | −8.948 | 68.230 | 55.894 | 1.00 | 31.99 | O |
| ATOM | 1602 | N | ASP | B | 93 | −9.696 | 66.098 | 55.765 | 1.00 | 32.42 | N |
| ATOM | 1603 | CA | ASP | B | 93 | −10.223 | 66.050 | 57.131 | 1.00 | 32.02 | C |
| ATOM | 1604 | C | ASP | B | 93 | −10.482 | 64.577 | 57.505 | 1.00 | 31.47 | C |
| ATOM | 1605 | O | ASP | B | 93 | −10.682 | 63.721 | 56.621 | 1.00 | 30.74 | O |
| ATOM | 1606 | CB | ASP | B | 93 | −11.468 | 66.936 | 57.272 | 1.00 | 32.07 | C |
| ATOM | 1607 | CG | ASP | B | 93 | −12.260 | 66.640 | 58.522 | 1.00 | 32.22 | C |
| ATOM | 1608 | OD1 | ASP | B | 93 | −13.295 | 65.950 | 58.415 | 1.00 | 32.43 | O |
| ATOM | 1609 | OD2 | ASP | B | 93 | −11.915 | 67.035 | 59.657 | 1.00 | 33.64 | O |
| ATOM | 1610 | N | TYR | B | 94 | −10.421 | 64.287 | 58.808 | 1.00 | 30.71 | N |
| ATOM | 1611 | CA | TYR | B | 94 | −10.430 | 62.905 | 59.294 | 1.00 | 30.32 | C |
| ATOM | 1612 | C | TYR | B | 94 | −11.721 | 62.175 | 58.944 | 1.00 | 29.29 | C |
| ATOM | 1613 | O | TYR | B | 94 | −11.677 | 61.040 | 58.486 | 1.00 | 29.11 | O |
| ATOM | 1614 | CB | TYR | B | 94 | −10.162 | 62.821 | 60.811 | 1.00 | 30.66 | C |
| ATOM | 1615 | CG | TYR | B | 94 | −10.018 | 61.390 | 61.314 | 1.00 | 32.23 | C |
| ATOM | 1616 | CD1 | TYR | B | 94 | −9.185 | 60.479 | 60.655 | 1.00 | 33.94 | C |
| ATOM | 1617 | CD2 | TYR | B | 94 | −10.733 | 60.939 | 62.426 | 1.00 | 33.45 | C |
| ATOM | 1618 | CE1 | TYR | B | 94 | −9.055 | 59.166 | 61.099 | 1.00 | 34.92 | C |
| ATOM | 1619 | CE2 | TYR | B | 94 | −10.611 | 59.618 | 62.878 | 1.00 | 34.33 | C |
| ATOM | 1620 | CZ | TYR | B | 94 | −9.769 | 58.736 | 62.208 | 1.00 | 35.76 | C |
| ATOM | 1621 | OH | TYR | B | 94 | −9.635 | 57.423 | 62.629 | 1.00 | 37.28 | O |
| ATOM | 1622 | N | ASN | B | 95 | −12.862 | 62.829 | 59.137 | 1.00 | 28.16 | N |
| ATOM | 1623 | CA | ASN | B | 95 | −14.144 | 62.221 | 58.784 | 1.00 | 27.21 | C |
| ATOM | 1624 | C | ASN | B | 95 | −14.461 | 62.276 | 57.279 | 1.00 | 26.08 | C |
| ATOM | 1625 | O | ASN | B | 95 | −15.162 | 61.393 | 56.787 | 1.00 | 26.22 | O |
| ATOM | 1626 | CB | ASN | B | 95 | −15.296 | 62.844 | 59.589 | 1.00 | 27.50 | C |
| ATOM | 1627 | CG | ASN | B | 95 | −15.025 | 62.868 | 61.093 | 1.00 | 28.06 | C |
| ATOM | 1628 | OD1 | ASN | B | 95 | −15.185 | 61.861 | 61.784 | 1.00 | 29.15 | O |
| ATOM | 1629 | ND2 | ASN | B | 95 | −14.616 | 64.025 | 61.600 | 1.00 | 28.91 | N |
| ATOM | 1630 | N | TYR | B | 96 | −13.931 | 63.265 | 56.545 | 1.00 | 24.35 | N |
| ATOM | 1631 | CA | TYR | B | 96 | −14.346 | 63.501 | 55.145 | 1.00 | 23.11 | C |
| ATOM | 1632 | C | TYR | B | 96 | −13.270 | 63.343 | 54.042 | 1.00 | 21.64 | C |
| ATOM | 1633 | O | TYR | B | 96 | −12.145 | 63.812 | 54.171 | 1.00 | 21.25 | O |
| ATOM | 1634 | CB | TYR | B | 96 | −15.001 | 64.882 | 55.013 | 1.00 | 23.06 | C |
| ATOM | 1635 | CG | TYR | B | 96 | −16.167 | 65.107 | 55.963 | 1.00 | 24.50 | C |
| ATOM | 1636 | CD1 | TYR | B | 96 | −16.118 | 66.099 | 56.952 | 1.00 | 25.24 | C |
| ATOM | 1637 | CD2 | TYR | B | 96 | −17.317 | 64.335 | 55.879 | 1.00 | 24.87 | C |
| ATOM | 1638 | CE1 | TYR | B | 96 | −17.191 | 66.306 | 57.827 | 1.00 | 25.86 | C |
| ATOM | 1639 | CE2 | TYR | B | 96 | −18.398 | 64.535 | 56.754 | 1.00 | 25.97 | C |
| ATOM | 1640 | CZ | TYR | B | 96 | −18.330 | 65.520 | 57.722 | 1.00 | 26.29 | C |
| ATOM | 1641 | OH | TYR | B | 96 | −19.395 | 65.713 | 58.586 | 1.00 | 26.82 | O |
| ATOM | 1642 | N | SER | B | 97 | −13.655 | 62.674 | 52.960 | 1.00 | 20.03 | N |
| ATOM | 1643 | CA | SER | B | 97 | −12.905 | 62.653 | 51.699 | 1.00 | 19.27 | C |
| ATOM | 1644 | C | SER | B | 97 | −13.869 | 62.771 | 50.523 | 1.00 | 18.44 | C |

APPENDIX I(b)-continued

| ATOM | 1645 | O | SER | B | 97 | −15.080 | 62.683 | 50.680 | 1.00 | 17.65 | O |
|---|---|---|---|---|---|---|---|---|---|---|---|
| ATOM | 1646 | CB | SER | B | 97 | −12.097 | 61.357 | 51.533 | 1.00 | 19.13 | C |
| ATOM | 1647 | OG | SER | B | 97 | −10.972 | 61.327 | 52.399 | 1.00 | 19.63 | O |
| ATOM | 1648 | N | LEU | B | 98 | −13.328 | 62.982 | 49.336 | 1.00 | 18.23 | N |
| ATOM | 1649 | CA | LEU | B | 98 | −14.162 | 63.093 | 48.161 | 1.00 | 18.60 | C |
| ATOM | 1650 | C | LEU | B | 98 | −14.082 | 61.839 | 47.355 | 1.00 | 17.81 | C |
| ATOM | 1651 | O | LEU | B | 98 | −13.018 | 61.400 | 46.967 | 1.00 | 17.98 | O |
| ATOM | 1652 | CB | LEU | B | 98 | −13.761 | 64.271 | 47.287 | 1.00 | 19.46 | C |
| ATOM | 1653 | CG | LEU | B | 98 | −14.959 | 65.100 | 46.824 | 1.00 | 20.85 | C |
| ATOM | 1654 | CD1 | LEU | B | 98 | −15.248 | 66.226 | 47.810 | 1.00 | 20.64 | C |
| ATOM | 1655 | CD2 | LEU | B | 98 | −14.699 | 65.623 | 45.416 | 1.00 | 22.29 | C |
| ATOM | 1656 | N | LEU | B | 99 | −15.243 | 61.265 | 47.125 | 1.00 | 17.25 | N |
| ATOM | 1657 | CA | LEU | B | 99 | −15.387 | 60.098 | 46.297 | 1.00 | 17.01 | C |
| ATOM | 1658 | C | LEU | B | 99 | −15.487 | 60.578 | 44.854 | 1.00 | 16.38 | C |
| ATOM | 1659 | O | LEU | B | 99 | −16.166 | 61.556 | 44.576 | 1.00 | 15.68 | O |
| ATOM | 1660 | CB | LEU | B | 99 | −16.682 | 59.387 | 46.654 | 1.00 | 17.31 | C |
| ATOM | 1661 | CG | LEU | B | 99 | −16.740 | 57.946 | 47.140 | 1.00 | 19.55 | C |
| ATOM | 1662 | CD1 | LEU | B | 99 | −18.108 | 57.398 | 46.718 | 1.00 | 21.25 | C |
| ATOM | 1663 | CD2 | LEU | B | 99 | −15.627 | 57.043 | 46.660 | 1.00 | 18.90 | C |
| ATOM | 1664 | N | PHE | B | 100 | −14.822 | 59.892 | 43.941 | 1.00 | 15.94 | N |
| ATOM | 1665 | CA | PHE | B | 100 | −14.995 | 60.202 | 42.535 | 1.00 | 16.65 | C |
| ATOM | 1666 | C | PHE | B | 100 | −15.046 | 58.977 | 41.629 | 1.00 | 16.49 | C |
| ATOM | 1667 | O | PHE | B | 100 | −14.625 | 57.896 | 41.988 | 1.00 | 16.43 | O |
| ATOM | 1668 | CB | PHE | B | 100 | −13.986 | 61.265 | 42.045 | 1.00 | 16.45 | C |
| ATOM | 1669 | CG | PHE | B | 100 | −12.550 | 60.818 | 42.013 | 1.00 | 16.97 | C |
| ATOM | 1670 | CD1 | PHE | B | 100 | −11.938 | 60.466 | 40.810 | 1.00 | 18.14 | C |
| ATOM | 1671 | CD2 | PHE | B | 100 | −11.788 | 60.798 | 43.176 | 1.00 | 16.86 | C |
| ATOM | 1672 | CE1 | PHE | B | 100 | −10.582 | 60.077 | 40.771 | 1.00 | 17.07 | C |
| ATOM | 1673 | CE2 | PHE | B | 100 | −10.445 | 60.405 | 43.145 | 1.00 | 18.19 | C |
| ATOM | 1674 | CZ | PHE | B | 100 | −9.840 | 60.053 | 41.930 | 1.00 | 17.19 | C |
| ATOM | 1675 | N | ARG | B | 101 | −15.608 | 59.200 | 40.450 | 1.00 | 17.08 | N |
| ATOM | 1676 | CA | ARG | B | 101 | −15.884 | 58.172 | 39.477 | 1.00 | 17.76 | C |
| ATOM | 1677 | C | ARG | B | 101 | −14.597 | 57.728 | 38.822 | 1.00 | 17.11 | C |
| ATOM | 1678 | O | ARG | B | 101 | −13.847 | 58.555 | 38.310 | 1.00 | 16.40 | O |
| ATOM | 1679 | CB | ARG | B | 101 | −16.824 | 58.737 | 38.395 | 1.00 | 18.57 | C |
| ATOM | 1680 | CG | ARG | B | 101 | −18.056 | 57.886 | 38.135 | 1.00 | 21.82 | C |
| ATOM | 1681 | CD | ARG | B | 101 | −19.196 | 58.631 | 37.439 | 1.00 | 24.74 | C |
| ATOM | 1682 | NE | ARG | B | 101 | −20.327 | 58.826 | 38.341 | 1.00 | 27.71 | N |
| ATOM | 1683 | CZ | ARG | B | 101 | −21.194 | 57.878 | 38.692 | 1.00 | 28.04 | C |
| ATOM | 1684 | NH1 | ARG | B | 101 | −21.081 | 56.639 | 38.235 | 1.00 | 29.97 | N |
| ATOM | 1685 | NH2 | ARG | B | 101 | −22.187 | 58.174 | 39.515 | 1.00 | 30.47 | N |
| ATOM | 1686 | N | GLY | B | 102 | −14.378 | 56.415 | 38.808 | 1.00 | 16.71 | N |
| ATOM | 1687 | CA | GLY | B | 102 | −13.265 | 55.820 | 38.094 | 1.00 | 16.36 | C |
| ATOM | 1688 | C | GLY | B | 102 | −13.731 | 55.107 | 36.836 | 1.00 | 16.19 | C |
| ATOM | 1689 | O | GLY | B | 102 | −14.804 | 55.376 | 36.305 | 1.00 | 15.43 | O |
| ATOM | 1690 | N | GLU | B | 103 | −12.947 | 54.131 | 36.411 | 1.00 | 15.92 | N |
| ATOM | 1691 | CA | GLU | B | 103 | −13.155 | 53.459 | 35.126 | 1.00 | 16.00 | C |
| ATOM | 1692 | C | GLU | B | 103 | −14.294 | 52.456 | 35.219 | 1.00 | 16.23 | C |
| ATOM | 1693 | O | GLU | B | 103 | −14.661 | 52.007 | 36.297 | 1.00 | 14.93 | O |
| ATOM | 1694 | CB | GLU | B | 103 | −11.882 | 52.731 | 34.703 | 1.00 | 15.57 | C |
| ATOM | 1695 | CG | GLU | B | 103 | −10.726 | 53.669 | 34.411 | 1.00 | 16.30 | C |
| ATOM | 1696 | CD | GLU | B | 103 | −9.986 | 54.115 | 35.652 | 1.00 | 16.19 | C |
| ATOM | 1697 | OE1 | GLU | B | 103 | −9.137 | 54.998 | 35.508 | 1.00 | 16.39 | O |
| ATOM | 1698 | OE2 | GLU | B | 103 | −10.260 | 53.592 | 36.777 | 1.00 | 15.82 | O |
| ATOM | 1699 | N | LYS | B | 104 | −14.828 | 52.096 | 34.063 | 1.00 | 17.04 | N |
| ATOM | 1700 | CA | LYS | B | 104 | −16.031 | 51.299 | 33.978 | 1.00 | 17.92 | C |
| ATOM | 1701 | C | LYS | B | 104 | −15.728 | 50.063 | 33.124 | 1.00 | 17.90 | C |
| ATOM | 1702 | O | LYS | B | 104 | −14.934 | 50.121 | 32.169 | 1.00 | 16.60 | O |
| ATOM | 1703 | CB | LYS | B | 104 | −17.150 | 52.159 | 33.363 | 1.00 | 18.66 | C |
| ATOM | 1704 | CG | LYS | B | 104 | −18.552 | 51.885 | 33.857 | 1.00 | 21.78 | C |
| ATOM | 1705 | CD | LYS | B | 104 | −19.605 | 52.757 | 33.118 | 1.00 | 24.78 | C |
| ATOM | 1706 | CE | LYS | B | 104 | −21.036 | 52.466 | 33.580 | 1.00 | 25.87 | C |
| ATOM | 1707 | NZ | LYS | B | 104 | −22.126 | 53.297 | 32.887 | 1.00 | 28.01 | N |
| ATOM | 1708 | N | GLY | B | 105 | −16.362 | 48.942 | 33.484 | 1.00 | 17.73 | N |
| ATOM | 1709 | CA | GLY | B | 105 | −16.316 | 47.745 | 32.677 | 1.00 | 17.68 | C |
| ATOM | 1710 | C | GLY | B | 105 | −16.960 | 47.943 | 31.323 | 1.00 | 17.40 | C |
| ATOM | 1711 | O | GLY | B | 105 | −17.822 | 48.799 | 31.162 | 1.00 | 17.93 | O |
| ATOM | 1712 | N | ALA | B | 106 | −16.523 | 47.159 | 30.343 | 1.00 | 16.99 | N |
| ATOM | 1713 | CA | ALA | B | 106 | −17.004 | 47.300 | 28.969 | 1.00 | 17.63 | C |
| ATOM | 1714 | C | ALA | B | 106 | −18.384 | 46.692 | 28.753 | 1.00 | 17.50 | C |
| ATOM | 1715 | O | ALA | B | 106 | −18.974 | 46.949 | 27.732 | 1.00 | 17.21 | O |
| ATOM | 1716 | CB | ALA | B | 106 | −16.013 | 46.688 | 27.977 | 1.00 | 17.39 | C |
| ATOM | 1717 | N | GLY | B | 107 | −18.860 | 45.882 | 29.704 | 1.00 | 17.48 | N |
| ATOM | 1718 | CA | GLY | B | 107 | −20.216 | 45.352 | 29.709 | 1.00 | 17.63 | C |
| ATOM | 1719 | C | GLY | B | 107 | −20.338 | 43.833 | 29.604 | 1.00 | 17.28 | C |
| ATOM | 1720 | O | GLY | B | 107 | −19.452 | 43.160 | 29.110 | 1.00 | 17.81 | O |
| ATOM | 1721 | N | THR | B | 108 | −21.478 | 43.316 | 30.052 | 1.00 | 17.48 | N |
| ATOM | 1722 | CA | THR | B | 108 | −21.879 | 41.917 | 29.908 | 1.00 | 16.91 | C |
| ATOM | 1723 | C | THR | B | 108 | −23.251 | 41.948 | 29.289 | 1.00 | 16.96 | C |
| ATOM | 1724 | O | THR | B | 108 | −24.159 | 42.543 | 29.874 | 1.00 | 16.69 | O |

APPENDIX I(b)-continued

| | | | | | | | | | | |
|---|---|---|---|---|---|---|---|---|---|---|
| ATOM | 1725 | CB | THR | B | 108 | −22.010 | 41.208 | 31.293 | 1.00 | 16.78 | C |
| ATOM | 1726 | OG1 | THR | B | 108 | −20.720 | 41.021 | 31.894 | 1.00 | 15.50 | O |
| ATOM | 1727 | CG2 | THR | B | 108 | −22.588 | 39.765 | 31.132 | 1.00 | 17.18 | C |
| ATOM | 1728 | N | ALA | B | 109 | −23.420 | 41.306 | 28.131 | 1.00 | 16.67 | N |
| ATOM | 1729 | CA | ALA | B | 109 | −24.706 | 41.262 | 27.448 | 1.00 | 16.55 | C |
| ATOM | 1730 | C | ALA | B | 109 | −25.353 | 39.961 | 27.846 | 1.00 | 16.99 | C |
| ATOM | 1731 | O | ALA | B | 109 | −24.939 | 38.896 | 27.394 | 1.00 | 17.11 | O |
| ATOM | 1732 | CB | ALA | B | 109 | −24.540 | 41.324 | 25.893 | 1.00 | 16.53 | C |
| ATOM | 1733 | N | LEU | B | 110 | −26.363 | 40.047 | 28.699 | 1.00 | 17.44 | N |
| ATOM | 1734 | CA | LEU | B | 110 | −27.059 | 38.870 | 29.180 | 1.00 | 17.82 | C |
| ATOM | 1735 | C | LEU | B | 110 | −28.334 | 38.654 | 28.402 | 1.00 | 18.45 | C |
| ATOM | 1736 | O | LEU | B | 110 | −29.121 | 39.585 | 28.200 | 1.00 | 18.97 | O |
| ATOM | 1737 | CB | LEU | B | 110 | −27.410 | 39.018 | 30.660 | 1.00 | 17.67 | C |
| ATOM | 1738 | CG | LEU | B | 110 | −28.233 | 37.905 | 31.297 | 1.00 | 16.52 | C |
| ATOM | 1739 | CD1 | LEU | B | 110 | −27.559 | 36.562 | 31.143 | 1.00 | 15.11 | C |
| ATOM | 1740 | CD2 | LEU | B | 110 | −28.502 | 38.236 | 32.784 | 1.00 | 17.55 | C |
| ATOM | 1741 | N | THR | B | 111 | −28.529 | 37.408 | 27.989 | 1.00 | 18.42 | N |
| ATOM | 1742 | CA | THR | B | 111 | −29.781 | 36.945 | 27.444 | 1.00 | 18.62 | C |
| ATOM | 1743 | C | THR | B | 111 | −30.320 | 35.854 | 28.342 | 1.00 | 18.54 | C |
| ATOM | 1744 | O | THR | B | 111 | −29.648 | 34.855 | 28.574 | 1.00 | 18.20 | O |
| ATOM | 1745 | CB | THR | B | 111 | −29.557 | 36.395 | 26.049 | 1.00 | 18.49 | C |
| ATOM | 1746 | OG1 | THR | B | 111 | −29.304 | 37.485 | 25.159 | 1.00 | 19.06 | O |
| ATOM | 1747 | CG2 | THR | B | 111 | −30.821 | 35.724 | 25.509 | 1.00 | 18.48 | C |
| ATOM | 1748 | N | VAL | B | 112 | −31.529 | 36.063 | 28.854 | 1.00 | 18.62 | N |
| ATOM | 1749 | CA | VAL | B | 112 | −32.203 | 35.061 | 29.650 | 1.00 | 18.98 | C |
| ATOM | 1750 | C | VAL | B | 112 | −33.437 | 34.563 | 28.897 | 1.00 | 19.41 | C |
| ATOM | 1751 | O | VAL | B | 112 | −34.285 | 35.347 | 28.455 | 1.00 | 19.07 | O |
| ATOM | 1752 | CB | VAL | B | 112 | −32.666 | 35.600 | 31.023 | 1.00 | 18.78 | C |
| ATOM | 1753 | CG1 | VAL | B | 112 | −33.204 | 34.452 | 31.902 | 1.00 | 18.38 | C |
| ATOM | 1754 | CG2 | VAL | B | 112 | −31.540 | 36.356 | 31.735 | 1.00 | 19.56 | C |
| ATOM | 1755 | N | LYS | B | 113 | −33.518 | 33.255 | 28.732 | 1.00 | 20.11 | N |
| ATOM | 1756 | CA | LYS | B | 113 | −34.805 | 32.612 | 28.521 | 1.00 | 20.80 | C |
| ATOM | 1757 | C | LYS | B | 113 | −34.736 | 31.166 | 28.964 | 1.00 | 20.93 | C |
| ATOM | 1758 | O | LYS | B | 113 | −35.505 | 30.751 | 29.825 | 1.00 | 21.05 | O |
| ATOM | 1759 | CB | LYS | B | 113 | −35.265 | 32.714 | 27.070 | 1.00 | 21.14 | C |
| ATOM | 1760 | CG | LYS | B | 113 | −36.797 | 32.926 | 26.932 | 1.00 | 21.95 | C |
| ATOM | 1761 | CD | LYS | B | 113 | −37.613 | 31.644 | 27.254 | 1.00 | 23.53 | C |
| ATOM | 1762 | CE | LYS | B | 113 | −38.619 | 31.803 | 28.420 | 1.00 | 23.96 | C |
| ATOM | 1763 | NZ | LYS | B | 113 | −38.373 | 30.833 | 29.560 | 1.00 | 24.62 | N |
| TER | 1764 | | LYS | B | 113 | | | | | | |
| HETATM | 1765 | O | HOH | | 1 | −3.603 | 22.565 | 27.326 | 1.00 | 32.62 | O |
| HETATM | 1766 | O | HOH | | 2 | −2.025 | 37.576 | 31.649 | 1.00 | 28.80 | O |
| HETATM | 1767 | O | HOH | | 3 | −11.564 | 37.382 | 17.647 | 1.00 | 29.79 | O |
| HETATM | 1768 | O | HOH | | 4 | −12.147 | 50.601 | 31.887 | 1.00 | 29.72 | O |
| HETATM | 1769 | O | HOH | | 5 | −14.153 | 45.214 | 30.485 | 1.00 | 27.66 | O |
| HETATM | 1770 | O | HOH | | 6 | −8.057 | 56.130 | 33.388 | 1.00 | 37.02 | O |
| HETATM | 1771 | O | HOH | | 7 | −17.902 | 51.226 | 29.662 | 1.00 | 34.89 | O |
| HETATM | 1772 | O | HOH | | 8 | −12.752 | 39.758 | 34.757 | 1.00 | 28.89 | O |
| HETATM | 1773 | O | HOH | | 9 | −8.631 | 55.669 | 45.707 | 1.00 | 41.15 | O |
| HETATM | 1774 | O | HOH | | 10 | 13.151 | 25.246 | 35.468 | 1.00 | 53.94 | O |
| HETATM | 1775 | O | HOH | | 11 | −20.020 | 44.397 | 48.086 | 1.00 | 34.26 | O |
| HETATM | 1776 | O | HOH | | 12 | −2.478 | 40.620 | 21.138 | 1.00 | 31.91 | O |
| HETATM | 1777 | O | HOH | | 13 | 6.817 | 45.918 | 20.781 | 1.00 | 34.15 | O |
| HETATM | 1778 | O | HOH | | 14 | −10.720 | 41.048 | 19.742 | 1.00 | 29.28 | O |
| HETATM | 1779 | O | HOH | | 15 | 5.136 | 27.001 | 33.682 | 1.00 | 34.01 | O |
| HETATM | 1780 | O | HOH | | 16 | −8.752 | 34.083 | 17.394 | 1.00 | 32.30 | O |
| HETATM | 1781 | O | HOH | | 17 | 6.370 | 25.987 | 36.062 | 1.00 | 46.53 | O |
| HETATM | 1782 | O | HOH | | 18 | −2.835 | 44.271 | 34.848 | 1.00 | 46.44 | O |
| HETATM | 1783 | O | HOH | | 19 | 12.329 | 46.062 | 32.976 | 1.00 | 41.31 | O |
| HETATM | 1784 | O | HOH | | 20 | 7.260 | 23.068 | 29.837 | 1.00 | 38.09 | O |
| HETATM | 1785 | O | HOH | | 21 | 9.196 | 26.047 | 36.490 | 1.00 | 47.12 | O |
| HETATM | 1786 | O | HOH | | 22 | −15.395 | 35.722 | 34.664 | 1.00 | 41.20 | O |
| HETATM | 1787 | O | HOH | | 23 | −0.653 | 40.172 | 17.501 | 1.00 | 37.13 | O |
| HETATM | 1788 | O | HOH | | 24 | −5.694 | 32.125 | 32.899 | 1.00 | 44.72 | O |
| HETATM | 1789 | O | HOH | | 25 | −12.701 | 48.162 | 29.678 | 1.00 | 45.56 | O |
| HETATM | 1790 | O | HOH | | 26 | −2.261 | 42.933 | 22.850 | 1.00 | 45.39 | O |
| HETATM | 1791 | O | HOH | | 27 | −1.180 | 27.915 | 31.872 | 1.00 | 44.10 | O |
| HETATM | 1792 | O | HOH | | 28 | −11.917 | 36.985 | 27.031 | 1.00 | 46.78 | O |
| HETATM | 1793 | O | HOH | | 29 | −22.053 | 53.082 | 44.383 | 1.00 | 57.53 | O |
| HETATM | 1794 | O | HOH | | 30 | 8.896 | 28.691 | 22.223 | 1.00 | 36.55 | O |
| HETATM | 1795 | O | HOH | | 31 | 11.139 | 27.149 | 35.370 | 1.00 | 40.73 | O |
| HETATM | 1796 | O | HOH | | 32 | 16.384 | 43.712 | 24.651 | 1.00 | 35.03 | O |
| HETATM | 1797 | O | HOH | | 33 | −1.673 | 32.550 | 31.734 | 1.00 | 53.95 | O |
| HETATM | 1798 | O | HOH | | 34 | −0.534 | 41.750 | 25.977 | 1.00 | 26.15 | O |
| HETATM | 1799 | O | HOH | | 35 | −25.707 | 49.370 | 30.021 | 1.00 | 55.33 | O |
| HETATM | 1800 | O | HOH | | 36 | 7.758 | 32.565 | 39.383 | 1.00 | 44.45 | O |
| HETATM | 1801 | O | HOH | | 37 | −9.122 | 42.014 | 49.736 | 1.00 | 40.33 | O |
| HETATM | 1802 | O | HOH | | 38 | −7.490 | 26.790 | 15.325 | 1.00 | 45.84 | O |
| HETATM | 1803 | O | HOH | | 39 | −15.093 | 35.774 | 21.413 | 1.00 | 58.89 | O |
| HETATM | 1804 | O | HOH | | 40 | −13.787 | 53.303 | 31.695 | 1.00 | 48.06 | O |

APPENDIX I(b)-continued

| | | | | | | | | | | |
|---|---|---|---|---|---|---|---|---|---|---|
| HETATM | 1805 | O | HOH | 41 | −26.881 | 36.152 | 44.074 | 1.00 | 45.18 | O |
| HETATM | 1806 | O | HOH | 42 | −31.999 | 47.971 | 25.667 | 1.00 | 45.30 | O |
| HETATM | 1807 | O | HOH | 43 | −2.869 | 45.128 | 37.465 | 1.00 | 51.46 | O |
| HETATM | 1808 | O | HOH | 44 | −11.522 | 33.793 | 24.204 | 1.00 | 48.27 | O |
| HETATM | 1809 | O | HOH | 45 | 0.741 | 49.839 | 30.801 | 1.00 | 64.89 | O |
| HETATM | 1810 | O | HOH | 46 | 3.995 | 28.946 | 34.996 | 1.00 | 46.15 | O |
| HETATM | 1811 | O | HOH | 47 | 1.716 | 24.921 | 22.872 | 1.00 | 50.97 | O |
| HETATM | 1812 | O | HOH | 48 | −14.528 | 49.967 | 29.489 | 1.00 | 32.12 | O |
| HETATM | 1813 | O | HOH | 49 | −3.397 | 54.514 | 35.732 | 1.00 | 75.25 | O |
| HETATM | 1814 | O | HOH | 50 | 7.350 | 36.188 | 38.637 | 1.00 | 44.58 | O |
| HETATM | 1815 | O | HOH | 51 | −11.258 | 36.392 | 32.460 | 1.00 | 64.14 | O |
| HETATM | 1816 | O | HOH | 52 | −5.919 | 28.213 | 33.670 | 1.00 | 53.43 | O |
| HETATM | 1817 | O | HOH | 53 | −29.035 | 35.826 | 45.961 | 1.00 | 52.26 | O |
| HETATM | 1818 | O | HOH | 54 | 0.619 | 37.563 | 35.722 | 1.00 | 36.13 | O |
| HETATM | 1819 | O | HOH | 55 | 17.630 | 44.800 | 22.683 | 0.50 | 19.47 | O |
| HETATM | 1820 | O | HOH | 56 | 10.658 | 48.432 | 27.654 | 1.00 | 57.06 | O |
| HETATM | 1821 | O | HOH | 57 | 12.883 | 47.166 | 27.270 | 1.00 | 47.82 | O |
| HETATM | 1822 | O | HOH | 58 | −10.204 | 43.420 | 20.875 | 1.00 | 54.59 | O |
| HETATM | 1823 | O | HOH | 59 | −17.821 | 36.045 | 26.779 | 1.00 | 48.73 | O |
| HETATM | 1824 | O | HOH | 60 | −33.575 | 46.023 | 24.555 | 0.50 | 57.14 | O |
| HETATM | 1825 | O | HOH | 61 | −9.513 | 32.401 | 30.497 | 1.00 | 49.08 | O |
| HETATM | 1826 | O | HOH | 62 | −22.035 | 32.931 | 35.329 | 1.00 | 53.74 | O |
| HETATM | 1827 | O | HOH | 63 | −26.276 | 37.813 | 25.169 | 1.00 | 43.04 | O |
| HETATM | 1828 | O | HOH | 64 | 6.554 | 36.026 | 15.888 | 1.00 | 49.25 | O |
| HETATM | 1829 | O | HOH | 65 | −14.945 | 36.915 | 28.030 | 1.00 | 55.95 | O |
| HETATM | 1830 | O | HOH | 66 | 11.110 | 41.062 | 21.523 | 1.00 | 47.74 | O |
| HETATM | 1831 | O | HOH | 67 | 3.797 | 45.196 | 35.142 | 1.00 | 49.98 | O |
| HETATM | 1832 | O | HOH | 68 | −7.103 | 48.353 | 46.125 | 1.00 | 63.67 | O |
| HETATM | 1833 | O | HOH | 69 | −26.227 | 28.904 | 36.563 | 1.00 | 67.40 | O |
| HETATM | 1834 | O | HOH | 70 | −21.008 | 37.879 | 44.773 | 1.00 | 38.83 | O |
| HETATM | 1835 | O | HOH | 71 | −8.401 | 39.932 | 48.004 | 1.00 | 59.32 | O |
| HETATM | 1836 | O | HOH | 72 | −7.060 | 55.805 | 37.587 | 1.00 | 36.59 | O |
| HETATM | 1837 | O | HOH | 73 | 2.254 | 43.055 | 28.212 | 1.00 | 37.43 | O |
| HETATM | 1838 | O | HOH | 74 | −15.957 | 41.782 | 22.346 | 1.00 | 52.21 | O |
| HETATM | 1839 | O | HOH | 75 | −30.836 | 46.157 | 27.026 | 1.00 | 41.75 | O |
| HETATM | 1840 | O | HOH | 76 | 0.243 | 30.979 | 36.033 | 1.00 | 54.97 | O |
| HETATM | 1841 | O | HOH | 77 | 0.247 | 38.128 | 13.711 | 1.00 | 71.28 | O |
| HETATM | 1842 | O | HOH | 78 | 5.404 | 42.527 | 18.589 | 1.00 | 45.84 | O |
| HETATM | 1843 | O | HOH | 79 | −10.308 | 34.296 | 26.893 | 1.00 | 53.88 | O |
| HETATM | 1844 | O | HOH | 80 | −6.664 | 53.994 | 39.217 | 1.00 | 42.65 | O |
| HETATM | 1845 | O | HOH | 81 | −5.087 | 41.168 | 17.628 | 1.00 | 50.54 | O |
| HETATM | 1846 | O | HOH | 82 | −22.020 | 51.083 | 47.018 | 1.00 | 63.47 | O |
| HETATM | 1847 | O | HOH | 83 | −5.142 | 35.512 | 13.750 | 1.00 | 49.89 | O |
| HETATM | 1848 | O | HOH | 84 | 10.297 | 24.970 | 22.199 | 1.00 | 54.97 | O |
| HETATM | 1849 | O | HOH | 85 | −3.029 | 49.876 | 30.159 | 1.00 | 67.18 | O |
| HETATM | 1850 | O | HOH | 86 | −15.585 | 36.101 | 16.657 | 1.00 | 62.06 | O |
| HETATM | 1851 | O | HOH | 87 | −31.964 | 47.184 | 41.589 | 1.00 | 51.59 | O |
| HETATM | 1852 | O | HOH | 88 | −32.818 | 49.890 | 32.367 | 1.00 | 49.76 | O |
| HETATM | 1853 | O | HOH | 89 | 15.015 | 43.317 | 14.283 | 1.00 | 57.75 | O |
| HETATM | 1854 | O | HOH | 90 | −21.719 | 31.012 | 37.760 | 1.00 | 72.98 | O |
| HETATM | 1855 | O | HOH | 91 | −32.335 | 46.485 | 39.125 | 1.00 | 68.68 | O |
| HETATM | 1856 | O | HOH | 92 | 0.069 | 40.947 | 11.925 | 1.00 | 58.64 | O |
| HETATM | 1857 | O | HOH | 93 | 15.333 | 44.973 | 29.047 | 1.00 | 58.06 | O |
| HETATM | 1858 | O | HOH | 94 | 4.602 | 29.902 | 37.670 | 1.00 | 58.96 | O |
| HETATM | 1859 | O | HOH | 95 | 8.321 | 46.401 | 37.041 | 1.00 | 79.54 | O |
| HETATM | 1860 | O | HOH | 96 | 16.844 | 44.827 | 27.035 | 1.00 | 53.07 | O |
| HETATM | 1861 | O | HOH | 97 | 8.643 | 34.976 | 14.645 | 1.00 | 61.34 | O |
| HETATM | 1862 | O | HOH | 98 | 15.081 | 30.053 | 40.624 | 1.00 | 58.50 | O |
| HETATM | 1863 | O | HOH | 99 | −29.173 | 38.671 | 49.216 | 1.00 | 77.24 | O |
| HETATM | 1864 | O | HOH | 100 | −34.367 | 30.230 | 40.676 | 1.00 | 87.45 | O |
| HETATM | 1865 | O | HOH | 101 | 13.024 | 40.796 | 42.706 | 1.00 | 66.67 | O |
| HETATM | 1866 | O | HOH | 102 | −24.986 | 34.816 | 45.384 | 1.00 | 54.92 | O |
| HETATM | 1867 | O | HOH | 103 | 3.596 | 42.385 | 20.233 | 1.00 | 37.71 | O |
| HETATM | 1868 | O | HOH | 104 | −23.493 | 49.334 | 44.992 | 1.00 | 44.76 | O |
| HETATM | 1869 | O | HOH | 105 | −22.358 | 44.809 | 26.526 | 1.00 | 68.31 | O |
| HETATM | 1870 | O | HOH | 106 | −17.446 | 32.842 | 37.601 | 1.00 | 65.30 | O |
| HETATM | 1871 | O | HOH | 107 | −22.821 | 52.720 | 29.818 | 1.00 | 71.05 | O |
| HETATM | 1872 | O | HOH | 108 | −8.572 | 26.810 | 23.048 | 1.00 | 81.52 | O |
| HETATM | 1873 | O | HOH | 109 | 4.419 | 46.453 | 27.301 | 1.00 | 63.98 | O |
| HETATM | 1874 | O | HOH | 110 | 23.410 | 26.310 | 29.884 | 1.00 | 72.88 | O |
| HETATM | 1875 | O | HOH | 111 | 9.649 | 42.598 | 19.288 | 1.00 | 58.11 | O |
| HETATM | 1876 | O | HOH | 112 | −15.692 | 35.133 | 41.149 | 1.00 | 63.89 | O |
| HETATM | 1877 | O | HOH | 113 | −26.983 | 54.986 | 35.486 | 1.00 | 87.73 | O |
| HETATM | 1878 | O | HOH | 114 | −24.223 | 45.040 | 24.854 | 0.50 | 34.45 | O |
| HETATM | 1879 | O | HOH | 115 | −5.537 | 55.893 | 46.218 | 1.00 | 46.13 | O |
| HETATM | 1880 | O | HOH | 116 | −22.125 | 35.353 | 45.825 | 1.00 | 54.11 | O |
| HETATM | 1881 | O | HOH | 117 | −4.303 | 38.534 | 32.607 | 1.00 | 65.18 | O |
| HETATM | 1882 | O | HOH | 118 | −24.701 | 49.655 | 42.592 | 1.00 | 44.09 | O |
| HETATM | 1883 | O | HOH | 119 | −6.344 | 37.080 | 33.536 | 1.00 | 56.70 | O |
| HETATM | 1884 | O | HOH | 120 | −16.010 | 39.018 | 19.540 | 1.00 | 47.12 | O |

APPENDIX I(b)-continued

| HETATM | 1885 | O | HOH | 121 | −27.762 | 40.565 | 50.157 | 1.00 | 65.48 | O |
|---|---|---|---|---|---|---|---|---|---|---|
| HETATM | 1886 | O | HOH | 122 | −38.022 | 50.782 | 33.568 | 1.00 | 73.64 | O |
| HETATM | 1887 | O | HOH | 123 | −1.625 | 52.480 | 34.057 | 1.00 | 74.28 | O |
| HETATM | 1888 | O | HOH | 124 | −21.663 | 35.323 | 48.955 | 1.00 | 65.30 | O |
| HETATM | 1889 | O | HOH | 125 | −6.821 | 48.170 | 48.922 | 1.00 | 73.82 | O |
| HETATM | 1890 | O | HOH | 126 | −13.845 | 39.478 | 40.011 | 1.00 | 60.84 | O |
| HETATM | 1891 | O | HOH | 127 | 6.927 | 41.038 | 17.007 | 1.00 | 68.49 | O |
| HETATM | 1892 | O | HOH | 128 | −1.966 | 52.839 | 44.944 | 1.00 | 87.28 | O |
| HETATM | 1893 | O | HOH | 129 | −7.847 | 23.965 | 22.241 | 1.00 | 58.88 | O |
| HETATM | 1894 | O | HOH | 130 | −3.206 | 50.463 | 45.678 | 1.00 | 81.46 | O |
| HETATM | 1895 | O | HOH | 131 | −20.734 | 33.268 | 29.612 | 1.00 | 65.97 | O |
| HETATM | 1896 | O | HOH | 132 | −3.239 | 43.318 | 28.931 | 1.00 | 60.99 | O |
| HETATM | 1897 | O | HOH | 133 | −40.181 | 49.870 | 32.489 | 1.00 | 76.03 | O |
| HETATM | 1898 | O | HOH | 134 | −13.701 | 39.202 | 25.401 | 1.00 | 64.57 | O |
| HETATM | 1899 | O | HOH | 135 | −28.332 | 46.062 | 26.011 | 1.00 | 50.13 | O |
| HETATM | 1900 | O | HOH | 136 | −14.074 | 29.707 | 23.160 | 1.00 | 83.09 | O |
| HETATM | 1901 | O | HOH | 137 | −4.377 | 47.534 | 39.617 | 1.00 | 61.39 | O |
| HETATM | 1902 | O | HOH | 138 | −14.674 | 39.434 | 43.947 | 1.00 | 61.24 | O |
| HETATM | 1903 | O | HOH | 139 | −28.314 | 52.582 | 28.145 | 1.00 | 60.30 | O |
| HETATM | 1904 | O | HOH | 140 | −18.687 | 49.110 | 26.208 | 1.00 | 54.09 | O |
| HETATM | 1905 | O | HOH | 141 | −15.685 | 39.305 | 23.521 | 1.00 | 65.29 | O |
| HETATM | 1906 | O | HOH | 142 | −33.598 | 49.435 | 41.980 | 1.00 | 83.02 | O |
| HETATM | 1907 | O | HOH | 143 | −38.646 | 26.243 | 29.939 | 1.00 | 92.35 | O |
| HETATM | 1908 | O | HOH | 144 | −20.693 | 42.535 | 25.536 | 1.00 | 61.60 | O |
| HETATM | 1909 | O | HOH | 145 | −21.614 | 55.217 | 35.058 | 1.00 | 54.35 | O |
| HETATM | 1910 | O | HOH | 146 | 20.340 | 33.477 | 28.720 | 1.00 | 57.13 | O |
| HETATM | 1911 | O | HOH | 147 | −14.937 | 35.262 | 30.134 | 1.00 | 80.62 | O |
| HETATM | 1912 | O | HOH | 148 | −30.357 | 41.475 | 51.126 | 1.00 | 55.90 | O |
| HETATM | 1913 | O | HOH | 149 | −7.343 | 19.838 | 22.057 | 1.00 | 58.33 | O |
| HETATM | 1914 | O | HOH | 150 | 10.363 | 41.633 | 41.955 | 1.00 | 80.85 | O |
| HETATM | 1915 | O | HOH | 151 | −28.516 | 56.353 | 29.977 | 1.00 | 67.64 | O |
| HETATM | 1916 | O | HOH | 152 | 0.289 | 49.396 | 28.161 | 1.00 | 82.96 | O |
| HETATM | 1917 | O | HOH | 153 | −5.197 | 44.204 | 39.334 | 1.00 | 57.87 | O |
| HETATM | 1918 | O | HOH | 154 | −1.892 | 29.898 | 33.032 | 1.00 | 81.31 | O |
| HETATM | 1919 | O | HOH | 155 | −6.354 | 40.306 | 40.369 | 1.00 | 64.96 | O |
| HETATM | 1920 | O | HOH | 156 | −35.505 | 42.575 | 36.471 | 1.00 | 61.68 | O |
| HETATM | 1921 | O | HOH | 157 | −11.766 | 41.049 | 25.763 | 1.00 | 67.31 | O |
| HETATM | 1922 | O | HOH | 158 | 24.549 | 41.790 | 44.796 | 1.00 | 94.46 | O |
| HETATM | 1923 | O | HOH | 159 | 21.990 | 42.199 | 17.194 | 1.00 | 71.97 | O |
| HETATM | 1924 | O | HOH | 160 | −21.524 | 48.235 | 45.392 | 1.00 | 38.60 | O |
| HETATM | 1925 | O | HOH | 161 | −8.232 | 11.927 | 11.548 | 1.00 | 77.25 | O |
| HETATM | 1926 | O | HOH | 162 | 18.993 | 45.611 | 24.121 | 0.50 | 48.25 | O |
| HETATM | 1927 | O | HOH | 163 | −3.423 | 33.004 | 33.502 | 1.00 | 46.87 | O |
| HETATM | 1928 | O | HOH | 164 | −12.067 | 38.301 | 39.035 | 1.00 | 66.32 | O |
| HETATM | 1929 | O | HOH | 165 | −19.240 | 57.453 | 34.326 | 1.00 | 62.19 | O |
| HETATM | 1930 | O | HOH | 166 | −15.369 | 57.421 | 34.820 | 1.00 | 56.53 | O |
| HETATM | 1931 | O | HOH | 167 | −12.383 | 46.024 | 24.556 | 0.50 | 107.60 | O |
| HETATM | 1932 | O | HOH | 168 | 9.582 | 23.067 | 37.226 | 1.00 | 68.06 | O |
| HETATM | 1933 | O | HOH | 169 | 13.979 | 44.653 | 23.993 | 1.00 | 59.28 | O |
| HETATM | 1934 | O | HOH | 170 | 7.020 | 20.778 | 33.662 | 1.00 | 55.70 | O |
| HETATM | 1935 | O | HOH | 171 | −6.632 | 18.659 | 6.953 | 1.00 | 57.16 | O |
| HETATM | 1936 | O | HOH | 172 | −40.140 | 40.092 | 30.271 | 1.00 | 83.42 | O |
| HETATM | 1937 | O | HOH | 173 | −25.859 | 49.080 | 46.581 | 1.00 | 72.05 | O |
| HETATM | 1938 | O | HOH | 174 | 11.903 | 33.915 | 42.794 | 1.00 | 62.47 | O |
| HETATM | 1939 | O | HOH | 175 | 4.443 | 37.316 | 14.253 | 1.00 | 54.63 | O |
| HETATM | 1940 | O | HOH | 176 | −23.109 | 32.164 | 39.230 | 1.00 | 58.67 | O |
| HETATM | 1941 | O | HOH | 177 | 16.134 | 23.618 | 36.264 | 1.00 | 72.38 | O |
| HETATM | 1942 | O | HOH | 178 | 6.026 | 27.145 | 18.930 | 1.00 | 77.90 | O |
| HETATM | 1943 | O | HOH | 179 | −9.688 | 38.334 | 40.737 | 1.00 | 61.53 | O |
| HETATM | 1944 | O | HOH | 180 | −22.696 | 49.211 | 25.803 | 1.00 | 65.15 | O |
| HETATM | 1945 | O | HOH | 181 | −30.846 | 54.695 | 38.649 | 1.00 | 60.05 | O |
| HETATM | 1946 | O | HOH | 182 | −19.785 | 63.595 | 61.341 | 1.00 | 89.42 | O |
| HETATM | 1947 | O | HOH | 183 | 13.553 | 19.460 | 30.403 | 1.00 | 79.86 | O |
| HETATM | 1948 | O | HOH | 184 | 4.577 | 49.300 | 32.750 | 1.00 | 64.93 | O |
| HETATM | 1949 | O | HOH | 185 | 1.307 | 28.028 | 35.709 | 1.00 | 65.55 | O |
| HETATM | 1950 | O | HOH | 186 | −4.209 | 8.016 | 10.568 | 1.00 | 76.31 | O |
| HETATM | 1951 | O | HOH | 187 | −7.990 | 57.550 | 66.176 | 1.00 | 84.96 | O |
| HETATM | 1952 | O | HOH | 188 | −11.759 | 70.211 | 53.014 | 1.00 | 68.57 | O |
| HETATM | 1953 | O | HOH | 189 | −15.093 | 31.958 | 14.184 | 1.00 | 77.18 | O |
| HETATM | 1954 | O | HOH | 190 | −23.127 | 28.574 | 35.811 | 1.00 | 84.33 | O |
| HETATM | 1955 | O | HOH | 191 | −12.687 | 42.314 | 29.442 | 1.00 | 56.81 | O |
| HETATM | 1956 | O | HOH | 192 | −3.637 | 39.435 | 35.154 | 1.00 | 57.23 | O |
| HETATM | 1957 | O | HOH | 193 | 13.948 | 40.445 | 14.939 | 1.00 | 74.56 | O |
| HETATM | 1958 | O | HOH | 194 | −24.452 | 59.655 | 41.252 | 1.00 | 95.39 | O |
| HETATM | 1959 | O | HOH | 195 | −35.101 | 41.960 | 42.068 | 1.00 | 74.52 | O |
| HETATM | 1960 | O | HOH | 196 | −21.224 | 54.576 | 30.539 | 1.00 | 93.57 | O |
| HETATM | 1961 | O | HOH | 197 | −6.699 | 59.049 | 64.130 | 1.00 | 90.32 | O |
| HETATM | 1962 | O | HOH | 198 | −12.852 | 44.654 | 28.015 | 1.00 | 65.04 | O |
| HETATM | 1963 | O | HOH | 199 | −35.270 | 35.608 | 25.394 | 1.00 | 91.63 | O |
| HETATM | 1964 | O | HOH | 200 | −27.591 | 55.725 | 41.984 | 1.00 | 78.78 | O |

APPENDIX I(b)-continued

| HETATM | 1965 | O | HOH | 201 | −2.304 | 42.014 | 35.867 | 1.00 | 60.76 | O |
|---|---|---|---|---|---|---|---|---|---|---|
| HETATM | 1966 | O | HOH | 202 | −7.873 | 38.784 | 35.085 | 1.00 | 60.96 | O |
| HETATM | 1967 | O | HOH | 203 | 1.437 | 49.049 | 33.215 | 1.00 | 91.38 | O |
| HETATM | 1968 | O | HOH | 204 | 9.087 | 29.635 | 19.856 | 1.00 | 44.92 | O |
| HETATM | 1969 | O | HOH | 205 | 4.632 | 27.259 | 38.041 | 1.00 | 73.19 | O |
| HETATM | 1970 | O | HOH | 206 | −6.312 | 40.374 | 36.109 | 1.00 | 54.83 | O |
| HETATM | 1971 | O | HOH | 207 | 16.399 | 32.078 | 23.121 | 1.00 | 87.24 | O |
| HETATM | 1972 | O | HOH | 208 | 15.627 | 25.767 | 26.517 | 1.00 | 68.61 | O |
| HETATM | 1973 | O | HOH | 209 | 22.940 | 40.400 | 23.162 | 1.00 | 66.19 | O |
| HETATM | 1974 | O | HOH | 210 | 9.044 | 42.885 | 39.388 | 1.00 | 52.86 | O |
| HETATM | 1975 | O | HOH | 211 | 2.686 | 10.774 | 3.076 | 1.00 | 86.36 | O |
| HETATM | 1976 | O | HOH | 212 | −21.576 | 32.568 | 32.413 | 1.00 | 63.08 | O |
| HETATM | 1977 | O | HOH | 213 | 12.714 | 21.953 | 33.512 | 1.00 | 69.19 | O |
| HETATM | 1978 | O | HOH | 214 | 18.333 | 25.494 | 30.728 | 1.00 | 59.02 | O |
| HETATM | 1979 | O | HOH | 215 | −10.477 | 70.874 | 59.283 | 1.00 | 90.02 | O |
| HETATM | 1980 | O | HOH | 216 | −24.719 | 51.729 | 41.022 | 1.00 | 46.48 | O |
| HETATM | 1981 | O | HOH | 217 | 14.511 | 48.063 | 37.259 | 1.00 | 60.62 | O |
| HETATM | 1982 | O | HOH | 218 | −10.655 | 26.875 | 15.002 | 1.00 | 83.41 | O |
| HETATM | 1983 | O | HOH | 219 | 11.207 | 48.612 | 31.720 | 1.00 | 62.53 | O |
| HETATM | 1984 | O | HOH | 220 | −12.020 | 30.028 | 27.373 | 1.00 | 74.67 | O |
| HETATM | 1985 | O | HOH | 221 | −37.489 | 47.701 | 29.803 | 1.00 | 68.54 | O |
| HETATM | 1986 | O | HOH | 222 | 6.582 | 42.620 | 37.908 | 1.00 | 52.68 | O |
| HETATM | 1987 | O | HOH | 223 | −5.169 | 54.977 | 49.059 | 1.00 | 81.54 | O |
| HETATM | 1988 | O | HOH | 224 | −11.648 | 73.225 | 58.749 | 1.00 | 71.11 | O |
| HETATM | 1989 | O | HOH | 225 | 1.769 | 39.751 | 36.817 | 1.00 | 83.19 | O |
| HETATM | 1990 | O | HOH | 226 | 12.017 | 35.767 | 45.531 | 1.00 | 87.64 | O |
| HETATM | 1991 | O | HOH | 227 | 21.914 | 39.637 | 26.810 | 1.00 | 61.56 | O |
| HETATM | 1992 | O | HOH | 228 | 13.853 | 42.384 | 18.211 | 1.00 | 47.88 | O |
| HETATM | 1993 | O | HOH | 229 | −2.593 | 54.747 | 48.184 | 1.00 | 85.82 | O |
| HETATM | 1994 | O | HOH | 230 | 16.494 | 26.070 | 37.419 | 1.00 | 66.70 | O |
| HETATM | 1995 | O | HOH | 231 | −9.482 | 37.452 | 37.786 | 1.00 | 78.29 | O |
| HETATM | 1996 | O | HOH | 232 | −13.412 | 29.804 | 19.190 | 1.00 | 95.07 | O |
| HETATM | 1997 | O | HOH | 233 | −11.326 | 24.573 | 13.894 | 1.00 | 85.94 | O |
| HETATM | 1998 | O | HOH | 234 | 18.269 | 38.041 | 21.145 | 1.00 | 51.57 | O |
| HETATM | 1999 | O | HOH | 235 | −11.946 | 37.393 | 36.577 | 1.00 | 61.47 | O |
| HETATM | 2000 | O | HOH | 236 | −29.656 | 56.618 | 26.887 | 1.00 | 77.90 | O |
| HETATM | 2001 | O | HOH | 237 | −12.732 | 32.774 | 38.409 | 1.00 | 74.56 | O |
| HETATM | 2002 | O | HOH | 238 | 17.956 | 23.840 | 34.384 | 1.00 | 63.80 | O |
| HETATM | 2003 | O | HOH | 239 | −9.416 | 37.923 | 44.514 | 1.00 | 90.86 | O |
| HETATM | 2004 | O | HOH | 240 | −14.456 | 60.996 | 37.550 | 1.00 | 80.66 | O |
| HETATM | 2005 | O | HOH | 241 | −1.720 | 44.079 | 26.371 | 1.00 | 64.22 | O |
| HETATM | 2006 | O | HOH | 242 | −10.339 | 38.706 | 33.728 | 1.00 | 67.90 | O |
| HETATM | 2007 | O | HOH | 243 | 24.244 | 36.669 | 35.828 | 1.00 | 53.46 | O |
| HETATM | 2008 | O | HOH | 244 | −7.769 | 23.449 | 11.359 | 1.00 | 84.35 | O |
| HETATM | 2009 | O | HOH | 245 | 11.242 | 21.377 | 31.295 | 1.00 | 59.50 | O |
| HETATM | 2010 | O | HOH | 246 | −29.651 | 41.449 | 25.764 | 1.00 | 55.60 | O |
| HETATM | 2011 | O | HOH | 247 | −13.689 | 59.872 | 55.361 | 1.00 | 57.65 | O |
| HETATM | 2012 | O | HOH | 248 | 4.670 | 26.514 | 16.406 | 1.00 | 78.28 | O |
| HETATM | 2013 | O | HOH | 249 | −38.061 | 52.151 | 30.188 | 1.00 | 74.73 | O |
| HETATM | 2014 | O | HOH | 250 | 13.040 | 26.819 | 19.529 | 1.00 | 73.16 | O |
| HETATM | 2015 | O | HOH | 251 | −17.381 | 34.165 | 33.393 | 1.00 | 64.24 | O |
| HETATM | 2016 | O | HOH | 252 | −2.223 | 34.352 | 37.730 | 1.00 | 83.71 | O |
| HETATM | 2017 | O | HOH | 253 | −16.079 | 31.443 | 19.478 | 1.00 | 84.26 | O |
| HETATM | 2018 | O | HOH | 254 | −8.067 | 30.366 | 34.807 | 1.00 | 75.21 | O |
| HETATM | 2019 | O | HOH | 255 | −16.052 | 32.626 | 17.086 | 1.00 | 111.60 | O |
| HETATM | 2020 | O | HOH | 256 | −3.151 | 32.317 | 36.134 | 1.00 | 76.07 | O |
| HETATM | 2021 | O | HOH | 257 | −28.340 | 43.292 | 26.140 | 1.00 | 84.47 | O |
| HETATM | 2022 | O | HOH | 258 | −13.201 | 34.779 | 40.218 | 1.00 | 78.14 | O |
| HETATM | 2023 | O | HOH | 259 | −28.742 | 28.673 | 28.253 | 1.00 | 65.42 | O |
| HETATM | 2024 | O | HOH | 260 | −20.148 | 45.068 | 25.903 | 0.50 | 74.24 | O |
| HETATM | 2025 | O | HOH | 261 | 11.073 | 36.391 | 42.363 | 1.00 | 95.30 | O |
| HETATM | 2026 | O | HOH | 262 | −15.738 | 48.828 | 48.039 | 1.00 | 55.95 | O |
| HETATM | 2027 | O | HOH | 263 | −19.088 | 33.527 | 26.503 | 1.00 | 87.58 | O |
| HETATM | 2028 | O | HOH | 264 | −0.687 | 47.729 | 38.514 | 1.00 | 82.39 | O |
| HETATM | 2029 | O | HOH | 265 | 13.291 | 35.265 | 47.736 | 1.00 | 85.03 | O |
| HETATM | 2030 | O | HOH | 266 | −2.672 | 19.489 | 1.571 | 1.00 | 72.65 | O |
| HETATM | 2031 | O | HOH | 267 | −39.451 | 43.535 | 26.005 | 0.50 | 61.33 | O |
| HETATM | 2032 | O | HOH | 268 | −0.307 | 24.319 | 23.263 | 1.00 | 61.23 | O |
| HETATM | 2033 | O | HOH | 269 | 18.114 | 42.357 | 14.347 | 1.00 | 74.03 | O |
| HETATM | 2034 | O | HOH | 270 | −1.953 | 37.146 | 36.068 | 1.00 | 98.52 | O |
| HETATM | 2035 | O | HOH | 271 | −37.503 | 39.278 | 41.064 | 1.00 | 73.24 | O |
| HETATM | 2036 | O | HOH | 272 | −40.189 | 28.850 | 28.128 | 1.00 | 87.08 | O |
| HETATM | 2037 | O | HOH | 273 | 24.328 | 34.368 | 36.983 | 1.00 | 75.80 | O |
| HETATM | 2038 | O | HOH | 274 | −37.020 | 37.405 | 24.990 | 1.00 | 71.53 | O |
| HETATM | 2039 | O | HOH | 275 | −19.465 | 36.641 | 43.076 | 1.00 | 67.93 | O |
| HETATM | 2040 | O | HOH | 276 | −7.655 | 24.826 | 31.230 | 1.00 | 49.77 | O |
| HETATM | 2041 | O | HOH | 277 | −2.621 | 23.763 | 22.594 | 1.00 | 88.43 | O |
| HETATM | 2042 | O | HOH | 278 | −2.830 | 35.434 | 33.849 | 1.00 | 88.49 | O |
| HETATM | 2043 | O | HOH | 279 | −32.334 | 34.377 | 45.004 | 1.00 | 93.57 | O |
| HETATM | 2044 | O | HOH | 280 | 1.641 | 44.356 | 34.318 | 1.00 | 50.87 | O |

APPENDIX I(b)-continued

| | | | | | | | | | | |
|---|---|---|---|---|---|---|---|---|---|---|
| HETATM | 2045 | O | HOH | 281 | −36.662 | 44.555 | 31.032 | 1.00 | 55.72 | O |
| HETATM | 2046 | O | HOH | 282 | −0.094 | 34.840 | 10.372 | 1.00 | 66.27 | O |
| HETATM | 2047 | O | HOH | 283 | −13.878 | 31.752 | 27.095 | 1.00 | 69.99 | O |
| HETATM | 2048 | O | HOH | 284 | 23.476 | 43.421 | 42.279 | 1.00 | 105.55 | O |
| HETATM | 2049 | O | HOH | 285 | −23.343 | 31.731 | 28.830 | 1.00 | 70.21 | O |
| HETATM | 2050 | O | HOH | 286 | 5.253 | 45.138 | 37.445 | 1.00 | 94.42 | O |
| HETATM | 2051 | O | HOH | 287 | 10.412 | 31.220 | 14.882 | 1.00 | 87.46 | O |
| HETATM | 2052 | O | HOH | 288 | 14.940 | 31.880 | 16.303 | 1.00 | 66.56 | O |
| HETATM | 2053 | O | HOH | 289 | 17.168 | 36.449 | 45.600 | 0.50 | 54.04 | O |
| HETATM | 2054 | O | HOH | 290 | 2.003 | 41.955 | 38.222 | 1.00 | 69.37 | O |
| HETATM | 2055 | O | HOH | 291 | 6.621 | 39.950 | 38.526 | 1.00 | 58.61 | O |
| HETATM | 2056 | O | HOH | 292 | −22.166 | 32.743 | 25.751 | 1.00 | 79.54 | O |
| HETATM | 2057 | O | HOH | 293 | −21.155 | 47.190 | 26.170 | 0.50 | 53.13 | O |
| HETATM | 2058 | O | HOH | 294 | 21.374 | 37.864 | 20.799 | 1.00 | 77.05 | O |
| HETATM | 2059 | O | HOH | 295 | −13.520 | 70.582 | 51.050 | 1.00 | 88.38 | O |
| HETATM | 2060 | O | HOH | 296 | 25.541 | 38.807 | 32.374 | 1.00 | 52.13 | O |
| HETATM | 2061 | O | HOH | 297 | −20.150 | 33.543 | 42.049 | 1.00 | 69.15 | O |
| HETATM | 2062 | O | HOH | 298 | −16.241 | 69.662 | 40.827 | 1.00 | 75.97 | O |
| HETATM | 2063 | O | HOH | 299 | −15.650 | 66.556 | 60.490 | 1.00 | 96.19 | O |
| HETATM | 2064 | O | HOH | 300 | −4.674 | 46.553 | 26.268 | 1.00 | 89.63 | O |
| HETATM | 2065 | O | HOH | 301 | −18.802 | 36.355 | 49.179 | 1.00 | 77.59 | O |
| HETATM | 2066 | O | HOH | 302 | −25.774 | 35.475 | 24.450 | 1.00 | 61.75 | O |
| HETATM | 2067 | O | HOH | 303 | −4.490 | 16.888 | 11.049 | 1.00 | 90.74 | O |
| HETATM | 2068 | O | HOH | 304 | −26.802 | 27.808 | 30.640 | 1.00 | 77.04 | O |
| HETATM | 2069 | O | HOH | 305 | 5.669 | 22.533 | 35.676 | 1.00 | 73.26 | O |
| HETATM | 2070 | O | HOH | 306 | −31.095 | 43.543 | 25.917 | 1.00 | 67.07 | O |
| HETATM | 2071 | O | HOH | 307 | −10.776 | 20.519 | 3.866 | 1.00 | 88.13 | O |
| HETATM | 2072 | O | HOH | 308 | −24.474 | 29.167 | 30.418 | 1.00 | 83.44 | O |
| HETATM | 2073 | O | HOH | 309 | 4.054 | 47.866 | 34.653 | 1.00 | 67.34 | O |
| HETATM | 2074 | O | HOH | 310 | −40.069 | 32.480 | 34.827 | 1.00 | 87.72 | O |
| HETATM | 2075 | O | HOH | 311 | −13.867 | 22.452 | 8.366 | 1.00 | 81.23 | O |
| HETATM | 2076 | O | HOH | 312 | −6.729 | 34.615 | 36.646 | 1.00 | 91.79 | O |
| HETATM | 2077 | O | HOH | 313 | −13.851 | 67.948 | 42.822 | 1.00 | 104.93 | O |
| HETATM | 2078 | O | HOH | 314 | −9.942 | 22.490 | 2.278 | 1.00 | 76.63 | O |
| HETATM | 2079 | O | HOH | 315 | −12.535 | 69.113 | 55.555 | 1.00 | 84.39 | O |
| HETATM | 2080 | O | HOH | 316 | −35.917 | 50.015 | 39.350 | 1.00 | 102.90 | O |
| HETATM | 2081 | O | HOH | 317 | 6.860 | 27.799 | 16.464 | 1.00 | 94.15 | O |
| HETATM | 2082 | O | HOH | 318 | −6.624 | 47.121 | 27.551 | 1.00 | 55.25 | O |
| HETATM | 2083 | O | HOH | 319 | 25.633 | 36.301 | 33.674 | 1.00 | 90.78 | O |
| HETATM | 2084 | O | HOH | 320 | −40.011 | 28.195 | 30.647 | 1.00 | 72.48 | O |
| HETATM | 2085 | O | HOH | 321 | −0.548 | 21.349 | 5.340 | 1.00 | 76.60 | O |
| HETATM | 2086 | O | HOH | 322 | −19.675 | 66.803 | 60.854 | 1.00 | 94.58 | O |
| HETATM | 2087 | O | HOH | 323 | −2.728 | 51.206 | 32.260 | 1.00 | 77.64 | O |
| HETATM | 2088 | O | HOH | 324 | −1.247 | 43.110 | 29.580 | 1.00 | 56.25 | O |
| HETATM | 2089 | O | HOH | 325 | −34.343 | 37.661 | 47.184 | 1.00 | 73.61 | O |
| HETATM | 2090 | O | HOH | 326 | −17.710 | 48.503 | 47.282 | 1.00 | 51.09 | O |
| HETATM | 2091 | O | HOH | 327 | 19.728 | 28.197 | 29.672 | 1.00 | 71.53 | O |
| HETATM | 2092 | O | HOH | 328 | −16.815 | 43.464 | 29.032 | 1.00 | 38.64 | O |
| HETATM | 2093 | O | HOH | 329 | −8.769 | 46.895 | 26.815 | 1.00 | 63.95 | O |
| HETATM | 2094 | O | HOH | 330 | 19.385 | 30.108 | 27.998 | 1.00 | 84.78 | O |
| HETATM | 2095 | O | HOH | 331 | 20.296 | 46.890 | 36.277 | 1.00 | 69.10 | O |
| HETATM | 2096 | O | HOH | 332 | 10.011 | 39.138 | 22.129 | 1.00 | 73.04 | O |
| HETATM | 2097 | O | HOH | 333 | −34.667 | 43.573 | 39.921 | 1.00 | 94.23 | O |
| HETATM | 2098 | O | HOH | 334 | 25.038 | 44.754 | 44.084 | 1.00 | 62.57 | O |
| HETATM | 2099 | O | HOH | 335 | 18.836 | 44.474 | 39.123 | 1.00 | 79.24 | O |
| HETATM | 2100 | O | HOH | 336 | 5.728 | 24.703 | 20.348 | 1.00 | 91.70 | O |
| HETATM | 2101 | O | HOH | 337 | −37.708 | 28.757 | 29.261 | 1.00 | 89.30 | O |
| HETATM | 2102 | O | HOH | 338 | 24.041 | 44.585 | 36.443 | 1.00 | 87.02 | O |
| HETATM | 2103 | O | HOH | 339 | −16.021 | 34.803 | 49.305 | 0.50 | 57.78 | O |
| HETATM | 2104 | O | HOH | 340 | −23.445 | 54.520 | 27.866 | 1.00 | 97.08 | O |
| HETATM | 2105 | O | HOH | 341 | 12.151 | 43.628 | 46.109 | 1.00 | 87.45 | O |
| HETATM | 2106 | O | HOH | 342 | 21.420 | 30.507 | 17.302 | 1.00 | 70.53 | O |
| HETATM | 2107 | O | HOH | 343 | −34.255 | 41.798 | 50.132 | 1.00 | 81.37 | O |
| HETATM | 2108 | O | HOH | 344 | 18.390 | 20.362 | 32.308 | 1.00 | 83.10 | O |
| HETATM | 2109 | O | HOH | 345 | −25.000 | 56.746 | 38.927 | 1.00 | 94.33 | O |
| HETATM | 2110 | O | HOH | 346 | −8.804 | 60.068 | 50.157 | 1.00 | 79.38 | O |
| HETATM | 2111 | O | HOH | 347 | −20.488 | 55.011 | 45.150 | 1.00 | 91.93 | O |
| HETATM | 2112 | O | HOH | 348 | −0.212 | 46.908 | 32.365 | 1.00 | 84.10 | O |
| HETATM | 2113 | O | HOH | 349 | −7.494 | 7.448 | 7.764 | 1.00 | 76.18 | O |
| HETATM | 2114 | O | HOH | 350 | −17.446 | 73.178 | 55.029 | 1.00 | 76.88 | O |
| HETATM | 2115 | O | HOH | 351 | −7.818 | 4.607 | 5.147 | 1.00 | 67.95 | O |
| HETATM | 2116 | O | HOH | 352 | 18.532 | 34.688 | 16.174 | 1.00 | 80.19 | O |
| HETATM | 2117 | O | HOH | 353 | −38.919 | 53.773 | 41.038 | 1.00 | 77.53 | O |
| HETATM | 2118 | O | HOH | 354 | 4.686 | 42.380 | 42.213 | 1.00 | 66.79 | O |
| HETATM | 2119 | O | HOH | 355 | −43.020 | 57.512 | 44.325 | 1.00 | 74.66 | O |
| HETATM | 2120 | O | HOH | 356 | −36.610 | 51.515 | 43.519 | 1.00 | 80.73 | O |
| HETATM | 2121 | O | HOH | 357 | −40.125 | 38.357 | 26.648 | 1.00 | 83.64 | O |
| HETATM | 2122 | O | HOH | 358 | −42.612 | 55.808 | 47.578 | 1.00 | 69.35 | O |
| CONECT | 168 | 649 | | | | | | | | |
| CONECT | 649 | 168 | | | | | | | | |

APPENDIX I(b)-continued

```
CONECT   1050  1531
CONECT   1531  1050
MASTER         377   0   0   2   26   0   0   6   2120   2   4   18
END
```

APPENDIX I(c)

```
HEADER   12A-9
COMPND   12A-9
REMARK   3
REMARK   3   REFINEMENT.
REMARK   3      PROGRAM        : REFMAC 5.2.0005
REMARK   3      AUTHORS        : MURSHUDOV, VAGIN, DODSON
REMARK   3
REMARK   3      REFINEMENT TARGET : MAXIMUM LIKELIHOOD
REMARK   3
REMARK   3   DATA USED IN REFINEMENT.
REMARK   3      RESOLUTION RANGE HIGH     (ANGSTROMS) :  2.10
REMARK   3      RESOLUTION RANGE LOW      (ANGSTROMS) : 34.20
REMARK   3      DATA CUTOFF               (SIGMA(F)) : NONE
REMARK   3      COMPLETENESS FOR RANGE        (%) : 98.55
REMARK   3      NUMBER OF REFLECTIONS              :  6040
REMARK   3
REMARK   3   FIT TO DATA USED IN REFINEMENT.
REMARK   3      CROSS-VALIDATION METHOD          : THROUGHOUT
REMARK   3      FREE R VALUE TEST SET SELECTION  : RANDOM
REMARK   3      R VALUE       (WORKING + TEST SET) : 0.22276
REMARK   3      R VALUE            (WORKING SET) : 0.21668
REMARK   3      FREE R VALUE                     : 0.34914
REMARK   3      FREE R VALUE TEST SET SIZE   (%) : 4.7
REMARK   3      FREE R VALUE TEST SET COUNT      :   297
REMARK   3
REMARK   3   FIT IN THE HIGHEST RESOLUTION BIN.
REMARK   3      TOTAL NUMBER OF BINS USED           :    20
REMARK   3      BIN RESOLUTION RANGE HIGH           :  2.100
REMARK   3      BIN RESOLUTION RANGE LOW            :  2.154
REMARK   3      REFLECTION IN BIN        (WORKING SET) :   432
REMARK   3      BIN COMPLETENESS    (WORKING + TEST) (%) : 100.00
REMARK   3      BIN R VALUE              (WORKING SET) :  0.261
REMARK   3      BIN FREE R VALUE SET COUNT          :    19
REMARK   3      BIN FREE R VALUE                    :  0.397
REMARK   3
REMARK   3   NUMBER OF NON-HYDROGEN ATOMS USED IN REFINEMENT.
REMARK   3      ALL ATOMS             :       963
REMARK   3
REMARK   3   B VALUES.
REMARK   3      FROM WILSON PLOT          (A**2) : NULL
REMARK   3      MEAN B VALUE       (OVERALL, A**2) :  46.514
REMARK   3      OVERALL ANISOTROPIC B VALUE.
REMARK   3        B11 (A**2)  :  -2.38
REMARK   3        B22 (A**2)  :   2.21
REMARK   3        B33 (A**2)  :   0.17
REMARK   3        B12 (A**2)  :   0.00
REMARK   3        B13 (A**2)  :   0.00
REMARK   3        B23 (A**2)  :   0.00
REMARK   3
REMARK   3   ESTIMATED OVERALL COORDINATE ERROR.
REMARK   3      ESU BASED ON R VALUE                     (A) :  0.308
REMARK   3      ESU BASED ON FREE R VALUE                (A) :  0.299
REMARK   3      ESU BASED ON MAXIMUM LIKELIHOOD          (A) :  0.266
REMARK   3      ESU FOR B VALUES BASED ON MAXIMUM LIKELIHOOD  (A**2) : 18.684
REMARK   3
REMARK   3   CORRELATION COEFFICIENTS.
REMARK   3      CORRELATION COEFFICIENT FO-FC       :  0.938
REMARK   3      CORRELATION COEFFICIENT FO-FC FREE  :  0.852
REMARK   3
REMARK   3   RMS DEVIATIONS FROM IDEAL VALUES           COUNT    RMS    WEIGHT
REMARK   3      BOND LENGTHS REFINED ATOMS      (A):    833;   0.013;   0.022
REMARK   3      BOND ANGLES REFINED ATOMS  (DEGREES):  1125;   1.589;   1.959
REMARK   3      TORSION ANGLES, PERIOD 1   (DEGREES):   107;   7.310;   5.000
REMARK   3      TORSION ANGLES, PERIOD 2   (DEGREES):    35;  31.640;  22.857
REMARK   3      TORSION ANGLES, PERIOD 3   (DEGREES):   149;  17.871;  15.000
REMARK   3      TORSION ANGLES, PERIOD 4   (DEGREES):     9;  15.120;  15.000
REMARK   3      CHIRAL-CENTER RESTRAINTS      (A**3):   132;   0.098;   0.200
REMARK   3      GENERAL PLANES REFINED ATOMS     (A):   610;   0.006;   0.020
REMARK   3      NON-BONDED CONTACTS REFINED ATOMS (A):  328;   0.262;   0.200
REMARK   3      NON-BONDED TORSION REFINED ATOMS  (A):  540;   0.307;   0.200
```

APPENDIX I(c)-continued

| | | | | | | | | | | |
|---|---|---|---|---|---|---|---|---|---|---|
| REMARK | 3 | H-BOND (X...Y) REFINED ATOMS | | | (A): | 88; | 0.234; | 0.200 | | |
| REMARK | 3 | SYMMETRY VDW REFINED ATOMS | | | (A): | 40; | 0.230; | 0.200 | | |
| REMARK | 3 | SYMMETRY H-BOND REFINED ATOMS | | | (A): | 34; | 0.251; | 0.200 | | |
| REMARK | 3 | | | | | | | | | |
| REMARK | 3 | ISOTROPIC THERMAL FACTOR RESTRAINTS. | | | | COUNT | RMS | WEIGHT | | |
| REMARK | 3 | MAIN-CHAIN BOND REFINED ATOMS | | | (A**2): | 542; | 0.684; | 1.500 | | |
| REMARK | 3 | MAIN-CHAIN ANGLE REFINED ATOMS | | | (A**2): | 853; | 1.129; | 2.000 | | |
| REMARK | 3 | SIDE-CHAIN BOND REFINED ATOMS | | | (A**2): | 327; | 1.950; | 3.000 | | |
| REMARK | 3 | SIDE-CHAIN ANGLE REFINED ATOMS | | | (A**2): | 272; | 2.921; | 4.500 | | |
| REMARK | 3 | | | | | | | | | |
| REMARK | 3 | NCS RESTRAINTS STATISTICS | | | | | | | | |
| REMARK | 3 | NUMBER OF NCS GROUPS: NULL | | | | | | | | |
| REMARK | 3 | | | | | | | | | |
| REMARK | 3 | | | | | | | | | |
| REMARK | 3 | TLS DETAILS | | | | | | | | |
| REMARK | 3 | NUMBER OF TLS GROUPS : | | 1 | | | | | | |
| REMARK | 3 | ATOM RECORD CONTAINS RESIDUAL B FACTORS ONLY | | | | | | | | |
| REMARK | 3 | | | | | | | | | |
| REMARK | 3 | TLS GROUP : | 1 | | | | | | | |
| REMARK | 3 | NUMBER OF COMPONENTS GROUP : | | 1 | | | | | | |
| REMARK | 3 | COMPONENTS | C SSSEQI | TO | C SSSEQI | | | | | |
| REMARK | 3 | RESIDUE RANGE: | A | 1 | A | 108 | | | | |
| REMARK | 3 | ORIGIN FOR THE GROUP (A): | | 6.9430 | 24.5360 | 17.1020 | | | | |
| REMARK | 3 | T TENSOR | | | | | | | | |
| REMARK | 3 | T11: | −0.1693 | T22: | −0.1046 | | | | | |
| REMARK | 3 | T33: | −0.2013 | T12: | 0.0063 | | | | | |
| REMARK | 3 | T13: | 0.0567 | T23: | 0.0059 | | | | | |
| REMARK | 3 | L TENSOR | | | | | | | | |
| REMARK | 3 | L11: | 6.2257 | L22: | 3.2213 | | | | | |
| REMARK | 3 | L33: | 3.2779 | L12: | 1.8504 | | | | | |
| REMARK | 3 | L13: | 1.5143 | L23: | 0.1677 | | | | | |
| REMARK | 3 | S TENSOR | | | | | | | | |
| REMARK | 3 | S11: | 0.0246 | S12: | 0.4407 | S13: | 0.2852 | | | |
| REMARK | 3 | S21: | −0.1471 | S22: | 0.0358 | S23: | −0.0174 | | | |
| REMARK | 3 | S31: | −0.1461 | S32: | −0.0338 | S33: | −0.0604 | | | |
| REMARK | 3 | | | | | | | | | |
| REMARK | 3 | | | | | | | | | |
| REMARK | 3 | BULK SOLVENT MODELLING. | | | | | | | | |
| REMARK | 3 | METHOD USED : MASK | | | | | | | | |
| REMARK | 3 | PARAMETERS FOR MASK CALCULATION | | | | | | | | |
| REMARK | 3 | VDW PROBE RADIUS : | | 1.20 | | | | | | |
| REMARK | 3 | ION PROBE RADIUS : | | 0.80 | | | | | | |
| REMARK | 3 | SHRINKAGE RADIUS : | | 0.80 | | | | | | |
| REMARK | 3 | | | | | | | | | |
| REMARK | 3 | OTHER REFINEMENT REMARKS: | | | | | | | | |
| REMARK | 3 | HYDROGENS HAVE BEEN ADDED IN THE RIDING POSITIONS | | | | | | | | |
| REMARK | 3 | | | | | | | | | |
| SSBOND | 1 | CYS | A | 22 | CYS | A | 83 | | | |
| SSBOND | 2 | CYS | A | 29 | CYS | A | 89 | | | |
| CISPEP | 1 | THR | A | 6 | PRO | A | 7 | 0.00 | | |
| CRYST1 | 38.268 | 68.324 | 39.511 | 90.00 | 90.00 | 90.00 P 21 21 2 | | | | |
| SCALE1 | | 0.026131 | 0.000000 | 0.000000 | 0.00000 | | | | | |
| SCALE2 | | 0.000000 | 0.014636 | 0.000000 | 0.00000 | | | | | |
| SCALE3 | | 0.000000 | 0.000000 | 0.025309 | 0.00000 | | | | | |
| ATOM | 1 | N | ALA | A | 1 | 4.330 | 25.995 | 2.005 | 1.00 | 43.85 N |
| ATOM | 2 | CA | ALA | A | 1 | 4.728 | 27.133 | 1.107 | 1.00 | 43.77 C |
| ATOM | 3 | CB | ALA | A | 1 | 3.593 | 27.517 | 0.176 | 1.00 | 43.63 C |
| ATOM | 4 | C | ALA | A | 1 | 5.151 | 28.332 | 1.936 | 1.00 | 43.39 C |
| ATOM | 5 | O | ALA | A | 1 | 5.918 | 29.172 | 1.470 | 1.00 | 43.85 O |
| ATOM | 6 | N | ARG | A | 2 | 4.579 | 28.432 | 3.132 | 1.00 | 42.78 N |
| ATOM | 7 | CA | ARG | A | 2 | 5.102 | 29.264 | 4.216 | 1.00 | 42.72 C |
| ATOM | 8 | CB | ARG | A | 2 | 4.780 | 30.749 | 4.023 | 1.00 | 42.82 C |
| ATOM | 9 | CG | ARG | A | 2 | 5.657 | 31.676 | 4.877 | 1.00 | 44.95 C |
| ATOM | 10 | CD | ARG | A | 2 | 5.472 | 33.132 | 4.480 | 1.00 | 47.25 C |
| ATOM | 11 | NE | ARG | A | 2 | 6.437 | 34.012 | 5.135 | 1.00 | 49.81 N |
| ATOM | 12 | CZ | ARG | A | 2 | 6.603 | 35.304 | 4.828 | 1.00 | 51.50 C |
| ATOM | 13 | NH1 | ARG | A | 2 | 5.863 | 35.873 | 3.885 | 1.00 | 51.25 N |
| ATOM | 14 | NH2 | ARG | A | 2 | 7.507 | 36.040 | 5.465 | 1.00 | 51.63 N |
| ATOM | 15 | C | ARG | A | 2 | 4.476 | 28.768 | 5.506 | 1.00 | 42.13 C |
| ATOM | 16 | O | ARG | A | 2 | 3.283 | 28.457 | 5.534 | 1.00 | 41.66 O |
| ATOM | 17 | N | VAL | A | 3 | 5.280 | 28.675 | 6.567 | 1.00 | 41.68 N |
| ATOM | 18 | CA | VAL | A | 3 | 4.755 | 28.407 | 7.899 | 1.00 | 41.27 C |
| ATOM | 19 | CB | VAL | A | 3 | 5.585 | 27.367 | 8.690 | 1.00 | 41.29 C |
| ATOM | 20 | CG1 | VAL | A | 3 | 5.631 | 26.054 | 7.981 | 1.00 | 41.79 C |
| ATOM | 21 | CG2 | VAL | A | 3 | 4.962 | 27.123 | 10.045 | 1.00 | 42.69 C |
| ATOM | 22 | C | VAL | A | 3 | 4.695 | 29.732 | 8.678 | 1.00 | 41.43 C |
| ATOM | 23 | O | VAL | A | 3 | 5.675 | 30.493 | 8.728 | 1.00 | 41.02 O |
| ATOM | 24 | N | ASP | A | 4 | 3.534 | 30.006 | 9.274 | 1.00 | 41.22 N |
| ATOM | 25 | CA | ASP | A | 4 | 3.393 | 31.135 | 10.171 | 1.00 | 40.99 C |
| ATOM | 26 | CB | ASP | A | 4 | 2.059 | 31.870 | 9.961 | 1.00 | 40.51 C |

APPENDIX I(c)-continued

| | | | | | | | | | | | |
|---|---|---|---|---|---|---|---|---|---|---|---|
| ATOM | 27 | CG | ASP | A | 4 | 1.862 | 32.377 | 8.537 | 1.00 | 43.34 | C |
| ATOM | 28 | OD1 | ASP | A | 4 | 0.693 | 32.684 | 8.183 | 1.00 | 44.24 | O |
| ATOM | 29 | OD2 | ASP | A | 4 | 2.854 | 32.502 | 7.779 | 1.00 | 45.58 | O |
| ATOM | 30 | C | ASP | A | 4 | 3.469 | 30.569 | 11.581 | 1.00 | 40.39 | C |
| ATOM | 31 | O | ASP | A | 4 | 2.629 | 29.730 | 11.968 | 1.00 | 40.91 | O |
| ATOM | 32 | N | GLN | A | 5 | 4.470 | 31.000 | 12.342 | 1.00 | 39.37 | N |
| ATOM | 33 | CA | GLN | A | 5 | 4.613 | 30.557 | 13.755 | 1.00 | 39.62 | C |
| ATOM | 34 | CB | GLN | A | 5 | 6.033 | 30.097 | 14.056 | 1.00 | 39.21 | C |
| ATOM | 35 | CG | GLN | A | 5 | 6.143 | 29.286 | 15.330 | 1.00 | 39.71 | C |
| ATOM | 36 | CD | GLN | A | 5 | 7.566 | 28.809 | 15.616 | 1.00 | 40.20 | C |
| ATOM | 37 | OE1 | GLN | A | 5 | 8.281 | 28.355 | 14.720 | 1.00 | 38.99 | O |
| ATOM | 38 | NE2 | GLN | A | 5 | 7.995 | 28.953 | 16.871 | 1.00 | 39.67 | N |
| ATOM | 39 | C | GLN | A | 5 | 4.305 | 31.695 | 14.702 | 1.00 | 39.74 | C |
| ATOM | 40 | O | GLN | A | 5 | 4.878 | 32.804 | 14.545 | 1.00 | 39.27 | O |
| ATOM | 41 | N | THR | A | 6 | 3.436 | 31.431 | 15.683 | 1.00 | 39.68 | N |
| ATOM | 42 | CA | THR | A | 6 | 3.127 | 32.446 | 16.692 | 1.00 | 39.83 | C |
| ATOM | 43 | CB | THR | A | 6 | 1.908 | 33.215 | 16.266 | 1.00 | 39.82 | C |
| ATOM | 44 | OG1 | THR | A | 6 | 1.666 | 34.263 | 17.204 | 1.00 | 43.51 | O |
| ATOM | 45 | CG2 | THR | A | 6 | 0.689 | 32.306 | 16.156 | 1.00 | 37.32 | C |
| ATOM | 46 | C | THR | A | 6 | 3.048 | 31.917 | 18.149 | 1.00 | 40.58 | C |
| ATOM | 47 | O | THR | A | 6 | 2.734 | 30.743 | 18.359 | 1.00 | 39.70 | O |
| ATOM | 48 | N | PRO | A | 7 | 3.405 | 32.748 | 19.163 | 1.00 | 41.05 | N |
| ATOM | 49 | CA | PRO | A | 7 | 3.870 | 34.153 | 19.132 | 1.00 | 41.58 | C |
| ATOM | 50 | CB | PRO | A | 7 | 3.722 | 34.616 | 20.587 | 1.00 | 41.21 | C |
| ATOM | 51 | CG | PRO | A | 7 | 3.829 | 33.371 | 21.381 | 1.00 | 42.26 | C |
| ATOM | 52 | CD | PRO | A | 7 | 3.378 | 32.213 | 20.535 | 1.00 | 40.83 | C |
| ATOM | 53 | C | PRO | A | 7 | 5.323 | 34.205 | 18.715 | 1.00 | 41.50 | C |
| ATOM | 54 | O | PRO | A | 7 | 5.996 | 33.179 | 18.810 | 1.00 | 40.92 | O |
| ATOM | 55 | N | ARG | A | 8 | 5.782 | 35.367 | 18.252 | 1.00 | 41.56 | N |
| ATOM | 56 | CA | ARG | A | 8 | 7.166 | 35.551 | 17.879 | 1.00 | 42.59 | C |
| ATOM | 57 | CB | ARG | A | 8 | 7.324 | 36.786 | 16.982 | 1.00 | 43.86 | C |
| ATOM | 58 | CG | ARG | A | 8 | 8.768 | 37.127 | 16.567 | 1.00 | 47.00 | C |
| ATOM | 59 | CD | ARG | A | 8 | 9.356 | 36.117 | 15.546 | 1.00 | 52.83 | C |
| ATOM | 60 | NE | ARG | A | 8 | 10.695 | 35.623 | 15.908 | 1.00 | 54.23 | N |
| ATOM | 61 | CZ | ARG | A | 8 | 11.824 | 36.329 | 15.838 | 1.00 | 55.74 | C |
| ATOM | 62 | NH1 | ARG | A | 8 | 12.973 | 35.762 | 16.189 | 1.00 | 55.74 | N |
| ATOM | 63 | NH2 | ARG | A | 8 | 11.817 | 37.602 | 15.438 | 1.00 | 55.73 | N |
| ATOM | 64 | C | ARG | A | 8 | 8.025 | 35.667 | 19.144 | 1.00 | 42.90 | C |
| ATOM | 65 | O | ARG | A | 8 | 9.165 | 35.198 | 19.172 | 1.00 | 42.04 | O |
| ATOM | 66 | N | ILE | A | 9 | 7.469 | 36.281 | 20.193 | 1.00 | 42.94 | N |
| ATOM | 67 | CA | ILE | A | 9 | 8.171 | 36.410 | 21.483 | 1.00 | 43.38 | C |
| ATOM | 68 | CB | ILE | A | 9 | 8.863 | 37.808 | 21.679 | 1.00 | 43.29 | C |
| ATOM | 69 | CG1 | ILE | A | 9 | 7.854 | 38.897 | 22.063 | 1.00 | 42.77 | C |
| ATOM | 70 | CD1 | ILE | A | 9 | 7.657 | 40.025 | 21.036 | 1.00 | 44.86 | C |
| ATOM | 71 | CG2 | ILE | A | 9 | 9.665 | 38.186 | 20.442 | 1.00 | 44.36 | C |
| ATOM | 72 | C | ILE | A | 9 | 7.211 | 36.153 | 22.641 | 1.00 | 43.85 | C |
| ATOM | 73 | O | ILE | A | 9 | 6.005 | 36.392 | 22.529 | 1.00 | 43.69 | O |
| ATOM | 74 | N | ALA | A | 10 | 7.754 | 35.682 | 23.758 | 1.00 | 44.25 | N |
| ATOM | 75 | CA | ALA | A | 10 | 6.946 | 35.359 | 24.930 | 1.00 | 44.42 | C |
| ATOM | 76 | CB | ALA | A | 10 | 6.407 | 33.930 | 24.805 | 1.00 | 44.54 | C |
| ATOM | 77 | C | ALA | A | 10 | 7.777 | 35.528 | 26.215 | 1.00 | 44.54 | C |
| ATOM | 78 | O | ALA | A | 10 | 8.956 | 35.154 | 26.271 | 1.00 | 44.06 | O |
| ATOM | 79 | N | THR | A | 11 | 7.180 | 36.136 | 27.231 | 1.00 | 44.75 | N |
| ATOM | 80 | CA | THR | A | 11 | 7.803 | 36.159 | 28.539 | 1.00 | 45.12 | C |
| ATOM | 81 | CB | THR | A | 11 | 8.201 | 37.568 | 28.982 | 1.00 | 45.29 | C |
| ATOM | 82 | OG1 | THR | A | 11 | 7.042 | 38.405 | 28.976 | 1.00 | 46.91 | O |
| ATOM | 83 | CG2 | THR | A | 11 | 9.283 | 38.154 | 28.075 | 1.00 | 46.06 | C |
| ATOM | 84 | C | THR | A | 11 | 6.833 | 35.565 | 29.545 | 1.00 | 45.16 | C |
| ATOM | 85 | O | THR | A | 11 | 5.795 | 36.146 | 29.848 | 1.00 | 45.26 | O |
| ATOM | 86 | N | LYS | A | 12 | 7.203 | 34.397 | 30.048 | 1.00 | 45.15 | N |
| ATOM | 87 | CA | LYS | A | 12 | 6.446 | 33.666 | 31.037 | 1.00 | 45.46 | C |
| ATOM | 88 | CB | LYS | A | 12 | 6.323 | 32.221 | 30.584 | 1.00 | 45.35 | C |
| ATOM | 89 | CG | LYS | A | 12 | 5.099 | 31.914 | 29.756 | 1.00 | 47.76 | C |
| ATOM | 90 | CD | LYS | A | 12 | 4.697 | 33.007 | 28.777 | 1.00 | 49.69 | C |
| ATOM | 91 | CE | LYS | A | 12 | 3.521 | 32.560 | 27.920 | 1.00 | 49.05 | C |
| ATOM | 92 | NZ | LYS | A | 12 | 2.306 | 32.457 | 28.739 | 1.00 | 49.64 | N |
| ATOM | 93 | C | LYS | A | 12 | 7.102 | 33.718 | 32.424 | 1.00 | 45.30 | C |
| ATOM | 94 | O | LYS | A | 12 | 8.283 | 34.053 | 32.569 | 1.00 | 45.21 | O |
| ATOM | 95 | N | GLU | A | 13 | 6.302 | 33.416 | 33.442 | 1.00 | 45.31 | N |
| ATOM | 96 | CA | GLU | A | 13 | 6.776 | 33.188 | 34.807 | 1.00 | 45.37 | C |
| ATOM | 97 | CB | GLU | A | 13 | 5.857 | 33.935 | 35.759 | 1.00 | 45.85 | C |
| ATOM | 98 | CG | GLU | A | 13 | 5.752 | 35.414 | 35.367 | 1.00 | 48.54 | C |
| ATOM | 99 | CD | GLU | A | 13 | 4.509 | 36.109 | 35.878 | 1.00 | 51.63 | C |
| ATOM | 100 | OE1 | GLU | A | 13 | 4.402 | 37.334 | 35.645 | 1.00 | 53.17 | O |
| ATOM | 101 | OE2 | GLU | A | 13 | 3.646 | 35.448 | 36.511 | 1.00 | 54.08 | O |
| ATOM | 102 | C | GLU | A | 13 | 6.797 | 31.674 | 35.096 | 1.00 | 44.83 | C |
| ATOM | 103 | O | GLU | A | 13 | 6.029 | 30.902 | 34.496 | 1.00 | 43.74 | O |
| ATOM | 104 | N | THR | A | 14 | 7.675 | 31.229 | 35.986 | 1.00 | 44.58 | N |
| ATOM | 105 | CA | THR | A | 14 | 7.792 | 29.794 | 36.199 | 1.00 | 45.00 | C |
| ATOM | 106 | CB | THR | A | 14 | 8.810 | 29.381 | 37.292 | 1.00 | 45.21 | C |

APPENDIX I(c)-continued

| | | | | | | | | | | | |
|---|---|---|---|---|---|---|---|---|---|---|---|
| ATOM | 107 | OG1 | THR | A | 14 | 8.341 | 29.745 | 38.606 | 1.00 | 44.01 | O |
| ATOM | 108 | CG2 | THR | A | 14 | 10.190 | 29.968 | 37.006 | 1.00 | 45.34 | C |
| ATOM | 109 | C | THR | A | 14 | 6.419 | 29.253 | 36.532 | 1.00 | 45.37 | C |
| ATOM | 110 | O | THR | A | 14 | 5.614 | 29.949 | 37.138 | 1.00 | 45.15 | O |
| ATOM | 111 | N | GLY | A | 15 | 6.141 | 28.031 | 36.099 | 1.00 | 45.55 | N |
| ATOM | 112 | CA | GLY | A | 15 | 4.838 | 27.446 | 36.328 | 1.00 | 45.89 | C |
| ATOM | 113 | C | GLY | A | 15 | 3.778 | 27.733 | 35.276 | 1.00 | 46.24 | C |
| ATOM | 114 | O | GLY | A | 15 | 2.773 | 27.020 | 35.217 | 1.00 | 47.04 | O |
| ATOM | 115 | N | GLU | A | 16 | 3.978 | 28.754 | 34.439 | 1.00 | 46.01 | N |
| ATOM | 116 | CA | GLU | A | 16 | 3.004 | 29.052 | 33.376 | 1.00 | 45.58 | C |
| ATOM | 117 | CB | GLU | A | 16 | 3.171 | 30.483 | 32.865 | 1.00 | 45.77 | C |
| ATOM | 118 | CG | GLU | A | 16 | 2.684 | 31.561 | 33.810 | 1.00 | 45.94 | C |
| ATOM | 119 | CD | GLU | A | 16 | 2.551 | 32.924 | 33.137 | 1.00 | 46.28 | C |
| ATOM | 120 | OE1 | GLU | A | 16 | 1.414 | 33.434 | 33.026 | 1.00 | 48.01 | O |
| ATOM | 121 | OE2 | GLU | A | 16 | 3.577 | 33.492 | 32.719 | 1.00 | 46.37 | O |
| ATOM | 122 | C | GLU | A | 16 | 3.100 | 28.042 | 32.214 | 1.00 | 44.90 | C |
| ATOM | 123 | O | GLU | A | 16 | 3.937 | 27.152 | 32.242 | 1.00 | 44.86 | O |
| ATOM | 124 | N | SER | A | 17 | 2.217 | 28.187 | 31.224 | 1.00 | 44.50 | N |
| ATOM | 125 | CA | SER | A | 17 | 2.222 | 27.396 | 29.989 | 1.00 | 44.60 | C |
| ATOM | 126 | CB | SER | A | 17 | 0.842 | 26.775 | 29.738 | 1.00 | 44.45 | C |
| ATOM | 127 | OG | SER | A | 17 | 0.453 | 25.965 | 30.811 | 1.00 | 44.72 | O |
| ATOM | 128 | C | SER | A | 17 | 2.523 | 28.302 | 28.823 | 1.00 | 44.08 | C |
| ATOM | 129 | O | SER | A | 17 | 2.185 | 29.476 | 28.861 | 1.00 | 44.27 | O |
| ATOM | 130 | N | LEU | A | 18 | 3.128 | 27.748 | 27.783 | 1.00 | 44.07 | N |
| ATOM | 131 | CA | LEU | A | 18 | 3.221 | 28.413 | 26.500 | 1.00 | 44.43 | C |
| ATOM | 132 | CB | LEU | A | 18 | 4.676 | 28.794 | 26.169 | 1.00 | 44.33 | C |
| ATOM | 133 | CG | LEU | A | 18 | 4.894 | 29.325 | 24.724 | 1.00 | 45.37 | C |
| ATOM | 134 | CD1 | LEU | A | 18 | 4.372 | 30.754 | 24.566 | 1.00 | 46.79 | C |
| ATOM | 135 | CD2 | LEU | A | 18 | 6.337 | 29.238 | 24.266 | 1.00 | 44.61 | C |
| ATOM | 136 | C | LEU | A | 18 | 2.643 | 27.515 | 25.389 | 1.00 | 44.31 | C |
| ATOM | 137 | O | LEU | A | 18 | 2.907 | 26.316 | 25.342 | 1.00 | 45.00 | O |
| ATOM | 138 | N | THR | A | 19 | 1.845 | 28.108 | 24.511 | 1.00 | 43.57 | N |
| ATOM | 139 | CA | THR | A | 19 | 1.392 | 27.424 | 23.329 | 1.00 | 42.81 | C |
| ATOM | 140 | CB | THR | A | 19 | −0.133 | 27.292 | 23.333 | 1.00 | 43.09 | C |
| ATOM | 141 | OG1 | THR | A | 19 | −0.529 | 26.408 | 24.397 | 1.00 | 41.89 | O |
| ATOM | 142 | CG2 | THR | A | 19 | −0.661 | 26.725 | 22.038 | 1.00 | 42.37 | C |
| ATOM | 143 | C | THR | A | 19 | 1.956 | 28.171 | 22.123 | 1.00 | 42.99 | C |
| ATOM | 144 | O | THR | A | 19 | 1.816 | 29.395 | 21.994 | 1.00 | 43.18 | O |
| ATOM | 145 | N | ILE | A | 20 | 2.676 | 27.437 | 21.289 | 1.00 | 42.98 | N |
| ATOM | 146 | CA | ILE | A | 20 | 3.236 | 27.974 | 20.038 | 1.00 | 42.80 | C |
| ATOM | 147 | CB | ILE | A | 20 | 4.705 | 27.584 | 19.883 | 1.00 | 43.04 | C |
| ATOM | 148 | CG1 | ILE | A | 20 | 5.526 | 28.107 | 21.081 | 1.00 | 43.37 | C |
| ATOM | 149 | CD1 | ILE | A | 20 | 6.953 | 27.570 | 21.100 | 1.00 | 44.96 | C |
| ATOM | 150 | CG2 | ILE | A | 20 | 5.277 | 28.026 | 18.480 | 1.00 | 43.19 | C |
| ATOM | 151 | C | ILE | A | 20 | 2.446 | 27.323 | 18.917 | 1.00 | 42.22 | C |
| ATOM | 152 | O | ILE | A | 20 | 2.329 | 26.084 | 18.880 | 1.00 | 41.41 | O |
| ATOM | 153 | N | ASN | A | 21 | 1.875 | 28.159 | 18.052 | 1.00 | 41.71 | N |
| ATOM | 154 | CA | ASN | A | 21 | 1.036 | 27.726 | 16.926 | 1.00 | 42.93 | C |
| ATOM | 155 | CB | ASN | A | 21 | −0.183 | 28.639 | 16.820 | 1.00 | 42.54 | C |
| ATOM | 156 | CG | ASN | A | 21 | −0.976 | 28.682 | 18.083 | 1.00 | 44.72 | C |
| ATOM | 157 | OD1 | ASN | A | 21 | −1.349 | 29.757 | 18.551 | 1.00 | 45.71 | O |
| ATOM | 158 | ND2 | ASN | A | 21 | −1.219 | 27.513 | 18.674 | 1.00 | 42.93 | N |
| ATOM | 159 | C | ASN | A | 21 | 1.770 | 27.795 | 15.592 | 1.00 | 43.02 | C |
| ATOM | 160 | O | ASN | A | 21 | 2.331 | 28.828 | 15.282 | 1.00 | 43.10 | O |
| ATOM | 161 | N | CYS | A | 22 | 1.766 | 26.706 | 14.818 | 1.00 | 43.57 | N |
| ATOM | 162 | CA | CYS | A | 22 | 2.380 | 26.727 | 13.466 | 1.00 | 44.69 | C |
| ATOM | 163 | CB | CYS | A | 22 | 3.504 | 25.707 | 13.321 | 1.00 | 44.60 | C |
| ATOM | 164 | SG | CYS | A | 22 | 4.986 | 26.277 | 14.143 | 1.00 | 50.05 | S |
| ATOM | 165 | C | CYS | A | 22 | 1.353 | 26.444 | 12.415 | 1.00 | 43.98 | C |
| ATOM | 166 | O | CYS | A | 22 | 0.883 | 25.306 | 12.305 | 1.00 | 44.31 | O |
| ATOM | 167 | N | VAL | A | 23 | 0.991 | 27.470 | 11.656 | 1.00 | 42.86 | N |
| ATOM | 168 | CA | VAL | A | 23 | 0.041 | 27.309 | 10.574 | 1.00 | 42.98 | C |
| ATOM | 169 | CB | VAL | A | 23 | −1.009 | 28.482 | 10.517 | 1.00 | 42.82 | C |
| ATOM | 170 | CG1 | VAL | A | 23 | −1.749 | 28.606 | 11.828 | 1.00 | 42.81 | C |
| ATOM | 171 | CG2 | VAL | A | 23 | −0.349 | 29.798 | 10.236 | 1.00 | 43.32 | C |
| ATOM | 172 | C | VAL | A | 23 | 0.776 | 27.117 | 9.224 | 1.00 | 42.77 | C |
| ATOM | 173 | O | VAL | A | 23 | 1.634 | 27.906 | 8.863 | 1.00 | 42.18 | O |
| ATOM | 174 | N | LEU | A | 24 | 0.440 | 26.055 | 8.498 | 1.00 | 43.14 | N |
| ATOM | 175 | CA | LEU | A | 24 | 1.036 | 25.814 | 7.191 | 1.00 | 43.73 | C |
| ATOM | 176 | CB | LEU | A | 24 | 1.249 | 24.329 | 6.928 | 1.00 | 43.14 | C |
| ATOM | 177 | CG | LEU | A | 24 | 1.546 | 23.903 | 5.485 | 1.00 | 43.95 | C |
| ATOM | 178 | CD1 | LEU | A | 24 | 1.681 | 22.390 | 5.387 | 1.00 | 43.88 | C |
| ATOM | 179 | CD2 | LEU | A | 24 | 2.799 | 24.576 | 4.951 | 1.00 | 41.94 | C |
| ATOM | 180 | C | LEU | A | 24 | 0.134 | 26.444 | 6.139 | 1.00 | 44.52 | C |
| ATOM | 181 | O | LEU | A | 24 | −0.906 | 25.887 | 5.749 | 1.00 | 44.87 | O |
| ATOM | 182 | N | ARG | A | 25 | 0.528 | 27.626 | 5.692 | 1.00 | 44.92 | N |
| ATOM | 183 | CA | ARG | A | 25 | −0.296 | 28.383 | 4.783 | 1.00 | 45.81 | C |
| ATOM | 184 | CB | ARG | A | 25 | −0.088 | 29.882 | 5.010 | 1.00 | 45.82 | C |
| ATOM | 185 | CG | ARG | A | 25 | −0.384 | 30.338 | 6.442 | 1.00 | 47.76 | C |
| ATOM | 186 | CD | ARG | A | 25 | −1.877 | 30.620 | 6.729 | 1.00 | 50.07 | C |

APPENDIX I(c)-continued

| | | | | | | | | | | | |
|---|---|---|---|---|---|---|---|---|---|---|---|
| ATOM | 187 | NE   | ARG | A | 25 | −2.337 | 31.949 | 6.312  | 1.00 | 53.50 | N |
| ATOM | 188 | CZ   | ARG | A | 25 | −1.548 | 32.969 | 5.958  | 1.00 | 55.85 | C |
| ATOM | 189 | NH1  | ARG | A | 25 | −0.231 | 32.824 | 5.983  | 1.00 | 56.20 | N |
| ATOM | 190 | NH2  | ARG | A | 25 | −2.074 | 34.141 | 5.571  | 1.00 | 55.64 | N |
| ATOM | 191 | C    | ARG | A | 25 | 0.043  | 27.961 | 3.361  | 1.00 | 46.02 | C |
| ATOM | 192 | O    | ARG | A | 25 | 1.085  | 28.348 | 2.822  | 1.00 | 45.99 | O |
| ATOM | 193 | N    | ARP | A | 26 | −0.843 | 27.155 | 2.777  | 1.00 | 46.53 | N |
| ATOM | 194 | CA   | ASP | A | 26 | −0.624 | 26.523 | 1.488  | 1.00 | 47.22 | C |
| ATOM | 195 | CB   | ASP | A | 26 | 0.407  | 25.390 | 1.604  | 1.00 | 47.06 | C |
| ATOM | 196 | CG   | ASP | A | 26 | 0.809  | 24.833 | 0.248  | 1.00 | 46.67 | C |
| ATOM | 197 | OD1  | ASP | A | 26 | 0.263  | 25.302 | −0.772 | 1.00 | 46.55 | O |
| ATOM | 198 | OD2  | ASP | A | 26 | 1.676  | 23.946 | 0.195  | 1.00 | 46.05 | O |
| ATOM | 199 | C    | ASP | A | 26 | −1.901 | 25.928 | 0.953  | 1.00 | 47.74 | C |
| ATOM | 200 | O    | ASP | A | 26 | −2.360 | 24.914 | 1.462  | 1.00 | 49.08 | O |
| ATOM | 201 | N    | THR | A | 27 | −2.452 | 26.524 | −0.096 | 1.00 | 48.30 | N |
| ATOM | 202 | CA   | THR | A | 27 | −3.694 | 26.029 | −0.712 | 1.00 | 48.55 | C |
| ATOM | 203 | CB   | THR | A | 27 | −4.261 | 27.048 | −1.707 | 1.00 | 48.30 | C |
| ATOM | 204 | OG1  | THR | A | 27 | −3.194 | 27.563 | −2.505 | 1.00 | 48.97 | O |
| ATOM | 205 | CG2  | THR | A | 27 | −4.952 | 28.201 | −0.984 | 1.00 | 48.44 | C |
| ATOM | 206 | C    | THR | A | 27 | −3.548 | 24.685 | −1.447 | 1.00 | 48.44 | C |
| ATOM | 207 | O    | THR | A | 27 | −4.559 | 24.048 | −1.785 | 1.00 | 48.34 | O |
| ATOM | 208 | N    | ALA | A | 28 | −2.300 | 24.264 | −1.679 | 1.00 | 47.65 | N |
| ATOM | 209 | CA   | ALA | A | 28 | −2.003 | 23.004 | −2.379 | 1.00 | 46.66 | C |
| ATOM | 210 | CB   | ALA | A | 28 | −0.974 | 23.244 | −3.482 | 1.00 | 46.92 | C |
| ATOM | 211 | C    | ALA | A | 28 | −1.610 | 21.758 | −1.522 | 1.00 | 46.70 | C |
| ATOM | 212 | O    | ALA | A | 28 | −1.761 | 20.627 | −2.016 | 1.00 | 46.77 | O |
| ATOM | 213 | N    | CYS | A | 29 | −1.129 | 21.935 | −0.279 | 1.00 | 45.33 | N |
| ATOM | 214 | CA   | CYS | A | 29 | −0.631 | 20.784 | 0.521  | 1.00 | 44.73 | C |
| ATOM | 215 | CB   | CYS | A | 29 | 0.909  | 20.674 | 0.491  | 1.00 | 44.19 | C |
| ATOM | 216 | SG   | CYS | A | 29 | 1.740  | 20.865 | −1.109 | 1.00 | 44.32 | S |
| ATOM | 217 | C    | CYS | A | 29 | −1.074 | 20.722 | 1.983  | 1.00 | 43.81 | C |
| ATOM | 218 | O    | CYS | A | 29 | −1.289 | 21.754 | 2.630  | 1.00 | 43.43 | O |
| ATOM | 219 | N    | ALA | A | 30 | −1.164 | 19.495 | 2.495  | 1.00 | 42.66 | N |
| ATOM | 220 | CA   | ALA | A | 30 | −1.505 | 19.233 | 3.886  | 1.00 | 42.28 | C |
| ATOM | 221 | CB   | ALA | A | 30 | −2.285 | 17.930 | 3.997  | 1.00 | 42.02 | C |
| ATOM | 222 | C    | ALA | A | 30 | −0.269 | 19.154 | 4.771  | 1.00 | 41.62 | C |
| ATOM | 223 | O    | ALA | A | 30 | 0.712  | 18.511 | 4.429  | 1.00 | 41.53 | O |
| ATOM | 224 | N    | LEU | A | 31 | −0.325 | 19.794 | 5.923  | 1.00 | 41.91 | N |
| ATOM | 225 | CA   | LEU | A | 31 | 0.662  | 19.561 | 6.967  | 1.00 | 42.25 | C |
| ATOM | 226 | CB   | LEU | A | 31 | 0.404  | 20.523 | 8.124  | 1.00 | 42.32 | C |
| ATOM | 227 | CG   | LEU | A | 31 | 1.190  | 20.318 | 9.432  | 1.00 | 43.10 | C |
| ATOM | 228 | CD1  | LEU | A | 31 | 0.828  | 21.343 | 10.499 | 1.00 | 44.14 | C |
| ATOM | 229 | CD2  | LEU | A | 31 | 2.648  | 20.360 | 9.184  | 1.00 | 41.11 | C |
| ATOM | 230 | C    | LEU | A | 31 | 0.556  | 18.104 | 7.445  | 1.00 | 42.95 | C |
| ATOM | 231 | O    | LEU | A | 31 | −0.355 | 17.764 | 8.187  | 1.00 | 42.73 | O |
| ATOM | 232 | N    | ASP | A | 32 | 1.461  | 17.234 | 7.017  | 1.00 | 44.01 | N |
| ATOM | 233 | CA   | ASP | A | 32 | 1.352  | 15.832 | 7.416  | 1.00 | 45.57 | C |
| ATOM | 234 | CB   | ASP | A | 32 | 1.979  | 14.882 | 6.399  | 1.00 | 45.87 | C |
| ATOM | 235 | CG   | ASP | A | 32 | 1.289  | 13.517 | 6.377  | 1.00 | 48.45 | C |
| ATOM | 236 | OD1  | ASP | A | 32 | 1.974  | 12.499 | 6.104  | 1.00 | 51.52 | O |
| ATOM | 237 | OD2  | ASP | A | 32 | 0.056  | 13.451 | 6.625  | 1.00 | 51.42 | O |
| ATOM | 238 | C    | ASP | A | 32 | 1.928  | 15.561 | 8.799  | 1.00 | 46.12 | C |
| ATOM | 239 | O    | ASP | A | 32 | 1.336  | 14.820 | 9.586  | 1.00 | 48.01 | O |
| ATOM | 240 | N    | SER | A | 33 | 3.060  | 16.168 | 9.112  | 1.00 | 45.67 | N |
| ATOM | 241 | CA   | SER | A | 33 | 3.754  | 15.910 | 10.367 | 1.00 | 45.25 | C |
| ATOM | 242 | CB   | SER | A | 33 | 4.803  | 14.811 | 10.179 | 1.00 | 45.41 | C |
| ATOM | 243 | OG   | SER | A | 33 | 4.209  | 13.522 | 10.260 | 1.00 | 47.47 | O |
| ATOM | 244 | C    | SER | A | 33 | 4.436  | 17.192 | 10.801 | 1.00 | 44.88 | C |
| ATOM | 245 | O    | SER | A | 33 | 4.494  | 18.142 | 10.048 | 1.00 | 44.07 | O |
| ATOM | 246 | N    | THR | A | 34 | 4.924  | 17.211 | 12.037 | 1.00 | 44.87 | N |
| ATOM | 247 | CA   | THR | A | 34 | 5.688  | 18.333 | 12.566 | 1.00 | 44.62 | C |
| ATOM | 248 | CB   | THR | A | 34 | 4.807  | 19.303 | 13.360 | 1.00 | 44.16 | C |
| ATOM | 249 | OG1  | THR | A | 34 | 3.591  | 19.534 | 12.654 | 1.00 | 45.91 | O |
| ATOM | 250 | CG2  | THR | A | 34 | 5.499  | 20.667 | 13.570 | 1.00 | 44.99 | C |
| ATOM | 251 | C    | THR | A | 34 | 6.725  | 17.760 | 13.515 | 1.00 | 44.44 | C |
| ATOM | 252 | O    | THR | A | 34 | 6.480  | 16.725 | 14.145 | 1.00 | 44.41 | O |
| ATOM | 253 | N    | ASN | A | 35 | 7.886  | 18.407 | 13.577 | 1.00 | 43.58 | N |
| ATOM | 254 | CA   | ASN | A | 35 | 8.814  | 18.241 | 14.693 | 1.00 | 42.87 | C |
| ATOM | 255 | CB   | ASN | A | 35 | 10.126 | 17.582 | 14.245 | 1.00 | 45.18 | C |
| ATOM | 256 | CG   | ASN | A | 35 | 9.995  | 16.083 | 13.991 | 1.00 | 47.53 | C |
| ATOM | 257 | OD1  | ASN | A | 35 | 9.134  | 15.403 | 14.564 | 1.00 | 54.08 | O |
| ATOM | 258 | ND2  | ASN | A | 35 | 10.873 | 15.555 | 13.136 | 1.00 | 49.76 | N |
| ATOM | 259 | C    | ASN | A | 35 | 9.074  | 19.624 | 15.301 | 1.00 | 41.97 | C |
| ATOM | 260 | O    | ASN | A | 35 | 8.830  | 20.677 | 14.667 | 1.00 | 40.57 | O |
| ATOM | 261 | N    | TRP | A | 36 | 9.528  | 19.609 | 16.542 | 1.00 | 40.82 | N |
| ATOM | 262 | CA   | TRP | A | 36 | 9.709  | 20.808 | 17.311 | 1.00 | 40.85 | C |
| ATOM | 263 | CB   | TRP | A | 36 | 8.676  | 20.850 | 18.471 | 1.00 | 41.37 | C |
| ATOM | 264 | CG   | TRP | A | 36 | 7.177  | 20.913 | 17.976 | 1.00 | 40.86 | C |
| ATOM | 265 | CD1  | TRP | A | 36 | 6.334  | 19.850 | 17.742 | 1.00 | 40.28 | C |
| ATOM | 266 | NE1  | TRP | A | 36 | 5.096  | 20.302 | 17.342 | 1.00 | 40.69 | N |

APPENDIX I(c)-continued

| ATOM | 267 | CE2 | TRP | A | 36 | 5.132 | 21.676 | 17.280 | 1.00 | 40.81 | C |
|------|-----|-----|-----|---|----|-------|--------|--------|------|-------|---|
| ATOM | 268 | CD2 | TRP | A | 36 | 6.426 | 22.091 | 17.646 | 1.00 | 39.78 | C |
| ATOM | 269 | CE3 | TRP | A | 36 | 6.709 | 23.467 | 17.680 | 1.00 | 42.09 | C |
| ATOM | 270 | CZ3 | TRP | A | 36 | 5.707 | 24.367 | 17.335 | 1.00 | 39.48 | C |
| ATOM | 271 | CH2 | TRP | A | 36 | 4.455 | 23.918 | 16.931 | 1.00 | 41.78 | C |
| ATOM | 272 | CZ2 | TRP | A | 36 | 4.136 | 22.578 | 16.914 | 1.00 | 40.38 | C |
| ATOM | 273 | C   | TRP | A | 36 | 11.133 | 20.823 | 17.820 | 1.00 | 40.66 | C |
| ATOM | 274 | O   | TRP | A | 36 | 11.659 | 19.781 | 18.190 | 1.00 | 38.51 | O |
| ATOM | 275 | N   | TYR | A | 37 | 11.749 | 22.013 | 17.804 | 1.00 | 40.65 | N |
| ATOM | 276 | CA  | TYR | A | 37 | 13.153 | 22.209 | 18.092 | 1.00 | 41.40 | C |
| ATOM | 277 | CB  | TYR | A | 37 | 13.942 | 22.596 | 16.813 | 1.00 | 42.81 | C |
| ATOM | 278 | CG  | TYR | A | 37 | 13.855 | 21.544 | 15.747 | 1.00 | 44.19 | C |
| ATOM | 279 | CD1 | TYR | A | 37 | 12.811 | 21.548 | 14.841 | 1.00 | 46.04 | C |
| ATOM | 280 | CE1 | TYR | A | 37 | 12.690 | 20.563 | 13.899 | 1.00 | 47.40 | C |
| ATOM | 281 | CZ  | TYR | A | 37 | 13.604 | 19.559 | 13.838 | 1.00 | 47.21 | C |
| ATOM | 282 | OH  | TYR | A | 37 | 13.457 | 18.596 | 12.859 | 1.00 | 47.93 | O |
| ATOM | 283 | CE2 | TYR | A | 37 | 14.669 | 19.518 | 14.740 | 1.00 | 46.59 | C |
| ATOM | 284 | CD2 | TYR | A | 37 | 14.769 | 20.499 | 15.698 | 1.00 | 44.56 | C |
| ATOM | 285 | C   | TYR | A | 37 | 13.333 | 23.320 | 19.098 | 1.00 | 42.34 | C |
| ATOM | 286 | O   | TYR | A | 37 | 12.664 | 24.359 | 19.009 | 1.00 | 42.93 | O |
| ATOM | 287 | N   | ARG | A | 38 | 14.264 | 23.110 | 20.015 | 1.00 | 42.19 | N |
| ATOM | 288 | CA  | ARG | A | 38 | 14.595 | 24.070 | 21.025 | 1.00 | 42.96 | C |
| ATOM | 289 | CB  | ARG | A | 38 | 14.270 | 23.477 | 22.397 | 1.00 | 42.92 | C |
| ATOM | 290 | CG  | ARG | A | 38 | 14.763 | 24.313 | 23.558 | 1.00 | 44.39 | C |
| ATOM | 291 | CD  | ARG | A | 38 | 14.561 | 23.598 | 24.854 | 1.00 | 44.38 | C |
| ATOM | 292 | NE  | ARG | A | 38 | 15.527 | 22.532 | 25.049 | 1.00 | 45.25 | N |
| ATOM | 293 | CZ  | ARG | A | 38 | 15.442 | 21.627 | 26.008 | 1.00 | 45.72 | C |
| ATOM | 294 | NH1 | ARG | A | 38 | 14.428 | 21.656 | 26.880 | 1.00 | 47.04 | N |
| ATOM | 295 | NH2 | ARG | A | 38 | 16.370 | 20.697 | 26.090 | 1.00 | 46.29 | N |
| ATOM | 296 | C   | ARG | A | 38 | 16.066 | 24.380 | 20.947 | 1.00 | 42.48 | C |
| ATOM | 297 | O   | ARG | A | 38 | 16.886 | 23.480 | 20.836 | 1.00 | 41.77 | O |
| ATOM | 298 | N   | THR | A | 39 | 16.385 | 25.665 | 20.950 | 1.00 | 42.48 | N |
| ATOM | 299 | CA  | THR | A | 39 | 17.734 | 26.114 | 21.184 | 1.00 | 42.41 | C |
| ATOM | 300 | CB  | THR | A | 39 | 18.241 | 27.037 | 20.048 | 1.00 | 42.54 | C |
| ATOM | 301 | OG1 | THR | A | 39 | 18.228 | 26.312 | 18.820 | 1.00 | 42.53 | O |
| ATOM | 302 | CG2 | THR | A | 39 | 19.673 | 27.527 | 20.311 | 1.00 | 41.06 | C |
| ATOM | 303 | C   | THR | A | 39 | 17.676 | 26.873 | 22.510 | 1.00 | 42.92 | C |
| ATOM | 304 | O   | THR | A | 39 | 17.003 | 27.900 | 22.564 | 1.00 | 42.88 | O |
| ATOM | 305 | N   | LYS | A | 40 | 18.365 | 26.371 | 23.548 | 1.00 | 42.04 | N |
| ATOM | 306 | CA  | LYS | A | 40 | 18.419 | 27.030 | 24.866 | 1.00 | 43.09 | C |
| ATOM | 307 | CB  | LYS | A | 40 | 19.207 | 26.194 | 25.881 | 1.00 | 42.59 | C |
| ATOM | 308 | CG  | LYS | A | 40 | 18.404 | 24.966 | 26.364 | 1.00 | 44.24 | C |
| ATOM | 309 | CD  | LYS | A | 40 | 19.096 | 24.238 | 27.544 | 1.00 | 44.63 | C |
| ATOM | 310 | CE  | LYS | A | 40 | 18.461 | 22.852 | 27.732 | 1.00 | 48.13 | C |
| ATOM | 311 | NZ  | LYS | A | 40 | 19.384 | 21.866 | 28.429 | 1.00 | 50.65 | N |
| ATOM | 312 | C   | LYS | A | 40 | 19.035 | 28.410 | 24.737 | 1.00 | 42.81 | C |
| ATOM | 313 | O   | LYS | A | 40 | 19.920 | 28.594 | 23.919 | 1.00 | 42.34 | O |
| ATOM | 314 | N   | LEU | A | 41 | 18.546 | 29.379 | 25.510 | 1.00 | 43.09 | N |
| ATOM | 315 | CA  | LEU | A | 41 | 19.033 | 30.752 | 25.382 | 1.00 | 44.01 | C |
| ATOM | 316 | CB  | LEU | A | 41 | 18.276 | 31.698 | 26.311 | 1.00 | 44.25 | C |
| ATOM | 317 | CG  | LEU | A | 41 | 17.782 | 33.024 | 25.744 | 1.00 | 43.95 | C |
| ATOM | 318 | CD1 | LEU | A | 41 | 16.729 | 32.793 | 24.645 | 1.00 | 46.04 | C |
| ATOM | 319 | CD2 | LEU | A | 41 | 17.186 | 33.805 | 26.889 | 1.00 | 42.63 | C |
| ATOM | 320 | C   | LEU | A | 41 | 20.491 | 30.797 | 25.743 | 1.00 | 44.32 | C |
| ATOM | 321 | O   | LEU | A | 41 | 20.875 | 30.255 | 26.776 | 1.00 | 44.32 | O |
| ATOM | 322 | N   | GLY | A | 42 | 21.276 | 31.465 | 24.894 | 1.00 | 44.48 | N |
| ATOM | 323 | CA  | GLY | A | 42 | 22.724 | 31.559 | 25.032 | 1.00 | 45.33 | C |
| ATOM | 324 | C   | GLY | A | 42 | 23.534 | 30.447 | 24.379 | 1.00 | 45.16 | C |
| ATOM | 325 | O   | GLY | A | 42 | 24.750 | 30.546 | 24.253 | 1.00 | 46.05 | O |
| ATOM | 326 | N   | SER | A | 43 | 22.866 | 29.382 | 23.979 | 1.00 | 45.58 | N |
| ATOM | 327 | CA  | SER | A | 43 | 23.513 | 28.241 | 23.342 | 1.00 | 45.64 | C |
| ATOM | 328 | CB  | SER | A | 43 | 22.919 | 26.938 | 23.886 | 1.00 | 45.67 | C |
| ATOM | 329 | OG  | SER | A | 43 | 23.459 | 25.792 | 23.251 | 1.00 | 46.70 | O |
| ATOM | 330 | C   | SER | A | 43 | 23.289 | 28.358 | 21.832 | 1.00 | 46.16 | C |
| ATOM | 331 | O   | SER | A | 43 | 22.467 | 29.164 | 21.372 | 1.00 | 45.71 | O |
| ATOM | 332 | N   | THR | A | 44 | 24.043 | 27.569 | 21.077 | 1.00 | 46.22 | N |
| ATOM | 333 | CA  | THR | A | 44 | 23.942 | 27.526 | 19.633 | 1.00 | 46.87 | C |
| ATOM | 334 | CB  | THR | A | 44 | 25.270 | 27.986 | 18.993 | 1.00 | 47.20 | C |
| ATOM | 335 | OG1 | THR | A | 44 | 25.567 | 29.313 | 19.456 | 1.00 | 50.26 | O |
| ATOM | 336 | CG2 | THR | A | 44 | 25.165 | 28.027 | 17.487 | 1.00 | 49.30 | C |
| ATOM | 337 | C   | THR | A | 44 | 23.531 | 26.104 | 19.198 | 1.00 | 46.11 | C |
| ATOM | 338 | O   | THR | A | 44 | 23.339 | 25.840 | 18.003 | 1.00 | 46.05 | O |
| ATOM | 339 | N   | LYS | A | 45 | 23.348 | 25.220 | 20.187 | 1.00 | 45.02 | N |
| ATOM | 340 | CA  | LYS | A | 45 | 22.925 | 23.823 | 19.974 | 1.00 | 43.74 | C |
| ATOM | 341 | CB  | LYS | A | 45 | 23.431 | 22.949 | 21.138 | 1.00 | 44.10 | C |
| ATOM | 342 | CG  | LYS | A | 45 | 23.218 | 21.441 | 20.990 | 1.00 | 41.77 | C |
| ATOM | 343 | CD  | LYS | A | 45 | 23.748 | 20.699 | 22.202 | 1.00 | 41.15 | C |
| ATOM | 344 | CE  | LYS | A | 45 | 23.276 | 19.255 | 22.208 | 1.00 | 40.36 | C |
| ATOM | 345 | NZ  | LYS | A | 45 | 24.119 | 18.427 | 23.140 | 1.00 | 35.82 | N |
| ATOM | 346 | C   | LYS | A | 45 | 21.406 | 23.683 | 19.838 | 1.00 | 44.15 | C |

APPENDIX I(c)-continued

| | | | | | | | | | | | |
|---|---|---|---|---|---|---|---|---|---|---|---|
| ATOM | 347 | O | LYS | A | 45 | 20.662 | 23.948 | 20.788 | 1.00 | 43.67 | O |
| ATOM | 348 | N | GLU | A | 46 | 20.948 | 23.234 | 18.669 | 1.00 | 44.10 | N |
| ATOM | 349 | CA | GLU | A | 46 | 19.534 | 22.901 | 18.453 | 1.00 | 44.73 | C |
| ATOM | 350 | CB | GLU | A | 46 | 19.187 | 23.050 | 16.961 | 1.00 | 44.68 | C |
| ATOM | 351 | CG | GLU | A | 46 | 17.697 | 22.939 | 16.568 | 1.00 | 46.37 | C |
| ATOM | 352 | CD | GLU | A | 46 | 17.489 | 23.212 | 15.065 | 1.00 | 46.94 | C |
| ATOM | 353 | OE1 | GLU | A | 46 | 16.943 | 24.286 | 14.702 | 1.00 | 51.63 | O |
| ATOM | 354 | OE2 | GLU | A | 46 | 17.922 | 22.371 | 14.253 | 1.00 | 48.82 | O |
| ATOM | 355 | C | GLU | A | 46 | 19.248 | 21.467 | 18.895 | 1.00 | 44.02 | C |
| ATOM | 356 | O | GLU | A | 46 | 20.008 | 20.526 | 18.582 | 1.00 | 43.31 | O |
| ATOM | 357 | N | GLN | A | 47 | 18.155 | 21.298 | 19.629 | 1.00 | 44.37 | N |
| ATOM | 358 | CA | GLN | A | 47 | 17.669 | 19.946 | 19.923 | 1.00 | 45.03 | C |
| ATOM | 359 | CB | GLN | A | 47 | 17.925 | 19.522 | 21.378 | 1.00 | 45.59 | C |
| ATOM | 360 | CG | GLN | A | 47 | 17.466 | 20.462 | 22.441 | 1.00 | 47.40 | C |
| ATOM | 361 | CD | GLN | A | 47 | 18.514 | 20.692 | 23.534 | 1.00 | 48.12 | C |
| ATOM | 362 | OE1 | GLN | A | 47 | 18.640 | 21.814 | 24.024 | 1.00 | 50.42 | O |
| ATOM | 363 | NE2 | GLN | A | 47 | 19.275 | 19.650 | 23.905 | 1.00 | 44.87 | N |
| ATOM | 364 | C | GLN | A | 47 | 16.232 | 19.743 | 19.520 | 1.00 | 44.93 | C |
| ATOM | 365 | O | GLN | A | 47 | 15.397 | 20.664 | 19.618 | 1.00 | 43.86 | O |
| ATOM | 366 | N | THR | A | 48 | 15.966 | 18.539 | 19.018 | 1.00 | 43.69 | N |
| ATOM | 367 | CA | THR | A | 48 | 14.612 | 18.113 | 18.772 | 1.00 | 43.60 | C |
| ATOM | 368 | CB | THR | A | 48 | 14.572 | 16.904 | 17.840 | 1.00 | 43.49 | C |
| ATOM | 369 | OG1 | THR | A | 48 | 15.501 | 17.082 | 16.774 | 1.00 | 43.99 | O |
| ATOM | 370 | CG2 | THR | A | 48 | 13.191 | 16.705 | 17.254 | 1.00 | 44.57 | C |
| ATOM | 371 | C | THR | A | 48 | 13.956 | 17.716 | 20.100 | 1.00 | 43.88 | C |
| ATOM | 372 | O | THR | A | 48 | 14.500 | 16.890 | 20.858 | 1.00 | 43.41 | O |
| ATOM | 373 | N | ILE | A | 49 | 12.763 | 18.250 | 20.342 | 1.00 | 43.65 | N |
| ATOM | 374 | CA | ILE | A | 49 | 11.949 | 17.867 | 21.500 | 1.00 | 44.19 | C |
| ATOM | 375 | CB | ILE | A | 49 | 10.965 | 18.986 | 21.860 | 1.00 | 44.86 | C |
| ATOM | 376 | CG1 | ILE | A | 49 | 11.703 | 20.311 | 22.079 | 1.00 | 44.80 | C |
| ATOM | 377 | CD1 | ILE | A | 49 | 10.772 | 21.515 | 22.217 | 1.00 | 45.75 | C |
| ATOM | 378 | CG2 | ILE | A | 49 | 10.129 | 18.577 | 23.090 | 1.00 | 44.23 | C |
| ATOM | 379 | C | ILE | A | 49 | 11.116 | 16.609 | 21.250 | 1.00 | 43.80 | C |
| ATOM | 380 | O | ILE | A | 49 | 10.322 | 16.569 | 20.311 | 1.00 | 44.87 | O |
| ATOM | 381 | N | SER | A | 50 | 11.268 | 15.587 | 22.068 | 1.00 | 42.75 | N |
| ATOM | 382 | CA | SER | A | 50 | 10.378 | 14.439 | 21.955 | 1.00 | 44.53 | C |
| ATOM | 383 | CB | SER | A | 50 | 11.064 | 13.151 | 22.440 | 1.00 | 44.13 | C |
| ATOM | 384 | OG | SER | A | 50 | 10.155 | 12.054 | 22.445 | 1.00 | 49.23 | O |
| ATOM | 385 | C | SER | A | 50 | 9.055 | 14.758 | 22.699 | 1.00 | 44.49 | C |
| ATOM | 386 | O | SER | A | 50 | 9.050 | 15.069 | 23.883 | 1.00 | 43.95 | O |
| ATOM | 387 | N | ILE | A | 51 | 7.943 | 14.733 | 21.953 | 1.00 | 44.98 | N |
| ATOM | 388 | CA | ILE | A | 51 | 6.609 | 15.076 | 22.454 | 1.00 | 44.02 | C |
| ATOM | 389 | CB | ILE | A | 51 | 5.605 | 15.221 | 21.273 | 1.00 | 44.92 | C |
| ATOM | 390 | CG1 | ILE | A | 51 | 6.024 | 16.366 | 20.349 | 1.00 | 45.18 | C |
| ATOM | 391 | CD1 | ILE | A | 51 | 6.216 | 17.701 | 21.070 | 1.00 | 45.42 | C |
| ATOM | 392 | CG2 | ILE | A | 51 | 4.160 | 15.429 | 21.770 | 1.00 | 44.94 | C |
| ATOM | 393 | C | ILE | A | 51 | 6.070 | 14.034 | 23.421 | 1.00 | 44.33 | C |
| ATOM | 394 | O | ILE | A | 51 | 6.006 | 12.838 | 23.094 | 1.00 | 43.52 | O |
| ATOM | 395 | N | GLY | A | 52 | 5.631 | 14.507 | 24.591 | 1.00 | 43.39 | N |
| ATOM | 396 | CA | GLY | A | 52 | 5.153 | 13.648 | 25.669 | 1.00 | 42.74 | C |
| ATOM | 397 | C | GLY | A | 52 | 5.393 | 14.348 | 26.998 | 1.00 | 41.31 | C |
| ATOM | 398 | O | GLY | A | 52 | 6.109 | 15.329 | 27.063 | 1.00 | 39.55 | O |
| ATOM | 399 | N | GLY | A | 53 | 4.766 | 13.856 | 28.052 | 1.00 | 41.80 | N |
| ATOM | 400 | CA | GLY | A | 53 | 4.940 | 14.458 | 29.386 | 1.00 | 41.49 | C |
| ATOM | 401 | C | GLY | A | 53 | 4.327 | 15.852 | 29.367 | 1.00 | 41.82 | C |
| ATOM | 402 | O | GLY | A | 53 | 3.170 | 16.016 | 28.982 | 1.00 | 41.84 | O |
| ATOM | 403 | N | ARG | A | 54 | 5.098 | 16.859 | 29.739 | 1.00 | 41.46 | N |
| ATOM | 404 | CA | ARG | A | 54 | 4.562 | 18.215 | 29.779 | 1.00 | 41.94 | C |
| ATOM | 405 | CB | ARG | A | 54 | 5.290 | 19.038 | 30.821 | 1.00 | 41.77 | C |
| ATOM | 406 | CG | ARG | A | 54 | 6.712 | 19.369 | 30.492 | 1.00 | 41.91 | C |
| ATOM | 407 | CD | ARG | A | 54 | 7.432 | 19.944 | 31.739 | 1.00 | 43.30 | C |
| ATOM | 408 | NE | ARG | A | 54 | 8.839 | 20.155 | 31.471 | 1.00 | 42.80 | N |
| ATOM | 409 | CZ | ARG | A | 54 | 9.386 | 21.335 | 31.194 | 1.00 | 41.93 | C |
| ATOM | 410 | NH1 | ARG | A | 54 | 10.684 | 21.405 | 30.941 | 1.00 | 39.03 | N |
| ATOM | 411 | NH2 | ARG | A | 54 | 8.645 | 22.441 | 31.186 | 1.00 | 40.55 | N |
| ATOM | 412 | C | ARG | A | 54 | 4.659 | 18.932 | 28.459 | 1.00 | 42.70 | C |
| ATOM | 413 | O | ARG | A | 54 | 4.402 | 20.152 | 28.406 | 1.00 | 42.87 | O |
| ATOM | 414 | N | TYR | A | 55 | 5.066 | 18.196 | 27.420 | 1.00 | 42.17 | N |
| ATOM | 415 | CA | TYR | A | 55 | 5.079 | 18.703 | 26.062 | 1.00 | 43.29 | C |
| ATOM | 416 | CB | TYR | A | 55 | 6.420 | 18.416 | 25.352 | 1.00 | 42.79 | C |
| ATOM | 417 | CG | TYR | A | 55 | 7.624 | 19.132 | 25.934 | 1.00 | 43.35 | C |
| ATOM | 418 | CD1 | TYR | A | 55 | 8.030 | 20.364 | 25.444 | 1.00 | 42.33 | C |
| ATOM | 419 | CE1 | TYR | A | 55 | 9.139 | 21.026 | 25.985 | 1.00 | 44.73 | C |
| ATOM | 420 | CZ | TYR | A | 55 | 9.859 | 20.423 | 27.010 | 1.00 | 45.08 | C |
| ATOM | 421 | OH | TYR | A | 55 | 10.973 | 21.049 | 27.536 | 1.00 | 44.82 | O |
| ATOM | 422 | CE2 | TYR | A | 55 | 9.472 | 19.194 | 27.498 | 1.00 | 42.19 | C |
| ATOM | 423 | CD2 | TYR | A | 55 | 8.369 | 18.559 | 26.963 | 1.00 | 44.00 | C |
| ATOM | 424 | C | TYR | A | 55 | 3.975 | 18.027 | 25.289 | 1.00 | 43.41 | C |
| ATOM | 425 | O | TYR | A | 55 | 3.931 | 16.785 | 25.178 | 1.00 | 43.01 | O |
| ATOM | 426 | N | SER | A | 56 | 3.073 | 18.826 | 24.742 | 1.00 | 43.44 | N |

APPENDIX I(c)-continued

| | | | | | | | | | | |
|---|---|---|---|---|---|---|---|---|---|---|
| ATOM | 427 | CA | SER | A | 56 | 2.012 | 18.211 | 23.977 | 1.00 | 44.15 C |
| ATOM | 428 | CB | SER | A | 56 | 0.701 | 18.153 | 24.797 | 1.00 | 44.77 C |
| ATOM | 429 | OG | SER | A | 56 | 0.143 | 19.440 | 25.022 | 1.00 | 46.86 O |
| ATOM | 430 | C | SER | A | 56 | 1.840 | 18.923 | 22.660 | 1.00 | 44.00 C |
| ATOM | 431 | O | SER | A | 56 | 2.180 | 20.104 | 22.539 | 1.00 | 44.53 O |
| ATOM | 432 | N | GLU | A | 57 | 1.343 | 18.188 | 21.669 | 1.00 | 43.36 N |
| ATOM | 433 | CA | GLU | A | 57 | 1.042 | 18.751 | 20.356 | 1.00 | 42.94 C |
| ATOM | 434 | CB | GLU | A | 57 | 1.886 | 18.064 | 19.275 | 1.00 | 42.52 C |
| ATOM | 435 | CG | GLU | A | 57 | 1.674 | 18.580 | 17.860 | 1.00 | 43.65 C |
| ATOM | 436 | CD | GLU | A | 57 | 2.473 | 17.808 | 16.828 | 1.00 | 43.95 C |
| ATOM | 437 | OE1 | GLU | A | 57 | 1.857 | 17.099 | 16.011 | 1.00 | 48.95 O |
| ATOM | 438 | OE2 | GLU | A | 57 | 3.718 | 17.895 | 16.815 | 1.00 | 45.70 O |
| ATOM | 439 | C | GLU | A | 57 | −0.426 | 18.594 | 20.058 | 1.00 | 42.25 C |
| ATOM | 440 | O | GLU | A | 57 | −0.988 | 17.502 | 20.203 | 1.00 | 43.26 O |
| ATOM | 441 | N | THR | A | 58 | −1.062 | 19.692 | 19.653 | 1.00 | 41.96 N |
| ATOM | 442 | CA | THR | A | 58 | −2.444 | 19.661 | 19.201 | 1.00 | 40.98 C |
| ATOM | 443 | CB | THR | A | 58 | −3.250 | 20.750 | 19.963 | 1.00 | 41.21 C |
| ATOM | 444 | OG1 | THR | A | 58 | −3.103 | 20.492 | 21.360 | 1.00 | 43.13 O |
| ATOM | 445 | CG2 | THR | A | 58 | −4.746 | 20.738 | 19.612 | 1.00 | 40.36 C |
| ATOM | 446 | C | THR | A | 58 | −2.464 | 19.839 | 17.687 | 1.00 | 40.68 C |
| ATOM | 447 | O | THR | A | 58 | −1.796 | 20.746 | 17.165 | 1.00 | 40.52 O |
| ATOM | 448 | N | VAL | A | 59 | −3.178 | 18.958 | 16.976 | 1.00 | 39.94 N |
| ATOM | 449 | CA | VAL | A | 59 | −3.346 | 19.089 | 15.503 | 1.00 | 39.87 C |
| ATOM | 450 | CB | VAL | A | 59 | −3.023 | 17.778 | 14.703 | 1.00 | 39.05 C |
| ATOM | 451 | CG1 | VAL | A | 59 | −1.591 | 17.390 | 14.896 | 1.00 | 41.22 C |
| ATOM | 452 | CG2 | VAL | A | 59 | −3.957 | 16.654 | 15.094 | 1.00 | 39.56 C |
| ATOM | 453 | C | VAL | A | 59 | −4.741 | 19.574 | 15.078 | 1.00 | 39.53 C |
| ATOM | 454 | O | VAL | A | 59 | −5.757 | 19.092 | 15.584 | 1.00 | 39.08 O |
| ATOM | 455 | N | ASP | A | 60 | −4.769 | 20.511 | 14.138 | 1.00 | 40.17 N |
| ATOM | 456 | CA | ASP | A | 60 | −6.023 | 20.986 | 13.552 | 1.00 | 41.52 C |
| ATOM | 457 | CB | ASP | A | 60 | −6.338 | 22.409 | 14.018 | 1.00 | 41.49 C |
| ATOM | 458 | CG | ASP | A | 60 | −7.695 | 22.896 | 13.549 | 1.00 | 44.26 C |
| ATOM | 459 | OD1 | ASP | A | 60 | −8.177 | 22.474 | 12.490 | 1.00 | 46.98 O |
| ATOM | 460 | OD2 | ASP | A | 60 | −8.294 | 23.739 | 14.230 | 1.00 | 48.31 O |
| ATOM | 461 | C | ASP | A | 60 | −5.961 | 20.849 | 12.023 | 1.00 | 41.63 C |
| ATOM | 462 | O | ASP | A | 60 | −5.348 | 21.657 | 11.308 | 1.00 | 41.42 O |
| ATOM | 463 | N | GLU | A | 61 | −6.583 | 19.788 | 11.539 | 1.00 | 41.59 N |
| ATOM | 464 | CA | GLU | A | 61 | −6.643 | 19.514 | 10.115 | 1.00 | 42.38 C |
| ATOM | 465 | CB | GLU | A | 61 | −7.324 | 18.169 | 9.908 | 1.00 | 42.35 C |
| ATOM | 466 | CG | GLU | A | 61 | −7.387 | 17.692 | 8.483 | 1.00 | 43.28 C |
| ATOM | 467 | CD | GLU | A | 61 | −7.987 | 16.328 | 8.417 | 1.00 | 42.95 C |
| ATOM | 468 | OE1 | GLU | A | 61 | −9.192 | 16.250 | 8.170 | 1.00 | 40.78 O |
| ATOM | 469 | OE2 | GLU | A | 61 | −7.261 | 15.343 | 8.679 | 1.00 | 46.17 O |
| ATOM | 470 | C | GLU | A | 61 | −7.318 | 20.621 | 9.273 | 1.00 | 42.62 C |
| ATOM | 471 | O | GLU | A | 61 | −6.886 | 20.941 | 8.155 | 1.00 | 43.01 O |
| ATOM | 472 | N | GLY | A | 62 | −8.351 | 21.235 | 9.812 | 1.00 | 42.12 N |
| ATOM | 473 | CA | GLY | A | 62 | −9.044 | 22.254 | 9.063 | 1.00 | 42.47 C |
| ATOM | 474 | C | GLY | A | 62 | −8.255 | 23.509 | 8.831 | 1.00 | 42.28 C |
| ATOM | 475 | O | GLY | A | 62 | −8.454 | 24.187 | 7.811 | 1.00 | 43.30 O |
| ATOM | 476 | N | SER | A | 63 | −7.372 | 23.819 | 9.775 | 1.00 | 41.92 N |
| ATOM | 477 | CA | SER | A | 63 | −6.541 | 25.022 | 9.746 | 1.00 | 41.93 C |
| ATOM | 478 | CB | SER | A | 63 | −6.436 | 25.625 | 11.158 | 1.00 | 42.03 C |
| ATOM | 479 | OG | SER | A | 63 | −7.720 | 25.762 | 11.737 | 1.00 | 45.80 O |
| ATOM | 480 | C | SER | A | 63 | −5.128 | 24.761 | 9.245 | 1.00 | 41.03 C |
| ATOM | 481 | O | SER | A | 63 | −4.339 | 25.696 | 9.181 | 1.00 | 40.56 O |
| ATOM | 482 | N | ASN | A | 64 | −4.820 | 23.501 | 8.912 | 1.00 | 40.57 N |
| ATOM | 483 | CA | ASN | A | 64 | −3.485 | 23.079 | 8.452 | 1.00 | 40.70 C |
| ATOM | 484 | CB | ASN | A | 64 | −3.129 | 23.764 | 7.117 | 1.00 | 40.66 C |
| ATOM | 485 | CG | ASN | A | 64 | −2.613 | 22.788 | 6.048 | 1.00 | 42.06 C |
| ATOM | 486 | OD1 | ASN | A | 64 | −2.632 | 21.575 | 6.233 | 1.00 | 44.67 O |
| ATOM | 487 | ND2 | ASN | A | 64 | −2.168 | 23.328 | 4.916 | 1.00 | 38.47 N |
| ATOM | 488 | C | ASN | A | 64 | −2.456 | 23.441 | 9.524 | 1.00 | 40.57 C |
| ATOM | 489 | O | ASN | A | 64 | −1.385 | 23.971 | 9.216 | 1.00 | 40.25 O |
| ATOM | 490 | N | SER | A | 65 | −2.791 | 23.178 | 10.789 | 1.00 | 40.60 N |
| ATOM | 491 | CA | SER | A | 65 | −1.956 | 23.646 | 11.894 | 1.00 | 40.94 C |
| ATOM | 492 | CB | SER | A | 65 | −2.596 | 24.855 | 12.605 | 1.00 | 41.18 C |
| ATOM | 493 | OG | SER | A | 65 | −3.789 | 24.507 | 13.278 | 1.00 | 42.58 O |
| ATOM | 494 | C | SER | A | 65 | −1.543 | 22.593 | 12.895 | 1.00 | 41.28 C |
| ATOM | 495 | O | SER | A | 65 | −2.160 | 21.526 | 12.983 | 1.00 | 41.22 O |
| ATOM | 496 | N | ALA | A | 66 | −0.462 | 22.895 | 13.627 | 1.00 | 42.01 N |
| ATOM | 497 | CA | ALA | A | 66 | 0.009 | 22.107 | 14.785 | 1.00 | 42.51 C |
| ATOM | 498 | CB | ALA | A | 66 | 1.128 | 21.099 | 14.370 | 1.00 | 41.63 C |
| ATOM | 499 | C | ALA | A | 66 | 0.533 | 23.080 | 15.839 | 1.00 | 43.50 C |
| ATOM | 500 | O | ALA | A | 66 | 1.302 | 24.014 | 15.501 | 1.00 | 44.12 O |
| ATOM | 501 | N | SER | A | 67 | 0.109 | 22.859 | 17.089 | 1.00 | 43.19 N |
| ATOM | 502 | CA | SER | A | 67 | 0.496 | 23.663 | 18.237 | 1.00 | 44.12 C |
| ATOM | 503 | CB | SER | A | 67 | −0.719 | 24.297 | 18.894 | 1.00 | 43.60 C |
| ATOM | 504 | OG | SER | A | 67 | −1.213 | 25.268 | 17.996 | 1.00 | 47.65 O |
| ATOM | 505 | C | SER | A | 67 | 1.242 | 22.870 | 19.293 | 1.00 | 43.95 C |
| ATOM | 506 | O | SER | A | 67 | 0.873 | 21.727 | 19.622 | 1.00 | 44.77 O |

APPENDIX I(c)-continued

| | | | | | | | | | | | |
|---|---|---|---|---|---|---|---|---|---|---|---|
| ATOM | 507 | N | LEU | A | 68 | 2.330 | 23.448 | 19.769 | 1.00 | 42.85 | N |
| ATOM | 508 | CA | LEU | A | 68 | 3.042 | 22.858 | 20.894 | 1.00 | 43.00 | C |
| ATOM | 509 | CB | LEU | A | 68 | 4.564 | 22.921 | 20.678 | 1.00 | 42.58 | C |
| ATOM | 510 | CG | LEU | A | 68 | 5.455 | 22.619 | 21.891 | 1.00 | 42.99 | C |
| ATOM | 511 | CD1 | LEU | A | 68 | 5.434 | 21.129 | 22.244 | 1.00 | 40.58 | C |
| ATOM | 512 | CD2 | LEU | A | 68 | 6.910 | 23.118 | 21.663 | 1.00 | 41.93 | C |
| ATOM | 513 | C | LEU | A | 68 | 2.665 | 23.549 | 22.192 | 1.00 | 42.19 | C |
| ATOM | 514 | O | LEU | A | 68 | 2.829 | 24.771 | 22.317 | 1.00 | 42.62 | O |
| ATOM | 515 | N | THR | A | 69 | 2.163 | 22.778 | 23.148 | 1.00 | 42.05 | N |
| ATOM | 516 | CA | THR | A | 69 | 1.989 | 23.296 | 24.507 | 1.00 | 42.43 | C |
| ATOM | 517 | CB | THR | A | 69 | 0.577 | 23.016 | 25.054 | 1.00 | 42.69 | C |
| ATOM | 518 | OG1 | THR | A | 69 | −0.358 | 23.689 | 24.216 | 1.00 | 42.54 | O |
| ATOM | 519 | CG2 | THR | A | 69 | 0.394 | 23.575 | 26.498 | 1.00 | 42.39 | C |
| ATOM | 520 | C | THR | A | 69 | 3.093 | 22.768 | 25.430 | 1.00 | 42.65 | C |
| ATOM | 521 | O | THR | A | 69 | 3.364 | 21.550 | 25.466 | 1.00 | 42.53 | O |
| ATOM | 522 | N | ILE | A | 70 | 3.781 | 23.689 | 26.105 | 1.00 | 42.73 | N |
| ATOM | 523 | CA | ILE | A | 70 | 4.745 | 23.320 | 27.168 | 1.00 | 43.57 | C |
| ATOM | 524 | CB | ILE | A | 70 | 6.118 | 24.002 | 26.988 | 1.00 | 43.71 | C |
| ATOM | 525 | CG1 | ILE | A | 70 | 6.679 | 23.746 | 25.576 | 1.00 | 44.37 | C |
| ATOM | 526 | CD1 | ILE | A | 70 | 7.838 | 24.682 | 25.237 | 1.00 | 43.90 | C |
| ATOM | 527 | CG2 | ILE | A | 70 | 7.092 | 23.524 | 28.033 | 1.00 | 44.26 | C |
| ATOM | 528 | C | ILE | A | 70 | 4.172 | 23.754 | 28.501 | 1.00 | 43.90 | C |
| ATOM | 529 | O | ILE | A | 70 | 3.967 | 24.947 | 28.725 | 1.00 | 43.83 | O |
| ATOM | 530 | N | ARG | A | 71 | 3.893 | 22.799 | 29.373 | 1.00 | 44.36 | N |
| ATOM | 531 | CA | ARG | A | 71 | 3.306 | 23.110 | 30.676 | 1.00 | 46.05 | C |
| ATOM | 532 | CB | ARG | A | 71 | 2.214 | 22.085 | 31.036 | 1.00 | 46.19 | C |
| ATOM | 533 | CG | ARG | A | 71 | 1.045 | 22.023 | 30.039 | 1.00 | 48.10 | C |
| ATOM | 534 | CD | ARG | A | 71 | 0.227 | 20.724 | 30.205 | 1.00 | 49.51 | C |
| ATOM | 535 | NE | ARG | A | 71 | 0.731 | 19.665 | 29.316 | 1.00 | 54.32 | N |
| ATOM | 536 | CZ | ARG | A | 71 | 0.397 | 18.364 | 29.365 | 1.00 | 55.91 | C |
| ATOM | 537 | NH1 | ARG | A | 71 | 0.952 | 17.520 | 28.489 | 1.00 | 53.43 | N |
| ATOM | 538 | NH2 | ARG | A | 71 | −0.473 | 17.893 | 30.281 | 1.00 | 54.28 | N |
| ATOM | 539 | C | ARG | A | 71 | 4.391 | 23.175 | 31.761 | 1.00 | 45.39 | C |
| ATOM | 540 | O | ARG | A | 71 | 5.536 | 22.769 | 31.521 | 1.00 | 45.67 | O |
| ATOM | 541 | N | ASP | A | 72 | 4.026 | 23.683 | 32.936 | 1.00 | 44.59 | N |
| ATOM | 542 | CA | ASP | A | 72 | 4.934 | 23.834 | 34.095 | 1.00 | 44.37 | C |
| ATOM | 543 | CB | ASP | A | 72 | 5.092 | 22.514 | 34.876 | 1.00 | 43.81 | C |
| ATOM | 544 | CG | ASP | A | 72 | 5.939 | 22.686 | 36.175 | 1.00 | 46.29 | C |
| ATOM | 545 | OD1 | ASP | A | 72 | 5.735 | 23.682 | 36.905 | 1.00 | 45.23 | O |
| ATOM | 546 | OD2 | ASP | A | 72 | 6.825 | 21.839 | 36.454 | 1.00 | 47.68 | O |
| ATOM | 547 | C | ASP | A | 72 | 6.308 | 24.455 | 33.780 | 1.00 | 43.81 | C |
| ATOM | 548 | O | ASP | A | 72 | 7.353 | 23.849 | 34.050 | 1.00 | 43.52 | O |
| ATOM | 549 | N | LEU | A | 73 | 6.304 | 25.675 | 33.239 | 1.00 | 43.67 | N |
| ATOM | 550 | CA | LEU | A | 73 | 7.543 | 26.258 | 32.634 | 1.00 | 43.28 | C |
| ATOM | 551 | CB | LEU | A | 73 | 7.266 | 27.548 | 31.842 | 1.00 | 42.21 | C |
| ATOM | 552 | CG | LEU | A | 73 | 6.698 | 27.428 | 30.420 | 1.00 | 41.64 | C |
| ATOM | 553 | CD1 | LEU | A | 73 | 6.099 | 28.774 | 29.995 | 1.00 | 40.11 | C |
| ATOM | 554 | CD2 | LEU | A | 73 | 7.740 | 26.946 | 29.357 | 1.00 | 36.14 | C |
| ATOM | 555 | C | LEU | A | 73 | 8.606 | 26.517 | 33.668 | 1.00 | 43.26 | C |
| ATOM | 556 | O | LEU | A | 73 | 8.292 | 26.835 | 34.809 | 1.00 | 43.51 | O |
| ATOM | 557 | N | ARG | A | 74 | 9.860 | 26.363 | 33.260 | 1.00 | 43.56 | N |
| ATOM | 558 | CA | ARG | A | 74 | 11.017 | 26.486 | 34.148 | 1.00 | 43.52 | C |
| ATOM | 559 | CB | ARG | A | 74 | 11.654 | 25.118 | 34.295 | 1.00 | 43.58 | C |
| ATOM | 560 | CG | ARG | A | 74 | 10.699 | 24.083 | 34.838 | 1.00 | 43.45 | C |
| ATOM | 561 | CD | ARG | A | 74 | 10.850 | 22.733 | 34.192 | 1.00 | 42.00 | C |
| ATOM | 562 | NE | ARG | A | 74 | 9.778 | 21.852 | 34.646 | 1.00 | 43.41 | N |
| ATOM | 563 | CZ | ARG | A | 74 | 9.833 | 20.523 | 34.615 | 1.00 | 44.43 | C |
| ATOM | 564 | NH1 | ARG | A | 74 | 8.827 | 19.802 | 35.075 | 1.00 | 41.62 | N |
| ATOM | 565 | NH2 | ARG | A | 74 | 10.914 | 19.910 | 34.152 | 1.00 | 46.68 | N |
| ATOM | 566 | C | ARG | A | 74 | 12.011 | 27.437 | 33.489 | 1.00 | 43.68 | C |
| ATOM | 567 | O | ARG | A | 74 | 12.044 | 27.522 | 32.275 | 1.00 | 43.51 | O |
| ATOM | 568 | N | VAL | A | 75 | 12.840 | 28.117 | 34.272 | 1.00 | 44.03 | N |
| ATOM | 569 | CA | VAL | A | 75 | 13.843 | 29.050 | 33.721 | 1.00 | 44.68 | C |
| ATOM | 570 | CB | VAL | A | 75 | 14.721 | 29.674 | 34.832 | 1.00 | 44.80 | C |
| ATOM | 571 | CG1 | VAL | A | 75 | 15.612 | 30.776 | 34.269 | 1.00 | 45.53 | C |
| ATOM | 572 | CG2 | VAL | A | 75 | 13.843 | 30.232 | 35.978 | 1.00 | 44.80 | C |
| ATOM | 573 | C | VAL | A | 75 | 14.709 | 28.404 | 32.615 | 1.00 | 44.75 | C |
| ATOM | 574 | O | VAL | A | 75 | 15.105 | 29.063 | 31.660 | 1.00 | 43.97 | O |
| ATOM | 575 | N | GLU | A | 76 | 14.940 | 27.099 | 32.726 | 1.00 | 45.06 | N |
| ATOM | 576 | CA | GLU | A | 76 | 15.736 | 26.364 | 31.737 | 1.00 | 45.93 | C |
| ATOM | 577 | CB | GLU | A | 76 | 16.321 | 25.095 | 32.381 | 1.00 | 46.31 | C |
| ATOM | 578 | CG | GLU | A | 76 | 15.275 | 24.161 | 32.999 | 1.00 | 48.76 | C |
| ATOM | 579 | CD | GLU | A | 76 | 15.109 | 24.314 | 34.520 | 1.00 | 51.57 | C |
| ATOM | 580 | OE1 | GLU | A | 76 | 14.648 | 23.325 | 35.150 | 1.00 | 52.40 | O |
| ATOM | 581 | OE2 | GLU | A | 76 | 15.425 | 25.395 | 35.082 | 1.00 | 50.39 | O |
| ATOM | 582 | C | GLU | A | 76 | 14.994 | 26.043 | 30.400 | 1.00 | 45.85 | C |
| ATOM | 583 | O | GLU | A | 76 | 15.585 | 25.503 | 29.447 | 1.00 | 45.45 | O |
| ATOM | 584 | N | ASP | A | 77 | 13.705 | 26.374 | 30.341 | 1.00 | 45.80 | N |
| ATOM | 585 | CA | ASP | A | 77 | 12.942 | 26.294 | 29.082 | 1.00 | 44.88 | C |
| ATOM | 586 | CB | ASP | A | 77 | 11.452 | 26.083 | 29.370 | 1.00 | 44.95 | C |

APPENDIX I(c)-continued

| ATOM | 587 | CG | ASP | A | 77 | 11.160 | 24.767 | 30.081 | 1.00 | 46.55 | C |
|---|---|---|---|---|---|---|---|---|---|---|---|
| ATOM | 588 | OD1 | ASP | A | 77 | 11.753 | 23.722 | 29.728 | 1.00 | 46.55 | O |
| ATOM | 589 | OD2 | ASP | A | 77 | 10.291 | 24.763 | 30.975 | 1.00 | 47.83 | O |
| ATOM | 590 | C | ASP | A | 77 | 13.162 | 27.535 | 28.204 | 1.00 | 44.03 | C |
| ATOM | 591 | O | ASP | A | 77 | 12.911 | 27.494 | 26.991 | 1.00 | 44.02 | O |
| ATOM | 592 | N | SER | A | 78 | 13.660 | 28.629 | 28.789 | 1.00 | 43.14 | N |
| ATOM | 593 | CA | SER | A | 78 | 14.077 | 29.796 | 27.985 | 1.00 | 42.43 | C |
| ATOM | 594 | CB | SER | A | 78 | 14.855 | 30.811 | 28.812 | 1.00 | 42.27 | C |
| ATOM | 595 | OG | SER | A | 78 | 14.061 | 31.325 | 29.855 | 1.00 | 45.22 | O |
| ATOM | 596 | C | SER | A | 78 | 14.916 | 29.363 | 26.764 | 1.00 | 41.89 | C |
| ATOM | 597 | O | SER | A | 78 | 15.849 | 28.570 | 26.889 | 1.00 | 42.32 | O |
| ATOM | 598 | N | GLY | A | 79 | 14.600 | 29.892 | 25.591 | 1.00 | 41.21 | N |
| ATOM | 599 | CA | GLY | A | 79 | 15.205 | 29.375 | 24.348 | 1.00 | 41.10 | C |
| ATOM | 600 | C | GLY | A | 79 | 14.457 | 29.849 | 23.125 | 1.00 | 41.37 | C |
| ATOM | 601 | O | GLY | A | 79 | 13.426 | 30.528 | 23.223 | 1.00 | 41.44 | O |
| ATOM | 602 | N | THR | A | 80 | 15.012 | 29.556 | 21.961 | 1.00 | 41.26 | N |
| ATOM | 603 | CA | THR | A | 80 | 14.302 | 29.778 | 20.702 | 1.00 | 41.23 | C |
| ATOM | 604 | CB | THR | A | 80 | 15.234 | 30.352 | 19.639 | 1.00 | 40.40 | C |
| ATOM | 605 | OG1 | THR | A | 80 | 15.748 | 31.599 | 20.124 | 1.00 | 40.92 | O |
| ATOM | 606 | CG2 | THR | A | 80 | 14.478 | 30.616 | 18.350 | 1.00 | 41.08 | C |
| ATOM | 607 | C | THR | A | 80 | 13.713 | 28.441 | 20.278 | 1.00 | 41.52 | C |
| ATOM | 608 | O | THR | A | 80 | 14.399 | 27.396 | 20.256 | 1.00 | 40.53 | O |
| ATOM | 609 | N | TYR | A | 81 | 12.427 | 28.479 | 19.975 | 1.00 | 42.20 | N |
| ATOM | 610 | CA | TYR | A | 81 | 11.701 | 27.273 | 19.624 | 1.00 | 42.88 | C |
| ATOM | 611 | CB | TYR | A | 81 | 10.517 | 27.079 | 20.576 | 1.00 | 42.50 | C |
| ATOM | 612 | CG | TYR | A | 81 | 10.876 | 26.675 | 21.993 | 1.00 | 43.04 | C |
| ATOM | 613 | CD1 | TYR | A | 81 | 11.258 | 27.628 | 22.947 | 1.00 | 42.08 | C |
| ATOM | 614 | CE1 | TYR | A | 81 | 11.591 | 27.248 | 24.246 | 1.00 | 40.82 | C |
| ATOM | 615 | CZ | TYR | A | 81 | 11.540 | 25.910 | 24.619 | 1.00 | 41.51 | C |
| ATOM | 616 | OH | TYR | A | 81 | 11.888 | 25.530 | 25.909 | 1.00 | 41.77 | O |
| ATOM | 617 | CE2 | TYR | A | 81 | 11.147 | 24.957 | 23.712 | 1.00 | 42.75 | C |
| ATOM | 618 | CD2 | TYR | A | 81 | 10.807 | 25.338 | 22.402 | 1.00 | 44.77 | C |
| ATOM | 619 | C | TYR | A | 81 | 11.244 | 27.466 | 18.192 | 1.00 | 43.89 | C |
| ATOM | 620 | O | TYR | A | 81 | 10.884 | 28.587 | 17.784 | 1.00 | 44.08 | O |
| ATOM | 621 | N | LYS | A | 82 | 11.309 | 26.390 | 17.414 | 1.00 | 44.31 | N |
| ATOM | 622 | CA | LYS | A | 82 | 10.903 | 26.405 | 16.020 | 1.00 | 44.69 | C |
| ATOM | 623 | CB | LYS | A | 82 | 12.116 | 26.515 | 15.090 | 1.00 | 45.16 | C |
| ATOM | 624 | CG | LYS | A | 82 | 12.764 | 27.870 | 14.991 | 1.00 | 47.79 | C |
| ATOM | 625 | CD | LYS | A | 82 | 14.103 | 27.702 | 14.313 | 1.00 | 50.84 | C |
| ATOM | 626 | CE | LYS | A | 82 | 15.117 | 28.697 | 14.882 | 1.00 | 57.07 | C |
| ATOM | 627 | NZ | LYS | A | 82 | 14.749 | 30.121 | 14.595 | 1.00 | 58.51 | N |
| ATOM | 628 | C | LYS | A | 82 | 10.180 | 25.096 | 15.722 | 1.00 | 44.51 | C |
| ATOM | 629 | O | LYS | A | 82 | 10.470 | 24.057 | 16.367 | 1.00 | 43.69 | O |
| ATOM | 630 | N | CYS | A | 83 | 9.252 | 25.164 | 14.756 | 1.00 | 43.58 | N |
| ATOM | 631 | CA | CYS | A | 83 | 8.637 | 23.975 | 14.139 | 1.00 | 43.92 | C |
| ATOM | 632 | CB | CYS | A | 83 | 7.118 | 24.116 | 14.069 | 1.00 | 44.57 | C |
| ATOM | 633 | SG | CYS | A | 83 | 6.599 | 25.545 | 13.076 | 1.00 | 45.39 | S |
| ATOM | 634 | C | CYS | A | 83 | 9.157 | 23.755 | 12.711 | 1.00 | 43.64 | C |
| ATOM | 635 | O | CYS | A | 83 | 9.508 | 24.712 | 12.004 | 1.00 | 41.71 | O |
| ATOM | 636 | N | LYS | A | 84 | 9.227 | 22.476 | 12.334 | 1.00 | 44.18 | N |
| ATOM | 637 | CA | LYS | A | 84 | 9.492 | 22.022 | 10.982 | 1.00 | 45.42 | C |
| ATOM | 638 | CB | LYS | A | 84 | 10.647 | 21.020 | 10.957 | 1.00 | 46.76 | C |
| ATOM | 639 | CG | LYS | A | 84 | 12.060 | 21.586 | 10.916 | 1.00 | 48.51 | C |
| ATOM | 640 | CD | LYS | A | 84 | 12.977 | 20.615 | 10.171 | 1.00 | 53.46 | C |
| ATOM | 641 | CE | LYS | A | 84 | 14.486 | 20.718 | 10.553 | 1.00 | 53.84 | C |
| ATOM | 642 | NZ | LYS | A | 84 | 15.072 | 22.085 | 10.793 | 1.00 | 53.72 | N |
| ATOM | 643 | C | LYS | A | 84 | 8.253 | 21.275 | 10.551 | 1.00 | 45.80 | C |
| ATOM | 644 | O | LYS | A | 84 | 7.891 | 20.280 | 11.175 | 1.00 | 47.54 | O |
| ATOM | 645 | N | ALA | A | 85 | 7.583 | 21.781 | 9.522 | 1.00 | 45.28 | N |
| ATOM | 646 | CA | ALA | A | 85 | 6.374 | 21.196 | 8.991 | 1.00 | 45.01 | C |
| ATOM | 647 | CB | ALA | A | 85 | 5.403 | 22.295 | 8.615 | 1.00 | 44.83 | C |
| ATOM | 648 | C | ALA | A | 85 | 6.708 | 20.343 | 7.787 | 1.00 | 45.27 | C |
| ATOM | 649 | O | ALA | A | 85 | 7.288 | 20.831 | 6.827 | 1.00 | 44.57 | O |
| ATOM | 650 | N | TYR | A | 86 | 6.363 | 19.058 | 7.861 | 1.00 | 45.35 | N |
| ATOM | 651 | CA | TYR | A | 86 | 6.435 | 18.160 | 6.717 | 1.00 | 45.77 | C |
| ATOM | 652 | CB | TYR | A | 86 | 6.775 | 16.736 | 7.174 | 1.00 | 46.34 | C |
| ATOM | 653 | CG | TYR | A | 86 | 8.056 | 16.762 | 7.964 | 1.00 | 48.76 | C |
| ATOM | 654 | CD1 | TYR | A | 86 | 8.038 | 16.975 | 9.343 | 1.00 | 50.37 | C |
| ATOM | 655 | CE1 | TYR | A | 86 | 9.214 | 17.058 | 10.084 | 1.00 | 51.40 | C |
| ATOM | 656 | CZ | TYR | A | 86 | 10.427 | 16.942 | 9.447 | 1.00 | 50.41 | C |
| ATOM | 657 | OH | TYR | A | 86 | 11.579 | 17.012 | 10.193 | 1.00 | 50.04 | O |
| ATOM | 658 | CE2 | TYR | A | 86 | 10.488 | 16.746 | 8.067 | 1.00 | 52.75 | C |
| ATOM | 659 | CD2 | TYR | A | 86 | 9.293 | 16.660 | 7.327 | 1.00 | 51.59 | C |
| ATOM | 660 | C | TYR | A | 86 | 5.110 | 18.260 | 5.970 | 1.00 | 45.44 | C |
| ATOM | 661 | O | TYR | A | 86 | 4.097 | 18.623 | 6.568 | 1.00 | 45.39 | O |
| ATOM | 662 | N | ARG | A | 87 | 5.113 | 17.970 | 4.671 | 1.00 | 44.88 | N |
| ATOM | 663 | CA | ARG | A | 87 | 3.922 | 18.186 | 3.839 | 1.00 | 45.04 | C |
| ATOM | 664 | CB | ARG | A | 87 | 4.082 | 19.422 | 2.940 | 1.00 | 44.90 | C |
| ATOM | 665 | CG | ARG | A | 87 | 4.795 | 20.547 | 3.675 | 1.00 | 46.39 | C |
| ATOM | 666 | CD | ARG | A | 87 | 4.537 | 21.958 | 3.168 | 1.00 | 46.94 | C |

APPENDIX I(c)-continued

| ATOM | 667 | NE | ARG | A | 87 | 4.855 | 22.168 | 1.775 | 1.00 | 44.54 | N |
|---|---|---|---|---|---|---|---|---|---|---|---|
| ATOM | 668 | CZ | ARG | A | 87 | 6.063 | 22.093 | 1.227 | 1.00 | 45.63 | C |
| ATOM | 669 | NH1 | ARG | A | 87 | 6.192 | 22.323 | −0.071 | 1.00 | 41.09 | N |
| ATOM | 670 | NH2 | ARG | A | 87 | 7.132 | 21.788 | 1.955 | 1.00 | 48.23 | N |
| ATOM | 671 | C | ARG | A | 87 | 3.533 | 16.958 | 3.023 | 1.00 | 44.92 | C |
| ATOM | 672 | O | ARG | A | 87 | 4.366 | 16.103 | 2.700 | 1.00 | 45.77 | O |
| ATOM | 673 | N | ARG | A | 88 | 2.248 | 16.881 | 2.721 | 1.00 | 44.30 | N |
| ATOM | 674 | CA | ARG | A | 88 | 1.668 | 15.817 | 1.928 | 1.00 | 43.99 | C |
| ATOM | 675 | CB | ARG | A | 88 | 0.696 | 15.000 | 2.807 | 1.00 | 43.99 | C |
| ATOM | 676 | CG | ARG | A | 88 | −0.252 | 14.029 | 2.076 | 1.00 | 45.06 | C |
| ATOM | 677 | CD | ARG | A | 88 | 0.460 | 12.944 | 1.277 | 1.00 | 47.65 | C |
| ATOM | 678 | NE | ARG | A | 88 | 1.605 | 12.336 | 1.965 | 1.00 | 51.20 | N |
| ATOM | 679 | CZ | ARG | A | 88 | 2.387 | 11.400 | 1.414 | 1.00 | 52.98 | C |
| ATOM | 680 | NH1 | ARG | A | 88 | 3.420 | 10.892 | 2.085 | 1.00 | 53.13 | N |
| ATOM | 681 | NH2 | ARG | A | 88 | 2.132 | 10.967 | 0.184 | 1.00 | 52.26 | N |
| ATOM | 682 | C | ARG | A | 88 | 0.952 | 16.583 | 0.837 | 1.00 | 43.43 | C |
| ATOM | 683 | O | ARG | A | 88 | 0.038 | 17.364 | 1.138 | 1.00 | 43.15 | O |
| ATOM | 684 | N | CYS | A | 89 | 1.415 | 16.420 | −0.415 | 1.00 | 43.21 | N |
| ATOM | 685 | CA | CYS | A | 89 | 0.884 | 17.212 | −1.507 | 1.00 | 42.95 | C |
| ATOM | 686 | CB | CYS | A | 89 | 2.000 | 17.979 | −2.229 | 1.00 | 42.90 | C |
| ATOM | 687 | SG | CYS | A | 89 | 2.955 | 19.217 | −1.275 | 1.00 | 43.42 | S |
| ATOM | 688 | C | CYS | A | 89 | 0.128 | 16.305 | −2.486 | 1.00 | 43.49 | C |
| ATOM | 689 | O | CYS | A | 89 | 0.348 | 15.066 | −2.527 | 1.00 | 43.18 | O |
| ATOM | 690 | N | ALA | A | 90 | −0.749 | 16.921 | −3.288 | 1.00 | 43.77 | N |
| ATOM | 691 | CA | ALA | A | 90 | −1.513 | 16.151 | −4.268 | 1.00 | 44.87 | C |
| ATOM | 692 | CB | ALA | A | 90 | −2.429 | 17.069 | −5.090 | 1.00 | 44.89 | C |
| ATOM | 693 | C | ALA | A | 90 | −0.644 | 15.288 | −5.199 | 1.00 | 45.28 | C |
| ATOM | 694 | O | ALA | A | 90 | −1.169 | 14.364 | −5.833 | 1.00 | 45.43 | O |
| ATOM | 695 | N | PHE | A | 91 | 0.667 | 15.576 | −5.273 | 1.00 | 45.99 | N |
| ATOM | 696 | CA | PHE | A | 91 | 1.545 | 14.830 | −6.195 | 1.00 | 46.92 | C |
| ATOM | 697 | CB | PHE | A | 91 | 2.393 | 15.747 | −7.132 | 1.00 | 46.28 | C |
| ATOM | 698 | CG | PHE | A | 91 | 2.962 | 16.963 | −6.455 | 1.00 | 44.74 | C |
| ATOM | 699 | CD1 | PHE | A | 91 | 4.151 | 16.888 | −5.738 | 1.00 | 44.41 | C |
| ATOM | 700 | CE1 | PHE | A | 91 | 4.667 | 18.003 | −5.081 | 1.00 | 44.69 | C |
| ATOM | 701 | CZ | PHE | A | 91 | 3.996 | 19.211 | −5.159 | 1.00 | 44.49 | C |
| ATOM | 702 | CE2 | PHE | A | 91 | 2.809 | 19.299 | −5.898 | 1.00 | 44.64 | C |
| ATOM | 703 | CD2 | PHE | A | 91 | 2.304 | 18.182 | −6.536 | 1.00 | 42.85 | C |
| ATOM | 704 | C | PHE | A | 91 | 2.414 | 13.763 | −5.536 | 1.00 | 48.05 | C |
| ATOM | 705 | O | PHE | A | 91 | 2.010 | 12.597 | −5.460 | 1.00 | 48.28 | O |
| ATOM | 706 | N | ASN | A | 92 | 3.598 | 14.166 | −5.067 | 1.00 | 49.62 | N |
| ATOM | 707 | CA | ASN | A | 92 | 4.708 | 13.232 | −4.837 | 1.00 | 51.06 | C |
| ATOM | 708 | CB | ASN | A | 92 | 5.379 | 12.890 | −6.178 | 1.00 | 50.88 | C |
| ATOM | 709 | CG | ASN | A | 92 | 4.729 | 11.730 | −6.890 | 1.00 | 50.22 | C |
| ATOM | 710 | OD1 | ASN | A | 92 | 4.899 | 11.570 | −8.092 | 1.00 | 50.52 | O |
| ATOM | 711 | ND2 | ASN | A | 92 | 3.991 | 10.909 | −6.156 | 1.00 | 49.11 | N |
| ATOM | 712 | C | ASN | A | 92 | 5.801 | 13.698 | −3.866 | 1.00 | 52.19 | C |
| ATOM | 713 | O | ASN | A | 92 | 5.677 | 14.734 | −3.197 | 1.00 | 52.40 | O |
| ATOM | 714 | N | THR | A | 93 | 6.880 | 12.914 | −3.824 | 1.00 | 53.42 | N |
| ATOM | 715 | CA | THR | A | 93 | 8.083 | 13.223 | −3.052 | 1.00 | 54.60 | C |
| ATOM | 716 | CB | THR | A | 93 | 8.994 | 11.972 | −2.916 | 1.00 | 54.62 | C |
| ATOM | 717 | OG1 | THR | A | 93 | 8.874 | 11.154 | −4.091 | 1.00 | 53.58 | O |
| ATOM | 718 | CG2 | THR | A | 93 | 8.596 | 11.159 | −1.685 | 1.00 | 54.51 | C |
| ATOM | 719 | C | THR | A | 93 | 8.868 | 14.414 | −3.632 | 1.00 | 55.41 | C |
| ATOM | 720 | O | THR | A | 93 | 9.611 | 14.280 | −4.620 | 1.00 | 55.67 | O |
| ATOM | 721 | N | GLY | A | 94 | 8.692 | 15.574 | −2.998 | 1.00 | 56.30 | N |
| ATOM | 722 | CA | GLY | A | 94 | 9.345 | 16.808 | −3.421 | 1.00 | 56.84 | C |
| ATOM | 723 | C | GLY | A | 94 | 9.800 | 17.601 | −2.212 | 1.00 | 57.51 | C |
| ATOM | 724 | O | GLY | A | 94 | 9.473 | 17.239 | −1.081 | 1.00 | 57.17 | O |
| ATOM | 725 | N | VAL | A | 95 | 10.551 | 18.680 | −2.472 | 1.00 | 58.10 | N |
| ATOM | 726 | CA | VAL | A | 95 | 11.176 | 19.569 | −1.456 | 1.00 | 58.30 | C |
| ATOM | 727 | CB | VAL | A | 95 | 11.911 | 20.790 | −2.131 | 1.00 | 58.41 | C |
| ATOM | 728 | CG1 | VAL | A | 95 | 13.412 | 20.494 | −2.326 | 1.00 | 58.19 | C |
| ATOM | 729 | CG2 | VAL | A | 95 | 11.712 | 22.104 | −1.347 | 1.00 | 58.50 | C |
| ATOM | 730 | C | VAL | A | 95 | 10.253 | 20.029 | −0.314 | 1.00 | 58.52 | C |
| ATOM | 731 | O | VAL | A | 95 | 9.675 | 21.124 | −0.345 | 1.00 | 59.14 | O |
| ATOM | 732 | N | GLY | A | 96 | 10.150 | 19.189 | 0.711 | 1.00 | 58.23 | N |
| ATOM | 733 | CA | GLY | A | 96 | 9.231 | 19.439 | 1.795 | 1.00 | 57.55 | C |
| ATOM | 734 | C | GLY | A | 96 | 9.904 | 19.629 | 3.128 | 1.00 | 57.16 | C |
| ATOM | 735 | O | GLY | A | 96 | 11.107 | 19.410 | 3.291 | 1.00 | 57.41 | O |
| ATOM | 736 | N | TYR | A | 97 | 9.080 | 19.986 | 4.097 | 1.00 | 56.75 | N |
| ATOM | 737 | CA | TYR | A | 97 | 9.536 | 20.547 | 5.355 | 1.00 | 55.42 | C |
| ATOM | 738 | CB | TYR | A | 97 | 10.632 | 19.684 | 6.021 | 1.00 | 55.74 | C |
| ATOM | 739 | CG | TYR | A | 97 | 11.960 | 20.312 | 6.399 | 1.00 | 56.10 | C |
| ATOM | 740 | CD1 | TYR | A | 97 | 12.041 | 21.541 | 7.057 | 1.00 | 56.27 | C |
| ATOM | 741 | CE1 | TYR | A | 97 | 13.296 | 22.095 | 7.410 | 1.00 | 57.14 | C |
| ATOM | 742 | CZ | TYR | A | 97 | 14.461 | 21.387 | 7.126 | 1.00 | 56.83 | C |
| ATOM | 743 | OH | TYR | A | 97 | 15.689 | 21.887 | 7.473 | 1.00 | 55.48 | O |
| ATOM | 744 | CE2 | TYR | A | 97 | 14.391 | 20.154 | 6.503 | 1.00 | 57.28 | C |
| ATOM | 745 | CD2 | TYR | A | 97 | 13.150 | 19.623 | 6.149 | 1.00 | 56.77 | C |
| ATOM | 746 | C | TYR | A | 97 | 9.846 | 22.013 | 5.115 | 1.00 | 54.29 | C |

APPENDIX I(c)-continued

| | | | | | | | | | | | |
|---|---|---|---|---|---|---|---|---|---|---|---|
| ATOM | 747 | O | TYR | A | 97 | 10.748 | 22.376 | 4.358 | 1.00 | 54.07 | O |
| ATOM | 748 | N | LYS | A | 98 | 8.963 | 22.829 | 5.671 | 1.00 | 52.88 | N |
| ATOM | 749 | CA | LYS | A | 98 | 9.117 | 24.254 | 5.774 | 1.00 | 52.16 | C |
| ATOM | 750 | CB | LYS | A | 98 | 7.918 | 24.963 | 5.146 | 1.00 | 52.30 | C |
| ATOM | 751 | CG | LYS | A | 98 | 7.868 | 24.902 | 3.594 | 1.00 | 51.71 | C |
| ATOM | 752 | CD | LYS | A | 98 | 8.873 | 25.820 | 2.951 | 1.00 | 51.20 | C |
| ATOM | 753 | CE | LYS | A | 98 | 9.000 | 25.574 | 1.445 | 1.00 | 52.94 | C |
| ATOM | 754 | NZ | LYS | A | 98 | 7.778 | 25.938 | 0.660 | 1.00 | 53.22 | N |
| ATOM | 755 | C | LYS | A | 98 | 9.216 | 24.543 | 7.260 | 1.00 | 51.92 | C |
| ATOM | 756 | O | LYS | A | 98 | 8.681 | 23.804 | 8.070 | 1.00 | 50.81 | O |
| ATOM | 757 | N | GLU | A | 99 | 9.931 | 25.603 | 7.610 | 1.00 | 52.28 | N |
| ATOM | 758 | CA | GLU | A | 99 | 10.230 | 25.940 | 9.000 | 1.00 | 53.27 | C |
| ATOM | 759 | CB | GLU | A | 99 | 11.721 | 26.262 | 9.140 | 1.00 | 53.26 | C |
| ATOM | 760 | CG | GLU | A | 99 | 12.638 | 25.140 | 9.605 | 1.00 | 55.49 | C |
| ATOM | 761 | CD | GLU | A | 99 | 13.946 | 25.678 | 10.221 | 1.00 | 56.41 | C |
| ATOM | 762 | OE1 | GLU | A | 99 | 14.761 | 24.867 | 10.720 | 1.00 | 60.13 | O |
| ATOM | 763 | OE2 | GLU | A | 99 | 14.168 | 26.916 | 10.214 | 1.00 | 60.48 | O |
| ATOM | 764 | C | GLU | A | 99 | 9.438 | 27.174 | 9.456 | 1.00 | 52.61 | C |
| ATOM | 765 | O | GLU | A | 99 | 9.172 | 28.086 | 8.651 | 1.00 | 52.40 | O |
| ATOM | 766 | N | GLY | A | 100 | 9.078 | 27.200 | 10.741 | 1.00 | 51.81 | N |
| ATOM | 767 | CA | GLY | A | 100 | 8.580 | 28.413 | 11.382 | 1.00 | 50.72 | C |
| ATOM | 768 | C | GLY | A | 100 | 9.744 | 29.356 | 11.618 | 1.00 | 50.01 | C |
| ATOM | 769 | O | GLY | A | 100 | 10.886 | 28.903 | 11.701 | 1.00 | 49.52 | O |
| ATOM | 770 | N | ALA | A | 101 | 9.466 | 30.662 | 11.717 | 1.00 | 49.16 | N |
| ATOM | 771 | CA | ALA | A | 101 | 10.527 | 31.661 | 11.904 | 1.00 | 48.33 | C |
| ATOM | 772 | CB | ALA | A | 101 | 10.100 | 33.021 | 11.324 | 1.00 | 48.12 | C |
| ATOM | 773 | C | ALA | A | 101 | 11.027 | 31.803 | 13.371 | 1.00 | 47.76 | C |
| ATOM | 774 | O | ALA | A | 101 | 11.992 | 32.535 | 13.634 | 1.00 | 47.69 | O |
| ATOM | 775 | N | GLY | A | 102 | 10.355 | 31.128 | 14.305 | 1.00 | 47.20 | N |
| ATOM | 776 | CA | GLY | A | 102 | 10.790 | 31.013 | 15.715 | 1.00 | 46.78 | C |
| ATOM | 777 | C | GLY | A | 102 | 9.916 | 31.710 | 16.745 | 1.00 | 46.63 | C |
| ATOM | 778 | O | GLY | A | 102 | 9.217 | 32.681 | 16.417 | 1.00 | 47.73 | O |
| ATOM | 779 | N | THR | A | 103 | 9.908 | 31.178 | 17.972 | 1.00 | 45.85 | N |
| ATOM | 780 | CA | THR | A | 103 | 9.426 | 31.883 | 19.169 | 1.00 | 44.12 | C |
| ATOM | 781 | CB | THR | A | 103 | 8.331 | 31.084 | 19.922 | 1.00 | 44.44 | C |
| ATOM | 782 | OG1 | THR | A | 103 | 7.235 | 30.802 | 19.052 | 1.00 | 45.90 | O |
| ATOM | 783 | CG2 | THR | A | 103 | 7.798 | 31.873 | 21.105 | 1.00 | 41.87 | C |
| ATOM | 784 | C | THR | A | 103 | 10.601 | 32.067 | 20.147 | 1.00 | 43.84 | C |
| ATOM | 785 | O | THR | A | 103 | 11.257 | 31.085 | 20.507 | 1.00 | 42.90 | O |
| ATOM | 786 | N | VAL | A | 104 | 10.862 | 33.304 | 20.589 | 1.00 | 42.99 | N |
| ATOM | 787 | CA | VAL | A | 104 | 11.821 | 33.546 | 21.693 | 1.00 | 42.66 | C |
| ATOM | 788 | CB | VAL | A | 104 | 12.627 | 34.863 | 21.516 | 1.00 | 42.32 | C |
| ATOM | 789 | CG1 | VAL | A | 104 | 13.729 | 34.905 | 22.549 | 1.00 | 42.52 | C |
| ATOM | 790 | CG2 | VAL | A | 104 | 13.198 | 34.982 | 20.109 | 1.00 | 42.86 | C |
| ATOM | 791 | C | VAL | A | 104 | 11.141 | 33.568 | 23.098 | 1.00 | 42.52 | C |
| ATOM | 792 | O | VAL | A | 104 | 10.465 | 34.543 | 23.488 | 1.00 | 41.37 | O |
| ATOM | 793 | N | LEU | A | 105 | 11.360 | 32.509 | 23.866 | 1.00 | 42.08 | N |
| ATOM | 794 | CA | LEU | A | 105 | 10.746 | 32.396 | 25.173 | 1.00 | 42.02 | C |
| ATOM | 795 | CB | LEU | A | 105 | 10.134 | 30.985 | 25.370 | 1.00 | 41.41 | C |
| ATOM | 796 | CG | LEU | A | 105 | 9.750 | 30.627 | 26.814 | 1.00 | 40.79 | C |
| ATOM | 797 | CD1 | LEU | A | 105 | 8.484 | 31.377 | 27.340 | 1.00 | 37.83 | C |
| ATOM | 798 | CD2 | LEU | A | 105 | 9.593 | 29.131 | 26.998 | 1.00 | 40.33 | C |
| ATOM | 799 | C | LEU | A | 105 | 11.753 | 32.736 | 26.272 | 1.00 | 42.74 | C |
| ATOM | 800 | O | LEU | A | 105 | 12.894 | 32.248 | 26.274 | 1.00 | 42.12 | O |
| ATOM | 801 | N | THR | A | 106 | 11.323 | 33.587 | 27.203 | 1.00 | 43.70 | N |
| ATOM | 802 | CA | THR | A | 106 | 12.051 | 33.796 | 28.459 | 1.00 | 44.17 | C |
| ATOM | 803 | CB | THR | A | 106 | 12.621 | 35.232 | 28.590 | 1.00 | 44.10 | C |
| ATOM | 804 | OG1 | THR | A | 106 | 13.521 | 35.493 | 27.512 | 1.00 | 43.79 | O |
| ATOM | 805 | CG2 | THR | A | 106 | 13.399 | 35.362 | 29.872 | 1.00 | 43.32 | C |
| ATOM | 806 | C | THR | A | 106 | 11.154 | 33.465 | 29.666 | 1.00 | 45.05 | C |
| ATOM | 807 | O | THR | A | 106 | 10.015 | 33.942 | 29.770 | 1.00 | 45.24 | O |
| ATOM | 808 | N | VAL | A | 107 | 11.679 | 32.648 | 30.574 | 1.00 | 45.71 | N |
| ATOM | 809 | CA | VAL | A | 107 | 10.946 | 32.265 | 31.780 | 1.00 | 46.23 | C |
| ATOM | 810 | CB | VAL | A | 107 | 10.790 | 30.730 | 31.916 | 1.00 | 45.95 | C |
| ATOM | 811 | CG1 | VAL | A | 107 | 9.747 | 30.402 | 32.993 | 1.00 | 45.73 | C |
| ATOM | 812 | CG2 | VAL | A | 107 | 10.394 | 30.105 | 30.561 | 1.00 | 44.60 | C |
| ATOM | 813 | C | VAL | A | 107 | 11.618 | 32.850 | 33.016 | 1.00 | 47.10 | C |
| ATOM | 814 | O | VAL | A | 107 | 12.778 | 32.556 | 33.301 | 1.00 | 46.92 | O |
| ATOM | 815 | N | LYS | A | 108 | 10.840 | 33.668 | 33.727 | 1.00 | 48.46 | N |
| ATOM | 816 | CA | LYS | A | 108 | 11.258 | 34.453 | 34.889 | 1.00 | 49.58 | C |
| ATOM | 817 | CB | LYS | A | 108 | 11.515 | 33.576 | 36.110 | 1.00 | 49.94 | C |
| ATOM | 818 | CG | LYS | A | 108 | 10.246 | 33.322 | 36.937 | 1.00 | 49.89 | C |
| ATOM | 819 | CD | LYS | A | 108 | 10.037 | 34.370 | 38.058 | 1.00 | 48.87 | C |
| ATOM | 820 | CE | LYS | A | 108 | 11.008 | 34.151 | 39.197 | 1.00 | 49.35 | C |
| ATOM | 821 | NZ | LYS | A | 108 | 11.300 | 32.697 | 39.377 | 1.00 | 47.83 | N |
| ATOM | 822 | C | LYS | A | 108 | 12.435 | 35.340 | 34.583 | 1.00 | 50.70 | C |
| ATOM | 823 | O | LYS | A | 108 | 12.374 | 36.115 | 33.626 | 1.00 | 52.01 | O |
| ATOM | 824 | O | HOH | W | 1 | 10.564 | 12.981 | 15.180 | 1.00 | 57.87 | O |
| ATOM | 825 | O | HOH | W | 2 | 4.884 | 38.038 | 19.422 | 1.00 | 39.09 | O |
| ATOM | 826 | O | HOH | W | 3 | 18.831 | 30.006 | 11.592 | 1.00 | 61.93 | O |

APPENDIX I(c)-continued

| ATOM | 827 | O | HOH | W | 4 | 1.789 | 33.404 | 36.744 | 1.00 | 54.79 | O |
|---|---|---|---|---|---|---|---|---|---|---|---|
| ATOM | 828 | O | HOH | W | 5 | 8.978 | 32.010 | 7.686 | 1.00 | 56.85 | O |
| ATOM | 829 | O | HOH | W | 6 | 6.845 | 33.982 | 8.593 | 1.00 | 71.15 | O |
| ATOM | 830 | O | HOH | W | 7 | 10.498 | 39.946 | 15.695 | 1.00 | 65.23 | O |
| ATOM | 831 | O | HOH | W | 8 | 13.932 | 22.652 | 30.685 | 1.00 | 42.16 | O |
| ATOM | 832 | O | HOH | W | 9 | −3.165 | 18.770 | 8.538 | 1.00 | 39.40 | O |
| ATOM | 833 | O | HOH | W | 10 | 18.047 | 27.608 | 16.064 | 1.00 | 55.15 | O |
| ATOM | 834 | O | HOH | W | 11 | −11.674 | 22.619 | 11.921 | 1.00 | 63.53 | O |
| ATOM | 835 | O | HOH | W | 12 | 12.389 | 9.964 | 5.651 | 1.00 | 63.77 | O |
| ATOM | 836 | O | HOH | W | 13 | −2.440 | 23.895 | 28.901 | 1.00 | 65.10 | O |
| ATOM | 837 | O | HOH | W | 14 | 1.615 | 35.824 | 29.148 | 1.00 | 52.11 | O |
| ATOM | 838 | O | HOH | W | 15 | 21.110 | 27.208 | 16.490 | 1.00 | 52.35 | O |
| ATOM | 839 | O | HOH | W | 16 | 0.817 | 32.375 | 23.701 | 1.00 | 50.69 | O |
| ATOM | 840 | O | HOH | W | 17 | 0.234 | 31.767 | 1.378 | 1.00 | 58.08 | O |
| ATOM | 841 | O | HOH | W | 18 | 15.129 | 33.987 | 33.625 | 1.00 | 67.94 | O |
| ATOM | 842 | O | HOH | W | 19 | 9.080 | 35.304 | 2.554 | 1.00 | 48.79 | O |
| ATOM | 843 | O | HOH | W | 20 | 15.507 | 38.561 | 33.060 | 1.00 | 40.13 | O |
| ATOM | 844 | O | HOH | W | 21 | 14.043 | 19.259 | 27.586 | 1.00 | 56.30 | O |
| ATOM | 845 | O | HOH | W | 22 | 11.011 | 38.760 | 11.090 | 1.00 | 52.13 | O |
| ATOM | 846 | O | HOH | W | 23 | 19.096 | 19.513 | 27.600 | 1.00 | 45.11 | O |
| ATOM | 847 | O | HOH | W | 24 | 8.529 | 10.231 | 23.841 | 1.00 | 54.09 | O |
| ATOM | 848 | O | HOH | W | 25 | 18.602 | 28.055 | 41.400 | 1.00 | 44.05 | O |
| ATOM | 849 | O | HOH | W | 26 | −0.858 | 32.893 | −3.524 | 1.00 | 48.46 | O |
| ATOM | 850 | O | HOH | W | 27 | 6.490 | 13.377 | 4.108 | 1.00 | 66.62 | O |
| ATOM | 851 | O | HOH | W | 28 | 3.930 | 14.910 | 13.874 | 1.00 | 30.35 | O |
| ATOM | 852 | O | HOH | W | 29 | −8.350 | 27.041 | 7.152 | 1.00 | 64.13 | O |
| ATOM | 853 | O | HOH | W | 30 | 19.016 | 32.914 | 41.473 | 1.00 | 53.57 | O |
| ATOM | 854 | O | HOH | W | 31 | 7.643 | 36.456 | 8.441 | 1.00 | 49.74 | O |
| ATOM | 855 | O | HOH | W | 32 | 0.695 | 30.653 | 25.517 | 1.00 | 40.63 | O |
| ATOM | 856 | O | HOH | W | 33 | 7.361 | 13.425 | 13.040 | 1.00 | 56.27 | O |
| ATOM | 857 | O | HOH | W | 34 | 16.881 | 31.557 | 10.306 | 1.00 | 60.57 | O |
| ATOM | 858 | O | HOH | W | 35 | 8.287 | 13.597 | 10.547 | 1.00 | 57.02 | O |
| ATOM | 859 | O | HOH | W | 36 | 8.039 | 13.358 | 19.018 | 1.00 | 34.10 | O |
| ATOM | 860 | O | HOH | W | 37 | 11.473 | 14.810 | 5.085 | 1.00 | 72.98 | O |
| ATOM | 861 | O | HOH | W | 38 | 18.961 | 23.256 | 8.032 | 1.00 | 45.71 | O |
| ATOM | 862 | O | HOH | W | 39 | 7.350 | 25.517 | 37.490 | 1.00 | 57.94 | O |
| ATOM | 863 | O | HOH | W | 40 | 0.871 | 15.567 | 22.621 | 1.00 | 36.05 | O |
| ATOM | 864 | O | HOH | W | 41 | 9.259 | 29.560 | 4.060 | 1.00 | 45.31 | O |
| ATOM | 865 | O | HOH | W | 42 | 15.495 | 16.208 | 13.522 | 1.00 | 48.14 | O |
| ATOM | 866 | O | HOH | W | 43 | −6.942 | 25.812 | 16.028 | 1.00 | 49.25 | O |
| ATOM | 867 | O | HOH | W | 44 | 8.961 | 33.009 | 1.653 | 1.00 | 58.96 | O |
| ATOM | 868 | O | HOH | W | 45 | 8.820 | 29.722 | 1.693 | 1.00 | 55.31 | O |
| ATOM | 869 | O | HOH | W | 46 | 0.934 | 10.101 | 7.881 | 1.00 | 46.26 | O |
| ATOM | 870 | O | HOH | W | 47 | 9.394 | 17.052 | 17.564 | 1.00 | 40.92 | O |
| ATOM | 871 | O | HOH | W | 48 | 15.096 | 33.948 | 15.334 | 1.00 | 51.10 | O |
| ATOM | 872 | O | HOH | W | 49 | 2.093 | 24.026 | 37.059 | 1.00 | 57.99 | O |
| ATOM | 873 | O | HOH | W | 50 | −0.613 | 16.821 | 11.553 | 1.00 | 40.82 | O |
| ATOM | 874 | O | HOH | W | 51 | 2.378 | 35.855 | 32.307 | 1.00 | 57.82 | O |
| ATOM | 875 | O | HOH | W | 52 | 10.646 | 16.132 | 25.937 | 1.00 | 28.33 | O |
| ATOM | 876 | O | HOH | W | 53 | 7.810 | 15.199 | 17.107 | 1.00 | 35.66 | O |
| ATOM | 877 | O | HOH | W | 54 | 7.946 | 10.228 | 19.423 | 1.00 | 58.71 | O |
| ATOM | 878 | O | HOH | W | 55 | −5.087 | 21.855 | 29.858 | 1.00 | 52.92 | O |
| ATOM | 879 | O | HOH | W | 56 | −2.460 | 30.063 | −6.344 | 1.00 | 63.51 | O |
| ATOM | 880 | O | HOH | W | 57 | −9.940 | 27.200 | 4.714 | 1.00 | 62.80 | O |
| ATOM | 881 | O | HOH | W | 58 | 7.680 | 43.303 | 24.786 | 1.00 | 54.95 | O |
| ATOM | 882 | O | HOH | W | 59 | 18.234 | 20.029 | 14.184 | 1.00 | 44.17 | O |
| ATOM | 883 | O | HOH | W | 60 | −8.225 | 25.875 | −4.166 | 1.00 | 54.98 | O |
| ATOM | 884 | O | HOH | W | 61 | 16.874 | 18.265 | 12.498 | 1.00 | 68.89 | O |
| ATOM | 885 | O | HOH | W | 62 | 7.892 | 14.001 | 1.905 | 1.00 | 65.53 | O |
| ATOM | 886 | O | HOH | W | 63 | −0.782 | 37.111 | 37.382 | 1.00 | 63.57 | O |
| ATOM | 887 | O | HOH | W | 64 | 22.498 | 23.044 | 16.311 | 1.00 | 36.02 | O |
| ATOM | 888 | O | HOH | W | 65 | 12.976 | 40.341 | 37.741 | 1.00 | 48.78 | O |
| ATOM | 889 | O | HOH | W | 66 | 20.503 | 26.080 | 31.957 | 1.00 | 53.38 | O |
| ATOM | 890 | O | HOH | W | 67 | 5.796 | 9.451 | 26.499 | 1.00 | 70.39 | O |
| ATOM | 891 | O | HOH | W | 68 | −1.275 | 15.214 | −8.910 | 1.00 | 52.06 | O |
| ATOM | 892 | O | HOH | W | 69 | 14.525 | 15.403 | 8.537 | 1.00 | 65.82 | O |
| ATOM | 893 | O | HOH | W | 70 | 12.969 | 42.361 | 34.897 | 1.00 | 82.78 | O |
| ATOM | 894 | O | HOH | W | 71 | 16.514 | 20.813 | 35.521 | 1.00 | 77.73 | O |
| ATOM | 895 | O | HOH | W | 72 | 9.910 | 10.781 | 13.915 | 1.00 | 58.26 | O |
| ATOM | 896 | O | HOH | W | 73 | 12.437 | 24.710 | 1.893 | 1.00 | 64.10 | O |
| ATOM | 897 | O | HOH | W | 74 | 20.747 | 31.422 | 22.103 | 1.00 | 41.64 | O |
| ATOM | 898 | O | HOH | W | 75 | 15.721 | 36.144 | 32.861 | 1.00 | 62.03 | O |
| ATOM | 899 | O | HOH | W | 76 | 0.635 | 31.352 | 13.751 | 1.00 | 31.08 | O |
| ATOM | 900 | O | HOH | W | 77 | 22.337 | 23.558 | 24.955 | 1.00 | 40.08 | O |
| ATOM | 901 | O | HOH | W | 78 | 7.932 | 13.265 | 7.088 | 1.00 | 67.66 | O |
| ATOM | 902 | O | HOH | W | 79 | 20.517 | 29.057 | 29.548 | 1.00 | 52.12 | O |
| ATOM | 903 | O | HOH | W | 80 | 15.259 | 17.514 | 0.795 | 1.00 | 60.37 | O |
| ATOM | 904 | O | HOH | W | 81 | −15.805 | 25.833 | 10.294 | 1.00 | 53.42 | O |
| ATOM | 905 | O | HOH | W | 82 | 3.946 | 10.765 | 28.247 | 1.00 | 71.57 | O |
| ATOM | 906 | O | HOH | W | 83 | −5.175 | 28.237 | 13.448 | 1.00 | 54.99 | O |

APPENDIX I(c)-continued

| ATOM | 907 | O | HOH | W | 84 | 5.447 | 39.199 | 25.619 | 1.00 | 52.76 | O |
|---|---|---|---|---|---|---|---|---|---|---|---|
| ATOM | 908 | O | HOH | W | 85 | 16.383 | 26.315 | 43.672 | 1.00 | 52.39 | O |
| ATOM | 909 | O | HOH | W | 86 | 8.064 | 40.405 | 25.323 | 1.00 | 54.14 | O |
| ATOM | 910 | O | HOH | W | 87 | 13.597 | 39.136 | 30.408 | 1.00 | 59.39 | O |
| ATOM | 911 | O | HOH | W | 88 | 7.974 | 10.662 | 16.213 | 1.00 | 48.90 | O |
| ATOM | 912 | O | HOH | W | 89 | 3.093 | 11.244 | 9.567 | 1.00 | 53.95 | O |
| ATOM | 913 | O | HOH | W | 90 | 11.935 | 23.245 | 26.965 | 1.00 | 25.98 | O |
| ATOM | 914 | O | HOH | W | 91 | 15.676 | 17.694 | 31.366 | 1.00 | 49.77 | O |
| ATOM | 915 | O | HOH | W | 92 | 1.434 | 28.589 | −1.853 | 1.00 | 61.65 | O |
| ATOM | 916 | O | HOH | W | 93 | −0.967 | 31.873 | 18.174 | 1.00 | 28.83 | O |
| ATOM | 917 | O | HOH | W | 94 | 3.569 | 19.724 | 15.627 | 1.00 | 69.29 | O |
| ATOM | 918 | O | HOH | W | 95 | 16.027 | 26.116 | 17.619 | 1.00 | 41.37 | O |
| ATOM | 919 | O | HOH | W | 96 | −3.179 | 23.176 | 16.288 | 1.00 | 35.67 | O |
| ATOM | 920 | O | HOH | W | 97 | 11.378 | 36.643 | 24.903 | 1.00 | 38.26 | O |
| ATOM | 921 | O | HOH | W | 98 | 11.275 | 12.570 | 12.614 | 1.00 | 61.05 | O |
| ATOM | 922 | O | HOH | W | 99 | 0.392 | 37.579 | 30.346 | 1.00 | 63.86 | O |
| ATOM | 923 | O | HOH | W | 100 | 3.615 | 36.054 | 27.042 | 1.00 | 52.83 | O |
| ATOM | 924 | O | HOH | W | 101 | 19.917 | 24.030 | 23.404 | 1.00 | 33.13 | O |
| ATOM | 925 | O | HOH | W | 102 | 25.442 | 22.459 | 25.169 | 1.00 | 52.27 | O |
| ATOM | 926 | O | HOH | W | 103 | 13.667 | 17.731 | 8.904 | 1.00 | 57.13 | O |
| ATOM | 927 | O | HOH | W | 104 | 12.838 | 33.231 | 16.397 | 1.00 | 49.03 | O |
| ATOM | 928 | O | HOH | W | 105 | −4.419 | 19.850 | 7.056 | 1.00 | 48.59 | O |
| ATOM | 929 | O | HOH | W | 106 | 2.163 | 14.571 | 24.878 | 1.00 | 58.28 | O |
| ATOM | 930 | O | HOH | W | 107 | 12.110 | 41.016 | 26.077 | 1.00 | 43.46 | O |
| ATOM | 931 | O | HOH | W | 108 | −6.767 | 22.389 | 4.829 | 1.00 | 51.02 | O |
| ATOM | 932 | O | HOH | W | 109 | −9.391 | 28.696 | 0.532 | 1.00 | 56.17 | O |
| ATOM | 933 | O | HOH | W | 110 | 12.664 | 12.157 | 15.211 | 1.00 | 69.74 | O |
| ATOM | 934 | O | HOH | W | 111 | 14.219 | 30.759 | 11.453 | 1.00 | 54.75 | O |
| ATOM | 935 | O | HOH | W | 112 | 22.000 | 34.294 | 19.285 | 1.00 | 54.23 | O |
| ATOM | 936 | O | HOH | W | 113 | −6.324 | 17.895 | 4.472 | 1.00 | 42.42 | O |
| ATOM | 937 | O | HOH | W | 114 | 26.863 | 26.038 | 22.840 | 1.00 | 52.75 | O |
| ATOM | 938 | O | HOH | W | 115 | 18.802 | 30.472 | 41.476 | 1.00 | 43.99 | O |
| ATOM | 939 | O | HOH | W | 116 | 7.804 | 8.898 | −3.753 | 1.00 | 69.67 | O |
| ATOM | 940 | O | HOH | W | 117 | 7.387 | 14.592 | −7.052 | 1.00 | 46.13 | O |
| ATOM | 941 | O | HOH | W | 118 | −0.533 | 19.834 | −3.700 | 1.00 | 61.81 | O |
| ATOM | 942 | O | HOH | W | 119 | 6.983 | 18.009 | 0.417 | 1.00 | 58.96 | O |
| ATOM | 943 | O | HOH | W | 120 | 7.436 | 17.165 | 3.342 | 1.00 | 61.89 | O |
| ATOM | 944 | O | HOH | W | 121 | 20.944 | 31.648 | 43.363 | 1.00 | 53.31 | O |
| ATOM | 945 | O | HOH | W | 122 | 21.826 | 26.911 | 29.579 | 1.00 | 67.75 | O |
| ATOM | 946 | O | HOH | W | 123 | 9.097 | 11.465 | 3.849 | 1.00 | 62.13 | O |
| ATOM | 947 | O | HOH | W | 124 | −1.826 | 21.461 | 28.064 | 1.00 | 60.67 | O |
| ATOM | 948 | O | HOH | W | 125 | 18.975 | 22.373 | 10.462 | 1.00 | 47.51 | O |
| ATOM | 949 | O | HOH | W | 126 | −10.791 | 27.326 | 7.417 | 1.00 | 58.06 | O |
| ATOM | 950 | O | HOH | W | 127 | 2.269 | 11.384 | 25.458 | 1.00 | 60.73 | O |
| ATOM | 951 | O | HOH | W | 128 | 9.714 | 36.832 | 6.517 | 1.00 | 60.04 | O |
| ATOM | 952 | O | HOH | W | 129 | 17.055 | 32.219 | 15.352 | 1.00 | 41.93 | O |
| ATOM | 953 | O | HOH | W | 130 | 1.590 | 20.061 | 27.434 | 1.00 | 37.17 | O |
| ATOM | 954 | O | HOH | W | 131 | 13.830 | 21.020 | 33.287 | 1.00 | 50.68 | O |
| ATOM | 955 | O | HOH | W | 132 | −6.693 | 16.372 | 13.047 | 1.00 | 45.15 | O |
| ATOM | 956 | O | HOH | W | 133 | 8.383 | 36.910 | 33.042 | 1.00 | 65.33 | O |
| ATOM | 957 | O | HOH | W | 134 | 11.374 | 41.068 | 32.503 | 1.00 | 54.93 | O |
| ATOM | 958 | O | HOH | W | 135 | 6.316 | 40.823 | 31.658 | 1.00 | 68.39 | O |
| ATOM | 959 | O | HOH | W | 136 | 12.324 | 14.149 | 2.727 | 1.00 | 67.01 | O |
| ATOM | 960 | O | HOH | W | 137 | −5.787 | 27.138 | −4.125 | 1.00 | 65.52 | O |
| ATOM | 961 | O | HOH | W | 138 | −9.802 | 27.322 | 11.236 | 1.00 | 60.08 | O |
| ATOM | 962 | O | HOH | W | 139 | −3.759 | 28.863 | −4.521 | 1.00 | 62.40 | O |
| ATOM | 963 | O | HOH | W | 140 | −2.672 | 19.413 | 11.260 | 1.00 | 45.75 | O |

APPENDIX I(d)

```
HEADER    1A-7
COMPND    1A-7
REMARK  3
REMARK  3  REFINEMENT.
REMARK  3     PROGRAM        : REFMAC 5.2.0011
REMARK  3     AUTHORS        : MURSHUDOV, VAGIN, DODSON
REMARK  3
REMARK  3     REFINEMENT TARGET : MAXIMUM LIKELIHOOD
REMARK  3
REMARK  3  DATA USED IN REFINEMENT.
REMARK  3     RESOLUTION RANGE HIGH    (ANGSTROMS) :   2.71
REMARK  3     RESOLUTION RANGE LOW     (ANGSTROMS) :  21.57
REMARK  3     DATA CUTOFF              (SIGMA(F))  : NONE
REMARK  3     COMPLETENESS FOR RANGE          (%)  :  95.14
REMARK  3     NUMBER OF REFLECTIONS           :     18372
REMARK  3
REMARK  3  FIT TO DATA USED IN REFINEMENT.
```

APPENDIX I(d)-continued

```
REMARK  3        CROSS-VALIDATION METHOD          : THROUGHOUT
REMARK  3        FREE R VALUE TEST SET SELECTION  : RANDOM
REMARK  3        R VALUE         (WORKING + TEST SET) : 0.18041
REMARK  3        R VALUE              (WORKING SET) : 0.17586
REMARK  3        FREE R VALUE                     : 0.26495
REMARK  3        FREE R VALUE TEST SET SIZE   (%) : 5.1
REMARK  3        FREE R VALUE TEST SET COUNT      : 982
REMARK  3
REMARK  3        FIT IN THE HIGHEST RESOLUTION BIN.
REMARK  3          TOTAL NUMBER OF BINS USED              : 20
REMARK  3          BIN RESOLUTION RANGE HIGH              : 2.709
REMARK  3          BIN RESOLUTION RANGE LOW               : 2.778
REMARK  3          REFLECTION IN BIN         (WORKING SET) : 1089
REMARK  3          BIN COMPLETENESS   (WORKING + TEST) (%) : 78.87
REMARK  3          BIN R VALUE              (WORKING SET) : 0.327
REMARK  3          BIN FREE R VALUE SET COUNT             : 46
REMARK  3          BIN FREE R VALUE                       : 0.328
REMARK  3
REMARK  3        NUMBER OF NON-HYDROGEN ATOMS USED IN REFINEMENT.
REMARK  3          ALL ATOMS              :      3765
REMARK  3
REMARK  3        B VALUES.
REMARK  3          FROM WILSON PLOT          (A**2) : NULL
REMARK  3          MEAN B VALUE      (OVERALL, A**2) : 43.346
REMARK  3          OVERALL ANISOTROPIC B VALUE.
REMARK  3           B11 (A**2):      4.16
REMARK  3           B22 (A**2):     -2.46
REMARK  3           B33 (A**2):     -1.70
REMARK  3           B12 (A**2):      0.00
REMARK  3           B13 (A**2):      0.00
REMARK  3           B23 (A**2):      0.00
REMARK  3
REMARK  3        ESTIMATED OVERALL COORDINATE ERROR.
REMARK  3          ESU BASED ON R VALUE                          (A) :  0.525
REMARK  3          ESU BASED ON FREE R VALUE                     (A) :  0.336
REMARK  3          ESU BASED ON MAXIMUM LIKELIHOOD               (A) :  0.258
REMARK  3          ESU FOR B VALUES BASED ON MAXIMUM LIKELIHOOD  (A**2) : 22.695
REMARK  3
REMARK  3        CORRELATION COEFFICIENTS.
REMARK  3            CORRELATION COEFFICIENT FO-FC       :  0.950
REMARK  3            CORRELATION COEFFICIENT FO-FC FREE  :  0.878
REMARK  3
REMARK  3        RMS DEVIATIONS FROM IDEAL VALUES              COUNT    RMS     WEIGHT
REMARK  3          BOND LENGTHS REFINED ATOMS        (A):      3328;   0.012;    0.022
REMARK  3          BOND ANGLES REFINED ATOMS    (DEGREES):     4492;   1.453;    1.954
REMARK  3          TORSION ANGLES, PERIOD 1     (DEGREES):      418;   6.864;    5.000
REMARK  3          TORSION ANGLES, PERIOD 2     (DEGREES):      144;  32.750;   23.611
REMARK  3          TORSION ANGLES, PERIOD 3     (DEGREES):      586;  20.512;   15.000
REMARK  3          TORSION ANGLES, PERIOD 4     (DEGREES):       28;  20.012;   15.000
REMARK  3          CHIRAL-CENTER RESTRAINTS       (A**3):       506;   0.102;    0.200
REMARK  3          GENERAL PLANES REFINED ATOMS      (A):      2460;   0.004;    0.020
REMARK  3          NON-BONDED CONTACTS REFINED ATOMS (A):      1638;   0.235;    0.200
REMARK  3          NON-BONDED TORSION REFINED ATOMS  (A):      2185;   0.308;    0.200
REMARK  3          H-BOND (X...Y) REFINED ATOMS      (A):       309;   0.191;    0.200
REMARK  3          SYMMETRY VDW REFINED ATOMS        (A):        72;   0.270;    0.200
REMARK  3          SYMMETRY H-BOND REFINED ATOMS     (A):        30;   0.292;    0.200
REMARK  3
REMARK  3        ISOTROPIC THERMAL FACTOR RESTRAINTS.          COUNT    RMS     WEIGHT
REMARK  3          MAIN-CHAIN BOND REFINED ATOMS   (A**2):     2116;   0.565;    1.500
REMARK  3          MAIN-CHAIN ANGLE REFINED ATOMS  (A**2):     3350;   1.077;    2.000
REMARK  3          SIDE-CHAIN BOND REFINED ATOMS   (A**2):     1368;   1.619;    3.000
REMARK  3          SIDE-CHAIN ANGLE REFINED ATOMS  (A**2):     1142;   2.840;    4.500
REMARK  3
REMARK  3        NCS RESTRAINTS STATISTICS
REMARK  3          NUMBER OF NCS GROUPS: NULL
REMARK  3
REMARK  3
REMARK  3        TLS DETAILS
REMARK  3          NUMBER OF TLS GROUPS: 4
REMARK  3          ATOM RECORD CONTAINS RESIDUAL B FACTORS ONLY
REMARK  3
REMARK  3          TLS GROUP:     1
REMARK  3            NUMBER OF COMPONENTS GROUP:    1
REMARK  3            COMPONENTS       C SSSEQI  TO   C SSSEQI
REMARK  3            RESIDUE RANGE :    A     1      A   111
REMARK  3          ORIGIN FOR THE GROUP (A):   42.6420   2.7110   11.2850
REMARK  3          T TENSOR
REMARK  3            T11:   -0.0556 T22:   -0.1040
REMARK  3            T33:   -0.1287 T12:   -0.0331
REMARK  3            T13:    0.0426 T23:   -0.0163
```

APPENDIX I(d)-continued

```
REMARK  3        L TENSOR
REMARK  3           L11:     6.4349 L22:      8.9791
REMARK  3           L33:     4.6108 L12:     -2.9273
REMARK  3           L13:    -0.1563 L23:     -1.8520
REMARK  3        S TENSOR
REMARK  3           S11:    -0.2306 S12:     -0.0310 S13:    -0.3199
REMARK  3           S21:     0.4291 S22:      0.2316 S23:     0.0525
REMARK  3           S31:     0.4464 S32:      0.0357 S33:    -0.0010
REMARK  3
REMARK  3     TLS GROUP: 2
REMARK  3        NUMBER OF COMPONENTS GROUP: 1
REMARK  3        COMPONENTS        C SSSEQI   TO   C SSSEQI
REMARK  3        RESIDUE RANGE :   B    1       B    111
REMARK  3        ORIGIN FOR THE GROUP (A):   57.2880   23.2710   9.5550
REMARK  3        T TENSOR
REMARK  3           T11:    -0.1637 T22:     -0.0898
REMARK  3           T33:    -0.0233 T12:      0.0302
REMARK  3           T13:    -0.0125 T23:     -0.0400
REMARK  3        L TENSOR
REMARK  3           L11:     2.6012 L22:      6.9682
REMARK  3           L33:     3.5725 L12:      2.9543
REMARK  3           L13:    -1.1259 L23:     -1.8219
REMARK  3        S TENSOR
REMARK  3           S11:     0.1344 S12:     -0.0679 S13:    -0.0673
REMARK  3           S21:     0.3029 S22:      0.0152 S23:    -0.1821
REMARK  3           S31:     0.2191 S32:     -0.1304 S33:    -0.1496
REMARK  3
REMARK  3     TLS GROUP: 3
REMARK  3        NUMBER OF COMPONENTS GROUP :   1
REMARK  3        COMPONENTS        C SSSEQI   TO   C SSSEQI
REMARK  3        RESIDUE RANGE :   C    1       C    111
REMARK  3        ORIGIN FOR THE GROUP (A):   25.8060   22.8210   23.0520
REMARK  3        T TENSOR
REMARK  3           T11:    -0.2263 T22:     -0.1090
REMARK  3           T33:    -0.0650 T12:      0.0097
REMARK  3           T13:    -0.0073 T23:      0.0251
REMARK  3        L TENSOR
REMARK  3           L11:     3.4989 L22:      7.7019
REMARK  3           L33:     6.6253 L12:      0.2165
REMARK  3           L13:    -0.5468 L23:      2.4276
REMARK  3        S TENSOR
REMARK  3           S11:    -0.0280 S12:     -0.0752 S13:     0.2877
REMARK  3           S21:     0.1903 S22:      0.2318 S23:    -0.2761
REMARK  3           S31:    -0.2228 S32:      0.2336 S33:    -0.2038
REMARK  3
REMARK  3     TLS GROUP :    4
REMARK  3        NUMBER OF COMPONENTS GROUP :    1
REMARK  3        COMPONENTS        C SSSEQI   TO   C SSSEQI
REMARK  3        RESIDUE RANGE :   D    1       D    111
REMARK  3        ORIGIN FOR THE GROUP (A):   19.7280    2.5210   36.8750
REMARK  3        T TENSOR
REMARK  3           T11:    -0.1365 T22:     -0.0747
REMARK  3           T33:    -0.1289 T12:      0.0351
REMARK  3           T13:     0.0176 T23:      0.0351
REMARK  3        L TENSOR
REMARK  3           L11:     3.3426 L22:      9.8078
REMARK  3           L33:     4.5159 L12:      0.8691
REMARK  3           L13:    -0.2683 L23:     -2.7373
REMARK  3        S TENSOR
REMARK  3           S11:    -0.1963 S12:      0.1431 S13:    -0.0334
REMARK  3           S21:     0.2425 S22:      0.2293 S23:    -0.2122
REMARK  3           S31:    -0.1809 S32:     -0.0589 S33:    -0.0330
REMARK  3
REMARK  3
REMARK  3     BULK SOLVENT MODELLING.
REMARK  3       METHOD USED: BABINET MODEL WITH MASK
REMARK  3       PARAMETERS FOR MASK CALCULATION
REMARK  3       VDW PROBE RADIUS :   1.20
REMARK  3       ION PROBE RADIUS :   0.80
REMARK  3       SHRINKAGE RADIUS :   0.80
REMARK  3
REMARK  3     OTHER REFINEMENT REMARKS:
REMARK  3     HYDROGENS HAVE BEEN ADDED IN THE RIDING POSITIONS
REMARK  3
SSBOND   1   CYS  A   22      CYS  A   83
SSBOND   2   CYS  B   22      CYS  B   83
SSBOND   3   CYS  C   22      CYS  C   83
SSBOND   4   CYS  D   22      CYS  D   83
CISPEP   1   THR  A    6      PRO  A    7                   0.00
CISPEP   2   THR  B    6      PRO  B    7                   0.00
```

APPENDIX I(d)-continued

| LINK | | | SER B | 88 | | | | PRO B | 99 | gap | | |
|---|---|---|---|---|---|---|---|---|---|---|---|---|
| CISPEP | 3 | THR | C | 6 | PRO | C | 7 | | 0.00 | | | |
| CISPEP | 4 | THR | D | 6 | PRO | D | 7 | | 0.00 | | | |
| LINK | | | SER D | 88 | | | | PRO D | 99 | gap | | |
| CRYST1 | 80.498 | 88.661 | 101.754 | 90.00 | 90.00 | 90.00 P 21 21 21 | | | | | | |
| SCALE1 | | 0.012423 | 0.000000 | 0.000000 | 0.00000 | | | | | | | |
| SCALE2 | | 0.000000 | 0.011279 | 0.000000 | 0.00000 | | | | | | | |
| SCALE3 | | 0.000000 | 0.000000 | 0.009828 | 0.00000 | | | | | | | |
| ATOM | 1 | N | ALA | A | 1 | 30.011 | 14.284 | 9.406 | 1.00 | 34.46 | N |
| ATOM | 2 | CA | ALA | A | 1 | 31.036 | 13.509 | 8.624 | 1.00 | 35.28 | C |
| ATOM | 3 | CB | ALA | A | 1 | 32.437 | 14.034 | 8.888 | 1.00 | 34.84 | C |
| ATOM | 4 | C | ALA | A | 1 | 30.972 | 11.997 | 8.877 | 1.00 | 35.65 | C |
| ATOM | 5 | O | ALA | A | 1 | 30.119 | 11.520 | 9.642 | 1.00 | 35.76 | O |
| ATOM | 6 | N | TRP | A | 2 | 31.857 | 11.254 | 8.206 | 1.00 | 35.69 | N |
| ATOM | 7 | CA | TRP | A | 2 | 31.947 | 9.799 | 8.343 | 1.00 | 36.00 | C |
| ATOM | 8 | CB | TRP | A | 2 | 30.700 | 9.112 | 7.776 | 1.00 | 35.89 | C |
| ATOM | 9 | CG | TRP | A | 2 | 30.730 | 8.902 | 6.299 | 1.00 | 35.28 | C |
| ATOM | 10 | CD1 | TRP | A | 2 | 31.303 | 7.856 | 5.637 | 1.00 | 35.33 | C |
| ATOM | 11 | NE1 | TRP | A | 2 | 31.147 | 8.010 | 4.281 | 1.00 | 35.24 | N |
| ATOM | 12 | CE2 | TRP | A | 2 | 30.442 | 9.158 | 4.042 | 1.00 | 34.88 | C |
| ATOM | 13 | CD2 | TRP | A | 2 | 30.168 | 9.753 | 5.293 | 1.00 | 34.55 | C |
| ATOM | 14 | CE3 | TRP | A | 2 | 29.451 | 10.952 | 5.327 | 1.00 | 34.74 | C |
| ATOM | 15 | CZ3 | TRP | A | 2 | 29.043 | 11.525 | 4.115 | 1.00 | 36.01 | C |
| ATOM | 16 | CH2 | TRP | A | 2 | 29.341 | 10.911 | 2.884 | 1.00 | 35.59 | C |
| ATOM | 17 | CZ2 | TRP | A | 2 | 30.026 | 9.724 | 2.830 | 1.00 | 35.60 | C |
| ATOM | 18 | C | TRP | A | 2 | 33.206 | 9.286 | 7.641 | 1.00 | 36.83 | C |
| ATOM | 19 | O | TRP | A | 2 | 33.787 | 9.979 | 6.789 | 1.00 | 37.05 | O |
| ATOM | 20 | N | VAL | A | 3 | 33.620 | 8.068 | 7.986 | 1.00 | 37.68 | N |
| ATOM | 21 | CA | VAL | A | 3 | 34.802 | 7.463 | 7.390 | 1.00 | 38.15 | C |
| ATOM | 22 | CB | VAL | A | 3 | 35.768 | 7.048 | 8.463 | 1.00 | 37.97 | C |
| ATOM | 23 | CG1 | VAL | A | 3 | 36.981 | 6.394 | 7.857 | 1.00 | 38.96 | C |
| ATOM | 24 | CG2 | VAL | A | 3 | 36.190 | 8.253 | 9.265 | 1.00 | 37.45 | C |
| ATOM | 25 | C | VAL | A | 3 | 34.433 | 6.260 | 6.529 | 1.00 | 39.32 | C |
| ATOM | 26 | O | VAL | A | 3 | 33.522 | 5.496 | 6.865 | 1.00 | 39.40 | O |
| ATOM | 27 | N | ASP | A | 4 | 35.127 | 6.129 | 5.398 | 1.00 | 40.83 | N |
| ATOM | 28 | CA | ASP | A | 4 | 35.007 | 4.981 | 4.485 | 1.00 | 42.50 | C |
| ATOM | 29 | CB | ASP | A | 4 | 35.128 | 5.449 | 3.040 | 1.00 | 42.10 | C |
| ATOM | 30 | CG | ASP | A | 4 | 33.831 | 5.916 | 2.470 | 1.00 | 44.06 | C |
| ATOM | 31 | OD1 | ASP | A | 4 | 33.877 | 6.414 | 1.321 | 1.00 | 46.56 | O |
| ATOM | 32 | OD2 | ASP | A | 4 | 32.771 | 5.783 | 3.148 | 1.00 | 45.25 | O |
| ATOM | 33 | C | ASP | A | 4 | 36.143 | 3.997 | 4.705 | 1.00 | 43.53 | C |
| ATOM | 34 | O | ASP | A | 4 | 37.294 | 4.316 | 4.382 | 1.00 | 44.43 | O |
| ATOM | 35 | N | GLN | A | 5 | 35.864 | 2.805 | 5.217 | 1.00 | 44.07 | N |
| ATOM | 36 | CA | GLN | A | 5 | 36.966 | 1.882 | 5.436 | 1.00 | 44.76 | C |
| ATOM | 37 | CB | GLN | A | 5 | 36.924 | 1.313 | 6.842 | 1.00 | 45.18 | C |
| ATOM | 38 | CG | GLN | A | 5 | 38.195 | 0.608 | 7.266 | 1.00 | 47.01 | C |
| ATOM | 39 | CD | GLN | A | 5 | 38.183 | 0.219 | 8.737 | 1.00 | 49.42 | C |
| ATOM | 40 | OE1 | GLN | A | 5 | 37.411 | 0.760 | 9.527 | 1.00 | 49.45 | O |
| ATOM | 41 | NE2 | GLN | A | 5 | 39.043 | −0.724 | 9.108 | 1.00 | 50.74 | N |
| ATOM | 42 | C | GLN | A | 5 | 36.945 | 0.779 | 4.411 | 1.00 | 44.79 | C |
| ATOM | 43 | O | GLN | A | 5 | 35.876 | 0.276 | 4.067 | 1.00 | 45.27 | O |
| ATOM | 44 | N | THR | A | 6 | 38.129 | 0.398 | 3.937 | 1.00 | 44.76 | N |
| ATOM | 45 | CA | THR | A | 6 | 38.278 | −0.648 | 2.915 | 1.00 | 44.58 | C |
| ATOM | 46 | CB | THR | A | 6 | 38.436 | 0.011 | 1.541 | 1.00 | 44.58 | C |
| ATOM | 47 | OG1 | THR | A | 6 | 37.159 | 0.471 | 1.104 | 1.00 | 44.70 | O |
| ATOM | 48 | CG2 | THR | A | 6 | 38.953 | −0.954 | 0.529 | 1.00 | 45.30 | C |
| ATOM | 49 | C | THR | A | 6 | 39.488 | −1.551 | 3.205 | 1.00 | 44.30 | C |
| ATOM | 50 | O | THR | A | 6 | 40.572 | −1.043 | 3.535 | 1.00 | 44.75 | O |
| ATOM | 51 | N | PRO | A | 7 | 39.318 | −2.886 | 3.115 | 1.00 | 43.66 | N |
| ATOM | 52 | CA | PRO | A | 7 | 38.111 | −3.683 | 2.896 | 1.00 | 43.45 | C |
| ATOM | 53 | CB | PRO | A | 7 | 38.670 | −5.030 | 2.455 | 1.00 | 43.29 | C |
| ATOM | 54 | CG | PRO | A | 7 | 39.953 | −5.128 | 3.166 | 1.00 | 43.32 | C |
| ATOM | 55 | CD | PRO | A | 7 | 40.513 | −3.742 | 3.203 | 1.00 | 43.44 | C |
| ATOM | 56 | C | PRO | A | 7 | 37.274 | −3.903 | 4.145 | 1.00 | 43.07 | C |
| ATOM | 57 | O | PRO | A | 7 | 37.737 | −3.660 | 5.254 | 1.00 | 42.77 | O |
| ATOM | 58 | N | ARG | A | 8 | 36.059 | −4.400 | 3.948 | 1.00 | 42.89 | N |
| ATOM | 59 | CA | ARG | A | 8 | 35.144 | −4.642 | 5.056 | 1.00 | 42.68 | C |
| ATOM | 60 | CB | ARG | A | 8 | 33.701 | −4.386 | 4.626 | 1.00 | 42.94 | C |
| ATOM | 61 | CG | ARG | A | 8 | 33.474 | −2.897 | 4.307 | 1.00 | 44.84 | C |
| ATOM | 62 | CD | ARG | A | 8 | 33.522 | −2.011 | 5.573 | 1.00 | 46.18 | C |
| ATOM | 63 | NE | ARG | A | 8 | 32.191 | −1.984 | 6.180 | 1.00 | 49.33 | N |
| ATOM | 64 | CZ | ARG | A | 8 | 31.770 | −2.747 | 7.193 | 1.00 | 49.53 | C |
| ATOM | 65 | NH1 | ARG | A | 8 | 32.579 | −3.612 | 7.796 | 1.00 | 50.15 | N |
| ATOM | 66 | NH2 | ARG | A | 8 | 30.520 | −2.623 | 7.616 | 1.00 | 49.55 | N |
| ATOM | 67 | C | ARG | A | 8 | 35.336 | −6.007 | 5.690 | 1.00 | 42.02 | C |
| ATOM | 68 | O | ARG | A | 8 | 35.204 | −6.143 | 6.907 | 1.00 | 41.82 | O |
| ATOM | 69 | N | SER | A | 9 | 35.653 | −7.007 | 4.869 | 1.00 | 41.36 | N |
| ATOM | 70 | CA | SER | A | 9 | 36.221 | −8.258 | 5.372 | 1.00 | 40.81 | C |
| ATOM | 71 | CB | SER | A | 9 | 35.140 | −9.293 | 5.702 | 1.00 | 40.66 | C |
| ATOM | 72 | OG | SER | A | 9 | 34.610 | −9.877 | 4.533 | 1.00 | 41.34 | O |

APPENDIX I(d)-continued

| ATOM | 73 | C | SER | A | 9 | 37.244 | −8.811 | 4.386 | 1.00 | 40.42 | C |
|---|---|---|---|---|---|---|---|---|---|---|---|
| ATOM | 74 | O | SER | A | 9 | 37.171 | −8.528 | 3.186 | 1.00 | 40.20 | O |
| ATOM | 75 | N | VAL | A | 10 | 38.196 | −9.593 | 4.897 | 1.00 | 39.89 | N |
| ATOM | 76 | CA | VAL | A | 10 | 39.313 | −10.077 | 4.095 | 1.00 | 39.33 | C |
| ATOM | 77 | CB | VAL | A | 10 | 40.314 | −8.932 | 3.746 | 1.00 | 39.54 | C |
| ATOM | 78 | CG1 | VAL | A | 10 | 41.033 | −8.411 | 4.992 | 1.00 | 39.50 | C |
| ATOM | 79 | CG2 | VAL | A | 10 | 41.309 | −9.365 | 2.663 | 1.00 | 39.48 | C |
| ATOM | 80 | C | VAL | A | 10 | 40.054 | −11.205 | 4.782 | 1.00 | 39.05 | C |
| ATOM | 81 | O | VAL | A | 10 | 40.350 | −11.144 | 5.977 | 1.00 | 38.79 | O |
| ATOM | 82 | N | THR | A | 11 | 40.337 | −12.241 | 3.999 | 1.00 | 38.97 | N |
| ATOM | 83 | CA | THR | A | 11 | 41.137 | −13.381 | 4.431 | 1.00 | 38.52 | C |
| ATOM | 84 | CB | THR | A | 11 | 40.544 | −14.672 | 3.897 | 1.00 | 38.36 | C |
| ATOM | 85 | OG1 | THR | A | 11 | 39.128 | −14.618 | 4.075 | 1.00 | 38.78 | O |
| ATOM | 86 | CG2 | THR | A | 11 | 41.095 | −15.879 | 4.643 | 1.00 | 38.38 | C |
| ATOM | 87 | C | THR | A | 11 | 42.542 | −13.197 | 3.890 | 1.00 | 38.21 | C |
| ATOM | 88 | O | THR | A | 11 | 42.723 | −12.656 | 2.802 | 1.00 | 38.36 | O |
| ATOM | 89 | N | LYS | A | 12 | 43.539 | −13.631 | 4.650 | 1.00 | 37.69 | N |
| ATOM | 90 | CA | LYS | A | 12 | 44.915 | −13.447 | 4.235 | 1.00 | 37.08 | C |
| ATOM | 91 | CB | LYS | A | 12 | 45.442 | −12.123 | 4.774 | 1.00 | 36.91 | C |
| ATOM | 92 | CG | LYS | A | 12 | 46.038 | −11.223 | 3.713 | 1.00 | 37.12 | C |
| ATOM | 93 | CD | LYS | A | 12 | 44.965 | −10.364 | 3.059 | 1.00 | 37.36 | C |
| ATOM | 94 | CE | LYS | A | 12 | 45.533 | −9.095 | 2.396 | 1.00 | 37.20 | C |
| ATOM | 95 | NZ | LYS | A | 12 | 46.627 | −9.346 | 1.416 | 1.00 | 36.82 | N |
| ATOM | 96 | C | LYS | A | 12 | 45.779 | −14.600 | 4.710 | 1.00 | 36.74 | C |
| ATOM | 97 | O | LYS | A | 12 | 45.567 | −15.138 | 5.790 | 1.00 | 36.56 | O |
| ATOM | 98 | N | GLU | A | 13 | 46.748 | −14.983 | 3.890 | 1.00 | 36.65 | N |
| ATOM | 99 | CA | GLU | A | 13 | 47.662 | −16.063 | 4.223 | 1.00 | 36.63 | C |
| ATOM | 100 | CB | GLU | A | 13 | 48.443 | −16.476 | 2.982 | 1.00 | 36.88 | C |
| ATOM | 101 | CG | GLU | A | 13 | 48.852 | −17.943 | 2.921 | 1.00 | 37.05 | C |
| ATOM | 102 | CD | GLU | A | 13 | 47.914 | −18.746 | 2.053 | 1.00 | 37.80 | C |
| ATOM | 103 | OE1 | GLU | A | 13 | 48.375 | −19.718 | 1.409 | 1.00 | 36.95 | O |
| ATOM | 104 | OE2 | GLU | A | 13 | 46.712 | −18.387 | 2.008 | 1.00 | 38.61 | O |
| ATOM | 105 | C | GLU | A | 13 | 48.640 | −15.558 | 5.257 | 1.00 | 36.50 | C |
| ATOM | 106 | O | GLU | A | 13 | 48.973 | −14.381 | 5.267 | 1.00 | 36.57 | O |
| ATOM | 107 | N | THR | A | 14 | 49.104 | −16.454 | 6.119 | 1.00 | 36.57 | N |
| ATOM | 108 | CA | THR | A | 14 | 50.154 | −16.149 | 7.087 | 1.00 | 36.76 | C |
| ATOM | 109 | CB | THR | A | 14 | 50.468 | −17.390 | 7.993 | 1.00 | 37.06 | C |
| ATOM | 110 | OG1 | THR | A | 14 | 49.284 | −18.190 | 8.178 | 1.00 | 37.72 | O |
| ATOM | 111 | CG2 | THR | A | 14 | 51.006 | −16.970 | 9.359 | 1.00 | 37.11 | C |
| ATOM | 112 | C | THR | A | 14 | 51.421 | −15.708 | 6.338 | 1.00 | 36.68 | C |
| ATOM | 113 | O | THR | A | 14 | 51.878 | −16.394 | 5.419 | 1.00 | 36.83 | O |
| ATOM | 114 | N | GLY | A | 15 | 51.973 | −14.562 | 6.724 | 1.00 | 36.57 | N |
| ATOM | 115 | CA | GLY | A | 15 | 53.222 | −14.066 | 6.142 | 1.00 | 36.88 | C |
| ATOM | 116 | C | GLY | A | 15 | 52.988 | −12.938 | 5.160 | 1.00 | 37.24 | C |
| ATOM | 117 | O | GLY | A | 15 | 53.925 | −12.306 | 4.684 | 1.00 | 37.22 | O |
| ATOM | 118 | N | GLU | A | 16 | 51.719 | −12.680 | 4.876 | 1.00 | 37.60 | N |
| ATOM | 119 | CA | GLU | A | 16 | 51.313 | −11.686 | 3.901 | 1.00 | 38.12 | C |
| ATOM | 120 | CB | GLU | A | 16 | 50.036 | −12.178 | 3.221 | 1.00 | 38.52 | C |
| ATOM | 121 | CG | GLU | A | 16 | 50.043 | −12.115 | 1.696 | 1.00 | 39.20 | C |
| ATOM | 122 | CD | GLU | A | 16 | 49.133 | −13.160 | 1.081 | 1.00 | 38.58 | C |
| ATOM | 123 | OE1 | GLU | A | 16 | 47.934 | −13.224 | 1.446 | 1.00 | 37.91 | O |
| ATOM | 124 | OE2 | GLU | A | 16 | 49.631 | −13.922 | 0.231 | 1.00 | 39.94 | O |
| ATOM | 125 | C | GLU | A | 16 | 51.078 | −10.307 | 4.545 | 1.00 | 38.27 | C |
| ATOM | 126 | O | GLU | A | 16 | 51.211 | −10.149 | 5.766 | 1.00 | 38.17 | O |
| ATOM | 127 | N | SER | A | 17 | 50.733 | −9.319 | 3.718 | 1.00 | 38.22 | N |
| ATOM | 128 | CA | SER | A | 17 | 50.527 | −7.952 | 4.181 | 1.00 | 38.25 | C |
| ATOM | 129 | CB | SER | A | 17 | 51.468 | −7.012 | 3.449 | 1.00 | 38.04 | C |
| ATOM | 130 | OG | SER | A | 17 | 52.526 | −6.633 | 4.292 | 1.00 | 38.21 | O |
| ATOM | 131 | C | SER | A | 17 | 49.100 | −7.463 | 4.016 | 1.00 | 38.42 | C |
| ATOM | 132 | O | SER | A | 17 | 48.468 | −7.715 | 3.001 | 1.00 | 38.73 | O |
| ATOM | 133 | N | LEU | A | 18 | 48.585 | −6.763 | 5.017 | 1.00 | 38.75 | N |
| ATOM | 134 | CA | LEU | A | 18 | 47.270 | −6.156 | 4.874 | 1.00 | 39.12 | C |
| ATOM | 135 | CB | LEU | A | 18 | 46.353 | −6.572 | 6.022 | 1.00 | 39.04 | C |
| ATOM | 136 | CG | LEU | A | 18 | 44.806 | −6.512 | 6.021 | 1.00 | 38.73 | C |
| ATOM | 137 | CD1 | LEU | A | 18 | 44.328 | −5.643 | 7.149 | 1.00 | 39.79 | C |
| ATOM | 138 | CD2 | LEU | A | 18 | 44.103 | −6.155 | 4.705 | 1.00 | 37.22 | C |
| ATOM | 139 | C | LEU | A | 18 | 47.373 | −4.634 | 4.760 | 1.00 | 39.48 | C |
| ATOM | 140 | O | LEU | A | 18 | 48.245 | −4.003 | 5.382 | 1.00 | 39.45 | O |
| ATOM | 141 | N | THR | A | 19 | 46.495 | −4.073 | 3.928 | 1.00 | 39.47 | N |
| ATOM | 142 | CA | THR | A | 19 | 46.365 | −2.639 | 3.747 | 1.00 | 39.18 | C |
| ATOM | 143 | CB | THR | A | 19 | 46.900 | −2.192 | 2.371 | 1.00 | 39.41 | C |
| ATOM | 144 | OG1 | THR | A | 19 | 48.101 | −2.914 | 2.076 | 1.00 | 39.32 | O |
| ATOM | 145 | CG2 | THR | A | 19 | 47.174 | −0.670 | 2.324 | 1.00 | 38.20 | C |
| ATOM | 146 | C | THR | A | 19 | 44.892 | −2.293 | 3.868 | 1.00 | 39.18 | C |
| ATOM | 147 | O | THR | A | 19 | 44.060 | −2.770 | 3.091 | 1.00 | 38.41 | O |
| ATOM | 148 | N | ILE | A | 20 | 44.597 | −1.478 | 4.876 | 1.00 | 39.56 | N |
| ATOM | 149 | CA | ILE | A | 20 | 43.260 | −0.955 | 5.138 | 1.00 | 39.76 | C |
| ATOM | 150 | CB | ILE | A | 20 | 42.903 | −1.040 | 6.652 | 1.00 | 39.03 | C |
| ATOM | 151 | CG1 | ILE | A | 20 | 42.854 | −2.492 | 7.109 | 1.00 | 37.40 | C |
| ATOM | 152 | CD1 | ILE | A | 20 | 42.677 | −2.673 | 8.576 | 1.00 | 34.93 | C |

APPENDIX I(d)-continued

| ATOM | 153 | CG2 | ILE | A | 20 | 41.561 | −0.422 | 6.915 | 1.00 | 39.48 | C |
|---|---|---|---|---|---|---|---|---|---|---|---|
| ATOM | 154 | C | ILE | A | 20 | 43.270 | 0.502 | 4.705 | 1.00 | 40.70 | C |
| ATOM | 155 | O | ILE | A | 20 | 44.093 | 1.289 | 5.200 | 1.00 | 41.44 | O |
| ATOM | 156 | N | ASN | A | 21 | 42.378 | 0.865 | 3.784 | 1.00 | 41.34 | N |
| ATOM | 157 | CA | ASN | A | 21 | 42.217 | 2.277 | 3.388 | 1.00 | 41.97 | C |
| ATOM | 158 | CB | ASN | A | 21 | 41.958 | 2.394 | 1.892 | 1.00 | 41.90 | C |
| ATOM | 159 | CG | ASN | A | 21 | 43.155 | 1.947 | 1.059 | 1.00 | 42.52 | C |
| ATOM | 160 | OD1 | ASN | A | 21 | 43.117 | 0.905 | 0.407 | 1.00 | 43.46 | O |
| ATOM | 161 | ND2 | ASN | A | 21 | 44.224 | 2.730 | 1.085 | 1.00 | 43.18 | N |
| ATOM | 162 | C | ASN | A | 21 | 41.136 | 2.997 | 4.190 | 1.00 | 42.22 | C |
| ATOM | 163 | O | ASN | A | 21 | 40.226 | 2.370 | 4.705 | 1.00 | 43.14 | O |
| ATOM | 164 | N | CYS | A | 22 | 41.260 | 4.305 | 4.327 | 1.00 | 42.28 | N |
| ATOM | 165 | CA | CYS | A | 22 | 40.265 | 5.101 | 5.027 | 1.00 | 42.84 | C |
| ATOM | 166 | CB | CYS | A | 22 | 40.554 | 5.158 | 6.527 | 1.00 | 43.14 | C |
| ATOM | 167 | SG | CYS | A | 22 | 40.171 | 3.613 | 7.438 | 1.00 | 48.94 | S |
| ATOM | 168 | C | CYS | A | 22 | 40.209 | 6.508 | 4.455 | 1.00 | 41.89 | C |
| ATOM | 169 | O | CYS | A | 22 | 41.239 | 7.124 | 4.182 | 1.00 | 42.35 | O |
| ATOM | 170 | N | ALA | A | 23 | 39.005 | 7.014 | 4.260 | 1.00 | 40.70 | N |
| ATOM | 171 | CA | ALA | A | 23 | 38.848 | 8.380 | 3.803 | 1.00 | 39.76 | C |
| ATOM | 172 | CB | ALA | A | 23 | 38.526 | 8.399 | 2.357 | 1.00 | 39.71 | C |
| ATOM | 173 | C | ALA | A | 23 | 37.762 | 9.084 | 4.612 | 1.00 | 39.14 | C |
| ATOM | 174 | O | ALA | A | 23 | 36.691 | 8.519 | 4.843 | 1.00 | 38.80 | O |
| ATOM | 175 | N | LEU | A | 24 | 38.076 | 10.305 | 5.056 | 1.00 | 38.04 | N |
| ATOM | 176 | CA | LEU | A | 24 | 37.170 | 11.133 | 5.840 | 1.00 | 37.40 | C |
| ATOM | 177 | CB | LEU | A | 24 | 37.981 | 12.023 | 6.793 | 1.00 | 37.06 | C |
| ATOM | 178 | CG | LEU | A | 24 | 37.310 | 13.044 | 7.730 | 1.00 | 37.11 | C |
| ATOM | 179 | CD1 | LEU | A | 24 | 38.333 | 13.654 | 8.690 | 1.00 | 34.67 | C |
| ATOM | 180 | CD2 | LEU | A | 24 | 36.106 | 12.470 | 8.501 | 1.00 | 35.66 | C |
| ATOM | 181 | C | LEU | A | 24 | 36.265 | 11.952 | 4.897 | 1.00 | 37.29 | C |
| ATOM | 182 | O | LEU | A | 24 | 36.746 | 12.790 | 4.117 | 1.00 | 36.95 | O |
| ATOM | 183 | N | LYS | A | 25 | 34.959 | 11.695 | 4.951 | 1.00 | 36.83 | N |
| ATOM | 184 | CA | LYS | A | 25 | 34.046 | 12.329 | 4.008 | 1.00 | 36.82 | C |
| ATOM | 185 | CB | LYS | A | 25 | 33.225 | 11.273 | 3.268 | 1.00 | 36.56 | C |
| ATOM | 186 | CG | LYS | A | 25 | 34.044 | 10.153 | 2.595 | 1.00 | 37.16 | C |
| ATOM | 187 | CD | LYS | A | 25 | 34.408 | 10.422 | 1.143 | 1.00 | 37.46 | C |
| ATOM | 188 | CE | LYS | A | 25 | 35.722 | 11.217 | 1.064 | 1.00 | 41.41 | C |
| ATOM | 189 | NZ | LYS | A | 25 | 36.517 | 11.096 | −0.229 | 1.00 | 41.89 | N |
| ATOM | 190 | C | LYS | A | 25 | 33.137 | 13.322 | 4.709 | 1.00 | 36.75 | C |
| ATOM | 191 | O | LYS | A | 25 | 32.758 | 13.096 | 5.854 | 1.00 | 37.04 | O |
| ATOM | 192 | N | ASN | A | 26 | 32.798 | 14.420 | 4.027 | 1.00 | 36.84 | N |
| ATOM | 193 | CA | ASN | A | 26 | 31.808 | 15.399 | 4.510 | 1.00 | 37.02 | C |
| ATOM | 194 | CB | ASN | A | 26 | 30.454 | 14.723 | 4.775 | 1.00 | 37.06 | C |
| ATOM | 195 | CG | ASN | A | 26 | 29.262 | 15.664 | 4.557 | 1.00 | 39.15 | C |
| ATOM | 196 | OD1 | ASN | A | 26 | 28.344 | 15.755 | 5.390 | 1.00 | 39.26 | O |
| ATOM | 197 | ND2 | ASN | A | 26 | 29.265 | 16.361 | 3.422 | 1.00 | 41.33 | N |
| ATOM | 198 | C | ASN | A | 26 | 32.254 | 16.157 | 5.759 | 1.00 | 37.24 | C |
| ATOM | 199 | O | ASN | A | 26 | 31.420 | 16.589 | 6.551 | 1.00 | 37.14 | O |
| ATOM | 200 | N | ALA | A | 27 | 33.567 | 16.296 | 5.941 | 1.00 | 37.46 | N |
| ATOM | 201 | CA | ALA | A | 27 | 34.131 | 17.028 | 7.069 | 1.00 | 37.86 | C |
| ATOM | 202 | CB | ALA | A | 27 | 35.300 | 16.289 | 7.631 | 1.00 | 37.64 | C |
| ATOM | 203 | C | ALA | A | 27 | 34.557 | 18.443 | 6.673 | 1.00 | 38.63 | C |
| ATOM | 204 | O | ALA | A | 27 | 35.473 | 18.630 | 5.839 | 1.00 | 39.12 | O |
| ATOM | 205 | N | ALA | A | 28 | 33.894 | 19.425 | 7.286 | 1.00 | 38.74 | N |
| ATOM | 206 | CA | ALA | A | 28 | 34.201 | 20.846 | 7.127 | 1.00 | 38.77 | C |
| ATOM | 207 | CB | ALA | A | 28 | 33.266 | 21.675 | 7.969 | 1.00 | 38.26 | C |
| ATOM | 208 | C | ALA | A | 28 | 35.650 | 21.212 | 7.468 | 1.00 | 39.27 | C |
| ATOM | 209 | O | ALA | A | 28 | 36.238 | 22.075 | 6.800 | 1.00 | 39.84 | O |
| ATOM | 210 | N | ASP | A | 29 | 36.227 | 20.579 | 8.495 | 1.00 | 39.15 | N |
| ATOM | 211 | CA | ASP | A | 29 | 37.529 | 21.012 | 9.011 | 1.00 | 39.27 | C |
| ATOM | 212 | CB | ASP | A | 29 | 37.435 | 21.193 | 10.516 | 1.00 | 39.55 | C |
| ATOM | 213 | CG | ASP | A | 29 | 36.715 | 22.467 | 10.909 | 1.00 | 40.83 | C |
| ATOM | 214 | OD1 | ASP | A | 29 | 36.915 | 23.522 | 10.253 | 1.00 | 40.47 | O |
| ATOM | 215 | OD2 | ASP | A | 29 | 35.946 | 22.409 | 11.894 | 1.00 | 43.52 | O |
| ATOM | 216 | C | ASP | A | 29 | 38.697 | 20.092 | 8.639 | 1.00 | 39.04 | C |
| ATOM | 217 | O | ASP | A | 29 | 38.481 | 19.056 | 8.035 | 1.00 | 39.18 | O |
| ATOM | 218 | N | ASP | A | 30 | 39.929 | 20.464 | 8.996 | 1.00 | 38.80 | N |
| ATOM | 219 | CA | ASP | A | 30 | 41.115 | 19.660 | 8.628 | 1.00 | 38.39 | C |
| ATOM | 220 | CB | ASP | A | 30 | 42.418 | 20.435 | 8.838 | 1.00 | 38.50 | C |
| ATOM | 221 | CG | ASP | A | 30 | 42.507 | 21.699 | 7.991 | 1.00 | 40.29 | C |
| ATOM | 222 | OD1 | ASP | A | 30 | 43.012 | 22.709 | 8.523 | 1.00 | 42.73 | O |
| ATOM | 223 | OD2 | ASP | A | 30 | 42.080 | 21.708 | 6.808 | 1.00 | 41.07 | O |
| ATOM | 224 | C | ASP | A | 30 | 41.210 | 18.370 | 9.419 | 1.00 | 37.92 | C |
| ATOM | 225 | O | ASP | A | 30 | 40.802 | 18.325 | 10.584 | 1.00 | 37.68 | O |
| ATOM | 226 | N | LEU | A | 31 | 41.751 | 17.332 | 8.774 | 1.00 | 37.28 | N |
| ATOM | 227 | CA | LEU | A | 31 | 42.173 | 16.113 | 9.441 | 1.00 | 36.52 | C |
| ATOM | 228 | CB | LEU | A | 31 | 42.727 | 15.118 | 8.438 | 1.00 | 36.34 | C |
| ATOM | 229 | CG | LEU | A | 31 | 42.508 | 13.612 | 8.605 | 1.00 | 35.92 | C |
| ATOM | 230 | CD1 | LEU | A | 31 | 42.219 | 13.184 | 10.047 | 1.00 | 35.84 | C |
| ATOM | 231 | CD2 | LEU | A | 31 | 43.676 | 12.876 | 8.037 | 1.00 | 35.02 | C |
| ATOM | 232 | C | LEU | A | 31 | 43.304 | 16.505 | 10.330 | 1.00 | 36.82 | C |

APPENDIX I(d)-continued

| ATOM | 233 | O | LEU | A | 31 | 44.265 | 17.147 | 9.883 | 1.00 | 36.89 | O |
|---|---|---|---|---|---|---|---|---|---|---|---|
| ATOM | 234 | N | GLU | A | 32 | 43.213 | 16.090 | 11.583 | 1.00 | 37.16 | N |
| ATOM | 235 | CA | GLU | A | 32 | 44.153 | 16.520 | 12.603 | 1.00 | 37.77 | C |
| ATOM | 236 | CB | GLU | A | 32 | 43.443 | 17.502 | 13.557 | 1.00 | 37.94 | C |
| ATOM | 237 | CG | GLU | A | 32 | 44.338 | 18.432 | 14.370 | 1.00 | 40.70 | C |
| ATOM | 238 | CD | GLU | A | 32 | 45.128 | 19.438 | 13.530 | 1.00 | 43.57 | C |
| ATOM | 239 | OE1 | GLU | A | 32 | 46.360 | 19.572 | 13.769 | 1.00 | 43.94 | O |
| ATOM | 240 | OE2 | GLU | A | 32 | 44.521 | 20.097 | 12.649 | 1.00 | 44.41 | O |
| ATOM | 241 | C | GLU | A | 32 | 44.820 | 15.312 | 13.319 | 1.00 | 37.53 | C |
| ATOM | 242 | O | GLU | A | 32 | 46.000 | 15.347 | 13.645 | 1.00 | 37.47 | O |
| ATOM | 243 | N | ARG | A | 33 | 44.089 | 14.228 | 13.514 | 1.00 | 37.63 | N |
| ATOM | 244 | CA | ARG | A | 33 | 44.650 | 13.069 | 14.176 | 1.00 | 38.59 | C |
| ATOM | 245 | CB | ARG | A | 33 | 44.330 | 13.124 | 15.668 | 1.00 | 38.27 | C |
| ATOM | 246 | CG | ARG | A | 33 | 45.405 | 12.524 | 16.561 | 1.00 | 39.74 | C |
| ATOM | 247 | CD | ARG | A | 33 | 44.978 | 12.402 | 18.023 | 1.00 | 40.86 | C |
| ATOM | 248 | NE | ARG | A | 33 | 43.765 | 11.591 | 18.189 | 1.00 | 48.81 | N |
| ATOM | 249 | CZ | ARG | A | 33 | 42.619 | 12.005 | 18.751 | 1.00 | 51.82 | C |
| ATOM | 250 | NH1 | ARG | A | 33 | 42.484 | 13.241 | 19.247 | 1.00 | 50.95 | N |
| ATOM | 251 | NH2 | ARG | A | 33 | 41.589 | 11.161 | 18.828 | 1.00 | 54.87 | N |
| ATOM | 252 | C | ARG | A | 33 | 44.081 | 11.800 | 13.573 | 1.00 | 38.68 | C |
| ATOM | 253 | O | ARG | A | 33 | 42.887 | 11.731 | 13.269 | 1.00 | 38.65 | O |
| ATOM | 254 | N | THR | A | 34 | 44.924 | 10.790 | 13.392 | 1.00 | 39.54 | N |
| ATOM | 255 | CA | THR | A | 34 | 44.442 | 9.476 | 12.933 | 1.00 | 40.35 | C |
| ATOM | 256 | CB | THR | A | 34 | 44.987 | 9.118 | 11.559 | 1.00 | 40.18 | C |
| ATOM | 257 | OG1 | THR | A | 34 | 46.414 | 9.263 | 11.560 | 1.00 | 39.67 | O |
| ATOM | 258 | CG2 | THR | A | 34 | 44.382 | 10.023 | 10.501 | 1.00 | 40.31 | C |
| ATOM | 259 | C | THR | A | 34 | 44.827 | 8.383 | 13.927 | 1.00 | 41.31 | C |
| ATOM | 260 | O | THR | A | 34 | 45.953 | 8.373 | 14.447 | 1.00 | 41.94 | O |
| ATOM | 261 | N | ASP | A | 35 | 43.891 | 7.478 | 14.210 | 1.00 | 41.83 | N |
| ATOM | 262 | CA | ASP | A | 35 | 44.126 | 6.393 | 15.161 | 1.00 | 42.20 | C |
| ATOM | 263 | CB | ASP | A | 35 | 43.274 | 6.571 | 16.421 | 1.00 | 42.42 | C |
| ATOM | 264 | CG | ASP | A | 35 | 43.737 | 7.747 | 17.302 | 1.00 | 46.01 | C |
| ATOM | 265 | OD1 | ASP | A | 35 | 42.966 | 8.226 | 18.195 | 1.00 | 47.52 | O |
| ATOM | 266 | OD2 | ASP | A | 35 | 44.892 | 8.195 | 17.112 | 1.00 | 50.48 | O |
| ATOM | 267 | C | ASP | A | 35 | 43.762 | 5.095 | 14.470 | 1.00 | 42.09 | C |
| ATOM | 268 | O | ASP | A | 35 | 43.012 | 5.105 | 13.485 | 1.00 | 41.93 | O |
| ATOM | 269 | N | TRP | A | 36 | 44.322 | 3.985 | 14.959 | 1.00 | 42.03 | N |
| ATOM | 270 | CA | TRP | A | 36 | 43.935 | 2.646 | 14.501 | 1.00 | 41.95 | C |
| ATOM | 271 | CB | TRP | A | 36 | 44.964 | 2.073 | 13.553 | 1.00 | 41.75 | C |
| ATOM | 272 | CG | TRP | A | 36 | 45.116 | 2.870 | 12.337 | 1.00 | 41.84 | C |
| ATOM | 273 | CD1 | TRP | A | 36 | 45.928 | 3.949 | 12.162 | 1.00 | 41.60 | C |
| ATOM | 274 | NE1 | TRP | A | 36 | 45.799 | 4.440 | 10.884 | 1.00 | 42.39 | N |
| ATOM | 275 | CE2 | TRP | A | 36 | 44.890 | 3.669 | 10.210 | 1.00 | 42.33 | C |
| ATOM | 276 | CD2 | TRP | A | 36 | 44.428 | 2.677 | 11.105 | 1.00 | 41.80 | C |
| ATOM | 277 | CE3 | TRP | A | 36 | 43.487 | 1.749 | 10.660 | 1.00 | 40.90 | C |
| ATOM | 278 | CZ3 | TRP | A | 36 | 43.037 | 1.839 | 9.374 | 1.00 | 41.85 | C |
| ATOM | 279 | CH2 | TRP | A | 36 | 43.520 | 2.840 | 8.497 | 1.00 | 42.44 | C |
| ATOM | 280 | CZ2 | TRP | A | 36 | 44.442 | 3.758 | 8.900 | 1.00 | 41.87 | C |
| ATOM | 281 | C | TRP | A | 36 | 43.767 | 1.722 | 15.680 | 1.00 | 42.21 | C |
| ATOM | 282 | O | TRP | A | 36 | 44.588 | 1.736 | 16.604 | 1.00 | 42.22 | O |
| ATOM | 283 | N | TYR | A | 37 | 42.706 | 0.918 | 15.632 | 1.00 | 42.73 | N |
| ATOM | 284 | CA | TYR | A | 37 | 42.263 | 0.091 | 16.763 | 1.00 | 43.04 | C |
| ATOM | 285 | CB | TYR | A | 37 | 40.951 | 0.612 | 17.329 | 1.00 | 42.85 | C |
| ATOM | 286 | CG | TYR | A | 37 | 41.021 | 2.037 | 17.776 | 1.00 | 43.46 | C |
| ATOM | 287 | CD1 | TYR | A | 37 | 41.456 | 2.361 | 19.068 | 1.00 | 43.11 | C |
| ATOM | 288 | CE1 | TYR | A | 37 | 41.548 | 3.664 | 19.490 | 1.00 | 41.58 | C |
| ATOM | 289 | CZ | TYR | A | 37 | 41.189 | 4.677 | 18.626 | 1.00 | 43.27 | C |
| ATOM | 290 | OH | TYR | A | 37 | 41.261 | 5.989 | 19.050 | 1.00 | 44.70 | O |
| ATOM | 291 | CE2 | TYR | A | 37 | 40.746 | 4.390 | 17.333 | 1.00 | 43.92 | C |
| ATOM | 292 | CD2 | TYR | A | 37 | 40.671 | 3.070 | 16.914 | 1.00 | 43.64 | C |
| ATOM | 293 | C | TYR | A | 37 | 42.029 | −1.325 | 16.317 | 1.00 | 43.46 | C |
| ATOM | 294 | O | TYR | A | 37 | 41.591 | −1.566 | 15.187 | 1.00 | 44.17 | O |
| ATOM | 295 | N | ARG | A | 38 | 42.312 | −2.259 | 17.206 | 1.00 | 43.57 | N |
| ATOM | 296 | CA | ARG | A | 38 | 42.024 | −3.648 | 16.947 | 1.00 | 44.06 | C |
| ATOM | 297 | CB | ARG | A | 38 | 43.299 | −4.422 | 16.565 | 1.00 | 44.12 | C |
| ATOM | 298 | CG | ARG | A | 38 | 44.193 | −4.794 | 17.743 | 1.00 | 45.46 | C |
| ATOM | 299 | CD | ARG | A | 38 | 45.022 | −6.017 | 17.472 | 1.00 | 48.46 | C |
| ATOM | 300 | NE | ARG | A | 38 | 46.019 | −5.760 | 16.436 | 1.00 | 51.96 | N |
| ATOM | 301 | CZ | ARG | A | 38 | 46.772 | −6.693 | 15.850 | 1.00 | 53.24 | C |
| ATOM | 302 | NH1 | ARG | A | 38 | 47.654 | −6.345 | 14.908 | 1.00 | 52.53 | N |
| ATOM | 303 | NH2 | ARG | A | 38 | 46.645 | −7.970 | 16.203 | 1.00 | 54.34 | N |
| ATOM | 304 | C | ARG | A | 38 | 41.370 | −4.276 | 18.164 | 1.00 | 44.18 | C |
| ATOM | 305 | O | ARG | A | 38 | 41.730 | −3.980 | 19.313 | 1.00 | 43.93 | O |
| ATOM | 306 | N | THR | A | 39 | 40.383 | −5.122 | 17.903 | 1.00 | 44.59 | N |
| ATOM | 307 | CA | THR | A | 39 | 39.980 | −6.125 | 18.879 | 1.00 | 44.78 | C |
| ATOM | 308 | CB | THR | A | 39 | 38.506 | −5.944 | 19.441 | 1.00 | 44.80 | C |
| ATOM | 309 | OG1 | THR | A | 39 | 37.647 | −6.999 | 18.988 | 1.00 | 45.17 | O |
| ATOM | 310 | CG2 | THR | A | 39 | 37.902 | −4.568 | 19.101 | 1.00 | 44.19 | C |
| ATOM | 311 | C | THR | A | 39 | 40.241 | −7.490 | 18.222 | 1.00 | 44.86 | C |
| ATOM | 312 | O | THR | A | 39 | 39.614 | −7.850 | 17.217 | 1.00 | 44.92 | O |

APPENDIX I(d)-continued

| ATOM | 313 | N   | THR | A | 40 | 41.211 | −8.218  | 18.763 | 1.00 | 44.69 | N |
|------|-----|-----|-----|---|----|--------|---------|--------|------|-------|---|
| ATOM | 314 | CA  | THR | A | 40 | 41.535 | −9.535  | 18.250 | 1.00 | 44.78 | C |
| ATOM | 315 | CB  | THR | A | 40 | 42.888 | −10.006 | 18.768 | 1.00 | 44.70 | C |
| ATOM | 316 | OG1 | THR | A | 40 | 43.112 | −9.450  | 20.065 | 1.00 | 43.69 | O |
| ATOM | 317 | CG2 | THR | A | 40 | 43.997 | −9.535  | 17.823 | 1.00 | 44.71 | C |
| ATOM | 318 | C   | THR | A | 40 | 40.429 | −10.519 | 18.611 | 1.00 | 45.11 | C |
| ATOM | 319 | O   | THR | A | 40 | 39.598 | −10.220 | 19.467 | 1.00 | 45.36 | O |
| ATOM | 320 | N   | LEU | A | 41 | 40.398 | −11.666 | 17.930 | 1.00 | 45.34 | N |
| ATOM | 321 | CA  | LEU | A | 41 | 39.405 | −12.708 | 18.185 | 1.00 | 45.60 | C |
| ATOM | 322 | CB  | LEU | A | 41 | 39.650 | −13.923 | 17.284 | 1.00 | 45.75 | C |
| ATOM | 323 | CG  | LEU | A | 41 | 39.027 | −13.992 | 15.886 | 1.00 | 46.10 | C |
| ATOM | 324 | CD1 | LEU | A | 41 | 39.400 | −15.309 | 15.218 | 1.00 | 45.39 | C |
| ATOM | 325 | CD2 | LEU | A | 41 | 37.504 | −13.847 | 15.936 | 1.00 | 46.64 | C |
| ATOM | 326 | C   | LEU | A | 41 | 39.377 | −13.162 | 19.646 | 1.00 | 45.78 | C |
| ATOM | 327 | O   | LEU | A | 41 | 40.419 | −13.282 | 20.296 | 1.00 | 45.53 | O |
| ATOM | 328 | N   | GLY | A | 42 | 38.171 | −13.406 | 20.149 | 1.00 | 46.12 | N |
| ATOM | 329 | CA  | GLY | A | 42 | 37.968 | −13.838 | 21.526 | 1.00 | 46.62 | C |
| ATOM | 330 | C   | GLY | A | 42 | 38.330 | −12.787 | 22.561 | 1.00 | 46.95 | C |
| ATOM | 331 | O   | GLY | A | 42 | 38.450 | −13.096 | 23.744 | 1.00 | 47.22 | O |
| ATOM | 332 | N   | SER | A | 43 | 38.496 | −11.544 | 22.120 | 1.00 | 47.14 | N |
| ATOM | 333 | CA  | SER | A | 43 | 38.904 | −10.461 | 23.002 | 1.00 | 47.51 | C |
| ATOM | 334 | CB  | SER | A | 43 | 40.172 | −9.807  | 22.452 | 1.00 | 47.44 | C |
| ATOM | 335 | OG  | SER | A | 43 | 40.588 | −8.718  | 23.250 | 1.00 | 47.84 | O |
| ATOM | 336 | C   | SER | A | 43 | 37.782 | −9.438  | 23.139 | 1.00 | 47.74 | C |
| ATOM | 337 | O   | SER | A | 43 | 37.201 | −9.029  | 22.138 | 1.00 | 47.93 | O |
| ATOM | 338 | N   | THR | A | 44 | 37.491 | −9.024  | 24.374 | 1.00 | 48.06 | N |
| ATOM | 339 | CA  | THR | A | 44 | 36.372 | −8.104  | 24.675 | 1.00 | 48.47 | C |
| ATOM | 340 | CB  | THR | A | 44 | 36.037 | −8.081  | 26.193 | 1.00 | 48.56 | C |
| ATOM | 341 | OG1 | THR | A | 44 | 36.312 | −9.358  | 26.790 | 1.00 | 49.42 | O |
| ATOM | 342 | CG2 | THR | A | 44 | 34.566 | −7.694  | 26.424 | 1.00 | 48.79 | C |
| ATOM | 343 | C   | THR | A | 44 | 36.584 | −6.636  | 24.258 | 1.00 | 48.60 | C |
| ATOM | 344 | O   | THR | A | 44 | 35.606 | −5.879  | 24.132 | 1.00 | 48.74 | O |
| ATOM | 345 | N   | ASN | A | 45 | 37.841 | −6.227  | 24.064 | 1.00 | 48.29 | N |
| ATOM | 346 | CA  | ASN | A | 45 | 38.146 | −4.801  | 23.989 | 1.00 | 47.93 | C |
| ATOM | 347 | CB  | ASN | A | 45 | 38.709 | −4.286  | 25.321 | 1.00 | 48.18 | C |
| ATOM | 348 | CG  | ASN | A | 45 | 40.194 | −4.610  | 25.510 | 1.00 | 47.74 | C |
| ATOM | 349 | OD1 | ASN | A | 45 | 40.583 | −5.160  | 26.535 | 1.00 | 48.34 | O |
| ATOM | 350 | ND2 | ASN | A | 45 | 41.024 | −4.252  | 24.532 | 1.00 | 47.01 | N |
| ATOM | 351 | C   | ASN | A | 45 | 39.064 | −4.353  | 22.875 | 1.00 | 47.68 | C |
| ATOM | 352 | O   | ASN | A | 45 | 39.969 | −5.080  | 22.450 | 1.00 | 47.62 | O |
| ATOM | 353 | N   | GLU | A | 46 | 38.830 | −3.107  | 22.475 | 1.00 | 47.03 | N |
| ATOM | 354 | CA  | GLU | A | 46 | 39.563 | −2.405  | 21.446 | 1.00 | 46.44 | C |
| ATOM | 355 | CB  | GLU | A | 46 | 38.666 | −1.289  | 20.929 | 1.00 | 46.92 | C |
| ATOM | 356 | CG  | GLU | A | 46 | 38.808 | −0.975  | 19.478 | 1.00 | 49.14 | C |
| ATOM | 357 | CD  | GLU | A | 46 | 37.665 | −0.129  | 18.953 | 1.00 | 52.82 | C |
| ATOM | 358 | OE1 | GLU | A | 46 | 36.756 | 0.231   | 19.743 | 1.00 | 53.98 | O |
| ATOM | 359 | OE2 | GLU | A | 46 | 37.671 | 0.181   | 17.738 | 1.00 | 55.31 | O |
| ATOM | 360 | C   | GLU | A | 46 | 40.834 | −1.792  | 22.019 | 1.00 | 45.39 | C |
| ATOM | 361 | O   | GLU | A | 46 | 40.779 | −1.015  | 22.969 | 1.00 | 45.55 | O |
| ATOM | 362 | N   | GLN | A | 47 | 41.979 | −2.146  | 21.452 | 1.00 | 44.11 | N |
| ATOM | 363 | CA  | GLN | A | 47 | 43.235 | −1.524  | 21.856 | 1.00 | 43.28 | C |
| ATOM | 364 | CB  | GLN | A | 47 | 44.246 | −2.584  | 22.324 | 1.00 | 43.08 | C |
| ATOM | 365 | CG  | GLN | A | 47 | 44.622 | −3.594  | 21.239 | 1.00 | 44.55 | C |
| ATOM | 366 | CD  | GLN | A | 47 | 45.149 | −4.939  | 21.765 | 1.00 | 45.07 | C |
| ATOM | 367 | OE1 | GLN | A | 47 | 45.388 | −5.115  | 22.972 | 1.00 | 48.41 | O |
| ATOM | 368 | NE2 | GLN | A | 47 | 45.326 | −5.899  | 20.846 | 1.00 | 45.13 | N |
| ATOM | 369 | C   | GLN | A | 47 | 43.764 | −0.656  | 20.703 | 1.00 | 41.76 | C |
| ATOM | 370 | O   | GLN | A | 47 | 43.516 | −0.952  | 19.538 | 1.00 | 41.19 | O |
| ATOM | 371 | N   | LYS | A | 48 | 44.446 | 0.438   | 21.035 | 1.00 | 40.40 | N |
| ATOM | 372 | CA  | LYS | A | 48 | 45.041 | 1.298   | 20.027 | 1.00 | 39.25 | C |
| ATOM | 373 | CB  | LYS | A | 48 | 45.258 | 2.703   | 20.566 | 1.00 | 39.55 | C |
| ATOM | 374 | CG  | LYS | A | 48 | 46.022 | 3.635   | 19.626 | 1.00 | 41.07 | C |
| ATOM | 375 | CD  | LYS | A | 48 | 45.976 | 5.054   | 20.154 | 1.00 | 44.06 | C |
| ATOM | 376 | CE  | LYS | A | 48 | 47.037 | 5.918   | 19.518 | 1.00 | 45.73 | C |
| ATOM | 377 | NZ  | LYS | A | 48 | 46.515 | 6.731   | 18.397 | 1.00 | 47.48 | N |
| ATOM | 378 | C   | LYS | A | 48 | 46.359 | 0.714   | 19.568 | 1.00 | 38.35 | C |
| ATOM | 379 | O   | LYS | A | 48 | 47.164 | 0.259   | 20.380 | 1.00 | 37.69 | O |
| ATOM | 380 | N   | ILE | A | 49 | 46.556 | 0.722   | 18.251 | 1.00 | 37.55 | N |
| ATOM | 381 | CA  | ILE | A | 49 | 47.776 | 0.228   | 17.632 | 1.00 | 36.50 | C |
| ATOM | 382 | CB  | ILE | A | 49 | 47.546 | −0.204  | 16.169 | 1.00 | 36.80 | C |
| ATOM | 383 | CG1 | ILE | A | 49 | 46.439 | −1.272  | 16.078 | 1.00 | 35.88 | C |
| ATOM | 384 | CD1 | ILE | A | 49 | 46.064 | −1.701  | 14.656 | 1.00 | 35.50 | C |
| ATOM | 385 | CG2 | ILE | A | 49 | 48.895 | −0.667  | 15.549 | 1.00 | 36.79 | C |
| ATOM | 386 | C   | ILE | A | 49 | 48.865 | 1.298   | 17.664 | 1.00 | 36.12 | C |
| ATOM | 387 | O   | ILE | A | 49 | 48.694 | 2.395   | 17.125 | 1.00 | 36.62 | O |
| ATOM | 388 | N   | SER | A | 50 | 49.977 | 0.995   | 18.318 | 1.00 | 35.10 | N |
| ATOM | 389 | CA  | SER | A | 50 | 51.093 | 1.906   | 18.311 | 1.00 | 34.20 | C |
| ATOM | 390 | CB  | SER | A | 50 | 51.986 | 1.645   | 19.515 | 1.00 | 33.93 | C |
| ATOM | 391 | OG  | SER | A | 50 | 53.288 | 2.161   | 19.314 | 1.00 | 34.04 | O |
| ATOM | 392 | C   | SER | A | 50 | 51.835 | 1.757   | 16.972 | 1.00 | 33.93 | C |

APPENDIX I(d)-continued

| ATOM | 393 | O | SER | A | 50 | 52.425 | 0.706 | 16.694 | 1.00 | 34.24 | O |
|---|---|---|---|---|---|---|---|---|---|---|---|
| ATOM | 394 | N | ILE | A | 51 | 51.770 | 2.805 | 16.142 | 1.00 | 33.13 | N |
| ATOM | 395 | CA | ILE | A | 51 | 52.425 | 2.857 | 14.825 | 1.00 | 32.31 | C |
| ATOM | 396 | CB | ILE | A | 51 | 51.963 | 4.106 | 14.044 | 1.00 | 32.15 | C |
| ATOM | 397 | CG1 | ILE | A | 51 | 50.426 | 4.185 | 13.996 | 1.00 | 31.76 | C |
| ATOM | 398 | CD1 | ILE | A | 51 | 49.747 | 3.145 | 13.130 | 1.00 | 32.12 | C |
| ATOM | 399 | CG2 | ILE | A | 51 | 52.599 | 4.194 | 12.654 | 1.00 | 31.09 | C |
| ATOM | 400 | C | ILE | A | 51 | 53.954 | 2.829 | 14.912 | 1.00 | 32.65 | C |
| ATOM | 401 | O | ILE | A | 51 | 54.564 | 3.433 | 15.791 | 1.00 | 32.80 | O |
| ATOM | 402 | N | GLY | A | 52 | 54.567 | 2.124 | 13.976 | 1.00 | 33.09 | N |
| ATOM | 403 | CA | GLY | A | 52 | 56.002 | 1.887 | 13.991 | 1.00 | 33.42 | C |
| ATOM | 404 | C | GLY | A | 52 | 56.221 | 0.399 | 13.838 | 1.00 | 33.74 | C |
| ATOM | 405 | O | GLY | A | 52 | 55.305 | −0.393 | 14.056 | 1.00 | 33.66 | O |
| ATOM | 406 | N | GLY | A | 53 | 57.432 | 0.015 | 13.460 | 1.00 | 34.29 | N |
| ATOM | 407 | CA | GLY | A | 53 | 57.763 | −1.397 | 13.322 | 1.00 | 35.04 | C |
| ATOM | 408 | C | GLY | A | 53 | 56.957 | −1.991 | 12.195 | 1.00 | 35.46 | C |
| ATOM | 409 | O | GLY | A | 53 | 56.982 | −1.476 | 11.080 | 1.00 | 35.74 | O |
| ATOM | 410 | N | ARG | A | 54 | 56.213 | −3.050 | 12.490 | 1.00 | 35.90 | N |
| ATOM | 411 | CA | ARG | A | 54 | 55.433 | −3.725 | 11.461 | 1.00 | 36.34 | C |
| ATOM | 412 | CB | ARG | A | 54 | 55.022 | −5.121 | 11.923 | 1.00 | 36.49 | C |
| ATOM | 413 | CG | ARG | A | 54 | 54.076 | −5.157 | 13.113 | 1.00 | 37.52 | C |
| ATOM | 414 | CD | ARG | A | 54 | 53.998 | −6.557 | 13.716 | 1.00 | 40.03 | C |
| ATOM | 415 | NE | ARG | A | 54 | 53.427 | −7.539 | 12.792 | 1.00 | 41.16 | N |
| ATOM | 416 | CZ | ARG | A | 54 | 52.182 | −8.028 | 12.856 | 1.00 | 42.21 | C |
| ATOM | 417 | NH1 | ARG | A | 54 | 51.329 | −7.666 | 13.819 | 1.00 | 40.89 | N |
| ATOM | 418 | NH2 | ARG | A | 54 | 51.795 | −8.918 | 11.953 | 1.00 | 42.90 | N |
| ATOM | 419 | C | ARG | A | 54 | 54.217 | −2.927 | 10.989 | 1.00 | 36.53 | C |
| ATOM | 420 | O | ARG | A | 54 | 53.644 | −3.246 | 9.948 | 1.00 | 36.70 | O |
| ATOM | 421 | N | TYR | A | 55 | 53.822 | −1.902 | 11.747 | 1.00 | 36.80 | N |
| ATOM | 422 | CA | TYR | A | 55 | 52.639 | −1.088 | 11.404 | 1.00 | 37.20 | C |
| ATOM | 423 | CB | TYR | A | 55 | 51.798 | −0.746 | 12.635 | 1.00 | 37.76 | C |
| ATOM | 424 | CG | TYR | A | 55 | 51.512 | −1.949 | 13.486 | 1.00 | 38.65 | C |
| ATOM | 425 | CD1 | TYR | A | 55 | 50.408 | −2.756 | 13.232 | 1.00 | 39.27 | C |
| ATOM | 426 | CE1 | TYR | A | 55 | 50.159 | −3.879 | 14.009 | 1.00 | 40.17 | C |
| ATOM | 427 | CZ | TYR | A | 55 | 51.043 | −4.206 | 15.042 | 1.00 | 39.69 | C |
| ATOM | 428 | OH | TYR | A | 55 | 50.821 | −5.328 | 15.824 | 1.00 | 40.19 | O |
| ATOM | 429 | CE2 | TYR | A | 55 | 52.150 | −3.421 | 15.296 | 1.00 | 39.05 | C |
| ATOM | 430 | CD2 | TYR | A | 55 | 52.375 | −2.302 | 14.528 | 1.00 | 38.92 | C |
| ATOM | 431 | C | TYR | A | 55 | 53.092 | 0.188 | 10.765 | 1.00 | 36.81 | C |
| ATOM | 432 | O | TYR | A | 55 | 53.922 | 0.898 | 11.327 | 1.00 | 36.76 | O |
| ATOM | 433 | N | VAL | A | 56 | 52.554 | 0.483 | 9.586 | 1.00 | 36.40 | N |
| ATOM | 434 | CA | VAL | A | 56 | 52.999 | 1.679 | 8.866 | 1.00 | 35.90 | C |
| ATOM | 435 | CB | VAL | A | 56 | 54.262 | 1.420 | 7.938 | 1.00 | 35.20 | C |
| ATOM | 436 | CG1 | VAL | A | 56 | 54.243 | 0.050 | 7.360 | 1.00 | 35.04 | C |
| ATOM | 437 | CG2 | VAL | A | 56 | 54.393 | 2.462 | 6.867 | 1.00 | 34.11 | C |
| ATOM | 438 | C | VAL | A | 56 | 51.859 | 2.475 | 8.230 | 1.00 | 35.61 | C |
| ATOM | 439 | O | VAL | A | 56 | 51.327 | 2.092 | 7.216 | 1.00 | 36.11 | O |
| ATOM | 440 | N | GLU | A | 57 | 51.515 | 3.588 | 8.863 | 1.00 | 35.55 | N |
| ATOM | 441 | CA | GLU | A | 57 | 50.453 | 4.475 | 8.427 | 1.00 | 35.99 | C |
| ATOM | 442 | CB | GLU | A | 57 | 49.955 | 5.271 | 9.617 | 1.00 | 36.06 | C |
| ATOM | 443 | CG | GLU | A | 57 | 48.594 | 5.851 | 9.404 | 1.00 | 36.87 | C |
| ATOM | 444 | CD | GLU | A | 57 | 48.199 | 6.813 | 10.501 | 1.00 | 38.36 | C |
| ATOM | 445 | OE1 | GLU | A | 57 | 49.107 | 7.427 | 11.114 | 1.00 | 37.22 | O |
| ATOM | 446 | OE2 | GLU | A | 57 | 46.970 | 6.965 | 10.720 | 1.00 | 39.11 | O |
| ATOM | 447 | C | GLU | A | 57 | 50.892 | 5.463 | 7.363 | 1.00 | 36.29 | C |
| ATOM | 448 | O | GLU | A | 57 | 51.989 | 6.024 | 7.424 | 1.00 | 36.57 | O |
| ATOM | 449 | N | THR | A | 58 | 50.011 | 5.701 | 6.404 | 1.00 | 36.94 | N |
| ATOM | 450 | CA | THR | A | 58 | 50.256 | 6.677 | 5.354 | 1.00 | 38.04 | C |
| ATOM | 451 | CB | THR | A | 58 | 50.400 | 5.991 | 3.978 | 1.00 | 38.06 | C |
| ATOM | 452 | OG1 | THR | A | 58 | 51.539 | 5.115 | 4.017 | 1.00 | 38.61 | O |
| ATOM | 453 | CG2 | THR | A | 58 | 50.600 | 7.016 | 2.871 | 1.00 | 37.85 | C |
| ATOM | 454 | C | THR | A | 58 | 49.101 | 7.656 | 5.367 | 1.00 | 38.73 | C |
| ATOM | 455 | O | THR | A | 58 | 47.935 | 7.256 | 5.228 | 1.00 | 39.47 | O |
| ATOM | 456 | N | VAL | A | 59 | 49.412 | 8.936 | 5.581 | 1.00 | 39.11 | N |
| ATOM | 457 | CA | VAL | A | 59 | 48.358 | 9.934 | 5.774 | 1.00 | 38.99 | C |
| ATOM | 458 | CB | VAL | A | 59 | 48.384 | 10.521 | 7.203 | 1.00 | 39.19 | C |
| ATOM | 459 | CG1 | VAL | A | 59 | 47.438 | 11.723 | 7.355 | 1.00 | 38.40 | C |
| ATOM | 460 | CG2 | VAL | A | 59 | 48.013 | 9.435 | 8.204 | 1.00 | 39.01 | C |
| ATOM | 461 | C | VAL | A | 59 | 48.441 | 10.994 | 4.704 | 1.00 | 39.04 | C |
| ATOM | 462 | O | VAL | A | 59 | 49.527 | 11.445 | 4.368 | 1.00 | 39.20 | O |
| ATOM | 463 | N | ASN | A | 60 | 47.288 | 11.329 | 4.123 | 1.00 | 39.25 | N |
| ATOM | 464 | CA | ASN | A | 60 | 47.167 | 12.432 | 3.159 | 1.00 | 38.89 | C |
| ATOM | 465 | CB | ASN | A | 60 | 46.856 | 11.903 | 1.766 | 1.00 | 38.66 | C |
| ATOM | 466 | CG | ASN | A | 60 | 46.808 | 13.004 | 0.716 | 1.00 | 39.92 | C |
| ATOM | 467 | OD1 | ASN | A | 60 | 46.683 | 14.195 | 1.023 | 1.00 | 40.70 | O |
| ATOM | 468 | ND2 | ASN | A | 60 | 46.898 | 12.602 | −0.542 | 1.00 | 41.09 | N |
| ATOM | 469 | C | ASN | A | 60 | 46.088 | 13.417 | 3.620 | 1.00 | 38.71 | C |
| ATOM | 470 | O | ASN | A | 60 | 44.905 | 13.256 | 3.309 | 1.00 | 38.65 | O |
| ATOM | 471 | N | LYS | A | 61 | 46.514 | 14.431 | 4.370 | 1.00 | 38.57 | N |
| ATOM | 472 | CA | LYS | A | 61 | 45.602 | 15.383 | 4.996 | 1.00 | 38.16 | C |

APPENDIX I(d)-continued

| ATOM | 473 | CB | LYS | A | 61 | 46.355 | 16.271 | 5.980 | 1.00 | 37.56 | C |
|---|---|---|---|---|---|---|---|---|---|---|---|
| ATOM | 474 | CG | LYS | A | 61 | 46.886 | 15.543 | 7.172 | 1.00 | 35.28 | C |
| ATOM | 475 | CD | LYS | A | 61 | 47.561 | 16.502 | 8.098 | 1.00 | 32.88 | C |
| ATOM | 476 | CE | LYS | A | 61 | 47.572 | 15.971 | 9.495 | 1.00 | 31.84 | C |
| ATOM | 477 | NZ | LYS | A | 61 | 48.779 | 16.466 | 10.203 | 1.00 | 33.28 | N |
| ATOM | 478 | C | LYS | A | 61 | 44.841 | 16.234 | 3.966 | 1.00 | 38.90 | C |
| ATOM | 479 | O | LYS | A | 61 | 43.655 | 16.544 | 4.180 | 1.00 | 38.97 | O |
| ATOM | 480 | N | GLY | A | 62 | 45.521 | 16.606 | 2.869 | 1.00 | 39.06 | N |
| ATOM | 481 | CA | GLY | A | 62 | 44.897 | 17.316 | 1.742 | 1.00 | 39.10 | C |
| ATOM | 482 | C | GLY | A | 62 | 43.622 | 16.614 | 1.292 | 1.00 | 39.43 | C |
| ATOM | 483 | O | GLY | A | 62 | 42.535 | 17.195 | 1.319 | 1.00 | 39.28 | O |
| ATOM | 484 | N | SER | A | 63 | 43.735 | 15.345 | 0.914 | 1.00 | 39.54 | N |
| ATOM | 485 | CA | SER | A | 63 | 42.556 | 14.614 | 0.471 | 1.00 | 39.91 | C |
| ATOM | 486 | CB | SER | A | 63 | 42.924 | 13.630 | −0.640 | 1.00 | 40.15 | C |
| ATOM | 487 | OG | SER | A | 63 | 43.499 | 12.450 | −0.115 | 1.00 | 40.82 | O |
| ATOM | 488 | C | SER | A | 63 | 41.827 | 13.907 | 1.618 | 1.00 | 39.94 | C |
| ATOM | 489 | O | SER | A | 63 | 40.885 | 13.162 | 1.382 | 1.00 | 39.93 | O |
| ATOM | 490 | N | LYS | A | 64 | 42.260 | 14.157 | 2.853 | 1.00 | 39.99 | N |
| ATOM | 491 | CA | LYS | A | 64 | 41.631 | 13.589 | 4.054 | 1.00 | 40.06 | C |
| ATOM | 492 | CB | LYS | A | 64 | 40.267 | 14.231 | 4.317 | 1.00 | 39.53 | C |
| ATOM | 493 | CG | LYS | A | 64 | 40.306 | 15.555 | 5.036 | 1.00 | 38.57 | C |
| ATOM | 494 | CD | LYS | A | 64 | 39.285 | 16.496 | 4.420 | 1.00 | 38.14 | C |
| ATOM | 495 | CE | LYS | A | 64 | 38.478 | 17.277 | 5.453 | 1.00 | 37.99 | C |
| ATOM | 496 | NZ | LYS | A | 64 | 38.684 | 18.747 | 5.347 | 1.00 | 38.34 | N |
| ATOM | 497 | C | LYS | A | 64 | 41.506 | 12.060 | 4.015 | 1.00 | 40.63 | C |
| ATOM | 498 | O | LYS | A | 64 | 40.515 | 11.491 | 4.507 | 1.00 | 40.91 | O |
| ATOM | 499 | N | SER | A | 65 | 42.507 | 11.399 | 3.439 | 1.00 | 40.85 | N |
| ATOM | 500 | CA | SER | A | 65 | 42.524 | 9.940 | 3.393 | 1.00 | 41.61 | C |
| ATOM | 501 | CB | SER | A | 65 | 42.351 | 9.465 | 1.974 | 1.00 | 41.33 | C |
| ATOM | 502 | OG | SER | A | 65 | 43.517 | 9.807 | 1.261 | 1.00 | 42.19 | O |
| ATOM | 503 | C | SER | A | 65 | 43.839 | 9.391 | 3.938 | 1.00 | 42.06 | C |
| ATOM | 504 | O | SER | A | 65 | 44.880 | 10.055 | 3.886 | 1.00 | 42.51 | O |
| ATOM | 505 | N | PHE | A | 66 | 43.797 | 8.164 | 4.438 | 1.00 | 42.21 | N |
| ATOM | 506 | CA | PHE | A | 66 | 44.934 | 7.603 | 5.135 | 1.00 | 42.56 | C |
| ATOM | 507 | CB | PHE | A | 66 | 45.006 | 8.173 | 6.554 | 1.00 | 42.69 | C |
| ATOM | 508 | CG | PHE | A | 66 | 43.749 | 7.977 | 7.340 | 1.00 | 43.57 | C |
| ATOM | 509 | CD1 | PHE | A | 66 | 43.747 | 7.183 | 8.488 | 1.00 | 45.35 | C |
| ATOM | 510 | CE1 | PHE | A | 66 | 42.560 | 6.982 | 9.215 | 1.00 | 45.15 | C |
| ATOM | 511 | CZ | PHE | A | 66 | 41.365 | 7.585 | 8.792 | 1.00 | 44.06 | C |
| ATOM | 512 | CE2 | PHE | A | 66 | 41.364 | 8.380 | 7.656 | 1.00 | 43.63 | C |
| ATOM | 513 | CD2 | PHE | A | 66 | 42.554 | 8.569 | 6.935 | 1.00 | 44.35 | C |
| ATOM | 514 | C | PHE | A | 66 | 44.757 | 6.106 | 5.157 | 1.00 | 42.46 | C |
| ATOM | 515 | O | PHE | A | 66 | 43.636 | 5.617 | 5.036 | 1.00 | 42.37 | O |
| ATOM | 516 | N | SER | A | 67 | 45.859 | 5.381 | 5.301 | 1.00 | 42.29 | N |
| ATOM | 517 | CA | SER | A | 67 | 45.826 | 3.926 | 5.227 | 1.00 | 42.43 | C |
| ATOM | 518 | CB | SER | A | 67 | 46.278 | 3.454 | 3.846 | 1.00 | 42.23 | C |
| ATOM | 519 | OG | SER | A | 67 | 47.595 | 3.886 | 3.538 | 1.00 | 42.43 | O |
| ATOM | 520 | C | SER | A | 67 | 46.708 | 3.319 | 6.301 | 1.00 | 42.62 | C |
| ATOM | 521 | O | SER | A | 67 | 47.547 | 4.022 | 6.869 | 1.00 | 43.30 | O |
| ATOM | 522 | N | LEU | A | 68 | 46.503 | 2.032 | 6.599 | 1.00 | 42.30 | N |
| ATOM | 523 | CA | LEU | A | 68 | 47.421 | 1.276 | 7.460 | 1.00 | 41.69 | C |
| ATOM | 524 | CB | LEU | A | 68 | 46.731 | 0.905 | 8.771 | 1.00 | 42.08 | C |
| ATOM | 525 | CG | LEU | A | 68 | 47.490 | 0.038 | 9.789 | 1.00 | 41.64 | C |
| ATOM | 526 | CD1 | LEU | A | 68 | 48.609 | 0.829 | 10.433 | 1.00 | 40.86 | C |
| ATOM | 527 | CD2 | LEU | A | 68 | 46.532 | −0.537 | 10.837 | 1.00 | 40.59 | C |
| ATOM | 528 | C | LEU | A | 68 | 47.899 | 0.010 | 6.766 | 1.00 | 41.78 | C |
| ATOM | 529 | O | LEU | A | 68 | 47.109 | −0.693 | 6.130 | 1.00 | 41.90 | O |
| ATOM | 530 | N | ARG | A | 69 | 49.188 | −0.286 | 6.892 | 1.00 | 41.68 | N |
| ATOM | 531 | CA | ARG | A | 69 | 49.758 | −1.526 | 6.355 | 1.00 | 41.58 | C |
| ATOM | 532 | CB | ARG | A | 69 | 50.780 | −1.257 | 5.265 | 1.00 | 41.79 | C |
| ATOM | 533 | CG | ARG | A | 69 | 50.930 | −2.417 | 4.305 | 1.00 | 44.13 | C |
| ATOM | 534 | CD | ARG | A | 69 | 51.683 | −2.018 | 3.041 | 1.00 | 48.20 | C |
| ATOM | 535 | NE | ARG | A | 69 | 53.069 | −2.481 | 3.086 | 1.00 | 52.28 | N |
| ATOM | 536 | CZ | ARG | A | 69 | 54.101 | −1.792 | 3.584 | 1.00 | 54.41 | C |
| ATOM | 537 | NH1 | ARG | A | 69 | 55.322 | −2.331 | 3.571 | 1.00 | 55.41 | N |
| ATOM | 538 | NH2 | ARG | A | 69 | 53.933 | −0.569 | 4.083 | 1.00 | 54.08 | N |
| ATOM | 539 | C | ARG | A | 69 | 50.410 | −2.320 | 7.458 | 1.00 | 41.10 | C |
| ATOM | 540 | O | ARG | A | 69 | 51.175 | −1.776 | 8.258 | 1.00 | 41.13 | O |
| ATOM | 541 | N | ILE | A | 70 | 50.092 | −3.610 | 7.501 | 1.00 | 40.76 | N |
| ATOM | 542 | CA | ILE | A | 70 | 50.601 | −4.510 | 8.535 | 1.00 | 39.88 | C |
| ATOM | 543 | CB | ILE | A | 70 | 49.453 | −5.222 | 9.325 | 1.00 | 39.36 | C |
| ATOM | 544 | CG1 | ILE | A | 70 | 48.347 | −4.228 | 9.728 | 1.00 | 37.87 | C |
| ATOM | 545 | CD1 | ILE | A | 70 | 47.792 | −4.439 | 11.089 | 1.00 | 35.40 | C |
| ATOM | 546 | CG2 | ILE | A | 70 | 50.006 | −5.964 | 10.520 | 1.00 | 38.83 | C |
| ATOM | 547 | C | ILE | A | 70 | 51.449 | −5.521 | 7.808 | 1.00 | 40.36 | C |
| ATOM | 548 | O | ILE | A | 70 | 50.957 | −6.225 | 6.941 | 1.00 | 40.44 | O |
| ATOM | 549 | N | ARG | A | 71 | 52.733 | −5.552 | 8.130 | 1.00 | 41.10 | N |
| ATOM | 550 | CA | ARG | A | 71 | 53.666 | −6.476 | 7.528 | 1.00 | 41.96 | C |
| ATOM | 551 | CB | ARG | A | 71 | 55.068 | −5.884 | 7.626 | 1.00 | 42.48 | C |
| ATOM | 552 | CG | ARG | A | 71 | 56.093 | −6.426 | 6.622 | 1.00 | 46.49 | C |

APPENDIX I(d)-continued

| ATOM | 553 | CD | ARG | A | 71 | 56.065 | −5.651 | 5.276 | 1.00 | 52.49 | C |
|---|---|---|---|---|---|---|---|---|---|---|---|
| ATOM | 554 | NE | ARG | A | 71 | 57.001 | −6.185 | 4.271 | 1.00 | 55.71 | N |
| ATOM | 555 | CZ | ARG | A | 71 | 57.090 | −5.751 | 3.010 | 1.00 | 57.32 | C |
| ATOM | 556 | NH1 | ARG | A | 71 | 56.295 | −4.773 | 2.577 | 1.00 | 58.00 | N |
| ATOM | 557 | NH2 | ARG | A | 71 | 57.975 | −6.293 | 2.177 | 1.00 | 57.14 | N |
| ATOM | 558 | C | ARG | A | 71 | 53.606 | −7.790 | 8.309 | 1.00 | 42.06 | C |
| ATOM | 559 | O | ARG | A | 71 | 53.359 | −7.772 | 9.522 | 1.00 | 41.88 | O |
| ATOM | 560 | N | ASP | A | 72 | 53.816 | −8.917 | 7.615 | 1.00 | 42.18 | N |
| ATOM | 561 | CA | ASP | A | 72 | 53.979 | −10.243 | 8.237 | 1.00 | 42.19 | C |
| ATOM | 562 | CB | ASP | A | 72 | 55.119 | −10.225 | 9.257 | 1.00 | 42.61 | C |
| ATOM | 563 | CG | ASP | A | 72 | 56.476 | −10.361 | 8.625 | 1.00 | 44.47 | C |
| ATOM | 564 | OD1 | ASP | A | 72 | 57.153 | −11.381 | 8.916 | 1.00 | 45.25 | O |
| ATOM | 565 | OD2 | ASP | A | 72 | 56.867 | −9.447 | 7.850 | 1.00 | 46.70 | O |
| ATOM | 566 | C | ASP | A | 72 | 52.756 | −10.734 | 8.969 | 1.00 | 41.93 | C |
| ATOM | 567 | O | ASP | A | 72 | 52.819 | −10.966 | 10.178 | 1.00 | 41.95 | O |
| ATOM | 568 | N | LEU | A | 73 | 51.645 | −10.913 | 8.268 | 1.00 | 41.73 | N |
| ATOM | 569 | CA | LEU | A | 73 | 50.422 | −11.332 | 8.954 | 1.00 | 41.47 | C |
| ATOM | 570 | CB | LEU | A | 73 | 49.222 | −11.373 | 8.010 | 1.00 | 41.11 | C |
| ATOM | 571 | CG | LEU | A | 73 | 48.727 | −9.994 | 7.567 | 1.00 | 40.12 | C |
| ATOM | 572 | CD1 | LEU | A | 73 | 47.903 | −10.146 | 6.326 | 1.00 | 40.41 | C |
| ATOM | 573 | CD2 | LEU | A | 73 | 47.941 | −9.265 | 8.650 | 1.00 | 37.17 | C |
| ATOM | 574 | C | LEU | A | 73 | 50.648 | −12.664 | 9.644 | 1.00 | 41.62 | C |
| ATOM | 575 | O | LEU | A | 73 | 51.502 | −13.438 | 9.224 | 1.00 | 41.48 | O |
| ATOM | 576 | N | ARG | A | 74 | 49.904 | −12.903 | 10.720 | 1.00 | 42.02 | N |
| ATOM | 577 | CA | ARG | A | 74 | 50.122 | −14.067 | 11.589 | 1.00 | 42.54 | C |
| ATOM | 578 | CB | ARG | A | 74 | 51.235 | −13.788 | 12.614 | 1.00 | 42.53 | C |
| ATOM | 579 | CG | ARG | A | 74 | 51.179 | −12.388 | 13.256 | 1.00 | 43.61 | C |
| ATOM | 580 | CD | ARG | A | 74 | 52.125 | −12.257 | 14.459 | 1.00 | 43.83 | C |
| ATOM | 581 | NE | ARG | A | 74 | 53.394 | −11.580 | 14.167 | 1.00 | 46.03 | N |
| ATOM | 582 | CZ | ARG | A | 74 | 53.748 | −10.386 | 14.649 | 1.00 | 46.33 | C |
| ATOM | 583 | NH1 | ARG | A | 74 | 52.936 | −9.706 | 15.457 | 1.00 | 45.42 | N |
| ATOM | 584 | NH2 | ARG | A | 74 | 54.924 | −9.870 | 14.317 | 1.00 | 46.76 | N |
| ATOM | 585 | C | ARG | A | 74 | 48.833 | −14.489 | 12.290 | 1.00 | 42.15 | C |
| ATOM | 586 | O | ARG | A | 74 | 47.851 | −13.742 | 12.296 | 1.00 | 42.15 | O |
| ATOM | 587 | N | VAL | A | 75 | 48.839 | −15.691 | 12.863 | 1.00 | 41.96 | N |
| ATOM | 588 | CA | VAL | A | 75 | 47.655 | −16.259 | 13.526 | 1.00 | 41.57 | C |
| ATOM | 589 | CB | VAL | A | 75 | 48.010 | −17.568 | 14.298 | 1.00 | 41.47 | C |
| ATOM | 590 | CG1 | VAL | A | 75 | 46.806 | −18.116 | 15.058 | 1.00 | 41.34 | C |
| ATOM | 591 | CG2 | VAL | A | 75 | 48.559 | −18.619 | 13.334 | 1.00 | 41.54 | C |
| ATOM | 592 | C | VAL | A | 75 | 47.012 | −15.202 | 14.444 | 1.00 | 41.29 | C |
| ATOM | 593 | O | VAL | A | 75 | 45.917 | −14.683 | 14.150 | 1.00 | 41.52 | O |
| ATOM | 594 | N | GLU | A | 76 | 47.737 | −14.853 | 15.509 | 1.00 | 40.35 | N |
| ATOM | 595 | CA | GLU | A | 76 | 47.289 | −13.910 | 16.530 | 1.00 | 39.34 | C |
| ATOM | 596 | CB | GLU | A | 76 | 48.455 | −13.586 | 17.474 | 1.00 | 39.48 | C |
| ATOM | 597 | CG | GLU | A | 76 | 49.647 | −12.919 | 16.786 | 1.00 | 41.25 | C |
| ATOM | 598 | CD | GLU | A | 76 | 51.012 | −13.380 | 17.305 | 1.00 | 43.35 | C |
| ATOM | 599 | OE1 | GLU | A | 76 | 51.405 | −14.537 | 17.015 | 1.00 | 43.69 | O |
| ATOM | 600 | OE2 | GLU | A | 76 | 51.711 | −12.568 | 17.962 | 1.00 | 43.92 | O |
| ATOM | 601 | C | GLU | A | 76 | 46.646 | −12.637 | 15.963 | 1.00 | 38.30 | C |
| ATOM | 602 | O | GLU | A | 76 | 45.830 | −12.017 | 16.631 | 1.00 | 38.03 | O |
| ATOM | 603 | N | ASP | A | 77 | 46.995 | −12.285 | 14.725 | 1.00 | 37.35 | N |
| ATOM | 604 | CA | ASP | A | 77 | 46.562 | −11.037 | 14.072 | 1.00 | 36.49 | C |
| ATOM | 605 | CB | ASP | A | 77 | 47.430 | −10.761 | 12.852 | 1.00 | 36.49 | C |
| ATOM | 606 | CG | ASP | A | 77 | 48.581 | −9.848 | 13.147 | 1.00 | 37.31 | C |
| ATOM | 607 | OD1 | ASP | A | 77 | 48.488 | −9.031 | 14.082 | 1.00 | 39.17 | O |
| ATOM | 608 | OD2 | ASP | A | 77 | 49.587 | −9.934 | 12.419 | 1.00 | 37.91 | O |
| ATOM | 609 | C | ASP | A | 77 | 45.104 | −10.946 | 13.614 | 1.00 | 35.90 | C |
| ATOM | 610 | O | ASP | A | 77 | 44.686 | −9.903 | 13.119 | 1.00 | 35.62 | O |
| ATOM | 611 | N | SER | A | 78 | 44.338 | −12.026 | 13.750 | 1.00 | 35.37 | N |
| ATOM | 612 | CA | SER | A | 78 | 42.955 | −12.026 | 13.270 | 1.00 | 34.66 | C |
| ATOM | 613 | CB | SER | A | 78 | 42.436 | −13.451 | 13.134 | 1.00 | 34.45 | C |
| ATOM | 614 | OG | SER | A | 78 | 43.376 | −14.247 | 12.450 | 1.00 | 34.25 | O |
| ATOM | 615 | C | SER | A | 78 | 42.050 | −11.228 | 14.199 | 1.00 | 34.40 | C |
| ATOM | 616 | O | SER | A | 78 | 42.061 | −11.442 | 15.412 | 1.00 | 34.25 | O |
| ATOM | 617 | N | GLY | A | 79 | 41.277 | −10.307 | 13.625 | 1.00 | 34.06 | N |
| ATOM | 618 | CA | GLY | A | 79 | 40.327 | −9.506 | 14.395 | 1.00 | 33.98 | C |
| ATOM | 619 | C | GLY | A | 79 | 39.751 | −8.336 | 13.625 | 1.00 | 34.18 | C |
| ATOM | 620 | O | GLY | A | 79 | 39.807 | −8.317 | 12.390 | 1.00 | 34.12 | O |
| ATOM | 621 | N | THR | A | 80 | 39.207 | −7.355 | 14.354 | 1.00 | 34.22 | N |
| ATOM | 622 | CA | THR | A | 80 | 38.551 | −6.189 | 13.742 | 1.00 | 34.52 | C |
| ATOM | 623 | CB | THR | A | 80 | 37.118 | −5.930 | 14.301 | 1.00 | 34.52 | C |
| ATOM | 624 | OG1 | THR | A | 80 | 36.338 | −7.125 | 14.215 | 1.00 | 35.18 | O |
| ATOM | 625 | CG2 | THR | A | 80 | 36.405 | −4.848 | 13.507 | 1.00 | 34.49 | C |
| ATOM | 626 | C | THR | A | 80 | 39.387 | −4.922 | 13.888 | 1.00 | 34.82 | C |
| ATOM | 627 | O | THR | A | 80 | 39.666 | −4.458 | 15.003 | 1.00 | 35.04 | O |
| ATOM | 628 | N | TYR | A | 81 | 39.775 | −4.365 | 12.750 | 1.00 | 34.80 | N |
| ATOM | 629 | CA | TYR | A | 81 | 40.543 | −3.143 | 12.732 | 1.00 | 35.18 | C |
| ATOM | 630 | CB | TYR | A | 81 | 41.690 | −3.274 | 11.738 | 1.00 | 34.34 | C |
| ATOM | 631 | CG | TYR | A | 81 | 42.654 | −4.335 | 12.154 | 1.00 | 33.32 | C |
| ATOM | 632 | CD1 | TYR | A | 81 | 43.933 | −4.010 | 12.556 | 1.00 | 33.55 | C |

APPENDIX I(d)-continued

| ATOM | 633 | CE1 | TYR | A | 81 | 44.822 | −5.002 | 12.958 | 1.00 | 33.31 | C |
|---|---|---|---|---|---|---|---|---|---|---|---|
| ATOM | 634 | CZ | TYR | A | 81 | 44.424 | −6.321 | 12.966 | 1.00 | 32.64 | C |
| ATOM | 635 | OH | TYR | A | 81 | 45.292 | −7.296 | 13.373 | 1.00 | 31.77 | O |
| ATOM | 636 | CE2 | TYR | A | 81 | 43.147 | −6.660 | 12.586 | 1.00 | 32.62 | C |
| ATOM | 637 | CD2 | TYR | A | 81 | 42.275 | −5.670 | 12.182 | 1.00 | 32.26 | C |
| ATOM | 638 | C | TYR | A | 81 | 39.629 | −1.958 | 12.393 | 1.00 | 36.14 | C |
| ATOM | 639 | O | TYR | A | 81 | 38.818 | −2.057 | 11.461 | 1.00 | 36.07 | O |
| ATOM | 640 | N | LYS | A | 82 | 39.751 | −0.865 | 13.161 | 1.00 | 36.60 | N |
| ATOM | 641 | CA | LYS | A | 82 | 38.958 | 0.330 | 12.934 | 1.00 | 37.79 | C |
| ATOM | 642 | CB | LYS | A | 82 | 37.866 | 0.467 | 13.980 | 1.00 | 37.18 | C |
| ATOM | 643 | CG | LYS | A | 82 | 36.568 | −0.098 | 13.582 | 1.00 | 36.88 | C |
| ATOM | 644 | CD | LYS | A | 82 | 35.673 | −0.167 | 14.774 | 1.00 | 37.48 | C |
| ATOM | 645 | CE | LYS | A | 82 | 34.371 | −0.857 | 14.437 | 1.00 | 38.70 | C |
| ATOM | 646 | NZ | LYS | A | 82 | 33.540 | −1.153 | 15.653 | 1.00 | 40.07 | N |
| ATOM | 647 | C | LYS | A | 82 | 39.830 | 1.555 | 12.997 | 1.00 | 39.37 | C |
| ATOM | 648 | O | LYS | A | 82 | 40.507 | 1.786 | 14.000 | 1.00 | 40.01 | O |
| ATOM | 649 | N | CYS | A | 83 | 39.797 | 2.358 | 11.936 | 1.00 | 41.01 | N |
| ATOM | 650 | CA | CYS | A | 83 | 40.517 | 3.629 | 11.915 | 1.00 | 42.65 | C |
| ATOM | 651 | CB | CYS | A | 83 | 40.841 | 4.047 | 10.473 | 1.00 | 43.26 | C |
| ATOM | 652 | SG | CYS | A | 83 | 39.421 | 4.180 | 9.326 | 1.00 | 47.78 | S |
| ATOM | 653 | C | CYS | A | 83 | 39.696 | 4.707 | 12.617 | 1.00 | 42.57 | C |
| ATOM | 654 | O | CYS | A | 83 | 38.468 | 4.634 | 12.641 | 1.00 | 43.03 | O |
| ATOM | 655 | N | GLY | A | 84 | 40.365 | 5.701 | 13.197 | 1.00 | 42.24 | N |
| ATOM | 656 | CA | GLY | A | 84 | 39.667 | 6.825 | 13.803 | 1.00 | 41.51 | C |
| ATOM | 657 | C | GLY | A | 84 | 40.216 | 8.090 | 13.221 | 1.00 | 41.19 | C |
| ATOM | 658 | O | GLY | A | 84 | 41.428 | 8.307 | 13.271 | 1.00 | 41.93 | O |
| ATOM | 659 | N | ALA | A | 85 | 39.338 | 8.907 | 12.640 | 1.00 | 40.68 | N |
| ATOM | 660 | CA | ALA | A | 85 | 39.721 | 10.194 | 12.043 | 1.00 | 40.26 | C |
| ATOM | 661 | CB | ALA | A | 85 | 39.171 | 10.280 | 10.648 | 1.00 | 39.48 | C |
| ATOM | 662 | C | ALA | A | 85 | 39.229 | 11.380 | 12.890 | 1.00 | 40.43 | C |
| ATOM | 663 | O | ALA | A | 85 | 38.024 | 11.524 | 13.095 | 1.00 | 40.41 | O |
| ATOM | 664 | N | TYR | A | 86 | 40.144 | 12.217 | 13.389 | 1.00 | 40.96 | N |
| ATOM | 665 | CA | TYR | A | 86 | 39.770 | 13.398 | 14.230 | 1.00 | 41.74 | C |
| ATOM | 666 | CB | TYR | A | 86 | 40.395 | 13.287 | 15.633 | 1.00 | 42.59 | C |
| ATOM | 667 | CG | TYR | A | 86 | 39.840 | 12.049 | 16.256 | 1.00 | 44.45 | C |
| ATOM | 668 | CD1 | TYR | A | 86 | 40.464 | 10.820 | 16.075 | 1.00 | 46.20 | C |
| ATOM | 669 | CE1 | TYR | A | 86 | 39.898 | 9.655 | 16.575 | 1.00 | 47.13 | C |
| ATOM | 670 | CZ | TYR | A | 86 | 38.677 | 9.716 | 17.243 | 1.00 | 47.00 | C |
| ATOM | 671 | OH | TYR | A | 86 | 38.110 | 8.570 | 17.743 | 1.00 | 47.11 | O |
| ATOM | 672 | CE2 | TYR | A | 86 | 38.022 | 10.920 | 17.411 | 1.00 | 47.20 | C |
| ATOM | 673 | CD2 | TYR | A | 86 | 38.602 | 12.076 | 16.903 | 1.00 | 46.80 | C |
| ATOM | 674 | C | TYR | A | 86 | 40.025 | 14.730 | 13.541 | 1.00 | 41.34 | C |
| ATOM | 675 | O | TYR | A | 86 | 41.040 | 14.901 | 12.903 | 1.00 | 41.73 | O |
| ATOM | 676 | N | PHE | A | 87 | 39.080 | 15.650 | 13.608 | 1.00 | 41.28 | N |
| ATOM | 677 | CA | PHE | A | 87 | 39.166 | 16.845 | 12.782 | 1.00 | 41.56 | C |
| ATOM | 678 | CB | PHE | A | 87 | 38.374 | 16.639 | 11.477 | 1.00 | 41.06 | C |
| ATOM | 679 | CG | PHE | A | 87 | 36.932 | 16.274 | 11.676 | 1.00 | 39.53 | C |
| ATOM | 680 | CD1 | PHE | A | 87 | 35.947 | 17.257 | 11.679 | 1.00 | 39.73 | C |
| ATOM | 681 | CE1 | PHE | A | 87 | 34.586 | 16.931 | 11.869 | 1.00 | 39.72 | C |
| ATOM | 682 | CZ | PHE | A | 87 | 34.210 | 15.602 | 12.037 | 1.00 | 39.61 | C |
| ATOM | 683 | CE2 | PHE | A | 87 | 35.196 | 14.600 | 12.011 | 1.00 | 39.83 | C |
| ATOM | 684 | CD2 | PHE | A | 87 | 36.550 | 14.948 | 11.824 | 1.00 | 39.38 | C |
| ATOM | 685 | C | PHE | A | 87 | 38.748 | 18.133 | 13.494 | 1.00 | 42.67 | C |
| ATOM | 686 | O | PHE | A | 87 | 37.823 | 18.117 | 14.298 | 1.00 | 42.45 | O |
| ATOM | 687 | N | SER | A | 88 | 39.422 | 19.249 | 13.208 | 1.00 | 44.36 | N |
| ATOM | 688 | CA | SER | A | 88 | 38.983 | 20.548 | 13.756 | 1.00 | 46.58 | C |
| ATOM | 689 | CB | SER | A | 88 | 39.254 | 20.623 | 15.262 | 1.00 | 46.54 | C |
| ATOM | 690 | OG | SER | A | 88 | 38.249 | 21.402 | 15.909 | 1.00 | 47.58 | O |
| ATOM | 691 | C | SER | A | 88 | 39.537 | 21.793 | 13.046 | 1.00 | 47.83 | C |
| ATOM | 692 | O | SER | A | 88 | 40.136 | 21.682 | 11.982 | 1.00 | 48.24 | O |
| ATOM | 693 | N | ASP | A | 89 | 39.280 | 22.973 | 13.611 | 1.00 | 49.69 | N |
| ATOM | 694 | CA | ASP | A | 89 | 39.998 | 24.207 | 13.237 | 1.00 | 51.76 | C |
| ATOM | 695 | CB | ASP | A | 89 | 39.034 | 25.388 | 13.018 | 1.00 | 51.71 | C |
| ATOM | 696 | CG | ASP | A | 89 | 37.997 | 25.525 | 14.126 | 1.00 | 52.05 | C |
| ATOM | 697 | OD1 | ASP | A | 89 | 37.313 | 24.520 | 14.445 | 1.00 | 51.33 | O |
| ATOM | 698 | OD2 | ASP | A | 89 | 37.854 | 26.652 | 14.656 | 1.00 | 52.53 | O |
| ATOM | 699 | C | ASP | A | 89 | 41.078 | 24.545 | 14.284 | 1.00 | 53.06 | C |
| ATOM | 700 | O | ASP | A | 89 | 41.313 | 23.760 | 15.207 | 1.00 | 53.58 | O |
| ATOM | 701 | N | ALA | A | 90 | 41.754 | 25.683 | 14.147 | 1.00 | 54.40 | N |
| ATOM | 702 | CA | ALA | A | 90 | 42.727 | 26.075 | 15.167 | 1.00 | 55.85 | C |
| ATOM | 703 | CB | ALA | A | 90 | 43.719 | 27.092 | 14.620 | 1.00 | 55.91 | C |
| ATOM | 704 | C | ALA | A | 90 | 42.008 | 26.617 | 16.406 | 1.00 | 56.94 | C |
| ATOM | 705 | O | ALA | A | 90 | 42.408 | 26.311 | 17.536 | 1.00 | 57.01 | O |
| ATOM | 706 | N | MET | A | 91 | 40.941 | 27.391 | 16.163 | 1.00 | 58.11 | N |
| ATOM | 707 | CA | MET | A | 91 | 40.091 | 28.038 | 17.187 | 1.00 | 59.30 | C |
| ATOM | 708 | CB | MET | A | 91 | 38.880 | 28.721 | 16.498 | 1.00 | 59.40 | C |
| ATOM | 709 | CG | MET | A | 91 | 37.535 | 28.722 | 17.267 | 1.00 | 60.45 | C |
| ATOM | 710 | SD | MET | A | 91 | 37.156 | 30.177 | 18.308 | 1.00 | 63.23 | S |
| ATOM | 711 | CE | MET | A | 91 | 36.666 | 31.394 | 17.075 | 1.00 | 61.90 | C |
| ATOM | 712 | C | MET | A | 91 | 39.652 | 27.166 | 18.396 | 1.00 | 59.86 | C |

APPENDIX I(d)-continued

| ATOM | 713 | O | MET | A | 91 | 39.717 | 27.622 | 19.549 | 1.00 | 59.93 | O |
|---|---|---|---|---|---|---|---|---|---|---|---|
| ATOM | 714 | N | SER | A | 92 | 39.226 | 25.926 | 18.131 | 1.00 | 60.49 | N |
| ATOM | 715 | CA | SER | A | 92 | 38.665 | 25.034 | 19.166 | 1.00 | 60.99 | C |
| ATOM | 716 | CB | SER | A | 92 | 37.804 | 23.923 | 18.536 | 1.00 | 61.05 | C |
| ATOM | 717 | OG | SER | A | 92 | 37.490 | 24.177 | 17.178 | 1.00 | 61.70 | O |
| ATOM | 718 | C | SER | A | 92 | 39.749 | 24.388 | 20.036 | 1.00 | 61.12 | C |
| ATOM | 719 | O | SER | A | 92 | 40.158 | 23.246 | 19.782 | 1.00 | 61.30 | O |
| ATOM | 720 | N | ASN | A | 93 | 40.184 | 25.096 | 21.078 | 1.00 | 61.18 | N |
| ATOM | 721 | CA | ASN | A | 93 | 41.338 | 24.655 | 21.873 | 1.00 | 61.19 | C |
| ATOM | 722 | CB | ASN | A | 93 | 41.617 | 25.608 | 23.059 | 1.00 | 61.23 | C |
| ATOM | 723 | CG | ASN | A | 93 | 40.859 | 25.241 | 24.321 | 1.00 | 61.10 | C |
| ATOM | 724 | OD1 | ASN | A | 93 | 40.047 | 26.018 | 24.809 | 1.00 | 60.02 | O |
| ATOM | 725 | ND2 | ASN | A | 93 | 41.145 | 24.065 | 24.870 | 1.00 | 61.37 | N |
| ATOM | 726 | C | ASN | A | 93 | 41.293 | 23.171 | 22.270 | 1.00 | 61.09 | C |
| ATOM | 727 | O | ASN | A | 93 | 40.238 | 22.645 | 22.631 | 1.00 | 61.14 | O |
| ATOM | 728 | N | TYR | A | 94 | 42.447 | 22.513 | 22.186 | 1.00 | 61.01 | N |
| ATOM | 729 | CA | TYR | A | 94 | 42.527 | 21.044 | 22.190 | 1.00 | 60.82 | C |
| ATOM | 730 | CB | TYR | A | 94 | 43.727 | 20.577 | 21.348 | 1.00 | 61.25 | C |
| ATOM | 731 | CG | TYR | A | 94 | 43.596 | 20.802 | 19.846 | 1.00 | 62.15 | C |
| ATOM | 732 | CD1 | TYR | A | 94 | 43.511 | 19.718 | 18.956 | 1.00 | 62.46 | C |
| ATOM | 733 | CE1 | TYR | A | 94 | 43.406 | 19.923 | 17.572 | 1.00 | 62.67 | C |
| ATOM | 734 | CZ | TYR | A | 94 | 43.387 | 21.228 | 17.067 | 1.00 | 62.76 | C |
| ATOM | 735 | OH | TYR | A | 94 | 43.280 | 21.469 | 15.707 | 1.00 | 62.36 | O |
| ATOM | 736 | CE2 | TYR | A | 94 | 43.478 | 22.312 | 17.932 | 1.00 | 63.17 | C |
| ATOM | 737 | CD2 | TYR | A | 94 | 43.582 | 22.096 | 19.311 | 1.00 | 62.95 | C |
| ATOM | 738 | C | TYR | A | 94 | 42.581 | 20.366 | 23.567 | 1.00 | 60.23 | C |
| ATOM | 739 | O | TYR | A | 94 | 42.718 | 19.140 | 23.641 | 1.00 | 60.11 | O |
| ATOM | 740 | N | SER | A | 95 | 42.461 | 21.141 | 24.646 | 1.00 | 59.52 | N |
| ATOM | 741 | CA | SER | A | 95 | 42.581 | 20.582 | 26.002 | 1.00 | 58.81 | C |
| ATOM | 742 | CB | SER | A | 95 | 42.852 | 21.672 | 27.042 | 1.00 | 58.71 | C |
| ATOM | 743 | OG | SER | A | 95 | 41.818 | 22.630 | 27.053 | 1.00 | 58.55 | O |
| ATOM | 744 | C | SER | A | 95 | 41.415 | 19.669 | 26.431 | 1.00 | 58.41 | C |
| ATOM | 745 | O | SER | A | 95 | 41.552 | 18.918 | 27.404 | 1.00 | 58.61 | O |
| ATOM | 746 | N | TYR | A | 96 | 40.280 | 19.744 | 25.725 | 1.00 | 57.56 | N |
| ATOM | 747 | CA | TYR | A | 96 | 39.262 | 18.672 | 25.743 | 1.00 | 56.62 | C |
| ATOM | 748 | CB | TYR | A | 96 | 37.920 | 19.112 | 26.373 | 1.00 | 57.07 | C |
| ATOM | 749 | CG | TYR | A | 96 | 37.741 | 18.806 | 27.868 | 1.00 | 57.61 | C |
| ATOM | 750 | CD1 | TYR | A | 96 | 37.940 | 17.510 | 28.391 | 1.00 | 57.75 | C |
| ATOM | 751 | CE1 | TYR | A | 96 | 37.767 | 17.247 | 29.764 | 1.00 | 57.76 | C |
| ATOM | 752 | CZ | TYR | A | 96 | 37.377 | 18.287 | 30.616 | 1.00 | 58.09 | C |
| ATOM | 753 | OH | TYR | A | 96 | 37.191 | 18.084 | 31.966 | 1.00 | 57.64 | O |
| ATOM | 754 | CE2 | TYR | A | 96 | 37.167 | 19.565 | 30.118 | 1.00 | 58.28 | C |
| ATOM | 755 | CD2 | TYR | A | 96 | 37.343 | 19.813 | 28.753 | 1.00 | 58.03 | C |
| ATOM | 756 | C | TYR | A | 96 | 39.086 | 18.199 | 24.297 | 1.00 | 55.45 | C |
| ATOM | 757 | O | TYR | A | 96 | 39.520 | 18.902 | 23.381 | 1.00 | 55.68 | O |
| ATOM | 758 | N | PRO | A | 97 | 38.437 | 17.029 | 24.084 | 1.00 | 54.13 | N |
| ATOM | 759 | CA | PRO | A | 97 | 38.603 | 16.250 | 22.842 | 1.00 | 52.71 | C |
| ATOM | 760 | CB | PRO | A | 97 | 37.814 | 14.964 | 23.119 | 1.00 | 52.84 | C |
| ATOM | 761 | CG | PRO | A | 97 | 37.584 | 14.952 | 24.598 | 1.00 | 53.79 | C |
| ATOM | 762 | CD | PRO | A | 97 | 37.472 | 16.380 | 24.989 | 1.00 | 54.03 | C |
| ATOM | 763 | C | PRO | A | 97 | 38.060 | 16.910 | 21.592 | 1.00 | 51.10 | C |
| ATOM | 764 | O | PRO | A | 97 | 37.344 | 17.897 | 21.657 | 1.00 | 50.84 | O |
| ATOM | 765 | N | ILE | A | 98 | 38.401 | 16.347 | 20.448 | 1.00 | 49.60 | N |
| ATOM | 766 | CA | ILE | A | 98 | 37.932 | 16.909 | 19.185 | 1.00 | 47.94 | C |
| ATOM | 767 | CB | ILE | A | 98 | 39.116 | 17.382 | 18.274 | 1.00 | 48.04 | C |
| ATOM | 768 | CG1 | ILE | A | 98 | 40.146 | 16.264 | 18.054 | 1.00 | 47.50 | C |
| ATOM | 769 | CD1 | ILE | A | 98 | 41.275 | 16.645 | 17.088 | 1.00 | 47.86 | C |
| ATOM | 770 | CG2 | ILE | A | 98 | 39.769 | 18.647 | 18.881 | 1.00 | 48.04 | C |
| ATOM | 771 | C | ILE | A | 98 | 36.983 | 15.953 | 18.469 | 1.00 | 46.38 | C |
| ATOM | 772 | O | ILE | A | 98 | 37.126 | 14.733 | 18.617 | 1.00 | 46.53 | O |
| ATOM | 773 | N | PRO | A | 99 | 35.988 | 16.498 | 17.726 | 1.00 | 44.56 | N |
| ATOM | 774 | CA | PRO | A | 99 | 35.087 | 15.693 | 16.891 | 1.00 | 43.02 | C |
| ATOM | 775 | CB | PRO | A | 99 | 34.375 | 16.736 | 16.023 | 1.00 | 42.91 | C |
| ATOM | 776 | CG | PRO | A | 99 | 35.076 | 18.025 | 16.282 | 1.00 | 43.57 | C |
| ATOM | 777 | CD | PRO | A | 99 | 35.638 | 17.922 | 17.647 | 1.00 | 44.32 | C |
| ATOM | 778 | C | PRO | A | 99 | 35.819 | 14.672 | 16.015 | 1.00 | 41.63 | C |
| ATOM | 779 | O | PRO | A | 99 | 36.930 | 14.920 | 15.542 | 1.00 | 41.07 | O |
| ATOM | 780 | N | GLY | A | 100 | 35.210 | 13.515 | 15.819 | 1.00 | 40.25 | N |
| ATOM | 781 | CA | GLY | A | 100 | 35.838 | 12.516 | 14.992 | 1.00 | 38.90 | C |
| ATOM | 782 | C | GLY | A | 100 | 34.862 | 11.434 | 14.664 | 1.00 | 38.33 | C |
| ATOM | 783 | O | GLY | A | 100 | 33.789 | 11.369 | 15.265 | 1.00 | 38.01 | O |
| ATOM | 784 | N | GLU | A | 101 | 35.247 | 10.592 | 13.707 | 1.00 | 37.69 | N |
| ATOM | 785 | CA | GLU | A | 101 | 34.459 | 9.460 | 13.277 | 1.00 | 37.26 | C |
| ATOM | 786 | CB | GLU | A | 101 | 33.817 | 9.732 | 11.925 | 1.00 | 37.40 | C |
| ATOM | 787 | CG | GLU | A | 101 | 32.802 | 10.844 | 11.894 | 1.00 | 39.41 | C |
| ATOM | 788 | CD | GLU | A | 101 | 31.489 | 10.480 | 12.574 | 1.00 | 42.64 | C |
| ATOM | 789 | OE1 | GLU | A | 101 | 31.156 | 9.266 | 12.657 | 1.00 | 44.09 | O |
| ATOM | 790 | OE2 | GLU | A | 101 | 30.784 | 11.422 | 13.015 | 1.00 | 42.76 | O |
| ATOM | 791 | C | GLU | A | 101 | 35.362 | 8.271 | 13.110 | 1.00 | 37.21 | C |
| ATOM | 792 | O | GLU | A | 101 | 36.540 | 8.394 | 12.789 | 1.00 | 36.41 | O |

APPENDIX I(d)-continued

| ATOM | 793 | N | LYS | A | 102 | 34.783 | 7.098 | 13.306 | 1.00 | 38.04 | N |
|------|-----|-----|-----|---|-----|--------|--------|--------|------|-------|---|
| ATOM | 794 | CA | LYS | A | 102 | 35.478 | 5.831 | 13.085 | 1.00 | 38.38 | C |
| ATOM | 795 | CB | LYS | A | 102 | 35.316 | 4.910 | 14.300 | 1.00 | 38.22 | C |
| ATOM | 796 | CG | LYS | A | 102 | 35.999 | 5.442 | 15.541 | 1.00 | 39.05 | C |
| ATOM | 797 | CD | LYS | A | 102 | 35.674 | 4.610 | 16.753 | 1.00 | 41.78 | C |
| ATOM | 798 | CE | LYS | A | 102 | 36.545 | 3.369 | 16.826 | 1.00 | 43.99 | C |
| ATOM | 799 | NZ | LYS | A | 102 | 36.106 | 2.510 | 17.964 | 1.00 | 47.98 | N |
| ATOM | 800 | C | LYS | A | 102 | 34.936 | 5.168 | 11.823 | 1.00 | 38.37 | C |
| ATOM | 801 | O | LYS | A | 102 | 33.815 | 5.468 | 11.379 | 1.00 | 38.58 | O |
| ATOM | 802 | N | GLY | A | 103 | 35.741 | 4.289 | 11.232 | 1.00 | 38.20 | N |
| ATOM | 803 | CA | GLY | A | 103 | 35.315 | 3.531 | 10.069 | 1.00 | 37.94 | C |
| ATOM | 804 | C | GLY | A | 103 | 34.398 | 2.432 | 10.546 | 1.00 | 37.97 | C |
| ATOM | 805 | O | GLY | A | 103 | 34.407 | 2.098 | 11.738 | 1.00 | 37.93 | O |
| ATOM | 806 | N | ALA | A | 104 | 33.597 | 1.878 | 9.631 | 1.00 | 37.92 | N |
| ATOM | 807 | CA | ALA | A | 104 | 32.750 | 0.702 | 9.939 | 1.00 | 37.58 | C |
| ATOM | 808 | CB | ALA | A | 104 | 31.765 | 0.432 | 8.801 | 1.00 | 37.08 | C |
| ATOM | 809 | C | ALA | A | 104 | 33.551 | −0.583 | 10.315 | 1.00 | 37.23 | C |
| ATOM | 810 | O | ALA | A | 104 | 32.987 | −1.493 | 10.913 | 1.00 | 36.83 | O |
| ATOM | 811 | N | GLY | A | 105 | 34.848 | −0.639 | 9.980 | 1.00 | 36.70 | N |
| ATOM | 812 | CA | GLY | A | 105 | 35.717 | −1.739 | 10.405 | 1.00 | 36.63 | C |
| ATOM | 813 | C | GLY | A | 105 | 36.121 | −2.751 | 9.334 | 1.00 | 36.82 | C |
| ATOM | 814 | O | GLY | A | 105 | 35.447 | −2.898 | 8.310 | 1.00 | 36.82 | O |
| ATOM | 815 | N | THR | A | 106 | 37.228 | −3.452 | 9.586 | 1.00 | 36.84 | N |
| ATOM | 816 | CA | THR | A | 106 | 37.735 | −4.539 | 8.727 | 1.00 | 36.57 | C |
| ATOM | 817 | CB | THR | A | 106 | 39.140 | −4.208 | 8.153 | 1.00 | 36.36 | C |
| ATOM | 818 | OG1 | THR | A | 106 | 39.057 | −3.079 | 7.270 | 1.00 | 36.90 | O |
| ATOM | 819 | CG2 | THR | A | 106 | 39.716 | −5.390 | 7.393 | 1.00 | 36.01 | C |
| ATOM | 820 | C | THR | A | 106 | 37.848 | −5.826 | 9.540 | 1.00 | 36.39 | C |
| ATOM | 821 | O | THR | A | 106 | 38.609 | −5.895 | 10.499 | 1.00 | 36.67 | O |
| ATOM | 822 | N | VAL | A | 107 | 37.093 | −6.848 | 9.183 | 1.00 | 36.21 | N |
| ATOM | 823 | CA | VAL | A | 107 | 37.282 | −8.113 | 9.871 | 1.00 | 36.14 | C |
| ATOM | 824 | CB | VAL | A | 107 | 35.938 | −8.872 | 10.219 | 1.00 | 36.19 | C |
| ATOM | 825 | CG1 | VAL | A | 107 | 34.747 | −8.302 | 9.454 | 1.00 | 36.06 | C |
| ATOM | 826 | CG2 | VAL | A | 107 | 36.078 | −10.400 | 10.048 | 1.00 | 35.72 | C |
| ATOM | 827 | C | VAL | A | 107 | 38.315 | −8.942 | 9.111 | 1.00 | 36.04 | C |
| ATOM | 828 | O | VAL | A | 107 | 38.114 | −9.330 | 7.953 | 1.00 | 36.06 | O |
| ATOM | 829 | N | LEU | A | 108 | 39.439 | −9.173 | 9.780 | 1.00 | 35.79 | N |
| ATOM | 830 | CA | LEU | A | 108 | 40.553 | −9.902 | 9.202 | 1.00 | 35.32 | C |
| ATOM | 831 | CB | LEU | A | 108 | 41.836 | −9.135 | 9.469 | 1.00 | 35.00 | C |
| ATOM | 832 | CG | LEU | A | 108 | 43.135 | −9.811 | 9.049 | 1.00 | 35.77 | C |
| ATOM | 833 | CD1 | LEU | A | 108 | 43.114 | −10.166 | 7.569 | 1.00 | 34.89 | C |
| ATOM | 834 | CD2 | LEU | A | 108 | 44.303 | −8.880 | 9.385 | 1.00 | 36.41 | C |
| ATOM | 835 | C | LEU | A | 108 | 40.665 | −11.351 | 9.707 | 1.00 | 34.96 | C |
| ATOM | 836 | O | LEU | A | 108 | 40.651 | −11.607 | 10.914 | 1.00 | 34.93 | O |
| ATOM | 837 | N | THR | A | 109 | 40.763 | −12.291 | 8.771 | 1.00 | 34.40 | N |
| ATOM | 838 | CA | THR | A | 109 | 41.047 | −13.679 | 9.108 | 1.00 | 33.95 | C |
| ATOM | 839 | CB | THR | A | 109 | 40.034 | −14.648 | 8.489 | 1.00 | 33.87 | C |
| ATOM | 840 | OG1 | THR | A | 109 | 38.720 | −14.118 | 8.645 | 1.00 | 34.49 | O |
| ATOM | 841 | CG2 | THR | A | 109 | 40.092 | −15.997 | 9.177 | 1.00 | 34.16 | C |
| ATOM | 842 | C | THR | A | 109 | 42.411 | −13.992 | 8.553 | 1.00 | 33.64 | C |
| ATOM | 843 | O | THR | A | 109 | 42.731 | −13.599 | 7.432 | 1.00 | 33.51 | O |
| ATOM | 844 | N | VAL | A | 110 | 43.214 | −14.689 | 9.351 | 1.00 | 33.46 | N |
| ATOM | 845 | CA | VAL | A | 110 | 44.557 | −15.120 | 8.951 | 1.00 | 33.20 | C |
| ATOM | 846 | CB | VAL | A | 110 | 45.644 | −14.520 | 9.895 | 1.00 | 33.18 | C |
| ATOM | 847 | CG1 | VAL | A | 110 | 47.033 | −14.974 | 9.497 | 1.00 | 32.89 | C |
| ATOM | 848 | CG2 | VAL | A | 110 | 45.576 | −12.990 | 9.876 | 1.00 | 33.11 | C |
| ATOM | 849 | C | VAL | A | 110 | 44.628 | −16.662 | 8.879 | 1.00 | 33.14 | C |
| ATOM | 850 | O | VAL | A | 110 | 43.820 | −17.352 | 9.508 | 1.00 | 33.15 | O |
| ATOM | 851 | N | LYS | A | 111 | 45.569 | −17.176 | 8.076 | 1.00 | 32.96 | N |
| ATOM | 852 | CA | LYS | A | 111 | 45.863 | −18.614 | 7.908 | 1.00 | 32.47 | C |
| ATOM | 853 | CB | LYS | A | 111 | 46.047 | −19.310 | 9.266 | 1.00 | 32.42 | C |
| ATOM | 854 | CG | LYS | A | 111 | 47.301 | −20.173 | 9.401 | 1.00 | 32.16 | C |
| ATOM | 855 | CD | LYS | A | 111 | 47.322 | −21.337 | 8.439 | 1.00 | 30.51 | C |
| ATOM | 856 | CE | LYS | A | 111 | 48.666 | −21.373 | 7.765 | 1.00 | 29.84 | C |
| ATOM | 857 | NZ | LYS | A | 111 | 48.509 | −21.849 | 6.325 | 1.00 | 28.97 | N |
| ATOM | 858 | C | LYS | A | 111 | 44.803 | −19.337 | 7.075 | 1.00 | 32.50 | C |
| ATOM | 859 | O | LYS | A | 111 | 43.688 | −18.840 | 6.886 | 1.00 | 32.44 | O |
| ATOM | 860 | N | ALA | B | 1 | 61.374 | 15.952 | 26.666 | 1.00 | 40.58 | N |
| ATOM | 861 | CA | ALA | B | 1 | 61.194 | 15.867 | 25.190 | 1.00 | 40.32 | C |
| ATOM | 862 | CB | ALA | B | 1 | 59.746 | 15.561 | 24.857 | 1.00 | 40.27 | C |
| ATOM | 863 | C | ALA | B | 1 | 61.595 | 17.183 | 24.574 | 1.00 | 40.31 | C |
| ATOM | 864 | O | ALA | B | 1 | 61.451 | 18.221 | 25.207 | 1.00 | 40.46 | O |
| ATOM | 865 | N | TRP | B | 2 | 62.100 | 17.137 | 23.345 | 1.00 | 40.50 | N |
| ATOM | 866 | CA | TRP | B | 2 | 62.339 | 18.351 | 22.545 | 1.00 | 40.64 | C |
| ATOM | 867 | CB | TRP | B | 2 | 63.662 | 19.036 | 22.923 | 1.00 | 40.90 | C |
| ATOM | 868 | CG | TRP | B | 2 | 64.853 | 18.232 | 22.538 | 1.00 | 41.26 | C |
| ATOM | 869 | CD1 | TRP | B | 2 | 65.313 | 17.111 | 23.157 | 1.00 | 41.31 | C |
| ATOM | 870 | NE1 | TRP | B | 2 | 66.415 | 16.634 | 22.506 | 1.00 | 41.61 | N |
| ATOM | 871 | CE2 | TRP | B | 2 | 66.688 | 17.445 | 21.435 | 1.00 | 41.51 | C |
| ATOM | 872 | CD2 | TRP | B | 2 | 65.721 | 18.465 | 21.426 | 1.00 | 41.52 | C |

APPENDIX I(d)-continued

| ATOM | 873 | CE3 | TRP | B | 2 | 65.776 | 19.445 | 20.419 | 1.00 | 42.43 | C |
|---|---|---|---|---|---|---|---|---|---|---|---|
| ATOM | 874 | CZ3 | TRP | B | 2 | 66.798 | 19.376 | 19.467 | 1.00 | 41.87 | C |
| ATOM | 875 | CH2 | TRP | B | 2 | 67.753 | 18.344 | 19.507 | 1.00 | 42.06 | C |
| ATOM | 876 | CZ2 | TRP | B | 2 | 67.716 | 17.373 | 20.482 | 1.00 | 42.00 | C |
| ATOM | 877 | C | TRP | B | 2 | 62.302 | 18.017 | 21.058 | 1.00 | 40.47 | C |
| ATOM | 878 | O | TRP | B | 2 | 62.361 | 16.852 | 20.678 | 1.00 | 40.26 | O |
| ATOM | 879 | N | VAL | B | 3 | 62.187 | 19.050 | 20.231 | 1.00 | 40.69 | N |
| ATOM | 880 | CA | VAL | B | 3 | 62.056 | 18.889 | 18.794 | 1.00 | 40.91 | C |
| ATOM | 881 | CB | VAL | B | 3 | 60.770 | 19.529 | 18.257 | 1.00 | 40.88 | C |
| ATOM | 882 | CG1 | VAL | B | 3 | 60.727 | 19.412 | 16.755 | 1.00 | 40.86 | C |
| ATOM | 883 | CG2 | VAL | B | 3 | 59.540 | 18.863 | 18.860 | 1.00 | 40.88 | C |
| ATOM | 884 | C | VAL | B | 3 | 63.222 | 19.534 | 18.093 | 1.00 | 41.36 | C |
| ATOM | 885 | O | VAL | B | 3 | 63.461 | 20.727 | 18.240 | 1.00 | 41.24 | O |
| ATOM | 886 | N | ASP | B | 4 | 63.942 | 18.720 | 17.329 | 1.00 | 42.15 | N |
| ATOM | 887 | CA | ASP | B | 4 | 65.052 | 19.174 | 16.502 | 1.00 | 42.71 | C |
| ATOM | 888 | CB | ASP | B | 4 | 66.056 | 18.034 | 16.348 | 1.00 | 43.16 | C |
| ATOM | 889 | CG | ASP | B | 4 | 67.427 | 18.503 | 15.884 | 1.00 | 45.21 | C |
| ATOM | 890 | OD1 | ASP | B | 4 | 68.205 | 17.616 | 15.462 | 1.00 | 47.92 | O |
| ATOM | 891 | OD2 | ASP | B | 4 | 67.739 | 19.725 | 15.948 | 1.00 | 45.46 | O |
| ATOM | 892 | C | ASP | B | 4 | 64.510 | 19.559 | 15.141 | 1.00 | 42.38 | C |
| ATOM | 893 | O | ASP | B | 4 | 64.014 | 18.697 | 14.419 | 1.00 | 42.71 | O |
| ATOM | 894 | N | GLN | B | 5 | 64.585 | 20.842 | 14.795 | 1.00 | 42.02 | N |
| ATOM | 895 | CA | GLN | B | 5 | 64.012 | 21.321 | 13.537 | 1.00 | 42.00 | C |
| ATOM | 896 | CB | GLN | B | 5 | 62.884 | 22.316 | 13.775 | 1.00 | 41.95 | C |
| ATOM | 897 | CG | GLN | B | 5 | 62.484 | 23.088 | 12.544 | 1.00 | 42.24 | C |
| ATOM | 898 | CD | GLN | B | 5 | 61.343 | 24.061 | 12.775 | 1.00 | 42.53 | C |
| ATOM | 899 | OE1 | GLN | B | 5 | 61.122 | 24.946 | 11.957 | 1.00 | 44.45 | O |
| ATOM | 900 | NE2 | GLN | B | 5 | 60.601 | 23.896 | 13.871 | 1.00 | 42.54 | N |
| ATOM | 901 | C | GLN | B | 5 | 65.070 | 21.925 | 12.647 | 1.00 | 42.01 | C |
| ATOM | 902 | O | GLN | B | 5 | 65.737 | 22.873 | 13.020 | 1.00 | 41.81 | O |
| ATOM | 903 | N | THR | B | 6 | 65.165 | 21.383 | 11.442 | 1.00 | 42.28 | N |
| ATOM | 904 | CA | THR | B | 6 | 66.276 | 21.604 | 10.539 | 1.00 | 42.29 | C |
| ATOM | 905 | CB | THR | B | 6 | 67.123 | 20.300 | 10.533 | 1.00 | 42.26 | C |
| ATOM | 906 | OG1 | THR | B | 6 | 68.506 | 20.595 | 10.360 | 1.00 | 42.75 | O |
| ATOM | 907 | CG2 | THR | B | 6 | 66.646 | 19.280 | 9.494 | 1.00 | 43.12 | C |
| ATOM | 908 | C | THR | B | 6 | 65.656 | 21.970 | 9.174 | 1.00 | 42.28 | C |
| ATOM | 909 | O | THR | B | 6 | 64.656 | 21.372 | 8.774 | 1.00 | 43.46 | O |
| ATOM | 910 | N | PRO | B | 7 | 66.161 | 23.007 | 8.485 | 1.00 | 41.61 | N |
| ATOM | 911 | CA | PRO | B | 7 | 67.250 | 23.902 | 8.768 | 1.00 | 41.37 | C |
| ATOM | 912 | CB | PRO | B | 7 | 67.673 | 24.367 | 7.382 | 1.00 | 41.15 | C |
| ATOM | 913 | CG | PRO | B | 7 | 66.448 | 24.287 | 6.546 | 1.00 | 40.63 | C |
| ATOM | 914 | CD | PRO | B | 7 | 65.479 | 23.370 | 7.229 | 1.00 | 41.21 | C |
| ATOM | 915 | C | PRO | B | 7 | 66.795 | 25.105 | 9.578 | 1.00 | 41.83 | C |
| ATOM | 916 | O | PRO | B | 7 | 65.605 | 25.469 | 9.587 | 1.00 | 41.92 | O |
| ATOM | 917 | N | ARG | B | 8 | 67.767 | 25.729 | 10.227 | 1.00 | 42.11 | N |
| ATOM | 918 | CA | ARG | B | 8 | 67.546 | 26.866 | 11.084 | 1.00 | 42.31 | C |
| ATOM | 919 | CB | ARG | B | 8 | 68.804 | 27.107 | 11.904 | 1.00 | 42.89 | C |
| ATOM | 920 | CG | ARG | B | 8 | 68.536 | 27.677 | 13.253 | 1.00 | 46.29 | C |
| ATOM | 921 | CD | ARG | B | 8 | 69.820 | 27.906 | 14.054 | 1.00 | 52.71 | C |
| ATOM | 922 | NE | ARG | B | 8 | 70.453 | 26.647 | 14.446 | 1.00 | 57.86 | N |
| ATOM | 923 | CZ | ARG | B | 8 | 71.641 | 26.231 | 14.005 | 1.00 | 60.60 | C |
| ATOM | 924 | NH1 | ARG | B | 8 | 72.133 | 25.061 | 14.415 | 1.00 | 61.06 | N |
| ATOM | 925 | NH2 | ARG | B | 8 | 72.348 | 26.988 | 13.166 | 1.00 | 61.41 | N |
| ATOM | 926 | C | ARG | B | 8 | 67.214 | 28.067 | 10.209 | 1.00 | 41.73 | C |
| ATOM | 927 | O | ARG | B | 8 | 66.308 | 28.843 | 10.507 | 1.00 | 42.11 | O |
| ATOM | 928 | N | SER | B | 9 | 67.934 | 28.205 | 9.109 | 1.00 | 41.12 | N |
| ATOM | 929 | CA | SER | B | 9 | 67.642 | 29.256 | 8.158 | 1.00 | 41.01 | C |
| ATOM | 930 | CB | SER | B | 9 | 68.452 | 30.518 | 8.468 | 1.00 | 41.19 | C |
| ATOM | 931 | OG | SER | B | 9 | 69.842 | 30.315 | 8.271 | 1.00 | 40.95 | O |
| ATOM | 932 | C | SER | B | 9 | 67.933 | 28.761 | 6.752 | 1.00 | 40.85 | C |
| ATOM | 933 | O | SER | B | 9 | 68.813 | 27.924 | 6.553 | 1.00 | 41.20 | O |
| ATOM | 934 | N | VAL | B | 10 | 67.174 | 29.264 | 5.780 | 1.00 | 40.24 | N |
| ATOM | 935 | CA | VAL | B | 10 | 67.441 | 28.996 | 4.368 | 1.00 | 38.90 | C |
| ATOM | 936 | CB | VAL | B | 10 | 66.828 | 27.641 | 3.924 | 1.00 | 38.87 | C |
| ATOM | 937 | CG1 | VAL | B | 10 | 65.327 | 27.586 | 4.213 | 1.00 | 38.32 | C |
| ATOM | 938 | CG2 | VAL | B | 10 | 67.124 | 27.343 | 2.465 | 1.00 | 38.15 | C |
| ATOM | 939 | C | VAL | B | 10 | 66.940 | 30.164 | 3.519 | 1.00 | 38.48 | C |
| ATOM | 940 | O | VAL | B | 10 | 65.913 | 30.783 | 3.827 | 1.00 | 38.34 | O |
| ATOM | 941 | N | THR | B | 11 | 67.686 | 30.501 | 2.476 | 1.00 | 37.98 | N |
| ATOM | 942 | CA | THR | B | 11 | 67.104 | 31.341 | 1.447 | 1.00 | 37.86 | C |
| ATOM | 943 | CB | THR | B | 11 | 67.902 | 32.620 | 1.151 | 1.00 | 37.76 | C |
| ATOM | 944 | OG1 | THR | B | 11 | 68.567 | 32.460 | -0.094 | 1.00 | 39.82 | O |
| ATOM | 945 | CG2 | THR | B | 11 | 68.917 | 32.956 | 2.258 | 1.00 | 37.12 | C |
| ATOM | 946 | C | THR | B | 11 | 66.833 | 30.522 | 0.164 | 1.00 | 37.54 | C |
| ATOM | 947 | O | THR | B | 11 | 67.627 | 29.640 | -0.225 | 1.00 | 37.27 | O |
| ATOM | 948 | N | LYS | B | 12 | 65.683 | 30.803 | -0.457 | 1.00 | 36.76 | N |
| ATOM | 949 | CA | LYS | B | 12 | 65.231 | 30.116 | -1.671 | 1.00 | 35.59 | C |
| ATOM | 950 | CB | LYS | B | 12 | 64.089 | 29.143 | -1.356 | 1.00 | 35.82 | C |
| ATOM | 951 | CG | LYS | B | 12 | 64.455 | 27.976 | -0.437 | 1.00 | 36.08 | C |
| ATOM | 952 | CD | LYS | B | 12 | 65.410 | 27.000 | -1.110 | 1.00 | 35.78 | C |

APPENDIX I(d)-continued

| | | | | | | | | | | | |
|---|---|---|---|---|---|---|---|---|---|---|---|
| ATOM | 953 | CE | LYS | B | 12 | 65.351 | 25.656 | −0.461 | 1.00 | 35.08 | C |
| ATOM | 954 | NZ | LYS | B | 12 | 66.015 | 24.710 | −1.348 | 1.00 | 35.28 | N |
| ATOM | 955 | C | LYS | B | 12 | 64.736 | 31.152 | −2.664 | 1.00 | 34.87 | C |
| ATOM | 956 | O | LYS | B | 12 | 64.335 | 32.253 | −2.247 | 1.00 | 35.65 | O |
| ATOM | 957 | N | GLU | B | 13 | 64.771 | 30.801 | −3.956 | 1.00 | 33.28 | N |
| ATOM | 958 | CA | GLU | B | 13 | 64.308 | 31.653 | −5.056 | 1.00 | 31.58 | C |
| ATOM | 959 | CB | GLU | B | 13 | 65.119 | 31.370 | −6.306 | 1.00 | 31.34 | C |
| ATOM | 960 | CG | GLU | B | 13 | 66.376 | 32.163 | −6.380 | 1.00 | 31.28 | C |
| ATOM | 961 | CD | GLU | B | 13 | 67.229 | 31.761 | −7.540 | 1.00 | 32.53 | C |
| ATOM | 962 | OE1 | GLU | B | 13 | 68.028 | 30.799 | −7.409 | 1.00 | 32.67 | O |
| ATOM | 963 | OE2 | GLU | B | 13 | 67.106 | 32.426 | −8.586 | 1.00 | 32.70 | O |
| ATOM | 964 | C | GLU | B | 13 | 62.837 | 31.432 | −5.359 | 1.00 | 31.03 | C |
| ATOM | 965 | O | GLU | B | 13 | 62.301 | 30.362 | −5.087 | 1.00 | 31.03 | O |
| ATOM | 966 | N | THR | B | 14 | 62.184 | 32.442 | −5.923 | 1.00 | 30.46 | N |
| ATOM | 967 | CA | THR | B | 14 | 60.759 | 32.369 | −6.200 | 1.00 | 30.13 | C |
| ATOM | 968 | CB | THR | B | 14 | 60.240 | 33.634 | −6.893 | 1.00 | 29.79 | C |
| ATOM | 969 | OG1 | THR | B | 14 | 60.521 | 34.754 | −6.071 | 1.00 | 29.96 | O |
| ATOM | 970 | CG2 | THR | B | 14 | 58.743 | 33.592 | −7.055 | 1.00 | 29.82 | C |
| ATOM | 971 | C | THR | B | 14 | 60.559 | 31.177 | −7.101 | 1.00 | 30.18 | C |
| ATOM | 972 | O | THR | B | 14 | 61.333 | 30.971 | −8.031 | 1.00 | 30.27 | O |
| ATOM | 973 | N | GLY | B | 15 | 59.553 | 30.369 | −6.791 | 1.00 | 30.03 | N |
| ATOM | 974 | CA | GLY | B | 15 | 59.248 | 29.200 | −7.588 | 1.00 | 30.02 | C |
| ATOM | 975 | C | GLY | B | 15 | 59.658 | 27.906 | −6.923 | 1.00 | 30.20 | C |
| ATOM | 976 | O | GLY | B | 15 | 59.023 | 26.880 | −7.150 | 1.00 | 31.13 | O |
| ATOM | 977 | N | GLU | B | 16 | 60.707 | 27.941 | −6.105 | 1.00 | 30.13 | N |
| ATOM | 978 | CA | GLU | B | 16 | 61.317 | 26.720 | −5.575 | 1.00 | 30.09 | C |
| ATOM | 979 | CB | GLU | B | 16 | 62.734 | 26.998 | −5.097 | 1.00 | 29.57 | C |
| ATOM | 980 | CG | GLU | B | 16 | 63.685 | 27.421 | −6.154 | 1.00 | 28.93 | C |
| ATOM | 981 | CD | GLU | B | 16 | 65.140 | 27.353 | −5.687 | 1.00 | 30.00 | C |
| ATOM | 982 | OE1 | GLU | B | 16 | 65.563 | 28.203 | −4.863 | 1.00 | 28.19 | O |
| ATOM | 983 | OE2 | GLU | B | 16 | 65.877 | 26.449 | −6.162 | 1.00 | 30.14 | O |
| ATOM | 984 | C | GLU | B | 16 | 60.509 | 26.160 | −4.421 | 1.00 | 30.54 | C |
| ATOM | 985 | O | GLU | B | 16 | 59.576 | 26.799 | −3.965 | 1.00 | 30.94 | O |
| ATOM | 986 | N | SER | B | 17 | 60.885 | 24.966 | −3.961 | 1.00 | 31.53 | N |
| ATOM | 987 | CA | SER | B | 17 | 60.337 | 24.316 | −2.742 | 1.00 | 32.44 | C |
| ATOM | 988 | CB | SER | B | 17 | 60.147 | 22.809 | −2.963 | 1.00 | 32.39 | C |
| ATOM | 989 | OG | SER | B | 17 | 59.425 | 22.522 | −4.143 | 1.00 | 34.08 | O |
| ATOM | 990 | C | SER | B | 17 | 61.245 | 24.448 | −1.511 | 1.00 | 32.74 | C |
| ATOM | 991 | O | SER | B | 17 | 62.466 | 24.648 | −1.628 | 1.00 | 32.92 | O |
| ATOM | 992 | N | LEU | B | 18 | 60.647 | 24.275 | −0.334 | 1.00 | 33.17 | N |
| ATOM | 993 | CA | LEU | B | 18 | 61.402 | 24.112 | 0.902 | 1.00 | 33.49 | C |
| ATOM | 994 | CB | LEU | B | 18 | 61.090 | 25.264 | 1.839 | 1.00 | 33.92 | C |
| ATOM | 995 | CG | LEU | B | 18 | 62.099 | 25.810 | 2.846 | 1.00 | 35.15 | C |
| ATOM | 996 | CD1 | LEU | B | 18 | 61.288 | 26.335 | 4.010 | 1.00 | 36.95 | C |
| ATOM | 997 | CD2 | LEU | B | 18 | 63.143 | 24.818 | 3.319 | 1.00 | 36.58 | C |
| ATOM | 998 | C | LEU | B | 18 | 60.962 | 22.843 | 1.590 | 1.00 | 33.50 | C |
| ATOM | 999 | O | LEU | B | 18 | 59.751 | 22.616 | 1.741 | 1.00 | 33.48 | O |
| ATOM | 1000 | N | THR | B | 19 | 61.917 | 22.020 | 2.014 | 1.00 | 33.67 | N |
| ATOM | 1001 | CA | THR | B | 19 | 61.592 | 21.011 | 3.034 | 1.00 | 34.29 | C |
| ATOM | 1002 | CB | THR | B | 19 | 62.028 | 19.597 | 2.665 | 1.00 | 33.80 | C |
| ATOM | 1003 | OG1 | THR | B | 19 | 61.709 | 19.353 | 1.297 | 1.00 | 33.83 | O |
| ATOM | 1004 | CG2 | THR | B | 19 | 61.269 | 18.597 | 3.500 | 1.00 | 33.92 | C |
| ATOM | 1005 | C | THR | B | 19 | 62.128 | 21.359 | 4.415 | 1.00 | 34.84 | C |
| ATOM | 1006 | O | THR | B | 19 | 63.333 | 21.594 | 4.583 | 1.00 | 35.20 | O |
| ATOM | 1007 | N | ILE | B | 20 | 61.213 | 21.412 | 5.382 | 1.00 | 35.38 | N |
| ATOM | 1008 | CA | ILE | B | 20 | 61.551 | 21.554 | 6.789 | 1.00 | 36.25 | C |
| ATOM | 1009 | CB | ILE | B | 20 | 60.621 | 22.549 | 7.507 | 1.00 | 36.25 | C |
| ATOM | 1010 | CG1 | ILE | B | 20 | 60.585 | 23.884 | 6.750 | 1.00 | 35.44 | C |
| ATOM | 1011 | CD1 | ILE | B | 20 | 59.842 | 25.014 | 7.450 | 1.00 | 35.83 | C |
| ATOM | 1012 | CG2 | ILE | B | 20 | 61.041 | 22.685 | 9.009 | 1.00 | 36.74 | C |
| ATOM | 1013 | C | ILE | B | 20 | 61.369 | 20.187 | 7.443 | 1.00 | 37.37 | C |
| ATOM | 1014 | O | ILE | B | 20 | 60.321 | 19.573 | 7.293 | 1.00 | 37.80 | O |
| ATOM | 1015 | N | ASN | B | 21 | 62.393 | 19.721 | 8.160 | 1.00 | 38.67 | N |
| ATOM | 1016 | CA | ASN | B | 21 | 62.363 | 18.449 | 8.884 | 1.00 | 39.53 | C |
| ATOM | 1017 | CB | ASN | B | 21 | 63.610 | 17.644 | 8.584 | 1.00 | 39.82 | C |
| ATOM | 1018 | CG | ASN | B | 21 | 63.536 | 16.947 | 7.256 | 1.00 | 41.31 | C |
| ATOM | 1019 | OD1 | ASN | B | 21 | 64.121 | 17.392 | 6.280 | 1.00 | 43.13 | O |
| ATOM | 1020 | ND2 | ASN | B | 21 | 62.793 | 15.855 | 7.203 | 1.00 | 44.31 | N |
| ATOM | 1021 | C | ASN | B | 21 | 62.315 | 18.677 | 10.368 | 1.00 | 39.99 | C |
| ATOM | 1022 | O | ASN | B | 21 | 62.958 | 19.585 | 10.874 | 1.00 | 40.44 | O |
| ATOM | 1023 | N | CYS | B | 22 | 61.567 | 17.835 | 11.065 | 1.00 | 40.38 | N |
| ATOM | 1024 | CA | CYS | B | 22 | 61.545 | 17.849 | 12.507 | 1.00 | 40.90 | C |
| ATOM | 1025 | CB | CYS | B | 22 | 60.276 | 18.529 | 13.026 | 1.00 | 41.39 | C |
| ATOM | 1026 | SG | CYS | B | 22 | 60.092 | 20.330 | 12.606 | 1.00 | 45.04 | S |
| ATOM | 1027 | C | CYS | B | 22 | 61.625 | 16.422 | 13.020 | 1.00 | 40.81 | C |
| ATOM | 1028 | O | CYS | B | 22 | 61.075 | 15.493 | 12.427 | 1.00 | 40.89 | O |
| ATOM | 1029 | N | ALA | B | 23 | 62.341 | 16.246 | 14.122 | 1.00 | 40.97 | N |
| ATOM | 1030 | CA | ALA | B | 23 | 62.338 | 14.972 | 14.852 | 1.00 | 40.61 | C |
| ATOM | 1031 | CB | ALA | B | 23 | 63.660 | 14.228 | 14.663 | 1.00 | 40.21 | C |
| ATOM | 1032 | C | ALA | B | 23 | 62.056 | 15.228 | 16.333 | 1.00 | 40.31 | C |

APPENDIX I(d)-continued

| ATOM | 1033 | O | ALA | B | 23 | 62.728 | 16.051 | 16.970 | 1.00 | 40.42 | O |
|---|---|---|---|---|---|---|---|---|---|---|---|
| ATOM | 1034 | N | LEU | B | 24 | 61.034 | 14.558 | 16.859 | 1.00 | 39.95 | N |
| ATOM | 1035 | CA | LEU | B | 24 | 60.761 | 14.558 | 18.295 | 1.00 | 40.06 | C |
| ATOM | 1036 | CB | LEU | B | 24 | 59.343 | 14.053 | 18.581 | 1.00 | 39.89 | C |
| ATOM | 1037 | CG | LEU | B | 24 | 58.860 | 13.966 | 20.025 | 1.00 | 39.41 | C |
| ATOM | 1038 | CD1 | LEU | B | 24 | 57.522 | 13.239 | 20.086 | 1.00 | 39.03 | C |
| ATOM | 1039 | CD2 | LEU | B | 24 | 58.767 | 15.349 | 20.667 | 1.00 | 40.01 | C |
| ATOM | 1040 | C | LEU | B | 24 | 61.800 | 13.669 | 18.972 | 1.00 | 40.18 | C |
| ATOM | 1041 | O | LEU | B | 24 | 61.938 | 12.504 | 18.625 | 1.00 | 40.40 | O |
| ATOM | 1042 | N | LYS | B | 25 | 62.537 | 14.230 | 19.922 | 1.00 | 40.26 | N |
| ATOM | 1043 | CA | LYS | B | 25 | 63.727 | 13.593 | 20.444 | 1.00 | 40.45 | C |
| ATOM | 1044 | CB | LYS | B | 25 | 64.936 | 14.452 | 20.092 | 1.00 | 40.39 | C |
| ATOM | 1045 | CG | LYS | B | 25 | 66.143 | 13.668 | 19.606 | 1.00 | 41.77 | C |
| ATOM | 1046 | CD | LYS | B | 25 | 66.036 | 13.256 | 18.143 | 1.00 | 43.39 | C |
| ATOM | 1047 | CE | LYS | B | 25 | 66.106 | 14.451 | 17.218 | 1.00 | 45.53 | C |
| ATOM | 1048 | NZ | LYS | B | 25 | 67.340 | 15.285 | 17.411 | 1.00 | 46.91 | N |
| ATOM | 1049 | C | LYS | B | 25 | 63.586 | 13.471 | 21.947 | 1.00 | 40.69 | C |
| ATOM | 1050 | O | LYS | B | 25 | 63.041 | 14.373 | 22.579 | 1.00 | 41.02 | O |
| ATOM | 1051 | N | ASN | B | 26 | 64.070 | 12.364 | 22.512 | 1.00 | 40.94 | N |
| ATOM | 1052 | CA | ASN | B | 26 | 63.968 | 12.075 | 23.952 | 1.00 | 41.43 | C |
| ATOM | 1053 | CB | ASN | B | 26 | 64.633 | 13.169 | 24.793 | 1.00 | 41.74 | C |
| ATOM | 1054 | CG | ASN | B | 26 | 66.142 | 13.104 | 24.770 | 1.00 | 42.51 | C |
| ATOM | 1055 | OD1 | ASN | B | 26 | 66.748 | 12.119 | 25.209 | 1.00 | 43.67 | O |
| ATOM | 1056 | ND2 | ASN | B | 26 | 66.766 | 14.179 | 24.287 | 1.00 | 42.58 | N |
| ATOM | 1057 | C | ASN | B | 26 | 62.544 | 11.867 | 24.473 | 1.00 | 41.54 | C |
| ATOM | 1058 | O | ASN | B | 26 | 62.279 | 12.075 | 25.662 | 1.00 | 41.37 | O |
| ATOM | 1059 | N | ALA | B | 27 | 61.634 | 11.468 | 23.593 | 1.00 | 41.65 | N |
| ATOM | 1060 | CA | ALA | B | 27 | 60.277 | 11.196 | 24.010 | 1.00 | 42.12 | C |
| ATOM | 1061 | CB | ALA | B | 27 | 59.331 | 12.088 | 23.278 | 1.00 | 42.06 | C |
| ATOM | 1062 | C | ALA | B | 27 | 59.937 | 9.734 | 23.764 | 1.00 | 42.77 | C |
| ATOM | 1063 | O | ALA | B | 27 | 60.152 | 9.219 | 22.665 | 1.00 | 43.05 | O |
| ATOM | 1064 | N | ALA | B | 28 | 59.412 | 9.067 | 24.792 | 1.00 | 43.31 | N |
| ATOM | 1065 | CA | ALA | B | 28 | 59.003 | 7.658 | 24.693 | 1.00 | 43.96 | C |
| ATOM | 1066 | CB | ALA | B | 28 | 59.334 | 6.914 | 25.977 | 1.00 | 43.78 | C |
| ATOM | 1067 | C | ALA | B | 28 | 57.512 | 7.525 | 24.359 | 1.00 | 44.39 | C |
| ATOM | 1068 | O | ALA | B | 28 | 57.020 | 6.441 | 24.023 | 1.00 | 44.65 | O |
| ATOM | 1069 | N | ASP | B | 29 | 56.803 | 8.641 | 24.445 | 1.00 | 44.56 | N |
| ATOM | 1070 | CA | ASP | B | 29 | 55.377 | 8.684 | 24.176 | 1.00 | 44.63 | C |
| ATOM | 1071 | CB | ASP | B | 29 | 54.830 | 9.999 | 24.713 | 1.00 | 45.08 | C |
| ATOM | 1072 | CG | ASP | B | 29 | 55.468 | 10.387 | 26.038 | 1.00 | 47.13 | C |
| ATOM | 1073 | OD1 | ASP | B | 29 | 56.306 | 11.328 | 26.063 | 1.00 | 48.02 | O |
| ATOM | 1074 | OD2 | ASP | B | 29 | 55.154 | 9.712 | 27.051 | 1.00 | 50.45 | O |
| ATOM | 1075 | C | ASP | B | 29 | 55.147 | 8.581 | 22.676 | 1.00 | 44.03 | C |
| ATOM | 1076 | O | ASP | B | 29 | 56.040 | 8.913 | 21.893 | 1.00 | 43.92 | O |
| ATOM | 1077 | N | ASP | B | 30 | 53.968 | 8.112 | 22.277 | 1.00 | 43.17 | N |
| ATOM | 1078 | CA | ASP | B | 30 | 53.645 | 8.001 | 20.858 | 1.00 | 42.91 | C |
| ATOM | 1079 | CB | ASP | B | 30 | 52.414 | 7.092 | 20.649 | 1.00 | 43.11 | C |
| ATOM | 1080 | CG | ASP | B | 30 | 52.744 | 5.580 | 20.769 | 1.00 | 43.85 | C |
| ATOM | 1081 | OD1 | ASP | B | 30 | 53.889 | 5.165 | 20.448 | 1.00 | 44.60 | O |
| ATOM | 1082 | OD2 | ASP | B | 30 | 51.845 | 4.801 | 21.180 | 1.00 | 42.81 | O |
| ATOM | 1083 | C | ASP | B | 30 | 53.418 | 9.389 | 20.238 | 1.00 | 42.32 | C |
| ATOM | 1084 | O | ASP | B | 30 | 52.808 | 10.239 | 20.871 | 1.00 | 42.41 | O |
| ATOM | 1085 | N | LEU | B | 31 | 53.922 | 9.627 | 19.024 | 1.00 | 41.59 | N |
| ATOM | 1086 | CA | LEU | B | 31 | 53.573 | 10.839 | 18.262 | 1.00 | 41.02 | C |
| ATOM | 1087 | CB | LEU | B | 31 | 54.483 | 11.003 | 17.049 | 1.00 | 40.87 | C |
| ATOM | 1088 | CG | LEU | B | 31 | 54.888 | 12.417 | 16.609 | 1.00 | 41.41 | C |
| ATOM | 1089 | CD1 | LEU | B | 31 | 53.857 | 13.498 | 16.958 | 1.00 | 42.54 | C |
| ATOM | 1090 | CD2 | LEU | B | 31 | 55.243 | 12.466 | 15.126 | 1.00 | 40.70 | C |
| ATOM | 1091 | C | LEU | B | 31 | 52.112 | 10.778 | 17.776 | 1.00 | 40.93 | C |
| ATOM | 1092 | O | LEU | B | 31 | 51.776 | 9.952 | 16.921 | 1.00 | 40.54 | O |
| ATOM | 1093 | N | GLU | B | 32 | 51.260 | 11.658 | 18.309 | 1.00 | 40.64 | N |
| ATOM | 1094 | CA | GLU | B | 32 | 49.828 | 11.619 | 18.018 | 1.00 | 40.28 | C |
| ATOM | 1095 | CB | GLU | B | 32 | 48.993 | 11.809 | 19.287 | 1.00 | 40.23 | C |
| ATOM | 1096 | CG | GLU | B | 32 | 49.122 | 10.694 | 20.299 | 1.00 | 42.07 | C |
| ATOM | 1097 | CD | GLU | B | 32 | 48.607 | 9.314 | 19.806 | 1.00 | 46.47 | C |
| ATOM | 1098 | OE1 | GLU | B | 32 | 48.930 | 8.303 | 20.502 | 1.00 | 47.39 | O |
| ATOM | 1099 | OE2 | GLU | B | 32 | 47.886 | 9.226 | 18.756 | 1.00 | 45.59 | O |
| ATOM | 1100 | C | GLU | B | 32 | 49.390 | 12.594 | 16.927 | 1.00 | 39.99 | C |
| ATOM | 1101 | O | GLU | B | 32 | 48.651 | 12.215 | 16.027 | 1.00 | 39.79 | O |
| ATOM | 1102 | N | ARG | B | 33 | 49.824 | 13.846 | 17.000 | 1.00 | 40.07 | N |
| ATOM | 1103 | CA | ARG | B | 33 | 49.492 | 14.790 | 15.941 | 1.00 | 40.54 | C |
| ATOM | 1104 | CB | ARG | B | 33 | 48.153 | 15.483 | 16.185 | 1.00 | 40.81 | C |
| ATOM | 1105 | CG | ARG | B | 33 | 48.136 | 16.524 | 17.257 | 1.00 | 41.98 | C |
| ATOM | 1106 | CD | ARG | B | 33 | 46.826 | 17.280 | 17.238 | 1.00 | 45.56 | C |
| ATOM | 1107 | NE | ARG | B | 33 | 46.749 | 18.207 | 18.365 | 1.00 | 49.98 | N |
| ATOM | 1108 | CZ | ARG | B | 33 | 47.272 | 19.437 | 18.352 | 1.00 | 53.89 | C |
| ATOM | 1109 | NH1 | ARG | B | 33 | 47.168 | 20.217 | 19.434 | 1.00 | 54.30 | N |
| ATOM | 1110 | NH2 | ARG | B | 33 | 47.903 | 19.894 | 17.255 | 1.00 | 54.63 | N |
| ATOM | 1111 | C | ARG | B | 33 | 50.601 | 15.780 | 15.708 | 1.00 | 40.70 | C |
| ATOM | 1112 | O | ARG | B | 33 | 51.439 | 15.977 | 16.567 | 1.00 | 40.72 | O |

APPENDIX I(d)-continued

| ATOM | 1113 | N | THR | B | 34 | 50.607 | 16.390 | 14.531 | 1.00 | 41.39 | N |
| ATOM | 1114 | CA | THR | B | 34 | 51.682 | 17.299 | 14.136 | 1.00 | 42.45 | C |
| ATOM | 1115 | CB | THR | B | 34 | 52.565 | 16.654 | 13.051 | 1.00 | 42.54 | C |
| ATOM | 1116 | OG1 | THR | B | 34 | 51.735 | 16.068 | 12.036 | 1.00 | 43.44 | O |
| ATOM | 1117 | CG2 | THR | B | 34 | 53.409 | 15.560 | 13.650 | 1.00 | 42.44 | C |
| ATOM | 1118 | C | THR | B | 34 | 51.123 | 18.643 | 13.657 | 1.00 | 42.88 | C |
| ATOM | 1119 | O | THR | B | 34 | 50.017 | 18.702 | 13.129 | 1.00 | 43.42 | O |
| ATOM | 1120 | N | ASP | B | 35 | 51.884 | 19.715 | 13.848 | 1.00 | 43.44 | N |
| ATOM | 1121 | CA | ASP | B | 35 | 51.423 | 21.088 | 13.586 | 1.00 | 43.97 | C |
| ATOM | 1122 | CB | ASP | B | 35 | 51.229 | 21.841 | 14.892 | 1.00 | 44.87 | C |
| ATOM | 1123 | CG | ASP | B | 35 | 49.801 | 21.859 | 15.358 | 1.00 | 49.02 | C |
| ATOM | 1124 | OD1 | ASP | B | 35 | 48.923 | 21.176 | 14.748 | 1.00 | 51.38 | O |
| ATOM | 1125 | OD2 | ASP | B | 35 | 49.570 | 22.578 | 16.366 | 1.00 | 52.82 | O |
| ATOM | 1126 | C | ASP | B | 35 | 52.478 | 21.866 | 12.859 | 1.00 | 43.37 | C |
| ATOM | 1127 | O | ASP | B | 35 | 53.678 | 21.613 | 13.029 | 1.00 | 43.51 | O |
| ATOM | 1128 | N | TRP | B | 36 | 52.027 | 22.850 | 12.088 | 1.00 | 42.37 | N |
| ATOM | 1129 | CA | TRP | B | 36 | 52.906 | 23.794 | 11.423 | 1.00 | 41.24 | C |
| ATOM | 1130 | CB | TRP | B | 36 | 53.162 | 23.366 | 9.974 | 1.00 | 40.25 | C |
| ATOM | 1131 | CG | TRP | B | 36 | 53.820 | 22.010 | 9.910 | 1.00 | 39.18 | C |
| ATOM | 1132 | CD1 | TRP | B | 36 | 53.189 | 20.808 | 9.912 | 1.00 | 39.03 | C |
| ATOM | 1133 | NE1 | TRP | B | 36 | 54.105 | 19.784 | 9.875 | 1.00 | 39.65 | N |
| ATOM | 1134 | CE2 | TRP | B | 36 | 55.365 | 20.311 | 9.861 | 1.00 | 37.81 | C |
| ATOM | 1135 | CD2 | TRP | B | 36 | 55.231 | 21.719 | 9.889 | 1.00 | 37.66 | C |
| ATOM | 1136 | CE3 | TRP | B | 36 | 56.383 | 22.508 | 9.886 | 1.00 | 36.22 | C |
| ATOM | 1137 | CZ3 | TRP | B | 36 | 57.604 | 21.887 | 9.856 | 1.00 | 38.69 | C |
| ATOM | 1138 | CH2 | TRP | B | 36 | 57.707 | 20.471 | 9.833 | 1.00 | 39.76 | C |
| ATOM | 1139 | CZ2 | TRP | B | 36 | 56.593 | 19.674 | 9.839 | 1.00 | 38.23 | C |
| ATOM | 1140 | C | TRP | B | 36 | 52.325 | 25.204 | 11.545 | 1.00 | 41.48 | C |
| ATOM | 1141 | O | TRP | B | 36 | 51.133 | 25.424 | 11.358 | 1.00 | 41.17 | O |
| ATOM | 1142 | N | TYR | B | 37 | 53.187 | 26.148 | 11.899 | 1.00 | 42.11 | N |
| ATOM | 1143 | CA | TYR | B | 37 | 52.801 | 27.525 | 12.143 | 1.00 | 42.12 | C |
| ATOM | 1144 | CB | TYR | B | 37 | 52.809 | 27.793 | 13.641 | 1.00 | 43.09 | C |
| ATOM | 1145 | CG | TYR | B | 37 | 51.595 | 27.209 | 14.331 | 1.00 | 44.97 | C |
| ATOM | 1146 | CD1 | TYR | B | 37 | 51.643 | 25.957 | 14.942 | 1.00 | 46.07 | C |
| ATOM | 1147 | CE1 | TYR | B | 37 | 50.518 | 25.408 | 15.566 | 1.00 | 45.11 | C |
| ATOM | 1148 | CZ | TYR | B | 37 | 49.328 | 26.125 | 15.579 | 1.00 | 45.99 | C |
| ATOM | 1149 | OH | TYR | B | 37 | 48.193 | 25.612 | 16.193 | 1.00 | 47.09 | O |
| ATOM | 1150 | CE2 | TYR | B | 37 | 49.256 | 27.373 | 14.979 | 1.00 | 46.28 | C |
| ATOM | 1151 | CD2 | TYR | B | 37 | 50.383 | 27.902 | 14.351 | 1.00 | 46.48 | C |
| ATOM | 1152 | C | TYR | B | 37 | 53.774 | 28.430 | 11.435 | 1.00 | 41.70 | C |
| ATOM | 1153 | O | TYR | B | 37 | 54.956 | 28.087 | 11.285 | 1.00 | 41.41 | O |
| ATOM | 1154 | N | ARG | B | 38 | 53.280 | 29.572 | 10.972 | 1.00 | 41.33 | N |
| ATOM | 1155 | CA | ARG | B | 38 | 54.138 | 30.506 | 10.257 | 1.00 | 41.41 | C |
| ATOM | 1156 | CB | ARG | B | 38 | 54.109 | 30.221 | 8.748 | 1.00 | 41.64 | C |
| ATOM | 1157 | CG | ARG | B | 38 | 52.855 | 30.715 | 8.033 | 1.00 | 43.80 | C |
| ATOM | 1158 | CD | ARG | B | 38 | 52.500 | 29.877 | 6.808 | 1.00 | 48.30 | C |
| ATOM | 1159 | NE | ARG | B | 38 | 53.297 | 30.168 | 5.608 | 1.00 | 51.15 | N |
| ATOM | 1160 | CZ | ARG | B | 38 | 52.875 | 30.864 | 4.545 | 1.00 | 51.98 | C |
| ATOM | 1161 | NH1 | ARG | B | 38 | 51.638 | 31.388 | 4.478 | 1.00 | 48.85 | N |
| ATOM | 1162 | NH2 | ARG | B | 38 | 53.722 | 31.042 | 3.537 | 1.00 | 52.22 | N |
| ATOM | 1163 | C | ARG | B | 38 | 53.808 | 31.967 | 10.558 | 1.00 | 40.80 | C |
| ATOM | 1164 | O | ARG | B | 38 | 52.644 | 32.328 | 10.714 | 1.00 | 40.56 | O |
| ATOM | 1165 | N | THR | B | 39 | 54.855 | 32.784 | 10.665 | 1.00 | 40.49 | N |
| ATOM | 1166 | CA | THR | B | 39 | 54.737 | 34.245 | 10.769 | 1.00 | 40.14 | C |
| ATOM | 1167 | CB | THR | B | 39 | 55.282 | 34.757 | 12.108 | 1.00 | 39.95 | C |
| ATOM | 1168 | OG1 | THR | B | 39 | 54.467 | 34.241 | 13.161 | 1.00 | 40.90 | O |
| ATOM | 1169 | CG2 | THR | B | 39 | 55.296 | 36.288 | 12.165 | 1.00 | 38.83 | C |
| ATOM | 1170 | C | THR | B | 39 | 55.517 | 34.853 | 9.604 | 1.00 | 40.12 | C |
| ATOM | 1171 | O | THR | B | 39 | 56.759 | 34.847 | 9.588 | 1.00 | 39.84 | O |
| ATOM | 1172 | N | THR | B | 40 | 54.787 | 35.362 | 8.619 | 1.00 | 39.67 | N |
| ATOM | 1173 | CA | THR | B | 40 | 55.403 | 35.647 | 7.341 | 1.00 | 39.66 | C |
| ATOM | 1174 | CB | THR | B | 40 | 54.873 | 34.699 | 6.241 | 1.00 | 39.69 | C |
| ATOM | 1175 | OG1 | THR | B | 40 | 53.465 | 34.856 | 6.095 | 1.00 | 40.00 | O |
| ATOM | 1176 | CG2 | THR | B | 40 | 55.165 | 33.264 | 6.577 | 1.00 | 40.25 | C |
| ATOM | 1177 | C | THR | B | 40 | 55.161 | 37.070 | 6.941 | 1.00 | 39.57 | C |
| ATOM | 1178 | O | THR | B | 40 | 54.336 | 37.741 | 7.553 | 1.00 | 39.87 | O |
| ATOM | 1179 | N | LEU | B | 41 | 55.876 | 37.529 | 5.918 | 1.00 | 39.69 | N |
| ATOM | 1180 | CA | LEU | B | 41 | 55.682 | 38.881 | 5.389 | 1.00 | 40.14 | C |
| ATOM | 1181 | CB | LEU | B | 41 | 56.620 | 39.170 | 4.218 | 1.00 | 39.45 | C |
| ATOM | 1182 | CG | LEU | B | 41 | 58.064 | 39.377 | 4.651 | 1.00 | 38.18 | C |
| ATOM | 1183 | CD1 | LEU | B | 41 | 58.992 | 39.498 | 3.463 | 1.00 | 36.16 | C |
| ATOM | 1184 | CD2 | LEU | B | 41 | 58.149 | 40.591 | 5.544 | 1.00 | 35.87 | C |
| ATOM | 1185 | C | LEU | B | 41 | 54.248 | 39.101 | 4.977 | 1.00 | 41.07 | C |
| ATOM | 1186 | O | LEU | B | 41 | 53.558 | 38.183 | 4.564 | 1.00 | 40.61 | O |
| ATOM | 1187 | N | GLY | B | 42 | 53.803 | 40.334 | 5.132 | 1.00 | 43.06 | N |
| ATOM | 1188 | CA | GLY | B | 42 | 52.443 | 40.730 | 4.778 | 1.00 | 45.64 | C |
| ATOM | 1189 | C | GLY | B | 42 | 51.375 | 40.327 | 5.791 | 1.00 | 47.14 | C |
| ATOM | 1190 | O | GLY | B | 42 | 50.738 | 41.196 | 6.426 | 1.00 | 47.26 | O |
| ATOM | 1191 | N | SER | B | 43 | 51.163 | 39.008 | 5.915 | 1.00 | 48.13 | N |
| ATOM | 1192 | CA | SER | B | 43 | 50.160 | 38.442 | 6.811 | 1.00 | 48.78 | C |

APPENDIX I(d)-continued

| ATOM | 1193 | CB | SER | B | 43 | 50.174 | 36.927 | 6.713 | 1.00 | 48.76 | C |
|---|---|---|---|---|---|---|---|---|---|---|---|
| ATOM | 1194 | OG | SER | B | 43 | 49.508 | 36.361 | 7.829 | 1.00 | 50.24 | O |
| ATOM | 1195 | C | SER | B | 43 | 50.424 | 38.895 | 8.242 | 1.00 | 49.01 | C |
| ATOM | 1196 | O | SER | B | 43 | 51.549 | 38.788 | 8.734 | 1.00 | 49.17 | O |
| ATOM | 1197 | N | THR | B | 44 | 49.390 | 39.417 | 8.892 | 1.00 | 49.44 | N |
| ATOM | 1198 | CA | THR | B | 44 | 49.549 | 40.109 | 10.184 | 1.00 | 50.08 | C |
| ATOM | 1199 | CB | THR | B | 44 | 48.264 | 40.935 | 10.579 | 1.00 | 50.34 | C |
| ATOM | 1200 | OG1 | THR | B | 44 | 47.092 | 40.110 | 10.468 | 1.00 | 50.77 | O |
| ATOM | 1201 | CG2 | THR | B | 44 | 48.093 | 42.184 | 9.689 | 1.00 | 49.96 | C |
| ATOM | 1202 | C | THR | B | 44 | 50.054 | 39.236 | 11.366 | 1.00 | 50.19 | C |
| ATOM | 1203 | O | THR | B | 44 | 51.145 | 39.497 | 11.902 | 1.00 | 50.45 | O |
| ATOM | 1204 | N | ASN | B | 45 | 49.289 | 38.202 | 11.747 | 1.00 | 49.88 | N |
| ATOM | 1205 | CA | ASN | B | 45 | 49.637 | 37.347 | 12.898 | 1.00 | 49.63 | C |
| ATOM | 1206 | CB | ASN | B | 45 | 48.430 | 37.140 | 13.819 | 1.00 | 50.02 | C |
| ATOM | 1207 | CG | ASN | B | 45 | 47.471 | 38.339 | 13.840 | 1.00 | 50.87 | C |
| ATOM | 1208 | OD1 | ASN | B | 45 | 47.891 | 39.490 | 13.728 | 1.00 | 51.82 | O |
| ATOM | 1209 | ND2 | ASN | B | 45 | 46.170 | 38.060 | 13.999 | 1.00 | 51.34 | N |
| ATOM | 1210 | C | ASN | B | 45 | 50.178 | 35.982 | 12.492 | 1.00 | 49.19 | C |
| ATOM | 1211 | O | ASN | B | 45 | 50.131 | 35.621 | 11.325 | 1.00 | 48.90 | O |
| ATOM | 1212 | N | GLU | B | 46 | 50.703 | 35.239 | 13.465 | 1.00 | 48.83 | N |
| ATOM | 1213 | CA | GLU | B | 46 | 51.098 | 33.839 | 13.274 | 1.00 | 48.89 | C |
| ATOM | 1214 | CB | GLU | B | 46 | 51.616 | 33.236 | 14.602 | 1.00 | 48.72 | C |
| ATOM | 1215 | CG | GLU | B | 46 | 51.589 | 31.680 | 14.656 | 1.00 | 51.01 | C |
| ATOM | 1216 | CD | GLU | B | 46 | 52.026 | 31.059 | 16.009 | 1.00 | 51.85 | C |
| ATOM | 1217 | OE1 | GLU | B | 46 | 53.085 | 30.355 | 16.022 | 1.00 | 55.28 | O |
| ATOM | 1218 | OE2 | GLU | B | 46 | 51.310 | 31.250 | 17.040 | 1.00 | 54.03 | O |
| ATOM | 1219 | C | GLU | B | 46 | 49.877 | 33.051 | 12.783 | 1.00 | 47.40 | C |
| ATOM | 1220 | O | GLU | B | 46 | 48.776 | 33.279 | 13.296 | 1.00 | 47.31 | O |
| ATOM | 1221 | N | GLN | B | 47 | 50.055 | 32.156 | 11.797 | 1.00 | 45.67 | N |
| ATOM | 1222 | CA | GLN | B | 47 | 48.959 | 31.256 | 11.382 | 1.00 | 44.20 | C |
| ATOM | 1223 | CB | GLN | B | 47 | 48.202 | 31.758 | 10.146 | 1.00 | 44.02 | C |
| ATOM | 1224 | CG | GLN | B | 47 | 49.018 | 32.205 | 8.958 | 1.00 | 44.67 | C |
| ATOM | 1225 | CD | GLN | B | 47 | 48.193 | 33.053 | 7.957 | 1.00 | 45.30 | C |
| ATOM | 1226 | OE1 | GLN | B | 47 | 48.624 | 33.293 | 6.825 | 1.00 | 47.08 | O |
| ATOM | 1227 | NE2 | GLN | B | 47 | 47.014 | 33.512 | 8.383 | 1.00 | 46.34 | N |
| ATOM | 1228 | C | GLN | B | 47 | 49.271 | 29.767 | 11.249 | 1.00 | 42.77 | C |
| ATOM | 1229 | O | GLN | B | 47 | 50.388 | 29.374 | 10.902 | 1.00 | 43.17 | O |
| ATOM | 1230 | N | LYS | B | 48 | 48.263 | 28.948 | 11.536 | 1.00 | 40.86 | N |
| ATOM | 1231 | CA | LYS | B | 48 | 48.381 | 27.516 | 11.355 | 1.00 | 39.42 | C |
| ATOM | 1232 | CB | LYS | B | 48 | 47.374 | 26.754 | 12.192 | 1.00 | 39.66 | C |
| ATOM | 1233 | CG | LYS | B | 48 | 47.668 | 25.273 | 12.204 | 1.00 | 40.68 | C |
| ATOM | 1234 | CD | LYS | B | 48 | 46.769 | 24.546 | 13.155 | 1.00 | 44.74 | C |
| ATOM | 1235 | CE | LYS | B | 48 | 46.885 | 23.054 | 12.934 | 1.00 | 47.87 | C |
| ATOM | 1236 | NZ | LYS | B | 48 | 45.989 | 22.323 | 13.869 | 1.00 | 51.09 | N |
| ATOM | 1237 | C | LYS | B | 48 | 48.188 | 27.139 | 9.908 | 1.00 | 38.04 | C |
| ATOM | 1238 | O | LYS | B | 48 | 47.173 | 27.468 | 9.302 | 1.00 | 38.20 | O |
| ATOM | 1239 | N | ILE | B | 49 | 49.164 | 26.424 | 9.371 | 1.00 | 36.39 | N |
| ATOM | 1240 | CA | ILE | B | 49 | 49.139 | 25.983 | 7.993 | 1.00 | 34.41 | C |
| ATOM | 1241 | CB | ILE | B | 49 | 50.536 | 25.543 | 7.541 | 1.00 | 34.65 | C |
| ATOM | 1242 | CG1 | ILE | B | 49 | 51.581 | 26.630 | 7.910 | 1.00 | 33.56 | C |
| ATOM | 1243 | CD1 | ILE | B | 49 | 52.977 | 26.419 | 7.414 | 1.00 | 32.67 | C |
| ATOM | 1244 | CG2 | ILE | B | 49 | 50.480 | 25.172 | 6.067 | 1.00 | 34.42 | C |
| ATOM | 1245 | C | ILE | B | 49 | 48.189 | 24.815 | 7.822 | 1.00 | 33.90 | C |
| ATOM | 1246 | O | ILE | B | 49 | 48.299 | 23.837 | 8.534 | 1.00 | 33.80 | O |
| ATOM | 1247 | N | SER | B | 50 | 47.240 | 24.946 | 6.897 | 1.00 | 33.32 | N |
| ATOM | 1248 | CA | SER | B | 50 | 46.433 | 23.828 | 6.427 | 1.00 | 32.90 | C |
| ATOM | 1249 | CB | SER | B | 50 | 45.206 | 24.350 | 5.696 | 1.00 | 32.66 | C |
| ATOM | 1250 | OG | SER | B | 50 | 44.029 | 24.100 | 6.418 | 1.00 | 33.04 | O |
| ATOM | 1251 | C | SER | B | 50 | 47.225 | 22.981 | 5.441 | 1.00 | 32.69 | C |
| ATOM | 1252 | O | SER | B | 50 | 47.443 | 23.401 | 4.317 | 1.00 | 33.31 | O |
| ATOM | 1253 | N | ILE | B | 51 | 47.659 | 21.793 | 5.842 | 1.00 | 32.40 | N |
| ATOM | 1254 | CA | ILE | B | 51 | 48.216 | 20.831 | 4.880 | 1.00 | 31.95 | C |
| ATOM | 1255 | CB | ILE | B | 51 | 48.520 | 19.488 | 5.559 | 1.00 | 31.82 | C |
| ATOM | 1256 | CG1 | ILE | B | 51 | 49.417 | 19.700 | 6.788 | 1.00 | 31.72 | C |
| ATOM | 1257 | CD1 | ILE | B | 51 | 50.781 | 20.302 | 6.518 | 1.00 | 30.73 | C |
| ATOM | 1258 | CG2 | ILE | B | 51 | 49.112 | 18.514 | 4.573 | 1.00 | 30.78 | C |
| ATOM | 1259 | C | ILE | B | 51 | 47.270 | 20.612 | 3.681 | 1.00 | 31.79 | C |
| ATOM | 1260 | O | ILE | B | 51 | 46.052 | 20.534 | 3.839 | 1.00 | 31.18 | O |
| ATOM | 1261 | N | GLY | B | 52 | 47.856 | 20.530 | 2.493 | 1.00 | 32.00 | N |
| ATOM | 1262 | CA | GLY | B | 52 | 47.115 | 20.377 | 1.246 | 1.00 | 32.81 | C |
| ATOM | 1263 | C | GLY | B | 52 | 47.671 | 21.388 | 0.271 | 1.00 | 33.29 | C |
| ATOM | 1264 | O | GLY | B | 52 | 48.433 | 22.266 | 0.701 | 1.00 | 34.33 | O |
| ATOM | 1265 | N | GLY | B | 53 | 47.316 | 21.271 | −1.020 | 1.00 | 32.93 | N |
| ATOM | 1266 | CA | GLY | B | 53 | 47.797 | 22.167 | −2.079 | 1.00 | 32.74 | C |
| ATOM | 1267 | C | GLY | B | 53 | 49.317 | 22.310 | −2.101 | 1.00 | 33.58 | C |
| ATOM | 1268 | O | GLY | B | 53 | 50.035 | 21.328 | −2.253 | 1.00 | 33.62 | O |
| ATOM | 1269 | N | ARG | B | 54 | 49.800 | 23.545 | −1.957 | 1.00 | 33.84 | N |
| ATOM | 1270 | CA | ARG | B | 54 | 51.210 | 23.856 | −1.783 | 1.00 | 34.22 | C |
| ATOM | 1271 | CB | ARG | B | 54 | 51.356 | 25.337 | −1.403 | 1.00 | 34.14 | C |
| ATOM | 1272 | CG | ARG | B | 54 | 51.572 | 26.240 | −2.549 | 1.00 | 35.30 | C |

APPENDIX I(d)-continued

| ATOM | 1273 | CD | ARG | B | 54 | 50.951 | 27.636 | −2.377 | 1.00 | 38.06 | C |
|---|---|---|---|---|---|---|---|---|---|---|---|
| ATOM | 1274 | NE | ARG | B | 54 | 51.387 | 28.432 | −1.220 | 1.00 | 38.60 | N |
| ATOM | 1275 | CZ | ARG | B | 54 | 52.637 | 28.827 | −0.962 | 1.00 | 38.97 | C |
| ATOM | 1276 | NH1 | ARG | B | 54 | 53.655 | 28.462 | −1.727 | 1.00 | 37.92 | N |
| ATOM | 1277 | NH2 | ARG | B | 54 | 52.877 | 29.574 | 0.105 | 1.00 | 39.13 | N |
| ATOM | 1278 | C | ARG | B | 54 | 51.876 | 23.037 | −0.670 | 1.00 | 34.59 | C |
| ATOM | 1279 | O | ARG | B | 54 | 53.099 | 22.842 | −0.690 | 1.00 | 35.21 | O |
| ATOM | 1280 | N | TYR | B | 55 | 51.096 | 22.605 | 0.318 | 1.00 | 34.28 | N |
| ATOM | 1281 | CA | TYR | B | 55 | 51.680 | 22.114 | 1.558 | 1.00 | 35.05 | C |
| ATOM | 1282 | CB | TYR | B | 55 | 51.012 | 22.750 | 2.778 | 1.00 | 35.40 | C |
| ATOM | 1283 | CG | TYR | B | 55 | 51.104 | 24.245 | 2.771 | 1.00 | 36.76 | C |
| ATOM | 1284 | CD1 | TYR | B | 55 | 49.993 | 25.022 | 2.453 | 1.00 | 36.78 | C |
| ATOM | 1285 | CE1 | TYR | B | 55 | 50.076 | 26.389 | 2.425 | 1.00 | 36.81 | C |
| ATOM | 1286 | CZ | TYR | B | 55 | 51.282 | 27.001 | 2.706 | 1.00 | 36.69 | C |
| ATOM | 1287 | OH | TYR | B | 55 | 51.353 | 28.363 | 2.682 | 1.00 | 37.75 | O |
| ATOM | 1288 | CE2 | TYR | B | 55 | 52.408 | 26.269 | 3.026 | 1.00 | 36.76 | C |
| ATOM | 1289 | CD2 | TYR | B | 55 | 52.319 | 24.893 | 3.053 | 1.00 | 37.99 | C |
| ATOM | 1290 | C | TYR | B | 55 | 51.546 | 20.621 | 1.650 | 1.00 | 35.30 | C |
| ATOM | 1291 | O | TYR | B | 55 | 50.418 | 20.093 | 1.689 | 1.00 | 35.71 | O |
| ATOM | 1292 | N | VAL | B | 56 | 52.691 | 19.942 | 1.680 | 1.00 | 34.77 | N |
| ATOM | 1293 | CA | VAL | B | 56 | 52.700 | 18.500 | 1.816 | 1.00 | 34.57 | C |
| ATOM | 1294 | CB | VAL | B | 56 | 52.930 | 17.723 | 0.423 | 1.00 | 34.43 | C |
| ATOM | 1295 | CG1 | VAL | B | 56 | 53.441 | 18.632 | −0.682 | 1.00 | 34.03 | C |
| ATOM | 1296 | CG2 | VAL | B | 56 | 53.758 | 16.472 | 0.581 | 1.00 | 33.69 | C |
| ATOM | 1297 | C | VAL | B | 56 | 53.522 | 18.045 | 3.026 | 1.00 | 34.81 | C |
| ATOM | 1298 | O | VAL | B | 56 | 54.724 | 18.312 | 3.129 | 1.00 | 35.06 | O |
| ATOM | 1299 | N | GLU | B | 57 | 52.821 | 17.406 | 3.963 | 1.00 | 35.01 | N |
| ATOM | 1300 | CA | GLU | B | 57 | 53.408 | 16.847 | 5.178 | 1.00 | 35.49 | C |
| ATOM | 1301 | CB | GLU | B | 57 | 52.474 | 17.028 | 6.364 | 1.00 | 35.34 | C |
| ATOM | 1302 | CG | GLU | B | 57 | 53.180 | 16.934 | 7.704 | 1.00 | 35.90 | C |
| ATOM | 1303 | CD | GLU | B | 57 | 52.231 | 17.058 | 8.896 | 1.00 | 36.90 | C |
| ATOM | 1304 | OE1 | GLU | B | 57 | 51.089 | 16.531 | 8.854 | 1.00 | 38.87 | O |
| ATOM | 1305 | OE2 | GLU | B | 57 | 52.642 | 17.678 | 9.898 | 1.00 | 39.53 | O |
| ATOM | 1306 | C | GLU | B | 57 | 53.679 | 15.368 | 5.034 | 1.00 | 35.42 | C |
| ATOM | 1307 | O | GLU | B | 57 | 52.834 | 14.617 | 4.549 | 1.00 | 35.57 | O |
| ATOM | 1308 | N | THR | B | 58 | 54.863 | 14.956 | 5.458 | 1.00 | 35.55 | N |
| ATOM | 1309 | CA | THR | B | 58 | 55.173 | 13.552 | 5.566 | 1.00 | 36.03 | C |
| ATOM | 1310 | CB | THR | B | 58 | 56.332 | 13.180 | 4.668 | 1.00 | 36.37 | C |
| ATOM | 1311 | OG1 | THR | B | 58 | 55.971 | 13.500 | 3.324 | 1.00 | 38.93 | O |
| ATOM | 1312 | CG2 | THR | B | 58 | 56.624 | 11.680 | 4.753 | 1.00 | 35.97 | C |
| ATOM | 1313 | C | THR | B | 58 | 55.510 | 13.227 | 6.999 | 1.00 | 35.82 | C |
| ATOM | 1314 | O | THR | B | 58 | 56.478 | 13.750 | 7.558 | 1.00 | 35.98 | O |
| ATOM | 1315 | N | VAL | B | 59 | 54.708 | 12.363 | 7.597 | 1.00 | 35.52 | N |
| ATOM | 1316 | CA | VAL | B | 59 | 54.956 | 11.955 | 8.968 | 1.00 | 35.20 | C |
| ATOM | 1317 | CB | VAL | B | 59 | 53.757 | 12.247 | 9.820 | 1.00 | 35.04 | C |
| ATOM | 1318 | CG1 | VAL | B | 59 | 53.952 | 11.715 | 11.241 | 1.00 | 34.11 | C |
| ATOM | 1319 | CG2 | VAL | B | 59 | 53.536 | 13.760 | 9.802 | 1.00 | 35.87 | C |
| ATOM | 1320 | C | VAL | B | 59 | 55.377 | 10.504 | 9.106 | 1.00 | 34.93 | C |
| ATOM | 1321 | O | VAL | B | 59 | 54.740 | 9.610 | 8.560 | 1.00 | 35.10 | O |
| ATOM | 1322 | N | ASN | B | 60 | 56.471 | 10.286 | 9.825 | 1.00 | 34.54 | N |
| ATOM | 1323 | CA | ASN | B | 60 | 56.872 | 8.949 | 10.196 | 1.00 | 34.43 | C |
| ATOM | 1324 | CB | ASN | B | 60 | 58.304 | 8.695 | 9.772 | 1.00 | 34.56 | C |
| ATOM | 1325 | CG | ASN | B | 60 | 58.665 | 7.231 | 9.819 | 1.00 | 34.65 | C |
| ATOM | 1326 | OD1 | ASN | B | 60 | 58.226 | 6.482 | 10.704 | 1.00 | 34.77 | O |
| ATOM | 1327 | ND2 | ASN | B | 60 | 59.474 | 6.812 | 8.867 | 1.00 | 33.75 | N |
| ATOM | 1328 | C | ASN | B | 60 | 56.707 | 8.692 | 11.692 | 1.00 | 34.35 | C |
| ATOM | 1329 | O | ASN | B | 60 | 57.659 | 8.801 | 12.473 | 1.00 | 34.37 | O |
| ATOM | 1330 | N | LYS | B | 61 | 55.486 | 8.333 | 12.082 | 1.00 | 34.32 | N |
| ATOM | 1331 | CA | LYS | B | 61 | 55.153 | 8.102 | 13.496 | 1.00 | 33.79 | C |
| ATOM | 1332 | CB | LYS | B | 61 | 53.712 | 7.595 | 13.640 | 1.00 | 33.51 | C |
| ATOM | 1333 | CG | LYS | B | 61 | 52.707 | 8.696 | 13.922 | 1.00 | 32.45 | C |
| ATOM | 1334 | CD | LYS | B | 61 | 51.272 | 8.203 | 13.746 | 1.00 | 31.18 | C |
| ATOM | 1335 | CE | LYS | B | 61 | 50.270 | 9.348 | 13.855 | 1.00 | 31.36 | C |
| ATOM | 1336 | NZ | LYS | B | 61 | 48.882 | 8.975 | 13.458 | 1.00 | 32.24 | N |
| ATOM | 1337 | C | LYS | B | 61 | 56.126 | 7.150 | 14.184 | 1.00 | 33.58 | C |
| ATOM | 1338 | O | LYS | B | 61 | 56.344 | 7.252 | 15.386 | 1.00 | 33.17 | O |
| ATOM | 1339 | N | GLY | B | 62 | 56.717 | 6.248 | 13.402 | 1.00 | 33.71 | N |
| ATOM | 1340 | CA | GLY | B | 62 | 57.582 | 5.197 | 13.927 | 1.00 | 33.75 | C |
| ATOM | 1341 | C | GLY | B | 62 | 58.902 | 5.716 | 14.449 | 1.00 | 33.69 | C |
| ATOM | 1342 | O | GLY | B | 62 | 59.342 | 5.338 | 15.535 | 1.00 | 33.29 | O |
| ATOM | 1343 | N | SER | B | 63 | 59.537 | 6.581 | 13.669 | 1.00 | 33.94 | N |
| ATOM | 1344 | CA | SER | B | 63 | 60.816 | 7.159 | 14.062 | 1.00 | 34.47 | C |
| ATOM | 1345 | CB | SER | B | 63 | 61.758 | 7.243 | 12.859 | 1.00 | 34.55 | C |
| ATOM | 1346 | OG | SER | B | 63 | 61.291 | 8.202 | 11.912 | 1.00 | 35.26 | O |
| ATOM | 1347 | C | SER | B | 63 | 60.605 | 8.538 | 14.678 | 1.00 | 34.60 | C |
| ATOM | 1348 | O | SER | B | 63 | 61.561 | 9.279 | 14.908 | 1.00 | 35.09 | O |
| ATOM | 1349 | N | LYS | B | 64 | 59.344 | 8.866 | 14.939 | 1.00 | 34.69 | N |
| ATOM | 1350 | CA | LYS | B | 64 | 58.925 | 10.171 | 15.447 | 1.00 | 34.92 | C |
| ATOM | 1351 | CB | LYS | B | 64 | 59.258 | 10.326 | 16.933 | 1.00 | 34.30 | C |
| ATOM | 1352 | CG | LYS | B | 64 | 58.467 | 9.412 | 17.849 | 1.00 | 34.05 | C |

APPENDIX I(d)-continued

| | | | | | | | | | | | |
|---|---|---|---|---|---|---|---|---|---|---|---|
| ATOM | 1353 | CD | LYS | B | 64 | 59.356 | 8.857 | 18.921 | 1.00 | 34.38 | C |
| ATOM | 1354 | CE | LYS | B | 64 | 58.612 | 8.736 | 20.206 | 1.00 | 35.46 | C |
| ATOM | 1355 | NZ | LYS | B | 64 | 57.842 | 7.479 | 20.278 | 1.00 | 37.44 | N |
| ATOM | 1356 | C | LYS | B | 64 | 59.430 | 11.374 | 14.647 | 1.00 | 35.47 | C |
| ATOM | 1357 | O | LYS | B | 64 | 59.438 | 12.485 | 15.153 | 1.00 | 36.15 | O |
| ATOM | 1358 | N | SER | B | 65 | 59.826 | 11.185 | 13.398 | 1.00 | 35.85 | N |
| ATOM | 1359 | CA | SER | B | 65 | 60.164 | 12.354 | 12.588 | 1.00 | 36.57 | C |
| ATOM | 1360 | CB | SER | B | 65 | 61.428 | 12.116 | 11.773 | 1.00 | 36.71 | C |
| ATOM | 1361 | OG | SER | B | 65 | 61.349 | 10.872 | 11.103 | 1.00 | 38.46 | O |
| ATOM | 1362 | C | SER | B | 65 | 59.000 | 12.777 | 11.692 | 1.00 | 36.53 | C |
| ATOM | 1363 | O | SER | B | 65 | 58.031 | 12.039 | 11.510 | 1.00 | 36.24 | O |
| ATOM | 1364 | N | PHE | B | 66 | 59.093 | 13.983 | 11.157 | 1.00 | 36.84 | N |
| ATOM | 1365 | CA | PHE | B | 66 | 58.081 | 14.495 | 10.254 | 1.00 | 37.54 | C |
| ATOM | 1366 | CB | PHE | B | 66 | 56.744 | 14.728 | 10.981 | 1.00 | 38.07 | C |
| ATOM | 1367 | CG | PHE | B | 66 | 56.815 | 15.713 | 12.127 | 1.00 | 38.99 | C |
| ATOM | 1368 | CD1 | PHE | B | 66 | 56.073 | 16.894 | 12.082 | 1.00 | 39.56 | C |
| ATOM | 1369 | CE1 | PHE | B | 66 | 56.129 | 17.808 | 13.131 | 1.00 | 39.86 | C |
| ATOM | 1370 | CZ | PHE | B | 66 | 56.932 | 17.540 | 14.245 | 1.00 | 40.09 | C |
| ATOM | 1371 | CE2 | PHE | B | 66 | 57.673 | 16.363 | 14.308 | 1.00 | 39.63 | C |
| ATOM | 1372 | CD2 | PHE | B | 66 | 57.603 | 15.456 | 13.253 | 1.00 | 39.81 | C |
| ATOM | 1373 | C | PHE | B | 66 | 58.567 | 15.744 | 9.527 | 1.00 | 37.56 | C |
| ATOM | 1374 | O | PHE | B | 66 | 59.251 | 16.573 | 10.114 | 1.00 | 37.86 | O |
| ATOM | 1375 | N | SER | B | 67 | 58.202 | 15.868 | 8.253 | 1.00 | 37.40 | N |
| ATOM | 1376 | CA | SER | B | 67 | 58.668 | 16.953 | 7.398 | 1.00 | 37.02 | C |
| ATOM | 1377 | CB | SER | B | 67 | 59.562 | 16.388 | 6.297 | 1.00 | 37.25 | C |
| ATOM | 1378 | OG | SER | B | 67 | 58.769 | 15.703 | 5.328 | 1.00 | 38.81 | O |
| ATOM | 1379 | C | SER | B | 67 | 57.522 | 17.681 | 6.735 | 1.00 | 36.30 | C |
| ATOM | 1380 | O | SER | B | 67 | 56.477 | 17.113 | 6.508 | 1.00 | 36.04 | O |
| ATOM | 1381 | N | LEU | B | 68 | 57.747 | 18.944 | 6.405 | 1.00 | 36.52 | N |
| ATOM | 1382 | CA | LEU | B | 68 | 56.812 | 19.747 | 5.625 | 1.00 | 36.48 | C |
| ATOM | 1383 | CB | LEU | B | 68 | 56.319 | 20.943 | 6.429 | 1.00 | 35.99 | C |
| ATOM | 1384 | CG | LEU | B | 68 | 55.589 | 22.029 | 5.647 | 1.00 | 36.04 | C |
| ATOM | 1385 | CD1 | LEU | B | 68 | 54.180 | 21.550 | 5.246 | 1.00 | 38.31 | C |
| ATOM | 1386 | CD2 | LEU | B | 68 | 55.518 | 23.352 | 6.412 | 1.00 | 35.68 | C |
| ATOM | 1387 | C | LEU | B | 68 | 57.520 | 20.240 | 4.371 | 1.00 | 37.35 | C |
| ATOM | 1388 | O | LEU | B | 68 | 58.662 | 20.744 | 4.436 | 1.00 | 37.12 | O |
| ATOM | 1389 | N | ARG | B | 69 | 56.844 | 20.082 | 3.232 | 1.00 | 37.75 | N |
| ATOM | 1390 | CA | ARG | B | 69 | 57.361 | 20.564 | 1.965 | 1.00 | 38.27 | C |
| ATOM | 1391 | CB | ARG | B | 69 | 57.563 | 19.402 | 1.011 | 1.00 | 38.49 | C |
| ATOM | 1392 | CG | ARG | B | 69 | 58.147 | 19.759 | −0.323 | 1.00 | 40.65 | C |
| ATOM | 1393 | CD | ARG | B | 69 | 58.789 | 18.518 | −0.879 | 1.00 | 47.79 | C |
| ATOM | 1394 | NE | ARG | B | 69 | 59.309 | 18.659 | −2.242 | 1.00 | 54.67 | N |
| ATOM | 1395 | CZ | ARG | B | 69 | 60.446 | 19.288 | −2.573 | 1.00 | 57.95 | C |
| ATOM | 1396 | NH1 | ARG | B | 69 | 60.826 | 19.348 | −3.855 | 1.00 | 57.88 | N |
| ATOM | 1397 | NH2 | ARG | B | 69 | 61.199 | 19.877 | −1.634 | 1.00 | 58.92 | N |
| ATOM | 1398 | C | ARG | B | 69 | 56.400 | 21.593 | 1.387 | 1.00 | 38.17 | C |
| ATOM | 1399 | O | ARG | B | 69 | 55.235 | 21.297 | 1.149 | 1.00 | 37.57 | O |
| ATOM | 1400 | N | ILE | B | 70 | 56.908 | 22.810 | 1.184 | 1.00 | 39.05 | N |
| ATOM | 1401 | CA | ILE | B | 70 | 56.128 | 23.927 | 0.615 | 1.00 | 39.54 | C |
| ATOM | 1402 | CB | ILE | B | 70 | 56.290 | 25.218 | 1.432 | 1.00 | 39.53 | C |
| ATOM | 1403 | CG1 | ILE | B | 70 | 55.884 | 24.995 | 2.883 | 1.00 | 38.64 | C |
| ATOM | 1404 | CD1 | ILE | B | 70 | 56.532 | 25.975 | 3.773 | 1.00 | 40.33 | C |
| ATOM | 1405 | CG2 | ILE | B | 70 | 55.443 | 26.333 | 0.848 | 1.00 | 40.01 | C |
| ATOM | 1406 | C | ILE | B | 70 | 56.579 | 24.194 | −0.810 | 1.00 | 39.97 | C |
| ATOM | 1407 | O | ILE | B | 70 | 57.765 | 24.444 | −1.075 | 1.00 | 40.13 | O |
| ATOM | 1408 | N | ARG | B | 71 | 55.633 | 24.120 | −1.732 | 1.00 | 40.24 | N |
| ATOM | 1409 | CA | ARG | B | 71 | 55.962 | 24.303 | −3.135 | 1.00 | 40.82 | C |
| ATOM | 1410 | CB | ARG | B | 71 | 55.148 | 23.348 | −3.993 | 1.00 | 41.16 | C |
| ATOM | 1411 | CG | ARG | B | 71 | 55.337 | 21.888 | −3.639 | 1.00 | 44.57 | C |
| ATOM | 1412 | CD | ARG | B | 71 | 54.725 | 20.992 | −4.710 | 1.00 | 49.70 | C |
| ATOM | 1413 | NE | ARG | B | 71 | 54.807 | 21.588 | −6.046 | 1.00 | 53.70 | N |
| ATOM | 1414 | CZ | ARG | B | 71 | 54.572 | 20.944 | −7.194 | 1.00 | 55.90 | C |
| ATOM | 1415 | NH1 | ARG | B | 71 | 54.674 | 21.597 | −8.352 | 1.00 | 56.14 | N |
| ATOM | 1416 | NH2 | ARG | B | 71 | 54.239 | 19.652 | −7.198 | 1.00 | 56.04 | N |
| ATOM | 1417 | C | ARG | B | 71 | 55.697 | 25.725 | −3.590 | 1.00 | 40.23 | C |
| ATOM | 1418 | O | ARG | B | 71 | 54.853 | 26.410 | −3.043 | 1.00 | 40.21 | O |
| ATOM | 1419 | N | ASP | B | 72 | 56.432 | 26.166 | −4.598 | 1.00 | 39.99 | N |
| ATOM | 1420 | CA | ASP | B | 72 | 56.074 | 27.365 | −5.311 | 1.00 | 39.63 | C |
| ATOM | 1421 | CB | ASP | B | 72 | 54.633 | 27.247 | −5.794 | 1.00 | 40.12 | C |
| ATOM | 1422 | CG | ASP | B | 72 | 54.453 | 27.755 | −7.197 | 1.00 | 43.50 | C |
| ATOM | 1423 | OD1 | ASP | B | 72 | 53.897 | 26.973 | −8.008 | 1.00 | 47.76 | O |
| ATOM | 1424 | OD2 | ASP | B | 72 | 54.870 | 28.909 | −7.500 | 1.00 | 45.42 | O |
| ATOM | 1425 | C | ASP | B | 72 | 56.216 | 28.575 | −4.419 | 1.00 | 38.78 | C |
| ATOM | 1426 | O | ASP | B | 72 | 55.359 | 29.435 | −4.391 | 1.00 | 39.10 | O |
| ATOM | 1427 | N | LEU | B | 73 | 57.306 | 28.639 | −3.681 | 1.00 | 38.19 | N |
| ATOM | 1428 | CA | LEU | B | 73 | 57.606 | 29.804 | −2.868 | 1.00 | 37.69 | C |
| ATOM | 1429 | CB | LEU | B | 73 | 59.012 | 29.684 | −2.307 | 1.00 | 37.08 | C |
| ATOM | 1430 | CG | LEU | B | 73 | 59.129 | 28.569 | −1.283 | 1.00 | 35.84 | C |
| ATOM | 1431 | CD1 | LEU | B | 73 | 60.549 | 28.541 | −0.791 | 1.00 | 37.26 | C |
| ATOM | 1432 | CD2 | LEU | B | 73 | 58.171 | 28.844 | −0.129 | 1.00 | 34.44 | C |

APPENDIX I(d)-continued

| ATOM | 1433 | C | LEU | B | 73 | 57.413 | 31.156 | −3.563 | 1.00 | 38.01 | C |
|---|---|---|---|---|---|---|---|---|---|---|---|
| ATOM | 1434 | O | LEU | B | 73 | 57.757 | 31.336 | −4.733 | 1.00 | 37.97 | O |
| ATOM | 1435 | N | ARG | B | 74 | 56.827 | 32.090 | −2.822 | 1.00 | 38.54 | N |
| ATOM | 1436 | CA | ARG | B | 74 | 56.692 | 33.480 | −3.231 | 1.00 | 39.03 | C |
| ATOM | 1437 | CB | ARG | B | 74 | 55.210 | 33.868 | −3.329 | 1.00 | 39.96 | C |
| ATOM | 1438 | CG | ARG | B | 74 | 54.303 | 32.933 | −4.150 | 1.00 | 42.17 | C |
| ATOM | 1439 | CD | ARG | B | 74 | 53.881 | 31.746 | −3.285 | 1.00 | 46.75 | C |
| ATOM | 1440 | NE | ARG | B | 74 | 52.745 | 30.999 | −3.823 | 1.00 | 50.63 | N |
| ATOM | 1441 | CZ | ARG | B | 74 | 51.483 | 31.425 | −3.764 | 1.00 | 53.30 | C |
| ATOM | 1442 | NH1 | ARG | B | 74 | 50.499 | 30.671 | −4.259 | 1.00 | 54.24 | N |
| ATOM | 1443 | NH2 | ARG | B | 74 | 51.201 | 32.612 | −3.214 | 1.00 | 53.43 | N |
| ATOM | 1444 | C | ARG | B | 74 | 57.359 | 34.300 | −2.150 | 1.00 | 38.76 | C |
| ATOM | 1445 | O | ARG | B | 74 | 57.595 | 33.785 | −1.062 | 1.00 | 38.68 | O |
| ATOM | 1446 | N | VAL | B | 75 | 57.666 | 35.564 | −2.409 | 1.00 | 39.03 | N |
| ATOM | 1447 | CA | VAL | B | 75 | 58.293 | 36.391 | −1.348 | 1.00 | 39.94 | C |
| ATOM | 1448 | CB | VAL | B | 75 | 58.755 | 37.808 | −1.812 | 1.00 | 39.90 | C |
| ATOM | 1449 | CG1 | VAL | B | 75 | 59.921 | 37.712 | −2.824 | 1.00 | 40.00 | C |
| ATOM | 1450 | CG2 | VAL | B | 75 | 57.599 | 38.585 | −2.382 | 1.00 | 40.10 | C |
| ATOM | 1451 | C | VAL | B | 75 | 57.447 | 36.512 | −0.072 | 1.00 | 40.09 | C |
| ATOM | 1452 | O | VAL | B | 75 | 57.986 | 36.505 | 1.021 | 1.00 | 40.49 | O |
| ATOM | 1453 | N | GLU | B | 76 | 56.131 | 36.583 | −0.212 | 1.00 | 40.25 | N |
| ATOM | 1454 | CA | GLU | B | 76 | 55.243 | 36.585 | 0.931 | 1.00 | 41.00 | C |
| ATOM | 1455 | CB | GLU | B | 76 | 53.794 | 36.502 | 0.475 | 1.00 | 41.62 | C |
| ATOM | 1456 | CG | GLU | B | 76 | 53.401 | 37.530 | −0.549 | 1.00 | 46.34 | C |
| ATOM | 1457 | CD | GLU | B | 76 | 53.603 | 37.033 | −1.981 | 1.00 | 51.96 | C |
| ATOM | 1458 | OE1 | GLU | B | 76 | 52.868 | 36.077 | −2.374 | 1.00 | 53.72 | O |
| ATOM | 1459 | OE2 | GLU | B | 76 | 54.479 | 37.611 | −2.699 | 1.00 | 52.46 | O |
| ATOM | 1460 | C | GLU | B | 76 | 55.488 | 35.438 | 1.899 | 1.00 | 40.60 | C |
| ATOM | 1461 | O | GLU | B | 76 | 55.188 | 35.558 | 3.068 | 1.00 | 40.70 | O |
| ATOM | 1462 | N | ASP | B | 77 | 55.995 | 34.314 | 1.412 | 1.00 | 40.65 | N |
| ATOM | 1463 | CA | ASP | B | 77 | 56.168 | 33.140 | 2.261 | 1.00 | 40.78 | C |
| ATOM | 1464 | CB | ASP | B | 77 | 56.366 | 31.865 | 1.430 | 1.00 | 40.99 | C |
| ATOM | 1465 | CG | ASP | B | 77 | 55.160 | 31.509 | 0.593 | 1.00 | 42.47 | C |
| ATOM | 1466 | OD1 | ASP | B | 77 | 54.012 | 31.891 | 0.925 | 1.00 | 43.22 | O |
| ATOM | 1467 | OD2 | ASP | B | 77 | 55.363 | 30.813 | −0.417 | 1.00 | 45.98 | O |
| ATOM | 1468 | C | ASP | B | 77 | 57.349 | 33.282 | 3.203 | 1.00 | 40.48 | C |
| ATOM | 1469 | O | ASP | B | 77 | 57.547 | 32.406 | 4.062 | 1.00 | 41.07 | O |
| ATOM | 1470 | N | SER | B | 78 | 58.144 | 34.343 | 3.026 | 1.00 | 39.20 | N |
| ATOM | 1471 | CA | SER | B | 78 | 59.263 | 34.613 | 3.919 | 1.00 | 38.61 | C |
| ATOM | 1472 | CB | SER | B | 78 | 60.034 | 35.853 | 3.479 | 1.00 | 38.59 | C |
| ATOM | 1473 | OG | SER | B | 78 | 60.749 | 35.584 | 2.287 | 1.00 | 39.13 | O |
| ATOM | 1474 | C | SER | B | 78 | 58.774 | 34.798 | 5.349 | 1.00 | 38.23 | C |
| ATOM | 1475 | O | SER | B | 78 | 57.725 | 35.412 | 5.566 | 1.00 | 38.16 | O |
| ATOM | 1476 | N | GLY | B | 79 | 59.526 | 34.264 | 6.310 | 1.00 | 37.06 | N |
| ATOM | 1477 | CA | GLY | B | 79 | 59.172 | 34.394 | 7.702 | 1.00 | 36.72 | C |
| ATOM | 1478 | C | GLY | B | 79 | 59.642 | 33.241 | 8.571 | 1.00 | 36.81 | C |
| ATOM | 1479 | O | GLY | B | 79 | 60.418 | 32.386 | 8.120 | 1.00 | 37.01 | O |
| ATOM | 1480 | N | THR | B | 80 | 59.182 | 33.215 | 9.820 | 1.00 | 35.82 | N |
| ATOM | 1481 | CA | THR | B | 80 | 59.539 | 32.136 | 10.723 | 1.00 | 35.70 | C |
| ATOM | 1482 | CB | THR | B | 80 | 59.759 | 32.708 | 12.113 | 1.00 | 35.62 | C |
| ATOM | 1483 | OG1 | THR | B | 80 | 60.574 | 33.869 | 11.970 | 1.00 | 35.54 | O |
| ATOM | 1484 | CG2 | THR | B | 80 | 60.452 | 31.710 | 13.024 | 1.00 | 34.98 | C |
| ATOM | 1485 | C | THR | B | 80 | 58.516 | 30.983 | 10.729 | 1.00 | 35.72 | C |
| ATOM | 1486 | O | THR | B | 80 | 57.311 | 31.195 | 10.948 | 1.00 | 35.81 | O |
| ATOM | 1487 | N | TYR | B | 81 | 59.010 | 29.773 | 10.482 | 1.00 | 35.54 | N |
| ATOM | 1488 | CA | TYR | B | 81 | 58.184 | 28.569 | 10.454 | 1.00 | 36.16 | C |
| ATOM | 1489 | CB | TYR | B | 81 | 58.423 | 27.801 | 9.156 | 1.00 | 36.56 | C |
| ATOM | 1490 | CG | TYR | B | 81 | 57.831 | 28.448 | 7.928 | 1.00 | 36.94 | C |
| ATOM | 1491 | CD1 | TYR | B | 81 | 58.527 | 29.423 | 7.216 | 1.00 | 36.56 | C |
| ATOM | 1492 | CE1 | TYR | B | 81 | 57.963 | 30.016 | 6.076 | 1.00 | 37.63 | C |
| ATOM | 1493 | CZ | TYR | B | 81 | 56.691 | 29.622 | 5.665 | 1.00 | 37.70 | C |
| ATOM | 1494 | OH | TYR | B | 81 | 56.095 | 30.186 | 4.569 | 1.00 | 38.04 | O |
| ATOM | 1495 | CE2 | TYR | B | 81 | 55.998 | 28.655 | 6.355 | 1.00 | 37.62 | C |
| ATOM | 1496 | CD2 | TYR | B | 81 | 56.562 | 28.078 | 7.477 | 1.00 | 37.71 | C |
| ATOM | 1497 | C | TYR | B | 81 | 58.519 | 27.653 | 11.625 | 1.00 | 36.66 | C |
| ATOM | 1498 | O | TYR | B | 81 | 59.681 | 27.295 | 11.816 | 1.00 | 36.33 | O |
| ATOM | 1499 | N | LYS | B | 82 | 57.512 | 27.275 | 12.416 | 1.00 | 37.35 | N |
| ATOM | 1500 | CA | LYS | B | 82 | 57.738 | 26.370 | 13.551 | 1.00 | 37.75 | C |
| ATOM | 1501 | CB | LYS | B | 82 | 57.561 | 27.102 | 14.872 | 1.00 | 37.28 | C |
| ATOM | 1502 | CG | LYS | B | 82 | 58.401 | 28.335 | 15.050 | 1.00 | 36.86 | C |
| ATOM | 1503 | CD | LYS | B | 82 | 58.600 | 28.661 | 16.530 | 1.00 | 37.26 | C |
| ATOM | 1504 | CE | LYS | B | 82 | 59.231 | 30.041 | 16.696 | 1.00 | 38.77 | C |
| ATOM | 1505 | NZ | LYS | B | 82 | 60.333 | 30.124 | 17.734 | 1.00 | 38.13 | N |
| ATOM | 1506 | C | LYS | B | 82 | 56.820 | 25.141 | 13.513 | 1.00 | 38.47 | C |
| ATOM | 1507 | O | LYS | B | 82 | 55.628 | 25.258 | 13.236 | 1.00 | 39.02 | O |
| ATOM | 1508 | N | CYS | B | 83 | 57.376 | 23.967 | 13.795 | 1.00 | 39.00 | N |
| ATOM | 1509 | CA | CYS | B | 83 | 56.578 | 22.739 | 13.854 | 1.00 | 39.64 | C |
| ATOM | 1510 | CB | CYS | B | 83 | 57.339 | 21.546 | 13.248 | 1.00 | 39.79 | C |
| ATOM | 1511 | SG | CYS | B | 83 | 58.916 | 21.142 | 14.085 | 1.00 | 41.25 | S |
| ATOM | 1512 | C | CYS | B | 83 | 56.183 | 22.432 | 15.302 | 1.00 | 39.76 | C |

APPENDIX I(d)-continued

| | | | | | | | | | | | |
|---|---|---|---|---|---|---|---|---|---|---|---|
| ATOM | 1513 | O | CYS | B | 83 | 56.962 | 22.700 | 16.229 | 1.00 | 39.86 | O |
| ATOM | 1514 | N | GLY | B | 84 | 54.981 | 21.879 | 15.487 | 1.00 | 39.61 | N |
| ATOM | 1515 | CA | GLY | B | 84 | 54.527 | 21.428 | 16.805 | 1.00 | 39.36 | C |
| ATOM | 1516 | C | GLY | B | 84 | 54.312 | 19.928 | 16.816 | 1.00 | 39.37 | C |
| ATOM | 1517 | O | GLY | B | 84 | 53.726 | 19.372 | 15.893 | 1.00 | 39.74 | O |
| ATOM | 1518 | N | ALA | B | 85 | 54.809 | 19.262 | 17.846 | 1.00 | 39.35 | N |
| ATOM | 1519 | CA | ALA | B | 85 | 54.593 | 17.833 | 18.008 | 1.00 | 39.38 | C |
| ATOM | 1520 | CB | ALA | B | 85 | 55.897 | 17.091 | 17.945 | 1.00 | 39.21 | C |
| ATOM | 1521 | C | ALA | B | 85 | 53.871 | 17.562 | 19.327 | 1.00 | 39.54 | C |
| ATOM | 1522 | O | ALA | B | 85 | 54.252 | 18.090 | 20.364 | 1.00 | 39.26 | O |
| ATOM | 1523 | N | TYR | B | 86 | 52.814 | 16.755 | 19.253 | 1.00 | 40.01 | N |
| ATOM | 1524 | CA | TYR | B | 86 | 51.962 | 16.400 | 20.392 | 1.00 | 40.48 | C |
| ATOM | 1525 | CB | TYR | B | 86 | 50.556 | 16.923 | 20.161 | 1.00 | 40.34 | C |
| ATOM | 1526 | CG | TYR | B | 86 | 50.584 | 18.401 | 19.902 | 1.00 | 40.96 | C |
| ATOM | 1527 | CD1 | TYR | B | 86 | 51.003 | 18.895 | 18.666 | 1.00 | 41.70 | C |
| ATOM | 1528 | CE1 | TYR | B | 86 | 51.062 | 20.246 | 18.420 | 1.00 | 42.23 | C |
| ATOM | 1529 | CZ | TYR | B | 86 | 50.698 | 21.129 | 19.424 | 1.00 | 41.82 | C |
| ATOM | 1530 | OH | TYR | B | 86 | 50.760 | 22.479 | 19.169 | 1.00 | 42.60 | O |
| ATOM | 1531 | CE2 | TYR | B | 86 | 50.269 | 20.667 | 20.660 | 1.00 | 40.71 | C |
| ATOM | 1532 | CD2 | TYR | B | 86 | 50.227 | 19.312 | 20.896 | 1.00 | 40.41 | C |
| ATOM | 1533 | C | TYR | B | 86 | 51.951 | 14.894 | 20.626 | 1.00 | 41.00 | C |
| ATOM | 1534 | O | TYR | B | 86 | 51.743 | 14.103 | 19.693 | 1.00 | 40.55 | O |
| ATOM | 1535 | N | PHE | B | 87 | 52.190 | 14.506 | 21.877 | 1.00 | 41.83 | N |
| ATOM | 1536 | CA | PHE | B | 87 | 52.457 | 13.106 | 22.201 | 1.00 | 42.83 | C |
| ATOM | 1537 | CB | PHE | B | 87 | 53.977 | 12.835 | 22.309 | 1.00 | 42.90 | C |
| ATOM | 1538 | CG | PHE | B | 87 | 54.726 | 13.842 | 23.133 | 1.00 | 43.47 | C |
| ATOM | 1539 | CD1 | PHE | B | 87 | 55.350 | 14.932 | 22.522 | 1.00 | 43.68 | C |
| ATOM | 1540 | CE1 | PHE | B | 87 | 56.058 | 15.887 | 23.293 | 1.00 | 45.01 | C |
| ATOM | 1541 | CZ | PHE | B | 87 | 56.141 | 15.741 | 24.701 | 1.00 | 45.10 | C |
| ATOM | 1542 | CE2 | PHE | B | 87 | 55.516 | 14.636 | 25.316 | 1.00 | 45.18 | C |
| ATOM | 1543 | CD2 | PHE | B | 87 | 54.817 | 13.699 | 24.524 | 1.00 | 43.90 | C |
| ATOM | 1544 | C | PHE | B | 87 | 51.726 | 12.583 | 23.432 | 1.00 | 43.25 | C |
| ATOM | 1545 | O | PHE | B | 87 | 51.548 | 13.314 | 24.408 | 1.00 | 43.61 | O |
| ATOM | 1546 | N | SER | B | 88 | 51.315 | 11.312 | 23.360 | 1.00 | 43.83 | N |
| ATOM | 1547 | CA | SER | B | 88 | 50.744 | 10.558 | 24.482 | 1.00 | 44.35 | C |
| ATOM | 1548 | CB | SER | B | 88 | 49.311 | 10.125 | 24.156 | 1.00 | 44.34 | C |
| ATOM | 1549 | OG | SER | B | 88 | 49.310 | 9.090 | 23.186 | 1.00 | 44.40 | O |
| ATOM | 1550 | C | SER | B | 88 | 51.610 | 9.322 | 24.808 | 1.00 | 44.75 | C |
| ATOM | 1551 | O | SER | B | 88 | 51.280 | 8.488 | 25.676 | 1.00 | 45.27 | O |
| ATOM | 1552 | N | PRO | B | 99 | 50.592 | 16.449 | 26.451 | 1.00 | 49.45 | N |
| ATOM | 1553 | CA | PRO | B | 99 | 51.216 | 17.750 | 26.211 | 1.00 | 48.89 | C |
| ATOM | 1554 | CB | PRO | B | 99 | 52.227 | 17.885 | 27.369 | 1.00 | 49.12 | C |
| ATOM | 1555 | CG | PRO | B | 99 | 52.424 | 16.435 | 27.917 | 1.00 | 49.96 | C |
| ATOM | 1556 | CD | PRO | B | 99 | 51.517 | 15.505 | 27.109 | 1.00 | 49.56 | C |
| ATOM | 1557 | C | PRO | B | 99 | 51.926 | 17.713 | 24.875 | 1.00 | 48.30 | C |
| ATOM | 1558 | O | PRO | B | 99 | 51.682 | 16.788 | 24.100 | 1.00 | 47.97 | O |
| ATOM | 1559 | N | GLY | B | 100 | 52.795 | 18.696 | 24.616 | 1.00 | 47.85 | N |
| ATOM | 1560 | CA | GLY | B | 100 | 53.472 | 18.823 | 23.322 | 1.00 | 47.04 | C |
| ATOM | 1561 | C | GLY | B | 100 | 54.567 | 19.872 | 23.223 | 1.00 | 46.58 | C |
| ATOM | 1562 | O | GLY | B | 100 | 54.601 | 20.824 | 23.997 | 1.00 | 46.58 | O |
| ATOM | 1563 | N | GLU | B | 101 | 55.432 | 19.709 | 22.226 | 1.00 | 46.07 | N |
| ATOM | 1564 | CA | GLU | B | 101 | 56.662 | 20.482 | 22.107 | 1.00 | 45.71 | C |
| ATOM | 1565 | CB | GLU | B | 101 | 57.818 | 19.564 | 22.490 | 1.00 | 45.87 | C |
| ATOM | 1566 | CG | GLU | B | 101 | 58.927 | 20.251 | 23.221 | 1.00 | 47.85 | C |
| ATOM | 1567 | CD | GLU | B | 101 | 58.610 | 20.469 | 24.686 | 1.00 | 50.59 | C |
| ATOM | 1568 | OE1 | GLU | B | 101 | 58.886 | 21.582 | 25.191 | 1.00 | 52.40 | O |
| ATOM | 1569 | OE2 | GLU | B | 101 | 58.096 | 19.533 | 25.337 | 1.00 | 51.15 | O |
| ATOM | 1570 | C | GLU | B | 101 | 56.892 | 21.092 | 20.691 | 1.00 | 44.89 | C |
| ATOM | 1571 | O | GLU | B | 101 | 56.642 | 20.439 | 19.685 | 1.00 | 44.67 | O |
| ATOM | 1572 | N | LYS | B | 102 | 57.376 | 22.336 | 20.630 | 1.00 | 44.18 | N |
| ATOM | 1573 | CA | LYS | B | 102 | 57.632 | 23.060 | 19.367 | 1.00 | 43.65 | C |
| ATOM | 1574 | CB | LYS | B | 102 | 57.152 | 24.511 | 19.470 | 1.00 | 43.65 | C |
| ATOM | 1575 | CG | LYS | B | 102 | 55.651 | 24.743 | 19.306 | 1.00 | 44.74 | C |
| ATOM | 1576 | CD | LYS | B | 102 | 55.342 | 26.238 | 19.111 | 1.00 | 45.16 | C |
| ATOM | 1577 | CE | LYS | B | 102 | 53.864 | 26.562 | 19.392 | 1.00 | 49.60 | C |
| ATOM | 1578 | NZ | LYS | B | 102 | 53.568 | 28.028 | 19.318 | 1.00 | 50.55 | N |
| ATOM | 1579 | C | LYS | B | 102 | 59.113 | 23.095 | 18.990 | 1.00 | 42.61 | C |
| ATOM | 1580 | O | LYS | B | 102 | 59.981 | 23.114 | 19.859 | 1.00 | 42.56 | O |
| ATOM | 1581 | N | GLY | B | 103 | 59.410 | 23.128 | 17.696 | 1.00 | 41.72 | N |
| ATOM | 1582 | CA | GLY | B | 103 | 60.808 | 23.232 | 17.259 | 1.00 | 40.69 | C |
| ATOM | 1583 | C | GLY | B | 103 | 61.291 | 24.672 | 17.305 | 1.00 | 39.71 | C |
| ATOM | 1584 | O | GLY | B | 103 | 60.478 | 25.592 | 17.294 | 1.00 | 39.87 | O |
| ATOM | 1585 | N | ALA | B | 104 | 62.601 | 24.884 | 17.338 | 1.00 | 38.38 | N |
| ATOM | 1586 | CA | ALA | B | 104 | 63.122 | 26.246 | 17.337 | 1.00 | 37.74 | C |
| ATOM | 1587 | CB | ALA | B | 104 | 64.632 | 26.254 | 17.379 | 1.00 | 37.58 | C |
| ATOM | 1588 | C | ALA | B | 104 | 62.620 | 27.082 | 16.151 | 1.00 | 37.52 | C |
| ATOM | 1589 | O | ALA | B | 104 | 62.298 | 28.245 | 16.315 | 1.00 | 38.11 | O |
| ATOM | 1590 | N | GLY | B | 105 | 62.558 | 26.513 | 14.957 | 1.00 | 36.98 | N |
| ATOM | 1591 | CA | GLY | B | 105 | 62.085 | 27.286 | 13.830 | 1.00 | 36.46 | C |
| ATOM | 1592 | C | GLY | B | 105 | 63.021 | 27.273 | 12.645 | 1.00 | 36.61 | C |

APPENDIX I(d)-continued

| | | | | | | | | | | | |
|---|---|---|---|---|---|---|---|---|---|---|---|
| ATOM | 1593 | O | GLY | B | 105 | 64.185 | 26.891 | 12.750 | 1.00 | 36.81 | O |
| ATOM | 1594 | N | THR | B | 106 | 62.488 | 27.689 | 11.507 | 1.00 | 36.30 | N |
| ATOM | 1595 | CA | THR | B | 106 | 63.245 | 27.842 | 10.289 | 1.00 | 35.99 | C |
| ATOM | 1596 | CB | THR | B | 106 | 62.713 | 26.880 | 9.195 | 1.00 | 36.37 | C |
| ATOM | 1597 | OG1 | THR | B | 106 | 62.974 | 25.531 | 9.571 | 1.00 | 35.72 | O |
| ATOM | 1598 | CG2 | THR | B | 106 | 63.395 | 27.128 | 7.874 | 1.00 | 37.55 | C |
| ATOM | 1599 | C | THR | B | 106 | 62.994 | 29.269 | 9.859 | 1.00 | 35.39 | C |
| ATOM | 1600 | O | THR | B | 106 | 61.844 | 29.677 | 9.772 | 1.00 | 35.20 | O |
| ATOM | 1601 | N | VAL | B | 107 | 64.051 | 30.042 | 9.624 | 1.00 | 34.99 | N |
| ATOM | 1602 | CA | VAL | B | 107 | 63.879 | 31.398 | 9.085 | 1.00 | 34.84 | C |
| ATOM | 1603 | CB | VAL | B | 107 | 64.838 | 32.416 | 9.701 | 1.00 | 34.41 | C |
| ATOM | 1604 | CG1 | VAL | B | 107 | 64.662 | 33.759 | 9.026 | 1.00 | 33.11 | C |
| ATOM | 1605 | CG2 | VAL | B | 107 | 64.589 | 32.524 | 11.189 | 1.00 | 33.77 | C |
| ATOM | 1606 | C | VAL | B | 107 | 64.046 | 31.362 | 7.568 | 1.00 | 35.66 | C |
| ATOM | 1607 | O | VAL | B | 107 | 65.165 | 31.227 | 7.029 | 1.00 | 35.61 | O |
| ATOM | 1608 | N | LEU | B | 108 | 62.914 | 31.458 | 6.879 | 1.00 | 36.39 | N |
| ATOM | 1609 | CA | LEU | B | 108 | 62.894 | 31.320 | 5.427 | 1.00 | 37.02 | C |
| ATOM | 1610 | CB | LEU | B | 108 | 61.650 | 30.552 | 4.959 | 1.00 | 36.96 | C |
| ATOM | 1611 | CG | LEU | B | 108 | 61.371 | 30.622 | 3.453 | 1.00 | 37.20 | C |
| ATOM | 1612 | CD1 | LEU | B | 108 | 62.500 | 29.997 | 2.636 | 1.00 | 36.00 | C |
| ATOM | 1613 | CD2 | LEU | B | 108 | 60.030 | 29.999 | 3.113 | 1.00 | 36.84 | C |
| ATOM | 1614 | C | LEU | B | 108 | 62.908 | 32.685 | 4.794 | 1.00 | 37.27 | C |
| ATOM | 1615 | O | LEU | B | 108 | 62.029 | 33.513 | 5.069 | 1.00 | 37.99 | O |
| ATOM | 1616 | N | THR | B | 109 | 63.897 | 32.932 | 3.951 | 1.00 | 37.20 | N |
| ATOM | 1617 | CA | THR | B | 109 | 63.800 | 34.092 | 3.081 | 1.00 | 37.29 | C |
| ATOM | 1618 | CB | THR | B | 109 | 64.859 | 35.169 | 3.392 | 1.00 | 37.40 | C |
| ATOM | 1619 | OG1 | THR | B | 109 | 65.039 | 35.985 | 2.230 | 1.00 | 38.63 | O |
| ATOM | 1620 | CG2 | THR | B | 109 | 66.182 | 34.552 | 3.782 | 1.00 | 37.84 | C |
| ATOM | 1621 | C | THR | B | 109 | 63.716 | 33.702 | 1.584 | 1.00 | 36.85 | C |
| ATOM | 1622 | O | THR | B | 109 | 64.405 | 32.776 | 1.110 | 1.00 | 36.94 | O |
| ATOM | 1623 | N | VAL | B | 110 | 62.823 | 34.388 | 0.867 | 1.00 | 36.01 | N |
| ATOM | 1624 | CA | VAL | B | 110 | 62.546 | 34.084 | −0.551 | 1.00 | 35.02 | C |
| ATOM | 1625 | CB | VAL | B | 110 | 61.059 | 33.691 | −0.773 | 1.00 | 34.55 | C |
| ATOM | 1626 | CG1 | VAL | B | 110 | 60.822 | 33.302 | −2.206 | 1.00 | 33.34 | C |
| ATOM | 1627 | CG2 | VAL | B | 110 | 60.697 | 32.549 | 0.109 | 1.00 | 34.63 | C |
| ATOM | 1628 | C | VAL | B | 110 | 62.946 | 35.212 | −1.532 | 1.00 | 34.56 | C |
| ATOM | 1629 | O | VAL | B | 110 | 62.394 | 36.325 | −1.477 | 1.00 | 34.65 | O |
| ATOM | 1630 | N | LYS | B | 111 | 63.918 | 34.887 | −2.390 | 1.00 | 33.54 | N |
| ATOM | 1631 | CA | LYS | B | 111 | 64.353 | 35.612 | −3.609 | 1.00 | 32.70 | C |
| ATOM | 1632 | CB | LYS | B | 111 | 63.710 | 36.984 | −3.859 | 1.00 | 32.41 | C |
| ATOM | 1633 | CG | LYS | B | 111 | 62.878 | 37.004 | −5.146 | 1.00 | 31.57 | C |
| ATOM | 1634 | CD | LYS | B | 111 | 62.464 | 38.390 | −5.630 | 1.00 | 31.59 | C |
| ATOM | 1635 | CE | LYS | B | 111 | 63.615 | 39.127 | −6.288 | 1.00 | 29.56 | C |
| ATOM | 1636 | NZ | LYS | B | 111 | 64.096 | 38.345 | −7.446 | 1.00 | 28.53 | N |
| ATOM | 1637 | C | LYS | B | 111 | 65.872 | 35.660 | −3.696 | 1.00 | 33.30 | C |
| ATOM | 1638 | O | LYS | B | 111 | 66.523 | 36.251 | −2.841 | 1.00 | 33.69 | O |
| ATOM | 1639 | N | ALA | C | 1 | 27.731 | 10.932 | 10.845 | 1.00 | 36.73 | N |
| ATOM | 1640 | CA | ALA | C | 1 | 26.819 | 11.600 | 11.783 | 1.00 | 37.06 | C |
| ATOM | 1641 | CB | ALA | C | 1 | 26.956 | 10.995 | 13.140 | 1.00 | 36.58 | C |
| ATOM | 1642 | C | ALA | C | 1 | 27.172 | 13.073 | 11.784 | 1.00 | 37.88 | C |
| ATOM | 1643 | O | ALA | C | 1 | 28.275 | 13.436 | 11.393 | 1.00 | 38.55 | O |
| ATOM | 1644 | N | TRP | C | 2 | 26.234 | 13.929 | 12.184 | 1.00 | 38.85 | N |
| ATOM | 1645 | CA | TRP | C | 2 | 26.434 | 15.391 | 12.169 | 1.00 | 39.92 | C |
| ATOM | 1646 | CB | TRP | C | 2 | 26.369 | 15.963 | 10.730 | 1.00 | 39.79 | C |
| ATOM | 1647 | CG | TRP | C | 2 | 25.004 | 15.897 | 10.161 | 1.00 | 39.52 | C |
| ATOM | 1648 | CD1 | TRP | C | 2 | 24.394 | 14.800 | 9.651 | 1.00 | 39.33 | C |
| ATOM | 1649 | NE1 | TRP | C | 2 | 23.119 | 15.102 | 9.263 | 1.00 | 39.75 | N |
| ATOM | 1650 | CE2 | TRP | C | 2 | 22.882 | 16.424 | 9.523 | 1.00 | 40.28 | C |
| ATOM | 1651 | CD2 | TRP | C | 2 | 24.048 | 16.955 | 10.092 | 1.00 | 39.55 | C |
| ATOM | 1652 | CE3 | TRP | C | 2 | 24.067 | 18.304 | 10.444 | 1.00 | 39.87 | C |
| ATOM | 1653 | CZ3 | TRP | C | 2 | 22.936 | 19.067 | 10.220 | 1.00 | 38.76 | C |
| ATOM | 1654 | CH2 | TRP | C | 2 | 21.800 | 18.517 | 9.656 | 1.00 | 39.45 | C |
| ATOM | 1655 | CZ2 | TRP | C | 2 | 21.745 | 17.196 | 9.298 | 1.00 | 40.40 | C |
| ATOM | 1656 | C | TRP | C | 2 | 25.350 | 16.008 | 13.051 | 1.00 | 40.73 | C |
| ATOM | 1657 | O | TRP | C | 2 | 24.265 | 15.425 | 13.181 | 1.00 | 41.56 | O |
| ATOM | 1658 | N | VAL | C | 3 | 25.635 | 17.161 | 13.664 | 1.00 | 41.60 | N |
| ATOM | 1659 | CA | VAL | C | 3 | 24.695 | 17.809 | 14.601 | 1.00 | 42.64 | C |
| ATOM | 1660 | CB | VAL | C | 3 | 25.381 | 18.237 | 15.920 | 1.00 | 42.63 | C |
| ATOM | 1661 | CG1 | VAL | C | 3 | 24.368 | 18.848 | 16.874 | 1.00 | 43.03 | C |
| ATOM | 1662 | CG2 | VAL | C | 3 | 26.027 | 17.038 | 16.593 | 1.00 | 42.94 | C |
| ATOM | 1663 | C | VAL | C | 3 | 23.982 | 19.013 | 13.975 | 1.00 | 43.23 | C |
| ATOM | 1664 | O | VAL | C | 3 | 24.639 | 19.915 | 13.460 | 1.00 | 44.10 | O |
| ATOM | 1665 | N | ASP | C | 4 | 22.646 | 19.001 | 14.000 | 1.00 | 43.73 | N |
| ATOM | 1666 | CA | ASP | C | 4 | 21.816 | 20.094 | 13.498 | 1.00 | 43.97 | C |
| ATOM | 1667 | CB | ASP | C | 4 | 20.470 | 19.545 | 13.016 | 1.00 | 43.97 | C |
| ATOM | 1668 | CG | ASP | C | 4 | 19.696 | 20.533 | 12.151 | 1.00 | 45.56 | C |
| ATOM | 1669 | OD1 | ASP | C | 4 | 18.573 | 20.188 | 11.732 | 1.00 | 46.90 | O |
| ATOM | 1670 | OD2 | ASP | C | 4 | 20.190 | 21.651 | 11.867 | 1.00 | 48.30 | O |
| ATOM | 1671 | C | ASP | C | 4 | 21.575 | 21.057 | 14.651 | 1.00 | 44.27 | C |
| ATOM | 1672 | O | ASP | C | 4 | 20.836 | 20.719 | 15.580 | 1.00 | 44.63 | O |

APPENDIX I(d)-continued

| | | | | | | | | | | |
|---|---|---|---|---|---|---|---|---|---|---|
| ATOM | 1673 | N | GLN | C | 5 | 22.187 | 22.245 | 14.611 | 1.00 | 44.42 N |
| ATOM | 1674 | CA | GLN | C | 5 | 21.982 | 23.243 | 15.675 | 1.00 | 44.16 C |
| ATOM | 1675 | CB | GLN | C | 5 | 23.317 | 23.653 | 16.240 | 1.00 | 44.58 C |
| ATOM | 1676 | CG | GLN | C | 5 | 23.245 | 24.644 | 17.374 | 1.00 | 44.79 C |
| ATOM | 1677 | CD | GLN | C | 5 | 24.625 | 25.031 | 17.833 | 1.00 | 45.01 C |
| ATOM | 1678 | OE1 | GLN | C | 5 | 25.593 | 24.300 | 17.586 | 1.00 | 42.96 O |
| ATOM | 1679 | NE2 | GLN | C | 5 | 24.733 | 26.188 | 18.496 | 1.00 | 45.43 N |
| ATOM | 1680 | C | GLN | C | 5 | 21.209 | 24.490 | 15.245 | 1.00 | 43.80 C |
| ATOM | 1681 | O | GLN | C | 5 | 21.529 | 25.095 | 14.240 | 1.00 | 43.89 O |
| ATOM | 1682 | N | THR | C | 6 | 20.190 | 24.850 | 16.020 | 1.00 | 43.48 N |
| ATOM | 1683 | CA | THR | C | 6 | 19.359 | 26.039 | 15.793 | 1.00 | 43.34 C |
| ATOM | 1684 | CB | THR | C | 6 | 17.908 | 25.659 | 15.350 | 1.00 | 43.54 C |
| ATOM | 1685 | OG1 | THR | C | 6 | 17.288 | 24.832 | 16.341 | 1.00 | 42.46 O |
| ATOM | 1686 | CG2 | THR | C | 6 | 17.890 | 24.904 | 14.013 | 1.00 | 43.93 C |
| ATOM | 1687 | C | THR | C | 6 | 19.277 | 26.803 | 17.122 | 1.00 | 43.40 C |
| ATOM | 1688 | O | THR | C | 6 | 19.339 | 26.165 | 18.188 | 1.00 | 43.20 O |
| ATOM | 1689 | N | PRO | C | 7 | 19.166 | 28.159 | 17.086 | 1.00 | 43.22 N |
| ATOM | 1690 | CA | PRO | C | 7 | 19.201 | 29.027 | 15.922 | 1.00 | 43.33 C |
| ATOM | 1691 | CB | PRO | C | 7 | 18.603 | 30.348 | 16.434 | 1.00 | 43.14 C |
| ATOM | 1692 | CG | PRO | C | 7 | 18.411 | 30.213 | 17.881 | 1.00 | 42.62 C |
| ATOM | 1693 | CD | PRO | C | 7 | 19.035 | 28.945 | 18.329 | 1.00 | 43.17 C |
| ATOM | 1694 | C | PRO | C | 7 | 20.644 | 29.269 | 15.507 | 1.00 | 43.73 C |
| ATOM | 1695 | O | PRO | C | 7 | 21.538 | 29.273 | 16.358 | 1.00 | 44.00 O |
| ATOM | 1696 | N | ARG | C | 8 | 20.875 | 29.441 | 14.213 | 1.00 | 43.91 N |
| ATOM | 1697 | CA | ARG | C | 8 | 22.203 | 29.804 | 13.741 | 1.00 | 44.42 C |
| ATOM | 1698 | CB | ARG | C | 8 | 22.288 | 29.736 | 12.203 | 1.00 | 44.66 C |
| ATOM | 1699 | CG | ARG | C | 8 | 21.908 | 28.355 | 11.559 | 1.00 | 47.05 C |
| ATOM | 1700 | CD | ARG | C | 8 | 23.002 | 27.235 | 11.669 | 1.00 | 48.64 C |
| ATOM | 1701 | NE | ARG | C | 8 | 24.326 | 27.765 | 12.042 | 1.00 | 50.62 N |
| ATOM | 1702 | CZ | ARG | C | 8 | 25.368 | 27.927 | 11.221 | 1.00 | 49.49 C |
| ATOM | 1703 | NH1 | ARG | C | 8 | 26.492 | 28.442 | 11.696 | 1.00 | 47.43 N |
| ATOM | 1704 | NH2 | ARG | C | 8 | 25.306 | 27.560 | 9.943 | 1.00 | 49.11 N |
| ATOM | 1705 | C | ARG | C | 8 | 22.622 | 31.191 | 14.313 | 1.00 | 43.96 C |
| ATOM | 1706 | O | ARG | C | 8 | 23.704 | 31.331 | 14.886 | 1.00 | 44.32 O |
| ATOM | 1707 | N | SER | C | 9 | 21.774 | 32.205 | 14.189 | 1.00 | 43.09 N |
| ATOM | 1708 | CA | SER | C | 9 | 22.056 | 33.463 | 14.876 | 1.00 | 42.40 C |
| ATOM | 1709 | CB | SER | C | 9 | 22.735 | 34.495 | 13.951 | 1.00 | 42.53 C |
| ATOM | 1710 | OG | SER | C | 9 | 21.816 | 35.166 | 13.109 | 1.00 | 42.75 O |
| ATOM | 1711 | C | SER | C | 9 | 20.802 | 34.007 | 15.545 | 1.00 | 41.72 C |
| ATOM | 1712 | O | SER | C | 9 | 19.681 | 33.687 | 15.126 | 1.00 | 41.94 O |
| ATOM | 1713 | N | VAL | C | 10 | 20.995 | 34.806 | 16.593 | 1.00 | 40.57 N |
| ATOM | 1714 | CA | VAL | C | 10 | 19.877 | 35.325 | 17.371 | 1.00 | 39.60 C |
| ATOM | 1715 | CB | VAL | C | 10 | 19.254 | 34.205 | 18.270 | 1.00 | 39.41 C |
| ATOM | 1716 | CG1 | VAL | C | 10 | 20.299 | 33.568 | 19.163 | 1.00 | 39.02 C |
| ATOM | 1717 | CG2 | VAL | C | 10 | 18.079 | 34.712 | 19.075 | 1.00 | 38.83 C |
| ATOM | 1718 | C | VAL | C | 10 | 20.258 | 36.565 | 18.174 | 1.00 | 39.27 C |
| ATOM | 1719 | O | VAL | C | 10 | 21.374 | 36.694 | 18.670 | 1.00 | 39.55 O |
| ATOM | 1720 | N | THR | C | 11 | 19.317 | 37.488 | 18.275 | 1.00 | 38.96 N |
| ATOM | 1721 | CA | THR | C | 11 | 19.461 | 38.661 | 19.129 | 1.00 | 38.39 C |
| ATOM | 1722 | CB | THR | C | 11 | 19.299 | 39.939 | 18.320 | 1.00 | 38.22 C |
| ATOM | 1723 | OG1 | THR | C | 11 | 20.199 | 39.883 | 17.211 | 1.00 | 38.20 O |
| ATOM | 1724 | CG2 | THR | C | 11 | 19.625 | 41.165 | 19.161 | 1.00 | 38.24 C |
| ATOM | 1725 | C | THR | C | 11 | 18.445 | 38.597 | 20.269 | 1.00 | 38.23 C |
| ATOM | 1726 | O | THR | C | 11 | 17.265 | 38.289 | 20.052 | 1.00 | 38.08 O |
| ATOM | 1727 | N | LYS | C | 12 | 18.924 | 38.844 | 21.485 | 1.00 | 38.02 N |
| ATOM | 1728 | CA | LYS | C | 12 | 18.089 | 38.828 | 22.677 | 1.00 | 38.13 C |
| ATOM | 1729 | CB | LYS | C | 12 | 18.255 | 37.518 | 23.457 | 1.00 | 38.13 C |
| ATOM | 1730 | CG | LYS | C | 12 | 17.558 | 36.338 | 22.799 | 1.00 | 38.06 C |
| ATOM | 1731 | CD | LYS | C | 12 | 16.847 | 35.434 | 23.786 | 1.00 | 37.36 C |
| ATOM | 1732 | CE | LYS | C | 12 | 15.673 | 34.699 | 23.122 | 1.00 | 36.90 C |
| ATOM | 1733 | NZ | LYS | C | 12 | 14.422 | 35.519 | 23.128 | 1.00 | 37.18 N |
| ATOM | 1734 | C | LYS | C | 12 | 18.465 | 39.995 | 23.549 | 1.00 | 38.34 C |
| ATOM | 1735 | O | LYS | C | 12 | 19.636 | 40.304 | 23.688 | 1.00 | 38.48 O |
| ATOM | 1736 | N | GLU | C | 13 | 17.473 | 40.650 | 24.134 | 1.00 | 38.77 N |
| ATOM | 1737 | CA | GLU | C | 13 | 17.743 | 41.773 | 25.018 | 1.00 | 39.16 C |
| ATOM | 1738 | CB | GLU | C | 13 | 16.521 | 42.674 | 25.120 | 1.00 | 39.34 C |
| ATOM | 1739 | CG | GLU | C | 13 | 16.396 | 43.631 | 23.945 | 1.00 | 40.22 C |
| ATOM | 1740 | CD | GLU | C | 13 | 14.957 | 43.847 | 23.517 | 1.00 | 41.71 C |
| ATOM | 1741 | OE1 | GLU | C | 13 | 14.657 | 44.910 | 22.915 | 1.00 | 41.36 O |
| ATOM | 1742 | OE2 | GLU | C | 13 | 14.126 | 42.948 | 23.784 | 1.00 | 42.65 O |
| ATOM | 1743 | C | GLU | C | 13 | 18.207 | 41.306 | 26.391 | 1.00 | 39.19 C |
| ATOM | 1744 | O | GLU | C | 13 | 17.979 | 40.158 | 26.771 | 1.00 | 39.29 O |
| ATOM | 1745 | N | THR | C | 14 | 18.884 | 42.194 | 27.111 | 1.00 | 39.39 N |
| ATOM | 1746 | CA | THR | C | 14 | 19.417 | 41.901 | 28.436 | 1.00 | 39.66 C |
| ATOM | 1747 | CB | THR | C | 14 | 20.096 | 43.159 | 29.020 | 1.00 | 39.57 C |
| ATOM | 1748 | OG1 | THR | C | 14 | 21.151 | 43.562 | 28.138 | 1.00 | 39.75 O |
| ATOM | 1749 | CG2 | THR | C | 14 | 20.671 | 42.907 | 30.415 | 1.00 | 39.37 C |
| ATOM | 1750 | C | THR | C | 14 | 18.313 | 41.392 | 29.358 | 1.00 | 40.11 C |
| ATOM | 1751 | O | THR | C | 14 | 17.199 | 41.920 | 29.347 | 1.00 | 40.08 O |
| ATOM | 1752 | N | GLY | C | 15 | 18.614 | 40.346 | 30.124 | 1.00 | 40.51 N |

APPENDIX I(d)-continued

| ATOM | 1753 | CA | GLY | C | 15 | 17.666 | 39.811 | 31.098 | 1.00 | 41.18 | C |
|---|---|---|---|---|---|---|---|---|---|---|---|
| ATOM | 1754 | C | GLY | C | 15 | 16.780 | 38.700 | 30.563 | 1.00 | 41.82 | C |
| ATOM | 1755 | O | GLY | C | 15 | 16.190 | 37.945 | 31.337 | 1.00 | 42.17 | O |
| ATOM | 1756 | N | GLU | C | 16 | 16.679 | 38.593 | 29.241 | 1.00 | 42.08 | N |
| ATOM | 1757 | CA | GLU | C | 16 | 15.961 | 37.491 | 28.613 | 1.00 | 42.31 | C |
| ATOM | 1758 | CB | GLU | C | 16 | 15.680 | 37.811 | 27.148 | 1.00 | 42.35 | C |
| ATOM | 1759 | CG | GLU | C | 16 | 14.839 | 39.050 | 26.948 | 1.00 | 42.99 | C |
| ATOM | 1760 | CD | GLU | C | 16 | 14.079 | 39.046 | 25.640 | 1.00 | 44.31 | C |
| ATOM | 1761 | OE1 | GLU | C | 16 | 13.949 | 40.129 | 25.026 | 1.00 | 44.89 | O |
| ATOM | 1762 | OE2 | GLU | C | 16 | 13.600 | 37.966 | 25.232 | 1.00 | 44.98 | O |
| ATOM | 1763 | C | GLU | C | 16 | 16.795 | 36.222 | 28.738 | 1.00 | 42.46 | C |
| ATOM | 1764 | O | GLU | C | 16 | 17.864 | 36.247 | 29.343 | 1.00 | 42.47 | O |
| ATOM | 1765 | N | SER | C | 17 | 16.311 | 35.115 | 28.180 | 1.00 | 42.67 | N |
| ATOM | 1766 | CA | SER | C | 17 | 17.070 | 33.867 | 28.200 | 1.00 | 43.22 | C |
| ATOM | 1767 | CB | SER | C | 17 | 16.598 | 32.956 | 29.336 | 1.00 | 43.10 | C |
| ATOM | 1768 | OG | SER | C | 17 | 15.213 | 32.696 | 29.259 | 1.00 | 43.49 | C |
| ATOM | 1769 | C | SER | C | 17 | 17.028 | 33.133 | 26.867 | 1.00 | 43.49 | C |
| ATOM | 1770 | O | SER | C | 17 | 16.053 | 33.244 | 26.138 | 1.00 | 43.98 | O |
| ATOM | 1771 | N | LEU | C | 18 | 18.088 | 32.386 | 26.559 | 1.00 | 43.91 | N |
| ATOM | 1772 | CA | LEU | C | 18 | 18.195 | 31.625 | 25.300 | 1.00 | 44.39 | C |
| ATOM | 1773 | CB | LEU | C | 18 | 19.588 | 31.817 | 24.686 | 1.00 | 43.94 | C |
| ATOM | 1774 | CG | LEU | C | 18 | 19.822 | 32.059 | 23.187 | 1.00 | 43.64 | C |
| ATOM | 1775 | CD1 | LEU | C | 18 | 21.247 | 31.649 | 22.849 | 1.00 | 44.22 | C |
| ATOM | 1776 | CD2 | LEU | C | 18 | 18.821 | 31.411 | 22.214 | 1.00 | 42.64 | C |
| ATOM | 1777 | C | LEU | C | 18 | 17.988 | 30.115 | 25.485 | 1.00 | 44.89 | C |
| ATOM | 1778 | O | LEU | C | 18 | 18.428 | 29.525 | 26.491 | 1.00 | 45.55 | O |
| ATOM | 1779 | N | THR | C | 19 | 17.345 | 29.491 | 24.507 | 1.00 | 44.93 | N |
| ATOM | 1780 | CA | THR | C | 19 | 17.395 | 28.044 | 24.375 | 1.00 | 45.04 | C |
| ATOM | 1781 | CB | THR | C | 19 | 15.991 | 27.418 | 24.390 | 1.00 | 44.97 | C |
| ATOM | 1782 | OG1 | THR | C | 19 | 15.299 | 27.824 | 25.571 | 1.00 | 45.74 | O |
| ATOM | 1783 | CG2 | THR | C | 19 | 16.080 | 25.921 | 24.401 | 1.00 | 45.54 | C |
| ATOM | 1784 | C | THR | C | 19 | 18.080 | 27.704 | 23.066 | 1.00 | 45.01 | C |
| ATOM | 1785 | O | THR | C | 19 | 17.667 | 28.159 | 22.012 | 1.00 | 45.60 | O |
| ATOM | 1786 | N | ILE | C | 20 | 19.137 | 26.919 | 23.135 | 1.00 | 45.26 | N |
| ATOM | 1787 | CA | ILE | C | 20 | 19.728 | 26.320 | 21.949 | 1.00 | 45.56 | C |
| ATOM | 1788 | CB | ILE | C | 20 | 21.280 | 26.416 | 21.988 | 1.00 | 45.39 | C |
| ATOM | 1789 | CG1 | ILE | C | 20 | 21.706 | 27.836 | 22.365 | 1.00 | 45.10 | C |
| ATOM | 1790 | CD1 | ILE | C | 20 | 23.194 | 28.035 | 22.546 | 1.00 | 45.39 | C |
| ATOM | 1791 | CG2 | ILE | C | 20 | 21.888 | 26.037 | 20.644 | 1.00 | 45.52 | C |
| ATOM | 1792 | C | ILE | C | 20 | 19.255 | 24.851 | 21.904 | 1.00 | 46.07 | C |
| ATOM | 1793 | O | ILE | C | 20 | 19.294 | 24.158 | 22.916 | 1.00 | 46.16 | O |
| ATOM | 1794 | N | ASN | C | 21 | 18.781 | 24.393 | 20.747 | 1.00 | 46.49 | N |
| ATOM | 1795 | CA | ASN | C | 21 | 18.442 | 22.980 | 20.551 | 1.00 | 46.90 | C |
| ATOM | 1796 | CB | ASN | C | 21 | 17.019 | 22.815 | 20.012 | 1.00 | 46.94 | C |
| ATOM | 1797 | CG | ASN | C | 21 | 15.994 | 23.612 | 20.799 | 1.00 | 48.31 | C |
| ATOM | 1798 | OD1 | ASN | C | 21 | 15.564 | 24.676 | 20.361 | 1.00 | 49.34 | O |
| ATOM | 1799 | ND2 | ASN | C | 21 | 15.592 | 23.100 | 21.965 | 1.00 | 49.90 | N |
| ATOM | 1800 | C | ASN | C | 21 | 19.390 | 22.387 | 19.542 | 1.00 | 46.87 | C |
| ATOM | 1801 | O | ASN | C | 21 | 19.539 | 22.928 | 18.468 | 1.00 | 47.41 | O |
| ATOM | 1802 | N | CYS | C | 22 | 20.035 | 21.282 | 19.883 | 1.00 | 46.92 | N |
| ATOM | 1803 | CA | CYS | C | 22 | 20.816 | 20.516 | 18.917 | 1.00 | 46.98 | C |
| ATOM | 1804 | CB | CYS | C | 22 | 22.261 | 20.348 | 19.412 | 1.00 | 47.47 | C |
| ATOM | 1805 | SG | CYS | C | 22 | 23.260 | 21.888 | 19.588 | 1.00 | 53.20 | S |
| ATOM | 1806 | C | CYS | C | 22 | 20.188 | 19.123 | 18.685 | 1.00 | 45.66 | C |
| ATOM | 1807 | O | CYS | C | 22 | 19.582 | 18.548 | 19.599 | 1.00 | 45.62 | O |
| ATOM | 1808 | N | ALA | C | 23 | 20.335 | 18.579 | 17.477 | 1.00 | 43.90 | N |
| ATOM | 1809 | CA | ALA | C | 23 | 19.989 | 17.185 | 17.252 | 1.00 | 42.45 | C |
| ATOM | 1810 | CB | ALA | C | 23 | 18.682 | 17.045 | 16.532 | 1.00 | 42.68 | C |
| ATOM | 1811 | C | ALA | C | 23 | 21.095 | 16.436 | 16.524 | 1.00 | 42.11 | C |
| ATOM | 1812 | O | ALA | C | 23 | 21.709 | 16.947 | 15.561 | 1.00 | 41.96 | O |
| ATOM | 1813 | N | LEU | C | 24 | 21.359 | 15.222 | 17.019 | 1.00 | 40.74 | N |
| ATOM | 1814 | CA | LEU | C | 24 | 22.336 | 14.323 | 16.417 | 1.00 | 39.93 | C |
| ATOM | 1815 | CB | LEU | C | 24 | 22.925 | 13.351 | 17.474 | 1.00 | 39.48 | C |
| ATOM | 1816 | CG | LEU | C | 24 | 24.008 | 12.327 | 17.060 | 1.00 | 38.90 | C |
| ATOM | 1817 | CD1 | LEU | C | 24 | 24.451 | 11.459 | 18.251 | 1.00 | 36.33 | C |
| ATOM | 1818 | CD2 | LEU | C | 24 | 25.205 | 12.958 | 16.367 | 1.00 | 32.90 | C |
| ATOM | 1819 | C | LEU | C | 24 | 21.636 | 13.575 | 15.281 | 1.00 | 39.20 | C |
| ATOM | 1820 | O | LEU | C | 24 | 20.666 | 12.842 | 15.537 | 1.00 | 38.96 | O |
| ATOM | 1821 | N | LYS | C | 25 | 22.095 | 13.789 | 14.042 | 1.00 | 37.85 | N |
| ATOM | 1822 | CA | LYS | C | 25 | 21.501 | 13.105 | 12.903 | 1.00 | 37.40 | C |
| ATOM | 1823 | CB | LYS | C | 25 | 20.947 | 14.081 | 11.875 | 1.00 | 37.17 | C |
| ATOM | 1824 | CG | LYS | C | 25 | 20.575 | 15.394 | 12.436 | 1.00 | 38.56 | C |
| ATOM | 1825 | CD | LYS | C | 25 | 19.242 | 15.866 | 11.907 | 1.00 | 41.52 | C |
| ATOM | 1826 | CE | LYS | C | 25 | 18.086 | 15.341 | 12.746 | 1.00 | 41.53 | C |
| ATOM | 1827 | NZ | LYS | C | 25 | 17.003 | 16.347 | 12.725 | 1.00 | 44.19 | N |
| ATOM | 1828 | C | LYS | C | 25 | 22.475 | 12.155 | 12.219 | 1.00 | 37.29 | C |
| ATOM | 1829 | O | LYS | C | 25 | 23.690 | 12.393 | 12.187 | 1.00 | 36.68 | O |
| ATOM | 1830 | N | ASN | C | 26 | 21.899 | 11.096 | 11.648 | 1.00 | 37.08 | N |
| ATOM | 1831 | CA | ASN | C | 26 | 22.619 | 10.045 | 10.951 | 1.00 | 36.94 | C |
| ATOM | 1832 | CB | ASN | C | 26 | 23.183 | 10.554 | 9.637 | 1.00 | 36.73 | C |

APPENDIX I(d)-continued

| ATOM | 1833 | CG | ASN | C | 26 | 23.422 | 9.445 | 8.640 | 1.00 | 36.96 | C |
|---|---|---|---|---|---|---|---|---|---|---|---|
| ATOM | 1834 | OD1 | ASN | C | 26 | 24.386 | 9.500 | 7.886 | 1.00 | 37.38 | O |
| ATOM | 1835 | ND2 | ASN | C | 26 | 22.554 | 8.429 | 8.630 | 1.00 | 37.00 | N |
| ATOM | 1836 | C | ASN | C | 26 | 23.693 | 9.383 | 11.800 | 1.00 | 37.21 | C |
| ATOM | 1837 | O | ASN | C | 26 | 24.818 | 9.162 | 11.347 | 1.00 | 37.58 | O |
| ATOM | 1838 | N | ALA | C | 27 | 23.324 | 9.063 | 13.036 | 1.00 | 37.26 | N |
| ATOM | 1839 | CA | ALA | C | 27 | 24.168 | 8.297 | 13.926 | 1.00 | 37.54 | C |
| ATOM | 1840 | CB | ALA | C | 27 | 24.279 | 9.001 | 15.233 | 1.00 | 37.73 | C |
| ATOM | 1841 | C | ALA | C | 27 | 23.610 | 6.889 | 14.126 | 1.00 | 37.64 | C |
| ATOM | 1842 | O | ALA | C | 27 | 22.456 | 6.720 | 14.500 | 1.00 | 37.87 | O |
| ATOM | 1843 | N | ALA | C | 28 | 24.427 | 5.877 | 13.860 | 1.00 | 38.19 | N |
| ATOM | 1844 | CA | ALA | C | 28 | 24.031 | 4.483 | 14.114 | 1.00 | 38.86 | C |
| ATOM | 1845 | CB | ALA | C | 28 | 25.016 | 3.490 | 13.457 | 1.00 | 38.12 | C |
| ATOM | 1846 | C | ALA | C | 28 | 23.966 | 4.271 | 15.621 | 1.00 | 39.37 | C |
| ATOM | 1847 | O | ALA | C | 28 | 23.060 | 3.640 | 16.125 | 1.00 | 39.79 | O |
| ATOM | 1848 | N | ASP | C | 29 | 24.917 | 4.867 | 16.329 | 1.00 | 39.97 | N |
| ATOM | 1849 | CA | ASP | C | 29 | 25.115 | 4.646 | 17.740 | 1.00 | 40.44 | C |
| ATOM | 1850 | CB | ASP | C | 29 | 26.597 | 4.825 | 18.041 | 1.00 | 40.96 | C |
| ATOM | 1851 | CG | ASP | C | 29 | 27.479 | 3.880 | 17.226 | 1.00 | 43.39 | C |
| ATOM | 1852 | OD1 | ASP | C | 29 | 27.169 | 2.654 | 17.165 | 1.00 | 44.27 | O |
| ATOM | 1853 | OD2 | ASP | C | 29 | 28.495 | 4.369 | 16.657 | 1.00 | 46.39 | O |
| ATOM | 1854 | C | ASP | C | 29 | 24.293 | 5.571 | 18.634 | 1.00 | 40.24 | C |
| ATOM | 1855 | O | ASP | C | 29 | 23.689 | 6.523 | 18.171 | 1.00 | 39.90 | O |
| ATOM | 1856 | N | ASP | C | 30 | 24.312 | 5.275 | 19.929 | 1.00 | 40.41 | N |
| ATOM | 1857 | CA | ASP | C | 30 | 23.546 | 5.989 | 20.938 | 1.00 | 40.34 | C |
| ATOM | 1858 | CB | ASP | C | 30 | 23.311 | 5.049 | 22.117 | 1.00 | 40.32 | C |
| ATOM | 1859 | CG | ASP | C | 30 | 22.420 | 3.865 | 21.764 | 1.00 | 42.22 | C |
| ATOM | 1860 | OD1 | ASP | C | 30 | 22.419 | 2.885 | 22.530 | 1.00 | 43.42 | O |
| ATOM | 1861 | OD2 | ASP | C | 30 | 21.694 | 3.901 | 20.742 | 1.00 | 45.93 | O |
| ATOM | 1862 | C | ASP | C | 30 | 24.234 | 7.271 | 21.441 | 1.00 | 40.30 | C |
| ATOM | 1863 | O | ASP | C | 30 | 25.457 | 7.289 | 21.620 | 1.00 | 40.36 | O |
| ATOM | 1864 | N | LEU | C | 31 | 23.444 | 8.326 | 21.680 | 1.00 | 40.03 | N |
| ATOM | 1865 | CA | LEU | C | 31 | 23.909 | 9.550 | 22.316 | 1.00 | 40.03 | C |
| ATOM | 1866 | CB | LEU | C | 31 | 22.763 | 10.513 | 22.468 | 1.00 | 39.83 | C |
| ATOM | 1867 | CG | LEU | C | 31 | 22.910 | 12.041 | 22.408 | 1.00 | 40.23 | C |
| ATOM | 1868 | CD1 | LEU | C | 31 | 24.306 | 12.606 | 22.614 | 1.00 | 38.68 | C |
| ATOM | 1869 | CD2 | LEU | C | 31 | 21.917 | 12.646 | 23.374 | 1.00 | 39.10 | C |
| ATOM | 1870 | C | LEU | C | 31 | 24.411 | 9.204 | 23.703 | 1.00 | 40.85 | C |
| ATOM | 1871 | O | LEU | C | 31 | 23.685 | 8.625 | 24.518 | 1.00 | 40.98 | O |
| ATOM | 1872 | N | GLU | C | 32 | 25.657 | 9.566 | 23.973 | 1.00 | 41.58 | N |
| ATOM | 1873 | CA | GLU | C | 32 | 26.345 | 9.082 | 25.147 | 1.00 | 42.36 | C |
| ATOM | 1874 | CB | GLU | C | 32 | 27.489 | 8.170 | 24.722 | 1.00 | 42.52 | C |
| ATOM | 1875 | CG | GLU | C | 32 | 28.036 | 7.284 | 25.826 | 1.00 | 45.19 | C |
| ATOM | 1876 | CD | GLU | C | 32 | 27.062 | 6.205 | 26.317 | 1.00 | 48.72 | C |
| ATOM | 1877 | OE1 | GLU | C | 32 | 27.214 | 5.790 | 27.491 | 1.00 | 49.89 | O |
| ATOM | 1878 | OE2 | GLU | C | 32 | 26.165 | 5.763 | 25.549 | 1.00 | 49.60 | O |
| ATOM | 1879 | C | GLU | C | 32 | 26.868 | 10.200 | 26.015 | 1.00 | 42.59 | C |
| ATOM | 1880 | O | GLU | C | 32 | 26.954 | 10.040 | 27.222 | 1.00 | 42.66 | O |
| ATOM | 1881 | N | ARG | C | 33 | 27.219 | 11.326 | 25.400 | 1.00 | 43.15 | N |
| ATOM | 1882 | CA | ARG | C | 33 | 27.768 | 12.463 | 26.119 | 1.00 | 44.02 | C |
| ATOM | 1883 | CB | ARG | C | 33 | 29.297 | 12.366 | 26.188 | 1.00 | 43.78 | C |
| ATOM | 1884 | CG | ARG | C | 33 | 29.835 | 12.760 | 27.549 | 1.00 | 45.32 | C |
| ATOM | 1885 | CD | ARG | C | 33 | 31.358 | 12.861 | 27.670 | 1.00 | 45.61 | C |
| ATOM | 1886 | NE | ARG | C | 33 | 31.932 | 13.600 | 26.555 | 1.00 | 50.54 | N |
| ATOM | 1887 | CZ | ARG | C | 33 | 32.936 | 13.160 | 25.790 | 1.00 | 53.62 | C |
| ATOM | 1888 | NH1 | ARG | C | 33 | 33.538 | 11.995 | 26.050 | 1.00 | 53.13 | N |
| ATOM | 1889 | NH2 | ARG | C | 33 | 33.358 | 13.903 | 24.765 | 1.00 | 55.14 | N |
| ATOM | 1890 | C | ARG | C | 33 | 27.351 | 13.751 | 25.436 | 1.00 | 44.08 | C |
| ATOM | 1891 | O | ARG | C | 33 | 27.274 | 13.827 | 24.214 | 1.00 | 43.84 | O |
| ATOM | 1892 | N | THR | C | 34 | 27.061 | 14.775 | 26.222 | 1.00 | 44.90 | N |
| ATOM | 1893 | CA | THR | C | 34 | 26.716 | 16.070 | 25.638 | 1.00 | 45.49 | C |
| ATOM | 1894 | CB | THR | C | 34 | 25.222 | 16.398 | 25.769 | 1.00 | 45.88 | C |
| ATOM | 1895 | OG1 | THR | C | 34 | 24.788 | 16.134 | 27.120 | 1.00 | 46.31 | O |
| ATOM | 1896 | CG2 | THR | C | 34 | 24.389 | 15.552 | 24.764 | 1.00 | 45.54 | C |
| ATOM | 1897 | C | THR | C | 34 | 27.523 | 17.126 | 26.324 | 1.00 | 45.65 | C |
| ATOM | 1898 | O | THR | C | 34 | 27.620 | 17.130 | 27.542 | 1.00 | 46.28 | O |
| ATOM | 1899 | N | ASP | C | 35 | 28.131 | 17.987 | 25.526 | 1.00 | 45.98 | N |
| ATOM | 1900 | CA | ASP | C | 35 | 28.961 | 19.075 | 25.991 | 1.00 | 46.47 | C |
| ATOM | 1901 | CB | ASP | C | 35 | 30.409 | 18.798 | 25.635 | 1.00 | 47.14 | C |
| ATOM | 1902 | CG | ASP | C | 35 | 31.034 | 17.710 | 26.502 | 1.00 | 50.19 | C |
| ATOM | 1903 | OD1 | ASP | C | 35 | 32.229 | 17.369 | 26.281 | 1.00 | 53.29 | O |
| ATOM | 1904 | OD2 | ASP | C | 35 | 30.348 | 17.206 | 27.421 | 1.00 | 52.72 | O |
| ATOM | 1905 | C | ASP | C | 35 | 28.517 | 20.367 | 25.319 | 1.00 | 46.41 | C |
| ATOM | 1906 | O | ASP | C | 35 | 27.873 | 20.354 | 24.265 | 1.00 | 46.40 | O |
| ATOM | 1907 | N | TRP | C | 36 | 28.838 | 21.493 | 25.944 | 1.00 | 46.29 | N |
| ATOM | 1908 | CA | TRP | C | 36 | 28.516 | 22.792 | 25.370 | 1.00 | 45.80 | C |
| ATOM | 1909 | CB | TRP | C | 36 | 27.312 | 23.395 | 26.055 | 1.00 | 45.82 | C |
| ATOM | 1910 | CG | TRP | C | 36 | 26.112 | 22.609 | 25.833 | 1.00 | 45.99 | C |
| ATOM | 1911 | CD1 | TRP | C | 36 | 25.717 | 21.508 | 26.528 | 1.00 | 46.28 | C |
| ATOM | 1912 | NE1 | TRP | C | 36 | 24.519 | 21.038 | 26.036 | 1.00 | 46.83 | N |

APPENDIX I(d)-continued

| ATOM | 1913 | CE2 | TRP | C | 36 | 24.122 | 21.842 | 25.002 | 1.00 | 46.87 | C |
|---|---|---|---|---|---|---|---|---|---|---|---|
| ATOM | 1914 | CD2 | TRP | C | 36 | 25.113 | 22.844 | 24.843 | 1.00 | 47.02 | C |
| ATOM | 1915 | CE3 | TRP | C | 36 | 24.947 | 23.815 | 23.840 | 1.00 | 46.90 | C |
| ATOM | 1916 | CZ3 | TRP | C | 36 | 23.798 | 23.755 | 23.030 | 1.00 | 46.94 | C |
| ATOM | 1917 | CH2 | TRP | C | 36 | 22.833 | 22.738 | 23.216 | 1.00 | 47.13 | C |
| ATOM | 1918 | CZ2 | TRP | C | 36 | 22.979 | 21.776 | 24.197 | 1.00 | 46.61 | C |
| ATOM | 1919 | C | TRP | C | 36 | 29.697 | 23.706 | 25.502 | 1.00 | 45.48 | C |
| ATOM | 1920 | O | TRP | C | 36 | 30.303 | 23.798 | 26.569 | 1.00 | 45.64 | O |
| ATOM | 1921 | N | TYR | C | 37 | 30.034 | 24.366 | 24.403 | 1.00 | 45.28 | N |
| ATOM | 1922 | CA | TYR | C | 37 | 31.184 | 25.251 | 24.366 | 1.00 | 45.14 | C |
| ATOM | 1923 | CB | TYR | C | 37 | 32.265 | 24.695 | 23.430 | 1.00 | 45.42 | C |
| ATOM | 1924 | CG | TYR | C | 37 | 32.608 | 23.242 | 23.684 | 1.00 | 46.04 | C |
| ATOM | 1925 | CD1 | TYR | C | 37 | 33.584 | 22.885 | 24.635 | 1.00 | 47.25 | C |
| ATOM | 1926 | CE1 | TYR | C | 37 | 33.911 | 21.545 | 24.887 | 1.00 | 46.32 | C |
| ATOM | 1927 | CZ | TYR | C | 37 | 33.257 | 20.541 | 24.177 | 1.00 | 47.31 | C |
| ATOM | 1928 | OH | TYR | C | 37 | 33.571 | 19.210 | 24.415 | 1.00 | 47.35 | O |
| ATOM | 1929 | CE2 | TYR | C | 37 | 32.278 | 20.869 | 23.222 | 1.00 | 47.25 | C |
| ATOM | 1930 | CD2 | TYR | C | 37 | 31.962 | 22.218 | 22.984 | 1.00 | 45.98 | C |
| ATOM | 1931 | C | TYR | C | 37 | 30.748 | 26.670 | 23.972 | 1.00 | 44.95 | C |
| ATOM | 1932 | O | TYR | C | 37 | 29.651 | 26.877 | 23.426 | 1.00 | 44.59 | O |
| ATOM | 1933 | N | ARG | C | 38 | 31.610 | 27.641 | 24.278 | 1.00 | 44.40 | N |
| ATOM | 1934 | CA | ARG | C | 38 | 31.307 | 29.039 | 24.092 | 1.00 | 43.78 | C |
| ATOM | 1935 | CB | ARG | C | 38 | 30.628 | 29.570 | 25.337 | 1.00 | 43.85 | C |
| ATOM | 1936 | CG | ARG | C | 38 | 30.200 | 31.012 | 25.249 | 1.00 | 45.64 | C |
| ATOM | 1937 | CD | ARG | C | 38 | 29.858 | 31.527 | 26.618 | 1.00 | 49.42 | C |
| ATOM | 1938 | NE | ARG | C | 38 | 31.043 | 31.607 | 27.462 | 1.00 | 53.90 | N |
| ATOM | 1939 | CZ | ARG | C | 38 | 31.040 | 31.582 | 28.791 | 1.00 | 56.65 | C |
| ATOM | 1940 | NH1 | ARG | C | 38 | 29.903 | 31.460 | 29.479 | 1.00 | 57.56 | N |
| ATOM | 1941 | NH2 | ARG | C | 38 | 32.193 | 31.662 | 29.440 | 1.00 | 58.12 | N |
| ATOM | 1942 | C | ARG | C | 38 | 32.576 | 29.832 | 23.839 | 1.00 | 43.49 | C |
| ATOM | 1943 | O | ARG | C | 38 | 33.589 | 29.651 | 24.519 | 1.00 | 42.68 | O |
| ATOM | 1944 | N | THR | C | 39 | 32.510 | 30.716 | 22.849 | 1.00 | 43.42 | N |
| ATOM | 1945 | CA | THR | C | 39 | 33.577 | 31.660 | 22.624 | 1.00 | 43.33 | C |
| ATOM | 1946 | CB | THR | C | 39 | 34.408 | 31.326 | 21.347 | 1.00 | 43.01 | C |
| ATOM | 1947 | OG1 | THR | C | 39 | 35.397 | 32.334 | 21.135 | 1.00 | 42.59 | O |
| ATOM | 1948 | CG2 | THR | C | 39 | 33.536 | 31.219 | 20.132 | 1.00 | 43.58 | C |
| ATOM | 1949 | C | THR | C | 39 | 33.029 | 33.087 | 22.701 | 1.00 | 43.51 | C |
| ATOM | 1950 | O | THR | C | 39 | 32.229 | 33.508 | 21.877 | 1.00 | 43.35 | O |
| ATOM | 1951 | N | THR | C | 40 | 33.459 | 33.781 | 23.756 | 1.00 | 44.12 | N |
| ATOM | 1952 | CA | THR | C | 40 | 33.087 | 35.157 | 24.122 | 1.00 | 44.52 | C |
| ATOM | 1953 | CB | THR | C | 40 | 33.779 | 35.506 | 25.480 | 1.00 | 44.65 | C |
| ATOM | 1954 | OG1 | THR | C | 40 | 33.014 | 34.951 | 26.554 | 1.00 | 45.14 | O |
| ATOM | 1955 | CG2 | THR | C | 40 | 33.954 | 37.006 | 25.708 | 1.00 | 44.21 | C |
| ATOM | 1956 | C | THR | C | 40 | 33.487 | 36.188 | 23.076 | 1.00 | 44.68 | C |
| ATOM | 1957 | O | THR | C | 40 | 34.551 | 36.065 | 22.477 | 1.00 | 44.77 | O |
| ATOM | 1958 | N | LEU | C | 41 | 32.643 | 37.201 | 22.864 | 1.00 | 45.08 | N |
| ATOM | 1959 | CA | LEU | C | 41 | 33.025 | 38.378 | 22.051 | 1.00 | 45.59 | C |
| ATOM | 1960 | CB | LEU | C | 41 | 31.924 | 39.452 | 22.017 | 1.00 | 45.38 | C |
| ATOM | 1961 | CG | LEU | C | 41 | 30.982 | 39.627 | 20.817 | 1.00 | 45.01 | C |
| ATOM | 1962 | CD1 | LEU | C | 41 | 30.413 | 41.035 | 20.861 | 1.00 | 44.32 | C |
| ATOM | 1963 | CD2 | LEU | C | 41 | 31.648 | 39.368 | 19.461 | 1.00 | 44.21 | C |
| ATOM | 1964 | C | LEU | C | 41 | 34.334 | 39.029 | 22.525 | 1.00 | 46.09 | C |
| ATOM | 1965 | O | LEU | C | 41 | 34.413 | 39.563 | 23.642 | 1.00 | 46.07 | O |
| ATOM | 1966 | N | GLY | C | 42 | 35.345 | 38.988 | 21.658 | 1.00 | 46.41 | N |
| ATOM | 1967 | CA | GLY | C | 42 | 36.662 | 39.511 | 21.981 | 1.00 | 46.86 | C |
| ATOM | 1968 | C | GLY | C | 42 | 37.653 | 38.393 | 22.218 | 1.00 | 47.32 | C |
| ATOM | 1969 | O | GLY | C | 42 | 38.805 | 38.480 | 21.808 | 1.00 | 47.49 | O |
| ATOM | 1970 | N | SER | C | 43 | 37.196 | 37.334 | 22.875 | 1.00 | 47.84 | N |
| ATOM | 1971 | CA | SER | C | 43 | 38.051 | 36.205 | 23.232 | 1.00 | 48.37 | C |
| ATOM | 1972 | CB | SER | C | 43 | 37.381 | 35.356 | 24.333 | 1.00 | 48.73 | C |
| ATOM | 1973 | OG | SER | C | 43 | 38.327 | 34.801 | 25.247 | 1.00 | 49.16 | O |
| ATOM | 1974 | C | SER | C | 43 | 38.353 | 35.339 | 22.008 | 1.00 | 48.25 | C |
| ATOM | 1975 | O | SER | C | 43 | 37.471 | 35.057 | 21.198 | 1.00 | 48.08 | O |
| ATOM | 1976 | N | THR | C | 44 | 39.608 | 34.932 | 21.881 | 1.00 | 48.32 | N |
| ATOM | 1977 | CA | THR | C | 44 | 40.017 | 34.007 | 20.826 | 1.00 | 48.49 | C |
| ATOM | 1978 | CB | THR | C | 44 | 41.540 | 34.209 | 20.436 | 1.00 | 48.64 | C |
| ATOM | 1979 | OG1 | THR | C | 44 | 42.070 | 33.032 | 19.818 | 1.00 | 48.40 | O |
| ATOM | 1980 | CG2 | THR | C | 44 | 42.410 | 34.586 | 21.648 | 1.00 | 48.71 | C |
| ATOM | 1981 | C | THR | C | 44 | 39.665 | 32.550 | 21.192 | 1.00 | 48.58 | C |
| ATOM | 1982 | O | THR | C | 44 | 39.325 | 31.741 | 20.315 | 1.00 | 48.51 | O |
| ATOM | 1983 | N | ASN | C | 45 | 39.702 | 32.245 | 22.493 | 1.00 | 48.49 | N |
| ATOM | 1984 | CA | ASN | C | 45 | 39.609 | 30.870 | 22.991 | 1.00 | 48.39 | C |
| ATOM | 1985 | CB | ASN | C | 45 | 40.476 | 30.692 | 24.234 | 1.00 | 48.45 | C |
| ATOM | 1986 | CG | ASN | C | 45 | 41.908 | 30.257 | 23.900 | 1.00 | 48.98 | C |
| ATOM | 1987 | OD1 | ASN | C | 45 | 42.128 | 29.275 | 23.172 | 1.00 | 50.20 | O |
| ATOM | 1988 | ND2 | ASN | C | 45 | 42.884 | 30.978 | 24.444 | 1.00 | 47.76 | N |
| ATOM | 1989 | C | ASN | C | 45 | 38.205 | 30.403 | 23.290 | 1.00 | 48.21 | C |
| ATOM | 1990 | O | ASN | C | 45 | 37.398 | 31.158 | 23.829 | 1.00 | 48.83 | O |
| ATOM | 1991 | N | GLU | C | 46 | 37.926 | 29.153 | 22.935 | 1.00 | 47.64 | N |
| ATOM | 1992 | CA | GLU | C | 46 | 36.613 | 28.541 | 23.128 | 1.00 | 47.23 | C |

APPENDIX I(d)-continued

| ATOM | 1993 | CB | GLU | C | 46 | 36.369 | 27.536 | 22.021 | 1.00 | 47.36 | C |
| ATOM | 1994 | CG | GLU | C | 46 | 34.963 | 27.003 | 21.947 | 1.00 | 49.62 | C |
| ATOM | 1995 | CD | GLU | C | 46 | 34.877 | 25.764 | 21.083 | 1.00 | 52.95 | C |
| ATOM | 1996 | OE1 | GLU | C | 46 | 35.885 | 25.005 | 21.073 | 1.00 | 54.92 | O |
| ATOM | 1997 | OE2 | GLU | C | 46 | 33.822 | 25.558 | 20.419 | 1.00 | 52.26 | O |
| ATOM | 1998 | C | GLU | C | 46 | 36.576 | 27.839 | 24.480 | 1.00 | 46.59 | C |
| ATOM | 1999 | O | GLU | C | 46 | 37.566 | 27.244 | 24.880 | 1.00 | 46.90 | O |
| ATOM | 2000 | N | GLN | C | 47 | 35.442 | 27.896 | 25.174 | 1.00 | 45.60 | N |
| ATOM | 2001 | CA | GLN | C | 47 | 35.379 | 27.529 | 26.589 | 1.00 | 45.13 | C |
| ATOM | 2002 | CB | GLN | C | 47 | 35.248 | 28.810 | 27.441 | 1.00 | 45.06 | C |
| ATOM | 2003 | CG | GLN | C | 47 | 34.469 | 28.693 | 28.769 | 1.00 | 46.54 | C |
| ATOM | 2004 | CD | GLN | C | 47 | 34.892 | 29.728 | 29.833 | 1.00 | 47.69 | C |
| ATOM | 2005 | OE1 | GLN | C | 47 | 35.066 | 29.383 | 31.013 | 1.00 | 50.91 | O |
| ATOM | 2006 | NE2 | GLN | C | 47 | 35.058 | 30.998 | 29.422 | 1.00 | 50.13 | N |
| ATOM | 2007 | C | GLN | C | 47 | 34.267 | 26.542 | 26.895 | 1.00 | 43.75 | C |
| ATOM | 2008 | O | GLN | C | 47 | 33.147 | 26.682 | 26.408 | 1.00 | 43.68 | O |
| ATOM | 2009 | N | LYS | C | 48 | 34.558 | 25.546 | 27.717 | 1.00 | 42.65 | N |
| ATOM | 2010 | CA | LYS | C | 48 | 33.512 | 24.584 | 28.070 | 1.00 | 42.13 | C |
| ATOM | 2011 | CB | LYS | C | 48 | 34.111 | 23.260 | 28.577 | 1.00 | 42.14 | C |
| ATOM | 2012 | CG | LYS | C | 48 | 33.146 | 22.080 | 28.531 | 1.00 | 42.28 | C |
| ATOM | 2013 | CD | LYS | C | 48 | 33.755 | 20.854 | 29.227 | 1.00 | 42.97 | C |
| ATOM | 2014 | CE | LYS | C | 48 | 32.995 | 19.550 | 28.896 | 1.00 | 44.44 | C |
| ATOM | 2015 | NZ | LYS | C | 48 | 31.730 | 19.382 | 29.689 | 1.00 | 41.90 | N |
| ATOM | 2016 | C | LYS | C | 48 | 32.529 | 25.167 | 29.088 | 1.00 | 40.86 | C |
| ATOM | 2017 | O | LYS | C | 48 | 32.927 | 25.559 | 30.186 | 1.00 | 41.16 | O |
| ATOM | 2018 | N | ILE | C | 49 | 31.258 | 25.234 | 28.704 | 1.00 | 39.24 | N |
| ATOM | 2019 | CA | ILE | C | 49 | 30.177 | 25.610 | 29.612 | 1.00 | 38.21 | C |
| ATOM | 2020 | CB | ILE | C | 49 | 28.876 | 25.902 | 28.832 | 1.00 | 38.04 | C |
| ATOM | 2021 | CG1 | ILE | C | 49 | 29.063 | 27.160 | 27.970 | 1.00 | 37.36 | C |
| ATOM | 2022 | CD1 | ILE | C | 49 | 27.998 | 27.395 | 26.955 | 1.00 | 35.52 | C |
| ATOM | 2023 | CG2 | ILE | C | 49 | 27.708 | 26.058 | 29.785 | 1.00 | 37.96 | C |
| ATOM | 2024 | C | ILE | C | 49 | 29.946 | 24.511 | 30.657 | 1.00 | 37.86 | C |
| ATOM | 2025 | O | ILE | C | 49 | 29.840 | 23.332 | 30.336 | 1.00 | 38.22 | O |
| ATOM | 2026 | N | SER | C | 50 | 29.871 | 24.893 | 31.914 | 1.00 | 36.99 | N |
| ATOM | 2027 | CA | SER | C | 50 | 29.823 | 23.911 | 32.974 | 1.00 | 36.24 | C |
| ATOM | 2028 | CB | SER | C | 50 | 30.936 | 24.211 | 33.985 | 1.00 | 36.03 | C |
| ATOM | 2029 | OG | SER | C | 50 | 30.705 | 23.597 | 35.226 | 1.00 | 35.67 | O |
| ATOM | 2030 | C | SER | C | 50 | 28.423 | 23.953 | 33.586 | 1.00 | 36.12 | C |
| ATOM | 2031 | O | SER | C | 50 | 28.101 | 24.893 | 34.305 | 1.00 | 36.47 | O |
| ATOM | 2032 | N | ILE | C | 51 | 27.604 | 22.937 | 33.276 | 1.00 | 35.77 | N |
| ATOM | 2033 | CA | ILE | C | 51 | 26.161 | 22.887 | 33.591 | 1.00 | 35.08 | C |
| ATOM | 2034 | CB | ILE | C | 51 | 25.489 | 21.636 | 32.962 | 1.00 | 34.76 | C |
| ATOM | 2035 | CG1 | ILE | C | 51 | 25.814 | 21.504 | 31.470 | 1.00 | 35.07 | C |
| ATOM | 2036 | CD1 | ILE | C | 51 | 25.313 | 22.612 | 30.586 | 1.00 | 34.14 | C |
| ATOM | 2037 | CG2 | ILE | C | 51 | 23.998 | 21.633 | 33.170 | 1.00 | 34.35 | C |
| ATOM | 2038 | C | ILE | C | 51 | 25.862 | 22.927 | 35.089 | 1.00 | 35.53 | C |
| ATOM | 2039 | O | ILE | C | 51 | 26.594 | 22.356 | 35.904 | 1.00 | 36.01 | O |
| ATOM | 2040 | N | GLY | C | 52 | 24.764 | 23.590 | 35.433 | 1.00 | 35.65 | N |
| ATOM | 2041 | CA | GLY | C | 52 | 24.432 | 23.962 | 36.802 | 1.00 | 36.14 | C |
| ATOM | 2042 | C | GLY | C | 52 | 24.077 | 25.434 | 36.781 | 1.00 | 36.66 | C |
| ATOM | 2043 | O | GLY | C | 52 | 24.461 | 26.143 | 35.855 | 1.00 | 37.19 | O |
| ATOM | 2044 | N | GLY | C | 53 | 23.337 | 25.905 | 37.775 | 1.00 | 37.19 | N |
| ATOM | 2045 | CA | GLY | C | 53 | 23.034 | 27.339 | 37.883 | 1.00 | 38.04 | C |
| ATOM | 2046 | C | GLY | C | 53 | 22.202 | 27.937 | 36.755 | 1.00 | 38.59 | C |
| ATOM | 2047 | O | GLY | C | 53 | 21.063 | 27.520 | 36.526 | 1.00 | 38.17 | O |
| ATOM | 2048 | N | ARG | C | 54 | 22.770 | 28.924 | 36.058 | 1.00 | 39.36 | N |
| ATOM | 2049 | CA | ARG | C | 54 | 22.070 | 29.587 | 34.952 | 1.00 | 40.47 | C |
| ATOM | 2050 | CB | ARG | C | 54 | 22.486 | 31.070 | 34.796 | 1.00 | 40.52 | C |
| ATOM | 2051 | CG | ARG | C | 54 | 23.987 | 31.389 | 34.836 | 1.00 | 42.08 | C |
| ATOM | 2052 | CD | ARG | C | 54 | 24.603 | 31.668 | 33.450 | 1.00 | 44.40 | C |
| ATOM | 2053 | NE | ARG | C | 54 | 24.062 | 32.872 | 32.798 | 1.00 | 45.39 | N |
| ATOM | 2054 | CZ | ARG | C | 54 | 24.681 | 33.569 | 31.840 | 1.00 | 44.83 | C |
| ATOM | 2055 | NH1 | ARG | C | 54 | 25.889 | 33.225 | 31.399 | 1.00 | 43.88 | N |
| ATOM | 2056 | NH2 | ARG | C | 54 | 24.083 | 34.626 | 31.317 | 1.00 | 44.61 | N |
| ATOM | 2057 | C | ARG | C | 54 | 22.091 | 28.819 | 33.612 | 1.00 | 40.93 | C |
| ATOM | 2058 | O | ARG | C | 54 | 21.457 | 29.234 | 32.642 | 1.00 | 41.07 | O |
| ATOM | 2059 | N | TYR | C | 55 | 22.801 | 27.699 | 33.559 | 1.00 | 41.75 | N |
| ATOM | 2060 | CA | TYR | C | 55 | 22.718 | 26.824 | 32.397 | 1.00 | 42.73 | C |
| ATOM | 2061 | CB | TYR | C | 55 | 24.098 | 26.431 | 31.892 | 1.00 | 43.59 | C |
| ATOM | 2062 | CG | TYR | C | 55 | 25.028 | 27.569 | 31.597 | 1.00 | 45.26 | C |
| ATOM | 2063 | CD1 | TYR | C | 55 | 25.972 | 27.983 | 32.547 | 1.00 | 46.23 | C |
| ATOM | 2064 | CE1 | TYR | C | 55 | 26.853 | 29.032 | 32.277 | 1.00 | 47.06 | C |
| ATOM | 2065 | CZ | TYR | C | 55 | 26.803 | 29.669 | 31.035 | 1.00 | 47.17 | C |
| ATOM | 2066 | OH | TYR | C | 55 | 27.678 | 30.699 | 30.758 | 1.00 | 47.13 | O |
| ATOM | 2067 | CE2 | TYR | C | 55 | 25.877 | 29.270 | 30.072 | 1.00 | 47.60 | C |
| ATOM | 2068 | CD2 | TYR | C | 55 | 24.994 | 28.220 | 30.356 | 1.00 | 46.94 | C |
| ATOM | 2069 | C | TYR | C | 55 | 21.971 | 25.549 | 32.739 | 1.00 | 42.70 | C |
| ATOM | 2070 | O | TYR | C | 55 | 22.483 | 24.719 | 33.478 | 1.00 | 42.39 | O |
| ATOM | 2071 | N | VAL | C | 56 | 20.765 | 25.382 | 32.209 | 1.00 | 43.05 | N |
| ATOM | 2072 | CA | VAL | C | 56 | 20.072 | 24.108 | 32.374 | 1.00 | 43.44 | C |

APPENDIX I(d)-continued

| ATOM | 2073 | CB | VAL | C | 56 | 18.679 | 24.247 | 33.084 | 1.00 | 43.19 | C |
|---|---|---|---|---|---|---|---|---|---|---|---|
| ATOM | 2074 | CG1 | VAL | C | 56 | 18.404 | 25.681 | 33.477 | 1.00 | 42.32 | C |
| ATOM | 2075 | CG2 | VAL | C | 56 | 17.554 | 23.658 | 32.252 | 1.00 | 43.66 | C |
| ATOM | 2076 | C | VAL | C | 56 | 20.073 | 23.330 | 31.053 | 1.00 | 43.90 | C |
| ATOM | 2077 | O | VAL | C | 56 | 19.914 | 23.910 | 29.984 | 1.00 | 44.29 | O |
| ATOM | 2078 | N | GLU | C | 57 | 20.332 | 22.029 | 31.134 | 1.00 | 44.13 | N |
| ATOM | 2079 | CA | GLU | C | 57 | 20.446 | 21.205 | 29.944 | 1.00 | 44.49 | C |
| ATOM | 2080 | CB | GLU | C | 57 | 21.808 | 20.522 | 29.886 | 1.00 | 44.65 | C |
| ATOM | 2081 | CG | GLU | C | 57 | 22.020 | 19.738 | 28.595 | 1.00 | 46.62 | C |
| ATOM | 2082 | CD | GLU | C | 57 | 23.221 | 18.801 | 28.631 | 1.00 | 48.99 | C |
| ATOM | 2083 | OE1 | GLU | C | 57 | 23.449 | 18.116 | 29.660 | 1.00 | 50.79 | O |
| ATOM | 2084 | OE2 | GLU | C | 57 | 23.929 | 18.739 | 27.609 | 1.00 | 48.49 | O |
| ATOM | 2085 | C | GLU | C | 57 | 19.371 | 20.151 | 29.952 | 1.00 | 44.38 | C |
| ATOM | 2086 | O | GLU | C | 57 | 19.189 | 19.466 | 30.957 | 1.00 | 44.68 | O |
| ATOM | 2087 | N | THR | C | 58 | 18.659 | 20.008 | 28.842 | 1.00 | 44.32 | N |
| ATOM | 2088 | CA | THR | C | 58 | 17.661 | 18.956 | 28.754 | 1.00 | 44.58 | C |
| ATOM | 2089 | CB | THR | C | 58 | 16.228 | 19.474 | 28.495 | 1.00 | 44.59 | C |
| ATOM | 2090 | OG1 | THR | C | 58 | 15.977 | 20.647 | 29.276 | 1.00 | 44.71 | O |
| ATOM | 2091 | CG2 | THR | C | 58 | 15.209 | 18.400 | 28.881 | 1.00 | 44.79 | C |
| ATOM | 2092 | C | THR | C | 58 | 18.065 | 18.005 | 27.661 | 1.00 | 44.55 | C |
| ATOM | 2093 | O | THR | C | 58 | 18.231 | 18.413 | 26.525 | 1.00 | 44.96 | O |
| ATOM | 2094 | N | VAL | C | 59 | 18.233 | 16.736 | 28.016 | 1.00 | 44.53 | N |
| ATOM | 2095 | CA | VAL | C | 59 | 18.661 | 15.736 | 27.054 | 1.00 | 44.23 | C |
| ATOM | 2096 | CB | VAL | C | 59 | 20.023 | 15.095 | 27.445 | 1.00 | 44.24 | C |
| ATOM | 2097 | CG1 | VAL | C | 59 | 20.517 | 14.143 | 26.360 | 1.00 | 41.77 | C |
| ATOM | 2098 | CG2 | VAL | C | 59 | 21.062 | 16.196 | 27.706 | 1.00 | 44.53 | C |
| ATOM | 2099 | C | VAL | C | 59 | 17.587 | 14.681 | 26.850 | 1.00 | 44.53 | C |
| ATOM | 2100 | O | VAL | C | 59 | 16.892 | 14.274 | 27.784 | 1.00 | 44.23 | O |
| ATOM | 2101 | N | ASN | C | 60 | 17.454 | 14.271 | 25.594 | 1.00 | 44.94 | N |
| ATOM | 2102 | CA | ASN | C | 60 | 16.609 | 13.153 | 25.202 | 1.00 | 44.74 | C |
| ATOM | 2103 | CB | ASN | C | 60 | 15.389 | 13.655 | 24.428 | 1.00 | 44.71 | C |
| ATOM | 2104 | CG | ASN | C | 60 | 14.358 | 12.588 | 24.221 | 1.00 | 45.15 | C |
| ATOM | 2105 | OD1 | ASN | C | 60 | 14.689 | 11.424 | 24.010 | 1.00 | 45.39 | O |
| ATOM | 2106 | ND2 | ASN | C | 60 | 13.085 | 12.974 | 24.284 | 1.00 | 46.47 | N |
| ATOM | 2107 | C | ASN | C | 60 | 17.438 | 12.204 | 24.346 | 1.00 | 44.60 | C |
| ATOM | 2108 | O | ASN | C | 60 | 17.329 | 12.215 | 23.106 | 1.00 | 44.87 | O |
| ATOM | 2109 | N | LYS | C | 61 | 18.315 | 11.434 | 25.004 | 1.00 | 44.25 | N |
| ATOM | 2110 | CA | LYS | C | 61 | 18.902 | 10.245 | 24.388 | 1.00 | 43.60 | C |
| ATOM | 2111 | CB | LYS | C | 61 | 19.676 | 9.391 | 25.396 | 1.00 | 42.97 | C |
| ATOM | 2112 | CG | LYS | C | 61 | 20.685 | 10.109 | 26.240 | 1.00 | 41.15 | C |
| ATOM | 2113 | CD | LYS | C | 61 | 21.355 | 9.167 | 27.219 | 1.00 | 36.07 | C |
| ATOM | 2114 | CE | LYS | C | 61 | 22.521 | 9.853 | 27.842 | 1.00 | 33.75 | C |
| ATOM | 2115 | NZ | LYS | C | 61 | 22.941 | 9.168 | 29.069 | 1.00 | 33.84 | N |
| ATOM | 2116 | C | LYS | C | 61 | 17.678 | 9.457 | 23.981 | 1.00 | 44.03 | C |
| ATOM | 2117 | O | LYS | C | 61 | 16.789 | 9.233 | 24.809 | 1.00 | 45.15 | O |
| ATOM | 2118 | N | GLY | C | 62 | 17.578 | 9.052 | 22.733 | 1.00 | 43.61 | N |
| ATOM | 2119 | CA | GLY | C | 62 | 16.386 | 8.324 | 22.349 | 1.00 | 43.74 | C |
| ATOM | 2120 | C | GLY | C | 62 | 15.924 | 8.921 | 21.068 | 1.00 | 43.99 | C |
| ATOM | 2121 | O | GLY | C | 62 | 15.804 | 8.220 | 20.077 | 1.00 | 44.34 | O |
| ATOM | 2122 | N | SER | C | 63 | 15.682 | 10.226 | 21.085 | 1.00 | 44.18 | N |
| ATOM | 2123 | CA | SER | C | 63 | 15.540 | 10.990 | 19.854 | 1.00 | 44.37 | C |
| ATOM | 2124 | CB | SER | C | 63 | 14.384 | 11.981 | 19.985 | 1.00 | 44.33 | C |
| ATOM | 2125 | OG | SER | C | 63 | 14.601 | 12.876 | 21.053 | 1.00 | 45.03 | O |
| ATOM | 2126 | C | SER | C | 63 | 16.865 | 11.692 | 19.512 | 1.00 | 44.34 | C |
| ATOM | 2127 | O | SER | C | 63 | 16.941 | 12.475 | 18.573 | 1.00 | 44.35 | O |
| ATOM | 2128 | N | LYS | C | 64 | 17.910 | 11.374 | 20.278 | 1.00 | 44.70 | N |
| ATOM | 2129 | CA | LYS | C | 64 | 19.263 | 11.956 | 20.120 | 1.00 | 44.84 | C |
| ATOM | 2130 | CB | LYS | C | 64 | 20.001 | 11.365 | 18.913 | 1.00 | 44.66 | C |
| ATOM | 2131 | CG | LYS | C | 64 | 20.685 | 10.054 | 19.177 | 1.00 | 43.38 | C |
| ATOM | 2132 | CD | LYS | C | 64 | 20.732 | 9.199 | 17.938 | 1.00 | 40.42 | C |
| ATOM | 2133 | CE | LYS | C | 64 | 20.708 | 7.747 | 18.313 | 1.00 | 39.27 | C |
| ATOM | 2134 | NZ | LYS | C | 64 | 20.923 | 6.914 | 17.106 | 1.00 | 40.81 | N |
| ATOM | 2135 | C | LYS | C | 64 | 19.224 | 13.475 | 20.021 | 1.00 | 45.39 | C |
| ATOM | 2136 | O | LYS | C | 64 | 19.916 | 14.079 | 19.195 | 1.00 | 45.63 | O |
| ATOM | 2137 | N | SER | C | 65 | 18.391 | 14.092 | 20.853 | 1.00 | 45.61 | N |
| ATOM | 2138 | CA | SER | C | 65 | 18.313 | 15.543 | 20.860 | 1.00 | 45.22 | C |
| ATOM | 2139 | CB | SER | C | 65 | 17.015 | 16.014 | 20.197 | 1.00 | 45.32 | C |
| ATOM | 2140 | OG | SER | C | 65 | 15.940 | 15.981 | 21.107 | 1.00 | 45.97 | O |
| ATOM | 2141 | C | SER | C | 65 | 18.483 | 16.105 | 22.275 | 1.00 | 44.72 | C |
| ATOM | 2142 | O | SER | C | 65 | 18.097 | 15.479 | 23.274 | 1.00 | 44.33 | O |
| ATOM | 2143 | N | PHE | C | 66 | 19.082 | 17.285 | 22.341 | 1.00 | 44.16 | N |
| ATOM | 2144 | CA | PHE | C | 66 | 19.394 | 17.928 | 23.606 | 1.00 | 43.60 | C |
| ATOM | 2145 | CB | PHE | C | 66 | 20.721 | 17.387 | 24.160 | 1.00 | 44.01 | C |
| ATOM | 2146 | CG | PHE | C | 66 | 21.873 | 17.540 | 23.220 | 1.00 | 44.66 | C |
| ATOM | 2147 | CD1 | PHE | C | 66 | 22.961 | 18.342 | 23.571 | 1.00 | 46.00 | C |
| ATOM | 2148 | CE1 | PHE | C | 66 | 24.045 | 18.504 | 22.703 | 1.00 | 47.22 | C |
| ATOM | 2149 | CZ | PHE | C | 66 | 24.025 | 17.865 | 21.454 | 1.00 | 47.14 | C |
| ATOM | 2150 | CE2 | PHE | C | 66 | 22.922 | 17.064 | 21.084 | 1.00 | 45.67 | C |
| ATOM | 2151 | CD2 | PHE | C | 66 | 21.866 | 16.904 | 21.974 | 1.00 | 45.23 | C |
| ATOM | 2152 | C | PHE | C | 66 | 19.448 | 19.431 | 23.413 | 1.00 | 42.65 | C |

APPENDIX I(d)-continued

| ATOM | 2153 | O | PHE | C | 66 | 19.643 | 19.916 | 22.290 | 1.00 | 41.90 | O |
|------|------|------|------|---|----|--------|--------|--------|------|-------|---|
| ATOM | 2154 | N | SER | C | 67 | 19.265 | 20.164 | 24.508 | 1.00 | 42.04 | N |
| ATOM | 2155 | CA | SER | C | 67 | 19.212 | 21.634 | 24.453 | 1.00 | 41.52 | C |
| ATOM | 2156 | CB | SER | C | 67 | 17.773 | 22.110 | 24.283 | 1.00 | 41.21 | C |
| ATOM | 2157 | OG | SER | C | 67 | 17.141 | 22.180 | 25.545 | 1.00 | 41.07 | O |
| ATOM | 2158 | C | SER | C | 67 | 19.821 | 22.316 | 25.671 | 1.00 | 40.87 | C |
| ATOM | 2159 | O | SER | C | 67 | 19.828 | 21.765 | 26.756 | 1.00 | 40.62 | O |
| ATOM | 2160 | N | LEU | C | 68 | 20.314 | 23.528 | 25.474 | 1.00 | 40.64 | N |
| ATOM | 2161 | CA | LEU | C | 68 | 20.846 | 24.326 | 26.563 | 1.00 | 41.10 | C |
| ATOM | 2162 | CB | LEU | C | 68 | 22.261 | 24.794 | 26.222 | 1.00 | 40.90 | C |
| ATOM | 2163 | CG | LEU | C | 68 | 22.953 | 25.633 | 27.287 | 1.00 | 40.77 | C |
| ATOM | 2164 | CD1 | LEU | C | 68 | 23.220 | 24.788 | 28.519 | 1.00 | 40.99 | C |
| ATOM | 2165 | CD2 | LEU | C | 68 | 24.238 | 26.207 | 26.730 | 1.00 | 41.39 | C |
| ATOM | 2166 | C | LEU | C | 68 | 19.965 | 25.529 | 26.797 | 1.00 | 41.39 | C |
| ATOM | 2167 | O | LEU | C | 68 | 19.555 | 26.174 | 25.862 | 1.00 | 41.94 | O |
| ATOM | 2168 | N | ARG | C | 69 | 19.657 | 25.835 | 28.038 | 1.00 | 42.12 | N |
| ATOM | 2169 | CA | ARG | C | 69 | 18.930 | 27.057 | 28.318 | 1.00 | 43.31 | C |
| ATOM | 2170 | CB | ARG | C | 69 | 17.610 | 26.778 | 29.037 | 1.00 | 43.32 | C |
| ATOM | 2171 | CG | ARG | C | 69 | 16.830 | 28.037 | 29.423 | 1.00 | 43.69 | C |
| ATOM | 2172 | CD | ARG | C | 69 | 15.456 | 27.700 | 29.985 | 1.00 | 44.45 | C |
| ATOM | 2173 | NE | ARG | C | 69 | 14.953 | 28.792 | 30.821 | 1.00 | 49.97 | N |
| ATOM | 2174 | CZ | ARG | C | 69 | 13.979 | 29.651 | 30.485 | 1.00 | 52.04 | C |
| ATOM | 2175 | NH1 | ARG | C | 69 | 13.348 | 29.550 | 29.313 | 1.00 | 52.62 | N |
| ATOM | 2176 | NH2 | ARG | C | 69 | 13.619 | 30.613 | 31.337 | 1.00 | 51.20 | N |
| ATOM | 2177 | C | ARG | C | 69 | 19.820 | 27.926 | 29.177 | 1.00 | 43.74 | C |
| ATOM | 2178 | O | ARG | C | 69 | 20.365 | 27.445 | 30.181 | 1.00 | 43.66 | O |
| ATOM | 2179 | N | ILE | C | 70 | 19.986 | 29.190 | 28.775 | 1.00 | 44.17 | N |
| ATOM | 2180 | CA | ILE | C | 70 | 20.771 | 30.139 | 29.568 | 1.00 | 44.24 | C |
| ATOM | 2181 | CB | ILE | C | 70 | 21.924 | 30.764 | 28.766 | 1.00 | 44.29 | C |
| ATOM | 2182 | CG1 | ILE | C | 70 | 22.500 | 29.748 | 27.767 | 1.00 | 44.55 | C |
| ATOM | 2183 | CD1 | ILE | C | 70 | 23.618 | 30.268 | 26.893 | 1.00 | 44.09 | C |
| ATOM | 2184 | CG2 | ILE | C | 70 | 22.985 | 31.293 | 29.727 | 1.00 | 44.12 | C |
| ATOM | 2185 | C | ILE | C | 70 | 19.888 | 31.247 | 30.090 | 1.00 | 44.26 | C |
| ATOM | 2186 | O | ILE | C | 70 | 19.388 | 32.025 | 29.305 | 1.00 | 44.12 | O |
| ATOM | 2187 | N | ARG | C | 71 | 19.689 | 31.296 | 31.406 | 1.00 | 44.56 | N |
| ATOM | 2188 | CA | ARG | C | 71 | 18.986 | 32.406 | 32.067 | 1.00 | 45.41 | C |
| ATOM | 2189 | CB | ARG | C | 71 | 18.490 | 31.964 | 33.444 | 1.00 | 46.04 | C |
| ATOM | 2190 | CG | ARG | C | 71 | 17.001 | 31.601 | 33.524 | 1.00 | 49.75 | C |
| ATOM | 2191 | CD | ARG | C | 71 | 16.720 | 30.125 | 33.165 | 1.00 | 54.75 | C |
| ATOM | 2192 | NE | ARG | C | 71 | 17.547 | 29.154 | 33.902 | 1.00 | 58.55 | N |
| ATOM | 2193 | CZ | ARG | C | 71 | 17.526 | 28.965 | 35.227 | 1.00 | 60.09 | C |
| ATOM | 2194 | NH1 | ARG | C | 71 | 18.324 | 28.047 | 35.771 | 1.00 | 60.34 | N |
| ATOM | 2195 | NH2 | ARG | C | 71 | 16.729 | 29.700 | 36.014 | 1.00 | 60.07 | N |
| ATOM | 2196 | C | ARG | C | 71 | 19.818 | 33.693 | 32.251 | 1.00 | 45.00 | C |
| ATOM | 2197 | O | ARG | C | 71 | 21.059 | 33.651 | 32.249 | 1.00 | 44.88 | O |
| ATOM | 2198 | N | ASP | C | 72 | 19.118 | 34.823 | 32.420 | 1.00 | 44.67 | N |
| ATOM | 2199 | CA | ASP | C | 72 | 19.710 | 36.111 | 32.831 | 1.00 | 44.50 | C |
| ATOM | 2200 | CB | ASP | C | 72 | 20.197 | 36.015 | 34.283 | 1.00 | 44.75 | C |
| ATOM | 2201 | CG | ASP | C | 72 | 20.246 | 37.369 | 34.988 | 1.00 | 47.01 | C |
| ATOM | 2202 | OD1 | ASP | C | 72 | 20.443 | 37.358 | 36.224 | 1.00 | 49.08 | O |
| ATOM | 2203 | OD2 | ASP | C | 72 | 20.089 | 38.440 | 34.337 | 1.00 | 48.36 | O |
| ATOM | 2204 | C | ASP | C | 72 | 20.829 | 36.639 | 31.906 | 1.00 | 43.99 | C |
| ATOM | 2205 | O | ASP | C | 72 | 21.917 | 36.997 | 32.360 | 1.00 | 43.48 | O |
| ATOM | 2206 | N | LEU | C | 73 | 20.536 | 36.697 | 30.612 | 1.00 | 43.65 | N |
| ATOM | 2207 | CA | LEU | C | 73 | 21.500 | 37.109 | 29.608 | 1.00 | 43.40 | C |
| ATOM | 2208 | CB | LEU | C | 73 | 20.887 | 36.973 | 28.222 | 1.00 | 43.00 | C |
| ATOM | 2209 | CG | LEU | C | 73 | 20.582 | 35.582 | 27.701 | 1.00 | 42.57 | C |
| ATOM | 2210 | CD1 | LEU | C | 73 | 19.672 | 35.690 | 26.497 | 1.00 | 42.05 | C |
| ATOM | 2211 | CD2 | LEU | C | 73 | 21.878 | 34.850 | 27.348 | 1.00 | 42.76 | C |
| ATOM | 2212 | C | LEU | C | 73 | 21.970 | 38.546 | 29.785 | 1.00 | 43.85 | C |
| ATOM | 2213 | O | LEU | C | 73 | 21.148 | 39.456 | 29.963 | 1.00 | 44.05 | O |
| ATOM | 2214 | N | ARG | C | 74 | 23.288 | 38.744 | 29.738 | 1.00 | 44.09 | N |
| ATOM | 2215 | CA | ARG | C | 74 | 23.878 | 40.083 | 29.681 | 1.00 | 44.58 | C |
| ATOM | 2216 | CB | ARG | C | 74 | 24.739 | 40.384 | 30.906 | 1.00 | 45.11 | C |
| ATOM | 2217 | CG | ARG | C | 74 | 24.366 | 39.609 | 32.152 | 1.00 | 48.62 | C |
| ATOM | 2218 | CD | ARG | C | 74 | 25.269 | 38.395 | 32.294 | 1.00 | 54.44 | C |
| ATOM | 2219 | NE | ARG | C | 74 | 24.804 | 37.482 | 33.336 | 1.00 | 59.52 | N |
| ATOM | 2220 | CZ | ARG | C | 74 | 25.390 | 36.322 | 33.637 | 1.00 | 62.37 | C |
| ATOM | 2221 | NH1 | ARG | C | 74 | 26.477 | 35.920 | 32.979 | 1.00 | 63.92 | N |
| ATOM | 2222 | NH2 | ARG | C | 74 | 24.877 | 35.550 | 34.589 | 1.00 | 62.66 | N |
| ATOM | 2223 | C | ARG | C | 74 | 24.720 | 40.168 | 28.423 | 1.00 | 43.88 | C |
| ATOM | 2224 | O | ARG | C | 74 | 25.009 | 39.136 | 27.822 | 1.00 | 43.92 | O |
| ATOM | 2225 | N | VAL | C | 75 | 25.100 | 41.389 | 28.028 | 1.00 | 43.11 | N |
| ATOM | 2226 | CA | VAL | C | 75 | 25.871 | 41.629 | 26.797 | 1.00 | 42.05 | C |
| ATOM | 2227 | CB | VAL | C | 75 | 26.188 | 43.144 | 26.576 | 1.00 | 42.25 | C |
| ATOM | 2228 | CG1 | VAL | C | 75 | 24.909 | 43.964 | 26.518 | 1.00 | 41.91 | C |
| ATOM | 2229 | CG2 | VAL | C | 75 | 27.026 | 43.369 | 25.298 | 1.00 | 42.12 | C |
| ATOM | 2230 | C | VAL | C | 75 | 27.152 | 40.794 | 26.807 | 1.00 | 41.41 | C |
| ATOM | 2231 | O | VAL | C | 75 | 27.569 | 40.274 | 25.766 | 1.00 | 41.57 | O |
| ATOM | 2232 | N | GLU | C | 76 | 27.742 | 40.634 | 27.990 | 1.00 | 40.22 | N |

APPENDIX I(d)-continued

| ATOM | 2233 | CA | GLU | C | 76 | 28.939 | 39.824 | 28.146 | 1.00 | 39.57 | C |
|---|---|---|---|---|---|---|---|---|---|---|---|
| ATOM | 2234 | CB | GLU | C | 76 | 29.438 | 39.893 | 29.583 | 1.00 | 39.22 | C |
| ATOM | 2235 | CG | GLU | C | 76 | 28.705 | 38.991 | 30.548 | 1.00 | 38.56 | C |
| ATOM | 2236 | CD | GLU | C | 76 | 29.132 | 39.200 | 31.985 | 1.00 | 37.76 | C |
| ATOM | 2237 | OE1 | GLU | C | 76 | 28.491 | 38.596 | 32.881 | 1.00 | 37.15 | O |
| ATOM | 2238 | OE2 | GLU | C | 76 | 30.098 | 39.971 | 32.217 | 1.00 | 36.57 | O |
| ATOM | 2239 | C | GLU | C | 76 | 28.770 | 38.353 | 27.706 | 1.00 | 39.68 | C |
| ATOM | 2240 | O | GLU | C | 76 | 29.759 | 37.642 | 27.548 | 1.00 | 39.67 | O |
| ATOM | 2241 | N | ASP | C | 77 | 27.529 | 37.906 | 27.511 | 1.00 | 39.47 | N |
| ATOM | 2242 | CA | ASP | C | 77 | 27.264 | 36.553 | 27.029 | 1.00 | 39.18 | C |
| ATOM | 2243 | CB | ASP | C | 77 | 25.975 | 36.015 | 27.621 | 1.00 | 39.36 | C |
| ATOM | 2244 | CG | ASP | C | 77 | 26.069 | 35.792 | 29.095 | 1.00 | 40.54 | C |
| ATOM | 2245 | OD1 | ASP | C | 77 | 27.103 | 35.279 | 29.564 | 1.00 | 43.00 | O |
| ATOM | 2246 | OD2 | ASP | C | 77 | 25.097 | 36.120 | 29.795 | 1.00 | 42.29 | O |
| ATOM | 2247 | C | ASP | C | 77 | 27.187 | 36.459 | 25.510 | 1.00 | 38.97 | C |
| ATOM | 2248 | O | ASP | C | 77 | 26.956 | 35.371 | 24.969 | 1.00 | 38.86 | O |
| ATOM | 2249 | N | SER | C | 78 | 27.362 | 37.590 | 24.823 | 1.00 | 38.67 | N |
| ATOM | 2250 | CA | SER | C | 78 | 27.479 | 37.581 | 23.362 | 1.00 | 38.39 | C |
| ATOM | 2251 | CB | SER | C | 78 | 27.564 | 38.997 | 22.814 | 1.00 | 38.08 | C |
| ATOM | 2252 | OG | SER | C | 78 | 26.390 | 39.703 | 23.145 | 1.00 | 37.55 | O |
| ATOM | 2253 | C | SER | C | 78 | 28.691 | 36.771 | 22.905 | 1.00 | 38.40 | C |
| ATOM | 2254 | O | SER | C | 78 | 29.781 | 36.858 | 23.489 | 1.00 | 38.36 | O |
| ATOM | 2255 | N | GLY | C | 79 | 28.490 | 35.973 | 21.867 | 1.00 | 38.28 | N |
| ATOM | 2256 | CA | GLY | C | 79 | 29.555 | 35.151 | 21.334 | 1.00 | 38.15 | C |
| ATOM | 2257 | C | GLY | C | 79 | 28.959 | 33.959 | 20.654 | 1.00 | 38.36 | C |
| ATOM | 2258 | O | GLY | C | 79 | 27.741 | 33.866 | 20.490 | 1.00 | 38.35 | O |
| ATOM | 2259 | N | THR | C | 80 | 29.823 | 33.041 | 20.249 | 1.00 | 38.98 | N |
| ATOM | 2260 | CA | THR | C | 80 | 29.392 | 31.847 | 19.538 | 1.00 | 39.37 | C |
| ATOM | 2261 | CB | THR | C | 80 | 30.273 | 31.554 | 18.304 | 1.00 | 39.13 | C |
| ATOM | 2262 | OG1 | THR | C | 80 | 30.166 | 32.641 | 17.377 | 1.00 | 38.93 | O |
| ATOM | 2263 | CG2 | THR | C | 80 | 29.814 | 30.290 | 17.600 | 1.00 | 39.77 | C |
| ATOM | 2264 | C | THR | C | 80 | 29.366 | 30.674 | 20.496 | 1.00 | 39.89 | C |
| ATOM | 2265 | O | THR | C | 80 | 30.323 | 30.457 | 21.243 | 1.00 | 40.12 | O |
| ATOM | 2266 | N | TYR | C | 81 | 28.245 | 29.946 | 20.463 | 1.00 | 40.31 | N |
| ATOM | 2267 | CA | TYR | C | 81 | 27.987 | 28.748 | 21.270 | 1.00 | 40.42 | C |
| ATOM | 2268 | CB | TYR | C | 81 | 26.673 | 28.921 | 22.051 | 1.00 | 40.48 | C |
| ATOM | 2269 | CG | TYR | C | 81 | 26.736 | 29.991 | 23.111 | 1.00 | 40.67 | C |
| ATOM | 2270 | CD1 | TYR | C | 81 | 26.667 | 29.655 | 24.463 | 1.00 | 39.50 | C |
| ATOM | 2271 | CE1 | TYR | C | 81 | 26.752 | 30.623 | 25.444 | 1.00 | 38.60 | C |
| ATOM | 2272 | CZ | TYR | C | 81 | 26.911 | 31.954 | 25.085 | 1.00 | 40.20 | C |
| ATOM | 2273 | OH | TYR | C | 81 | 26.993 | 32.905 | 26.065 | 1.00 | 41.07 | O |
| ATOM | 2274 | CE2 | TYR | C | 81 | 26.992 | 32.330 | 23.753 | 1.00 | 40.63 | C |
| ATOM | 2275 | CD2 | TYR | C | 81 | 26.905 | 31.344 | 22.767 | 1.00 | 41.34 | C |
| ATOM | 2276 | C | TYR | C | 81 | 27.887 | 27.500 | 20.384 | 1.00 | 40.61 | C |
| ATOM | 2277 | O | TYR | C | 81 | 27.270 | 27.534 | 19.317 | 1.00 | 40.48 | O |
| ATOM | 2278 | N | LYS | C | 82 | 28.486 | 26.400 | 20.830 | 1.00 | 40.98 | N |
| ATOM | 2279 | CA | LYS | C | 82 | 28.456 | 25.142 | 20.082 | 1.00 | 41.31 | C |
| ATOM | 2280 | CB | LYS | C | 82 | 29.769 | 24.890 | 19.354 | 1.00 | 40.81 | C |
| ATOM | 2281 | CG | LYS | C | 82 | 29.929 | 25.735 | 18.144 | 1.00 | 41.85 | C |
| ATOM | 2282 | CD | LYS | C | 82 | 31.152 | 25.386 | 17.339 | 1.00 | 42.31 | C |
| ATOM | 2283 | CE | LYS | C | 82 | 31.591 | 26.597 | 16.549 | 1.00 | 42.93 | C |
| ATOM | 2284 | NZ | LYS | C | 82 | 32.191 | 26.236 | 15.242 | 1.00 | 45.16 | N |
| ATOM | 2285 | C | LYS | C | 82 | 28.209 | 23.989 | 21.020 | 1.00 | 42.03 | C |
| ATOM | 2286 | O | LYS | C | 82 | 28.641 | 24.009 | 22.173 | 1.00 | 42.66 | O |
| ATOM | 2287 | N | CYS | C | 83 | 27.522 | 22.976 | 20.513 | 1.00 | 42.37 | N |
| ATOM | 2288 | CA | CYS | C | 83 | 27.318 | 21.760 | 21.230 | 1.00 | 42.93 | C |
| ATOM | 2289 | CB | CYS | C | 83 | 25.854 | 21.368 | 21.137 | 1.00 | 43.61 | C |
| ATOM | 2290 | SG | CYS | C | 83 | 25.278 | 21.291 | 19.462 | 1.00 | 48.55 | S |
| ATOM | 2291 | C | CYS | C | 83 | 28.179 | 20.680 | 20.613 | 1.00 | 42.42 | C |
| ATOM | 2292 | O | CYS | C | 83 | 28.563 | 20.766 | 19.447 | 1.00 | 41.85 | O |
| ATOM | 2293 | N | GLY | C | 84 | 28.480 | 19.664 | 21.418 | 1.00 | 42.34 | N |
| ATOM | 2294 | CA | GLY | C | 84 | 29.137 | 18.459 | 20.952 | 1.00 | 41.90 | C |
| ATOM | 2295 | C | GLY | C | 84 | 28.389 | 17.233 | 21.437 | 1.00 | 41.74 | C |
| ATOM | 2296 | O | GLY | C | 84 | 28.168 | 17.077 | 22.622 | 1.00 | 41.50 | O |
| ATOM | 2297 | N | ALA | C | 85 | 28.009 | 16.359 | 20.510 | 1.00 | 42.01 | N |
| ATOM | 2298 | CA | ALA | C | 85 | 27.327 | 15.111 | 20.825 | 1.00 | 42.63 | C |
| ATOM | 2299 | CB | ALA | C | 85 | 26.066 | 14.957 | 19.949 | 1.00 | 41.98 | C |
| ATOM | 2300 | C | ALA | C | 85 | 28.298 | 13.972 | 20.576 | 1.00 | 43.38 | C |
| ATOM | 2301 | O | ALA | C | 85 | 28.840 | 13.859 | 19.484 | 1.00 | 43.85 | O |
| ATOM | 2302 | N | TYR | C | 86 | 28.538 | 13.138 | 21.580 | 1.00 | 44.65 | N |
| ATOM | 2303 | CA | TYR | C | 86 | 29.488 | 12.036 | 21.454 | 1.00 | 46.09 | C |
| ATOM | 2304 | CB | TYR | C | 86 | 30.651 | 12.223 | 22.446 | 1.00 | 47.37 | C |
| ATOM | 2305 | CG | TYR | C | 86 | 31.336 | 13.560 | 22.219 | 1.00 | 49.85 | C |
| ATOM | 2306 | CD1 | TYR | C | 86 | 32.450 | 13.669 | 21.367 | 1.00 | 52.79 | C |
| ATOM | 2307 | CE1 | TYR | C | 86 | 33.072 | 14.925 | 21.103 | 1.00 | 53.92 | C |
| ATOM | 2308 | CZ | TYR | C | 86 | 32.554 | 16.087 | 21.694 | 1.00 | 53.39 | C |
| ATOM | 2309 | OH | TYR | C | 86 | 33.154 | 17.324 | 21.465 | 1.00 | 52.01 | O |
| ATOM | 2310 | CE2 | TYR | C | 86 | 31.438 | 15.995 | 22.552 | 1.00 | 53.89 | C |
| ATOM | 2311 | CD2 | TYR | C | 86 | 30.838 | 14.734 | 22.804 | 1.00 | 52.16 | C |
| ATOM | 2312 | C | TYR | C | 86 | 28.726 | 10.721 | 21.616 | 1.00 | 46.42 | C |

APPENDIX I(d)-continued

| | | | | | | | | | | | |
|---|---|---|---|---|---|---|---|---|---|---|---|
| ATOM | 2313 | O | TYR | C | 86 | 27.858 | 10.622 | 22.476 | 1.00 | 46.61 | O |
| ATOM | 2314 | N | PHE | C | 87 | 29.009 | 9.738 | 20.760 | 1.00 | 46.89 | N |
| ATOM | 2315 | CA | PHE | C | 87 | 28.226 | 8.492 | 20.697 | 1.00 | 47.55 | C |
| ATOM | 2316 | CB | PHE | C | 87 | 27.264 | 8.519 | 19.513 | 1.00 | 46.60 | C |
| ATOM | 2317 | CG | PHE | C | 87 | 27.872 | 9.054 | 18.263 | 1.00 | 45.28 | C |
| ATOM | 2318 | CD1 | PHE | C | 87 | 27.886 | 10.413 | 18.012 | 1.00 | 44.33 | C |
| ATOM | 2319 | CE1 | PHE | C | 87 | 28.459 | 10.907 | 16.867 | 1.00 | 43.16 | C |
| ATOM | 2320 | CZ | PHE | C | 87 | 29.027 | 10.041 | 15.963 | 1.00 | 43.21 | C |
| ATOM | 2321 | CE2 | PHE | C | 87 | 29.017 | 8.699 | 16.203 | 1.00 | 42.62 | C |
| ATOM | 2322 | CD2 | PHE | C | 87 | 28.445 | 8.208 | 17.344 | 1.00 | 43.83 | C |
| ATOM | 2323 | C | PHE | C | 87 | 29.105 | 7.274 | 20.573 | 1.00 | 49.03 | C |
| ATOM | 2324 | O | PHE | C | 87 | 30.146 | 7.331 | 19.944 | 1.00 | 49.13 | O |
| ATOM | 2325 | N | SER | C | 88 | 28.684 | 6.162 | 21.157 | 1.00 | 51.17 | N |
| ATOM | 2326 | CA | SER | C | 88 | 29.484 | 4.956 | 21.068 | 1.00 | 53.66 | C |
| ATOM | 2327 | CB | SER | C | 88 | 30.316 | 4.764 | 22.341 | 1.00 | 53.69 | C |
| ATOM | 2328 | OG | SER | C | 88 | 31.025 | 3.521 | 22.304 | 1.00 | 54.67 | O |
| ATOM | 2329 | C | SER | C | 88 | 28.667 | 3.707 | 20.792 | 1.00 | 55.16 | C |
| ATOM | 2330 | O | SER | C | 88 | 27.476 | 3.658 | 21.088 | 1.00 | 55.08 | O |
| ATOM | 2331 | N | ASP | C | 89 | 29.326 | 2.710 | 20.206 | 1.00 | 57.59 | N |
| ATOM | 2332 | CA | ASP | C | 89 | 28.792 | 1.345 | 20.138 | 1.00 | 60.14 | C |
| ATOM | 2333 | CB | ASP | C | 89 | 29.255 | 0.596 | 18.860 | 1.00 | 60.31 | C |
| ATOM | 2334 | CG | ASP | C | 89 | 30.771 | 0.736 | 18.578 | 1.00 | 60.98 | C |
| ATOM | 2335 | OD1 | ASP | C | 89 | 31.489 | −0.289 | 18.629 | 1.00 | 60.55 | O |
| ATOM | 2336 | OD2 | ASP | C | 89 | 31.242 | 1.864 | 18.295 | 1.00 | 61.88 | O |
| ATOM | 2337 | C | ASP | C | 89 | 29.230 | 0.615 | 21.407 | 1.00 | 61.54 | C |
| ATOM | 2338 | O | ASP | C | 89 | 30.423 | 0.368 | 21.598 | 1.00 | 61.77 | O |
| ATOM | 2339 | N | ALA | C | 90 | 28.262 | 0.298 | 22.270 | 1.00 | 63.36 | N |
| ATOM | 2340 | CA | ALA | C | 90 | 28.512 | −0.238 | 23.625 | 1.00 | 65.20 | C |
| ATOM | 2341 | CB | ALA | C | 90 | 27.406 | −1.231 | 24.018 | 1.00 | 65.05 | C |
| ATOM | 2342 | C | ALA | C | 90 | 29.919 | −0.852 | 23.843 | 1.00 | 66.45 | C |
| ATOM | 2343 | O | ALA | C | 90 | 30.731 | −0.331 | 24.634 | 1.00 | 66.70 | O |
| ATOM | 2344 | N | MET | C | 91 | 30.199 | −1.945 | 23.131 | 1.00 | 67.72 | N |
| ATOM | 2345 | CA | MET | C | 91 | 31.524 | −2.562 | 23.135 | 1.00 | 68.99 | C |
| ATOM | 2346 | CB | MET | C | 91 | 31.458 | −4.008 | 22.613 | 1.00 | 69.19 | C |
| ATOM | 2347 | CG | MET | C | 91 | 32.749 | −4.832 | 22.774 | 1.00 | 70.93 | C |
| ATOM | 2348 | SD | MET | C | 91 | 33.834 | −4.849 | 21.310 | 1.00 | 74.22 | S |
| ATOM | 2349 | CE | MET | C | 91 | 35.173 | −3.747 | 21.787 | 1.00 | 74.42 | C |
| ATOM | 2350 | C | MET | C | 91 | 32.507 | −1.714 | 22.319 | 1.00 | 69.40 | C |
| ATOM | 2351 | O | MET | C | 91 | 32.507 | −1.744 | 21.080 | 1.00 | 69.57 | O |
| ATOM | 2352 | N | SER | C | 92 | 33.308 | −0.929 | 23.035 | 1.00 | 69.79 | N |
| ATOM | 2353 | CA | SER | C | 92 | 34.469 | −0.223 | 22.475 | 1.00 | 70.05 | C |
| ATOM | 2354 | CB | SER | C | 92 | 34.066 | 0.939 | 21.541 | 1.00 | 69.93 | C |
| ATOM | 2355 | OG | SER | C | 92 | 32.806 | 1.491 | 21.881 | 1.00 | 70.35 | O |
| ATOM | 2356 | C | SER | C | 92 | 35.356 | 0.249 | 23.627 | 1.00 | 70.02 | C |
| ATOM | 2357 | O | SER | C | 92 | 36.583 | 0.306 | 23.506 | 1.00 | 70.09 | O |
| ATOM | 2358 | N | ASN | C | 93 | 34.704 | 0.541 | 24.750 | 1.00 | 70.00 | N |
| ATOM | 2359 | CA | ASN | C | 93 | 35.333 | 1.018 | 25.993 | 1.00 | 69.95 | C |
| ATOM | 2360 | CB | ASN | C | 93 | 36.362 | 0.031 | 26.561 | 1.00 | 69.90 | C |
| ATOM | 2361 | CG | ASN | C | 93 | 36.387 | 0.021 | 28.090 | 1.00 | 69.71 | C |
| ATOM | 2362 | OD1 | ASN | C | 93 | 37.241 | −0.629 | 28.699 | 1.00 | 69.74 | O |
| ATOM | 2363 | ND2 | ASN | C | 93 | 35.444 | 0.729 | 28.715 | 1.00 | 68.27 | N |
| ATOM | 2364 | C | ASN | C | 93 | 35.884 | 2.439 | 25.943 | 1.00 | 69.86 | C |
| ATOM | 2365 | O | ASN | C | 93 | 36.587 | 2.838 | 25.004 | 1.00 | 69.97 | O |
| ATOM | 2366 | N | TYR | C | 94 | 35.549 | 3.185 | 26.993 | 1.00 | 69.43 | N |
| ATOM | 2367 | CA | TYR | C | 94 | 35.704 | 4.627 | 27.041 | 1.00 | 68.88 | C |
| ATOM | 2368 | CB | TYR | C | 94 | 34.510 | 5.236 | 27.776 | 1.00 | 69.45 | C |
| ATOM | 2369 | CG | TYR | C | 94 | 33.164 | 4.883 | 27.172 | 1.00 | 70.37 | C |
| ATOM | 2370 | CD1 | TYR | C | 94 | 32.364 | 5.872 | 26.584 | 1.00 | 71.10 | C |
| ATOM | 2371 | CE1 | TYR | C | 94 | 31.121 | 5.562 | 26.038 | 1.00 | 71.14 | C |
| ATOM | 2372 | CZ | TYR | C | 94 | 30.669 | 4.244 | 26.062 | 1.00 | 71.31 | C |
| ATOM | 2373 | OH | TYR | C | 94 | 29.439 | 3.939 | 25.516 | 1.00 | 71.43 | O |
| ATOM | 2374 | CE2 | TYR | C | 94 | 31.448 | 3.238 | 26.634 | 1.00 | 71.20 | C |
| ATOM | 2375 | CD2 | TYR | C | 94 | 32.684 | 3.563 | 27.190 | 1.00 | 70.47 | C |
| ATOM | 2376 | C | TYR | C | 94 | 37.018 | 5.019 | 27.706 | 1.00 | 68.05 | C |
| ATOM | 2377 | O | TYR | C | 94 | 37.054 | 5.864 | 28.607 | 1.00 | 67.95 | O |
| ATOM | 2378 | N | SER | C | 95 | 38.092 | 4.370 | 27.262 | 1.00 | 67.01 | N |
| ATOM | 2379 | CA | SER | C | 95 | 39.454 | 4.775 | 27.598 | 1.00 | 65.81 | C |
| ATOM | 2380 | CB | SER | C | 95 | 40.366 | 3.558 | 27.764 | 1.00 | 65.66 | C |
| ATOM | 2381 | OG | SER | C | 95 | 39.725 | 2.552 | 28.519 | 1.00 | 65.34 | O |
| ATOM | 2382 | C | SER | C | 95 | 39.966 | 5.672 | 26.471 | 1.00 | 64.95 | C |
| ATOM | 2383 | O | SER | C | 95 | 40.638 | 6.676 | 26.716 | 1.00 | 65.24 | O |
| ATOM | 2384 | N | TYR | C | 96 | 39.641 | 5.301 | 25.234 | 1.00 | 63.43 | N |
| ATOM | 2385 | CA | TYR | C | 96 | 40.027 | 6.088 | 24.083 | 1.00 | 61.77 | C |
| ATOM | 2386 | CB | TYR | C | 96 | 40.629 | 5.210 | 22.985 | 1.00 | 62.04 | C |
| ATOM | 2387 | CG | TYR | C | 96 | 42.014 | 4.706 | 23.347 | 1.00 | 62.12 | C |
| ATOM | 2388 | CD1 | TYR | C | 96 | 43.086 | 5.598 | 23.492 | 1.00 | 62.12 | C |
| ATOM | 2389 | CE1 | TYR | C | 96 | 44.360 | 5.147 | 23.841 | 1.00 | 62.47 | C |
| ATOM | 2390 | CZ | TYR | C | 96 | 44.572 | 3.786 | 24.046 | 1.00 | 62.64 | C |
| ATOM | 2391 | OH | TYR | C | 96 | 45.834 | 3.324 | 24.384 | 1.00 | 62.52 | O |
| ATOM | 2392 | CE2 | TYR | C | 96 | 43.517 | 2.882 | 23.907 | 1.00 | 62.40 | C |

APPENDIX I(d)-continued

| | | | | | | | | | | |
|---|---|---|---|---|---|---|---|---|---|---|
| ATOM | 2393 | CD2 | TYR | C | 96 | 42.249 | 3.347 | 23.564 | 1.00 | 61.75 C |
| ATOM | 2394 | C | TYR | C | 96 | 38.817 | 6.849 | 23.608 | 1.00 | 60.49 C |
| ATOM | 2395 | O | TYR | C | 96 | 37.695 | 6.345 | 23.720 | 1.00 | 60.66 O |
| ATOM | 2396 | N | PRO | C | 97 | 39.038 | 8.077 | 23.094 | 1.00 | 59.03 N |
| ATOM | 2397 | CA | PRO | C | 97 | 37.958 | 8.995 | 22.751 | 1.00 | 57.45 C |
| ATOM | 2398 | CB | PRO | C | 97 | 38.693 | 10.221 | 22.199 | 1.00 | 57.62 C |
| ATOM | 2399 | CG | PRO | C | 97 | 40.034 | 9.721 | 21.798 | 1.00 | 58.56 C |
| ATOM | 2400 | CD | PRO | C | 97 | 40.359 | 8.663 | 22.798 | 1.00 | 59.07 C |
| ATOM | 2401 | C | PRO | C | 97 | 36.994 | 8.426 | 21.718 | 1.00 | 55.87 C |
| ATOM | 2402 | O | PRO | C | 97 | 37.393 | 7.996 | 20.634 | 1.00 | 55.50 O |
| ATOM | 2403 | N | ILE | C | 98 | 35.723 | 8.421 | 22.096 | 1.00 | 54.16 N |
| ATOM | 2404 | CA | ILE | C | 98 | 34.623 | 8.020 | 21.222 | 1.00 | 52.19 C |
| ATOM | 2405 | CB | ILE | C | 98 | 33.325 | 7.702 | 22.058 | 1.00 | 52.52 C |
| ATOM | 2406 | CG1 | ILE | C | 98 | 32.930 | 8.888 | 22.953 | 1.00 | 51.84 C |
| ATOM | 2407 | CD1 | ILE | C | 98 | 31.665 | 8.676 | 23.761 | 1.00 | 51.89 C |
| ATOM | 2408 | CG2 | ILE | C | 98 | 33.536 | 6.406 | 22.894 | 1.00 | 53.12 C |
| ATOM | 2409 | C | ILE | C | 98 | 34.371 | 9.087 | 20.141 | 1.00 | 50.11 C |
| ATOM | 2410 | O | ILE | C | 98 | 34.661 | 10.264 | 20.364 | 1.00 | 49.77 O |
| ATOM | 2411 | N | PRO | C | 99 | 33.874 | 8.671 | 18.954 | 1.00 | 48.00 N |
| ATOM | 2412 | CA | PRO | C | 99 | 33.470 | 9.652 | 17.944 | 1.00 | 46.52 C |
| ATOM | 2413 | CB | PRO | C | 99 | 32.852 | 8.782 | 16.836 | 1.00 | 46.16 C |
| ATOM | 2414 | CG | PRO | C | 99 | 32.689 | 7.435 | 17.411 | 1.00 | 46.14 C |
| ATOM | 2415 | CD | PRO | C | 99 | 33.698 | 7.291 | 18.470 | 1.00 | 47.41 C |
| ATOM | 2416 | C | PRO | C | 99 | 32.465 | 10.715 | 18.468 | 1.00 | 45.21 C |
| ATOM | 2417 | O | PRO | C | 99 | 31.867 | 10.534 | 19.526 | 1.00 | 44.67 O |
| ATOM | 2418 | N | GLY | C | 100 | 32.312 | 11.816 | 17.733 | 1.00 | 43.96 N |
| ATOM | 2419 | CA | GLY | C | 100 | 31.368 | 12.871 | 18.082 | 1.00 | 42.29 C |
| ATOM | 2420 | C | GLY | C | 100 | 31.376 | 13.977 | 17.049 | 1.00 | 41.74 C |
| ATOM | 2421 | O | GLY | C | 100 | 32.229 | 13.994 | 16.162 | 1.00 | 41.65 O |
| ATOM | 2422 | N | GLU | C | 101 | 30.427 | 14.900 | 17.162 | 1.00 | 41.32 N |
| ATOM | 2423 | CA | GLU | C | 101 | 30.302 | 16.039 | 16.238 | 1.00 | 41.63 C |
| ATOM | 2424 | CB | GLC | C | 101 | 29.265 | 15.742 | 15.137 | 1.00 | 41.77 C |
| ATOM | 2425 | CG | GLU | C | 101 | 29.525 | 14.511 | 14.274 | 1.00 | 42.85 C |
| ATOM | 2426 | CD | GLU | C | 101 | 30.562 | 14.728 | 13.171 | 1.00 | 44.72 C |
| ATOM | 2427 | OE1 | GLU | C | 101 | 30.820 | 15.899 | 12.792 | 1.00 | 46.56 O |
| ATOM | 2428 | OE2 | GLU | C | 101 | 31.107 | 13.715 | 12.671 | 1.00 | 43.10 O |
| ATOM | 2429 | C | GLU | C | 101 | 29.874 | 17.319 | 16.981 | 1.00 | 41.54 C |
| ATOM | 2430 | O | GLU | C | 101 | 29.267 | 17.249 | 18.056 | 1.00 | 41.68 O |
| ATOM | 2431 | N | LYS | C | 102 | 30.163 | 18.483 | 16.402 | 1.00 | 41.21 N |
| ATOM | 2432 | CA | LYS | C | 102 | 29.770 | 19.770 | 16.988 | 1.00 | 40.46 C |
| ATOM | 2433 | CB | LYS | C | 102 | 30.967 | 20.706 | 17.088 | 1.00 | 40.30 C |
| ATOM | 2434 | CG | LYS | C | 102 | 32.213 | 20.088 | 17.663 | 1.00 | 39.49 C |
| ATOM | 2435 | CD | LYS | C | 102 | 32.482 | 20.613 | 19.048 | 1.00 | 41.83 C |
| ATOM | 2436 | CE | LYS | C | 102 | 33.185 | 21.983 | 19.030 | 1.00 | 42.84 C |
| ATOM | 2437 | NZ | LYS | C | 102 | 34.685 | 21.860 | 19.033 | 1.00 | 43.61 N |
| ATOM | 2438 | C | LYS | C | 102 | 28.754 | 20.404 | 16.071 | 1.00 | 40.70 C |
| ATOM | 2439 | O | LYS | C | 102 | 28.812 | 20.218 | 14.849 | 1.00 | 40.87 O |
| ATOM | 2440 | N | GLY | C | 103 | 27.818 | 21.152 | 16.645 | 1.00 | 40.80 N |
| ATOM | 2441 | CA | GLY | C | 103 | 26.904 | 21.976 | 15.847 | 1.00 | 40.56 C |
| ATOM | 2442 | C | GLY | C | 103 | 27.714 | 23.051 | 15.128 | 1.00 | 40.72 C |
| ATOM | 2443 | O | GLY | C | 103 | 28.852 | 23.346 | 15.515 | 1.00 | 41.01 O |
| ATOM | 2444 | N | ALA | C | 104 | 27.147 | 23.618 | 14.066 | 1.00 | 40.34 N |
| ATOM | 2445 | CA | ALA | C | 104 | 27.760 | 24.720 | 13.340 | 1.00 | 39.68 C |
| ATOM | 2446 | CB | ALA | C | 104 | 26.978 | 24.993 | 12.093 | 1.00 | 39.30 C |
| ATOM | 2447 | C | ALA | C | 104 | 27.870 | 25.986 | 14.218 | 1.00 | 39.81 C |
| ATOM | 2448 | O | ALA | C | 104 | 28.731 | 26.839 | 13.982 | 1.00 | 39.91 O |
| ATOM | 2449 | N | GLY | C | 105 | 26.994 | 26.091 | 15.225 | 1.00 | 39.76 N |
| ATOM | 2450 | CA | GLY | C | 105 | 27.052 | 27.139 | 16.252 | 1.00 | 39.33 C |
| ATOM | 2451 | C | GLY | C | 105 | 25.873 | 28.105 | 16.348 | 1.00 | 39.20 C |
| ATOM | 2452 | O | GLY | C | 105 | 25.136 | 28.310 | 15.380 | 1.00 | 39.37 O |
| ATOM | 2453 | N | THR | C | 106 | 25.699 | 28.711 | 17.521 | 1.00 | 38.80 N |
| ATOM | 2454 | CA | THR | C | 106 | 24.851 | 29.894 | 17.654 | 1.00 | 38.05 C |
| ATOM | 2455 | CB | THR | C | 106 | 23.814 | 29.727 | 18.751 | 1.00 | 38.38 C |
| ATOM | 2456 | OG1 | THR | C | 106 | 22.999 | 28.579 | 18.467 | 1.00 | 38.76 O |
| ATOM | 2457 | CG2 | THR | C | 106 | 22.944 | 30.990 | 18.828 | 1.00 | 38.21 C |
| ATOM | 2458 | C | THR | C | 106 | 25.658 | 31.154 | 17.950 | 1.00 | 37.36 C |
| ATOM | 2459 | O | THR | C | 106 | 26.361 | 31.242 | 18.955 | 1.00 | 36.52 O |
| ATOM | 2460 | N | VAL | C | 107 | 25.558 | 32.130 | 17.057 | 1.00 | 37.43 N |
| ATOM | 2461 | CA | VAL | C | 107 | 26.119 | 33.466 | 17.343 | 1.00 | 37.35 C |
| ATOM | 2462 | CB | VAL | C | 107 | 26.932 | 34.118 | 16.152 | 1.00 | 36.69 C |
| ATOM | 2463 | CG1 | VAL | C | 107 | 26.857 | 33.283 | 14.897 | 1.00 | 36.10 C |
| ATOM | 2464 | CG2 | VAL | C | 107 | 26.520 | 35.538 | 15.904 | 1.00 | 35.96 C |
| ATOM | 2465 | C | VAL | C | 107 | 25.050 | 34.350 | 18.024 | 1.00 | 37.47 C |
| ATOM | 2466 | O | VAL | C | 107 | 24.023 | 34.712 | 17.424 | 1.00 | 37.06 O |
| ATOM | 2467 | N | LEU | C | 108 | 25.290 | 34.607 | 19.313 | 1.00 | 37.38 N |
| ATOM | 2468 | CA | LEU | C | 108 | 24.324 | 35.267 | 20.170 | 1.00 | 37.59 C |
| ATOM | 2469 | CB | LEU | C | 108 | 24.245 | 34.574 | 21.537 | 1.00 | 37.38 C |
| ATOM | 2470 | CG | LEU | C | 108 | 23.406 | 35.266 | 22.624 | 1.00 | 37.81 C |
| ATOM | 2471 | CD1 | LEU | C | 108 | 21.924 | 35.419 | 22.243 | 1.00 | 37.73 C |
| ATOM | 2472 | CD2 | LEU | C | 108 | 23.539 | 34.545 | 23.957 | 1.00 | 37.81 C |

APPENDIX I(d)-continued

| | | | | | | | | | | |
|---|---|---|---|---|---|---|---|---|---|---|
| ATOM | 2473 | C | LEU | C | 108 | 24.675 | 36.743 | 20.326 | 1.00 | 37.73 C |
| ATOM | 2474 | O | LEU | C | 108 | 25.790 | 37.083 | 20.743 | 1.00 | 38.29 O |
| ATOM | 2475 | N | THR | C | 109 | 23.732 | 37.615 | 19.976 | 1.00 | 37.18 N |
| ATOM | 2476 | CA | THR | C | 109 | 23.913 | 39.038 | 20.198 | 1.00 | 36.88 C |
| ATOM | 2477 | CB | THR | C | 109 | 23.741 | 39.834 | 18.895 | 1.00 | 36.94 C |
| ATOM | 2478 | OG1 | THR | C | 109 | 24.714 | 39.382 | 17.947 | 1.00 | 36.86 O |
| ATOM | 2479 | CG2 | THR | C | 109 | 23.935 | 41.315 | 19.139 | 1.00 | 35.69 C |
| ATOM | 2480 | C | THR | C | 109 | 22.941 | 39.512 | 21.265 | 1.00 | 36.68 C |
| ATOM | 2481 | O | THR | C | 109 | 21.738 | 39.344 | 21.123 | 1.00 | 36.74 O |
| ATOM | 2482 | N | VAL | C | 110 | 23.458 | 40.079 | 22.344 | 1.00 | 36.39 N |
| ATOM | 2483 | CA | VAL | C | 110 | 22.571 | 40.545 | 23.397 | 1.00 | 36.75 C |
| ATOM | 2484 | CB | VAL | C | 110 | 22.731 | 39.744 | 24.730 | 1.00 | 37.01 C |
| ATOM | 2485 | CG1 | VAL | C | 110 | 24.026 | 38.942 | 24.754 | 1.00 | 37.71 C |
| ATOM | 2486 | CG2 | VAL | C | 110 | 22.567 | 40.628 | 25.965 | 1.00 | 36.58 C |
| ATOM | 2487 | C | VAL | C | 110 | 22.527 | 42.067 | 23.571 | 1.00 | 36.82 C |
| ATOM | 2488 | O | VAL | C | 110 | 23.561 | 42.727 | 23.705 | 1.00 | 36.88 O |
| ATOM | 2489 | N | LYS | C | 111 | 21.293 | 42.581 | 23.564 | 1.00 | 36.66 N |
| ATOM | 2490 | CA | LYS | C | 111 | 20.954 | 44.004 | 23.539 | 1.00 | 36.40 C |
| ATOM | 2491 | CB | LYS | C | 111 | 21.921 | 44.857 | 24.364 | 1.00 | 36.13 C |
| ATOM | 2492 | CG | LYS | C | 111 | 21.539 | 45.007 | 25.813 | 1.00 | 34.53 C |
| ATOM | 2493 | CD | LYS | C | 111 | 21.941 | 46.406 | 26.332 | 1.00 | 31.44 C |
| ATOM | 2494 | CE | LYS | C | 111 | 20.798 | 47.369 | 26.236 | 1.00 | 28.66 C |
| ATOM | 2495 | NZ | LYS | C | 111 | 19.648 | 46.791 | 26.962 | 1.00 | 27.06 N |
| ATOM | 2496 | C | LYS | C | 111 | 20.864 | 44.514 | 22.100 | 1.00 | 36.68 C |
| ATOM | 2497 | O | LYS | C | 111 | 19.774 | 44.832 | 21.605 | 1.00 | 36.91 O |
| ATOM | 2498 | N | ALA | D | 1 | 34.772 | 10.109 | 45.854 | 1.00 | 43.36 N |
| ATOM | 2499 | CA | ALA | D | 1 | 33.646 | 9.989 | 44.886 | 1.00 | 43.10 C |
| ATOM | 2500 | CB | ALA | D | 1 | 34.122 | 10.324 | 43.477 | 1.00 | 42.95 C |
| ATOM | 2501 | C | ALA | D | 1 | 33.055 | 8.587 | 44.935 | 1.00 | 43.06 C |
| ATOM | 2502 | O | ALA | D | 1 | 33.793 | 7.610 | 44.856 | 1.00 | 42.97 O |
| ATOM | 2503 | N | TRP | D | 2 | 31.730 | 8.511 | 45.084 | 1.00 | 43.13 N |
| ATOM | 2504 | CA | TRP | D | 2 | 30.958 | 7.260 | 45.071 | 1.00 | 43.20 C |
| ATOM | 2505 | CB | TRP | D | 2 | 31.000 | 6.574 | 46.443 | 1.00 | 43.77 C |
| ATOM | 2506 | CG | TRP | D | 2 | 30.328 | 7.378 | 47.539 | 1.00 | 44.78 C |
| ATOM | 2507 | CD1 | TRP | D | 2 | 30.826 | 8.489 | 48.173 | 1.00 | 45.33 C |
| ATOM | 2508 | NE1 | TRP | D | 2 | 29.927 | 8.949 | 49.107 | 1.00 | 45.42 N |
| ATOM | 2509 | CE2 | TRP | D | 2 | 28.816 | 8.146 | 49.089 | 1.00 | 45.11 C |
| ATOM | 2510 | CD2 | TRP | D | 2 | 29.033 | 7.138 | 48.115 | 1.00 | 45.97 C |
| ATOM | 2511 | CE3 | TRP | D | 2 | 28.032 | 6.169 | 47.901 | 1.00 | 46.79 C |
| ATOM | 2512 | CZ3 | TRP | D | 2 | 26.866 | 6.236 | 48.668 | 1.00 | 45.73 C |
| ATOM | 2513 | CH2 | TRP | D | 2 | 26.684 | 7.263 | 49.630 | 1.00 | 45.13 C |
| ATOM | 2514 | CZ2 | TRP | D | 2 | 27.643 | 8.218 | 49.850 | 1.00 | 44.55 C |
| ATOM | 2515 | C | TRP | D | 2 | 29.512 | 7.575 | 44.695 | 1.00 | 43.00 C |
| ATOM | 2516 | O | TRP | D | 2 | 29.031 | 8.676 | 44.936 | 1.00 | 42.89 O |
| ATOM | 2517 | N | VAL | D | 3 | 28.820 | 6.609 | 44.107 | 1.00 | 43.01 N |
| ATOM | 2518 | CA | VAL | D | 3 | 27.434 | 6.802 | 43.677 | 1.00 | 42.86 C |
| ATOM | 2519 | CB | VAL | D | 3 | 27.170 | 6.184 | 42.285 | 1.00 | 42.67 C |
| ATOM | 2520 | CG1 | VAL | D | 3 | 25.709 | 6.364 | 41.868 | 1.00 | 42.34 C |
| ATOM | 2521 | CG2 | VAL | D | 3 | 28.087 | 6.780 | 41.255 | 1.00 | 41.96 C |
| ATOM | 2522 | C | VAL | D | 3 | 26.463 | 6.196 | 44.687 | 1.00 | 43.26 C |
| ATOM | 2523 | O | VAL | D | 3 | 26.535 | 5.004 | 45.005 | 1.00 | 43.57 O |
| ATOM | 2524 | N | ASP | D | 4 | 25.562 | 7.033 | 45.187 | 1.00 | 43.43 N |
| ATOM | 2525 | CA | ASP | D | 4 | 24.540 | 6.614 | 46.132 | 1.00 | 43.57 C |
| ATOM | 2526 | CB | ASP | D | 4 | 24.272 | 7.750 | 47.116 | 1.00 | 44.05 C |
| ATOM | 2527 | CG | ASP | D | 4 | 23.139 | 7.448 | 48.077 | 1.00 | 45.86 C |
| ATOM | 2528 | OD1 | ASP | D | 4 | 22.408 | 8.395 | 48.442 | 1.00 | 49.43 O |
| ATOM | 2529 | OD2 | ASP | D | 4 | 22.971 | 6.279 | 48.479 | 1.00 | 48.18 O |
| ATOM | 2530 | C | ASP | D | 4 | 23.274 | 6.245 | 45.368 | 1.00 | 43.18 C |
| ATOM | 2531 | O | ASP | D | 4 | 22.517 | 7.130 | 44.958 | 1.00 | 43.45 O |
| ATOM | 2532 | N | GLN | D | 5 | 23.051 | 4.944 | 45.176 | 1.00 | 42.32 N |
| ATOM | 2533 | CA | GLN | D | 5 | 21.927 | 4.460 | 44.372 | 1.00 | 41.43 C |
| ATOM | 2534 | CB | GLN | D | 5 | 22.409 | 3.374 | 43.385 | 1.00 | 41.53 C |
| ATOM | 2535 | CG | GLN | D | 5 | 21.300 | 2.779 | 42.500 | 1.00 | 40.66 C |
| ATOM | 2536 | CD | GLN | D | 5 | 21.731 | 1.644 | 41.584 | 1.00 | 40.39 C |
| ATOM | 2537 | OE1 | GLN | D | 5 | 20.885 | 0.938 | 41.081 | 1.00 | 40.73 O |
| ATOM | 2538 | NE2 | GLN | D | 5 | 23.029 | 1.467 | 41.362 | 1.00 | 39.34 N |
| ATOM | 2539 | C | GLN | D | 5 | 20.789 | 3.935 | 45.253 | 1.00 | 41.27 C |
| ATOM | 2540 | O | GLN | D | 5 | 21.027 | 3.140 | 46.160 | 1.00 | 41.45 O |
| ATOM | 2541 | N | THR | D | 6 | 19.564 | 4.389 | 44.996 | 1.00 | 40.95 N |
| ATOM | 2542 | CA | THR | D | 6 | 18.367 | 3.871 | 45.687 | 1.00 | 41.01 C |
| ATOM | 2543 | CB | THR | D | 6 | 17.824 | 4.824 | 46.783 | 1.00 | 40.94 C |
| ATOM | 2544 | OG1 | THR | D | 6 | 17.629 | 6.131 | 46.236 | 1.00 | 40.98 O |
| ATOM | 2545 | CG2 | THR | D | 6 | 18.770 | 4.899 | 47.984 | 1.00 | 41.61 C |
| ATOM | 2546 | C | THR | D | 6 | 17.236 | 3.649 | 44.699 | 1.00 | 41.11 C |
| ATOM | 2547 | O | THR | D | 6 | 17.199 | 4.313 | 43.654 | 1.00 | 41.48 O |
| ATOM | 2548 | N | PRO | D | 7 | 16.303 | 2.724 | 45.022 | 1.00 | 40.93 N |
| ATOM | 2549 | CA | PRO | D | 7 | 16.351 | 1.883 | 46.205 | 1.00 | 40.58 C |
| ATOM | 2550 | CB | PRO | D | 7 | 14.889 | 1.449 | 46.374 | 1.00 | 40.12 C |
| ATOM | 2551 | CG | PRO | D | 7 | 14.425 | 1.292 | 45.019 | 1.00 | 40.41 C |
| ATOM | 2552 | CD | PRO | D | 7 | 15.090 | 2.435 | 44.234 | 1.00 | 40.87 C |

APPENDIX I(d)-continued

| ATOM | 2553 | C | PRO | D | 7 | 17.252 | 0.669 | 45.987 | 1.00 | 40.46 | C |
|---|---|---|---|---|---|---|---|---|---|---|---|
| ATOM | 2554 | O | PRO | D | 7 | 17.582 | 0.319 | 44.854 | 1.00 | 40.53 | O |
| ATOM | 2555 | N | ARG | D | 8 | 17.633 | 0.048 | 47.093 | 1.00 | 40.39 | N |
| ATOM | 2556 | CA | ARG | D | 8 | 18.525 | −1.089 | 47.134 | 1.00 | 40.01 | C |
| ATOM | 2557 | CB | ARG | D | 8 | 18.900 | −1.298 | 48.590 | 1.00 | 39.76 | C |
| ATOM | 2558 | CG | ARG | D | 8 | 20.053 | −2.176 | 48.842 | 1.00 | 39.97 | C |
| ATOM | 2559 | CD | ARG | D | 8 | 20.407 | −2.076 | 50.299 | 1.00 | 42.10 | C |
| ATOM | 2560 | NE | ARG | D | 8 | 19.339 | −2.586 | 51.160 | 1.00 | 42.46 | N |
| ATOM | 2561 | CZ | ARG | D | 8 | 19.409 | −2.597 | 52.485 | 1.00 | 43.23 | C |
| ATOM | 2562 | NH1 | ARG | D | 8 | 20.498 | −2.134 | 53.081 | 1.00 | 44.37 | N |
| ATOM | 2563 | NH2 | ARG | D | 8 | 18.413 | −3.086 | 53.215 | 1.00 | 43.34 | N |
| ATOM | 2564 | C | ARG | D | 8 | 17.789 | −2.303 | 46.598 | 1.00 | 39.86 | C |
| ATOM | 2565 | O | ARG | D | 8 | 18.333 | −3.081 | 45.830 | 1.00 | 39.97 | O |
| ATOM | 2566 | N | SER | D | 9 | 16.543 | −2.452 | 47.026 | 1.00 | 39.86 | N |
| ATOM | 2567 | CA | SER | D | 9 | 15.663 | −3.511 | 46.557 | 1.00 | 39.98 | C |
| ATOM | 2568 | CB | SER | D | 9 | 15.726 | −4.729 | 47.481 | 1.00 | 39.97 | C |
| ATOM | 2569 | OG | SER | D | 9 | 14.958 | −4.536 | 48.652 | 1.00 | 39.70 | O |
| ATOM | 2570 | C | SER | D | 9 | 14.240 | −2.982 | 46.491 | 1.00 | 39.96 | C |
| ATOM | 2571 | O | SER | D | 9 | 13.845 | −2.127 | 47.288 | 1.00 | 39.56 | O |
| ATOM | 2572 | N | VAL | D | 10 | 13.480 | −3.485 | 45.529 | 1.00 | 40.04 | N |
| ATOM | 2573 | CA | VAL | D | 10 | 12.106 | −3.059 | 45.352 | 1.00 | 40.38 | C |
| ATOM | 2574 | CB | VAL | D | 10 | 12.034 | −1.736 | 44.553 | 1.00 | 40.44 | C |
| ATOM | 2575 | CG1 | VAL | D | 10 | 12.452 | −1.947 | 43.106 | 1.00 | 40.88 | C |
| ATOM | 2576 | CG2 | VAL | D | 10 | 10.643 | −1.117 | 44.642 | 1.00 | 40.75 | C |
| ATOM | 2577 | C | VAL | D | 10 | 11.319 | −4.173 | 44.665 | 1.00 | 40.45 | C |
| ATOM | 2578 | O | VAL | D | 10 | 11.888 | −4.981 | 43.919 | 1.00 | 40.68 | O |
| ATOM | 2579 | N | THR | D | 11 | 10.021 | −4.245 | 44.932 | 1.00 | 40.08 | N |
| ATOM | 2580 | CA | THR | D | 11 | 9.202 | −5.202 | 44.212 | 1.00 | 40.05 | C |
| ATOM | 2581 | CB | THR | D | 11 | 8.863 | −6.446 | 45.065 | 1.00 | 39.92 | C |
| ATOM | 2582 | OG1 | THR | D | 11 | 7.702 | −7.098 | 44.549 | 1.00 | 39.40 | O |
| ATOM | 2583 | CG2 | THR | D | 11 | 8.615 | −6.066 | 46.497 | 1.00 | 41.25 | C |
| ATOM | 2584 | C | THR | D | 11 | 7.981 | −4.526 | 43.622 | 1.00 | 40.02 | C |
| ATOM | 2585 | O | THR | D | 11 | 7.228 | −3.871 | 44.327 | 1.00 | 40.41 | O |
| ATOM | 2586 | N | LYS | D | 12 | 7.815 | −4.662 | 42.312 | 1.00 | 40.23 | N |
| ATOM | 2587 | CA | LYS | D | 12 | 6.727 | −4.003 | 41.595 | 1.00 | 40.27 | C |
| ATOM | 2588 | CB | LYS | D | 12 | 7.298 | −3.086 | 40.521 | 1.00 | 39.94 | C |
| ATOM | 2589 | CG | LYS | D | 12 | 8.109 | −1.918 | 41.063 | 1.00 | 39.68 | C |
| ATOM | 2590 | CD | LYS | D | 12 | 7.202 | −0.867 | 41.722 | 1.00 | 39.52 | C |
| ATOM | 2591 | CE | LYS | D | 12 | 7.858 | 0.503 | 41.808 | 1.00 | 38.17 | C |
| ATOM | 2592 | NZ | LYS | D | 12 | 7.254 | 1.335 | 42.866 | 1.00 | 36.86 | N |
| ATOM | 2593 | C | LYS | D | 12 | 5.831 | −5.056 | 40.965 | 1.00 | 40.58 | C |
| ATOM | 2594 | O | LYS | D | 12 | 6.268 | −6.194 | 40.790 | 1.00 | 41.22 | O |
| ATOM | 2595 | N | GLU | D | 13 | 4.587 | −4.696 | 40.645 | 1.00 | 40.41 | N |
| ATOM | 2596 | CA | GLU | D | 13 | 3.679 | −5.590 | 39.909 | 1.00 | 40.35 | C |
| ATOM | 2597 | CB | GLU | D | 13 | 2.225 | −5.341 | 40.311 | 1.00 | 40.65 | C |
| ATOM | 2598 | CG | GLU | D | 13 | 1.969 | −5.174 | 41.814 | 1.00 | 43.08 | C |
| ATOM | 2599 | CD | GLU | D | 13 | 1.647 | −6.484 | 42.499 | 1.00 | 47.17 | C |
| ATOM | 2600 | OE1 | GLU | D | 13 | 1.336 | −6.478 | 43.720 | 1.00 | 48.20 | O |
| ATOM | 2601 | OE2 | GLU | D | 13 | 1.706 | −7.529 | 41.808 | 1.00 | 49.59 | O |
| ATOM | 2602 | C | GLU | D | 13 | 3.832 | −5.363 | 38.400 | 1.00 | 39.74 | C |
| ATOM | 2603 | O | GLU | D | 13 | 4.165 | −4.257 | 37.979 | 1.00 | 40.12 | O |
| ATOM | 2604 | N | THR | D | 14 | 3.605 | −6.407 | 37.598 | 1.00 | 38.94 | N |
| ATOM | 2605 | CA | THR | D | 14 | 3.528 | −6.298 | 36.137 | 1.00 | 38.18 | C |
| ATOM | 2606 | CB | THR | D | 14 | 2.909 | −7.588 | 35.497 | 1.00 | 38.05 | C |
| ATOM | 2607 | OG1 | THR | D | 14 | 3.918 | −8.583 | 35.345 | 1.00 | 37.69 | O |
| ATOM | 2608 | CG2 | THR | D | 14 | 2.344 | −7.322 | 34.125 | 1.00 | 38.04 | C |
| ATOM | 2609 | C | THR | D | 14 | 2.702 | −5.071 | 35.754 | 1.00 | 38.15 | C |
| ATOM | 2610 | O | THR | D | 14 | 1.628 | −4.827 | 36.318 | 1.00 | 38.34 | O |
| ATOM | 2611 | N | GLY | D | 15 | 3.201 | −4.294 | 34.804 | 1.00 | 37.78 | N |
| ATOM | 2612 | CA | GLY | D | 15 | 2.475 | −3.124 | 34.362 | 1.00 | 38.18 | C |
| ATOM | 2613 | C | GLY | D | 15 | 2.970 | −1.835 | 34.984 | 1.00 | 38.45 | C |
| ATOM | 2614 | O | GLY | D | 15 | 3.058 | −0.818 | 34.305 | 1.00 | 38.92 | O |
| ATOM | 2615 | N | GLU | D | 16 | 3.302 | −1.866 | 36.269 | 1.00 | 38.44 | N |
| ATOM | 2616 | CA | GLU | D | 16 | 3.815 | −0.684 | 36.957 | 1.00 | 38.61 | C |
| ATOM | 2617 | CB | GLU | D | 16 | 3.957 | −0.971 | 38.448 | 1.00 | 38.77 | C |
| ATOM | 2618 | CG | GLU | D | 16 | 2.671 | −1.434 | 39.101 | 1.00 | 39.56 | C |
| ATOM | 2619 | CD | GLU | D | 16 | 2.848 | −1.834 | 40.546 | 1.00 | 40.65 | C |
| ATOM | 2620 | OE1 | GLU | D | 16 | 3.990 | −2.076 | 40.972 | 1.00 | 41.80 | O |
| ATOM | 2621 | OE2 | GLU | D | 16 | 1.831 | −1.915 | 41.264 | 1.00 | 42.46 | O |
| ATOM | 2622 | C | GLU | D | 16 | 5.161 | −0.247 | 36.396 | 1.00 | 38.77 | C |
| ATOM | 2623 | O | GLU | D | 16 | 5.758 | −0.944 | 35.574 | 1.00 | 38.73 | O |
| ATOM | 2624 | N | SER | D | 17 | 5.638 | 0.910 | 36.847 | 1.00 | 39.08 | N |
| ATOM | 2625 | CA | SER | D | 17 | 6.974 | 1.402 | 36.472 | 1.00 | 39.29 | C |
| ATOM | 2626 | CB | SER | D | 17 | 6.871 | 2.684 | 35.627 | 1.00 | 39.33 | C |
| ATOM | 2627 | OG | SER | D | 17 | 6.001 | 3.630 | 36.215 | 1.00 | 39.01 | O |
| ATOM | 2628 | C | SER | D | 17 | 7.920 | 1.603 | 37.664 | 1.00 | 39.41 | C |
| ATOM | 2629 | O | SER | D | 17 | 7.495 | 1.628 | 38.822 | 1.00 | 39.97 | O |
| ATOM | 2630 | N | LEU | D | 18 | 9.204 | 1.764 | 37.373 | 1.00 | 39.54 | N |
| ATOM | 2631 | CA | LEU | D | 18 | 10.223 | 1.787 | 38.410 | 1.00 | 39.59 | C |
| ATOM | 2632 | CB | LEU | D | 18 | 10.987 | 0.468 | 38.377 | 1.00 | 39.57 | C |

APPENDIX I(d)-continued

| ATOM | 2633 | CG | LEU | D | 18 | 12.098 | 0.062 | 39.357 | 1.00 | 39.70 | C |
|---|---|---|---|---|---|---|---|---|---|---|---|
| ATOM | 2634 | CD1 | LEU | D | 18 | 13.508 | 0.127 | 38.738 | 1.00 | 39.39 | C |
| ATOM | 2635 | CD2 | LEU | D | 18 | 11.996 | 0.804 | 40.688 | 1.00 | 39.58 | C |
| ATOM | 2636 | C | LEU | D | 18 | 11.172 | 2.963 | 38.222 | 1.00 | 39.76 | C |
| ATOM | 2637 | O | LEU | D | 18 | 11.634 | 3.225 | 37.116 | 1.00 | 39.81 | O |
| ATOM | 2638 | N | THR | D | 19 | 11.450 | 3.681 | 39.304 | 1.00 | 39.94 | N |
| ATOM | 2639 | CA | THR | D | 19 | 12.433 | 4.755 | 39.250 | 1.00 | 40.07 | C |
| ATOM | 2640 | CB | THR | D | 19 | 11.777 | 6.130 | 39.561 | 1.00 | 39.79 | C |
| ATOM | 2641 | OG1 | THR | D | 19 | 10.617 | 6.287 | 38.738 | 1.00 | 39.06 | O |
| ATOM | 2642 | CG2 | THR | D | 19 | 12.730 | 7.279 | 39.253 | 1.00 | 39.70 | C |
| ATOM | 2643 | C | THR | D | 19 | 13.671 | 4.441 | 40.125 | 1.00 | 40.27 | C |
| ATOM | 2644 | O | THR | D | 19 | 13.560 | 4.176 | 41.308 | 1.00 | 40.53 | O |
| ATOM | 2645 | N | ILE | D | 20 | 14.842 | 4.427 | 39.512 | 1.00 | 40.71 | N |
| ATOM | 2646 | CA | ILE | D | 20 | 16.089 | 4.283 | 40.245 | 1.00 | 41.31 | C |
| ATOM | 2647 | CB | ILE | D | 20 | 17.049 | 3.257 | 39.606 | 1.00 | 41.02 | C |
| ATOM | 2648 | CG1 | ILE | D | 20 | 16.387 | 1.881 | 39.544 | 1.00 | 41.44 | C |
| ATOM | 2649 | CD1 | ILE | D | 20 | 17.149 | 0.833 | 38.810 | 1.00 | 40.40 | C |
| ATOM | 2650 | CG2 | ILE | D | 20 | 18.309 | 3.165 | 40.424 | 1.00 | 41.51 | C |
| ATOM | 2651 | C | ILE | D | 20 | 16.757 | 5.637 | 40.264 | 1.00 | 41.93 | C |
| ATOM | 2652 | O | ILE | D | 20 | 16.885 | 6.291 | 39.231 | 1.00 | 41.92 | O |
| ATOM | 2653 | N | ASN | D | 21 | 17.181 | 6.046 | 41.448 | 1.00 | 42.92 | N |
| ATOM | 2654 | CA | ASN | D | 21 | 17.777 | 7.347 | 41.653 | 1.00 | 43.80 | C |
| ATOM | 2655 | CB | ASN | D | 21 | 17.076 | 8.052 | 42.802 | 1.00 | 44.06 | C |
| ATOM | 2656 | CG | ASN | D | 21 | 15.876 | 8.846 | 42.345 | 1.00 | 45.31 | C |
| ATOM | 2657 | OD1 | ASN | D | 21 | 14.749 | 8.618 | 42.794 | 1.00 | 46.50 | O |
| ATOM | 2658 | ND2 | ASN | D | 21 | 16.108 | 9.790 | 41.439 | 1.00 | 47.41 | N |
| ATOM | 2659 | C | ASN | D | 21 | 19.242 | 7.193 | 41.974 | 1.00 | 44.17 | C |
| ATOM | 2660 | O | ASN | D | 21 | 19.605 | 6.366 | 42.809 | 1.00 | 44.37 | O |
| ATOM | 2661 | N | CYS | D | 22 | 20.077 | 7.977 | 41.299 | 1.00 | 44.32 | N |
| ATOM | 2662 | CA | CYS | D | 22 | 21.512 | 7.971 | 41.546 | 1.00 | 44.68 | C |
| ATOM | 2663 | CB | CYS | D | 22 | 22.230 | 7.277 | 40.411 | 1.00 | 44.52 | C |
| ATOM | 2664 | SG | CYS | D | 22 | 21.830 | 5.539 | 40.404 | 1.00 | 47.27 | S |
| ATOM | 2665 | C | CYS | D | 22 | 22.081 | 9.369 | 41.775 | 1.00 | 44.46 | C |
| ATOM | 2666 | O | CYS | D | 22 | 21.656 | 10.338 | 41.146 | 1.00 | 45.03 | O |
| ATOM | 2667 | N | ALA | D | 23 | 23.031 | 9.484 | 42.690 | 1.00 | 43.59 | N |
| ATOM | 2668 | CA | ALA | D | 23 | 23.610 | 10.769 | 42.961 | 1.00 | 43.17 | C |
| ATOM | 2669 | CB | ALA | D | 23 | 22.952 | 11.383 | 44.181 | 1.00 | 43.11 | C |
| ATOM | 2670 | C | ALA | D | 23 | 25.104 | 10.613 | 43.162 | 1.00 | 42.94 | C |
| ATOM | 2671 | O | ALA | D | 23 | 25.533 | 9.852 | 44.016 | 1.00 | 43.43 | O |
| ATOM | 2672 | N | LEU | D | 24 | 25.893 | 11.319 | 42.366 | 1.00 | 42.39 | N |
| ATOM | 2673 | CA | LEU | D | 24 | 27.329 | 11.290 | 42.510 | 1.00 | 42.25 | C |
| ATOM | 2674 | CB | LEU | D | 24 | 28.014 | 11.786 | 41.226 | 1.00 | 41.99 | C |
| ATOM | 2675 | CG | LEU | D | 24 | 29.546 | 11.743 | 41.100 | 1.00 | 41.36 | C |
| ATOM | 2676 | CD1 | LEU | D | 24 | 29.985 | 12.221 | 39.726 | 1.00 | 39.92 | C |
| ATOM | 2677 | CD2 | LEU | D | 24 | 30.137 | 10.363 | 41.416 | 1.00 | 40.07 | C |
| ATOM | 2678 | C | LEU | D | 24 | 27.694 | 12.139 | 43.726 | 1.00 | 42.66 | C |
| ATOM | 2679 | O | LEU | D | 24 | 27.288 | 13.293 | 43.825 | 1.00 | 42.82 | O |
| ATOM | 2680 | N | LYS | D | 25 | 28.459 | 11.549 | 44.643 | 1.00 | 43.03 | N |
| ATOM | 2681 | CA | LYS | D | 25 | 28.717 | 12.120 | 45.961 | 1.00 | 43.39 | C |
| ATOM | 2682 | CB | LYS | D | 25 | 28.177 | 11.174 | 47.035 | 1.00 | 43.45 | C |
| ATOM | 2683 | CG | LYS | D | 25 | 26.648 | 11.033 | 47.048 | 1.00 | 45.23 | C |
| ATOM | 2684 | CD | LYS | D | 25 | 26.001 | 11.935 | 48.110 | 1.00 | 48.02 | C |
| ATOM | 2685 | CE | LYS | D | 25 | 24.522 | 12.163 | 47.822 | 1.00 | 49.24 | C |
| ATOM | 2686 | NZ | LYS | D | 25 | 24.301 | 13.275 | 46.839 | 1.00 | 49.27 | N |
| ATOM | 2687 | C | LYS | D | 25 | 30.211 | 12.354 | 46.178 | 1.00 | 43.55 | C |
| ATOM | 2688 | O | LYS | D | 25 | 31.033 | 11.601 | 45.656 | 1.00 | 43.60 | O |
| ATOM | 2689 | N | ASN | D | 26 | 30.549 | 13.387 | 46.961 | 1.00 | 43.74 | N |
| ATOM | 2690 | CA | ASN | D | 26 | 31.936 | 13.792 | 47.222 | 1.00 | 43.66 | C |
| ATOM | 2691 | CB | ASN | D | 26 | 32.611 | 12.840 | 48.205 | 1.00 | 44.13 | C |
| ATOM | 2692 | CG | ASN | D | 26 | 31.987 | 12.885 | 49.585 | 1.00 | 45.64 | C |
| ATOM | 2693 | OD1 | ASN | D | 26 | 31.277 | 11.955 | 49.994 | 1.00 | 46.22 | O |
| ATOM | 2694 | ND2 | ASN | D | 26 | 32.248 | 13.975 | 50.318 | 1.00 | 47.54 | N |
| ATOM | 2695 | C | ASN | D | 26 | 32.743 | 13.883 | 45.941 | 1.00 | 43.44 | C |
| ATOM | 2696 | O | ASN | D | 26 | 33.828 | 13.314 | 45.828 | 1.00 | 43.10 | O |
| ATOM | 2697 | N | ALA | D | 27 | 32.181 | 14.601 | 44.975 | 1.00 | 43.45 | N |
| ATOM | 2698 | CA | ALA | D | 27 | 32.735 | 14.706 | 43.637 | 1.00 | 43.52 | C |
| ATOM | 2699 | CB | ALA | D | 27 | 31.751 | 14.115 | 42.613 | 1.00 | 43.25 | C |
| ATOM | 2700 | C | ALA | D | 27 | 33.016 | 16.171 | 43.334 | 1.00 | 43.60 | C |
| ATOM | 2701 | O | ALA | D | 27 | 32.096 | 16.926 | 43.022 | 1.00 | 44.03 | O |
| ATOM | 2702 | N | ALA | D | 28 | 34.281 | 16.576 | 43.429 | 1.00 | 43.66 | N |
| ATOM | 2703 | CA | ALA | D | 28 | 34.687 | 17.981 | 43.175 | 1.00 | 43.69 | C |
| ATOM | 2704 | CB | ALA | D | 28 | 35.955 | 18.348 | 44.014 | 1.00 | 43.65 | C |
| ATOM | 2705 | C | ALA | D | 28 | 34.909 | 18.282 | 41.678 | 1.00 | 43.33 | C |
| ATOM | 2706 | O | ALA | D | 28 | 35.829 | 19.028 | 41.310 | 1.00 | 43.35 | O |
| ATOM | 2707 | N | ASP | D | 29 | 34.044 | 17.709 | 40.837 | 1.00 | 42.76 | N |
| ATOM | 2708 | CA | ASP | D | 29 | 34.268 | 17.592 | 39.389 | 1.00 | 42.30 | C |
| ATOM | 2709 | CB | ASP | D | 29 | 35.440 | 16.633 | 39.099 | 1.00 | 42.53 | C |
| ATOM | 2710 | CG | ASP | D | 29 | 35.551 | 15.492 | 40.124 | 1.00 | 43.66 | C |
| ATOM | 2711 | OD1 | ASP | D | 29 | 34.729 | 14.549 | 40.059 | 1.00 | 43.69 | O |
| ATOM | 2712 | OD2 | ASP | D | 29 | 36.465 | 15.537 | 40.993 | 1.00 | 44.75 | O |

APPENDIX I(d)-continued

| ATOM | 2713 | C | ASP | D | 29 | 32.979 | 17.162 | 38.661 | 1.00 | 41.65 | C |
|---|---|---|---|---|---|---|---|---|---|---|---|
| ATOM | 2714 | O | ASP | D | 29 | 32.044 | 16.666 | 39.294 | 1.00 | 41.73 | O |
| ATOM | 2715 | N | ASP | D | 30 | 32.942 | 17.338 | 37.337 | 1.00 | 40.69 | N |
| ATOM | 2716 | CA | ASP | D | 30 | 31.681 | 17.393 | 36.577 | 1.00 | 39.53 | C |
| ATOM | 2717 | CB | ASP | D | 30 | 31.845 | 18.356 | 35.405 | 1.00 | 39.73 | C |
| ATOM | 2718 | CG | ASP | D | 30 | 31.748 | 19.795 | 35.824 | 1.00 | 39.85 | C |
| ATOM | 2719 | OD1 | ASP | D | 30 | 30.886 | 20.105 | 36.669 | 1.00 | 41.59 | O |
| ATOM | 2720 | OD2 | ASP | D | 30 | 32.519 | 20.618 | 35.302 | 1.00 | 39.35 | O |
| ATOM | 2721 | C | ASP | D | 30 | 31.146 | 16.090 | 36.022 | 1.00 | 38.75 | C |
| ATOM | 2722 | O | ASP | D | 30 | 31.856 | 15.384 | 35.318 | 1.00 | 38.85 | O |
| ATOM | 2723 | N | LEU | D | 31 | 29.876 | 15.803 | 36.293 | 1.00 | 37.73 | N |
| ATOM | 2724 | CA | LEU | D | 31 | 29.184 | 14.694 | 35.646 | 1.00 | 36.84 | C |
| ATOM | 2725 | CB | LEU | D | 31 | 27.740 | 14.595 | 36.132 | 1.00 | 36.24 | C |
| ATOM | 2726 | CG | LEU | D | 31 | 27.011 | 13.284 | 35.847 | 1.00 | 33.49 | C |
| ATOM | 2727 | CD1 | LEU | D | 31 | 27.607 | 12.166 | 36.663 | 1.00 | 31.25 | C |
| ATOM | 2728 | CD2 | LEU | D | 31 | 25.556 | 13.427 | 36.163 | 1.00 | 30.41 | C |
| ATOM | 2729 | C | LEU | D | 31 | 29.209 | 14.870 | 34.133 | 1.00 | 37.41 | C |
| ATOM | 2730 | O | LEU | D | 31 | 28.792 | 15.918 | 33.607 | 1.00 | 37.39 | O |
| ATOM | 2731 | N | GLU | D | 32 | 29.713 | 13.849 | 33.441 | 1.00 | 37.95 | N |
| ATOM | 2732 | CA | GLU | D | 32 | 29.931 | 13.924 | 31.995 | 1.00 | 38.71 | C |
| ATOM | 2733 | CB | GLU | D | 32 | 31.416 | 13.801 | 31.645 | 1.00 | 39.12 | C |
| ATOM | 2734 | CG | GLU | D | 32 | 32.193 | 15.115 | 31.740 | 1.00 | 41.10 | C |
| ATOM | 2735 | CD | GLU | D | 32 | 31.764 | 16.157 | 30.685 | 1.00 | 44.44 | C |
| ATOM | 2736 | OE1 | GLU | D | 32 | 32.662 | 16.820 | 30.113 | 1.00 | 45.38 | O |
| ATOM | 2737 | OE2 | GLU | D | 32 | 30.539 | 16.313 | 30.421 | 1.00 | 45.39 | O |
| ATOM | 2738 | C | GLU | D | 32 | 29.149 | 12.895 | 31.241 | 1.00 | 38.85 | C |
| ATOM | 2739 | O | GLU | D | 32 | 28.616 | 13.177 | 30.188 | 1.00 | 39.30 | O |
| ATOM | 2740 | N | ARG | D | 33 | 29.058 | 11.702 | 31.808 | 1.00 | 39.42 | N |
| ATOM | 2741 | CA | ARG | D | 33 | 28.430 | 10.574 | 31.160 | 1.00 | 39.72 | C |
| ATOM | 2742 | CB | ARG | D | 33 | 29.499 | 9.789 | 30.410 | 1.00 | 39.85 | C |
| ATOM | 2743 | CG | ARG | D | 33 | 28.985 | 8.742 | 29.472 | 1.00 | 41.45 | C |
| ATOM | 2744 | CD | ARG | D | 33 | 30.062 | 8.322 | 28.491 | 1.00 | 43.89 | C |
| ATOM | 2745 | NE | ARG | D | 33 | 31.197 | 7.689 | 29.152 | 1.00 | 47.25 | N |
| ATOM | 2746 | CZ | ARG | D | 33 | 31.193 | 6.455 | 29.661 | 1.00 | 49.38 | C |
| ATOM | 2747 | NH1 | ARG | D | 33 | 32.292 | 5.974 | 30.243 | 1.00 | 49.45 | N |
| ATOM | 2748 | NH2 | ARG | D | 33 | 30.099 | 5.694 | 29.593 | 1.00 | 50.00 | N |
| ATOM | 2749 | C | ARG | D | 33 | 27.774 | 9.727 | 32.243 | 1.00 | 39.94 | C |
| ATOM | 2750 | O | ARG | D | 33 | 28.273 | 9.661 | 33.356 | 1.00 | 39.64 | O |
| ATOM | 2751 | N | THR | D | 34 | 26.638 | 9.112 | 31.915 | 1.00 | 40.75 | N |
| ATOM | 2752 | CA | THR | D | 34 | 25.871 | 8.276 | 32.835 | 1.00 | 41.14 | C |
| ATOM | 2753 | CB | THR | D | 34 | 24.679 | 9.027 | 33.461 | 1.00 | 40.95 | C |
| ATOM | 2754 | OG1 | THR | D | 34 | 24.020 | 9.814 | 32.468 | 1.00 | 41.22 | O |
| ATOM | 2755 | CG2 | THR | D | 34 | 25.134 | 9.920 | 34.570 | 1.00 | 41.33 | C |
| ATOM | 2756 | C | THR | D | 34 | 25.310 | 7.031 | 32.141 | 1.00 | 41.81 | C |
| ATOM | 2757 | O | THR | D | 34 | 24.571 | 7.142 | 31.161 | 1.00 | 42.34 | O |
| ATOM | 2758 | N | ASP | D | 35 | 25.639 | 5.850 | 32.671 | 1.00 | 42.29 | N |
| ATOM | 2759 | CA | ASP | D | 35 | 25.209 | 4.573 | 32.092 | 1.00 | 42.11 | C |
| ATOM | 2760 | CB | ASP | D | 35 | 26.425 | 3.829 | 31.537 | 1.00 | 42.03 | C |
| ATOM | 2761 | CG | ASP | D | 35 | 26.968 | 4.499 | 30.278 | 1.00 | 43.56 | C |
| ATOM | 2762 | OD1 | ASP | D | 35 | 27.842 | 3.941 | 29.560 | 1.00 | 46.61 | O |
| ATOM | 2763 | OD2 | ASP | D | 35 | 26.498 | 5.615 | 29.983 | 1.00 | 44.89 | O |
| ATOM | 2764 | C | ASP | D | 35 | 24.354 | 3.722 | 33.035 | 1.00 | 41.77 | C |
| ATOM | 2765 | O | ASP | D | 35 | 24.261 | 4.011 | 34.230 | 1.00 | 41.58 | O |
| ATOM | 2766 | N | TRP | D | 36 | 23.696 | 2.711 | 32.472 | 1.00 | 41.34 | N |
| ATOM | 2767 | CA | TRP | D | 36 | 22.739 | 1.884 | 33.202 | 1.00 | 41.40 | C |
| ATOM | 2768 | CB | TRP | D | 36 | 21.307 | 2.381 | 32.986 | 1.00 | 40.76 | C |
| ATOM | 2769 | CG | TRP | D | 36 | 21.035 | 3.735 | 33.560 | 1.00 | 39.98 | C |
| ATOM | 2770 | CD1 | TRP | D | 36 | 21.121 | 4.928 | 32.914 | 1.00 | 39.38 | C |
| ATOM | 2771 | NE1 | TRP | D | 36 | 20.809 | 5.962 | 33.768 | 1.00 | 39.12 | N |
| ATOM | 2772 | CE2 | TRP | D | 36 | 20.510 | 5.439 | 34.996 | 1.00 | 39.10 | C |
| ATOM | 2773 | CD2 | TRP | D | 36 | 20.639 | 4.035 | 34.901 | 1.00 | 39.48 | C |
| ATOM | 2774 | CE3 | TRP | D | 36 | 20.366 | 3.252 | 36.030 | 1.00 | 40.06 | C |
| ATOM | 2775 | CZ3 | TRP | D | 36 | 19.991 | 3.894 | 37.212 | 1.00 | 40.06 | C |
| ATOM | 2776 | CH2 | TRP | D | 36 | 19.874 | 5.295 | 37.269 | 1.00 | 40.13 | C |
| ATOM | 2777 | CZ2 | TRP | D | 36 | 20.125 | 6.080 | 36.173 | 1.00 | 39.66 | C |
| ATOM | 2778 | C | TRP | D | 36 | 22.849 | 0.462 | 32.690 | 1.00 | 41.89 | C |
| ATOM | 2779 | O | TRP | D | 36 | 22.709 | 0.233 | 31.494 | 1.00 | 41.74 | O |
| ATOM | 2780 | N | TYR | D | 37 | 23.125 | −0.482 | 33.591 | 1.00 | 42.42 | N |
| ATOM | 2781 | CA | TYR | D | 37 | 23.262 | −1.892 | 33.219 | 1.00 | 42.74 | C |
| ATOM | 2782 | CB | TYR | D | 37 | 24.695 | −2.390 | 33.386 | 1.00 | 43.39 | C |
| ATOM | 2783 | CG | TYR | D | 37 | 25.702 | −1.467 | 32.789 | 1.00 | 44.09 | C |
| ATOM | 2784 | CD1 | TYR | D | 37 | 26.041 | −0.301 | 33.448 | 1.00 | 47.02 | C |
| ATOM | 2785 | CE1 | TYR | D | 37 | 26.962 | 0.583 | 32.913 | 1.00 | 47.92 | C |
| ATOM | 2786 | CZ | TYR | D | 37 | 27.550 | 0.293 | 31.705 | 1.00 | 45.40 | C |
| ATOM | 2787 | OH | TYR | D | 37 | 28.443 | 1.214 | 31.238 | 1.00 | 46.33 | O |
| ATOM | 2788 | CE2 | TYR | D | 37 | 27.242 | −0.871 | 31.016 | 1.00 | 43.86 | C |
| ATOM | 2789 | CD2 | TYR | D | 37 | 26.314 | −1.746 | 31.569 | 1.00 | 44.21 | C |
| ATOM | 2790 | C | TYR | D | 37 | 22.333 | −2.758 | 34.028 | 1.00 | 42.45 | C |
| ATOM | 2791 | O | TYR | D | 37 | 22.056 | −2.467 | 35.184 | 1.00 | 42.79 | O |
| ATOM | 2792 | N | ARG | D | 38 | 21.846 | −3.817 | 33.399 | 1.00 | 42.06 | N |

APPENDIX I(d)-continued

| ATOM | 2793 | CA | ARG | D | 38 | 20.942 | −4.754 | 34.029 | 1.00 | 41.73 | C |
|---|---|---|---|---|---|---|---|---|---|---|---|
| ATOM | 2794 | CB | ARG | D | 38 | 19.524 | −4.627 | 33.446 | 1.00 | 41.95 | C |
| ATOM | 2795 | CG | ARG | D | 38 | 19.491 | −4.486 | 31.905 | 1.00 | 43.17 | C |
| ATOM | 2796 | CD | ARG | D | 38 | 18.362 | −5.245 | 31.218 | 1.00 | 45.32 | C |
| ATOM | 2797 | NE | ARG | D | 38 | 17.039 | −4.888 | 31.732 | 1.00 | 48.41 | N |
| ATOM | 2798 | CZ | ARG | D | 38 | 15.878 | −5.170 | 31.133 | 1.00 | 48.65 | C |
| ATOM | 2799 | NH1 | ARG | D | 38 | 15.851 | −5.819 | 29.974 | 1.00 | 48.23 | N |
| ATOM | 2800 | NH2 | ARG | D | 38 | 14.736 | −4.786 | 31.697 | 1.00 | 48.73 | N |
| ATOM | 2801 | C | ARG | D | 38 | 21.486 | −6.137 | 33.744 | 1.00 | 41.23 | C |
| ATOM | 2802 | O | ARG | D | 38 | 21.930 | −6.399 | 32.625 | 1.00 | 40.92 | O |
| ATOM | 2803 | N | THR | D | 39 | 21.494 | −6.983 | 34.776 | 1.00 | 40.78 | N |
| ATOM | 2804 | CA | THR | D | 39 | 21.560 | −8.433 | 34.640 | 1.00 | 40.44 | C |
| ATOM | 2805 | CB | THR | D | 39 | 22.682 | −9.065 | 35.492 | 1.00 | 40.56 | C |
| ATOM | 2806 | OG1 | THR | D | 39 | 23.930 | −8.409 | 35.236 | 1.00 | 40.48 | O |
| ATOM | 2807 | CG2 | THR | D | 39 | 22.824 | −10.534 | 35.161 | 1.00 | 40.93 | C |
| ATOM | 2808 | C | THR | D | 39 | 20.201 | −8.971 | 35.094 | 1.00 | 39.94 | C |
| ATOM | 2809 | O | THR | D | 39 | 19.828 | −8.841 | 36.243 | 1.00 | 39.94 | O |
| ATOM | 2810 | N | THR | D | 40 | 19.466 | −9.575 | 34.178 | 1.00 | 40.03 | N |
| ATOM | 2811 | CA | THR | D | 40 | 18.077 | −9.928 | 34.414 | 1.00 | 39.98 | C |
| ATOM | 2812 | CB | THR | D | 40 | 17.135 | −9.038 | 33.601 | 1.00 | 40.00 | C |
| ATOM | 2813 | OG1 | THR | D | 40 | 17.394 | −9.208 | 32.198 | 1.00 | 39.47 | O |
| ATOM | 2814 | CG2 | THR | D | 40 | 17.323 | −7.590 | 33.990 | 1.00 | 40.09 | C |
| ATOM | 2815 | C | THR | D | 40 | 17.780 | −11.357 | 34.040 | 1.00 | 40.30 | C |
| ATOM | 2816 | O | THR | D | 40 | 18.631 | −12.051 | 33.494 | 1.00 | 40.34 | O |
| ATOM | 2817 | N | LEU | D | 41 | 16.557 | −11.788 | 34.341 | 1.00 | 41.15 | N |
| ATOM | 2818 | CA | LEU | D | 41 | 16.086 | −13.107 | 33.976 | 1.00 | 42.05 | C |
| ATOM | 2819 | CB | LEU | D | 41 | 14.669 | −13.308 | 34.496 | 1.00 | 41.61 | C |
| ATOM | 2820 | CG | LEU | D | 41 | 14.465 | −13.519 | 36.001 | 1.00 | 41.14 | C |
| ATOM | 2821 | CD1 | LEU | D | 41 | 12.964 | −13.520 | 36.401 | 1.00 | 37.89 | C |
| ATOM | 2822 | CD2 | LEU | D | 41 | 15.160 | −14.796 | 36.463 | 1.00 | 40.23 | C |
| ATOM | 2823 | C | LEU | D | 41 | 16.127 | −13.290 | 32.459 | 1.00 | 43.36 | C |
| ATOM | 2824 | O | LEU | D | 41 | 16.391 | −14.387 | 31.969 | 1.00 | 43.43 | O |
| ATOM | 2825 | N | GLY | D | 42 | 15.891 | −12.198 | 31.729 | 1.00 | 44.83 | N |
| ATOM | 2826 | CA | GLY | D | 42 | 15.787 | −12.219 | 30.271 | 1.00 | 46.70 | C |
| ATOM | 2827 | C | GLY | D | 42 | 17.086 | −12.250 | 29.483 | 1.00 | 48.04 | C |
| ATOM | 2828 | O | GLY | D | 42 | 17.183 | −12.965 | 28.491 | 1.00 | 48.50 | O |
| ATOM | 2829 | N | SER | D | 43 | 18.054 | −11.433 | 29.897 | 1.00 | 49.46 | N |
| ATOM | 2830 | CA | SER | D | 43 | 19.426 | −11.415 | 29.360 | 1.00 | 50.33 | C |
| ATOM | 2831 | CB | SER | D | 43 | 20.173 | −10.173 | 29.896 | 1.00 | 51.06 | C |
| ATOM | 2832 | OG | SER | D | 43 | 20.572 | −10.313 | 31.275 | 1.00 | 50.27 | O |
| ATOM | 2833 | C | SER | D | 43 | 20.176 | −12.646 | 29.828 | 1.00 | 50.79 | C |
| ATOM | 2834 | O | SER | D | 43 | 19.790 | −13.264 | 30.819 | 1.00 | 50.86 | O |
| ATOM | 2835 | N | THR | D | 44 | 21.262 | −12.985 | 29.149 | 1.00 | 51.44 | N |
| ATOM | 2836 | CA | THR | D | 44 | 22.135 | −14.060 | 29.625 | 1.00 | 52.24 | C |
| ATOM | 2837 | CB | THR | D | 44 | 22.661 | −14.911 | 28.462 | 1.00 | 52.50 | C |
| ATOM | 2838 | OG1 | THR | D | 44 | 21.557 | −15.301 | 27.637 | 1.00 | 53.69 | O |
| ATOM | 2839 | CG2 | THR | D | 44 | 23.363 | −16.167 | 28.971 | 1.00 | 52.93 | C |
| ATOM | 2840 | C | THR | D | 44 | 23.284 | −13.459 | 30.431 | 1.00 | 52.40 | C |
| ATOM | 2841 | O | THR | D | 44 | 23.462 | −13.767 | 31.617 | 1.00 | 52.64 | O |
| ATOM | 2842 | N | ASN | D | 45 | 24.050 | −12.589 | 29.781 | 1.00 | 52.56 | N |
| ATOM | 2843 | CA | ASN | D | 45 | 25.082 | −11.803 | 30.456 | 1.00 | 52.43 | C |
| ATOM | 2844 | CB | ASN | D | 45 | 26.345 | −11.710 | 29.582 | 1.00 | 52.75 | C |
| ATOM | 2845 | CG | ASN | D | 45 | 27.157 | −13.001 | 29.571 | 1.00 | 53.08 | C |
| ATOM | 2846 | OD1 | ASN | D | 45 | 27.717 | −13.380 | 28.538 | 1.00 | 54.49 | O |
| ATOM | 2847 | ND2 | ASN | D | 45 | 27.247 | −13.667 | 30.723 | 1.00 | 52.75 | N |
| ATOM | 2848 | C | ASN | D | 45 | 24.558 | −10.406 | 30.782 | 1.00 | 51.79 | C |
| ATOM | 2849 | O | ASN | D | 45 | 23.413 | −10.080 | 30.457 | 1.00 | 51.44 | O |
| ATOM | 2850 | N | GLU | D | 46 | 25.403 | −9.596 | 31.422 | 1.00 | 51.23 | N |
| ATOM | 2851 | CA | GLU | D | 46 | 25.113 | −8.184 | 31.685 | 1.00 | 50.85 | C |
| ATOM | 2852 | CB | GLU | D | 46 | 26.312 | −7.517 | 32.370 | 1.00 | 51.14 | C |
| ATOM | 2853 | CG | GLU | D | 46 | 26.299 | −5.989 | 32.412 | 1.00 | 53.38 | C |
| ATOM | 2854 | CD | GLU | D | 46 | 27.037 | −5.420 | 33.640 | 1.00 | 57.60 | C |
| ATOM | 2855 | OE1 | GLU | D | 46 | 26.496 | −5.533 | 34.777 | 1.00 | 58.34 | O |
| ATOM | 2856 | OE2 | GLU | D | 46 | 28.148 | −4.847 | 33.465 | 1.00 | 58.29 | O |
| ATOM | 2857 | C | GLU | D | 46 | 24.796 | −7.485 | 30.376 | 1.00 | 50.00 | C |
| ATOM | 2858 | O | GLU | D | 46 | 25.308 | −7.888 | 29.321 | 1.00 | 50.44 | O |
| ATOM | 2859 | N | GLN | D | 47 | 23.941 | −6.464 | 30.433 | 1.00 | 48.59 | N |
| ATOM | 2860 | CA | GLN | D | 47 | 23.627 | −5.672 | 29.242 | 1.00 | 47.33 | C |
| ATOM | 2861 | CB | GLN | D | 47 | 22.468 | −6.295 | 28.442 | 1.00 | 47.28 | C |
| ATOM | 2862 | CG | GLN | D | 47 | 21.113 | −6.289 | 29.144 | 1.00 | 48.85 | C |
| ATOM | 2863 | CD | GLN | D | 47 | 19.949 | −6.605 | 28.208 | 1.00 | 48.87 | C |
| ATOM | 2864 | OE1 | GLN | D | 47 | 20.006 | −6.316 | 27.011 | 1.00 | 50.60 | O |
| ATOM | 2865 | NE2 | GLN | D | 47 | 18.884 | −7.200 | 28.755 | 1.00 | 49.96 | N |
| ATOM | 2866 | C | GLN | D | 47 | 23.384 | −4.190 | 29.540 | 1.00 | 45.66 | C |
| ATOM | 2867 | O | GLN | D | 47 | 22.830 | −3.834 | 30.581 | 1.00 | 45.01 | O |
| ATOM | 2868 | N | LYS | D | 48 | 23.817 | −3.340 | 28.611 | 1.00 | 44.18 | N |
| ATOM | 2869 | CA | LYS | D | 48 | 23.660 | −1.897 | 28.723 | 1.00 | 42.86 | C |
| ATOM | 2870 | CB | LYS | D | 48 | 24.693 | −1.174 | 27.859 | 1.00 | 43.14 | C |
| ATOM | 2871 | CG | LYS | D | 48 | 24.906 | 0.292 | 28.233 | 1.00 | 44.48 | C |
| ATOM | 2872 | CD | LYS | D | 48 | 25.770 | 1.001 | 27.209 | 1.00 | 46.74 | C |

APPENDIX I(d)-continued

| ATOM | 2873 | CE | LYS | D | 48 | 25.329 | 2.458 | 27.073 | 1.00 | 48.04 | C |
|---|---|---|---|---|---|---|---|---|---|---|---|
| ATOM | 2874 | NZ | LYS | D | 48 | 25.345 | 2.926 | 25.633 | 1.00 | 49.15 | N |
| ATOM | 2875 | C | LYS | D | 48 | 22.258 | −1.496 | 28.311 | 1.00 | 41.75 | C |
| ATOM | 2876 | O | LYS | D | 48 | 21.802 | −1.823 | 27.217 | 1.00 | 41.56 | O |
| ATOM | 2877 | N | ILE | D | 49 | 21.562 | −0.811 | 29.206 | 1.00 | 40.59 | N |
| ATOM | 2878 | CA | ILE | D | 49 | 20.252 | −0.283 | 28.889 | 1.00 | 39.63 | C |
| ATOM | 2879 | CB | ILE | D | 49 | 19.520 | 0.215 | 30.119 | 1.00 | 39.09 | C |
| ATOM | 2880 | CG1 | ILE | D | 49 | 19.200 | −0.969 | 31.043 | 1.00 | 38.06 | C |
| ATOM | 2881 | CD1 | ILE | D | 49 | 18.812 | −0.625 | 32.475 | 1.00 | 34.62 | C |
| ATOM | 2882 | CG2 | ILE | D | 49 | 18.277 | 0.944 | 29.668 | 1.00 | 38.69 | C |
| ATOM | 2883 | C | ILE | D | 49 | 20.412 | 0.859 | 27.889 | 1.00 | 39.78 | C |
| ATOM | 2884 | O | ILE | D | 49 | 21.253 | 1.747 | 28.064 | 1.00 | 40.00 | O |
| ATOM | 2885 | N | SER | D | 50 | 19.629 | 0.801 | 26.819 | 1.00 | 39.45 | N |
| ATOM | 2886 | CA | SER | D | 50 | 19.691 | 1.788 | 25.771 | 1.00 | 39.01 | C |
| ATOM | 2887 | CB | SER | D | 50 | 19.518 | 1.088 | 24.433 | 1.00 | 39.12 | C |
| ATOM | 2888 | OG | SER | D | 50 | 20.086 | 1.839 | 23.372 | 1.00 | 40.32 | O |
| ATOM | 2889 | C | SER | D | 50 | 18.545 | 2.751 | 26.011 | 1.00 | 38.51 | C |
| ATOM | 2890 | O | SER | D | 50 | 17.384 | 2.349 | 25.909 | 1.00 | 39.42 | O |
| ATOM | 2891 | N | ILE | D | 51 | 18.853 | 4.004 | 26.340 | 1.00 | 37.35 | N |
| ATOM | 2892 | CA | ILE | D | 51 | 17.814 | 4.982 | 26.670 | 1.00 | 36.74 | C |
| ATOM | 2893 | CB | ILE | D | 51 | 18.406 | 6.284 | 27.263 | 1.00 | 36.75 | C |
| ATOM | 2894 | CG1 | ILE | D | 51 | 19.193 | 5.982 | 28.542 | 1.00 | 34.81 | C |
| ATOM | 2895 | CD1 | ILE | D | 51 | 18.418 | 5.319 | 29.576 | 1.00 | 32.25 | C |
| ATOM | 2896 | CG2 | ILE | D | 51 | 17.315 | 7.328 | 27.527 | 1.00 | 36.15 | C |
| ATOM | 2897 | C | ILE | D | 51 | 16.914 | 5.303 | 25.475 | 1.00 | 36.75 | C |
| ATOM | 2898 | O | ILE | D | 51 | 17.390 | 5.558 | 24.373 | 1.00 | 36.49 | O |
| ATOM | 2899 | N | GLY | D | 52 | 15.609 | 5.287 | 25.718 | 1.00 | 36.69 | N |
| ATOM | 2900 | CA | GLY | D | 52 | 14.612 | 5.423 | 24.670 | 1.00 | 36.76 | C |
| ATOM | 2901 | C | GLY | D | 52 | 13.431 | 4.548 | 25.008 | 1.00 | 37.07 | C |
| ATOM | 2902 | O | GLY | D | 52 | 13.513 | 3.681 | 25.896 | 1.00 | 36.81 | O |
| ATOM | 2903 | N | GLY | D | 53 | 12.323 | 4.777 | 24.313 | 1.00 | 37.51 | N |
| ATOM | 2904 | CA | GLY | D | 53 | 11.138 | 3.932 | 24.472 | 1.00 | 38.10 | C |
| ATOM | 2905 | C | GLY | D | 53 | 10.635 | 3.891 | 25.902 | 1.00 | 38.54 | C |
| ATOM | 2906 | O | GLY | D | 53 | 10.205 | 4.914 | 26.438 | 1.00 | 38.60 | O |
| ATOM | 2907 | N | ARG | D | 54 | 10.703 | 2.718 | 26.530 | 1.00 | 38.89 | N |
| ATOM | 2908 | CA | ARG | D | 54 | 10.225 | 2.570 | 27.904 | 1.00 | 39.33 | C |
| ATOM | 2909 | CB | ARG | D | 54 | 9.540 | 1.219 | 28.116 | 1.00 | 38.67 | C |
| ATOM | 2910 | CG | ARG | D | 54 | 10.409 | 0.023 | 27.897 | 1.00 | 38.93 | C |
| ATOM | 2911 | CD | ARG | D | 54 | 9.664 | −1.276 | 28.255 | 1.00 | 39.46 | C |
| ATOM | 2912 | NE | ARG | D | 54 | 10.631 | −2.322 | 28.599 | 1.00 | 39.95 | N |
| ATOM | 2913 | CZ | ARG | D | 54 | 10.716 | −2.956 | 29.769 | 1.00 | 39.82 | C |
| ATOM | 2914 | NH1 | ARG | D | 54 | 9.870 | −2.722 | 30.766 | 1.00 | 40.34 | N |
| ATOM | 2915 | NH2 | ARG | D | 54 | 11.658 | −3.860 | 29.935 | 1.00 | 40.00 | N |
| ATOM | 2916 | C | ARG | D | 54 | 11.296 | 2.863 | 28.973 | 1.00 | 40.11 | C |
| ATOM | 2917 | O | ARG | D | 54 | 11.017 | 2.779 | 30.177 | 1.00 | 40.31 | O |
| ATOM | 2918 | N | TYR | D | 55 | 12.501 | 3.236 | 28.536 | 1.00 | 40.47 | N |
| ATOM | 2919 | CA | TYR | D | 55 | 13.535 | 3.637 | 29.467 | 1.00 | 41.02 | C |
| ATOM | 2920 | CB | TYR | D | 55 | 14.841 | 2.917 | 29.181 | 1.00 | 41.30 | C |
| ATOM | 2921 | CG | TYR | D | 55 | 14.767 | 1.417 | 29.167 | 1.00 | 41.64 | C |
| ATOM | 2922 | CD1 | TYR | D | 55 | 15.056 | 0.676 | 30.308 | 1.00 | 41.45 | C |
| ATOM | 2923 | CE1 | TYR | D | 55 | 15.006 | −0.716 | 30.285 | 1.00 | 41.62 | C |
| ATOM | 2924 | CZ | TYR | D | 55 | 14.665 | −1.364 | 29.103 | 1.00 | 42.18 | C |
| ATOM | 2925 | OH | TYR | D | 55 | 14.611 | −2.741 | 29.054 | 1.00 | 42.97 | O |
| ATOM | 2926 | CE2 | TYR | D | 55 | 14.376 | −0.646 | 27.965 | 1.00 | 40.93 | C |
| ATOM | 2927 | CD2 | TYR | D | 55 | 14.437 | 0.733 | 27.999 | 1.00 | 41.27 | C |
| ATOM | 2928 | C | TYR | D | 55 | 13.753 | 5.128 | 29.311 | 1.00 | 41.65 | C |
| ATOM | 2929 | O | TYR | D | 55 | 14.221 | 5.585 | 28.259 | 1.00 | 42.12 | O |
| ATOM | 2930 | N | VAL | D | 56 | 13.413 | 5.902 | 30.338 | 1.00 | 41.86 | N |
| ATOM | 2931 | CA | VAL | D | 56 | 13.590 | 7.350 | 30.237 | 1.00 | 42.12 | C |
| ATOM | 2932 | CB | VAL | D | 56 | 12.245 | 8.166 | 30.156 | 1.00 | 41.91 | C |
| ATOM | 2933 | CG1 | VAL | D | 56 | 11.098 | 7.449 | 30.817 | 1.00 | 42.53 | C |
| ATOM | 2934 | CG2 | VAL | D | 56 | 12.407 | 9.551 | 30.750 | 1.00 | 42.26 | C |
| ATOM | 2935 | C | VAL | D | 56 | 14.521 | 7.827 | 31.335 | 1.00 | 42.34 | C |
| ATOM | 2936 | O | VAL | D | 56 | 14.225 | 7.655 | 32.532 | 1.00 | 42.74 | O |
| ATOM | 2937 | N | GLU | D | 57 | 15.656 | 8.391 | 30.899 | 1.00 | 42.10 | N |
| ATOM | 2938 | CA | GLU | D | 57 | 16.706 | 8.880 | 31.786 | 1.00 | 41.85 | C |
| ATOM | 2939 | CB | GLU | D | 57 | 18.105 | 8.616 | 31.218 | 1.00 | 41.42 | C |
| ATOM | 2940 | CG | GLU | D | 57 | 19.172 | 8.651 | 32.301 | 1.00 | 41.99 | C |
| ATOM | 2941 | CD | GLU | D | 57 | 20.576 | 8.851 | 31.778 | 1.00 | 44.29 | C |
| ATOM | 2942 | OE1 | GLU | D | 57 | 20.726 | 9.397 | 30.666 | 1.00 | 44.38 | O |
| ATOM | 2943 | OE2 | GLU | D | 57 | 21.540 | 8.478 | 32.494 | 1.00 | 45.27 | O |
| ATOM | 2944 | C | GLU | D | 57 | 16.539 | 10.365 | 32.055 | 1.00 | 41.91 | C |
| ATOM | 2945 | O | GLU | D | 57 | 16.238 | 11.144 | 31.147 | 1.00 | 42.23 | O |
| ATOM | 2946 | N | THR | D | 58 | 16.725 | 10.743 | 33.315 | 1.00 | 41.83 | N |
| ATOM | 2947 | CA | THR | D | 58 | 16.747 | 12.147 | 33.726 | 1.00 | 41.66 | C |
| ATOM | 2948 | CB | THR | D | 58 | 15.622 | 12.454 | 34.708 | 1.00 | 41.70 | C |
| ATOM | 2949 | OG1 | THR | D | 58 | 14.383 | 12.354 | 34.006 | 1.00 | 42.93 | O |
| ATOM | 2950 | CG2 | THR | D | 58 | 15.756 | 13.871 | 35.282 | 1.00 | 41.32 | C |
| ATOM | 2951 | C | THR | D | 58 | 18.086 | 12.473 | 34.355 | 1.00 | 41.29 | C |
| ATOM | 2952 | O | THR | D | 58 | 18.552 | 11.779 | 35.263 | 1.00 | 41.34 | O |

APPENDIX I(d)-continued

| | | | | | | | | | | |
|---|---|---|---|---|---|---|---|---|---|---|
| ATOM | 2953 | N    | VAL | D | 59 | 18.705 | 13.533 | 33.851 | 1.00 | 40.74 N |
| ATOM | 2954 | CA   | VAL | D | 59 | 19.994 | 13.939 | 34.347 | 1.00 | 40.11 C |
| ATOM | 2955 | CB   | VAL | D | 59 | 21.116 | 13.635 | 33.336 | 1.00 | 40.28 C |
| ATOM | 2956 | CG1  | VAL | D | 59 | 22.440 | 14.177 | 33.838 | 1.00 | 41.06 C |
| ATOM | 2957 | CG2  | VAL | D | 59 | 21.237 | 12.132 | 33.094 | 1.00 | 40.21 C |
| ATOM | 2958 | C    | VAL | D | 59 | 19.979 | 15.409 | 34.728 | 1.00 | 39.52 C |
| ATOM | 2959 | O    | VAL | D | 59 | 19.682 | 16.284 | 33.904 | 1.00 | 39.63 O |
| ATOM | 2960 | N    | ASN | D | 60 | 20.266 | 15.642 | 36.005 | 1.00 | 38.53 N |
| ATOM | 2961 | CA   | ASN | D | 60 | 20.559 | 16.944 | 36.555 | 1.00 | 37.66 C |
| ATOM | 2962 | CB   | ASN | D | 60 | 19.751 | 17.135 | 37.841 | 1.00 | 37.63 C |
| ATOM | 2963 | CG   | ASN | D | 60 | 19.879 | 18.540 | 38.439 | 1.00 | 39.15 C |
| ATOM | 2964 | OD1  | ASN | D | 60 | 20.786 | 19.322 | 38.112 | 1.00 | 39.45 O |
| ATOM | 2965 | ND2  | ASN | D | 60 | 18.965 | 18.856 | 39.347 | 1.00 | 41.24 N |
| ATOM | 2966 | C    | ASN | D | 60 | 22.066 | 16.991 | 36.835 | 1.00 | 37.07 C |
| ATOM | 2967 | O    | ASN | D | 60 | 22.523 | 16.526 | 37.895 | 1.00 | 37.14 O |
| ATOM | 2968 | N    | LYS | D | 61 | 22.833 | 17.522 | 35.877 | 1.00 | 36.02 N |
| ATOM | 2969 | CA   | LYS | D | 61 | 24.284 | 17.681 | 36.029 | 1.00 | 35.34 C |
| ATOM | 2970 | CB   | LYS | D | 61 | 24.936 | 18.076 | 34.708 | 1.00 | 35.26 C |
| ATOM | 2971 | CG   | LYS | D | 61 | 25.277 | 16.898 | 33.825 | 1.00 | 35.03 C |
| ATOM | 2972 | CD   | LYS | D | 61 | 25.896 | 17.347 | 32.532 | 1.00 | 34.29 C |
| ATOM | 2973 | CE   | LYS | D | 61 | 25.631 | 16.329 | 31.473 | 1.00 | 34.80 C |
| ATOM | 2974 | NZ   | LYS | D | 61 | 26.224 | 16.730 | 30.180 | 1.00 | 36.67 N |
| ATOM | 2975 | C    | LYS | D | 61 | 24.681 | 18.683 | 37.112 | 1.00 | 35.17 C |
| ATOM | 2976 | O    | LYS | D | 61 | 25.735 | 18.538 | 37.727 | 1.00 | 34.89 O |
| ATOM | 2977 | N    | GLY | D | 62 | 23.841 | 19.692 | 37.330 | 1.00 | 35.04 N |
| ATOM | 2978 | CA   | GLY | D | 62 | 24.057 | 20.680 | 38.374 | 1.00 | 35.15 C |
| ATOM | 2979 | C    | GLY | D | 62 | 24.137 | 20.076 | 39.763 | 1.00 | 35.56 C |
| ATOM | 2980 | O    | GLY | D | 62 | 24.998 | 20.443 | 40.553 | 1.00 | 35.83 O |
| ATOM | 2981 | N    | SER | D | 63 | 23.240 | 19.153 | 40.073 | 1.00 | 35.78 N |
| ATOM | 2982 | CA   | SER | D | 63 | 23.276 | 18.484 | 41.369 | 1.00 | 36.29 C |
| ATOM | 2983 | CB   | SER | D | 63 | 21.865 | 18.429 | 41.969 | 1.00 | 36.47 C |
| ATOM | 2984 | OG   | SER | D | 63 | 21.008 | 17.558 | 41.243 | 1.00 | 36.43 O |
| ATOM | 2985 | C    | SER | D | 63 | 23.919 | 17.080 | 41.311 | 1.00 | 36.71 C |
| ATOM | 2986 | O    | SER | D | 63 | 23.928 | 16.350 | 42.300 | 1.00 | 36.84 O |
| ATOM | 2987 | N    | LYS | D | 64 | 24.440 | 16.710 | 40.140 | 1.00 | 37.00 N |
| ATOM | 2988 | CA   | LYS | D | 64 | 25.120 | 15.441 | 39.923 | 1.00 | 36.80 C |
| ATOM | 2989 | CB   | LYS | D | 64 | 26.417 | 15.374 | 40.727 | 1.00 | 36.46 C |
| ATOM | 2990 | CG   | LYS | D | 64 | 27.422 | 16.390 | 40.240 | 1.00 | 36.86 C |
| ATOM | 2991 | CD   | LYS | D | 64 | 28.631 | 16.570 | 41.140 | 1.00 | 37.76 C |
| ATOM | 2992 | CE   | LYS | D | 64 | 29.298 | 17.884 | 40.778 | 1.00 | 38.56 C |
| ATOM | 2993 | NZ   | LYS | D | 64 | 30.669 | 18.028 | 41.305 | 1.00 | 39.73 N |
| ATOM | 2994 | C    | LYS | D | 64 | 24.221 | 14.261 | 40.206 | 1.00 | 37.38 C |
| ATOM | 2995 | O    | LYS | D | 64 | 24.690 | 13.185 | 40.558 | 1.00 | 37.70 O |
| ATOM | 2996 | N    | SER | D | 65 | 22.921 | 14.451 | 40.037 | 1.00 | 37.84 N |
| ATOM | 2997 | CA   | SER | D | 65 | 21.999 | 13.328 | 40.174 | 1.00 | 38.63 C |
| ATOM | 2998 | CB   | SER | D | 65 | 20.867 | 13.671 | 41.136 | 1.00 | 38.71 C |
| ATOM | 2999 | OG   | SER | D | 65 | 20.203 | 14.855 | 40.734 | 1.00 | 39.23 O |
| ATOM | 3000 | C    | SER | D | 65 | 21.435 | 12.895 | 38.821 | 1.00 | 39.05 C |
| ATOM | 3001 | O    | SER | D | 65 | 21.436 | 13.658 | 37.864 | 1.00 | 39.10 O |
| ATOM | 3002 | N    | PHE | D | 66 | 20.971 | 11.657 | 38.754 | 1.00 | 39.85 N |
| ATOM | 3003 | CA   | PHE | D | 66 | 20.360 | 11.089 | 37.548 | 1.00 | 41.06 C |
| ATOM | 3004 | CB   | PHE | D | 66 | 21.412 | 10.655 | 36.503 | 1.00 | 41.00 C |
| ATOM | 3005 | CG   | PHE | D | 66 | 22.515 |  9.791 | 37.048 | 1.00 | 41.25 C |
| ATOM | 3006 | CD1  | PHE | D | 66 | 22.626 |  8.465 | 36.655 | 1.00 | 42.36 C |
| ATOM | 3007 | CE1  | PHE | D | 66 | 23.663 |  7.659 | 37.153 | 1.00 | 43.09 C |
| ATOM | 3008 | CZ   | PHE | D | 66 | 24.609 |  8.184 | 38.060 | 1.00 | 42.16 C |
| ATOM | 3009 | CE2  | PHE | D | 66 | 24.506 |  9.495 | 38.458 | 1.00 | 41.78 C |
| ATOM | 3010 | CD2  | PHE | D | 66 | 23.465 | 10.303 | 37.939 | 1.00 | 42.07 C |
| ATOM | 3011 | C    | PHE | D | 66 | 19.460 |  9.917 | 37.913 | 1.00 | 41.66 C |
| ATOM | 3012 | O    | PHE | D | 66 | 19.774 |  9.158 | 38.838 | 1.00 | 42.19 O |
| ATOM | 3013 | N    | SER | D | 67 | 18.351 |  9.760 | 37.201 | 1.00 | 41.87 N |
| ATOM | 3014 | CA   | SER | D | 67 | 17.450 |  8.665 | 37.497 | 1.00 | 42.54 C |
| ATOM | 3015 | CB   | SER | D | 67 | 16.204 |  9.199 | 38.191 | 1.00 | 42.49 C |
| ATOM | 3016 | OG   | SER | D | 67 | 15.374 |  9.911 | 37.288 | 1.00 | 44.07 O |
| ATOM | 3017 | C    | SER | D | 67 | 17.064 |  7.866 | 36.257 | 1.00 | 42.81 C |
| ATOM | 3018 | O    | SER | D | 67 | 17.043 |  8.393 | 35.153 | 1.00 | 43.06 O |
| ATOM | 3019 | N    | LEU | D | 68 | 16.750 |  6.591 | 36.430 | 1.00 | 43.18 N |
| ATOM | 3020 | CA   | LEU | D | 68 | 16.133 |  5.850 | 35.341 | 1.00 | 43.39 C |
| ATOM | 3021 | CB   | LEU | D | 68 | 16.901 |  4.558 | 35.088 | 1.00 | 43.37 C |
| ATOM | 3022 | CG   | LEU | D | 68 | 16.498 |  3.717 | 33.876 | 1.00 | 43.64 C |
| ATOM | 3023 | CD1  | LEU | D | 68 | 17.017 |  4.352 | 32.605 | 1.00 | 41.74 C |
| ATOM | 3024 | CD2  | LEU | D | 68 | 17.029 |  2.290 | 34.025 | 1.00 | 43.05 C |
| ATOM | 3025 | C    | LEU | D | 68 | 14.698 |  5.525 | 35.718 | 1.00 | 43.63 C |
| ATOM | 3026 | O    | LEU | D | 68 | 14.450 |  5.025 | 36.813 | 1.00 | 43.33 O |
| ATOM | 3027 | N    | ARG | D | 69 | 13.750 |  5.842 | 34.833 | 1.00 | 44.30 N |
| ATOM | 3028 | CA   | ARG | D | 69 | 12.365 |  5.310 | 34.934 | 1.00 | 44.40 C |
| ATOM | 3029 | CB   | ARG | D | 69 | 11.340 |  6.429 | 34.790 | 1.00 | 44.69 C |
| ATOM | 3030 | CG   | ARG | D | 69 |  9.877 |  6.025 | 34.925 | 1.00 | 46.02 C |
| ATOM | 3031 | CD   | ARG | D | 69 |  9.059 |  7.243 | 35.313 | 1.00 | 49.63 C |
| ATOM | 3032 | NE   | ARG | D | 69 |  7.640 |  7.148 | 34.949 | 1.00 | 54.97 N |

APPENDIX I(d)-continued

| | | | | | | | | | | |
|---|---|---|---|---|---|---|---|---|---|---|
| ATOM | 3033 | CZ | ARG | D | 69 | 6.625 | 6.943 | 35.805 | 1.00 | 56.63 C |
| ATOM | 3034 | NH1 | ARG | D | 69 | 5.374 | 6.895 | 35.352 | 1.00 | 56.12 N |
| ATOM | 3035 | NH2 | ARG | D | 69 | 6.842 | 6.782 | 37.112 | 1.00 | 57.83 N |
| ATOM | 3036 | C | ARG | D | 69 | 12.135 | 4.234 | 33.869 | 1.00 | 44.07 C |
| ATOM | 3037 | O | ARG | D | 69 | 12.376 | 4.469 | 32.672 | 1.00 | 44.43 O |
| ATOM | 3038 | N | ILE | D | 70 | 11.704 | 3.056 | 34.307 | 1.00 | 43.70 N |
| ATOM | 3039 | CA | ILE | D | 70 | 11.388 | 1.938 | 33.396 | 1.00 | 43.53 C |
| ATOM | 3040 | CB | ILE | D | 70 | 12.112 | 0.620 | 33.790 | 1.00 | 43.04 C |
| ATOM | 3041 | CG1 | ILE | D | 70 | 13.468 | 0.916 | 34.429 | 1.00 | 42.40 C |
| ATOM | 3042 | CD1 | ILE | D | 70 | 14.198 | −0.309 | 34.860 | 1.00 | 41.81 C |
| ATOM | 3043 | CG2 | ILE | D | 70 | 12.273 | −0.268 | 32.582 | 1.00 | 42.18 C |
| ATOM | 3044 | C | ILE | D | 70 | 9.878 | 1.693 | 33.352 | 1.00 | 43.87 C |
| ATOM | 3045 | O | ILE | D | 70 | 9.278 | 1.301 | 34.343 | 1.00 | 44.08 O |
| ATOM | 3046 | N | ARG | D | 71 | 9.268 | 1.947 | 32.205 | 1.00 | 44.38 N |
| ATOM | 3047 | CA | ARG | D | 71 | 7.823 | 1.787 | 32.037 | 1.00 | 44.93 C |
| ATOM | 3048 | CB | ARG | D | 71 | 7.364 | 2.627 | 30.851 | 1.00 | 45.25 C |
| ATOM | 3049 | CG | ARG | D | 71 | 7.092 | 4.069 | 31.159 | 1.00 | 47.04 C |
| ATOM | 3050 | CD | ARG | D | 71 | 5.746 | 4.407 | 30.570 | 1.00 | 51.66 C |
| ATOM | 3051 | NE | ARG | D | 71 | 5.701 | 4.424 | 29.099 | 1.00 | 55.58 N |
| ATOM | 3052 | CZ | ARG | D | 71 | 4.705 | 3.918 | 28.359 | 1.00 | 57.76 C |
| ATOM | 3053 | NH1 | ARG | D | 71 | 3.666 | 3.300 | 28.933 | 1.00 | 57.56 N |
| ATOM | 3054 | NH2 | ARG | D | 71 | 4.749 | 4.010 | 27.029 | 1.00 | 58.57 N |
| ATOM | 3055 | C | ARG | D | 71 | 7.423 | 0.337 | 31.789 | 1.00 | 44.65 C |
| ATOM | 3056 | O | ARG | D | 71 | 8.277 | −0.498 | 31.542 | 1.00 | 45.26 O |
| ATOM | 3057 | N | ASP | D | 72 | 6.128 | 0.054 | 31.863 | 1.00 | 44.46 N |
| ATOM | 3058 | CA | ASP | D | 72 | 5.533 | −1.215 | 31.422 | 1.00 | 44.72 C |
| ATOM | 3059 | CB | ASP | D | 72 | 5.390 | −1.223 | 29.901 | 1.00 | 45.19 C |
| ATOM | 3060 | CG | ASP | D | 72 | 4.368 | −0.194 | 29.403 | 1.00 | 48.24 C |
| ATOM | 3061 | OD1 | ASP | D | 72 | 4.666 | 0.561 | 28.434 | 1.00 | 50.91 O |
| ATOM | 3062 | OD2 | ASP | D | 72 | 3.258 | −0.133 | 29.989 | 1.00 | 50.87 O |
| ATOM | 3063 | C | ASP | D | 72 | 6.250 | −2.472 | 31.887 | 1.00 | 44.13 C |
| ATOM | 3064 | O | ASP | D | 72 | 6.593 | −3.322 | 31.066 | 1.00 | 44.33 O |
| ATOM | 3065 | N | LEU | D | 73 | 6.459 | −2.588 | 33.201 | 1.00 | 43.44 N |
| ATOM | 3066 | CA | LEU | D | 73 | 7.242 | −3.683 | 33.799 | 1.00 | 42.68 C |
| ATOM | 3067 | CB | LEU | D | 73 | 7.412 | −3.464 | 35.296 | 1.00 | 42.53 C |
| ATOM | 3068 | CG | LEU | D | 73 | 8.521 | −2.493 | 35.707 | 1.00 | 41.94 C |
| ATOM | 3069 | CD1 | LEU | D | 73 | 8.482 | −2.245 | 37.198 | 1.00 | 40.56 C |
| ATOM | 3070 | CD2 | LEU | D | 73 | 9.864 | −3.036 | 35.297 | 1.00 | 40.62 C |
| ATOM | 3071 | C | LEU | D | 73 | 6.699 | −5.082 | 33.556 | 1.00 | 42.39 C |
| ATOM | 3072 | O | LEU | D | 73 | 5.500 | −5.278 | 33.396 | 1.00 | 42.53 O |
| ATOM | 3073 | N | ARG | D | 74 | 7.610 | −6.044 | 33.521 | 1.00 | 42.33 N |
| ATOM | 3074 | CA | ARG | D | 74 | 7.276 | −7.445 | 33.280 | 1.00 | 42.60 C |
| ATOM | 3075 | CB | ARG | D | 74 | 7.176 | −7.727 | 31.777 | 1.00 | 42.97 C |
| ATOM | 3076 | CG | ARG | D | 74 | 8.472 | −7.524 | 31.014 | 1.00 | 45.79 C |
| ATOM | 3077 | CD | ARG | D | 74 | 8.253 | −7.753 | 29.528 | 1.00 | 50.87 C |
| ATOM | 3078 | NE | ARG | D | 74 | 9.227 | −7.043 | 28.690 | 1.00 | 54.09 N |
| ATOM | 3079 | CZ | ARG | D | 74 | 9.095 | −5.784 | 28.264 | 1.00 | 55.43 C |
| ATOM | 3080 | NH1 | ARG | D | 74 | 8.034 | −5.050 | 28.605 | 1.00 | 55.13 N |
| ATOM | 3081 | NH2 | ARG | D | 74 | 10.038 | −5.251 | 27.493 | 1.00 | 56.35 N |
| ATOM | 3082 | C | ARG | D | 74 | 8.301 | −8.378 | 33.935 | 1.00 | 42.04 C |
| ATOM | 3083 | O | ARG | D | 74 | 9.455 | −7.974 | 34.172 | 1.00 | 41.78 O |
| ATOM | 3084 | N | VAL | D | 75 | 7.881 | −9.619 | 34.204 | 1.00 | 41.25 N |
| ATOM | 3085 | CA | VAL | D | 75 | 8.697 | −10.608 | 34.943 | 1.00 | 40.84 C |
| ATOM | 3086 | CB | VAL | D | 75 | 8.015 | −12.017 | 34.960 | 1.00 | 40.73 C |
| ATOM | 3087 | CG1 | VAL | D | 75 | 8.891 | −13.070 | 35.649 | 1.00 | 41.36 C |
| ATOM | 3088 | CG2 | VAL | D | 75 | 6.686 | −11.937 | 35.672 | 1.00 | 40.25 C |
| ATOM | 3089 | C | VAL | D | 75 | 10.190 | −10.658 | 34.529 | 1.00 | 40.38 C |
| ATOM | 3090 | O | VAL | D | 75 | 11.079 | −10.478 | 35.365 | 1.00 | 39.84 O |
| ATOM | 3091 | N | GLU | D | 76 | 10.423 | −10.882 | 33.236 | 1.00 | 40.29 N |
| ATOM | 3092 | CA | GLU | D | 76 | 11.719 | −10.705 | 32.549 | 1.00 | 40.14 C |
| ATOM | 3093 | CB | GLU | D | 76 | 11.477 | −10.467 | 31.046 | 1.00 | 41.10 C |
| ATOM | 3094 | CG | GLU | D | 76 | 10.730 | −11.599 | 30.304 | 1.00 | 45.43 C |
| ATOM | 3095 | CD | GLU | D | 76 | 11.612 | −12.855 | 30.054 | 1.00 | 50.46 C |
| ATOM | 3096 | OE1 | GLU | D | 76 | 11.360 | −13.603 | 29.063 | 1.00 | 51.40 O |
| ATOM | 3097 | OE2 | GLU | D | 76 | 12.559 | −13.087 | 30.851 | 1.00 | 52.29 O |
| ATOM | 3098 | C | GLU | D | 76 | 12.602 | −9.568 | 33.052 | 1.00 | 38.84 C |
| ATOM | 3099 | O | GLU | D | 76 | 13.825 | −9.670 | 32.995 | 1.00 | 38.75 O |
| ATOM | 3100 | N | ASP | D | 77 | 11.995 | −8.475 | 33.503 | 1.00 | 37.42 N |
| ATOM | 3101 | CA | ASP | D | 77 | 12.781 | −7.340 | 33.974 | 1.00 | 36.19 C |
| ATOM | 3102 | CB | ASP | D | 77 | 11.960 | −6.041 | 34.024 | 1.00 | 36.54 C |
| ATOM | 3103 | CG | ASP | D | 77 | 11.370 | −5.644 | 32.675 | 1.00 | 37.48 C |
| ATOM | 3104 | OD1 | ASP | D | 77 | 12.078 | −5.751 | 31.648 | 1.00 | 37.44 O |
| ATOM | 3105 | OD2 | ASP | D | 77 | 10.192 | −5.205 | 32.656 | 1.00 | 38.17 O |
| ATOM | 3106 | C | ASP | D | 77 | 13.424 | −7.582 | 35.330 | 1.00 | 35.12 C |
| ATOM | 3107 | O | ASP | D | 77 | 14.403 | −6.903 | 35.649 | 1.00 | 35.09 O |
| ATOM | 3108 | N | SER | D | 78 | 12.882 | −8.525 | 36.118 | 1.00 | 33.83 N |
| ATOM | 3109 | CA | SER | D | 78 | 13.417 | −8.869 | 37.458 | 1.00 | 33.11 C |
| ATOM | 3110 | CB | SER | D | 78 | 12.750 | −10.123 | 38.039 | 1.00 | 33.10 C |
| ATOM | 3111 | OG | SER | D | 78 | 11.349 | −9.982 | 38.232 | 1.00 | 34.27 O |
| ATOM | 3112 | C | SER | D | 78 | 14.918 | −9.101 | 37.418 | 1.00 | 32.47 C |

APPENDIX I(d)-continued

| ATOM | 3113 | O | SER | D | 78 | 15.403 | −9.818 | 36.552 | 1.00 | 32.51 | O |
|---|---|---|---|---|---|---|---|---|---|---|---|
| ATOM | 3114 | N | GLY | D | 79 | 15.663 | −8.499 | 38.339 | 1.00 | 32.25 | N |
| ATOM | 3115 | CA | GLY | D | 79 | 17.132 | −8.599 | 38.302 | 1.00 | 31.92 | C |
| ATOM | 3116 | C | GLY | D | 79 | 17.871 | −7.446 | 38.939 | 1.00 | 31.96 | C |
| ATOM | 3117 | O | GLY | D | 79 | 17.330 | −6.760 | 39.809 | 1.00 | 31.58 | O |
| ATOM | 3118 | N | THR | D | 80 | 19.104 | −7.229 | 38.479 | 1.00 | 32.63 | N |
| ATOM | 3119 | CA | THR | D | 80 | 20.058 | −6.318 | 39.129 | 1.00 | 33.50 | C |
| ATOM | 3120 | CB | THR | D | 80 | 21.328 | −7.039 | 39.539 | 1.00 | 33.20 | C |
| ATOM | 3121 | OG1 | THR | D | 80 | 20.986 | −8.131 | 40.393 | 1.00 | 34.33 | O |
| ATOM | 3122 | CG2 | THR | D | 80 | 22.228 | −6.116 | 40.289 | 1.00 | 33.40 | C |
| ATOM | 3123 | C | THR | D | 80 | 20.442 | −5.192 | 38.197 | 1.00 | 34.18 | C |
| ATOM | 3124 | O | THR | D | 80 | 20.919 | −5.434 | 37.087 | 1.00 | 33.90 | O |
| ATOM | 3125 | N | TYR | D | 81 | 20.210 | −3.965 | 38.668 | 1.00 | 35.19 | N |
| ATOM | 3126 | CA | TYR | D | 81 | 20.462 | −2.735 | 37.913 | 1.00 | 35.91 | C |
| ATOM | 3127 | CB | TYR | D | 81 | 19.195 | −1.912 | 37.803 | 1.00 | 35.33 | C |
| ATOM | 3128 | CG | TYR | D | 81 | 18.114 | −2.593 | 37.010 | 1.00 | 34.85 | C |
| ATOM | 3129 | CD1 | TYR | D | 81 | 17.492 | −3.747 | 37.488 | 1.00 | 35.35 | C |
| ATOM | 3130 | CE1 | TYR | D | 81 | 16.506 | −4.389 | 36.753 | 1.00 | 35.81 | C |
| ATOM | 3131 | CZ | TYR | D | 81 | 16.132 | −3.866 | 35.535 | 1.00 | 35.53 | C |
| ATOM | 3132 | OH | TYR | D | 81 | 15.167 | −4.496 | 34.808 | 1.00 | 35.83 | O |
| ATOM | 3133 | CE2 | TYR | D | 81 | 16.733 | −2.724 | 35.044 | 1.00 | 35.04 | C |
| ATOM | 3134 | CD2 | TYR | D | 81 | 17.707 | −2.091 | 35.787 | 1.00 | 33.32 | C |
| ATOM | 3135 | C | TYR | D | 81 | 21.536 | −1.939 | 38.647 | 1.00 | 37.21 | C |
| ATOM | 3136 | O | TYR | D | 81 | 21.466 | −1.770 | 39.868 | 1.00 | 37.81 | O |
| ATOM | 3137 | N | LYS | D | 82 | 22.553 | −1.501 | 37.913 | 1.00 | 37.74 | N |
| ATOM | 3138 | CA | LYS | D | 82 | 23.568 | −0.638 | 38.456 | 1.00 | 38.35 | C |
| ATOM | 3139 | CB | LYS | D | 82 | 24.934 | −1.323 | 38.424 | 1.00 | 38.34 | C |
| ATOM | 3140 | CG | LYS | D | 82 | 25.392 | −1.989 | 39.709 | 1.00 | 37.40 | C |
| ATOM | 3141 | CD | LYS | D | 82 | 25.142 | −3.457 | 39.649 | 1.00 | 36.64 | C |
| ATOM | 3142 | CE | LYS | D | 82 | 26.282 | −4.240 | 40.237 | 1.00 | 34.73 | C |
| ATOM | 3143 | NZ | LYS | D | 82 | 26.197 | −4.327 | 41.696 | 1.00 | 35.21 | N |
| ATOM | 3144 | C | LYS | D | 82 | 23.595 | 0.578 | 37.557 | 1.00 | 39.27 | C |
| ATOM | 3145 | O | LYS | D | 82 | 23.505 | 0.452 | 36.339 | 1.00 | 39.29 | O |
| ATOM | 3146 | N | CYS | D | 83 | 23.701 | 1.753 | 38.161 | 1.00 | 40.62 | N |
| ATOM | 3147 | CA | CYS | D | 83 | 23.967 | 2.977 | 37.427 | 1.00 | 42.31 | C |
| ATOM | 3148 | CB | CYS | D | 83 | 23.147 | 4.119 | 38.004 | 1.00 | 42.45 | C |
| ATOM | 3149 | SG | CYS | D | 83 | 23.539 | 4.543 | 39.737 | 1.00 | 47.14 | S |
| ATOM | 3150 | C | CYS | D | 83 | 25.454 | 3.320 | 37.525 | 1.00 | 42.64 | C |
| ATOM | 3151 | O | CYS | D | 83 | 26.065 | 3.098 | 38.561 | 1.00 | 43.32 | O |
| ATOM | 3152 | N | GLY | D | 84 | 26.019 | 3.871 | 36.450 | 1.00 | 43.26 | N |
| ATOM | 3153 | CA | GLY | D | 84 | 27.425 | 4.309 | 36.406 | 1.00 | 42.90 | C |
| ATOM | 3154 | C | GLY | D | 84 | 27.562 | 5.762 | 35.971 | 1.00 | 42.52 | C |
| ATOM | 3155 | O | GLY | D | 84 | 26.877 | 6.201 | 35.065 | 1.00 | 41.68 | O |
| ATOM | 3156 | N | ALA | D | 85 | 28.464 | 6.488 | 36.633 | 1.00 | 42.86 | N |
| ATOM | 3157 | CA | ALA | D | 85 | 28.713 | 7.918 | 36.403 | 1.00 | 43.03 | C |
| ATOM | 3158 | CB | ALA | D | 85 | 28.307 | 8.728 | 37.624 | 1.00 | 42.74 | C |
| ATOM | 3159 | C | ALA | D | 85 | 30.183 | 8.120 | 36.126 | 1.00 | 43.30 | C |
| ATOM | 3160 | O | ALA | D | 85 | 31.014 | 7.609 | 36.860 | 1.00 | 43.69 | O |
| ATOM | 3161 | N | TYR | D | 86 | 30.510 | 8.847 | 35.065 | 1.00 | 43.66 | N |
| ATOM | 3162 | CA | TYR | D | 86 | 31.899 | 9.105 | 34.716 | 1.00 | 44.36 | C |
| ATOM | 3163 | CB | TYR | D | 86 | 32.219 | 8.530 | 33.340 | 1.00 | 44.95 | C |
| ATOM | 3164 | CG | TYR | D | 86 | 31.761 | 7.096 | 33.251 | 1.00 | 46.16 | C |
| ATOM | 3165 | CD1 | TYR | D | 86 | 30.403 | 6.796 | 33.028 | 1.00 | 47.23 | C |
| ATOM | 3166 | CE1 | TYR | D | 86 | 29.940 | 5.482 | 32.973 | 1.00 | 47.72 | C |
| ATOM | 3167 | CZ | TYR | D | 86 | 30.837 | 4.423 | 33.142 | 1.00 | 48.22 | C |
| ATOM | 3168 | OH | TYR | D | 86 | 30.343 | 3.123 | 33.084 | 1.00 | 47.41 | O |
| ATOM | 3169 | CE2 | TYR | D | 86 | 32.210 | 4.688 | 33.366 | 1.00 | 48.08 | C |
| ATOM | 3170 | CD2 | TYR | D | 86 | 32.657 | 6.033 | 33.432 | 1.00 | 46.88 | C |
| ATOM | 3171 | C | TYR | D | 86 | 32.105 | 10.602 | 34.795 | 1.00 | 44.66 | C |
| ATOM | 3172 | O | TYR | D | 86 | 31.162 | 11.360 | 34.575 | 1.00 | 44.79 | O |
| ATOM | 3173 | N | PHE | D | 87 | 33.307 | 11.041 | 35.162 | 1.00 | 44.81 | N |
| ATOM | 3174 | CA | PHE | D | 87 | 33.464 | 12.442 | 35.542 | 1.00 | 45.11 | C |
| ATOM | 3175 | CB | PHE | D | 87 | 33.095 | 12.677 | 37.019 | 1.00 | 45.03 | C |
| ATOM | 3176 | CG | PHE | D | 87 | 33.602 | 11.621 | 37.964 | 1.00 | 45.21 | C |
| ATOM | 3177 | CD1 | PHE | D | 87 | 34.890 | 11.693 | 38.486 | 1.00 | 45.51 | C |
| ATOM | 3178 | CE1 | PHE | D | 87 | 35.358 | 10.728 | 39.372 | 1.00 | 45.00 | C |
| ATOM | 3179 | CZ | PHE | D | 87 | 34.536 | 9.690 | 39.747 | 1.00 | 45.07 | C |
| ATOM | 3180 | CE2 | PHE | D | 87 | 33.246 | 9.611 | 39.238 | 1.00 | 44.96 | C |
| ATOM | 3181 | CD2 | PHE | D | 87 | 32.784 | 10.576 | 38.357 | 1.00 | 44.46 | C |
| ATOM | 3182 | C | PHE | D | 87 | 34.782 | 13.115 | 35.188 | 1.00 | 45.34 | C |
| ATOM | 3183 | O | PHE | D | 87 | 35.762 | 12.444 | 34.866 | 1.00 | 45.54 | O |
| ATOM | 3184 | N | SER | D | 88 | 34.756 | 14.451 | 35.255 | 1.00 | 45.64 | N |
| ATOM | 3185 | CA | SER | D | 88 | 35.821 | 15.349 | 34.811 | 1.00 | 45.97 | C |
| ATOM | 3186 | CB | SER | D | 88 | 35.297 | 16.247 | 33.694 | 1.00 | 46.20 | C |
| ATOM | 3187 | OG | SER | D | 88 | 35.337 | 15.595 | 32.433 | 1.00 | 47.34 | O |
| ATOM | 3188 | C | SER | D | 88 | 36.310 | 16.234 | 35.951 | 1.00 | 45.99 | C |
| ATOM | 3189 | O | SER | D | 88 | 37.402 | 16.800 | 35.897 | 1.00 | 46.11 | O |
| ATOM | 3190 | N | PRO | D | 99 | 37.620 | 8.378 | 34.147 | 1.00 | 41.32 | N |
| ATOM | 3191 | CA | PRO | D | 99 | 37.333 | 7.914 | 35.515 | 1.00 | 41.01 | C |
| ATOM | 3192 | CB | PRO | D | 99 | 37.997 | 8.983 | 36.403 | 1.00 | 41.21 | C |

APPENDIX I(d)-continued

| ATOM | 3193 | CG | PRO | D | 99 | 38.437 | 10.142 | 35.447 | 1.00 | 41.32 | C |
|---|---|---|---|---|---|---|---|---|---|---|---|
| ATOM | 3194 | CD | PRO | D | 99 | 37.888 | 9.829 | 34.076 | 1.00 | 41.24 | C |
| ATOM | 3195 | C | PRO | D | 99 | 35.827 | 7.848 | 35.777 | 1.00 | 40.76 | C |
| ATOM | 3196 | O | PRO | D | 99 | 35.075 | 8.620 | 35.183 | 1.00 | 40.78 | O |
| ATOM | 3197 | N | GLY | D | 100 | 35.390 | 6.940 | 36.652 | 1.00 | 40.55 | N |
| ATOM | 3198 | CA | GLY | D | 100 | 33.944 | 6.725 | 36.897 | 1.00 | 39.88 | C |
| ATOM | 3199 | C | GLY | D | 100 | 33.600 | 5.794 | 38.049 | 1.00 | 39.22 | C |
| ATOM | 3200 | O | GLY | D | 100 | 34.461 | 5.086 | 38.544 | 1.00 | 39.19 | O |
| ATOM | 3201 | N | GLU | D | 101 | 32.337 | 5.793 | 38.470 | 1.00 | 38.90 | N |
| ATOM | 3202 | CA | GLU | D | 101 | 31.895 | 5.043 | 39.662 | 1.00 | 38.56 | C |
| ATOM | 3203 | CB | GLU | D | 101 | 31.795 | 5.959 | 40.905 | 1.00 | 38.61 | C |
| ATOM | 3204 | CG | GLU | D | 101 | 33.089 | 6.543 | 41.423 | 1.00 | 39.35 | C |
| ATOM | 3205 | CD | GLU | D | 101 | 34.049 | 5.477 | 41.957 | 1.00 | 42.48 | C |
| ATOM | 3206 | OE1 | GLU | D | 101 | 35.275 | 5.773 | 42.085 | 1.00 | 41.06 | O |
| ATOM | 3207 | OE2 | GLU | D | 101 | 33.573 | 4.341 | 42.244 | 1.00 | 43.54 | O |
| ATOM | 3208 | C | GLU | D | 101 | 30.543 | 4.392 | 39.440 | 1.00 | 38.05 | C |
| ATOM | 3209 | O | GLU | D | 101 | 29.660 | 4.997 | 38.864 | 1.00 | 37.16 | O |
| ATOM | 3210 | N | LYS | D | 102 | 30.373 | 3.170 | 39.926 | 1.00 | 38.57 | N |
| ATOM | 3211 | CA | LYS | D | 102 | 29.047 | 2.525 | 39.897 | 1.00 | 39.26 | C |
| ATOM | 3212 | CB | LYS | D | 102 | 29.134 | 1.086 | 39.354 | 1.00 | 39.72 | C |
| ATOM | 3213 | CG | LYS | D | 102 | 29.719 | 0.974 | 37.951 | 1.00 | 42.83 | C |
| ATOM | 3214 | CD | LYS | D | 102 | 28.973 | −0.064 | 37.104 | 1.00 | 47.99 | C |
| ATOM | 3215 | CE | LYS | D | 102 | 29.772 | −1.371 | 36.971 | 1.00 | 51.61 | C |
| ATOM | 3216 | NZ | LYS | D | 102 | 29.020 | −2.452 | 36.233 | 1.00 | 53.94 | N |
| ATOM | 3217 | C | LYS | D | 102 | 28.308 | 2.529 | 41.252 | 1.00 | 38.60 | C |
| ATOM | 3218 | O | LYS | D | 102 | 28.917 | 2.359 | 42.306 | 1.00 | 38.71 | O |
| ATOM | 3219 | N | GLY | D | 103 | 26.992 | 2.723 | 41.207 | 1.00 | 38.22 | N |
| ATOM | 3220 | CA | GLY | D | 103 | 26.136 | 2.526 | 42.382 | 1.00 | 38.12 | C |
| ATOM | 3221 | C | GLY | D | 103 | 26.009 | 1.054 | 42.739 | 1.00 | 37.72 | C |
| ATOM | 3222 | O | GLY | D | 103 | 26.248 | 0.185 | 41.891 | 1.00 | 38.11 | O |
| ATOM | 3223 | N | ALA | D | 104 | 25.641 | 0.759 | 43.984 | 1.00 | 37.10 | N |
| ATOM | 3224 | CA | ALA | D | 104 | 25.685 | −0.624 | 44.471 | 1.00 | 36.84 | C |
| ATOM | 3225 | CB | ALA | D | 104 | 25.466 | −0.683 | 45.965 | 1.00 | 36.58 | C |
| ATOM | 3226 | C | ALA | D | 104 | 24.693 | −1.513 | 43.722 | 1.00 | 36.89 | C |
| ATOM | 3227 | O | ALA | D | 104 | 24.991 | −2.652 | 43.389 | 1.00 | 37.36 | O |
| ATOM | 3228 | N | GLY | D | 105 | 23.519 | −0.972 | 43.432 | 1.00 | 36.98 | N |
| ATOM | 3229 | CA | GLY | D | 105 | 22.539 | −1.667 | 42.623 | 1.00 | 36.50 | C |
| ATOM | 3230 | C | GLY | D | 105 | 21.135 | −1.498 | 43.141 | 1.00 | 36.28 | C |
| ATOM | 3231 | O | GLY | D | 105 | 20.917 | −0.997 | 44.244 | 1.00 | 36.50 | O |
| ATOM | 3232 | N | THR | D | 106 | 20.186 | −1.911 | 42.314 | 1.00 | 36.08 | N |
| ATOM | 3233 | CA | THR | D | 106 | 18.810 | −2.125 | 42.713 | 1.00 | 36.15 | C |
| ATOM | 3234 | CB | THR | D | 106 | 17.874 | −1.220 | 41.895 | 1.00 | 36.33 | C |
| ATOM | 3235 | OG1 | THR | D | 106 | 18.229 | 0.156 | 42.089 | 1.00 | 36.72 | O |
| ATOM | 3236 | CG2 | THR | D | 106 | 16.445 | −1.409 | 42.311 | 1.00 | 37.11 | C |
| ATOM | 3237 | C | THR | D | 106 | 18.515 | −3.595 | 42.386 | 1.00 | 36.03 | C |
| ATOM | 3238 | O | THR | D | 106 | 18.806 | −4.034 | 41.267 | 1.00 | 36.46 | O |
| ATOM | 3239 | N | VAL | D | 107 | 17.995 | −4.382 | 43.338 | 1.00 | 35.53 | N |
| ATOM | 3240 | CA | VAL | D | 107 | 17.420 | −5.678 | 42.927 | 1.00 | 34.79 | C |
| ATOM | 3241 | CB | VAL | D | 107 | 18.049 | −6.952 | 43.597 | 1.00 | 34.54 | C |
| ATOM | 3242 | CG1 | VAL | D | 107 | 17.254 | −7.451 | 44.711 | 1.00 | 35.41 | C |
| ATOM | 3243 | CG2 | VAL | D | 107 | 19.488 | −6.698 | 44.027 | 1.00 | 35.64 | C |
| ATOM | 3244 | C | VAL | D | 107 | 15.882 | −5.626 | 42.821 | 1.00 | 34.18 | C |
| ATOM | 3245 | O | VAL | D | 107 | 15.153 | −5.489 | 43.816 | 1.00 | 33.80 | O |
| ATOM | 3246 | N | LEU | D | 108 | 15.427 | −5.672 | 41.572 | 1.00 | 33.40 | N |
| ATOM | 3247 | CA | LEU | D | 108 | 14.026 | −5.543 | 41.235 | 1.00 | 33.01 | C |
| ATOM | 3248 | CB | LEU | D | 108 | 13.892 | −4.831 | 39.896 | 1.00 | 33.00 | C |
| ATOM | 3249 | CG | LEU | D | 108 | 12.566 | −4.235 | 39.374 | 1.00 | 33.86 | C |
| ATOM | 3250 | CD1 | LEU | D | 108 | 11.301 | −4.627 | 40.135 | 1.00 | 34.10 | C |
| ATOM | 3251 | CD2 | LEU | D | 108 | 12.415 | −4.524 | 37.875 | 1.00 | 32.03 | C |
| ATOM | 3252 | C | LEU | D | 108 | 13.417 | −6.919 | 41.091 | 1.00 | 32.57 | C |
| ATOM | 3253 | O | LEU | D | 108 | 14.015 | −7.807 | 40.508 | 1.00 | 32.64 | O |
| ATOM | 3254 | N | THR | D | 109 | 12.217 | −7.098 | 41.605 | 1.00 | 32.14 | N |
| ATOM | 3255 | CA | THR | D | 109 | 11.490 | −8.306 | 41.295 | 1.00 | 31.94 | C |
| ATOM | 3256 | CB | THR | D | 109 | 11.619 | −9.413 | 42.407 | 1.00 | 31.81 | C |
| ATOM | 3257 | OG1 | THR | D | 109 | 10.369 | −10.076 | 42.596 | 1.00 | 32.13 | O |
| ATOM | 3258 | CG2 | THR | D | 109 | 12.071 | −8.856 | 43.724 | 1.00 | 31.42 | C |
| ATOM | 3259 | C | THR | D | 109 | 10.069 | −7.932 | 40.901 | 1.00 | 31.92 | C |
| ATOM | 3260 | O | THR | D | 109 | 9.408 | −7.153 | 41.587 | 1.00 | 31.68 | O |
| ATOM | 3261 | N | VAL | D | 110 | 9.635 | −8.446 | 39.751 | 1.00 | 31.95 | N |
| ATOM | 3262 | CA | VAL | D | 110 | 8.332 | −8.099 | 39.186 | 1.00 | 31.54 | C |
| ATOM | 3263 | CB | VAL | D | 110 | 8.383 | −7.936 | 37.656 | 1.00 | 31.65 | C |
| ATOM | 3264 | CG1 | VAL | D | 110 | 7.082 | −7.284 | 37.146 | 1.00 | 30.75 | C |
| ATOM | 3265 | CG2 | VAL | D | 110 | 9.628 | −7.129 | 37.216 | 1.00 | 30.44 | C |
| ATOM | 3266 | C | VAL | D | 110 | 7.340 | −9.184 | 39.512 | 1.00 | 31.88 | C |
| ATOM | 3267 | O | VAL | D | 110 | 7.635 | −10.367 | 39.325 | 1.00 | 32.39 | O |
| ATOM | 3268 | N | LYS | D | 111 | 6.160 | −8.771 | 39.977 | 1.00 | 31.88 | N |
| ATOM | 3269 | CA | LYS | D | 111 | 5.113 | −9.670 | 40.445 | 1.00 | 31.62 | C |
| ATOM | 3270 | CB | LYS | D | 111 | 4.924 | −10.844 | 39.488 | 1.00 | 31.59 | C |
| ATOM | 3271 | CG | LYS | D | 111 | 4.107 | −10.551 | 38.264 | 1.00 | 30.11 | C |
| ATOM | 3272 | CD | LYS | D | 111 | 3.470 | −11.863 | 37.787 | 1.00 | 27.97 | C |

APPENDIX I(d)-continued

| ATOM | 3273 | CE | LYS | D | 111 | 2.016 | −11.633 | 37.521 | 1.00 | 26.09 | C |
|---|---|---|---|---|---|---|---|---|---|---|---|
| ATOM | 3274 | NZ | LYS | D | 111 | 1.418 | −11.163 | 38.781 | 1.00 | 24.52 | N |
| ATOM | 3275 | C | LYS | D | 111 | 5.422 | −10.184 | 41.856 | 1.00 | 31.99 | C |
| ATOM | 3276 | O | LYS | D | 111 | 4.582 | −10.094 | 42.774 | 1.00 | 32.43 | O |
| ATOM | 3277 | O | HOH | W | 1 | 20.434 | 11.911 | 29.836 | 1.00 | 28.88 | O |
| ATOM | 3278 | O | HOH | W | 2 | 51.173 | 8.997 | 9.730 | 1.00 | 44.36 | O |
| ATOM | 3279 | O | HOH | W | 3 | 47.689 | 11.742 | 13.593 | 1.00 | 27.86 | O |
| ATOM | 3280 | O | HOH | W | 4 | 11.612 | −6.756 | 46.515 | 1.00 | 30.22 | O |
| ATOM | 3281 | O | HOH | W | 5 | 50.210 | 12.148 | 9.875 | 1.00 | 31.20 | O |
| ATOM | 3282 | O | HOH | W | 6 | 49.395 | 14.702 | 4.881 | 1.00 | 23.52 | O |
| ATOM | 3283 | O | HOH | W | 7 | 32.057 | 7.039 | 10.045 | 1.00 | 27.86 | O |
| ATOM | 3284 | O | HOH | W | 8 | 13.846 | −7.318 | 45.160 | 1.00 | 37.92 | O |
| ATOM | 3285 | O | HOH | W | 9 | 45.367 | −5.972 | 1.806 | 1.00 | 56.96 | O |
| ATOM | 3286 | O | HOH | W | 10 | 50.323 | 2.945 | 4.830 | 1.00 | 31.28 | O |
| ATOM | 3287 | O | HOH | W | 11 | 50.653 | 13.787 | 7.807 | 1.00 | 31.34 | O |
| ATOM | 3288 | O | HOH | W | 12 | 55.639 | 7.497 | 18.084 | 1.00 | 28.59 | O |
| ATOM | 3289 | O | HOH | W | 13 | 50.800 | −9.586 | 17.024 | 1.00 | 31.78 | O |
| ATOM | 3290 | O | HOH | W | 14 | 30.173 | 21.846 | 12.570 | 1.00 | 47.23 | O |
| ATOM | 3291 | O | HOH | W | 15 | 22.770 | −0.220 | 48.758 | 1.00 | 43.83 | O |
| ATOM | 3292 | O | HOH | W | 16 | 14.574 | 24.569 | 28.773 | 1.00 | 50.25 | O |
| ATOM | 3293 | O | HOH | W | 17 | 17.273 | 23.275 | 28.770 | 1.00 | 32.25 | O |
| ATOM | 3294 | O | HOH | W | 18 | 15.628 | 9.857 | 28.519 | 1.00 | 31.38 | O |
| ATOM | 3295 | O | HOH | W | 19 | 47.486 | 29.840 | 6.150 | 1.00 | 53.53 | O |
| ATOM | 3296 | O | HOH | W | 20 | 64.546 | 22.854 | 17.164 | 1.00 | 47.54 | O |
| ATOM | 3297 | O | HOH | W | 21 | 13.831 | 9.756 | 34.661 | 1.00 | 48.11 | O |
| ATOM | 3298 | O | HOH | W | 22 | 53.874 | 4.595 | 9.539 | 1.00 | 29.77 | O |
| ATOM | 3299 | O | HOH | W | 23 | 17.826 | 11.221 | 28.000 | 1.00 | 37.97 | O |
| ATOM | 3300 | O | HOH | W | 24 | 21.478 | 16.649 | 31.244 | 1.00 | 29.30 | O |
| ATOM | 3301 | O | HOH | W | 25 | 61.648 | 23.163 | −6.346 | 1.00 | 41.07 | O |
| ATOM | 3302 | O | HOH | W | 26 | 17.685 | −4.024 | 28.143 | 1.00 | 45.65 | O |
| ATOM | 3303 | O | HOH | W | 27 | 18.676 | 48.553 | 28.572 | 1.00 | 49.95 | O |
| ATOM | 3304 | O | HOH | W | 28 | 28.883 | 35.475 | 31.748 | 1.00 | 65.90 | O |
| ATOM | 3305 | O | HOH | W | 29 | 26.495 | 13.768 | 28.887 | 1.00 | 28.89 | O |
| ATOM | 3306 | O | HOH | W | 30 | 20.570 | 7.084 | 21.442 | 1.00 | 45.88 | O |
| ATOM | 3307 | O | HOH | W | 31 | 25.634 | 10.403 | 29.395 | 1.00 | 35.32 | O |
| ATOM | 3308 | O | HOH | W | 32 | 62.535 | 39.022 | −0.570 | 1.00 | 46.92 | O |
| ATOM | 3309 | O | HOH | W | 33 | 67.283 | 26.093 | −4.127 | 1.00 | 33.73 | O |
| ATOM | 3310 | O | HOH | W | 34 | 27.566 | 41.774 | 33.161 | 1.00 | 68.26 | O |
| ATOM | 3311 | O | HOH | W | 35 | 24.143 | 13.706 | 28.178 | 1.00 | 29.46 | O |
| ATOM | 3312 | O | HOH | W | 36 | 30.372 | 26.293 | 12.250 | 1.00 | 72.48 | O |
| ATOM | 3313 | O | HOH | W | 37 | 45.656 | 20.943 | 8.052 | 1.00 | 33.27 | O |
| ATOM | 3314 | O | HOH | W | 38 | 48.649 | 7.010 | 15.549 | 1.00 | 53.94 | O |
| ATOM | 3315 | O | HOH | W | 39 | 31.570 | 18.599 | 13.713 | 1.00 | 41.28 | O |
| ATOM | 3316 | O | HOH | W | 40 | 53.663 | 7.208 | 10.450 | 1.00 | 34.57 | O |
| ATOM | 3317 | O | HOH | W | 41 | 38.580 | 12.260 | 2.002 | 1.00 | 37.67 | O |
| ATOM | 3318 | O | HOH | W | 42 | 68.611 | 36.093 | 1.637 | 1.00 | 58.68 | O |
| ATOM | 3319 | O | HOH | W | 43 | 66.806 | 32.948 | 6.043 | 1.00 | 28.02 | O |
| ATOM | 3320 | O | HOH | W | 44 | 50.597 | 16.056 | 2.995 | 1.00 | 20.92 | O |
| ATOM | 3321 | O | HOH | W | 45 | 32.402 | 18.632 | 9.245 | 1.00 | 57.58 | O |
| ATOM | 3322 | O | HOH | W | 46 | 17.826 | −1.585 | 26.168 | 1.00 | 33.42 | O |
| ATOM | 3323 | O | HOH | W | 47 | 27.978 | 18.431 | 13.061 | 1.00 | 32.36 | O |
| ATOM | 3324 | O | HOH | W | 48 | 31.130 | 23.731 | 14.541 | 1.00 | 49.15 | O |
| ATOM | 3325 | O | HOH | W | 49 | 42.973 | 18.176 | 6.181 | 1.00 | 33.87 | O |
| ATOM | 3326 | O | HOH | W | 50 | 32.854 | 1.573 | 13.656 | 1.00 | 69.40 | O |
| ATOM | 3327 | O | HOH | W | 51 | 61.024 | 21.580 | −8.223 | 1.00 | 33.81 | O |
| ATOM | 3328 | O | HOH | W | 52 | 21.853 | 18.003 | 33.363 | 1.00 | 35.88 | O |
| ATOM | 3329 | O | HOH | W | 53 | 28.214 | 18.749 | 29.985 | 1.00 | 36.72 | O |
| ATOM | 3330 | O | HOH | W | 54 | 47.190 | 27.455 | 4.981 | 1.00 | 33.48 | O |
| ATOM | 3331 | O | HOH | W | 55 | 48.698 | 14.899 | 12.805 | 1.00 | 36.47 | O |
| ATOM | 3332 | O | HOH | W | 56 | 22.007 | 13.901 | 29.964 | 1.00 | 43.41 | O |
| ATOM | 3333 | O | HOH | W | 57 | 22.817 | 3.633 | 29.513 | 1.00 | 56.91 | O |
| ATOM | 3334 | O | HOH | W | 58 | 58.369 | 24.559 | −5.982 | 1.00 | 20.15 | O |
| ATOM | 3335 | O | HOH | W | 59 | 24.791 | 22.275 | 12.738 | 1.00 | 29.00 | O |
| ATOM | 3336 | O | HOH | W | 60 | 32.506 | 39.375 | 33.303 | 1.00 | 38.43 | O |
| ATOM | 3337 | O | HOH | W | 61 | 53.833 | 40.967 | 1.428 | 1.00 | 45.08 | O |
| ATOM | 3338 | O | HOH | W | 62 | 57.058 | 27.269 | −9.143 | 1.00 | 40.00 | O |
| ATOM | 3339 | O | HOH | W | 63 | 69.526 | 32.652 | 5.064 | 1.00 | 33.59 | O |
| ATOM | 3340 | O | HOH | W | 64 | 26.026 | 46.491 | 29.214 | 1.00 | 49.43 | O |
| ATOM | 3341 | O | HOH | W | 65 | 7.535 | −12.277 | 43.624 | 1.00 | 38.83 | O |
| ATOM | 3342 | O | HOH | W | 66 | 57.673 | 36.036 | −4.990 | 1.00 | 58.18 | O |
| ATOM | 3343 | O | HOH | W | 67 | 25.219 | 2.698 | 45.646 | 1.00 | 63.61 | O |
| ATOM | 3344 | O | HOH | W | 68 | 15.224 | 15.226 | 16.533 | 1.00 | 44.99 | O |
| ATOM | 3345 | O | HOH | W | 69 | 14.303 | 30.312 | 26.773 | 1.00 | 55.43 | O |
| ATOM | 3346 | O | HOH | W | 70 | 27.473 | 17.640 | 8.014 | 1.00 | 44.24 | O |
| ATOM | 3347 | O | HOH | W | 71 | 33.541 | 14.753 | 28.074 | 1.00 | 57.64 | O |
| ATOM | 3348 | O | HOH | W | 72 | 24.106 | −5.245 | 36.422 | 1.00 | 35.69 | O |
| ATOM | 3349 | O | HOH | W | 73 | 19.945 | −3.453 | 25.718 | 1.00 | 62.43 | O |
| ATOM | 3350 | O | HOH | W | 74 | 27.055 | 43.217 | 29.667 | 1.00 | 36.48 | O |
| ATOM | 3351 | O | HOH | W | 75 | 61.808 | 21.334 | 21.511 | 1.00 | 41.05 | O |
| ATOM | 3352 | O | HOH | W | 76 | 28.392 | −1.577 | 41.924 | 1.00 | 40.31 | O |

APPENDIX I(d)-continued

| ATOM | 3353 | O | HOH | W | 77 | 41.700 | 24.432 | 10.528 | 1.00 | 50.92 | O |
|---|---|---|---|---|---|---|---|---|---|---|---|
| ATOM | 3354 | O | HOH | W | 78 | 56.356 | 17.804 | −2.343 | 1.00 | 37.41 | O |
| ATOM | 3355 | O | HOH | W | 79 | 36.787 | 28.401 | 12.252 | 1.00 | 59.49 | O |
| ATOM | 3356 | O | HOH | W | 80 | 47.719 | 11.922 | 11.398 | 1.00 | 44.13 | O |
| ATOM | 3357 | O | HOH | W | 81 | 4.122 | −2.877 | 44.501 | 1.00 | 47.12 | O |
| ATOM | 3358 | O | HOH | W | 82 | 52.740 | 31.000 | −8.756 | 1.00 | 43.99 | O |
| ATOM | 3359 | O | HOH | W | 83 | 7.919 | −11.057 | 46.234 | 1.00 | 41.46 | O |
| ATOM | 3360 | O | HOH | W | 84 | 32.706 | 34.935 | 19.255 | 1.00 | 42.71 | O |
| ATOM | 3361 | O | HOH | W | 85 | 59.882 | 27.603 | 19.759 | 1.00 | 61.63 | O |
| ATOM | 3362 | O | HOH | W | 86 | 32.168 | 6.815 | 13.604 | 1.00 | 49.25 | O |
| ATOM | 3363 | O | HOH | W | 87 | 59.729 | 2.501 | 13.133 | 1.00 | 38.27 | O |
| ATOM | 3364 | O | HOH | W | 88 | 56.064 | 4.299 | 10.903 | 1.00 | 35.41 | O |
| ATOM | 3365 | O | HOH | W | 89 | 30.138 | −2.702 | 33.252 | 1.00 | 47.19 | O |
| ATOM | 3366 | O | HOH | W | 90 | 38.708 | 21.593 | 5.409 | 1.00 | 46.41 | O |
| ATOM | 3367 | O | HOH | W | 91 | 28.192 | 17.922 | 37.236 | 1.00 | 50.27 | O |
| ATOM | 3368 | O | HOH | W | 92 | 29.568 | 3.973 | 44.497 | 1.00 | 56.59 | O |
| ATOM | 3369 | O | HOH | W | 93 | 34.862 | 20.140 | 13.615 | 1.00 | 58.79 | O |
| ATOM | 3370 | O | HOH | W | 94 | 68.056 | 37.171 | −4.566 | 1.00 | 46.07 | O |
| ATOM | 3371 | O | HOH | W | 95 | 20.067 | −18.415 | 28.488 | 1.00 | 39.57 | O |
| ATOM | 3372 | O | HOH | W | 96 | 64.699 | 22.658 | 1.365 | 1.00 | 35.36 | O |
| ATOM | 3373 | O | HOH | W | 97 | 66.830 | 20.070 | 6.461 | 1.00 | 40.73 | O |
| ATOM | 3374 | O | HOH | W | 98 | 21.629 | 21.137 | 36.271 | 1.00 | 45.67 | O |
| ATOM | 3375 | O | HOH | W | 99 | 35.422 | 2.703 | 41.956 | 1.00 | 52.70 | O |
| ATOM | 3376 | O | HOH | W | 100 | 24.037 | 1.650 | 19.799 | 1.00 | 58.56 | O |
| ATOM | 3377 | O | HOH | W | 101 | 61.498 | 2.982 | 15.930 | 1.00 | 55.15 | O |
| ATOM | 3378 | O | HOH | W | 102 | 35.953 | 15.608 | 4.118 | 1.00 | 25.75 | O |
| ATOM | 3379 | O | HOH | W | 103 | 25.517 | 31.363 | 12.480 | 1.00 | 39.04 | O |
| ATOM | 3380 | O | HOH | W | 104 | 16.726 | 21.992 | 15.197 | 1.00 | 52.30 | O |
| ATOM | 3381 | O | HOH | W | 105 | 52.552 | 23.250 | 25.811 | 1.00 | 48.16 | O |
| ATOM | 3382 | O | HOH | W | 106 | 24.153 | 12.188 | 30.527 | 1.00 | 27.39 | O |
| ATOM | 3383 | O | HOH | W | 107 | 53.933 | −9.516 | 4.486 | 1.00 | 42.89 | O |
| ATOM | 3384 | O | HOH | W | 108 | 23.827 | 37.285 | 16.265 | 1.00 | 54.62 | O |
| ATOM | 3385 | O | HOH | W | 109 | 28.396 | 33.187 | 28.407 | 1.00 | 53.09 | O |
| ATOM | 3386 | O | HOH | W | 110 | 31.985 | 20.657 | 32.687 | 1.00 | 58.85 | O |
| ATOM | 3387 | O | HOH | W | 111 | 18.171 | −15.401 | 30.507 | 1.00 | 56.89 | O |
| ATOM | 3388 | O | HOH | W | 112 | 22.082 | 0.773 | 46.243 | 1.00 | 48.16 | O |
| ATOM | 3389 | O | HOH | W | 113 | 34.526 | 22.736 | 14.520 | 1.00 | 41.26 | O |
| ATOM | 3390 | O | HOH | W | 114 | 22.419 | 6.371 | 28.995 | 1.00 | 56.85 | O |
| ATOM | 3391 | O | HOH | W | 115 | 67.422 | 16.825 | 11.168 | 1.00 | 60.46 | O |
| ATOM | 3392 | O | HOH | W | 116 | 67.448 | 23.130 | 0.776 | 1.00 | 33.43 | O |
| ATOM | 3393 | O | HOH | W | 117 | 18.592 | 16.299 | 30.811 | 1.00 | 42.83 | O |
| ATOM | 3394 | O | HOH | W | 118 | 34.587 | 24.867 | 10.841 | 1.00 | 54.23 | O |
| ATOM | 3395 | O | HOH | W | 119 | 30.859 | 34.219 | 31.592 | 1.00 | 42.88 | O |
| ATOM | 3396 | O | HOH | W | 120 | 49.605 | 4.517 | 19.934 | 1.00 | 62.19 | O |
| ATOM | 3397 | O | HOH | W | 121 | 5.422 | −5.622 | 26.696 | 1.00 | 68.49 | O |
| ATOM | 3398 | O | HOH | W | 122 | 17.557 | 13.571 | 16.130 | 1.00 | 43.21 | O |
| ATOM | 3399 | O | HOH | W | 123 | 27.902 | 37.884 | 19.254 | 1.00 | 64.98 | O |
| ATOM | 3400 | O | HOH | W | 124 | 17.490 | 12.457 | 13.620 | 1.00 | 56.86 | O |
| ATOM | 3401 | O | HOH | W | 125 | 25.374 | 44.666 | 33.403 | 1.00 | 46.35 | O |
| ATOM | 3402 | O | HOH | W | 126 | 12.246 | 0.705 | 24.754 | 1.00 | 56.61 | O |
| ATOM | 3403 | O | HOH | W | 127 | 22.142 | 5.206 | 26.086 | 1.00 | 40.68 | O |
| ATOM | 3404 | O | HOH | W | 128 | 37.638 | −12.506 | 6.296 | 1.00 | 57.01 | O |
| ATOM | 3405 | O | HOH | W | 129 | 48.345 | 16.352 | 1.698 | 1.00 | 30.83 | O |
| ATOM | 3406 | O | HOH | W | 130 | 20.648 | 20.480 | 33.583 | 1.00 | 34.60 | O |
| ATOM | 3407 | O | HOH | W | 131 | 64.275 | 41.462 | −8.991 | 1.00 | 47.63 | O |
| ATOM | 3408 | O | HOH | W | 132 | 60.760 | 12.924 | 7.514 | 1.00 | 49.20 | O |
| ATOM | 3409 | O | HOH | W | 133 | 50.675 | 6.054 | 17.267 | 1.00 | 41.28 | O |
| ATOM | 3410 | O | HOH | W | 134 | 33.273 | −5.842 | 12.720 | 1.00 | 54.10 | O |
| ATOM | 3411 | O | HOH | W | 135 | 32.026 | 34.506 | 33.860 | 1.00 | 62.11 | O |
| ATOM | 3412 | O | HOH | W | 136 | 30.538 | 27.830 | 33.165 | 1.00 | 49.21 | O |
| ATOM | 3413 | O | HOH | W | 137 | 46.775 | 19.029 | 10.612 | 1.00 | 52.46 | O |
| ATOM | 3414 | O | HOH | W | 138 | 67.563 | 23.044 | 3.123 | 1.00 | 36.24 | O |
| ATOM | 3415 | O | HOH | W | 139 | 39.108 | 16.251 | 0.823 | 1.00 | 51.06 | O |
| ATOM | 3416 | O | HOH | W | 140 | 20.593 | 22.210 | 39.321 | 1.00 | 53.90 | O |
| ATOM | 3417 | O | HOH | W | 141 | 46.106 | 8.016 | 1.533 | 1.00 | 37.88 | O |
| ATOM | 3418 | O | HOH | W | 142 | 52.095 | 35.903 | 9.125 | 1.00 | 32.61 | O |
| ATOM | 3419 | O | HOH | W | 143 | 75.389 | 25.371 | 16.968 | 1.00 | 35.99 | O |
| ATOM | 3420 | O | HOH | W | 144 | 15.057 | 9.817 | 16.549 | 1.00 | 65.48 | O |
| ATOM | 3421 | O | HOH | W | 145 | 37.631 | 28.173 | 28.732 | 1.00 | 38.60 | O |
| ATOM | 3422 | O | HOH | W | 146 | 66.515 | 22.664 | 20.027 | 1.00 | 52.17 | O |
| ATOM | 3423 | O | HOH | W | 147 | 42.528 | −7.022 | 23.940 | 1.00 | 71.26 | O |
| ATOM | 3424 | O | HOH | W | 148 | 54.947 | −3.340 | 6.545 | 1.00 | 55.11 | O |
| ATOM | 3425 | O | HOH | W | 149 | 28.775 | −10.352 | 32.112 | 1.00 | 44.73 | O |
| ATOM | 3426 | O | HOH | W | 150 | 18.892 | 31.401 | 12.777 | 1.00 | 37.43 | O |
| ATOM | 3427 | O | HOH | W | 151 | 9.905 | −12.495 | 39.620 | 1.00 | 32.28 | O |
| ATOM | 3428 | O | HOH | W | 152 | 38.303 | −19.018 | 4.482 | 1.00 | 70.97 | O |
| ATOM | 3429 | O | HOH | W | 153 | 15.856 | 34.267 | 36.720 | 1.00 | 58.14 | O |
| ATOM | 3430 | O | HOH | W | 154 | 30.760 | 5.017 | 7.768 | 1.00 | 43.73 | O |
| ATOM | 3431 | O | HOH | W | 155 | 16.890 | 20.222 | 33.788 | 1.00 | 49.43 | O |
| ATOM | 3432 | O | HOH | W | 156 | 33.273 | 2.733 | 7.110 | 1.00 | 39.05 | O |

APPENDIX I(d)-continued

| ATOM | 3433 | O | HOH | W | 157 | 49.572 | 43.793 | 7.514 | 1.00 | 43.22 | O |
| --- | --- | --- | --- | --- | --- | --- | --- | --- | --- | --- | --- |
| ATOM | 3434 | O | HOH | W | 158 | 30.541 | 3.798 | 48.182 | 1.00 | 55.17 | O |
| ATOM | 3435 | O | HOH | W | 159 | 16.015 | 34.924 | 32.024 | 1.00 | 48.83 | O |
| ATOM | 3436 | O | HOH | W | 160 | 51.712 | 35.074 | −4.804 | 1.00 | 64.25 | O |
| ATOM | 3437 | O | HOH | W | 161 | 36.464 | −3.007 | −0.285 | 1.00 | 38.44 | O |
| ATOM | 3438 | O | HOH | W | 162 | 16.182 | 15.269 | 31.037 | 1.00 | 66.49 | O |
| ATOM | 3439 | O | HOH | W | 163 | 35.025 | 8.191 | 26.758 | 1.00 | 58.94 | O |
| ATOM | 3440 | O | HOH | W | 164 | 66.113 | 10.299 | 20.931 | 1.00 | 56.12 | O |
| ATOM | 3441 | O | HOH | W | 165 | 55.630 | −22.839 | 7.058 | 1.00 | 40.94 | O |
| ATOM | 3442 | O | HOH | W | 166 | 70.597 | 24.001 | 10.339 | 1.00 | 38.15 | O |
| ATOM | 3443 | O | HOH | W | 167 | 33.827 | 8.257 | 29.433 | 1.00 | 47.62 | O |
| ATOM | 3444 | O | HOH | W | 168 | 38.651 | 3.562 | 1.821 | 1.00 | 46.00 | O |
| ATOM | 3445 | O | HOH | W | 169 | 17.931 | 8.596 | 15.903 | 1.00 | 63.55 | O |
| ATOM | 3446 | O | HOH | W | 170 | 53.590 | 12.112 | 2.058 | 1.00 | 52.40 | O |
| ATOM | 3447 | O | HOH | W | 171 | 12.498 | 6.890 | 22.243 | 1.00 | 48.61 | O |
| ATOM | 3448 | O | HOH | W | 172 | 45.282 | 16.726 | −1.766 | 1.00 | 53.43 | O |
| ATOM | 3449 | O | HOH | W | 173 | 33.374 | 0.766 | 3.579 | 1.00 | 48.57 | O |
| ATOM | 3450 | O | HOH | W | 174 | 17.563 | 13.972 | 38.450 | 1.00 | 48.25 | O |
| ATOM | 3451 | O | HOH | W | 175 | 68.951 | 20.742 | 22.836 | 1.00 | 58.59 | O |
| ATOM | 3452 | O | HOH | W | 176 | 37.600 | −19.066 | −0.214 | 1.00 | 54.28 | O |
| ATOM | 3453 | O | HOH | W | 177 | 58.850 | 2.171 | 16.664 | 1.00 | 66.83 | O |
| ATOM | 3454 | O | HOH | W | 178 | 37.338 | −18.592 | 14.900 | 1.00 | 66.88 | O |
| ATOM | 3455 | O | HOH | W | 179 | 9.482 | 6.134 | 21.968 | 1.00 | 71.18 | O |
| ATOM | 3456 | O | HOH | W | 180 | 15.502 | 31.876 | 18.773 | 1.00 | 54.02 | O |
| ATOM | 3457 | O | HOH | W | 181 | 14.514 | −4.130 | 26.924 | 1.00 | 55.36 | O |
| ATOM | 3458 | O | HOH | W | 182 | 70.672 | 29.846 | −1.684 | 1.00 | 60.93 | O |
| ATOM | 3459 | O | HOH | W | 183 | 51.258 | 13.722 | 1.255 | 1.00 | 43.34 | O |
| ATOM | 3460 | O | HOH | W | 184 | 10.716 | 1.766 | 47.290 | 1.00 | 67.75 | O |
| ATOM | 3461 | O | HOH | W | 185 | 58.832 | 8.512 | 6.813 | 1.00 | 53.65 | O |
| ATOM | 3462 | O | HOH | W | 186 | −4.086 | −12.572 | 36.744 | 1.00 | 62.79 | O |
| ATOM | 3463 | O | HOH | W | 187 | 46.508 | 24.691 | 2.250 | 1.00 | 47.04 | O |
| ATOM | 3464 | O | HOH | W | 188 | 13.873 | 5.882 | 44.387 | 1.00 | 58.50 | O |
| ATOM | 3465 | O | HOH | W | 189 | 51.139 | 28.495 | 18.297 | 1.00 | 57.53 | O |
| ATOM | 3466 | O | HOH | W | 190 | 30.947 | 10.141 | 52.110 | 1.00 | 57.16 | O |
| ATOM | 3467 | O | HOH | W | 191 | 65.605 | 25.389 | 14.283 | 1.00 | 43.24 | O |
| ATOM | 3468 | O | HOH | W | 192 | 18.126 | 13.182 | 30.638 | 1.00 | 41.72 | O |
| ATOM | 3469 | O | HOH | W | 193 | 55.794 | −1.873 | 17.214 | 1.00 | 36.16 | O |
| ATOM | 3470 | O | HOH | W | 194 | 33.783 | 33.110 | 17.457 | 1.00 | 54.55 | O |
| ATOM | 3471 | O | HOH | W | 195 | 38.853 | −14.910 | 11.939 | 1.00 | 63.88 | O |
| ATOM | 3472 | O | HOH | W | 196 | 49.456 | 22.757 | 10.865 | 1.00 | 63.46 | O |
| ATOM | 3473 | O | HOH | W | 197 | 28.587 | 7.862 | 11.381 | 1.00 | 52.03 | O |
| ATOM | 3474 | O | HOH | W | 198 | 34.947 | 35.941 | 19.703 | 1.00 | 70.80 | O |
| ATOM | 3475 | O | HOH | W | 199 | 55.475 | 24.490 | −7.980 | 1.00 | 51.18 | O |
| ATOM | 3476 | O | HOH | W | 200 | 56.743 | 13.758 | −6.598 | 1.00 | 65.21 | O |
| ATOM | 3477 | O | HOH | W | 201 | 12.911 | −7.264 | 23.286 | 1.00 | 60.82 | O |
| ATOM | 3478 | O | HOH | W | 202 | 5.138 | 2.264 | 22.647 | 1.00 | 62.03 | O |
| ATOM | 3479 | O | HOH | W | 203 | 13.304 | 35.163 | 27.777 | 1.00 | 46.47 | O |
| ATOM | 3480 | O | HOH | W | 204 | 25.888 | −4.844 | 26.526 | 1.00 | 48.34 | O |
| ATOM | 3481 | O | HOH | W | 205 | 14.760 | 20.897 | 17.935 | 1.00 | 40.89 | O |
| ATOM | 3482 | O | HOH | W | 206 | 53.987 | 26.147 | −11.062 | 1.00 | 49.82 | O |
| ATOM | 3483 | O | HOH | W | 207 | 68.989 | 21.658 | 5.489 | 1.00 | 44.82 | O |
| ATOM | 3484 | O | HOH | W | 208 | 4.346 | 1.281 | 33.781 | 1.00 | 35.17 | O |
| ATOM | 3485 | O | HOH | W | 209 | 43.654 | 22.216 | 2.326 | 1.00 | 56.61 | O |
| ATOM | 3486 | O | HOH | W | 210 | 57.660 | −0.011 | 17.662 | 1.00 | 57.39 | O |
| ATOM | 3487 | O | HOH | W | 211 | 21.597 | 34.434 | 36.749 | 1.00 | 53.23 | O |
| ATOM | 3488 | O | HOH | W | 212 | 14.578 | 8.819 | 26.105 | 1.00 | 36.35 | O |
| ATOM | 3489 | O | HOH | W | 213 | 13.688 | 13.351 | 16.929 | 1.00 | 60.60 | O |
| ATOM | 3490 | O | HOH | W | 214 | 6.756 | −7.170 | 24.322 | 1.00 | 56.84 | O |
| ATOM | 3491 | O | HOH | W | 215 | 67.898 | 11.572 | 28.182 | 1.00 | 55.11 | O |
| ATOM | 3492 | O | HOH | W | 216 | 57.714 | 24.233 | 22.731 | 1.00 | 44.21 | O |
| ATOM | 3493 | O | HOH | W | 217 | 58.213 | 41.336 | −4.038 | 1.00 | 57.86 | O |
| ATOM | 3494 | O | HOH | W | 218 | 12.270 | −5.061 | 48.893 | 1.00 | 43.21 | O |
| ATOM | 3495 | O | HOH | W | 219 | 70.379 | 28.854 | 2.049 | 1.00 | 42.00 | O |
| ATOM | 3496 | O | HOH | W | 220 | 50.260 | −5.040 | 1.589 | 1.00 | 48.18 | O |
| ATOM | 3497 | O | HOH | W | 221 | 56.271 | 31.125 | −7.728 | 1.00 | 52.70 | O |
| ATOM | 3498 | O | HOH | W | 222 | 14.596 | 5.260 | 21.037 | 1.00 | 66.32 | O |
| ATOM | 3499 | O | HOH | W | 223 | 34.755 | −8.144 | 17.238 | 1.00 | 51.05 | O |
| ATOM | 3500 | O | HOH | W | 224 | 48.049 | −5.297 | 0.350 | 1.00 | 51.97 | O |
| ATOM | 3501 | O | HOH | W | 225 | 39.891 | 10.372 | −0.744 | 1.00 | 57.12 | O |
| ATOM | 3502 | O | HOH | W | 226 | 56.777 | 16.253 | 3.098 | 1.00 | 44.22 | O |
| ATOM | 3503 | O | HOH | W | 227 | 41.686 | 6.425 | 30.801 | 1.00 | 58.48 | O |
| ATOM | 3504 | O | HOH | W | 228 | 31.152 | 3.461 | 14.490 | 1.00 | 61.32 | O |
| ATOM | 3505 | O | HOH | W | 229 | 20.483 | 5.907 | 24.097 | 1.00 | 54.34 | O |
| ATOM | 3506 | O | HOH | W | 230 | 19.242 | 7.120 | 14.031 | 1.00 | 41.44 | O |
| ATOM | 3507 | O | HOH | W | 231 | 31.016 | 13.010 | −0.673 | 1.00 | 38.51 | O |
| ATOM | 3508 | O | HOH | W | 232 | 70.871 | 26.732 | 9.211 | 1.00 | 50.35 | O |
| ATOM | 3509 | O | HOH | W | 233 | 62.530 | 5.381 | 16.924 | 1.00 | 69.00 | O |
| ATOM | 3510 | O | HOH | W | 234 | 58.689 | 10.135 | 26.681 | 1.00 | 61.24 | O |
| ATOM | 3511 | O | HOH | W | 235 | 48.099 | 28.707 | −1.499 | 1.00 | 41.34 | O |
| ATOM | 3512 | O | HOH | W | 236 | 56.075 | 11.436 | −8.202 | 1.00 | 72.01 | O |

APPENDIX I(d)-continued

| ATOM | 3513 | O | HOH | W | 237 | 44.741 | 25.584 | 8.874 | 1.00 | 56.34 | O |
|---|---|---|---|---|---|---|---|---|---|---|---|
| ATOM | 3514 | O | HOH | W | 238 | 25.074 | 2.290 | 49.071 | 1.00 | 61.02 | O |
| ATOM | 3515 | O | HOH | W | 239 | 13.166 | 21.601 | 29.112 | 1.00 | 61.73 | O |
| ATOM | 3516 | O | HOH | W | 240 | 27.871 | 0.758 | 7.409 | 1.00 | 58.43 | O |
| ATOM | 3517 | O | HOH | W | 241 | 29.447 | 3.216 | 9.465 | 1.00 | 45.36 | O |
| ATOM | 3518 | O | HOH | W | 242 | 33.613 | −4.885 | 10.263 | 1.00 | 47.86 | O |
| ATOM | 3519 | O | HOH | W | 243 | 53.720 | 6.429 | 0.325 | 1.00 | 57.39 | O |
| ATOM | 3520 | O | HOH | W | 244 | 29.614 | 2.734 | 6.372 | 1.00 | 50.86 | O |
| ATOM | 3521 | O | HOH | W | 245 | 17.179 | 1.833 | 49.731 | 1.00 | 29.82 | O |
| ATOM | 3522 | O | HOH | W | 246 | 19.272 | 8.281 | 10.603 | 1.00 | 48.32 | O |
| ATOM | 3523 | O | HOH | W | 247 | 40.725 | −15.193 | 24.266 | 1.00 | 53.01 | O |
| ATOM | 3524 | O | HOH | W | 248 | 29.119 | −7.888 | 30.396 | 1.00 | 49.32 | O |
| ATOM | 3525 | O | HOH | W | 249 | 49.189 | 23.307 | −5.216 | 1.00 | 42.80 | O |
| ATOM | 3526 | O | HOH | W | 250 | 54.694 | 28.682 | −11.150 | 1.00 | 66.83 | O |
| ATOM | 3527 | O | HOH | W | 251 | 60.944 | 16.846 | 0.662 | 1.00 | 52.36 | O |
| ATOM | 3528 | O | HOH | W | 252 | 16.228 | 18.028 | 33.087 | 1.00 | 49.65 | O |
| ATOM | 3529 | O | HOH | W | 253 | 45.158 | 30.281 | 11.427 | 1.00 | 45.27 | O |
| ATOM | 3530 | O | HOH | W | 254 | 26.898 | 6.397 | 13.473 | 1.00 | 50.93 | O |
| ATOM | 3531 | O | HOH | W | 255 | 57.476 | −18.207 | 3.515 | 1.00 | 68.56 | O |
| ATOM | 3532 | O | HOH | W | 256 | 32.813 | 19.282 | 2.967 | 1.00 | 36.17 | O |
| ATOM | 3533 | O | HOH | W | 257 | 9.491 | 2.419 | 44.597 | 1.00 | 52.45 | O |
| ATOM | 3534 | O | HOH | W | 258 | 35.271 | −3.932 | 16.911 | 1.00 | 66.53 | O |
| ATOM | 3535 | O | HOH | W | 259 | 49.732 | 14.842 | −2.401 | 1.00 | 43.97 | O |
| ATOM | 3536 | O | HOH | W | 260 | 27.521 | 20.972 | 11.308 | 1.00 | 47.00 | O |
| ATOM | 3537 | O | HOH | W | 261 | 43.115 | 10.114 | −1.913 | 1.00 | 35.84 | O |
| ATOM | 3538 | O | HOH | W | 262 | 21.275 | 0.044 | 21.585 | 1.00 | 67.57 | O |
| ATOM | 3539 | O | HOH | W | 263 | 37.120 | 20.797 | 18.864 | 1.00 | 79.96 | O |
| ATOM | 3540 | O | HOH | W | 264 | 47.410 | −17.381 | 18.378 | 1.00 | 74.12 | O |
| ATOM | 3541 | O | HOH | W | 265 | 62.924 | 21.666 | −0.960 | 1.00 | 50.01 | O |
| ATOM | 3542 | O | HOH | W | 266 | 35.999 | −1.885 | −2.786 | 1.00 | 49.94 | O |
| ATOM | 3543 | O | HOH | W | 267 | 74.941 | 28.538 | 16.431 | 1.00 | 59.06 | O |
| ATOM | 3544 | O | HOH | W | 268 | 46.761 | 1.281 | −0.475 | 1.00 | 67.06 | O |
| ATOM | 3545 | O | HOH | W | 269 | 48.670 | 8.707 | 0.836 | 1.00 | 49.88 | O |
| ATOM | 3546 | O | HOH | W | 270 | 66.079 | 13.752 | 6.762 | 1.00 | 42.69 | O |
| ATOM | 3547 | O | HOH | W | 271 | 16.090 | 16.729 | 37.464 | 1.00 | 69.24 | O |
| ATOM | 3548 | O | HOH | W | 272 | 77.143 | 27.199 | 11.644 | 1.00 | 52.10 | O |
| ATOM | 3549 | O | HOH | W | 273 | 51.882 | 22.494 | −6.310 | 1.00 | 59.08 | O |
| ATOM | 3550 | O | HOH | W | 274 | 50.771 | 43.361 | 4.510 | 1.00 | 48.05 | O |
| ATOM | 3551 | O | HOH | W | 275 | 46.898 | 34.616 | 12.107 | 1.00 | 65.71 | O |
| ATOM | 3552 | O | HOH | W | 276 | 23.075 | 46.450 | 29.289 | 1.00 | 47.04 | O |
| ATOM | 3553 | O | HOH | W | 277 | 14.404 | 12.889 | 31.126 | 1.00 | 57.95 | O |
| ATOM | 3554 | O | HOH | W | 278 | 36.453 | −11.467 | 1.613 | 1.00 | 57.63 | O |
| ATOM | 3555 | O | HOH | W | 279 | 8.112 | 9.700 | 21.211 | 1.00 | 59.50 | O |
| ATOM | 3556 | O | HOH | W | 280 | 46.998 | 14.682 | −2.760 | 1.00 | 52.71 | O |
| ATOM | 3557 | O | HOH | W | 281 | 17.921 | 3.335 | 17.731 | 1.00 | 49.98 | O |
| ATOM | 3558 | O | HOH | W | 282 | 32.865 | 28.042 | 19.693 | 1.00 | 50.59 | O |
| ATOM | 3559 | O | HOH | W | 283 | 25.586 | 31.869 | 10.003 | 1.00 | 63.81 | O |
| ATOM | 3560 | O | HOH | W | 284 | 31.186 | −6.345 | 2.371 | 1.00 | 49.17 | O |
| ATOM | 3561 | O | HOH | W | 285 | 15.416 | 17.750 | 24.533 | 1.00 | 48.35 | O |
| ATOM | 3562 | O | HOH | W | 286 | 38.078 | −16.872 | 18.075 | 1.00 | 71.42 | O |
| ATOM | 3563 | O | HOH | W | 287 | 9.244 | 3.329 | 41.771 | 1.00 | 50.93 | O |
| ATOM | 3564 | O | HOH | W | 288 | 52.401 | 34.885 | 3.571 | 1.00 | 60.33 | O |
| ATOM | 3565 | O | HOH | W | 289 | 31.377 | 39.196 | 25.255 | 1.00 | 51.58 | O |
| ATOM | 3566 | O | HOH | W | 290 | 14.500 | 17.886 | 22.018 | 1.00 | 50.10 | O |
| ATOM | 3567 | O | HOH | W | 291 | 40.282 | 7.206 | 17.126 | 1.00 | 42.88 | O |
| ATOM | 3568 | O | HOH | W | 292 | 30.260 | 17.132 | 9.954 | 1.00 | 55.27 | O |
| ATOM | 3569 | O | HOH | W | 293 | 38.681 | −1.970 | −2.008 | 1.00 | 60.38 | O |
| ATOM | 3570 | O | HOH | W | 294 | 19.629 | 9.142 | 21.868 | 1.00 | 62.74 | O |
| ATOM | 3571 | O | HOH | W | 295 | 15.109 | −8.962 | 30.732 | 1.00 | 50.70 | O |
| ATOM | 3572 | O | HOH | W | 296 | 20.081 | 2.438 | 49.837 | 1.00 | 47.62 | O |
| ATOM | 3573 | O | HOH | W | 297 | 56.603 | 15.529 | −0.198 | 1.00 | 46.06 | O |
| ATOM | 3574 | O | HOH | W | 298 | 27.818 | 6.514 | 7.376 | 1.00 | 50.96 | O |
| ATOM | 3575 | O | HOH | W | 299 | 24.897 | 22.369 | 9.701 | 1.00 | 32.90 | O |
| ATOM | 3576 | O | HOH | W | 300 | 54.872 | −12.316 | 12.229 | 1.00 | 64.45 | O |
| ATOM | 3577 | O | HOH | W | 301 | 47.153 | −4.394 | 19.519 | 1.00 | 51.72 | O |
| ATOM | 3578 | O | HOH | W | 302 | 28.548 | 27.445 | 38.300 | 1.00 | 57.61 | O |
| ATOM | 3579 | O | HOH | W | 303 | 44.013 | −17.633 | 4.722 | 1.00 | 75.42 | O |
| ATOM | 3580 | O | HOH | W | 304 | 48.151 | 26.251 | −1.702 | 1.00 | 38.80 | O |
| ATOM | 3581 | O | HOH | W | 305 | 19.193 | 10.914 | 11.697 | 1.00 | 47.15 | O |
| ATOM | 3582 | O | HOH | W | 306 | 22.985 | 24.448 | 10.233 | 1.00 | 42.45 | O |
| ATOM | 3583 | O | HOH | W | 307 | 37.607 | −9.929 | 15.371 | 1.00 | 54.35 | O |
| ATOM | 3584 | O | HOH | W | 308 | 53.957 | −16.667 | 11.106 | 1.00 | 73.02 | O |
| ATOM | 3585 | O | HOH | W | 309 | 11.604 | 28.463 | 23.443 | 1.00 | 76.29 | O |
| ATOM | 3586 | O | HOH | W | 310 | 31.389 | 2.126 | 35.240 | 1.00 | 54.80 | O |
| ATOM | 3587 | O | HOH | W | 311 | 41.669 | −17.196 | 13.469 | 1.00 | 55.16 | O |
| ATOM | 3588 | O | HOH | W | 312 | 23.733 | 40.464 | 35.441 | 1.00 | 58.58 | O |
| ATOM | 3589 | O | HOH | W | 313 | 20.071 | 8.403 | 45.139 | 1.00 | 55.44 | O |
| ATOM | 3590 | O | HOH | W | 314 | 68.778 | 28.533 | 17.512 | 1.00 | 45.32 | O |
| ATOM | 3591 | O | HOH | W | 315 | 64.181 | 14.152 | 10.857 | 1.00 | 51.72 | O |
| ATOM | 3592 | O | HOH | W | 316 | 29.049 | 1.903 | 46.292 | 1.00 | 43.97 | O |

APPENDIX I(d)-continued

| ATOM | 3593 | O | HOH | W | 317 | 62.143 | 14.172 | 9.271 | 1.00 | 63.02 | O |
|---|---|---|---|---|---|---|---|---|---|---|---|
| ATOM | 3594 | O | HOH | W | 318 | 24.107 | −2.007 | 49.865 | 1.00 | 38.66 | O |
| ATOM | 3595 | O | HOH | W | 319 | 41.007 | −7.072 | 0.043 | 1.00 | 56.35 | O |
| ATOM | 3596 | O | HOH | W | 320 | 68.195 | 21.721 | 14.142 | 1.00 | 46.50 | O |
| ATOM | 3597 | O | HOH | W | 321 | 22.462 | 39.174 | 37.178 | 1.00 | 69.52 | O |
| ATOM | 3598 | O | HOH | W | 322 | 17.783 | 6.183 | 19.862 | 1.00 | 54.61 | O |
| ATOM | 3599 | O | HOH | W | 323 | 46.953 | 22.632 | 18.131 | 1.00 | 51.51 | O |
| ATOM | 3600 | O | HOH | W | 324 | 30.988 | −1.282 | 12.374 | 1.00 | 50.56 | O |
| ATOM | 3601 | O | HOH | W | 325 | 46.824 | 9.645 | 16.570 | 1.00 | 76.67 | O |
| ATOM | 3602 | O | HOH | W | 326 | 47.709 | 3.790 | 27.072 | 1.00 | 52.42 | O |
| ATOM | 3603 | O | HOH | W | 327 | 37.100 | 14.801 | 1.681 | 1.00 | 49.38 | O |
| ATOM | 3604 | O | HOH | W | 328 | 41.476 | −1.502 | 0.396 | 1.00 | 58.29 | O |
| ATOM | 3605 | O | HOH | W | 329 | 67.547 | 38.430 | −0.728 | 1.00 | 44.88 | O |
| ATOM | 3606 | O | HOH | W | 330 | 62.517 | 25.184 | 21.058 | 1.00 | 64.10 | O |
| ATOM | 3607 | O | HOH | W | 331 | −0.557 | −2.635 | 37.863 | 1.00 | 45.19 | O |
| ATOM | 3608 | O | HOH | W | 332 | 69.664 | 27.202 | −0.020 | 1.00 | 51.53 | O |
| ATOM | 3609 | O | HOH | W | 333 | 30.130 | −0.340 | 29.038 | 1.00 | 57.18 | O |
| ATOM | 3610 | O | HOH | W | 334 | 51.237 | 27.533 | −6.173 | 1.00 | 47.91 | O |
| ATOM | 3611 | O | HOH | W | 335 | 0.933 | −1.230 | 32.070 | 1.00 | 57.36 | O |
| ATOM | 3612 | O | HOH | W | 336 | 31.115 | −13.376 | −0.361 | 1.00 | 45.10 | O |
| ATOM | 3613 | O | HOH | W | 337 | 45.532 | 6.225 | 27.169 | 1.00 | 66.83 | O |
| ATOM | 3614 | O | HOH | W | 338 | 38.789 | −3.517 | 28.225 | 1.00 | 63.88 | O |
| ATOM | 3615 | O | HOH | W | 339 | 21.603 | 23.747 | 35.437 | 1.00 | 58.20 | O |
| ATOM | 3616 | O | HOH | W | 340 | 51.744 | 32.705 | 1.437 | 1.00 | 69.55 | O |
| ATOM | 3617 | O | HOH | W | 341 | 53.285 | 23.459 | 20.176 | 1.00 | 50.19 | O |
| ATOM | 3618 | O | HOH | W | 342 | 50.116 | 30.832 | 6.312 | 1.00 | 31.41 | O |
| ATOM | 3619 | O | HOH | W | 343 | 56.433 | 5.701 | 7.393 | 1.00 | 42.02 | O |
| ATOM | 3620 | O | HOH | W | 344 | 37.416 | 20.918 | 24.575 | 1.00 | 55.74 | O |
| ATOM | 3621 | O | HOH | W | 345 | 67.567 | 26.023 | 15.813 | 1.00 | 43.48 | O |
| ATOM | 3622 | O | HOH | W | 346 | 14.406 | 44.657 | 26.427 | 1.00 | 65.51 | O |
| ATOM | 3623 | O | HOH | W | 347 | 17.703 | 5.856 | 16.750 | 1.00 | 45.27 | O |
| ATOM | 3624 | O | HOH | W | 348 | 44.529 | 25.367 | 21.896 | 1.00 | 61.22 | O |
| ATOM | 3625 | O | HOH | W | 349 | 43.676 | 8.317 | 25.804 | 1.00 | 47.68 | O |
| ATOM | 3626 | O | HOH | W | 350 | 59.266 | 11.361 | 7.848 | 1.00 | 69.95 | O |
| ATOM | 3627 | O | HOH | W | 351 | 50.382 | 13.506 | 12.091 | 1.00 | 35.61 | O |
| ATOM | 3628 | O | HOH | W | 352 | 52.344 | 20.190 | −3.908 | 1.00 | 41.33 | O |
| ATOM | 3629 | O | HOH | W | 353 | 70.633 | 22.306 | 8.035 | 1.00 | 49.69 | O |
| ATOM | 3630 | O | HOH | W | 354 | 20.918 | 9.448 | 14.526 | 1.00 | 49.51 | O |
| ATOM | 3631 | O | HOH | W | 355 | 46.850 | 29.538 | −5.784 | 1.00 | 55.83 | O |
| ATOM | 3632 | O | HOH | W | 356 | 7.257 | −10.627 | 28.472 | 1.00 | 75.56 | O |
| ATOM | 3633 | O | HOH | W | 357 | 29.522 | 21.084 | 28.772 | 1.00 | 29.76 | O |
| ATOM | 3634 | O | HOH | W | 358 | 58.141 | −5.422 | 8.999 | 1.00 | 72.75 | O |
| ATOM | 3635 | O | HOH | W | 359 | 44.287 | 32.961 | 31.887 | 1.00 | 52.80 | O |
| ATOM | 3636 | O | HOH | W | 360 | 52.292 | 13.939 | −1.485 | 1.00 | 45.87 | O |
| ATOM | 3637 | O | HOH | W | 361 | 38.838 | −12.010 | 13.154 | 1.00 | 53.39 | O |
| ATOM | 3638 | O | HOH | W | 362 | 71.746 | 29.166 | 11.917 | 1.00 | 66.84 | O |
| ATOM | 3639 | O | HOH | W | 363 | 34.791 | 26.989 | 17.836 | 1.00 | 58.17 | O |
| ATOM | 3640 | O | HOH | W | 364 | 49.720 | 18.422 | 10.244 | 1.00 | 58.39 | O |
| ATOM | 3641 | O | HOH | W | 365 | 36.609 | −19.691 | 18.159 | 1.00 | 56.62 | O |
| ATOM | 3642 | O | HOH | W | 366 | 52.019 | 34.567 | −0.128 | 1.00 | 62.35 | O |
| ATOM | 3643 | O | HOH | W | 367 | 8.099 | 4.733 | 38.644 | 1.00 | 59.14 | O |
| ATOM | 3644 | O | HOH | W | 368 | 24.162 | 43.585 | 29.340 | 1.00 | 54.80 | O |
| ATOM | 3645 | O | HOH | W | 369 | 12.065 | 11.038 | 40.551 | 1.00 | 50.21 | O |
| ATOM | 3646 | O | HOH | W | 370 | 51.445 | 34.226 | 7.596 | 1.00 | 46.49 | O |
| ATOM | 3647 | O | HOH | W | 371 | 46.917 | 37.194 | 10.718 | 1.00 | 47.06 | O |
| ATOM | 3648 | O | HOH | W | 372 | 37.530 | 8.417 | −1.409 | 1.00 | 50.26 | O |
| ATOM | 3649 | O | HOH | W | 373 | 16.046 | 20.046 | 23.951 | 1.00 | 62.38 | O |
| ATOM | 3650 | O | HOH | W | 374 | 31.497 | 29.299 | 30.333 | 1.00 | 55.86 | O |
| ATOM | 3651 | O | HOH | W | 375 | 55.680 | 31.078 | 13.913 | 1.00 | 66.00 | O |
| ATOM | 3652 | O | HOH | W | 376 | −1.126 | −12.205 | 37.405 | 1.00 | 46.93 | O |
| ATOM | 3653 | O | HOH | W | 377 | 57.780 | 19.822 | −4.481 | 1.00 | 52.77 | O |
| ATOM | 3654 | O | HOH | W | 378 | 20.558 | 24.848 | 11.749 | 1.00 | 44.63 | O |
| ATOM | 3655 | O | HOH | W | 379 | 18.424 | 49.479 | 19.940 | 1.00 | 56.67 | O |
| ATOM | 3656 | O | HOH | W | 380 | 22.486 | 31.556 | 10.000 | 1.00 | 50.34 | O |
| ATOM | 3657 | O | HOH | W | 381 | 53.741 | 23.702 | −9.251 | 1.00 | 48.43 | O |
| ATOM | 3658 | O | HOH | W | 382 | 34.525 | 24.186 | 16.557 | 1.00 | 65.32 | O |
| ATOM | 3659 | O | HOH | W | 383 | 17.235 | 19.518 | 21.375 | 1.00 | 58.33 | O |
| ATOM | 3660 | O | HOH | W | 384 | 57.882 | 3.621 | 8.079 | 1.00 | 39.82 | O |
| ATOM | 3661 | O | HOH | W | 385 | 26.561 | 28.879 | 35.275 | 1.00 | 73.69 | O |
| ATOM | 3662 | O | HOH | W | 386 | 45.960 | 30.047 | 14.517 | 1.00 | 40.29 | O |
| ATOM | 3663 | O | HOH | W | 387 | 24.745 | 5.242 | 28.231 | 1.00 | 77.59 | O |
| ATOM | 3664 | O | HOH | W | 388 | 38.843 | −22.197 | 1.181 | 1.00 | 69.86 | O |
| ATOM | 3665 | O | HOH | W | 389 | 24.914 | 45.052 | 21.953 | 1.00 | 47.80 | O |
| ATOM | 3666 | O | HOH | W | 390 | 23.968 | 5.180 | 9.472 | 1.00 | 36.09 | O |
| ATOM | 3667 | O | HOH | W | 391 | 45.167 | 22.341 | 10.168 | 1.00 | 58.85 | O |
| ATOM | 3668 | O | HOH | W | 392 | 63.994 | 23.103 | −6.623 | 1.00 | 41.36 | O |
| ATOM | 3669 | O | HOH | W | 393 | 43.211 | 28.094 | 26.866 | 1.00 | 64.82 | O |
| ATOM | 3670 | O | HOH | W | 394 | 12.463 | 10.420 | 17.753 | 1.00 | 51.83 | O |
| ATOM | 3671 | O | HOH | W | 395 | 23.822 | 27.573 | 41.487 | 1.00 | 37.27 | O |
| ATOM | 3672 | O | HOH | W | 396 | 13.987 | 41.496 | 29.635 | 1.00 | 62.16 | O |

APPENDIX I(d)-continued

| ATOM | 3673 | O | HOH | W | 397 | 33.026 | 22.598 | 37.699 | 1.00 | 51.26 | O |
|---|---|---|---|---|---|---|---|---|---|---|---|
| ATOM | 3674 | O | HOH | W | 398 | 64.548 | 15.778 | 25.784 | 1.00 | 73.76 | O |
| ATOM | 3675 | O | HOH | W | 399 | 4.456 | 6.820 | 31.188 | 1.00 | 52.61 | O |
| ATOM | 3676 | O | HOH | W | 400 | 56.245 | 22.603 | −12.779 | 1.00 | 69.18 | O |
| ATOM | 3677 | O | HOH | W | 401 | 21.852 | 21.246 | 43.752 | 1.00 | 49.06 | O |
| ATOM | 3678 | O | HOH | W | 402 | 53.672 | −4.770 | 2.592 | 1.00 | 66.30 | O |
| ATOM | 3679 | O | HOH | W | 403 | 40.577 | 22.543 | 17.517 | 1.00 | 55.37 | O |
| ATOM | 3680 | O | HOH | W | 404 | 39.682 | 23.255 | 9.179 | 1.00 | 40.71 | O |
| ATOM | 3681 | O | HOH | W | 405 | 26.738 | 24.263 | 8.013 | 1.00 | 54.59 | O |
| ATOM | 3682 | O | HOH | W | 406 | 50.210 | 0.374 | 1.209 | 1.00 | 50.49 | O |
| ATOM | 3683 | O | HOH | W | 407 | 60.590 | 19.355 | 27.471 | 1.00 | 47.33 | O |
| ATOM | 3684 | O | HOH | W | 408 | 4.171 | −0.693 | 25.748 | 1.00 | 66.54 | O |
| ATOM | 3685 | O | HOH | W | 409 | 45.385 | 8.836 | 27.640 | 1.00 | 48.88 | O |
| ATOM | 3686 | O | HOH | W | 410 | 37.725 | 11.971 | 26.053 | 1.00 | 62.01 | O |
| ATOM | 3687 | O | HOH | W | 411 | 45.832 | 8.800 | −1.281 | 1.00 | 46.54 | O |
| ATOM | 3688 | O | HOH | W | 412 | 13.221 | 11.782 | 28.251 | 1.00 | 39.21 | O |
| ATOM | 3689 | O | HOH | W | 413 | 23.976 | 47.982 | 18.021 | 1.00 | 53.62 | O |
| ATOM | 3690 | O | HOH | W | 414 | 63.898 | 17.108 | 27.312 | 1.00 | 46.28 | O |
| ATOM | 3691 | O | HOH | W | 415 | 5.585 | −10.312 | 33.042 | 1.00 | 48.81 | O |
| ATOM | 3692 | O | HOH | W | 416 | 38.213 | 2.921 | −0.615 | 1.00 | 52.43 | O |
| ATOM | 3693 | O | HOH | W | 417 | 11.363 | 8.700 | 42.372 | 1.00 | 63.77 | O |
| ATOM | 3694 | O | HOH | W | 418 | 38.189 | −2.578 | 16.862 | 1.00 | 48.54 | O |
| ATOM | 3695 | O | HOH | W | 419 | 35.880 | 21.127 | 45.601 | 1.00 | 56.00 | O |
| ATOM | 3696 | O | HOH | W | 420 | 57.494 | 8.004 | 2.119 | 1.00 | 53.09 | O |
| ATOM | 3697 | O | HOH | W | 421 | 59.320 | −4.060 | 11.061 | 1.00 | 53.50 | O |
| ATOM | 3698 | O | HOH | W | 422 | 31.364 | 1.362 | 44.832 | 1.00 | 47.58 | O |
| ATOM | 3699 | O | HOH | W | 423 | 64.047 | 11.643 | 27.376 | 1.00 | 58.29 | O |
| ATOM | 3700 | O | HOH | W | 424 | 32.930 | 3.782 | 19.596 | 1.00 | 51.49 | O |
| ATOM | 3701 | O | HOH | W | 425 | 38.784 | 17.343 | 41.490 | 1.00 | 60.60 | O |
| ATOM | 3702 | O | HOH | W | 426 | 37.274 | 22.305 | 27.368 | 1.00 | 46.16 | O |
| ATOM | 3703 | O | HOH | W | 427 | 2.920 | 3.818 | 31.574 | 1.00 | 48.85 | O |
| ATOM | 3704 | O | HOH | W | 428 | 31.322 | 4.264 | 17.113 | 1.00 | 61.45 | O |
| ATOM | 3705 | O | HOH | W | 429 | 37.349 | 2.399 | 44.067 | 1.00 | 59.80 | O |
| ATOM | 3706 | O | HOH | W | 430 | 30.656 | −2.719 | 19.246 | 1.00 | 52.57 | O |
| ATOM | 3707 | O | HOH | W | 431 | 45.180 | 15.640 | 19.348 | 1.00 | 58.43 | O |
| ATOM | 3708 | O | HOH | W | 432 | 5.372 | −7.792 | 47.576 | 1.00 | 69.85 | O |
| ATOM | 3709 | O | HOH | W | 433 | 25.527 | −3.157 | 21.992 | 1.00 | 66.96 | O |
| ATOM | 3710 | O | HOH | W | 434 | 44.619 | 27.583 | −3.072 | 1.00 | 47.84 | O |
| ATOM | 3711 | O | HOH | W | 435 | 13.783 | 30.570 | 33.920 | 1.00 | 58.04 | O |
| ATOM | 3712 | O | HOH | W | 436 | 34.166 | 8.815 | 47.993 | 1.00 | 56.17 | O |
| ATOM | 3713 | O | HOH | W | 437 | 43.341 | −13.044 | 19.673 | 1.00 | 57.24 | O |
| ATOM | 3714 | O | HOH | W | 438 | 73.346 | 13.204 | 25.504 | 1.00 | 60.85 | O |
| ATOM | 3715 | O | HOH | W | 439 | 46.736 | 20.265 | 31.497 | 1.00 | 68.57 | O |
| ATOM | 3716 | O | HOH | W | 440 | 3.829 | 1.129 | 41.666 | 1.00 | 52.32 | O |
| ATOM | 3717 | O | HOH | W | 441 | 52.231 | 13.277 | −7.024 | 1.00 | 64.60 | O |
| ATOM | 3718 | O | HOH | W | 442 | 40.476 | 19.912 | 31.528 | 1.00 | 38.49 | O |
| ATOM | 3719 | O | HOH | W | 443 | 42.835 | −13.097 | 16.910 | 1.00 | 50.34 | O |
| ATOM | 3720 | O | HOH | W | 444 | 28.031 | 15.763 | 48.184 | 1.00 | 40.06 | O |
| ATOM | 3721 | O | HOH | W | 445 | 9.673 | −9.229 | 46.054 | 1.00 | 51.46 | O |
| ATOM | 3722 | O | HOH | W | 446 | 29.683 | −16.115 | 27.350 | 1.00 | 54.29 | O |
| ATOM | 3723 | O | HOH | W | 447 | 54.239 | 5.891 | 5.248 | 1.00 | 61.23 | O |
| ATOM | 3724 | O | HOH | W | 448 | 19.031 | 2.254 | 54.929 | 1.00 | 48.57 | O |
| ATOM | 3725 | O | HOH | W | 449 | 61.677 | 7.330 | 6.963 | 1.00 | 74.94 | O |
| ATOM | 3726 | O | HOH | W | 450 | 31.932 | 44.220 | 19.866 | 1.00 | 59.36 | O |
| ATOM | 3727 | O | HOH | W | 451 | 10.482 | 48.704 | 30.828 | 1.00 | 65.80 | O |
| ATOM | 3728 | O | HOH | W | 452 | 6.561 | 11.748 | 10.662 | 1.00 | 54.13 | O |
| ATOM | 3729 | O | HOH | W | 453 | 15.435 | −0.867 | 49.670 | 1.00 | 45.56 | O |
| ATOM | 3730 | O | HOH | W | 454 | 51.570 | 37.652 | 4.006 | 1.00 | 42.09 | O |
| ATOM | 3731 | O | HOH | W | 455 | 23.910 | 26.874 | 14.030 | 1.00 | 52.57 | O |
| ATOM | 3732 | O | HOH | W | 456 | 27.085 | 29.781 | 13.934 | 1.00 | 25.46 | O |
| ATOM | 3733 | O | HOH | W | 457 | 27.900 | 28.627 | 9.182 | 1.00 | 45.79 | O |
| ATOM | 3734 | O | HOH | W | 458 | 32.738 | 29.266 | 13.968 | 1.00 | 42.91 | O |
| ATOM | 3735 | O | HOH | W | 459 | 29.835 | 30.314 | 13.852 | 1.00 | 48.08 | O |
| ATOM | 3736 | O | HOH | W | 460 | 30.248 | −10.934 | 4.378 | 1.00 | 51.32 | O |
| ATOM | 3737 | O | HOH | W | 461 | 32.581 | −10.951 | 9.228 | 1.00 | 64.63 | O |
| ATOM | 3738 | O | HOH | W | 462 | 32.498 | −10.742 | 12.543 | 1.00 | 54.22 | O |
| ATOM | 3739 | O | HOH | W | 463 | 11.813 | −0.334 | 48.643 | 1.00 | 57.91 | O |
| ATOM | 3740 | O | HOH | W | 464 | 4.172 | −6.148 | 31.453 | 1.00 | 65.05 | O |
| ATOM | 3741 | O | HOH | W | 465 | 38.613 | 13.637 | 20.404 | 1.00 | 83.38 | O |
| ATOM | 3742 | O | HOH | W | 466 | 25.868 | −18.454 | 28.422 | 1.00 | 60.00 | O |
| ATOM | 3743 | O | HOH | W | 467 | 65.059 | 16.988 | 12.215 | 1.00 | 49.23 | O |
| ATOM | 3744 | O | HOH | W | 468 | 30.433 | 21.112 | 45.165 | 1.00 | 58.66 | O |
| ATOM | 3745 | O | HOH | W | 469 | 63.211 | 34.666 | −5.360 | 1.00 | 44.44 | O |
| ATOM | 3746 | O | HOH | W | 470 | 46.034 | 24.452 | 16.370 | 1.00 | 47.25 | O |
| ATOM | 3747 | O | HOH | W | 471 | 38.317 | 37.251 | 29.410 | 1.00 | 57.97 | O |
| ATOM | 3748 | O | HOH | W | 472 | 45.601 | 16.935 | 22.457 | 1.00 | 50.56 | O |
| ATOM | 3749 | O | HOH | W | 473 | 57.386 | 3.823 | 5.277 | 1.00 | 47.98 | O |
| ATOM | 3750 | O | HOH | W | 474 | 48.907 | 41.483 | 3.217 | 1.00 | 46.27 | O |
| ATOM | 3751 | O | HOH | W | 475 | 60.742 | 15.315 | −2.406 | 1.00 | 47.15 | O |
| ATOM | 3752 | O | HOH | W | 476 | 11.472 | 30.114 | 17.903 | 1.00 | 50.81 | O |

APPENDIX I(d)-continued

| ATOM | 3753 | O | HOH | W | 477 | 27.442 | −5.736 | 4.830 | 1.00 | 50.01 | O |
| --- | --- | --- | --- | --- | --- | --- | --- | --- | --- | --- | --- |
| ATOM | 3754 | O | HOH | W | 478 | 15.963 | 19.233 | 13.604 | 1.00 | 40.24 | O |
| ATOM | 3755 | O | HOH | W | 479 | 11.847 | 16.803 | 29.315 | 1.00 | 51.87 | O |
| ATOM | 3756 | O | HOH | W | 480 | 25.373 | −1.129 | 6.145 | 1.00 | 69.33 | O |
| ATOM | 3757 | O | HOH | W | 481 | 21.061 | 27.210 | 7.262 | 1.00 | 43.87 | O |
| ATOM | 3758 | O | HOH | W | 482 | 11.657 | 12.994 | 20.711 | 1.00 | 62.23 | O |
| ATOM | 3759 | O | HOH | W | 483 | 55.094 | 2.305 | −3.240 | 1.00 | 66.83 | O |
| ATOM | 3760 | O | HOH | W | 484 | 19.281 | 0.887 | 18.463 | 1.00 | 65.62 | O |
| ATOM | 3761 | O | HOH | W | 485 | 44.026 | 16.214 | 28.232 | 1.00 | 64.82 | O |
| ATOM | 3762 | O | HOH | W | 486 | 53.605 | 24.910 | 16.745 | 1.00 | 73.45 | O |
| ATOM | 3763 | O | HOH | W | 487 | 15.314 | 30.821 | 22.775 | 1.00 | 45.14 | O |
| ATOM | 3764 | O | HOH | W | 488 | 20.855 | 2.452 | 52.883 | 1.00 | 51.84 | O |
| ATOM | 3765 | O | HOH | W | 489 | 32.918 | 5.487 | −2.045 | 1.00 | 45.08 | O |

The invention claimed is:

1. A method of modifying an I-set domain, said method comprising inserting and/or substituting one or more structural features from an IgNAR variable domain into the I-set domain.

2. The method of claim 1, wherein the structural feature is selected from the group consisting of a loop region from an IgNAR variable domain and the solvent exposed face at the C-terminus of the loop region 4 and in the C and D β-strands from an IgNAR variable domain.

3. The method of claim 2, wherein the loop region is selected from the group consisting of loop region 4 and loop region 8 from an IgNAR variable domain.

4. The method of claim 1, in which predetermined amino acids of the I-set domain are replaced with an insert comprising SEQ ID NO: 148 from the IgNAR variable domain.

5. The method of claim 1, in which all or a portion of the CDR2 loop of the I-set domain is removed.

6. The method of claim 1, in which amino acids of the I-set domain equivalent to amino acids Lys32, Asp33, Thr34, Gly 35, Tyr55, Glu 57 and Thr58 or a portion thereof are modified.

7. The method of claim 6, wherein the modification introduces charged or polar amino acids at these positions, improves the solubility of the I-set domain, or both.

8. The method of claim 1, wherein the (i) the I-set domain is selected from the group consisting of NCAM, VCAM, ICAM, Telokin, MADCAM-1, Twitchin and Titin.

* * * * *

```
                          SEQUENCE LISTING

<160> NUMBER OF SEQ ID NOS: 168

<210> SEQ ID NO 1
<211> LENGTH: 111
<212> TYPE: PRT
<213> ORGANISM: Artificial sequence
<220> FEATURE:
<223> OTHER INFORMATION: synthetic

<400> SEQUENCE: 1

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Tyr Gly Leu Glu
            20                  25                  30

Ser Thr Gly Trp Tyr Arg Thr Lys Leu Gly Ser Thr Asn Glu Gln Thr
        35                  40                  45

Ile Ser Ile Gly Gly Arg Tyr Val Glu Thr Val Asn Lys Gly Ser Lys
    50                  55                  60

Ser Phe Ser Leu Arg Ile Arg Asp Leu Arg Val Glu Asp Ser Gly Thr
65                  70                  75                  80

Tyr Lys Cys Gly Ala Phe Arg Phe Trp Leu Pro Tyr Gly Tyr Gly Ser
                85                  90                  95

Leu Pro Leu Ser Glu Lys Gly Ala Gly Thr Val Leu Thr Val Lys
            100                 105                 110

<210> SEQ ID NO 2
<211> LENGTH: 333
<212> TYPE: DNA
<213> ORGANISM: Artificial sequence
<220> FEATURE:
<223> OTHER INFORMATION: synthetic

<400> SEQUENCE: 2
gcatgggtag accaaacacc aagaacagca acaaaagaga cgggcgaatc actgaccatc      60
aactgcgtcc taagagatgc tagctacgga ttggagagca cgggctggta tcggacaaaa     120
ttgggttcaa caaacgagca gacaatatca attggcggac gatatgttga aacagtcaac     180
aagggatcaa agtccttttc tctgagaatt cgtgatctga gagttgaaga cagtggcacg     240
tataagtgtg gagcattccg gttttggctt ccttacggct atggtagcct tccgttgtcg     300
gagaaaggag ctggcaccgt attaaccgtg aaa                                  333

<210> SEQ ID NO 3
<211> LENGTH: 113
<212> TYPE: PRT
```

<213> ORGANISM: Artificial sequence
<220> FEATURE:
<223> OTHER INFORMATION: synthetic

<400> SEQUENCE: 3

```
Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Pro Leu Gly Asp Tyr Asn Tyr
                85                  90                  95

Ser Leu Leu Phe Arg Gly Glu Lys Gly Ala Gly Thr Ala Leu Thr Val
            100                 105                 110

Lys
```

<210> SEQ ID NO 4
<211> LENGTH: 339
<212> TYPE: DNA
<213> ORGANISM: Artificial sequence
<220> FEATURE:
<223> OTHER INFORMATION: synthetic

<400> SEQUENCE: 4

```
gcatgggtag accaaacacc aagaacagca acaaaagaga cgggcgaatc actgaccatc      60
aactgcgtcc taagagatgc tagttttgaa ttaaaagaca cgggctggta tcggacaaaa    120
ttgggttcaa caaatgagca gagtatatca attggcggac gatatgttga acagtcaac     180
aagggatcaa agtcctttc tctgagaatt agtgatctga gagttgaaga cagtggcacg    240
tataagtgtc aagcattcta ttctcttccg ttgggcgatt ataactattc tctgctgttt    300
aggggtgaga aggagctgg caccgcatta accgtgaaa                            339
```

<210> SEQ ID NO 5
<211> LENGTH: 111
<212> TYPE: PRT
<213> ORGANISM: Artificial sequence
<220> FEATURE:
<223> OTHER INFORMATION: synthetic

<400> SEQUENCE: 5

```
Ala Trp Val Asp Gln Thr Pro Arg Ser Val Thr Lys Glu Thr Gly Glu
1               5                   10                  15

Ser Leu Thr Ile Asn Cys Ala Leu Lys Asn Ala Ala Asp Asp Leu Glu
            20                  25                  30

Arg Thr Asp Trp Tyr Arg Thr Thr Leu Gly Ser Thr Asn Glu Gln Lys
        35                  40                  45

Ile Ser Ile Gly Gly Arg Tyr Val Glu Thr Val Asn Lys Gly Ser Lys
    50                  55                  60

Ser Phe Ser Leu Arg Ile Arg Asp Leu Arg Val Glu Asp Ser Gly Thr
65                  70                  75                  80

Tyr Lys Cys Gly Ala Tyr Phe Ser Asp Ala Met Ser Asn Tyr Ser Tyr
                85                  90                  95

Pro Ile Pro Gly Glu Lys Gly Ala Gly Thr Val Leu Thr Val Lys
```

<210> SEQ ID NO 6
<211> LENGTH: 333
<212> TYPE: DNA
<213> ORGANISM: Artificial sequence
<220> FEATURE:
<223> OTHER INFORMATION: synthetic

<400> SEQUENCE: 6

```
gcatgggtag accaaactcc gagatcagta acaaaagaga cgggcgaatc attgaccatc    60
aactgcgccc tgaaaaatgc tgcggacgac ttggagagga cggactggta tcggacaaca   120
ttgggttcaa caaacgagca gaaaatatca attggcggac gatatgttga acagtcaac    180
aagggatcaa agtcattttc tctgagaatt cgtgatctga gagtagaaga cagtggcacg   240
tataagtgtg gagcatactt ttctgatgct atgagcaatt acagctatcc gattcctggt   300
gagaaaggag ctggcaccgt attaaccgtg aaa                                333
```

<210> SEQ ID NO 7
<211> LENGTH: 111
<212> TYPE: PRT
<213> ORGANISM: Artificial sequence
<220> FEATURE:
<223> OTHER INFORMATION: synthetic

<400> SEQUENCE: 7

```
Ala Trp Val Asp Gln Thr Pro Arg Thr Ile Thr Lys Glu Thr Gly Glu
1               5                   10                  15
Ser Leu Thr Ile Lys Cys Val Leu Lys Asp His Ser Cys Gly Leu Ser
                20                  25                  30
Ser Thr Thr Trp Tyr Arg Thr Gln Leu Gly Ser Thr Asn Glu Lys Thr
            35                  40                  45
Ile Ser Ile Gly Gly Arg Tyr Asp Glu Thr Val Asp Lys Gly Ser Lys
        50                  55                  60
Ser Phe Ser Leu Arg Ile Ser Asp Leu Arg Val Glu Asp Ser Gly Thr
65                  70                  75                  80
Tyr Lys Cys Gln Ala Asp Tyr Ser Pro Ser Cys Tyr Ser Tyr Pro Ser
                85                  90                  95
Leu Glu Ser Ala Val Glu Gly Ala Gly Thr Val Leu Thr Val Lys
            100                 105                 110
```

<210> SEQ ID NO 8
<211> LENGTH: 333
<212> TYPE: DNA
<213> ORGANISM: Artificial sequence
<220> FEATURE:
<223> OTHER INFORMATION: synthetic

<400> SEQUENCE: 8

```
gcatgggtag accaaacacc aagaacaata acaaaagaga cgggcgaatc actgaccatc    60
aaatgcgtcc taaagatca tagttgtgga ttgtccagca caacctggta tcggacacaa   120
ttgggttcaa caaatgaaaa gacaatatca attggcggac gatatgatga acagtcgac    180
aagggatcaa agtccttttc tctgagaatt agtgatctga gagttgaaga cagtggcacg   240
tataagtgtc aagcagatta ttctccttcg tgctatagtt atccttctct tgagtctgcg   300
gttgagggag ctggcaccgt attaaccgtg aaa                                333
```

<210> SEQ ID NO 9
<211> LENGTH: 108

```
<212> TYPE: PRT
<213> ORGANISM: Artificial sequence
<220> FEATURE:
<223> OTHER INFORMATION: synthetic

<400> SEQUENCE: 9

Ala Arg Val Asp Gln Thr Pro Arg Ile Ala Thr Lys Glu Thr Gly Glu
1               5                   10                  15

Ser Leu Thr Ile Asn Cys Val Leu Arg Asp Thr Ala Cys Ala Leu Asp
            20                  25                  30

Ser Thr Asn Trp Tyr Arg Thr Lys Leu Gly Ser Thr Lys Glu Gln Thr
        35                  40                  45

Ile Ser Ile Gly Gly Arg Tyr Ser Glu Thr Val Asp Glu Gly Ser Asn
    50                  55                  60

Ser Ala Ser Leu Thr Ile Arg Asp Leu Arg Val Glu Asp Ser Gly Thr
65                  70                  75                  80

Tyr Lys Cys Lys Ala Tyr Arg Arg Cys Ala Phe Asn Thr Gly Val Gly
                85                  90                  95

Tyr Lys Glu Gly Ala Gly Thr Val Leu Thr Val Lys
            100                 105

<210> SEQ ID NO 10
<211> LENGTH: 324
<212> TYPE: DNA
<213> ORGANISM: Artificial sequence
<220> FEATURE:
<223> OTHER INFORMATION: synthetic

<400> SEQUENCE: 10
gcaagggtgg accaaacacc aagaatagca acaaaagaga cgggcgaatc actgaccatc        60
aattgcgtcc taagagatac tgcgtgtgca ttagacagta cgaattggta tcggacaaaa       120
ttgggttcaa caaggagca gacaatatca attggcggac gatatagtga aacagtcgac        180
gaaggatcaa actctgcttc tctgacaatt cgtgatctga gagttgaaga cagtggcacg       240
tataagtgta aagcatatag gagatgcgcc tttaatactg gagtgggata caaggaggga       300
gctggcaccg tattaaccgt gaaa                                              324

<210> SEQ ID NO 11
<211> LENGTH: 113
<212> TYPE: PRT
<213> ORGANISM: Artificial sequence
<220> FEATURE:
<223> OTHER INFORMATION: synthetic

<400> SEQUENCE: 11

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Leu Gly Asp Tyr Asn Tyr
                85                  90                  95

Ser Leu Leu Phe Arg Gly Glu Lys Gly Ala Gly Thr Ala Leu Thr Val
            100                 105                 110
```

Lys

<210> SEQ ID NO 12
<211> LENGTH: 339
<212> TYPE: DNA
<213> ORGANISM: Artificial sequence
<220> FEATURE:
<223> OTHER INFORMATION: synthetic

<400> SEQUENCE: 12

```
gcatgggtag accaaacacc aagaacagca acaaaagaga cgggcgaatc actgaccatc    60
aactgcgtcc taagagatgc tagttttgaa ttaaaagaca cgggctggta tcggacaaaa   120
ttgggttcaa caaatgagca gagtatatca attggcggac gatatgttga aacagtcaac   180
aagggatcaa agtccttttc tctgagaatt agtgatctga gagttgaaga cagtggcacg   240
tataagtgtc aagcattcta ttctcttctg ttgggcgatt ataactattc tctgctgttt   300
aggggtgaga aggagctgg caccgcatta accgtgaaa                            339
```

<210> SEQ ID NO 13
<211> LENGTH: 113
<212> TYPE: PRT
<213> ORGANISM: Artificial sequence
<220> FEATURE:
<223> OTHER INFORMATION: synthetic

<400> SEQUENCE: 13

```
Ala Trp Val Asp Gln Thr Pro Arg Thr Ala Thr Lys Glu Thr Gly Glu
1               5                   10                  15
Ser Leu Thr Ile Asn Cys Val Leu Arg Asp Ala Ser Phe Glu Leu Lys
            20                  25                  30
Asp Thr Gly Trp Tyr Arg Thr Lys Leu Gly Ser Thr Asn Glu Gln Ser
        35                  40                  45
Ile Ser Ile Gly Gly Arg Tyr Val Glu Thr Val Asn Lys Gly Ser Lys
    50                  55                  60
Ser Phe Ser Leu Arg Ile Ser Asp Leu Arg Val Glu Asp Ser Gly Thr
65                  70                  75                  80
Tyr Lys Cys Gln Ala Phe Tyr Ser Leu Leu Leu Gly Asp Tyr Asn Tyr
                85                  90                  95
Ser Leu Cys Phe Arg Gly Glu Lys Gly Ala Gly Thr Ala Leu Thr Val
            100                 105                 110
Lys
```

<210> SEQ ID NO 14
<211> LENGTH: 339
<212> TYPE: DNA
<213> ORGANISM: Artificial sequence
<220> FEATURE:
<223> OTHER INFORMATION: synthetic

<400> SEQUENCE: 14

```
gcatgggtag accaaacacc aagaacagca acaaaagaga cgggcgaatc actgaccatc    60
aactgcgtcc taagagatgc tagttttgaa ttaaaagaca cgggctggta tcggacaaaa   120
ttgggttcaa caaatgagca gagtatatca attggcggac gatatgttga aacagtcaac   180
aagggatcaa agtccttttc tctgagaatt agtgatctga gagttgaaga cagtggcacg   240
tataagtgtc aagcattcta ttctcttctg ttgggcgatt ataactattc tctgtgctttt  300
aggggtgaga aggagctgg caccgcatta accgtgaaa                            339
```

<210> SEQ ID NO 15
<211> LENGTH: 113
<212> TYPE: PRT
<213> ORGANISM: Artificial sequence
<220> FEATURE:
<223> OTHER INFORMATION: synthetic

<400> SEQUENCE: 15

```
Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Ser Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Leu Leu Gly Asp Tyr Asn Tyr
                85                  90                  95

Ser Leu Leu Phe Arg Gly Glu Lys Gly Ala Gly Thr Ala Leu Thr Val
                100                 105                 110

Lys
```

<210> SEQ ID NO 16
<211> LENGTH: 339
<212> TYPE: DNA
<213> ORGANISM: Artificial sequence
<220> FEATURE:
<223> OTHER INFORMATION: synthetic

<400> SEQUENCE: 16

```
gcatgggtag accaaacacc aagaacggca acaaaagaga cgggcgaatc actgaccatc      60
aactgcgtcc taagagatgc tagttttgaa ttaaaagaca cgggctggta tcggtcaaaa     120
ttgggttcaa caaatgagca gagtatatca attggcggac gatatgttga acagtcaac      180 aagggatcaa agtcctttc tctgagaatt agtgatctga gagttgaaga cagtggcacg      240
tataagtgtc aagcattcta ttctcttctg ttgggcgatt ataactattc tctgctgttt     300
aggggtgaga agggagccgg caccgcatta accgtgaaa                            339
```

<210> SEQ ID NO 17
<211> LENGTH: 113
<212> TYPE: PRT
<213> ORGANISM: Artificial sequence
<220> FEATURE:
<223> OTHER INFORMATION: synthetic

<400> SEQUENCE: 17

```
Val Arg Val Asp Gln Thr Pro His Thr Glu Lys Glu Thr Gly Glu
1               5                   10                  15

Ser Leu Thr Ile Asn Cys Val Leu Arg Ser Thr Asn Cys Ala Phe Ser
            20                  25                  30

Ser Thr Arg Trp Tyr Arg Thr Lys Leu Gly Ser Thr Asn Glu Gln Lys
        35                  40                  45

Val Ser Ile Gly Gly Arg Tyr Leu Glu Thr Val Asp Arg Gly Ser Lys
    50                  55                  60

Ser Phe Ser Leu Arg Ile Arg Asp Leu Arg Val Glu Asp Ser Gly Thr
65                  70                  75                  80
```

```
Phe Gln Cys Gln Ala Tyr Gly Thr Leu Leu Arg Gln Ser Gly Leu Ser
                85                  90                  95

Cys Tyr Asn Gly Asp Gly Leu Glu Gly Gly Leu Thr Val Leu Thr Val
            100                 105                 110

Lys

<210> SEQ ID NO 18
<211> LENGTH: 112
<212> TYPE: PRT
<213> ORGANISM: Artificial sequence
<220> FEATURE:
<223> OTHER INFORMATION: synthetic

<400> SEQUENCE: 18

Ala Leu Thr Asp Gln Thr Pro Arg Thr Val Thr Lys Glu Thr Gly Glu
1               5                   10                  15

Ser Leu Thr Ile Asn Cys Val Leu Arg Asp Thr His Cys Ala Leu Ser
            20                  25                  30

Asp Thr Tyr Trp Tyr Arg Thr Lys Leu Gly Ser Thr Asn Glu Gln Phe
            35                  40                  45

Ile Ser Ile Gly Gly Arg Tyr Val Glu Thr Val Asn Lys Gly Ser Lys
50                  55                  60

Ser Phe Ser Leu Arg Ile Ser Asp Leu Arg Val Glu Asp Ser Gly Thr
65                  70                  75                  80

Tyr Lys Cys His Ala Tyr Arg Asp Thr Arg Tyr Asp Arg Glu Cys Tyr
                85                  90                  95

Asp Trp Arg Tyr Pro Glu Lys Gly Val Gly Thr Val Leu Thr Val Arg
            100                 105                 110

<210> SEQ ID NO 19
<211> LENGTH: 110
<212> TYPE: PRT
<213> ORGANISM: Artificial sequence
<220> FEATURE:
<223> OTHER INFORMATION: synthetic

<400> SEQUENCE: 19

Ala Trp Val Glu Gln Pro Pro Arg Thr Ala Thr Lys Glu Thr Gly Gly
1               5                   10                  15

Ser Leu Thr Ile Asn Cys Val Val Arg Asn Ala Arg Cys Ala Leu Leu
            20                  25                  30

Arg Thr Asp Trp Tyr Arg Thr Lys Leu Asp Ser Thr Asn Glu Gln Thr
            35                  40                  45

Ile Ser Ile Gly Gly Arg Tyr Val Glu Thr Val Asp Leu Gly Ser Lys
50                  55                  60

Ser Phe Ser Leu Arg Ile Ser Asp Leu Arg Val Glu Asp Ser Gly Thr
65                  70                  75                  80

Tyr Lys Cys Gly Ala Phe Ser Phe Met Val Tyr Gly Leu Ser Cys Tyr
                85                  90                  95

Gly Gly Val Trp Trp Gly Ala Gly Thr Val Leu Thr Val Lys
            100                 105                 110

<210> SEQ ID NO 20
<211> LENGTH: 113
<212> TYPE: PRT
<213> ORGANISM: Artificial sequence
<220> FEATURE:
<223> OTHER INFORMATION: synthetic

<400> SEQUENCE: 20
```

```
Ala Arg Val Asp Gln Thr Pro Arg Thr Ala Thr Lys Glu Thr Gly Glu
1               5                   10                  15

Ser Leu Thr Ile His Cys Ala Leu Arg Asp Ser Glu Cys Ala Leu Gly
            20                  25                  30

Asp Thr Tyr Trp Tyr Arg Thr Lys Leu Gly Ser Thr Asn Glu Gln Thr
            35                  40                  45

Ile Ser Ile Gly Gly Arg Tyr Val Glu Thr Val Asp Arg Thr Ser Lys
        50                  55                  60

Ser Phe Ser Leu Ser Ile Arg Asp Leu Arg Val Glu Asp Ser Ala Thr
65                  70                  75                  80

Tyr Gln Cys Gln Ala Trp Gly Glu Lys Pro Arg Tyr Gly Glu Thr Arg
                85                  90                  95

Tyr Ala Cys Asn Gly Asp Tyr Lys Gly Gly Asp Thr Leu Leu Thr Val
                100                 105                 110

Lys
```

<210> SEQ ID NO 21
<211> LENGTH: 109
<212> TYPE: PRT
<213> ORGANISM: Artificial sequence
<220> FEATURE:
<223> OTHER INFORMATION: synthetic

<400> SEQUENCE: 21

```
Ala Arg Val Asp Gln Thr Pro Arg Thr Ala Thr Lys Glu Thr Gly Glu
1               5                   10                  15

Ser Leu Thr Ile Asn Cys Val Leu Arg Asp Ser Ser Tyr Lys Leu Glu
            20                  25                  30

Ser Thr Gly Trp Tyr Arg Thr Lys Leu Gly Ser Thr Asn Glu Gln Thr
            35                  40                  45

Ile Ser Ile Gly Gly Arg Tyr Val Glu Thr Val Asn Lys Gly Ser Lys
        50                  55                  60

Ser Phe Ser Leu Arg Ile Arg Asp Leu Arg Val Glu Asp Ser Gly Thr
65                  70                  75                  80

Tyr Lys Cys Ser Ala Cys Asp Asp Val Ala Asn Val Tyr Arg Arg Tyr
                85                  90                  95

Thr Tyr Glu Lys Gly Ala Gly Thr Ile Leu Thr Val Lys
                100                 105
```

<210> SEQ ID NO 22
<211> LENGTH: 109
<212> TYPE: PRT
<213> ORGANISM: Artificial sequence
<220> FEATURE:
<223> OTHER INFORMATION: synthetic

<400> SEQUENCE: 22

```
Gly Trp Val Asp Gln Thr Pro Thr Ser Ala Thr Lys Glu Thr Gly Glu
1               5                   10                  15

Ser Leu Thr Ile Asn Cys Val Leu Arg Glu Thr Ser Cys Ala Leu Ser
            20                  25                  30

Glu Thr Tyr Trp Tyr Arg Thr Lys Leu Gly Ser Thr Asn Glu Gln Ser
            35                  40                  45

Ile Ser Ile Gly Gly Arg Tyr Val Glu Thr Val Asn Lys Gly Ser Lys
        50                  55                  60

Ser Phe Ser Leu Arg Ile Ser Asp Leu Arg Val Glu Asp Ser Gly Thr
65                  70                  75                  80

Tyr Lys Cys Gln Ala Tyr Thr Val Tyr Asp Tyr Ser Cys Tyr Gly Asp
```

```
                    85                  90                  95
Tyr Ser Glu Lys Gly Ala Gly Thr Val Leu Thr Val Lys
                100                 105

<210> SEQ ID NO 23
<211> LENGTH: 110
<212> TYPE: PRT
<213> ORGANISM: Artificial sequence
<220> FEATURE:
<223> OTHER INFORMATION: synthetic

<400> SEQUENCE: 23

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Tyr Gly Ser Glu
            20                  25                  30

Arg Thr Gly Trp Tyr Arg Thr Lys Leu Gly Ser Thr Asn Glu Gln Thr
        35                  40                  45

Ile Ser Ile Gly Gly Arg Tyr Val Glu Thr Val Asn Lys Gly Ser Lys
    50                  55                  60

Ser Phe Ser Leu Arg Ile Arg Asp Leu Arg Val Glu Asp Ser Gly Thr
65                  70                  75                  80

Tyr Lys Cys Gly Gly Leu Ala Thr Leu Thr Ala Pro Tyr Glu Gln Leu
                85                  90                  95

Tyr Ser Tyr Glu Lys Gly Ala Gly Thr Val Leu Thr Val Lys
                100                 105                 110

<210> SEQ ID NO 24
<211> LENGTH: 111
<212> TYPE: PRT
<213> ORGANISM: Artificial sequence
<220> FEATURE:
<223> OTHER INFORMATION: synthetic

<400> SEQUENCE: 24

Ala Arg Ala Asp Gln Thr Pro Arg Pro Ala Thr Lys Glu Thr Gly Glu
1               5                   10                  15

Ser Leu Thr Ile Asn Cys Val Leu Arg Asp Thr Ser Cys Ser Phe Thr
            20                  25                  30

Ser Thr Tyr Trp Tyr Arg Thr Lys Leu Gly Ser Thr Asn Glu Gln Ser
        35                  40                  45

Met Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gly Ala Phe Gly Ala Thr Leu Thr Gly Pro Leu Leu Thr
                85                  90                  95

Leu Glu Ser Tyr Glu Lys Gly Ala Gly Thr Val Leu Thr Val Lys
                100                 105                 110

<210> SEQ ID NO 25
<211> LENGTH: 113
<212> TYPE: PRT
<213> ORGANISM: Artificial sequence
<220> FEATURE:
<223> OTHER INFORMATION: synthetic

<400> SEQUENCE: 25

Ala Arg Val Asp Gln Thr Pro Arg Pro Ala Thr Lys Glu Thr Gly Glu
1               5                   10                  15
```

```
Ser Leu Thr Ile Asn Cys Val Leu Arg Asp Thr Ser Cys Ala Phe Ser
            20                  25                  30

Ser Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
 50                  55                  60

Ser Phe Ser Leu Arg Ile Ser Asp Leu Arg Val Glu Asp Ser Gly Thr
 65                  70                  75                  80

Tyr Lys Cys Gln Ala Tyr Val Ile Ala Thr Met Ala Pro Leu Cys Tyr
                85                  90                  95

Ala Ser Tyr Ser Trp Asn Glu Lys Gly Ala Gly Thr Val Leu Thr Val
            100                 105                 110

Lys

<210> SEQ ID NO 26
<211> LENGTH: 112
<212> TYPE: PRT
<213> ORGANISM: Artificial sequence
<220> FEATURE:
<223> OTHER INFORMATION: synthetic

<400> SEQUENCE: 26

Ala Trp Val Asp Pro Lys Pro Arg Pro Val Thr Lys Glu Thr Gly Glu
 1               5                  10                  15

Ser Leu Thr Ile Asn Cys Val Leu Arg Asp Thr Asn Cys Ala Leu Gly
            20                  25                  30

Asp Thr Asp Trp Tyr Arg Thr Arg Leu Gly Ser Thr Lys Leu Gln Lys
        35                  40                  45

Ile Ser Ile Gly Gly Arg Tyr Val Glu Thr Val Asn Lys Gly Ser Lys
 50                  55                  60

Ser Phe Ser Leu Arg Ile Ser Glu Leu Ser Val Glu Asp Ser Ser Thr
 65                  70                  75                  80

Tyr Lys Cys Gln Ala Ser Arg Lys Trp Gly Arg Ser Cys Ala Gly Asp
                85                  90                  95

Arg Pro Tyr Asp Tyr Glu Lys Gly Ala Gly Thr Val Leu Thr Val Lys
            100                 105                 110

<210> SEQ ID NO 27
<211> LENGTH: 108
<212> TYPE: PRT
<213> ORGANISM: Artificial sequence
<220> FEATURE:
<223> OTHER INFORMATION: synthetic

<400> SEQUENCE: 27

Gln Arg Val Asp Gln Thr Pro Lys Thr Ala Thr Lys Glu Arg Gly Glu
 1               5                  10                  15

Ser Leu Thr Ile Tyr Cys Val Leu Lys Asp Thr Pro Cys Ser Leu Ser
            20                  25                  30

Ile Thr Trp Trp Tyr Arg Thr Lys Leu Gly Ser Thr Asn Glu Gln Lys
        35                  40                  45

Met Thr Leu Gly Gly Arg His Val Glu Thr Glu Asn Lys Glu Ser Lys
 50                  55                  60

Ser Phe Ser Leu Arg Ile Ser Asp Leu Arg Val Glu Asp Ser Gly Thr
 65                  70                  75                  80

Tyr Lys Cys Gln Val Tyr Asn Pro His Arg Ser Cys Pro Trp Thr Tyr
                85                  90                  95

Ala Asp Pro Gly Phe Gly Thr Asp Leu Thr Val Thr
            100                 105
```

<210> SEQ ID NO 28
<211> LENGTH: 111
<212> TYPE: PRT
<213> ORGANISM: Artificial sequence
<220> FEATURE:
<223> OTHER INFORMATION: synthetic

<400> SEQUENCE: 28

```
Ala Trp Val Asp Gln Thr Pro Lys Ser Ala Thr Lys Glu Thr Gly Glu
1               5                   10                  15
Ser Leu Thr Ile Ser Cys Val Ile Arg Asp Ala Thr Tyr Gly Val Glu
            20                  25                  30
Ser Thr Gly Trp Tyr Arg Thr Lys Leu Gly Ser Thr Asn Glu Gln Ala
        35                  40                  45
Ile Ser Ile Gly Gly Arg Tyr Val Glu Thr Val Asn Lys Gly Ser Lys
    50                  55                  60
Ser Phe Ser Leu Arg Ile Arg Asp Leu Arg Val Glu Asp Ser Gly Thr
65                  70                  75                  80
Tyr Lys Cys Gly Asn Cys Gly Tyr Ile Thr Thr Ile Thr Phe Arg Cys
                85                  90                  95
Asp Gly Arg Asp Glu Glu Gly Ala Gly Thr Val Leu Thr Val Lys
            100                 105                 110
```

<210> SEQ ID NO 29
<211> LENGTH: 108
<212> TYPE: PRT
<213> ORGANISM: Artificial sequence
<220> FEATURE:
<223> OTHER INFORMATION: synthetic

<400> SEQUENCE: 29

```
Ala Arg Val Asp Gln Thr Pro Lys Thr Ile Thr Lys Glu Thr Gly Glu
1               5                   10                  15
Ser Leu Thr Ile Asn Cys Val Leu Ser Asp Thr Ser Cys Ala Trp Asp
            20                  25                  30
Ser Thr Tyr Trp Tyr Arg Lys Lys Leu Asp Ser Thr Asn Glu Glu Ser
        35                  40                  45
Thr Ser Lys Gly Gly Arg Tyr Val Glu Thr Val Asn Ser Glu Ser Thr
    50                  55                  60
Ser Phe Ser Leu Arg Ile Asn Asp Leu Thr Val Glu Asp Ser Gly Thr
65                  70                  75                  80
Tyr Arg Cys Arg Ala Tyr Leu Tyr Cys Gly Ser Gln Leu Asp Ser Phe
                85                  90                  95
Asp Glu Tyr Gly Gly Thr Ile Val Thr Val Ser
            100                 105
```

<210> SEQ ID NO 30
<211> LENGTH: 108
<212> TYPE: PRT
<213> ORGANISM: Artificial sequence
<220> FEATURE:
<223> OTHER INFORMATION: synthetic

<400> SEQUENCE: 30

```
Ala Arg Val Asp Gln Thr Pro Lys Thr Ile Thr Lys Glu Thr Gly Glu
1               5                   10                  15
Ser Leu Thr Ile Asn Cys Val Leu Ser Asp Thr Ser Cys Ala Trp Asp
            20                  25                  30
```

```
Ser Thr Tyr Trp Tyr Arg Lys Lys Leu Asp Ser Thr Asn Glu Glu Ser
         35                  40                  45

Thr Ser Lys Gly Gly Arg Tyr Val Glu Thr Val Asn Ser Glu Ser Thr
 50                  55                  60

Ser Phe Ser Leu Arg Ile Asn Asp Leu Thr Val Glu Asp Ser Gly Thr
 65                  70                  75                  80

Tyr Arg Cys Arg Ala Tyr Leu Tyr Cys Gly Ala Glu Leu Asp Ser Phe
                 85                  90                  95

Asp Glu Tyr Gly Gly Gly Thr Ile Val Thr Val Asn
                100                 105

<210> SEQ ID NO 31
<211> LENGTH: 661
<212> TYPE: PRT
<213> ORGANISM: Artificial sequence
<220> FEATURE:
<223> OTHER INFORMATION: synthetic

<400> SEQUENCE: 31

Ala Trp Val Asp Gln Thr Pro Arg Thr Ala Thr Lys Glu Thr Asp Glu
 1               5                  10                  15

Ser Leu Thr Ile Asn Cys Val Leu Arg Glu Ser Pro Tyr Glu Leu Tyr
                 20                  25                  30

Asn Thr Gly Trp Tyr Arg Thr Lys Leu Gly Ser Thr Lys Glu Gln Arg
             35                  40                  45

Ile Ser Ile Gly Gly Arg Tyr Val Glu Thr Val Asp Lys Glu Ser Lys
 50                  55                  60

Ser Phe Ser Leu Arg Ile Ser Asp Leu Arg Ile Glu Asp Ser Gly Thr
 65                  70                  75                  80

Tyr Lys Cys Gly Ala Cys Asp Glu Pro Asp Gly Gly Tyr Gly Lys Tyr
                 85                  90                  95

Ser Cys Phe Thr Tyr Lys Lys Gly Thr Gly Thr Gly Leu Thr Val Lys
            100                 105                 110

Pro Gly Val Gln Pro Ser Pro Pro Val Ile Ser Leu Leu Tyr Ser Ala
115                 120                 125

Thr Glu Glu Gln Arg Gly Asn Gly Phe Val Gln Leu Ile Cys Leu Ile
130                 135                 140

Ser Gly Tyr Tyr Pro Glu Asn Ile Ala Val Ser Trp Gln Lys Asn Arg
145                 150                 155                 160

Asn Asp Ile Ser Ser Gly Phe Thr Thr Ser Pro Ser Met Lys Thr Ser
                165                 170                 175

Thr Asn Asp Phe Ser Ser Thr Ser Leu Leu Asn Val Pro Leu Gln Glu
            180                 185                 190

Trp Ser Gly Ser Val Tyr Ser Cys Arg Val Ser His Ser Ala Thr
        195                 200                 205

Asn Ser Asn Gln Arg Lys Glu Ile Arg Ser Thr Ser Glu Ile Ala Val
    210                 215                 220

Phe Leu Arg Asp Pro Ser Val Glu Glu Ile Trp Ile Asn Lys Ser Ala
225                 230                 235                 240

Thr Val Val Cys Glu Val Leu Ser Thr Val Ser Thr Gly Val Val Ile
                245                 250                 255

Ser Trp Met Val Asp Gly Lys Val Arg Thr Glu Gly Val Arg Ile Glu
            260                 265                 270

Ala Ala Lys Met Asp Gly Asn Gln Tyr Leu Thr Ile Ser Arg Leu Ser
        275                 280                 285

Ser Ser Val Glu Glu Trp Gln Ser Gly Val Glu Tyr Thr Cys Ser Ala
```

```
              290                 295                 300
Lys Gln Asp Gln Ser Ser Thr Pro Val Ser Lys Arg Thr Gly Lys Thr
305                 310                 315                 320

Lys Val Glu Pro Met Lys Pro Tyr Leu Arg Leu Leu Pro Pro Ser Pro
                325                 330                 335

Glu Glu Ile Gln Asn Ile Ser Ser Ala Ile Leu Thr Cys Leu Ile Arg
                340                 345                 350

Gly Phe Tyr Pro Asp Lys Ile Arg Val Ser Trp Glu Lys Asp Gly Ala
            355                 360                 365

Ala Val Ser Gly Asn Ile Thr Ser Phe Pro Thr Ala Leu Glu Gln Asp
        370                 375                 380

Leu Thr Phe Ser Thr Arg Ser Leu Leu Ile Leu Pro Ala Val Glu Trp
385                 390                 395                 400

Lys Ser Gly Ala Lys Tyr Thr Cys Ile Ala Ser His Pro Pro Ser Gln
                405                 410                 415

Ser Thr Val Lys Arg Val Ile Arg Ser Pro Lys Gly Asp Cys Gly Gln
                420                 425                 430

Pro Asp Ile Ser Val Asn Leu Leu Asn Pro Pro Phe Glu Glu Ile Trp
            435                 440                 445

Thr Gln Lys Thr Ala Thr Ile Val Cys Glu Ile Val Tyr Ser Asp Leu
        450                 455                 460

Glu Asn Val Asn Val Phe Trp Gln Val Asn Gly Ser Glu Arg Thr Glu
465                 470                 475                 480

Gly Val Glu Thr Gln Asn Pro Glu Trp Ser Gly Ser Lys Ser Thr Ile
                485                 490                 495

Val Ser Lys Leu Lys Val Thr Ser Ser Glu Trp Asp Ser Gly Val Glu
                500                 505                 510

Tyr Val Cys Leu Val Glu Asp Ser Glu Leu Pro Thr Pro Val Lys Ser
            515                 520                 525

Ser Ile Arg Lys Ala Lys Asp Arg Glu Met Tyr Pro Pro Lys Val Tyr
        530                 535                 540

Val Leu His Pro Ser Thr Asp Glu Ile Asp Thr Glu Asn Ser Ala Thr
545                 550                 555                 560

Leu Val Cys Leu Ala Thr Gly Phe Ser Pro Ala Glu Ile Tyr Val Gly
                565                 570                 575

Trp Met Ala Asn Asp Thr Leu Leu Asn Ser Gly Tyr Arg Ser Gln Val
                580                 585                 590

Glu Asn Glu Lys Gly Asn Gly Ser Asn Phe Ile Ile Asn Arg Leu Arg
            595                 600                 605

Leu Thr Ala Ala Glu Trp Asp Ser Asp Thr Thr Tyr Ser Cys Leu Val
        610                 615                 620

Gly His Pro Ser Leu Ser Arg Asp Leu Ile Arg Ser Ile Asn Lys Ser
625                 630                 635                 640

His Gly Lys Pro Thr Leu Val Asn Leu Ser Val Val Leu Ser Asp Thr
                645                 650                 655

Val Lys Ser Cys Thr
                660

<210> SEQ ID NO 32
<211> LENGTH: 2328
<212> TYPE: DNA
<213> ORGANISM: Orectolobus maculatus

<400> SEQUENCE: 32
gcatgggtag accaaacacc aagaacagca acaaaagaga cggacgaatc actgaccatc    60
```

```
aattgcgtcc tcagagagag tccctacgaa ttgtacaaca cgggctggta tcggacaaaa    120
ttgggttcaa caaggagca gagaatatca attggcggac gatatgttga aacagtcgac     180
aaagaatcaa agtccttttc tctgagaatt agtgatctga gaattgaaga cagtggcacg    240
tataagtgtg gagcatgtga tgaacctgac gggggctacg gtaagtatag ctgtttcacc    300
tacaagaaag gaactggcac cggactgacc gtgaaacctg gagtacagcc ttctccacca    360
gtcatcagtc tactttactc tgcaactgaa gaacagagag gaaacgggtt tgtgcagctg    420
atttgtctaa tcagcggata ctatcctgaa acattgcag tgagctggca aaagaacaga     480
aacgacataa gttctggctt tacaacttca ccctcaatga aaacatcgac caatgacttt    540
agctctacaa gtttacttaa tgtgcccctg caggaatgga gcagcggttc tgtgtacagt    600
tgtcgagttt ctcattctgc aaccaacagt aaccaaagga agaaattag atcaacatca     660 gagattgctg tattcctaag agatccatca gttgaagaaa tctggatcaa taaaagtgcc    720
actgtggttt gcgaagttct ttctacagtt tccactggag tcgtcatctc ttggatggtg    780
gatggaaagg taaggaccga aggcgttcga atcgaagcag ctaaaatgga tggaaaccaa    840
tatctgacca tcagccgctt gagcagcagc gtggaagagt ggcagagtgg ggtggaatac    900
acatgctccg caaaacagga tcaatcatcg accccggtat caaaacgaac aggaaaaaca    960
aaagtcgagc caatgaagcc atatcttcgc ctcctgcccc catcaccaga ggagattcaa    1020
aacatcagtt ctgctattct cacatgtttg ataagaggat tctaccctga caagatacgc    1080
gtttcctggg agaaggacgg agctgctgtg agtgggaaca tcaccagttt cccgactgct    1140
ctggaacagg acctgacctt cagcacccgg agcctcctca ttttgcctgc agtggaatgg    1200
aagagcggag caaaatacac ctgtatcgcc tcacatccac cgtcacaatc cactgtgaag    1260
agggtcatca ggagcccgaa aggtgattgc ggtcagccag acatttctgt caatctactg    1320
aaccctccgt ttgaagagat ttggacacaa aagacagcga ccattgtttg tgaaatcgtt    1380
tacagtgact tagaaaacgt caacgtgttc tggcaggtga atgggagtga gagaacggag    1440
ggagtcgaga cacaaaatcc tgagtggagt ggaagcaaat ccaccattgt cagcaaacta    1500
aaagtaacgt cttcggagtg ggacagtggt gtggaatatg tctgcttggt agaagacagt    1560
gaattaccaa caccagtgaa atcgtccatc aggaaggcaa aggaccgcga atgtaccct     1620 cctaaggttt atgtcctgca tccatcgacg gacgagattg acactgagaa ttcggctacc    1680
ctggtgtgtc tagccaccgg ctttttcccca gctgagattt acgtcggttg gatggccaat    1740
gacacacttt tgaattccgg gtaccggagc caagtagaga acgagaaagg gaatggttcc    1800
aatttcatta tcaacagatt aagactcaca gcggcggaat gggacagtga caccacttac    1860
tcctgtttag tgggtcaccc gtccctcagc cgggatttaa tcagaagtat aaataaatct    1920
cacggtaaac cgacattagt taatctttca gttgtactaa gcgacactgt taaatcctgt    1980
acataatttg cagtgattga ctaattgttt tctatagata agttcatgtt gttctggcaa    2040
taacggttta agcaaccgaa ccaatgcgtt ttcaattcaa cgcaaggcac agtcacattt    2100
ctgatgagag aacacgtttg taaaaataat tagctactat ttgaaatttt atctgtcaat    2160
gaaggacaat tatgattaga atctgatatg caaggataac ctgatcttgt cagtgcaatc    2220
gttctgaaga tcccttgacg tgtttcacgc cgttattgaa agaacagaaa atgatgcttt    2280
agtgtgtatg tggcgccgat agttgcaata aacgcagaat gaaaacttt                 2328
```

<210> SEQ ID NO 33
<211> LENGTH: 219

```
<212> TYPE: PRT
<213> ORGANISM: Artificial sequence
<220> FEATURE:
<223> OTHER INFORMATION: synthetic

<400> SEQUENCE: 33

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Pro Leu Gly Asp Tyr Asn Tyr
                85                  90                  95

Tyr Ser Leu Leu Phe Arg Gly Glu Lys Gly Ala Gly Thr Val Leu Thr
            100                 105                 110

Val Lys Pro Gly Val Pro Pro Ser Pro Pro Val Ile Ser Leu Leu Tyr
        115                 120                 125

Ser Ala Thr Glu Glu Gln Arg Gly Asn Gly Phe Val Gln Leu Ile Cys
    130                 135                 140

Leu Ile Ser Gly Tyr Tyr Pro Glu Asn Ile Ala Val Ser Trp Gln Lys
145                 150                 155                 160

Asn Arg Asn Asp Ile Ser Ser Gly Phe Thr Thr Ser Pro Ser Met Lys
                165                 170                 175

Thr Ser Thr Asn Asp Phe Ser Ser Thr Ser Leu Leu Asn Val Pro Leu
            180                 185                 190

Gln Glu Trp Arg Ser Gly Ser Val Tyr Ser Cys Arg Val Ser His Ser
        195                 200                 205

Ala Thr Asn Ser Asn Gln Arg Lys Glu Ile Arg
    210                 215

<210> SEQ ID NO 34
<211> LENGTH: 319
<212> TYPE: PRT
<213> ORGANISM: Artificial sequence
<220> FEATURE:
<223> OTHER INFORMATION: synthetic

<400> SEQUENCE: 34

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
    50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Pro Leu Gly Asp Tyr Asn Tyr
                85                  90                  95

Ser Leu Leu Phe Arg Gly Glu Lys Gly Ala Gly Thr Val Leu Thr Val
            100                 105                 110
```

```
Lys Pro Gly Val Gln Pro Ser Pro Val Ile Ser Leu Leu Tyr Ser
        115                 120                 125

Ala Thr Glu Glu Gln Arg Gly Asn Gly Phe Val Gln Leu Ile Cys Leu
        130                 135                 140

Ile Ser Gly Tyr Tyr Pro Glu Asn Ile Ala Val Ser Trp Gln Lys Asn
145                 150                 155                 160

Arg Asn Asp Ile Ser Ser Gly Phe Thr Thr Ser Pro Ser Met Lys Thr
                165                 170                 175

Ser Thr Asn Asp Phe Ser Ser Thr Ser Leu Leu Asn Val Pro Leu Gln
                180                 185                 190

Glu Trp Arg Ser Gly Ser Val Tyr Ser Cys Arg Val Ser His Ser Ala
        195                 200                 205

Thr Asn Ser Asn Gln Arg Lys Glu Ile Arg Ser Thr Ser Glu Ile Ala
    210                 215                 220

Val Leu Leu Arg Asp Pro Ser Val Glu Glu Ile Trp Ile Asn Lys Ser
225                 230                 235                 240

Ala Thr Val Val Cys Glu Val Leu Ser Thr Val Ser Thr Gly Val Val
                245                 250                 255

Ile Ser Trp Met Val Asp Gly Lys Val Arg Thr Lys Gly Val Arg Ile
                260                 265                 270

Glu Ala Ala Lys Met Asp Gly Asn Gln Tyr Leu Thr Ile Ser Arg Leu
            275                 280                 285

Ser Ser Ser Val Glu Glu Trp Gln Ser Gly Val Glu Tyr Thr Cys Ser
        290                 295                 300

Ala Lys Gln Asp Gln Ser Ser Pro Val Ser Lys Arg Thr Gly
305                 310                 315

<210> SEQ ID NO 35
<211> LENGTH: 425
<212> TYPE: PRT
<213> ORGANISM: Artificial sequence
<220> FEATURE:
<223> OTHER INFORMATION: synthetic

<400> SEQUENCE: 35

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ala Ser Phe Glu Leu Lys
            20                  25                  30

Asp Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn Lys Gly Ser Lys
50                  55                  60

Ser Phe Ser Leu Arg Ile Ser Asp Leu Arg Val Glu Asp Ser Gly Thr
65                  70                  75                  80

Tyr Lys Cys Gln Ala Phe Tyr Ser Leu Pro Leu Gly Asp Tyr Asn Tyr
                85                  90                  95

Ser Leu Leu Phe Arg Gly Glu Lys Gly Ala Gly Thr Val Leu Thr Val
            100                 105                 110

Lys Pro Gly Val Pro Pro Ser Pro Val Ile Ser Leu Leu Tyr Ser
        115                 120                 125

Ala Thr Glu Glu Gln Arg Gly Asn Gly Phe Val Gln Leu Ile Cys Leu
        130                 135                 140

Ile Ser Gly Tyr Tyr Pro Glu Asn Ile Ala Val Ser Trp Gln Lys Asn
145                 150                 155                 160

Arg Asn Asp Ile Ser Ser Gly Phe Thr Thr Ser Pro Ser Met Lys Thr
```

```
                       165                 170                 175
Ser Thr Asn Asp Phe Ser Ser Thr Ser Leu Leu Asn Val Pro Leu Gln
            180                 185                 190

Glu Trp Arg Ser Gly Ser Val Tyr Ser Cys Arg Val Ser His Ser Ala
        195                 200                 205

Thr Asn Ser Asn Gln Arg Lys Glu Ile Arg Ser Thr Ser Glu Ile Ala
    210                 215                 220

Val Leu Leu Arg Asp Pro Ser Val Glu Ile Trp Ile Asn Lys Ser
225                 230                 235                 240

Ala Thr Val Val Cys Glu Val Leu Ser Thr Val Ser Thr Gly Val Val
                245                 250                 255

Ile Ser Trp Met Val Asp Gly Lys Val Arg Thr Glu Gly Val Arg Ile
            260                 265                 270

Glu Ala Ala Lys Met Asp Gly Asn Gln Tyr Leu Thr Ile Ser Arg Leu
        275                 280                 285

Ser Ser Ser Val Glu Glu Trp Gln Ser Gly Val Glu Tyr Thr Cys Ser
    290                 295                 300

Ala Lys Gln Asp Gln Ser Ser Thr Pro Val Ser Lys Arg Thr Gly Lys
305                 310                 315                 320

Thr Lys Val Glu Pro Met Lys Pro Tyr Ile Arg Leu Leu Pro Pro Ser
                325                 330                 335

Pro Glu Glu Ile Gln Asp Ile Ser Ser Ala Ile Leu Thr Cys Leu Ile
            340                 345                 350

Arg Gly Phe Tyr Pro Asp Lys Ile Arg Val Ser Trp Glu Lys Asp Gly
        355                 360                 365

Ala Ala Val Ser Gly Asn Ile Thr Ser Phe Pro Thr Ala Leu Glu Gln
    370                 375                 380

Asp Leu Thr Phe Ser Thr Arg Ser Leu Leu Ile Leu Pro Ala Val Glu
385                 390                 395                 400

Trp Lys Ser Gly Ala Lys Tyr Thr Cys Ile Ala Ser His Ser Pro Ser
                405                 410                 415

Gln Ser Thr Val Lys Arg Val Ile Arg
            420                 425

<210> SEQ ID NO 36
<211> LENGTH: 97
<212> TYPE: PRT
<213> ORGANISM: Artificial sequence
<220> FEATURE:
<223> OTHER INFORMATION: synthetic

<400> SEQUENCE: 36

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Thr
65                  70                  75                  80

Gly Glu Asp Gly Ser Glu Ser Glu Ala Thr Val Asn Val Lys Ile Phe
                85                  90                  95

Gln
```

<210> SEQ ID NO 37
<211> LENGTH: 291
<212> TYPE: DNA
<213> ORGANISM: Orectolobus maculatus

<400> SEQUENCE: 37

```
ctgcaggtgg atattgttcc cagccagggg gagatcagcg ttggagagtc caaattcttc      60
ttatgccaag tggcaggaga tgccaaagat aaagacatct cctggttctc ccccaatgga     120
gaaaagctca ccccaaacca gcagcggatc tcagtggtgt ggaatgatga ttcctcctcc     180
accctcacca tctataacgc caacatcgac gacgccggca tttacaagtg tgtggttaca     240
ggcgaggatg gcagtgagtc agaggccacc gtcaacgtga agatctttca g              291
```

<210> SEQ ID NO 38
<211> LENGTH: 190
<212> TYPE: PRT
<213> ORGANISM: Artificial sequence
<220> FEATURE:
<223> OTHER INFORMATION: synthetic

<400> SEQUENCE: 38

```
Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Ser Thr Leu Thr Ile
    50                  55                  60

Tyr Asn Ala Asn Ile Asp Asp Ala Gly Ile Tyr Lys Cys Val Val Thr
65                  70                  75                  80

Gly Glu Asp Gly Ser Glu Ser Glu Ala Thr Val Asn Val Lys Ile Phe
                85                  90                  95

Gln Lys Leu Met Phe Lys Asn Ala Pro Thr Pro Gln Glu Phe Arg Glu
            100                 105                 110

Gly Glu Asp Ala Val Ile Val Cys Asp Val Val Ser Ser Leu Pro Pro
        115                 120                 125

Thr Ile Ile Trp Lys His Lys Gly Arg Asp Val Ile Leu Lys Lys Asp
    130                 135                 140

Val Arg Phe Ile Val Leu Ser Asn Asn Tyr Leu Gln Ile Arg Gly Ile
145                 150                 155                 160

Lys Lys Thr Asp Glu Gly Thr Tyr Arg Cys Glu Gly Arg Ile Leu Ala
                165                 170                 175

Arg Gly Glu Ile Asn Phe Lys Asp Ile Gln Val Ile Val Asn
            180                 185                 190
```

<210> SEQ ID NO 39
<211> LENGTH: 570
<212> TYPE: DNA
<213> ORGANISM: Orectolobus maculatus

<400> SEQUENCE: 39

```
ctgcaggtgg atattgttcc cagccagggg gagatcagcg ttggagagtc caaattcttc      60
ttatgccaag tggcaggaga tgccaaagat aaagacatct cctggttctc ccccaatgga     120
gaaaagctca ccccaaacca gcagcggatc tcagtggtgt ggaatgatga ttcctcctcc     180
accctcacca tctataacgc caacatcgac gacgccggca tttacaagtg tgtggttaca     240
```

```
ggcgaggatg gcagtgagtc agaggccacc gtcaacgtga agatctttca gaagctcatg    300
ttcaagaatg cgccaacccc acaggagttc cggagggg aagatgccgt gattgtgtgt       360
gatgtggtca gctccctccc accaaccatc atctggaaac acaaaggccg agatgtcatc    420
ctgaaaaaag atgtccgatt catagtcctg tccaacaact acctgcagat ccggggcatc    480
aagaaaacag atgagggcac ttatcgctgt gagggcagaa tcctggcacg ggggagatc     540 aacttcaagg acattcaggt cattgtgaat                                      570
```

<210> SEQ ID NO 40
<211> LENGTH: 105
<212> TYPE: PRT
<213> ORGANISM: Artificial sequence
<220> FEATURE:
<223> OTHER INFORMATION: synthetic

<400> SEQUENCE: 40

```
Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Thr
65                  70                  75                  80

Gly Ser Asp Ala Met Ser Asn Tyr Ser Tyr Pro Ile Ser Glu Ser Glu
                85                  90                  95

Ala Thr Val Asn Val Lys Ile Phe Gln
            100                 105
```

<210> SEQ ID NO 41
<211> LENGTH: 92
<212> TYPE: PRT
<213> ORGANISM: Artificial sequence
<220> FEATURE:
<223> OTHER INFORMATION: synthetic

<400> SEQUENCE: 41

```
Pro Tyr Phe Ser Lys Thr Ile Arg Asp Leu Glu Val Val Glu Gly Ser
1               5                   10                  15

Ala Ala Arg Phe Asp Cys Lys Ile Glu Gly Tyr Pro Asp Pro Glu Val
            20                  25                  30

Val Trp Phe Lys Asp Asp Gln Ser Ile Arg Glu Ser Arg His Phe Gln
        35                  40                  45

Ile Asp Tyr Asp Glu Asp Gly Asn Cys Ser Leu Ile Ile Ser Asp Val
    50                  55                  60

Cys Gly Asp Asp Asp Ala Lys Tyr Thr Cys Lys Ala Val Asn Ser Leu
65                  70                  75                  80

Gly Glu Ala Thr Cys Thr Ala Glu Leu Ile Val Glu
                85                  90
```

<210> SEQ ID NO 42
<211> LENGTH: 276
<212> TYPE: DNA
<213> ORGANISM: Orectolobus maculatus

<400> SEQUENCE: 42

```
ccctatttct ctaagaccat tcgcgattta gaagttgtgg agggaagtgc tgctagattt    60
```

```
gactgcaaga ttgaaggata cccagacccc gaggttgtct ggttcaaaga tgaccagtca    120
atcagggagt cccgccactt ccagatagac tacgatgagg acgggaactg ctctttaatt    180
attagtgatg tttgcgggga tgacgatgcc aagtacacct gcaaggctgt caacagtctt    240
ggagaagcca cctgcacagc agagctcatt gtggaa                              276
```

```
<210> SEQ ID NO 43
<211> LENGTH: 100
<212> TYPE: PRT
<213> ORGANISM: Artificial sequence
<220> FEATURE:
<223> OTHER INFORMATION: synthetic

<400> SEQUENCE: 43
```

```
Pro Tyr Phe Ser Lys Thr Ile Arg Asp Leu Glu Val Val Glu Gly Ser
1               5                   10                  15

Ala Ala Arg Phe Asp Cys Lys Ile Glu Gly Tyr Pro Asp Pro Glu Val
            20                  25                  30

Val Trp Phe Lys Asp Asp Gln Ser Ile Arg Glu Ser Arg His Phe Gln
        35                  40                  45

Ile Asp Tyr Asp Glu Asp Gly Asn Cys Ser Leu Ile Ile Ser Asp Val
    50                  55                  60

Cys Gly Asp Asp Asp Ala Lys Tyr Thr Cys Lys Tyr Phe Ser Asp Ala
65                  70                  75                  80

Met Ser Asn Tyr Ser Tyr Pro Ile Pro Gly Ala Thr Cys Thr Ala Glu
                85                  90                  95

Leu Ile Val Glu
            100
```

```
<210> SEQ ID NO 44
<211> LENGTH: 300
<212> TYPE: DNA
<213> ORGANISM: Orectolobus maculatus

<400> SEQUENCE: 44
```

```
ccctatttct ctaagaccat tcgcgattta gaagttgtgg agggaagtgc tgctagattt     60
gactgcaaga ttgaaggata cccagacccc gaggttgtct ggttcaaaga tgaccagtca    120
atcagggagt cccgccactt ccagatagac tacgatgagg acgggaactg ctctttaatt    180
attagtgatg tttgcgggga tgacgatgcc aagtacacct gcaagtattt tagcgatgcc    240
atgagcaact atagctatcc gattccgggc gccacctgca cagcagagct cattgtggaa    300
```

```
<210> SEQ ID NO 45
<211> LENGTH: 101
<212> TYPE: PRT
<213> ORGANISM: Artificial sequence
<220> FEATURE:
<223> OTHER INFORMATION: synthetic

<400> SEQUENCE: 45
```

```
Pro Tyr Phe Ser Lys Thr Ile Arg Asp Leu Glu Val Val Glu Gly Ser
1               5                   10                  15

Ala Ala Arg Phe Asp Cys Lys Ile Glu Gly Tyr Pro Asp Pro Glu Val
            20                  25                  30

Val Trp Phe Lys Asp Asp Gln Ser Ile Arg Glu Ser Arg His Phe Gln
        35                  40                  45

Ile Asp Tyr Asp Glu Asp Gly Asn Cys Ser Leu Ile Ile Ser Asp Val
    50                  55                  60
```

```
Cys Gly Asp Asp Asp Ala Lys Tyr Thr Cys Lys Ala Val Asn Ser Asp
 65                  70                  75                  80

Ala Met Ser Asn Tyr Ser Tyr Pro Ile Gly Glu Ala Thr Cys Thr Ala
                 85                  90                  95

Glu Leu Ile Val Glu
            100

<210> SEQ ID NO 46
<211> LENGTH: 303
<212> TYPE: DNA
<213> ORGANISM: Orectolobus maculatus

<400> SEQUENCE: 46
ccctatttct ctaagaccat tcgcgattta gaagttgtgg agggaagtgc tgctagattt      60
gactgcaaga ttgaaggata cccagacccc gaggttgtct ggttcaaaga tgaccagtca    120
atcagggagt cccgccactt ccagatagac tacgatgagg acgggaactg ctctttaatt    180
attagtgatg tttgcgggga tgacgatgcc aagtacacct gcaaggctgt caacagtgat    240
gccatgagca actatagcta tccgattgga gaagccacct gcacagcaga gctcattgtg    300
gaa                                                                  303

<210> SEQ ID NO 47
<211> LENGTH: 43
<212> TYPE: DNA
<213> ORGANISM: Artificial sequence
<220> FEATURE:
<223> OTHER INFORMATION: synthetic

<400> SEQUENCE: 47
tcgcggccca gccggccatg gccacaaggg tagaccaaac acc                       43

<210> SEQ ID NO 48
<211> LENGTH: 46
<212> TYPE: DNA
<213> ORGANISM: Artificial sequence
<220> FEATURE:
<223> OTHER INFORMATION: synthetic

<400> SEQUENCE: 48
gtctcgcggc ccagccggcc atggccacaa gggtagacca aacacc                    46

<210> SEQ ID NO 49
<211> LENGTH: 43
<212> TYPE: DNA
<213> ORGANISM: Artificial sequence
<220> FEATURE:
<223> OTHER INFORMATION: synthetic

<400> SEQUENCE: 49
tcgcggccca gccggccatg gccgcaaggg tggaccaaac acc                       43

<210> SEQ ID NO 50
<211> LENGTH: 46
<212> TYPE: DNA
<213> ORGANISM: Artificial sequence
<220> FEATURE:
<223> OTHER INFORMATION: synthetic

<400> SEQUENCE: 50
gtctcgcggc ccagccggcc atggccgcaa gggtggacca aacacc                    46

<210> SEQ ID NO 51
<211> LENGTH: 43
```

```
<212> TYPE: DNA
<213> ORGANISM: Artificial sequence
<220> FEATURE:
<223> OTHER INFORMATION: synthetic

<400> SEQUENCE: 51
tcgcggccca gccggccatg gccgcatggg tagaccaaac acc                    43

<210> SEQ ID NO 52
<211> LENGTH: 46
<212> TYPE: DNA
<213> ORGANISM: Artificial sequence
<220> FEATURE:
<223> OTHER INFORMATION: synthetic

<400> SEQUENCE: 52
gtctcgcggc ccagccggcc atggccgcat gggtagacca aacacc                 46

<210> SEQ ID NO 53
<211> LENGTH: 42
<212> TYPE: DNA
<213> ORGANISM: Artificial sequence
<220> FEATURE:
<223> OTHER INFORMATION: synthetic

<400> SEQUENCE: 53
cgcggcccag ccggccatgg ccgcaagcct ggaccaaaca cc                     42

<210> SEQ ID NO 54
<211> LENGTH: 42
<212> TYPE: DNA
<213> ORGANISM: Artificial sequence
<220> FEATURE:
<223> OTHER INFORMATION: synthetic

<400> SEQUENCE: 54
cgcggcccag ccggccatgg ccgcattgac ggaccaaaca cc                     42

<210> SEQ ID NO 55
<211> LENGTH: 33
<212> TYPE: DNA
<213> ORGANISM: Artificial sequence
<220> FEATURE:
<223> OTHER INFORMATION: synthetic

<400> SEQUENCE: 55
atctgcggcc gctttcacgg ttaatgcggt gcc                               33

<210> SEQ ID NO 56
<211> LENGTH: 39
<212> TYPE: DNA
<213> ORGANISM: Artificial sequence
<220> FEATURE:
<223> OTHER INFORMATION: synthetic

<400> SEQUENCE: 56
cacgttatct gcggccgctt tcacggttaa tgcggtgcc                         39

<210> SEQ ID NO 57
<211> LENGTH: 39
<212> TYPE: DNA
<213> ORGANISM: Artificial sequence
<220> FEATURE:
<223> OTHER INFORMATION: synthetic

<400> SEQUENCE: 57
atctgcggcc gctttcacgg ttaatacggt gccagctcc                         39
```

<210> SEQ ID NO 58
<211> LENGTH: 45
<212> TYPE: DNA
<213> ORGANISM: Artificial sequence
<220> FEATURE:
<223> OTHER INFORMATION: synthetic

<400> SEQUENCE: 58
cacgttatct gcggccgctt tcacggttaa tacggtgcca gctcc            45

<210> SEQ ID NO 59
<211> LENGTH: 33
<212> TYPE: DNA
<213> ORGANISM: Artificial sequence
<220> FEATURE:
<223> OTHER INFORMATION: synthetic

<400> SEQUENCE: 59
atctgcggcc gctttcacgg tcagtagggt gcc            33

<210> SEQ ID NO 60
<211> LENGTH: 33
<212> TYPE: DNA
<213> ORGANISM: Artificial sequence
<220> FEATURE:
<223> OTHER INFORMATION: synthetic

<400> SEQUENCE: 60
atctgcggcc gctctcacgg tcagtacggt gcc            33

<210> SEQ ID NO 61
<211> LENGTH: 87
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t

<400> SEQUENCE: 61
cacggttaat acggtgccag ctcctttctc nccmnnmnnm nnmnnryhry hryhmnnmnn    60
mnngnatgct tgacactcat acgtgcc                                       87

<210> SEQ ID NO 62
<211> LENGTH: 87
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(65)
<223> OTHER INFORMATION: n is a, c, g, or t

<400> SEQUENCE: 62
cacggttaat acggtgccag ctcctttctc mnnmnnmnnm nnryhryhry hmnnmnnmnn    60
mnngnatgct ccacacttat acgtgcc                                       87

<210> SEQ ID NO 63
<211> LENGTH: 84
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t

```
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 63
cacggttaat acggtgccag ctcctttctc nccmnnmnnm nnryhryhry hmnnmnnmnn      60
gnatgcttga cacttatacg tgcc                                            84

<210> SEQ ID NO 64
<211> LENGTH: 84
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 64
cacggttaat acggtgccag ctcctttctc mnnmnnmnnr yhryhryhmn nmnnmnnmnn      60
gnatgctcca cacttatacg tgcc                                            84

<210> SEQ ID NO 65
<211> LENGTH: 84
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (32)..(33)
<223> OTHER INFORMATION: n is a, c, g, or t
```

```
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t

<400> SEQUENCE: 65
cacggttaat acggtgccag ctcctttctc mnnmnnmnnr yhryhryhmn nmnnmnnmnn      60
gnatgctcca cacttatacg tgcc                                            84

<210> SEQ ID NO 66
<211> LENGTH: 102
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
```

<222> LOCATION: (77)..(78)
<223> OTHER INFORMATION: n is a, c, g, or t
<220> FEATURE:
<221> NAME/KEY: misc_feature
<222> LOCATION: (80)..(80)
<223> OTHER INFORMATION: n is a, c, g, or t

<400> SEQUENCE: 66
tttcacggtt aatacggtgc cagctccttt ctcmnnmnnm nnmnnmnnry hryhryhryh    60
ryhmnnmnnm nnmnnmnngn atgcttgaca cttatacgtg cc                     102

<210> SEQ ID NO 67
<211> LENGTH: 105
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
<220> FEATURE:
<221> NAME/KEY: misc_feature
<222> LOCATION: (83)..(83)
<223> OTHER INFORMATION: n is a, c, g, or t

<400> SEQUENCE: 67
tttcacggtt aatacggtgc cagctccttt ctcmnnmnnm nnmnnmnnmn nryhryhryh    60
ryhryhmnnm nnmnnmnnmn ngnatgcttg acacttatac gtgcc                  105

<210> SEQ ID NO 68
<211> LENGTH: 99
<212> TYPE: DNA
<213> ORGANISM: Artificial sequence

```
<220> FEATURE:
<223> OTHER INFORMATION: synthetic
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(77)
<223> OTHER INFORMATION: n is a, c, g, or t

<400> SEQUENCE: 68
tttcacggtt aatacggtgc cagctccttt ctcmnnmnnm nnmnnryhry hryhryhryh      60
mnnmnnmnnm nnmnngnatg ctccacactt atacgtgcc                            99

<210> SEQ ID NO 69
<211> LENGTH: 100
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
```

```
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t

<400> SEQUENCE: 69
ggttaatacg gtgccagctc ccyymnnmnn mnnmnnmnnm nnmnnryhry hryhryhmnn      60
mnnmnnmnnm nnmnntgctt gacacttata cgtgccactg                          100

<210> SEQ ID NO 70
<211> LENGTH: 94
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
```

<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t

<400> SEQUENCE: 70
ggttaatacg gtgccagctc ccyymnnmnn mnnmnnmnnr yhryhryhry hmnnmnnmnn    60
mnnmnnmnnt gctccacact tatacgtgcc actg                              94

<210> SEQ ID NO 71
<211> LENGTH: 95
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t

<400> SEQUENCE: 71
tttcacggtt aatgcggtgc cagctccttt ctcaccccta aacagmnsmn nmnnmnnmnn    60
mnnmnnmnna gaatagaatg cttgacactt atacg                              95

<210> SEQ ID NO 72
<211> LENGTH: 101
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature

```
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t

<400> SEQUENCE: 72
tttcacggtt aatgcggtgc cagctccttt ctcaccccta aacagmnsmn nmnnmnnmnn    60
mnnmnnmnnm nnmnnagaat agaatgcttg acacttatac g                      101

<210> SEQ ID NO 73
<211> LENGTH: 98
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (44)..(44)
<223> OTHER INFORMATION: n is a, c, g, or t
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t

<400> SEQUENCE: 73
tttcacggtt aatgcggtgc cagctccttt ctcaccccta aamnsmnsmn ngkrmnnmnn    60 gkrmnnngkrm nnagaataga atgcttgaca cttatacg                          98

<210> SEQ ID NO 74
<211> LENGTH: 104
<212> TYPE: DNA
<213> ORGANISM: Artificial sequence
```

```
<220> FEATURE:
<223> OTHER INFORMATION: synthetic
<220> FEATURE:
<221> NAME/KEY: misc_feature
<222> LOCATION: (47)..(47)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (71)..(72)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t

<400> SEQUENCE: 74
tttcacggtt aatgcggtgc cagctccttt ctcaccccta aacagmnsmn nmnnmnngkr      60
gkrgkrgkrm nnmnnmnnag aatagaatgc ttgacactta tacg                     104

<210> SEQ ID NO 75
<211> LENGTH: 107
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t
<220> FEATURE:
<221> NAME/KEY: misc_feature
<222> LOCATION: (80)..(81)
<223> OTHER INFORMATION: n is a, c, g, or t
```

<400> SEQUENCE: 75
tttcacggtt aatgcggtgc cagctccttt ctcaccccta aacagvnnvn nshwmnnmnn    60
vhwvnnvnnv hwmnnmnnmn nagaatagaa tgcttgacac ttatacg                107

<210> SEQ ID NO 76
<211> LENGTH: 107
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t
<220> FEATURE:
<221> NAME/KEY: misc_feature
<222> LOCATION: (68)..(69)
<223> OTHER INFORMATION: n is a, c, g, or t
<220> FEATURE:
<221> NAME/KEY: misc_feature
<222> LOCATION: (74)..(75)
<223> OTHER INFORMATION: n is a, c, g, or t
<220> FEATURE:
<221> NAME/KEY: misc_feature
<222> LOCATION: (77)..(78)
<223> OTHER INFORMATION: n is a, c, g, or t

<400> SEQUENCE: 76
tttcacggtt aatgcggtgc cagctccttt ctcaccccta aacagvnnvn nvhwmnnmnn    60
vhwvnnvnns hwmnnmnnvh wagaatagaa tgcttgacac ttatacg                107

<210> SEQ ID NO 77
<211> LENGTH: 53
<212> TYPE: DNA
<213> ORGANISM: Artificial sequence
<220> FEATURE:
<223> OTHER INFORMATION: synthetic

<400> SEQUENCE: 77
gtctcgcggc ccagccggcc atggccctgc aggtggatat tgttcccagc cag          53

<210> SEQ ID NO 78
<211> LENGTH: 42
<212> TYPE: DNA
<213> ORGANISM: Artificial sequence
<220> FEATURE:
<223> OTHER INFORMATION: synthetic

<400> SEQUENCE: 78
gctggttgcg gccgcctgaa agatcttcac gttgacggtg gc                     42

<210> SEQ ID NO 79
<211> LENGTH: 43

```
<212> TYPE: DNA
<213> ORGANISM: Artificial sequence
<220> FEATURE:
<223> OTHER INFORMATION: synthetic

<400> SEQUENCE: 79
gctggttgcg gccgcattca caatgacctg aatgtccttg aag                    43

<210> SEQ ID NO 80
<211> LENGTH: 74
<212> TYPE: DNA
<213> ORGANISM: Artificial sequence
<220> FEATURE:
<223> OTHER INFORMATION: synthetic

<400> SEQUENCE: 80
caggtggata ttgttcccag ccaggggag atcagcgttg gagagtccaa attcttctta   60
tgccaagtgg cagg                                                    74

<210> SEQ ID NO 81
<211> LENGTH: 93
<212> TYPE: DNA
<213> ORGANISM: Artificial sequence
<220> FEATURE:
<223> OTHER INFORMATION: synthetic

<400> SEQUENCE: 81
gatcttcacg ttgacggtgg cctctgactc actaatcgga taagagtaat ttgacatagc   60
gtcagagcct gtaaccacac acttgtaaat gcc                                93

<210> SEQ ID NO 82
<211> LENGTH: 69
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t

<400> SEQUENCE: 82
caaattcttc ttatgccaag tggcaggann knnknnknnk nnknnkatct cctggttctc   60
ccccaatgg                                                          69

<210> SEQ ID NO 83
<211> LENGTH: 72
<212> TYPE: DNA
<213> ORGANISM: Artificial sequence
```

```
<220> FEATURE:
<223> OTHER INFORMATION: synthetic
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 83
caaattcttc ttatgccaag tggcaggann knnknnknnk nnknnknnka tctcctggtt      60
ctcccccaat gg                                                         72

<210> SEQ ID NO 84
<211> LENGTH: 69
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 84
gatcttcacg ttgacggtgg cctcmnnmnn mnnmnnmnnm nnmnnmnnaa ccacacactt      60
``` gtaaatgcc 69

<210> SEQ ID NO 85
<211> LENGTH: 78
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 85
gatcttcacg ttgacggtgg cctcmnnmnn mnnmnnmnnm nnmnnmnnmn nmnnmnnaac    60
cacacacttg taaatgcc    78

<210> SEQ ID NO 86
<211> LENGTH: 87
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t

```
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t

<400> SEQUENCE: 86
gatcttcacg ttgacggtgg cctcmnnmnn mnnmnnmnnm nnmnnmnnmn nmnnmnnmnn    60
mnnmnnaacc acacacttgt aaatgcc                                        87

<210> SEQ ID NO 87
<211> LENGTH: 92
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
```

```
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(63)
<223> OTHER INFORMATION: n is a, c, g, or t
<220> FEATURE:
<221> NAME/KEY: misc_feature
<222> LOCATION: (65)..(66)
<223> OTHER INFORMATION: n is a, c, g, or t

<400> SEQUENCE: 87
gatcttcacg ttgacggtgg cctctgactc actmnnmnnm nmnnmnnmn nmnnmnnmnn    60 mnnmnngcct gtaaccacac acttgtaaat gc                                 92

<210> SEQ ID NO 88
<211> LENGTH: 53
<212> TYPE: DNA
<213> ORGANISM: Artificial sequence
<220> FEATURE:
<223> OTHER INFORMATION: synthetic

<400> SEQUENCE: 88
gtctcgcggc ccagccggcc atggccccct atttctctaa gaccattcgc gat          53

<210> SEQ ID NO 89
<211> LENGTH: 42
<212> TYPE: DNA
<213> ORGANISM: Artificial sequence
<220> FEATURE:
<223> OTHER INFORMATION: synthetic

<400> SEQUENCE: 89
acctgcacag cagagctcat tgtggaagcg gccgcaacca gc                      42

<210> SEQ ID NO 90
<211> LENGTH: 54
<212> TYPE: DNA
<213> ORGANISM: Artificial sequence
<220> FEATURE:
<223> OTHER INFORMATION: synthetic

<400> SEQUENCE: 90
atagctatag ttgctcatgg catcgctaaa atacttgcag gtgtacttgg catc         54

<210> SEQ ID NO 91
<211> LENGTH: 57
<212> TYPE: DNA
<213> ORGANISM: Artificial sequence
<220> FEATURE:
<223> OTHER INFORMATION: synthetic

<400> SEQUENCE: 91
aatgagctct gctgtgcagg tggcgcccgg aatcggatag ctatagttgc tcatggc      57

<210> SEQ ID NO 92
<211> LENGTH: 50
```

```
<212> TYPE: DNA
<213> ORGANISM: Artificial sequence
<220> FEATURE:
<223> OTHER INFORMATION: synthetic

<400> SEQUENCE: 92
atcggatagc tatagttgct catggcatca ctgttgacag ccttgcaggt                50

<210> SEQ ID NO 93
<211> LENGTH: 52
<212> TYPE: DNA
<213> ORGANISM: Artificial sequence
<220> FEATURE:
<223> OTHER INFORMATION: synthetic

<400> SEQUENCE: 93
aatgagctct gctgtgcagg tggcttctcc aatcggatag ctatagttgc tc            52

<210> SEQ ID NO 94
<211> LENGTH: 67
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t

<400> SEQUENCE: 94
gctgctagat ttgactgcaa gattnnknnk nnknnknnkn nknnkgttgt ctggttcaaa    60
gatgacc                                                              67

<210> SEQ ID NO 95
<211> LENGTH: 73
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (25)..(26)
<223> OTHER INFORMATION: n is a, c, g, or t
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
```

```
<222> LOCATION: (31)..(32)
<223> OTHER INFORMATION: n is a, c, g, or t
<220> FEATURE:
<221> NAME/KEY: misc_feature
<222> LOCATION: (34)..(35)
<223> OTHER INFORMATION: n is a, c, g, or t
<220> FEATURE:
<221> NAME/KEY: misc_feature
<222> LOCATION: (37)..(38)
<223> OTHER INFORMATION: n is a, c, g, or t
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t

<400> SEQUENCE: 95
gctgctagat tgactgcaa gattnnknnk nnknnknnkn nknnknnknn kgttgtctgg      60
ttcaaagatg acc                                                       73

<210> SEQ ID NO 96
<211> LENGTH: 51
<212> TYPE: DNA
<213> ORGANISM: Artificial sequence
<220> FEATURE:
<223> OTHER INFORMATION: synthetic

<400> SEQUENCE: 96
aagaccattc gcgatttaga agttgtggag ggaagtgctg ctagatttga c              51

<210> SEQ ID NO 97
<211> LENGTH: 60
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t

<400> SEQUENCE: 97
gagctctgct gtgcaggtgg cmnnmnnmnn mnnmnnmnna gccttgcagg tgtacttggc    60
```

<210> SEQ ID NO 98
<211> LENGTH: 69
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 98
gagctctgct gtgcaggtgg cmnmnnmnn mnnmnnmnm nnmnnmnnag ccttgcaggt      60
gtacttggc                                                            69

<210> SEQ ID NO 99
<211> LENGTH: 78
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature

```
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t

<400> SEQUENCE: 99
gagctctgct gtgcaggtgg cmnnmnnmnn mnnmnnmnnm nnmnnmnnmn nmnnmnnagc     60
cttgcaggtg tacttggc                                                  78

<210> SEQ ID NO 100
<211> LENGTH: 69
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (23)..(24)
<223> OTHER INFORMATION: n is a, c, g, or t
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (47)..(48)
<223> OTHER INFORMATION: n is a, c, g, or t

<400> SEQUENCE: 100
tgctgtgcag gtggcttctc cmnnmnnmnn mnnmnnmnnm nnmnnmnnaa gactgttgac     60
``` agccttgca 69

<210> SEQ ID NO 101
<211> LENGTH: 112
<212> TYPE: PRT
<213> ORGANISM: Artificial sequence
<220> FEATURE:
<223> OTHER INFORMATION: synthetic

<400> SEQUENCE: 101

Ala Trp Val Asp Gln Thr Pro Arg Thr Ala Thr Lys Glu Thr Gly Glu
1               5                   10                  15

Ser Leu Thr Ile Asn Cys Val Leu Arg Asp Thr Ser Cys Ala Phe Ser
                20                  25                  30

Ser Thr Gly Trp Tyr Arg Thr Lys Leu Gly Ser Thr Asn Glu Gln Ser
            35                  40                  45

Ile Ser Ile Gly Gly Arg Tyr Val Glu Thr Val Asn Lys Gly Ser Lys
50                  55                  60

Ser Phe Ser Leu Arg Ile Ser Asp Leu Arg Val Glu Asp Ser Gly Thr
65                  70                  75                  80

Tyr Lys Cys Gln Ala Ser Ile Lys Ser Lys Pro Gly Asn Cys Asn Cys
                85                  90                  95

Arg Cys Ile Gln Gln Thr Glu Gly Ala Gly Thr Ala Leu Thr Val Lys
            100                 105                 110

<210> SEQ ID NO 102
<211> LENGTH: 60
<212> TYPE: PRT
<213> ORGANISM: Artificial sequence
<220> FEATURE:
<223> OTHER INFORMATION: synthetic

<400> SEQUENCE: 102

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ser Asn Asp Ala Leu Gly
                20                  25                  30

Ser Thr Leu Trp Tyr Arg Thr Lys Leu Gly Ser Thr Asn Glu Gln Thr
            35                  40                  45

Ile Ser Ile Gly Gly Arg Tyr Val Glu Thr Val Asn
50                  55                  60

<210> SEQ ID NO 103
<211> LENGTH: 60
<212> TYPE: PRT
<213> ORGANISM: Artificial sequence
<220> FEATURE:
<223> OTHER INFORMATION: synthetic

<400> SEQUENCE: 103

Ala Trp Val Asp Gln Thr Pro Arg Ser Val Thr Lys Glu Thr Gly Glu
1               5                   10                  15

Ser Val Thr Ile Asn Cys Val Leu Glu Asp Ser Pro Cys Asp Leu Ala
                20                  25                  30

Asn Thr Leu Trp Tyr Arg Thr Lys Leu Gly Ser Lys Tyr Glu Gln Thr
            35                  40                  45

Val Ser Ile Gly Gly Arg Tyr Val Glu Thr Val Asn
50                  55                  60

<210> SEQ ID NO 104

```
<211> LENGTH: 60
<212> TYPE: PRT
<213> ORGANISM: Artificial sequence
<220> FEATURE:
<223> OTHER INFORMATION: synthetic

<400> SEQUENCE: 104

Ala Trp Val Asp Gln Thr Pro Arg Ser Val Thr Lys Glu Thr Gly Glu
1               5                   10                  15

Ser Leu Thr Ile Asn Cys Val Leu Arg Asp Thr Ser Cys Ala Phe Ser
            20                  25                  30

Ser Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn
    50                  55                  60

<210> SEQ ID NO 105
<211> LENGTH: 60
<212> TYPE: PRT
<213> ORGANISM: Artificial sequence
<220> FEATURE:
<223> OTHER INFORMATION: synthetic

<400> SEQUENCE: 105

Ala Trp Val Asp Gln Thr Pro Arg Ser Ala Thr Lys Glu Thr Gly Glu
1               5                   10                  15

Ser Leu Thr Ile Asn Cys Val Leu Arg Asp Thr Ser Cys Ala Phe Ser
            20                  25                  30

Ser Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn
    50                  55                  60

<210> SEQ ID NO 106
<211> LENGTH: 60
<212> TYPE: PRT
<213> ORGANISM: Artificial sequence
<220> FEATURE:
<223> OTHER INFORMATION: synthetic

<400> SEQUENCE: 106

Ala Trp Val Asp Gln Thr Gln Glu Thr Ala Thr Lys Glu Thr Gly Glu
1               5                   10                  15

Ser Leu Thr Ile Asn Cys Val Leu Arg Asp Thr Ser Cys Ala Phe Ser
            20                  25                  30

Ser Thr Gly Trp Tyr Arg Thr Lys Leu Gly Ser Thr Asn Glu Gln Ser
        35                  40                  45

Ile Ser Ile Gly Gly Arg Tyr Val Glu Thr Val Asn
    50                  55                  60

<210> SEQ ID NO 107
<211> LENGTH: 60
<212> TYPE: PRT
<213> ORGANISM: Artificial sequence
<220> FEATURE:
<223> OTHER INFORMATION: synthetic

<400> SEQUENCE: 107

Ala Trp Val Asp Gln Thr Pro Arg Thr Thr Thr Lys Glu Thr Gly Glu
1               5                   10                  15

Ser Leu Thr Ile Asn Cys Val Leu Thr Asp Thr Ile Cys Val Phe Ser
            20                  25                  30
```

-continued

Asn Thr Gly Trp Tyr Arg Thr Lys Leu Gly Ser Thr Asn Glu Gln Ser
         35                  40                  45

Ile Ser Ile Gly Gly Arg Tyr Val Glu Thr Val Asn
    50                  55                  60

<210> SEQ ID NO 108
<211> LENGTH: 60
<212> TYPE: PRT
<213> ORGANISM: Artificial sequence
<220> FEATURE:
<223> OTHER INFORMATION: synthetic

<400> SEQUENCE: 108

Ala Trp Val Asp Gln Thr Pro Arg Thr Ala Thr Lys Glu Thr Gly Glu
1               5                   10                  15

Ser Leu Thr Ile Asn Cys Val Leu Arg Asp Ser Cys Ala Phe Ser
                20                  25                  30

Ser Thr Gly Trp Tyr Arg Thr Lys Leu Gly Ser Thr Asn Glu Gln Arg
         35                  40                  45

Ile Ser Ile Gly Gly Arg Tyr Val Glu Thr Val Asn
    50                  55                  60

<210> SEQ ID NO 109
<211> LENGTH: 60
<212> TYPE: PRT
<213> ORGANISM: Artificial sequence
<220> FEATURE:
<223> OTHER INFORMATION: synthetic

<400> SEQUENCE: 109

Ala Trp Val Asp Gln Thr Pro Arg Thr Ala Thr Lys Glu Thr Gly Glu
1               5                   10                  15

Ser Leu Thr Ile Asn Cys Val Leu Arg Tyr Thr Ser Cys Ala Phe Asp
                20                  25                  30

Asn Thr Gly Trp Tyr Arg Thr Lys Leu Gly Ser Arg Asn Glu Arg Ser
         35                  40                  45

Ile Ser Ile Gly Gly Arg Tyr Val Glu Thr Val Asn
    50                  55                  60

<210> SEQ ID NO 110
<211> LENGTH: 60
<212> TYPE: PRT
<213> ORGANISM: Artificial sequence
<220> FEATURE:
<223> OTHER INFORMATION: synthetic

<400> SEQUENCE: 110

Ala Trp Val Asp Gln Thr Pro Arg Thr Val Thr Lys Glu Thr Gly Glu
1               5                   10                  15

Ser Leu Thr Ile Asn Cys Val Leu Arg Gly Thr Glu His Gly Leu Cys
                20                  25                  30

Arg Ala Asp Trp Ala Arg Thr Lys Leu Gly Ser Thr Asn Glu Gln Lys
         35                  40                  45

Met Ile Ile Gly Gly Arg Tyr Val Glu Thr Val Asn
    50                  55                  60

<210> SEQ ID NO 111
<211> LENGTH: 60
<212> TYPE: PRT
<213> ORGANISM: Artificial sequence
<220> FEATURE:
<223> OTHER INFORMATION: synthetic

```
<400> SEQUENCE: 111

Ala Trp Val Asp Gln Thr Pro Arg Thr Ala Thr Lys Glu Thr Gly Glu
1               5                   10                  15

Ser Leu Thr Ile Asn Cys Val Ile Arg Glu Gly Gly Cys Ala Ile Gly
            20                  25                  30

Ser Thr Tyr Trp Phe Arg Thr Lys Leu Gly Ser Thr Asn Glu Gln Lys
        35                  40                  45

Leu Ser Ile Gly Gly Arg Tyr Val Glu Thr Val Asn
    50                  55                  60

<210> SEQ ID NO 112
<211> LENGTH: 6
<212> TYPE: PRT
<213> ORGANISM: Artificial sequence
<220> FEATURE:
<223> OTHER INFORMATION: synthetic

<400> SEQUENCE: 112

Ser Tyr Gly Leu Glu Ser
1               5

<210> SEQ ID NO 113
<211> LENGTH: 6
<212> TYPE: PRT
<213> ORGANISM: Artificial sequence
<220> FEATURE:
<223> OTHER INFORMATION: synthetic

<400> SEQUENCE: 113

Ser Phe Glu Leu Lys Asp
1               5

<210> SEQ ID NO 114
<211> LENGTH: 5
<212> TYPE: PRT
<213> ORGANISM: Artificial sequence
<220> FEATURE:
<223> OTHER INFORMATION: synthetic

<400> SEQUENCE: 114

Gly Gly Gly Gly Ser
1               5

<210> SEQ ID NO 115
<211> LENGTH: 21
<212> TYPE: PRT
<213> ORGANISM: Artificial sequence
<220> FEATURE:
<223> OTHER INFORMATION: synthetic

<400> SEQUENCE: 115

Ala Ala Ala Asp Tyr Lys Asp Asp Asp Lys Ala Ala Asp Tyr Lys
1               5                   10                  15

Asp Asp Asp Asp Lys
            20

<210> SEQ ID NO 116
<211> LENGTH: 17
<212> TYPE: PRT
<213> ORGANISM: Artificial sequence
<220> FEATURE:
<223> OTHER INFORMATION: synthetic

<400> SEQUENCE: 116

Arg Val Gly Pro Tyr Ser Trp Asp Asp Ser Pro Gln Asp Asn Tyr Tyr
```

```
1               5                   10                  15
Met

<210> SEQ ID NO 117
<211> LENGTH: 9
<212> TYPE: PRT
<213> ORGANISM: Artificial sequence
<220> FEATURE:
<223> OTHER INFORMATION: synthetic

<400> SEQUENCE: 117

Cys Ser Lys Pro Ser Asp Ser Asn Cys
1               5

<210> SEQ ID NO 118
<211> LENGTH: 9
<212> TYPE: PRT
<213> ORGANISM: Artificial sequence
<220> FEATURE:
<223> OTHER INFORMATION: synthetic

<400> SEQUENCE: 118

Gly Tyr Arg Phe Ser Asn Phe Val Ile
1               5

<210> SEQ ID NO 119
<211> LENGTH: 11
<212> TYPE: PRT
<213> ORGANISM: Artificial sequence
<220> FEATURE:
<223> OTHER INFORMATION: synthetic

<400> SEQUENCE: 119

Arg Asp Thr Ser Cys Ala Phe Ser Ser Thr Gly
1               5                   10

<210> SEQ ID NO 120
<211> LENGTH: 105
<212> TYPE: PRT
<213> ORGANISM: Artificial sequence
<220> FEATURE:
<223> OTHER INFORMATION: synthetic

<400> SEQUENCE: 120

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
                20                  25                  30

Ile Ser Trp Phe Ser Pro Asn Gly Glu Lys Leu Thr Pro Asn Gln Gln
            35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Gly Ala Tyr
65                  70                  75                  80

Phe Ser Asp Ala Met Ser Asn Tyr Ser Tyr Pro Ile Pro Gly Glu Lys
                85                  90                  95

Ala Thr Val Asn Val Lys Ile Phe Gln
                100                 105

<210> SEQ ID NO 121
<211> LENGTH: 105
<212> TYPE: PRT
<213> ORGANISM: Artificial sequence
<220> FEATURE:
```

-continued

<223> OTHER INFORMATION: synthetic

<400> SEQUENCE: 121

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Ala Tyr
65                  70                  75                  80

Phe Ser Asp Ala Met Ser Asn Tyr Ser Tyr Pro Ile Pro Gly Glu Ser
                85                  90                  95

Ala Thr Val Asn Val Lys Ile Phe Gln
            100                 105

<210> SEQ ID NO 122
<211> LENGTH: 105
<212> TYPE: PRT
<213> ORGANISM: Artificial sequence
<220> FEATURE:
<223> OTHER INFORMATION: synthetic

<400> SEQUENCE: 122

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Tyr
65                  70                  75                  80

Phe Ser Asp Ala Met Ser Asn Tyr Ser Tyr Pro Ile Pro Gly Ser Glu
                85                  90                  95

Ala Thr Val Asn Val Lys Ile Phe Gln
            100                 105

<210> SEQ ID NO 123
<211> LENGTH: 105
<212> TYPE: PRT
<213> ORGANISM: Artificial sequence
<220> FEATURE:
<223> OTHER INFORMATION: synthetic

<400> SEQUENCE: 123

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
        35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Thr
65                  70                  75                  80

```
Phe Ser Asp Ala Met Ser Asn Tyr Ser Tyr Pro Ile Pro Glu Ser Glu
                85                  90                  95

Ala Thr Val Asn Val Lys Ile Phe Gln
            100                 105

<210> SEQ ID NO 124
<211> LENGTH: 105
<212> TYPE: PRT
<213> ORGANISM: Artificial sequence
<220> FEATURE:
<223> OTHER INFORMATION: synthetic

<400> SEQUENCE: 124

Leu Gln Val Asp Ile Val Pro Ser Gln Gly Glu Ile Ser Val Gly Glu
1               5                   10                  15

Ser Lys Phe Phe Leu Cys Gln Val Ala Gly Asp Ala Lys Asp Lys Asp
            20                  25                  30

Ile Ser Trp Phe Ser Pro Asn Gly Glu Lys Leu Thr Pro Asn Gln Gln
            35                  40                  45

Arg Ile Ser Val Val Trp Asn Asp Asp Ser Ser Thr Leu Thr Ile
    50                  55                  60

Tyr Asn Ala Asn Ile Asp Asp Ala Gly Ile Tyr Lys Cys Val Val Thr
65              70                  75                  80

Gly Ser Asp Ala Met Ser Asn Tyr Ser Tyr Pro Ile Ser Glu Ser Glu
                85                  90                  95

Ala Thr Val Asn Val Lys Ile Phe Gln
            100                 105

<210> SEQ ID NO 125
<211> LENGTH: 101
<212> TYPE: PRT
<213> ORGANISM: Artificial sequence
<220> FEATURE:
<223> OTHER INFORMATION: synthetic

<400> SEQUENCE: 125

Pro Tyr Phe Ser Lys Thr Ile Arg Asp Leu Glu Val Val Glu Gly Ser
1               5                   10                  15

Ala Ala Arg Phe Asp Cys Lys Ile Glu Gly Tyr Pro Asp Pro Glu Val
            20                  25                  30

Val Trp Phe Lys Asp Asp Gln Ser Ile Arg Glu Ser Arg His Phe Gln
            35                  40                  45

Ile Asp Tyr Asp Glu Asp Gly Asn Cys Ser Leu Ile Ile Ser Asp Val
            50                  55                  60

Cys Gly Asp Asp Asp Ala Lys Tyr Thr Cys Gly Ala Tyr Phe Ser Asp
65              70                  75                  80

Ala Met Ser Asn Tyr Ser Tyr Pro Ile Pro Gly Glu Lys Cys Thr Ala
                85                  90                  95

Glu Leu Ile Val Glu
            100

<210> SEQ ID NO 126
<211> LENGTH: 101
<212> TYPE: PRT
<213> ORGANISM: Artificial sequence
<220> FEATURE:
<223> OTHER INFORMATION: synthetic

<400> SEQUENCE: 126

Pro Tyr Phe Ser Lys Thr Ile Arg Asp Leu Glu Val Val Glu Gly Ser
```

-continued

```
                1               5                  10                  15
Ala Ala Arg Phe Asp Cys Lys Ile Glu Gly Tyr Pro Asp Pro Glu Val
                20                  25                  30

Val Trp Phe Lys Asp Asp Gln Ser Ile Arg Glu Ser Arg His Phe Gln
                35                  40                  45

Ile Asp Tyr Asp Glu Asp Gly Asn Cys Ser Leu Ile Ile Ser Asp Val
        50                  55                  60

Cys Gly Asp Asp Asp Ala Lys Tyr Thr Cys Lys Ala Tyr Phe Ser Asp
65                  70                  75                  80

Ala Met Ser Asn Tyr Ser Tyr Pro Ile Pro Gly Glu Thr Cys Thr Ala
                85                  90                  95

Glu Leu Ile Val Glu
            100
```

<210> SEQ ID NO 127
<211> LENGTH: 101
<212> TYPE: PRT
<213> ORGANISM: Artificial sequence
<220> FEATURE:
<223> OTHER INFORMATION: synthetic

<400> SEQUENCE: 127

```
Pro Tyr Phe Ser Lys Thr Ile Arg Asp Leu Glu Val Val Glu Gly Ser
1               5                   10                  15

Ala Ala Arg Phe Asp Cys Lys Ile Glu Gly Tyr Pro Asp Pro Glu Val
                20                  25                  30

Val Trp Phe Lys Asp Asp Gln Ser Ile Arg Glu Ser Arg His Phe Gln
                35                  40                  45

Ile Asp Tyr Asp Glu Asp Gly Asn Cys Ser Leu Ile Ile Ser Asp Val
        50                  55                  60

Cys Gly Asp Asp Asp Ala Lys Tyr Thr Cys Lys Ala Tyr Phe Ser Asp
65                  70                  75                  80

Ala Met Ser Asn Tyr Ser Tyr Pro Ile Pro Gly Ala Thr Cys Thr Ala
                85                  90                  95

Glu Leu Ile Val Glu
            100
```

<210> SEQ ID NO 128
<211> LENGTH: 101
<212> TYPE: PRT
<213> ORGANISM: Artificial sequence
<220> FEATURE:
<223> OTHER INFORMATION: synthetic

<400> SEQUENCE: 128

```
Pro Tyr Phe Ser Lys Thr Ile Arg Asp Leu Glu Val Val Glu Gly Ser
1               5                   10                  15

Ala Ala Arg Phe Asp Cys Lys Ile Glu Gly Tyr Pro Asp Pro Glu Val
                20                  25                  30

Val Trp Phe Lys Asp Asp Gln Ser Ile Arg Glu Ser Arg His Phe Gln
                35                  40                  45

Ile Asp Tyr Asp Glu Asp Gly Asn Cys Ser Leu Ile Ile Ser Asp Val
        50                  55                  60

Cys Gly Asp Asp Asp Ala Lys Tyr Thr Cys Lys Ala Val Phe Ser Asp
65                  70                  75                  80

Ala Met Ser Asn Tyr Ser Tyr Pro Ile Pro Glu Ala Thr Cys Thr Ala
                85                  90                  95

Glu Leu Ile Val Glu
```

```
                        100

<210> SEQ ID NO 129
<211> LENGTH: 101
<212> TYPE: PRT
<213> ORGANISM: Artificial sequence
<220> FEATURE:
<223> OTHER INFORMATION: synthetic

<400> SEQUENCE: 129

Pro Tyr Phe Ser Lys Thr Ile Arg Asp Leu Glu Val Val Glu Gly Ser
1               5                   10                  15

Ala Ala Arg Phe Asp Cys Lys Ile Glu Gly Tyr Pro Asp Pro Glu Val
            20                  25                  30

Val Trp Phe Lys Asp Asp Gln Ser Ile Arg Glu Ser Arg His Phe Gln
        35                  40                  45

Ile Asp Tyr Asp Glu Asp Gly Asn Cys Ser Leu Ile Ile Ser Asp Val
    50                  55                  60

Cys Gly Asp Asp Asp Ala Lys Tyr Thr Cys Lys Ala Val Asn Ser Asp
65                  70                  75                  80

Ala Met Ser Asn Tyr Ser Tyr Pro Ile Gly Glu Ala Thr Cys Thr Ala
                85                  90                  95

Glu Leu Ile Val Glu
            100

<210> SEQ ID NO 130
<211> LENGTH: 28
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: X is G or Q
<220> FEATURE:
<221> NAME/KEY: MISC_FEATURE
<222> LOCATION: (4)..(9)
<223> OTHER INFORMATION: X is any amino acid
<220> FEATURE:
<221> NAME/KEY: MISC_FEATURE
<222> LOCATION: (10)..(13)
<223> OTHER INFORMATION: X is C, S, G, Y, N or D
<220> FEATURE:
<221> NAME/KEY: MISC_FEATURE
<222> LOCATION: (14)..(18)
<223> OTHER INFORMATION: X is any amino acid
<220> FEATURE:
<221> NAME/KEY: MISC_FEATURE
<222> LOCATION: (19)..(19)
<223> OTHER INFORMATION: X is K, G, R or E
<220> FEATURE:
<221> NAME/KEY: MISC_FEATURE
<222> LOCATION: (24)..(24)
<223> OTHER INFORMATION: X is A or V

<400> SEQUENCE: 130

Cys Xaa Ala Xaa Xaa Xaa Xaa Xaa Xaa Xaa Xaa Xaa Xaa Xaa
1               5                   10                  15

Xaa Xaa Xaa Gly Ala Gly Thr Xaa Leu Thr Val Lys
            20                  25

<210> SEQ ID NO 131
<211> LENGTH: 30
<212> TYPE: PRT
<213> ORGANISM: Artificial sequence
<220> FEATURE:
<223> OTHER INFORMATION: synthetic
```

```
<220> FEATURE:
<221> NAME/KEY: MISC_FEATURE
<222> LOCATION: (2)..(2)
<223> OTHER INFORMATION: X = G or Q
<220> FEATURE:
<221> NAME/KEY: MISC_FEATURE
<222> LOCATION: (4)..(9)
<223> OTHER INFORMATION: X = any amino acid
<220> FEATURE:
<221> NAME/KEY: MISC_FEATURE
<222> LOCATION: (10)..(13)
<223> OTHER INFORMATION: X = C, S, G, Y, N or D
<220> FEATURE:
<221> NAME/KEY: MISC_FEATURE
<222> LOCATION: (14)..(20)
<223> OTHER INFORMATION: X = any amino acid
<220> FEATURE:
<221> NAME/KEY: MISC_FEATURE
<222> LOCATION: (21)..(21)
<223> OTHER INFORMATION: X = K, G, R or E
<220> FEATURE:
<221> NAME/KEY: MISC_FEATURE
<222> LOCATION: (26)..(26)
<223> OTHER INFORMATION: X = A or V

<400> SEQUENCE: 131

Cys Xaa Ala Xaa Xaa Xaa Xaa Xaa Xaa Xaa Xaa Xaa Xaa Xaa
1               5                   10                  15

Xaa Xaa Xaa Xaa Xaa Gly Ala Gly Thr Xaa Leu Thr Val Lys
            20                  25                  30

<210> SEQ ID NO 132
<211> LENGTH: 29
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (2)..(2)
<223> OTHER INFORMATION: X = G or Q
<220> FEATURE:
<221> NAME/KEY: MISC_FEATURE
<222> LOCATION: (4)..(4)
<223> OTHER INFORMATION: X = C, S, Y or F
<220> FEATURE:
<221> NAME/KEY: MISC_FEATURE
<222> LOCATION: (5)..(9)
<223> OTHER INFORMATION: X = any amino acid
<220> FEATURE:
<221> NAME/KEY: MISC_FEATURE
<222> LOCATION: (10)..(14)
<223> OTHER INFORMATION: X = C, S, G, Y, N, D
<220> FEATURE:
<221> NAME/KEY: MISC_FEATURE
<222> LOCATION: (15)..(18)
<223> OTHER INFORMATION: X = any amino acid
<220> FEATURE:
<221> NAME/KEY: MISC_FEATURE
<222> LOCATION: (25)..(25)
<223> OTHER INFORMATION: X = A or V

<400> SEQUENCE: 132

Cys Xaa Ala Xaa Xaa Xaa Xaa Xaa Xaa Xaa Xaa Xaa Xaa Xaa
1               5                   10                  15

Xaa Xaa Glu Lys Gly Ala Gly Thr Xaa Leu Thr Val Lys
            20                  25

<210> SEQ ID NO 133
<211> LENGTH: 31
<212> TYPE: PRT
<213> ORGANISM: Artificial sequence
<220> FEATURE:
<223> OTHER INFORMATION: synthetic
```

```
<220> FEATURE:
<221> NAME/KEY: MISC_FEATURE
<222> LOCATION: (2)..(2)
<223> OTHER INFORMATION: X = G or Q
<220> FEATURE:
<221> NAME/KEY: MISC_FEATURE
<222> LOCATION: (4)..(4)
<223> OTHER INFORMATION: X = C, S, Y or F
<220> FEATURE:
<221> NAME/KEY: MISC_FEATURE
<222> LOCATION: (5)..(9)
<223> OTHER INFORMATION: X = any amino acid
<220> FEATURE:
<221> NAME/KEY: MISC_FEATURE
<222> LOCATION: (10)..(14)
<223> OTHER INFORMATION: X = C, S, G, Y, N or D
<220> FEATURE:
<221> NAME/KEY: MISC_FEATURE
<222> LOCATION: (15)..(20)
<223> OTHER INFORMATION: X = any amino acid
<220> FEATURE:
<221> NAME/KEY: MISC_FEATURE
<222> LOCATION: (27)..(27)
<223> OTHER INFORMATION: X = A or V

<400> SEQUENCE: 133

Cys Xaa Ala Xaa Xaa Xaa Xaa Xaa Xaa Xaa Xaa Xaa Xaa Xaa
 1               5                  10                  15

Xaa Xaa Xaa Xaa Glu Lys Gly Ala Gly Thr Xaa Leu Thr Val Lys
            20                  25                  30

<210> SEQ ID NO 134
<211> LENGTH: 30
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X = C, S, Y or F
<220> FEATURE:
<221> NAME/KEY: MISC_FEATURE
<222> LOCATION: (5)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = C, S, G, Y, N or D
<220> FEATURE:
<221> NAME/KEY: MISC_FEATURE
<222> LOCATION: (11)..(15)
<223> OTHER INFORMATION: X = any amino acid
<220> FEATURE:
<221> NAME/KEY: misc_feature
<222> LOCATION: (16)..(19)
<223> OTHER INFORMATION: Xaa can be any naturally occurring amino acid
<220> FEATURE:
<221> NAME/KEY: MISC_FEATURE
<222> LOCATION: (26)..(26)
<223> OTHER INFORMATION: X = A or V

<400> SEQUENCE: 134

Cys Gln Ala Xaa Xaa Xaa Xaa Xaa Xaa Xaa Xaa Xaa Xaa Xaa Xaa
 1               5                  10                  15

Xaa Xaa Xaa Glu Lys Gly Ala Gly Thr Xaa Leu Thr Val Lys
            20                  25                  30

<210> SEQ ID NO 135
<211> LENGTH: 27
<212> TYPE: PRT
<213> ORGANISM: Artificial sequence
<220> FEATURE:
<223> OTHER INFORMATION: synthetic
```

```
<220> FEATURE:
<221> NAME/KEY: MISC_FEATURE
<222> LOCATION: (4)..(9)
<223> OTHER INFORMATION: X = any amino acid
<220> FEATURE:
<221> NAME/KEY: MISC_FEATURE
<222> LOCATION: (10)..(13)
<223> OTHER INFORMATION: X = C, S, G, Y, N or D
<220> FEATURE:
<221> NAME/KEY: MISC_FEATURE
<222> LOCATION: (14)..(17)
<223> OTHER INFORMATION: X = any amino acid
<220> FEATURE:
<221> NAME/KEY: MISC_FEATURE
<222> LOCATION: (18)..(18)
<223> OTHER INFORMATION: X = K, G, R or E
<220> FEATURE:
<221> NAME/KEY: MISC_FEATURE
<222> LOCATION: (23)..(23)
<223> OTHER INFORMATION: X = A or V

<400> SEQUENCE: 135

Cys Gly Ala Xaa Xaa Xaa Xaa Xaa Xaa Xaa Xaa Xaa Xaa Xaa Xaa
1               5                   10                  15

Xaa Xaa Gly Ala Gly Thr Xaa Leu Thr Val Lys
            20                  25

<210> SEQ ID NO 136
<211> LENGTH: 25
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X = C, S, Y OR F
<220> FEATURE:
<221> NAME/KEY: MISC_FEATURE
<222> LOCATION: (5)..(8)
<223> OTHER INFORMATION: X = any amino acid
<220> FEATURE:
<221> NAME/KEY: MISC_FEATURE
<222> LOCATION: (9)..(11)
<223> OTHER INFORMATION: X = C, S, G, Y, N or D
<220> FEATURE:
<221> NAME/KEY: MISC_FEATURE
<222> LOCATION: (12)..(14)
<223> OTHER INFORMATION: X = any amino acid
<220> FEATURE:
<221> NAME/KEY: MISC_FEATURE
<222> LOCATION: (21)..(21)
<223> OTHER INFORMATION: X = A or V

<400> SEQUENCE: 136

Cys Gly Ala Xaa Xaa Xaa Xaa Xaa Xaa Xaa Xaa Xaa Xaa Glu Lys
1               5                   10                  15

Gly Ala Gly Thr Xaa Leu Thr Val Lys
            20                  25

<210> SEQ ID NO 137
<211> LENGTH: 26
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X = C, S, Y or F
<220> FEATURE:
<221> NAME/KEY: MISC_FEATURE
<222> LOCATION: (5)..(8)
<223> OTHER INFORMATION: X = any amino acid
```

```
<220> FEATURE:
<221> NAME/KEY: MISC_FEATURE
<222> LOCATION: (9)..(11)
<223> OTHER INFORMATION: X = C, S, G, Y, N or D
<220> FEATURE:
<221> NAME/KEY: MISC_FEATURE
<222> LOCATION: (12)..(15)
<223> OTHER INFORMATION: X = any amino acid
<220> FEATURE:
<221> NAME/KEY: MISC_FEATURE
<222> LOCATION: (22)..(22)
<223> OTHER INFORMATION: X = A or V

<400> SEQUENCE: 137

Cys Gly Ala Xaa Xaa Xaa Xaa Xaa Xaa Xaa Xaa Xaa Xaa Xaa Glu
1               5                   10                  15

Lys Gly Ala Gly Thr Xaa Leu Thr Val Lys
            20                  25

<210> SEQ ID NO 138
<211> LENGTH: 25
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X = C, S, Y or F
<220> FEATURE:
<221> NAME/KEY: MISC_FEATURE
<222> LOCATION: (5)..(7)
<223> OTHER INFORMATION: X = any amino acid
<220> FEATURE:
<221> NAME/KEY: MISC_FEATURE
<222> LOCATION: (8)..(10)
<223> OTHER INFORMATION: X = C, S, G, Y, N or D
<220> FEATURE:
<221> NAME/KEY: MISC_FEATURE
<222> LOCATION: (11)..(13)
<223> OTHER INFORMATION: X = any amino acid
<220> FEATURE:
<221> NAME/KEY: MISC_FEATURE
<222> LOCATION: (21)..(21)
<223> OTHER INFORMATION: X = A or V

<400> SEQUENCE: 138

Cys Gln Ala Xaa Xaa Xaa Xaa Xaa Xaa Xaa Xaa Xaa Gly Glu Lys
1               5                   10                  15

Gly Ala Gly Thr Xaa Leu Thr Val Lys
            20                  25

<210> SEQ ID NO 139
<211> LENGTH: 26
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X = C, S, Y or F
<220> FEATURE:
<221> NAME/KEY: MISC_FEATURE
<222> LOCATION: (5)..(7)
<223> OTHER INFORMATION: X = any amino acid
<220> FEATURE:
<221> NAME/KEY: MISC_FEATURE
<222> LOCATION: (8)..(10)
<223> OTHER INFORMATION: X = C, S, G, Y, N or D
<220> FEATURE:
<221> NAME/KEY: MISC_FEATURE
<222> LOCATION: (11)..(14)
<223> OTHER INFORMATION: X = any amino acid
```

```
<220> FEATURE:
<221> NAME/KEY: MISC_FEATURE
<222> LOCATION: (22)..(22)
<223> OTHER INFORMATION: X = A or V

<400> SEQUENCE: 139

Cys Gln Ala Xaa Xaa Xaa Xaa Xaa Xaa Xaa Xaa Xaa Xaa Gly Glu
1               5                   10                  15

Lys Gly Ala Gly Thr Xaa Leu Thr Val Lys
            20                  25

<210> SEQ ID NO 140
<211> LENGTH: 31
<212> TYPE: PRT
<213> ORGANISM: Artificial sequence
<220> FEATURE:
<223> OTHER INFORMATION: synthetic

<400> SEQUENCE: 140

Cys Gln Ala Phe Tyr Ser Leu Pro Leu Gly Asp Tyr Asn Tyr Ser Leu
1               5                   10                  15

Leu Phe Arg Gly Glu Lys Gly Ala Gly Thr Ala Leu Thr Val Lys
            20                  25                  30

<210> SEQ ID NO 141
<211> LENGTH: 31
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (9)..(15)
<223> OTHER INFORMATION: X = any amino acid
<220> FEATURE:
<221> NAME/KEY: MISC_FEATURE
<222> LOCATION: (16)..(16)
<223> OTHER INFORMATION: X = L, V, P, A, H, Q, E, D, G, R

<400> SEQUENCE: 141

Cys Gln Ala Phe Tyr Ser Leu Pro Xaa Xaa Xaa Xaa Xaa Xaa Xaa Xaa
1               5                   10                  15

Leu Phe Arg Gly Glu Lys Gly Ala Gly Thr Ala Leu Thr Val Lys
            20                  25                  30

<210> SEQ ID NO 142
<211> LENGTH: 31
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (7)..(15)
<220> FEATURE:
<221> NAME/KEY: MISC_FEATURE
<222> LOCATION: (16)..(16)
<223> OTHER INFORMATION: X = L, V, P, A, H, Q, E, D, G, R

<400> SEQUENCE: 142

Cys Gln Ala Phe Tyr Ser Xaa Xaa Xaa Xaa Xaa Xaa Xaa Xaa Xaa Xaa
1               5                   10                  15

Leu Phe Arg Gly Glu Lys Gly Ala Gly Thr Ala Leu Thr Val Lys
            20                  25                  30

<210> SEQ ID NO 143
<211> LENGTH: 31
<212> TYPE: PRT
```

```
<213> ORGANISM: Artificial sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: X = any amino acid
<220> FEATURE:
<221> NAME/KEY: MISC_FEATURE
<222> LOCATION: (8)..(8)
<223> OTHER INFORMATION: X = S, Y, H or P
<220> FEATURE:
<221> NAME/KEY: MISC_FEATURE
<222> LOCATION: (9)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = S, Y, H or P
<220> FEATURE:
<221> NAME/KEY: MISC_FEATURE
<222> LOCATION: (11)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = S, Y, H or P
<220> FEATURE:
<221> NAME/KEY: MISC_FEATURE
<222> LOCATION: (14)..(14)
<223> OTHER INFORMATION: X = any amino acid
<220> FEATURE:
<221> NAME/KEY: MISC_FEATURE
<222> LOCATION: (15)..(15)
<223> OTHER INFORMATION: X = S, Y, H or P
<220> FEATURE:
<221> NAME/KEY: MISC_FEATURE
<222> LOCATION: (16)..(17)
<223> OTHER INFORMATION: X = L, V, P, A, H, Q, E, D, G or R

<400> SEQUENCE: 143

Cys Gln Ala Phe Tyr Ser Xaa Xaa Xaa Xaa Xaa Xaa Xaa Xaa Xaa
1               5                   10                  15

Xaa Phe Arg Gly Glu Lys Gly Ala Gly Thr Ala Leu Thr Val Lys
            20                  25                  30

<210> SEQ ID NO 144
<211> LENGTH: 32
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (7)..(9)
<223> OTHER INFORMATION: X = any amino acid
<220> FEATURE:
<221> NAME/KEY: MISC_FEATURE
<222> LOCATION: (10)..(13)
<223> OTHER INFORMATION: X = S, Y, H or P
<220> FEATURE:
<221> NAME/KEY: MISC_FEATURE
<222> LOCATION: (14)..(16)
<223> OTHER INFORMATION: X = any amino acid
<220> FEATURE:
<221> NAME/KEY: MISC_FEATURE
<222> LOCATION: (17)..(17)
<223> OTHER INFORMATION: X = L, V, P, A, H, Q, E, D, G or R

<400> SEQUENCE: 144

Cys Gln Ala Phe Tyr Ser Xaa Xaa Xaa Xaa Xaa Xaa Xaa Xaa Xaa
1               5                   10                  15

Xaa Leu Phe Arg Gly Glu Lys Gly Ala Gly Thr Ala Leu Thr Val Lys
            20                  25                  30
```

```
<210> SEQ ID NO 145
<211> LENGTH: 33
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (7)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = F, Y, C, I, M, N, K, R, S, W or L
<220> FEATURE:
<221> NAME/KEY: MISC_FEATURE
<222> LOCATION: (11)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = F, Y, C, I, M, N, K, R, S, W or L
<220> FEATURE:
<221> NAME/KEY: MISC_FEATURE
<222> LOCATION: (14)..(15)
<223> OTHER INFORMATION: X = any amino acid
<220> FEATURE:
<221> NAME/KEY: MISC_FEATURE
<222> LOCATION: (16)..(16)
<223> OTHER INFORMATION: X = F, Y, C, I, M, N, K, R, S, W or L
<220> FEATURE:
<221> NAME/KEY: MISC_FEATURE
<222> LOCATION: (17)..(18)
<223> OTHER INFORMATION: X = any amino acid

<400> SEQUENCE: 145

Cys Gln Ala Phe Tyr Ser Xaa Xaa Xaa Xaa Xaa Xaa Xaa Xaa Xaa
1               5                   10                  15

Xaa Xaa Leu Phe Arg Gly Glu Lys Gly Ala Gly Thr Ala Leu Thr Val
            20                  25                  30

Lys

<210> SEQ ID NO 146
<211> LENGTH: 33
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (7)..(7)
<223> OTHER INFORMATION: X = F, Y, C, I, M, N, K, R, S, W or L
<220> FEATURE:
<221> NAME/KEY: MISC_FEATURE
<222> LOCATION: (8)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = F, Y, C, I, M, N, K, R, S, W or L
<220> FEATURE:
<221> NAME/KEY: MISC_FEATURE
<222> LOCATION: (11)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = F, Y, C, I, M, N, K, R, S, W or L
<220> FEATURE:
<221> NAME/KEY: MISC_FEATURE
<222> LOCATION: (13)..(14)
<223> OTHER INFORMATION: X = any amino acid
<220> FEATURE:
<221> NAME/KEY: MISC_FEATURE
<222> LOCATION: (14)..(15)
```

```
<223> OTHER INFORMATION: X = any amino acid
<220> FEATURE:
<221> NAME/KEY: MISC_FEATURE
<222> LOCATION: (16)..(16)
<223> OTHER INFORMATION: X = F, Y, C, I, M, N, K, R, S, W or L
<220> FEATURE:
<221> NAME/KEY: MISC_FEATURE
<222> LOCATION: (17)..(18)
<223> OTHER INFORMATION: X = any amino acid

<400> SEQUENCE: 146

Cys Gln Ala Phe Tyr Ser Xaa Xaa Xaa Xaa Xaa Xaa Xaa Xaa Xaa
1               5                   10                  15

Xaa Xaa Leu Phe Arg Gly Glu Lys Gly Ala Gly Thr Ala Leu Thr Val
            20                  25                  30

Lys

<210> SEQ ID NO 147
<211> LENGTH: 16
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(10)
<223> OTHER INFORMATION: X = any amino acid
<220> FEATURE:
<221> NAME/KEY: MISC_FEATURE
<222> LOCATION: (11)..(11)
<223> OTHER INFORMATION: X = L, P, H, R, Q, V, A, N, G or E

<400> SEQUENCE: 147

Phe Tyr Ser Xaa Xaa Xaa Xaa Xaa Xaa Xaa Xaa Leu Phe Arg Gly Glu
1               5                   10                  15

<210> SEQ ID NO 148
<211> LENGTH: 18
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = L, P, H, R, Q, V, A, N, G or E

<400> SEQUENCE: 148

Phe Tyr Ser Xaa Xaa Xaa Xaa Xaa Xaa Xaa Xaa Xaa Xaa Leu Phe Arg
1               5                   10                  15

Gly Glu

<210> SEQ ID NO 149
<211> LENGTH: 19
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(6)
<223> OTHER INFORMATION: X = any amino acid
<220> FEATURE:
<221> NAME/KEY: MISC_FEATURE
<222> LOCATION: (7)..(10)
<223> OTHER INFORMATION: X = S, Y, P or H
<220> FEATURE:
```

```
<221> NAME/KEY: MISC_FEATURE
<222> LOCATION: (11)..(13)
<223> OTHER INFORMATION: X = any amino acid
<220> FEATURE:
<221> NAME/KEY: MISC_FEATURE
<222> LOCATION: (14)..(14)
<223> OTHER INFORMATION: X = L, P, H, R, Q, V, A, N, G or E

<400> SEQUENCE: 149

Phe Tyr Ser Xaa Xaa Xaa Xaa Xaa Xaa Xaa Xaa Xaa Xaa Leu Phe
1               5                   10                  15

Arg Gly Glu

<210> SEQ ID NO 150
<211> LENGTH: 18
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X = any amino acid
<220> FEATURE:
<221> NAME/KEY: MISC_FEATURE
<222> LOCATION: (5)..(5)
<223> OTHER INFORMATION: X = S, Y, P or H
<220> FEATURE:
<221> NAME/KEY: MISC_FEATURE
<222> LOCATION: (6)..(6)
<223> OTHER INFORMATION: X = any amino acid
<220> FEATURE:
<221> NAME/KEY: MISC_FEATURE
<222> LOCATION: (7)..(7)
<223> OTHER INFORMATION: X = S, Y, P or H
<220> FEATURE:
<221> NAME/KEY: MISC_FEATURE
<222> LOCATION: (8)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = S, Y, P or H
<220> FEATURE:
<221> NAME/KEY: MISC_FEATURE
<222> LOCATION: (11)..(11)
<223> OTHER INFORMATION: X = any amino acid
<220> FEATURE:
<221> NAME/KEY: MISC_FEATURE
<222> LOCATION: (12)..(12)
<223> OTHER INFORMATION: X = S, Y, P or H
<220> FEATURE:
<221> NAME/KEY: MISC_FEATURE
<222> LOCATION: (13)..(13)
<223> OTHER INFORMATION: X = L, P, H, R, Q, V, A, N, G or E

<400> SEQUENCE: 150

Phe Tyr Ser Xaa Xaa Xaa Xaa Xaa Xaa Xaa Xaa Xaa Leu Phe Arg
1               5                   10                  15

Gly Glu

<210> SEQ ID NO 151
<211> LENGTH: 20
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(6)
<223> OTHER INFORMATION: X = any amino acid
<220> FEATURE:
<221> NAME/KEY: MISC_FEATURE
<222> LOCATION: (7)..(7)
```

```
<223> OTHER INFORMATION: X = K, N, R, S, M, I, Y, W, C, L or F
<220> FEATURE:
<221> NAME/KEY: MISC_FEATURE
<222> LOCATION: (8)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = K, N, R, S, M, I, Y, W, C, L or F
<220> FEATURE:
<221> NAME/KEY: MISC_FEATURE
<222> LOCATION: (11)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = K, N, R, S, M, I, Y, W, C, L or F
<220> FEATURE:
<221> NAME/KEY: MISC_FEATURE
<222> LOCATION: (14)..(15)
<223> OTHER INFORMATION: X = any amino acid

<400> SEQUENCE: 151

Phe Tyr Ser Xaa Xaa Xaa Xaa Xaa Xaa Xaa Xaa Xaa Xaa Xaa Leu
1               5                   10                  15

Phe Arg Gly Glu
            20

<210> SEQ ID NO 152
<211> LENGTH: 20
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(4)
<223> OTHER INFORMATION: X = K, N, R, S, M, I, Y, W, C, L or F
<220> FEATURE:
<221> NAME/KEY: MISC_FEATURE
<222> LOCATION: (5)..(6)
<223> OTHER INFORMATION: X = any amino acid
<220> FEATURE:
<221> NAME/KEY: MISC_FEATURE
<222> LOCATION: (7)..(7)
<223> OTHER INFORMATION: X = K, N, R, S, M, I, Y, W, C, L or F
<220> FEATURE:
<221> NAME/KEY: MISC_FEATURE
<222> LOCATION: (8)..(9)
<223> OTHER INFORMATION: X = any amino acid
<220> FEATURE:
<221> NAME/KEY: MISC_FEATURE
<222> LOCATION: (10)..(10)
<223> OTHER INFORMATION: X = K, N, R, S, M, I, Y, W, C, L or F
<220> FEATURE:
<221> NAME/KEY: MISC_FEATURE
<222> LOCATION: (11)..(12)
<223> OTHER INFORMATION: X = any amino acid
<220> FEATURE:
<221> NAME/KEY: MISC_FEATURE
<222> LOCATION: (13)..(13)
<223> OTHER INFORMATION: X = K, N, R, S, M, I, Y, W, C, L or F
<220> FEATURE:
<221> NAME/KEY: MISC_FEATURE
<222> LOCATION: (14)..(15)
<223> OTHER INFORMATION: X = any amino acid

<400> SEQUENCE: 152

Phe Tyr Ser Xaa Xaa Xaa Xaa Xaa Xaa Xaa Xaa Xaa Xaa Xaa Leu
1               5                   10                  15

Phe Arg Gly Glu
            20

<210> SEQ ID NO 153
```

```
<211> LENGTH: 13
<212> TYPE: PRT
<213> ORGANISM: Artificial sequence
<220> FEATURE:
<223> OTHER INFORMATION: synthetic

<400> SEQUENCE: 153

Val Ala Gly Asp Ala Lys Asp Lys Asp Ile Ser Trp Phe
1               5                   10

<210> SEQ ID NO 154
<211> LENGTH: 13
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(9)
<223> OTHER INFORMATION: X = any amino acid

<400> SEQUENCE: 154

Val Ala Gly Xaa Xaa Xaa Xaa Xaa Xaa Ile Ser Trp Phe
1               5                   10

<210> SEQ ID NO 155
<211> LENGTH: 14
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(10)
<223> OTHER INFORMATION: X = any amino acid

<400> SEQUENCE: 155

Val Ala Gly Xaa Xaa Xaa Xaa Xaa Xaa Xaa Ile Ser Trp Phe
1               5                   10

<210> SEQ ID NO 156
<211> LENGTH: 21
<212> TYPE: PRT
<213> ORGANISM: Artificial sequence
<220> FEATURE:
<223> OTHER INFORMATION: synthetic

<400> SEQUENCE: 156

Cys Val Val Thr Gly Glu Asp Gly Ser Glu Ser Glu Ala Thr Val Asn
1               5                   10                  15

Val Lys Ile Phe Gln
            20

<210> SEQ ID NO 157
<211> LENGTH: 21
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(11)
<223> OTHER INFORMATION: X = any amino acid

<400> SEQUENCE: 157

Cys Val Val Xaa Xaa Xaa Xaa Xaa Xaa Xaa Xaa Glu Ala Thr Val Asn
1               5                   10                  15

Val Lys Ile Phe Gln
            20
```

<210> SEQ ID NO 158
<211> LENGTH: 24
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(14)
<223> OTHER INFORMATION: X = any amino acid

<400> SEQUENCE: 158

Cys Val Val Xaa Xaa Xaa Xaa Xaa Xaa Xaa Xaa Xaa Xaa Glu Ala
1               5                   10                  15

Thr Val Asn Val Lys Ile Phe Gln
            20

<210> SEQ ID NO 159
<211> LENGTH: 27
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(17)
<223> OTHER INFORMATION: X = any amino acid

<400> SEQUENCE: 159

Cys Val Val Xaa Xaa Xaa Xaa Xaa Xaa Xaa Xaa Xaa Xaa Xaa Xaa
1               5                   10                  15

Xaa Glu Ala Thr Val Asn Val Lys Ile Phe Gln
            20                  25

<210> SEQ ID NO 160
<211> LENGTH: 26
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (6)..(13)
<223> OTHER INFORMATION: X = any amino acid

<400> SEQUENCE: 160

Cys Val Val Thr Gly Xaa Xaa Xaa Xaa Xaa Xaa Xaa Xaa Ser Glu Ser
1               5                   10                  15

Glu Ala Thr Val Asn Val Lys Ile Phe Gln
            20                  25

<210> SEQ ID NO 161
<211> LENGTH: 14
<212> TYPE: PRT
<213> ORGANISM: Artificial sequence
<220> FEATURE:
<223> OTHER INFORMATION: synthetic

<400> SEQUENCE: 161

Cys Lys Ile Glu Gly Tyr Pro Asp Pro Glu Val Val Trp Phe
1               5                   10

<210> SEQ ID NO 162
<211> LENGTH: 14
<212> TYPE: PRT
<213> ORGANISM: Artificial sequence
<220> FEATURE:

```
<223> OTHER INFORMATION: synthetic
<220> FEATURE:
<221> NAME/KEY: MISC_FEATURE
<222> LOCATION: (4)..(10)
<223> OTHER INFORMATION: X = any amino acid

<400> SEQUENCE: 162

Cys Lys Ile Xaa Xaa Xaa Xaa Xaa Xaa Xaa Val Val Trp Phe
1               5                   10

<210> SEQ ID NO 163
<211> LENGTH: 16
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(12)
<223> OTHER INFORMATION: X = any amino acid

<400> SEQUENCE: 163

Cys Lys Ile Xaa Xaa Xaa Xaa Xaa Xaa Xaa Xaa Xaa Val Val Trp Phe
1               5                   10                  15

<210> SEQ ID NO 164
<211> LENGTH: 19
<212> TYPE: PRT
<213> ORGANISM: Artificial sequence
<220> FEATURE:
<223> OTHER INFORMATION: synthetic

<400> SEQUENCE: 164

Cys Lys Ala Val Asn Ser Leu Gly Glu Ala Thr Cys Thr Ala Glu Leu
1               5                   10                  15

Ile Val Glu

<210> SEQ ID NO 165
<211> LENGTH: 19
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(9)
<223> OTHER INFORMATION: X = any amino acid

<400> SEQUENCE: 165

Cys Lys Ala Xaa Xaa Xaa Xaa Xaa Xaa Ala Thr Cys Thr Ala Glu Leu
1               5                   10                  15

Ile Val Glu

<210> SEQ ID NO 166
<211> LENGTH: 22
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(12)
<223> OTHER INFORMATION: X = any amino acid

<400> SEQUENCE: 166

Cys Lys Ala Xaa Xaa Xaa Xaa Xaa Xaa Xaa Xaa Xaa Ala Thr Cys Thr
1               5                   10                  15

Ala Glu Leu Ile Val Glu
```

```
<210> SEQ ID NO 167
<211> LENGTH: 25
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (4)..(15)
<223> OTHER INFORMATION: X = any amino acid

<400> SEQUENCE: 167

Cys Lys Ala Xaa Xaa Xaa Xaa Xaa Xaa Xaa Xaa Xaa Xaa Xaa Xaa Ala
1               5                   10                  15

Thr Cys Thr Ala Glu Leu Ile Val Glu
            20                  25

<210> SEQ ID NO 168
<211> LENGTH: 28
<212> TYPE: PRT
<213> ORGANISM: Artificial sequence
<220> FEATURE:
<223> OTHER INFORMATION: synthetic
<220> FEATURE:
<221> NAME/KEY: MISC_FEATURE
<222> LOCATION: (8)..(16)
<223> OTHER INFORMATION: X = any amino acid

<400> SEQUENCE: 168

Cys Lys Ala Val Asn Ser Leu Xaa Xaa Xaa Xaa Xaa Xaa Xaa Xaa Xaa
1               5                   10                  15

Gly Glu Ala Thr Cys Thr Ala Glu Leu Ile Val Glu
            20                  25
```